US012673995B2

(12) United States Patent
Ganesan et al.

(10) Patent No.: US 12,673,995 B2
(45) Date of Patent: Jul. 7, 2026

(54) MATERIALS AND METHODS FOR MODULATING T CELL MEDIATED IMMUNITY

(71) Applicant: Janssen Biotech, Inc., Horsham, PA (US)

(72) Inventors: Rajkumar Ganesan, Blue Bell, PA (US); Iqbal S. Grewal, Newtown, PA (US); Sanjaya Singh, Blue Bell, PA (US)

(73) Assignee: Janssen Biotech, Inc., Horsham, PA (US)

( * ) Notice: Subject to any disclaimer, the term of this patent is extended or adjusted under 35 U.S.C. 154(b) by 511 days.

(21) Appl. No.: 18/306,401

(22) Filed: Apr. 25, 2023

(65) Prior Publication Data

US 2024/0150464 A1     May 9, 2024

Related U.S. Application Data

(63) Continuation of application No. 16/869,401, filed on May 7, 2020, now Pat. No. 11,667,712.

(60) Provisional application No. 62/844,966, filed on May 8, 2019, provisional application No. 62/844,976, filed on May 8, 2019, provisional application No. 62/844,959, filed on May 8, 2019, provisional application No. 62/844,970, filed on May 8, 2019, provisional application No. 62/844,995, filed on May 8, 2019.

(51) Int. Cl.
*C07K 16/28* (2006.01)
*A61K 38/17* (2006.01)

(52) U.S. Cl.
CPC ...... *C07K 16/2809* (2013.01); *A61K 38/1709* (2013.01); *C07K 16/2866* (2013.01); *C07K 2317/24* (2013.01); *C07K 2317/31* (2013.01); *C07K 2317/565* (2013.01)

(58) Field of Classification Search
CPC ............ C07K 16/2809; C07K 16/2866; C07K 2317/24; C07K 2317/31; C07K 2317/565; C07K 16/30; C07K 2317/92; A61K 38/1709; A61K 2039/505; A61P 35/00
USPC ...................................................... 424/133.1
See application file for complete search history.

(56) References Cited

U.S. PATENT DOCUMENTS

| | | | |
|---|---|---|---|
| 5,723,309 A | 3/1998 | Bonneville | |
| 6,737,056 B1 | 5/2004 | Presta | |
| 8,242,247 B2 | 8/2012 | Klein et al. | |
| 10,501,540 B2 | 12/2019 | Van Der Vliet et al. | |
| 11,466,082 B2 | 10/2022 | Diem et al. | |
| 11,603,405 B2 | 3/2023 | Gaudet et al. | |
| 11,667,712 B2 | 6/2023 | Ganesan et al. | |

| | | | |
|---|---|---|---|
| 2004/0018198 A1 | 1/2004 | Gudas et al. |
| 2007/0287170 A1 | 12/2007 | Davis et al. |
| 2009/0169547 A1 | 7/2009 | Sahin et al. |
| 2009/0182127 A1 | 7/2009 | Kjaergaard et al. |
| 2010/0015133 A1 | 1/2010 | Igawa et al. |
| 2010/0028637 A1 | 2/2010 | Tavsanli et al. |
| 2010/0261620 A1 | 10/2010 | Almagro et al. |
| 2011/0052488 A1 | 3/2011 | Dennis, Jr. et al. |
| 2011/0123532 A1 | 5/2011 | Gurney et al. |
| 2012/0149876 A1 | 6/2012 | von Kreudenstein et al. |
| 2013/0078249 A1 | 3/2013 | Ast et al. |
| 2013/0195849 A1 | 8/2013 | von Kreudenstein et al. |
| 2015/0119555 A1 | 4/2015 | Jung et al. |
| 2016/0068605 A1 | 3/2016 | Nemeth et al. |
| 2016/0175358 A1 | 6/2016 | Jakobovits et al. |
| 2017/0029506 A1 | 2/2017 | Van de Vliet et al. |
| 2018/0273602 A1 | 9/2018 | Alten et al. |
| 2019/0144540 A1 | 5/2019 | Koide et al. |
| 2019/0352397 A1 | 11/2019 | Takahashi et al. |
| 2021/0032338 A1 | 2/2021 | Ganesan et al. |
| 2021/0284731 A1 | 9/2021 | Ganesan et al. |
| 2022/0125947 A1 | 4/2022 | Ganesan et al. |
| 2022/0306739 A1 | 9/2022 | Ganesan et al. |
| 2023/0365683 A1 | 11/2023 | Doonan et al. |

FOREIGN PATENT DOCUMENTS

| | | | |
|---|---|---|---|
| CN | 105848484 A | 8/2016 |
| JP | H07-506495 A | 7/1995 |
| JP | 2017-529838 A | 10/2017 |
| JP | 2017-535292 A | 11/2017 |
| WO | WO 2006028936 A2 | 3/2006 |
| WO | WO 2006028936 A3 | 3/2006 |
| WO | WO 2009018386 A1 | 2/2009 |
| WO | WO 2009080251 A1 | 7/2009 |
| WO | WO 2009080252 A1 | 7/2009 |
| WO | WO 2009080254 A1 | 7/2009 |
| WO | WO 2011131746 A2 | 10/2011 |
| WO | WO 2011131746 A3 | 10/2011 |
| WO | WO 2012018767 A2 | 2/2012 |

(Continued)

OTHER PUBLICATIONS

Green, A.E. et al., "Recognition of nonpeptide antigens by human V gamma 9V delta 2 T cells requires contact with cells of human origin", Clin Exp Immunol, 136(3), pp. 472-482, Jun. 2004 (Jun. 2004).

(Continued)

*Primary Examiner* — Yan Xiao

(74) *Attorney, Agent, or Firm* — Troutman Pepper Locke LLP

(57) ABSTRACT

Anti-TRGV9 antibodies or antigen binding fragments thereof are described. Also described are nucleic acids encoding the antibodies, compositions comprising the antibodies, methods of producing the antibodies, and methods of using the antibodies for treating or preventing diseases, such as cancer.

6 Claims, 22 Drawing Sheets

Specification includes a Sequence Listing.

(56) References Cited

FOREIGN PATENT DOCUMENTS

| WO | WO 2012018767 A3 | 2/2012 |
| WO | WO 2015156673 A1 | 10/2015 |
| WO | WO 2016196237 A1 | 12/2016 |
| WO | 2019224711 A2 | 11/2019 |
| WO | 2020227457 A1 | 11/2020 |
| WO | WO 2021173896 A1 | 9/2021 |
| WO | WO 2022093888 A1 | 5/2022 |

OTHER PUBLICATIONS

Hans-Heinrich Oberg et al., Cellular Immunology Jul. 2015, vol. 296, No. 1, pp. 41-49.

Kugler et al., "A Recombinant Trispecific Single-Chain Fv Derivative Directed Against CD123 and CD33 Mediates Effective Elimination of Acute Myeloid Leukaemia Cells by Dual Targeting," British Journal of Hematology Jul. 2010, vol. 150, pp. 574-586.

Al-Lazikani et al., 1997, "Standard conformations for the canonical structures of immunoglobulins," J. Mol. Biol., 273(4):927-948.

Altschul et al., 1990, "Basic local alignment search tool," J. Mol. Biol., 215(3):403-410.

Altschul et al., 1997, "Gapped BLAST and PSI-BLAST: a new generation of protein database search programs," Nucleic Acids Res., 25(17):3389-3402.

Atwell et al., 1997, "Stable heterodimers from remodeling the domain interface of a homodimer using a phage display library," J. Mol. Biol., 270(1):26-35.

Belver et al., 2016, "The genetics and mechanisms of T cell acute lymphoblastic leukaemia," Nat. Rev. Cancer, 16(8):494-507.

Brown et al., 1998, "Affinity purification of human IgG using immobilised, mutated immunoglobulin-binding domains from protein A of Staphylococcus aureus," Biochem. Soc. Trans., 26(3):S249.

Bruin et al., 2017, "A bispecific nanobody approach to leverage the potent and widely applicable tumor cytolytic capacity of Vγ9Vδ2-T cells," Oncoimmunology, 7(1):e1375641 (15 pages).

Chames et al., 2009, "Bispecific antibodies for cancer therapy," Curr. Opin. Drug Discov. Devel., 12(2):276-283.

Chothia et al., 1987, "Canonical structures for the hypervariable regions of immunoglobulins," J. Mol. Biol., 196(4):901-917.

D'Asaro et al., 2010, "V gamma 9V delta 2 T lymphocytes efficiently recognize and kill zoledronate-sensitized, imatinib-sensitive, and imatinib-resistant chronic myelogenous leukemia cells," J. Immunol., 184(6):3260-3268.

Ebersbach et al., 2007, "Affilin-novel binding molecules based on human gamma-B-crystallin, an all beta-sheet protein," J. Mol. Biol., 372(1):172-185.

Ferrara et al., 2006, "Modulation of therapeutic antibody effector functions by glycosylation engineering: influence of Golgi enzyme localization domain and co-expression of heterologous betal, 4-N-acetylglucosaminyltransferase III and Golgi alpha-mannosidase II," Biotechnol. Bioeng., 93(5):851-861.

Ferrara et al., 2006, "The carbohydrate at FcgammaRIIIa Asn-162. An element required for high affinity binding to non-fucosylated IgG glycoforms," J. Biol. Chem., 281(8):5032-5036 (Epub 2005).

Ganesan et al., 2021, "Selective recruitment of γδ T cells by a bispecific antibody for the treatment of acute myeloid leukemia," Leukemia, 35(8):2274-2284.

Gebauer et al., 2009, "Engineered protein scaffolds as next-generation antibody therapeutics," Curr. Opin. Chem. Biol., 13(3):245-255.

GenBank Accession No. AY789109.1 (UnitProt P26951), "Interleukin-3 receptor subunit alpha · Homo sapiens (Human) • Gene: IL3RA (IL3R)," retrieved from internet <https://beta.uniprot.org/uniprotkb/P26951/entry> on Mar. 23, 2022, last released Feb. 23, 2022 (10 pages).

GenBank Accession No. BC028152.1 (UnitProt P20138), "Myeloid cell surface antigen CD33 • Homo sapiens (Human) · Gene: CD33 (SIGLEC3)," retrieved from internet <https://beta.uniprot.org/uniprotkb/P20138/entry> on Mar. 23, 2022, last released Feb. 23, 2022 (12 pages).

GenBank Accession No. NC_000007.14 (TRGC1), "Homo sapiens chromosome 7, GRCh38.p14 Primary Assembly," retrieved from internet <https://www.ncbi.nlm.nih.gov/nuccore/NC_000007.14?strand=2&report=genbank&from=38257879&to=38265678> on Sep. 20, 2022, last updated Apr. 6, 2022 (5 pages).

GenBank Accession No. NC_000007.14 (TRGC2), "Homo sapiens chromosome 7, GRCh38.p14 Primary Assembly," retrieved from internet <https://www.ncbi.nlm.nih.gov/nuccore/NC_000007.14?strand=2&report=genbank&from=38239580&to=38249572> on Sep. 20, 2022, last updated Apr. 6, 2022 (5 pages).

GenBank Accession No. NG_001336.2 (UnitProt Q99603), "T cell receptor gamma variable 9 • Homo sapiens (Human) · Gene: TRGV9 (TCRGV9)," retrieved from internet <https://beta.uniprot.org/uniprotkb/Q99603/entry> on Mar. 23, 2022, last released Feb. 23, 2022 (8 pages).

Grabulovski et al., 2007, "A novel, non-immunogenic Fyn SH3-derived binding protein with tumor vascular targeting properties," J. Biol. Chem., 282(5):3196-3204 (Epub 2006).

Hamuro et al., 2003, "Rapid analysis of protein structure and dynamics by hydrogen/deuteriuni exchange mass spectrometry," J. Biomol. Tech., 14(3):171-182.

Henikoff et al., 1992, "Amino acid substitution matrices from protein blocks," Proc. Natl. Acad. Sci. USA, 89(22):10915-10919.

Honegger et al., 2001, "Yet another numbering scheme for immunoglobulin variable domains: an automatic modeling and analysis tool," J. Mol. Biol., 309(3):657-670.

Horn et al., 2006, "The role of protein dynamics in increasing binding affinity for an engineered protein-protein interaction established by H/D exchange mass spectrometry," Biochemistry, 45(28):8488-8498.

Huang et al., 2018, "Hydrogen/deuterium exchange mass spectrometry and computational modeling reveal a discontinuous epitope of an antibody/TL1A Interaction," mAbs, 10(1):95-103 (Epub 2017).

International Search Authority, International Search Report and Written Opinion for International Patent Application No. PCT/US2020/031749 (Pub No. WO 2020227457) mailed Oct. 9, 2020 (16 pages).

International Search Authority, International Search Report and Written Opinion for International Patent Application No. PCT/US2021/019766 (Pub No. WO 2021173896) mailed Jul. 1, 2021 (10 pages).

International Search Authority, International Search Report and Written Opinion for International Patent Application No. PCT/US2021/056744 (Pub No. WO 2022093888) mailed Mar. 2, 2022 (12 pages).

Itohara et al., 1990, "Selection of gamma delta T cells with canonical T-cell antigen receptors in fetal thymus," Proc. Natl. Acad. Sci. USA, 87(20):7935-7938.

Kabat et al., 1977, "Unusual distributions of amino acids in complementarity-determining (hypervariable) segments of heavy and light chains of immunoglobulins and their possible roles in specificity of antibody-combining sites," J. Biol. Chem., 252(19):6609-6616.

Kabat, 1978, "The structural basis of antibody complementarity," Adv. Protein. Chem., 32:1-75.

Karlin et al., 1993, "Applications and statistics for multiple high-scoring segments in molecular sequences," Proc. Natl. Acad. Sci. USA, 90(12):5873-5877.

Kiladjian et al., 2008, "Activation of cytotoxic T-cell receptor gammadelta T lymphocytes in response to specific stimulation in myelodysplastic syndromes," Haematologica, 93(3):381-389.

Kirkland et al., 1986, "Analysis of the fine specificity and cross-reactivity of monoclonal anti-lipid A antibodies," J. Immunol., 137(11):3614-3619.

Koide et al., 2007, "Monobodies: antibody mimics based on the scaffold of the fibronectin type III domain," Methods Mol. Biol., 352:95-109.

Kolmar, 2008, "Alternative binding proteins: biological activity and therapeutic potential of cystine-knot miniproteins," FEBS J., 275(11):2684-2690.

(56)　　　　　References Cited

OTHER PUBLICATIONS

Konno et al., 2012, "Fucose content of monoclonal antibodies can be controlled by culture medium osmolality for high antibody-dependent cellular cytotoxicity," Cytotechnology, 64(3):249-265 (Epub 2011).

Krehenbrink et al., 2008, "Artificial binding proteins (Affitins) as probes for conformational changes in secretin PulD," J. Mol. Biol., 383(5):1058-1068.

Lefranc et al., 2003, "IMGT unique numbering for immunoglobulin and T cell receptor variable domains and Ig superfamily V-like domains," Dev. Comp. Immunol., 27(1):55-77.

Legut et al., 2015, "The promise of γδ T cells and the γδ cell receptor for cancer immunotherapy," Cell Mol. Immunol., 12(6):656-668.

Litzow et al., 2015, "How I treat T-cell acute lymphoblastic leukemia in adults," Blood, 126(7):833-841.

Liu et al., 2017, "The genomic landscape of pediatric and young adult T-lineage acute lymphoblastic leukemia," Nat. Genet., 49(8):1211-1218 and Online Methods (10 pages).

Moldenhauer et al., 1990, "Identity of HML-1 antigen on intestinal intraepithelial T cells and of B-ly7 antigen on hairy cell leukaemia," Scand. J. Immunol., 32(2):77-82.

Morea et al., 2000, "Antibody modeling: implications for engineering and design," Methods, 20(3):267-279.

Morel et al., 1988, "Monoclonal antibodies to bovine serum albumin: affinity and specificity determinations," Mol. Immunol., 25(1):7-15.

Mori et al., 2004, "Engineering Chinese hamster ovary cells to maximize effector function of produced antibodies using FUT8 siRNA," Biotechnol. Bioeng., 88(7):901-908.

Needleman et al., 1970, "A general method applicable to the search for similarities in the amino acid sequence of two proteins," J. Mol. Biol., 48(3):443-453.

Nixon et al., 2006, "Engineered protein inhibitors of proteases," Curr. Opin. Drug Discov. Devel., 9(2):261-268.

Nunez-Prado et al., 2015, "The coming of age of engineered multivalent antibodies," Drug Discov. Today, 20(5):588-594.

Nygren, 2008, "Alternative binding proteins: affibody binding proteins developed from a small three-helix bundle scaffold," FEBS J., 275(11):2668-2676.

Oberg et al., 2014, "Novel bispecific antibodies increase γδ T-cell cytotoxicity against pancreatic cancer cells," Cancer Res., 74(5):1349-1360.

Oberg et al., 2015, "γδ T cell activation by bispecific antibodies," Cell Immunol., 296(1):41-49.

Olivier et al., 2010, "EB66 cell line, a duck embryonic stem cell-derived substrate for the industrial production of therapeutic monoclonal antibodies with enhanced ADCC activity," mAbs, 2(4):405-415.

Pascal et al., 2012, "HDX workbench: software for the analysis of H/D exchange MS data," J. Am. Soc. Mass Spectrom., 23(9):1512-1521.

Pearson et al., 1988, "Improved tools for biological sequence comparison," Proc. Natl. Acad. Sci. USA, 85(8):2444-2448.

Pui et al., 2015, "Childhood Acute Lymphoblastic Leukemia: Progress Through Collaboration," J. Clin. Oncol., 33(27):2938-2948.

Shields et al., 2002, "Lack of fucose on human IgG1 N-linked oligosaccharide improves binding to human Fcgamma RIII and antibody-dependent cellular toxicity," J. Biol. Chem., 277(30):26733-26740.

Shinkawa et al., 2003, "The absence of fucose but not the presence of galactose or bisecting N-acetylglucosamine of human IgG1 complex-type oligosaccharides shows the critical role of enhancing antibody-dependent cellular cytotoxicity," J. Biol. Chem., 278(5):3466-3473 (Epub 2002).

Silverman et al., 2005, "Multivalent avimer proteins evolved by exon shuffling of a family of human receptor domains," Nat. Biotechnol., 23(12):1556-1561.

Singh et al., 2015, "Selective targeting of the IL23 pathway: Generation and characterization of a novel high-affinity humanized anti-IL23A antibody," mAbs, 7(4):778-791.

Skerra, 2008, "Alternative binding proteins: anticalins—harnessing the structural plasticity of the lipocalin ligand pocket to engineer novel binding activities" FEBS J., 275(11):2677-2683.

Smith et al., 1981, "Comparison of biosequences," Advances in Applied Mathematics, 2(4):482-489.

Stahli et al., 1983, "Distinction of epitopes by monoclonal antibodies," Methods Enzymol., 92:242-253.

Stumpp et al., 2008, "DARPins: a new generation of protein therapeutics," Drug Discov. Today, 13(15-16):695-701.

Wesselborg et al., 1991, "Selective activation of gamma/delta + T cell clones by single anti-CD2 antibodies," J. Exp. Med., 173(2):297-304.

Wranik et al., 2012, "LUZ-Y, a novel platform for the mammalian cell production of full-length IgG-bispecific antibodies," J. Biol. Chem., 287(52):43331-43339.

Zhang et al., 2019, "CellMarker: a manually curated resource of cell markers in human and mouse," Nucleic Acids Res., 47(D1):D721-D728 (Epub 2018).

Zhou et al., 2008, "Development of a simple and rapid method for producing non-fucosylated oligomannose containing antibodies with increased effector function," Biotechnol. Bioeng., 99(3):652-665.

European Patent Office, Supplemental European Search Report, for Related Patent Application No. EP20801607, May 2, 2023.

Office Action issued in corresponding Japanese Patent Application No. 2021-565723 dated Nov. 12, 2024 (including English Translation).

Airoldi et al. "γδ T-cell reconstitution after HLA-haploidentical hematopoietic transplantation depleted of TCR-γβ+/CD19+ lymphocytes". Blood. Apr. 9, 2015; vol. 125(15); pp. 2349-2358.

E:T (1:1)

$EC_{50}$ 160 pM

E:T (5:1)

$EC_{50}$ 167 pM

EC$_{50}$: 1-2 nM                low binding (S:B)

*FIG. 15*

MATERIALS AND METHODS FOR MODULATING T CELL MEDIATED IMMUNITY

CROSS-REFERENCE TO RELATED APPLICATIONS

This application is a continuation of U.S. application Ser. No. 16/869,401, filed May 7, 2020, which claims the benefit of U.S. Ser. No. 62/844,959 filed May 8, 2019; U.S. Ser. No. 62/844,966 filed May 8, 2019; U.S. Ser. No. 62/844,970 filed May 8, 2019; U.S. Ser. No. 62/844,976 filed May 8, 2019; and U.S. Ser. No. 62/844,995 filed May 8, 2019, each of which is incorporated herein by reference in its entirety.

FIELD

This invention relates to, among other things, anti-TRGV9 molecules, including anti-TRGV9 antibodies, anti-TRGV9/anti-cancer-associated antigen bispecific antibodies, as well as nucleic acids and expression vectors encoding the antibodies, recombinant cells containing the vectors, and compositions comprising the antibodies. Methods of making the antibodies, and methods of using the antibodies to kill cancer cells, are also provided.

REFERENCE TO SEQUENCE LISTING SUBMITTED ELECTRONICALLY

This application contains a sequence listing, which is submitted electronically via EFS-Web as an XML file formatted sequence listing with a file name 253505_000335_SL.xml and a creation date of Jul. 28, 2023 and having a size of 838,153 bytes. The sequence listing submitted via EFS-Web is part of the specification and is herein incorporated by reference in its entirety.

SUMMARY

In one aspect, provided herein is an antibody that binds to T Cell Receptor Gamma Variable 9 (TRGV9). In some embodiments, the antibody comprises a heavy chain variable region (VH) and a light chain variable region (VL).

In another aspect, provided herein is an antibody that binds to TRGV9, wherein the antibody comprises: (i) a VH comprising a VH complementarity determining region (CDR) 1 having an amino acid sequence of SEQ ID NO:1, a VH CDR2 having an amino acid sequence of SEQ ID NO:2, and a VH CDR3 having an amino acid sequence of SEQ ID NO:31; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In some embodiments, the antibody comprises a VH having an amino acid sequence of SEQ ID NO:34. In some embodiments, the antibody comprises a VL having an amino acid sequence of SEQ ID NO:8. In some embodiments, the antibody comprises a VH having an amino acid sequence of SEQ ID NO:34, and a VL having an amino acid sequence of SEQ ID NO:8. In some embodiments, the antibody specifically binds TRGV9. In other embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody. In some embodiments, the antibody is a bispecific antibody. In certain embodiments, the antibody is multivalent. In other embodiments, the antibody is capable of binding at least three antigens. In some embodiments, the antibody is capable of binding at least five antigens.

In another aspect, provided herein is an antibody that binds to TRGV9, wherein the antibody comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:32; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In some embodiments, the antibody comprises a VH having an amino acid sequence of SEQ ID NO:35. In some embodiments, the antibody comprises a VL having an amino acid sequence of SEQ ID NO:8. In some embodiments, the antibody comprises a VH having an amino acid sequence of SEQ ID NO:35, and a VL having an amino acid sequence of SEQ ID NO:8. In some embodiments, the antibody specifically binds TRGV9. In other embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody. In some embodiments, the antibody is a bispecific antibody. In certain embodiments, the antibody is multivalent. In other embodiments, the antibody is capable of binding at least three antigens. In some embodiments, the antibody is capable of binding at least five antigens.

In another aspect, provided herein is an antibody that binds to TRGV9, wherein the antibody comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:33; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In some embodiments, the antibody comprises a VH having an amino acid sequence of SEQ ID NO:36. In some embodiments, the antibody comprises a VL having an amino acid sequence of SEQ ID NO:8. In some embodiments, the antibody comprises a VH having an amino acid sequence of SEQ ID NO:36, and a VL having an amino acid sequence of SEQ ID NO:8. In some embodiments, the antibody specifically binds TRGV9. In other embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody. In some embodiments, the antibody is a bispecific antibody. In certain embodiments, the antibody is multivalent. In other embodiments, the antibody is capable of binding at least three antigens. In some embodiments, the antibody is capable of binding at least five antigens.

In another aspect, provided herein is an antibody that binds to TRGV9, wherein the antibody comprises: (i) a VH comprising a VH CDR1 having an amino acid sequence of SEQ ID NO:1, a VH CDR2 having an amino acid sequence of SEQ ID NO:76, and a VH CDR3 having an amino acid sequence of SEQ ID NO:3; and (ii) a VL comprising a VL CDR1 having an amino acid sequence of SEQ ID NO:77, a VL CDR2 having an amino acid sequence of SEQ ID NO:5, and a VL CDR3 having an amino acid sequence of SEQ ID NO:6. In another aspect, provided herein is an antibody that binds to TRGV9, wherein the antibody comprises: (i) a VH comprising a VH CDR1 having an amino acid sequence of SEQ ID NO:60, a VH CDR2 having an amino acid sequence of SEQ ID NO:61, and a VH CDR3 having an amino acid sequence of SEQ ID NO:62; and (ii) a VL comprising a VL CDR1 having an amino acid sequence of SEQ ID NO:63, a VL CDR2 having an amino acid sequence of SEQ ID NO:64, and a VL CDR3 having an amino acid sequence of SEQ ID NO:6. In some embodiments, the antibody comprises a VH having an amino acid sequence of SEQ ID NO:65. In some embodiments, the antibody comprises a VL having an amino acid sequence of SEQ ID NO:66. In some embodiments, the antibody comprises a VH having an amino acid sequence of SEQ ID NO:65, and a VL having an amino acid sequence of SEQ ID NO:66. In some embodiments, the antibody comprises a VH having an amino acid sequence of SEQ ID NO:67. In some embodiments, the antibody comprises a VL having an amino acid sequence of SEQ ID NO:68. In some embodiments, the antibody comprises a VH having an amino acid sequence of SEQ ID NO:67, and a VL having an amino acid sequence of SEQ ID NO:68. In some embodiments, the antibody specifically binds TRGV9. In other embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody. In some embodiments, the antibody is a bispecific antibody. In certain embodiments, the antibody is multivalent. In other embodiments, the antibody is capable of binding at least three antigens. In some embodiments, the antibody is capable of binding at least five antigens.

In another aspect, provided herein is an antibody that binds to TRGV9, wherein the antibody comprises: (i) a VH comprising a VH CDR1 having an amino acid sequence of SEQ ID NO:98, a VH CDR2 having an amino acid sequence of SEQ ID NO:99, and a VH CDR3 having an amino acid sequence of SEQ ID NO:100; and (ii) a VL comprising a VL CDR1 having an amino acid sequence of SEQ ID NO:101, a VL CDR2 having an amino acid sequence of SEQ ID NO:102, and a VL CDR3 having an amino acid sequence of SEQ ID NO:103. In some embodiments, the antibody comprises a VH having an amino acid sequence of SEQ ID NO:104. In some embodiments, the antibody comprises a VL having an amino acid sequence of SEQ ID NO:105. In some embodiments, the antibody comprises a VH having an amino acid sequence of SEQ ID NO:104, and a VL having an amino acid sequence of SEQ ID NO:105. In some embodiments, the antibody specifically binds TRGV9. In other embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody. In some embodiments, the antibody is a bispecific antibody. In certain embodiments, the antibody is multivalent. In other embodiments, the antibody is capable of binding at least three antigens. In some embodiments, the antibody is capable of binding at least five antigens.

In another aspect, provided herein is an antibody that binds to TRGV9, wherein the antibody comprises: (i) a VH comprising a VH CDR1 having an amino acid sequence of SEQ ID NO:107, a VH CDR2 having an amino acid sequence of SEQ ID NO:108, and a VH CDR3 having an amino acid sequence of SEQ ID NO: 109; and (ii) a VL comprising a VL CDR1 having an amino acid sequence of SEQ ID NO:110, a VL CDR2 having an amino acid sequence of SEQ ID NO:111, and a VL CDR3 having an amino acid sequence of SEQ ID NO:112. In some embodiments, the antibody comprises a VH having an amino acid sequence of SEQ ID NO:113. In some embodiments, the antibody comprises a VL having an amino acid sequence of SEQ ID NO:114. In some embodiments, the antibody comprises a VH having an amino acid sequence of SEQ ID NO:113, and a VL having an amino acid sequence of SEQ ID NO:114. In some embodiments, the antibody specifically binds TRGV9. In other embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody. In some embodiments, the antibody is a bispecific antibody. In certain embodiments, the antibody is multivalent. In other embodiments, the antibody is capable of binding at least three antigens. In some embodiments, the antibody is capable of binding at least five antigens.

In another aspect, provided herein is an antibody that binds to TRGV9, wherein the antibody comprises: (i) a VH comprising a VH CDR1 having an amino acid sequence of SEQ ID NO:117, a VH CDR2 having an amino acid sequence of SEQ ID NO:118, and a VH CDR3 having an amino acid sequence of SEQ ID NO:119; and (ii) a VL comprising a VL CDR1 having an amino acid sequence of SEQ ID NO:120, a VL CDR2 having an amino acid sequence of SEQ ID NO:121, and a VL CDR3 having an amino acid sequence of SEQ ID NO:122. In some embodiments, the antibody comprises a VH having an amino acid sequence of SEQ ID NO:123. In some embodiments, the antibody comprises a VL having an amino acid sequence of SEQ ID NO:124. In some embodiments, the antibody comprises a VH having an amino acid sequence of SEQ ID NO:123, and a VL having an amino acid sequence of SEQ ID NO:124. In some embodiments, the antibody specifically binds TRGV9. In other embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody. In some embodiments, the antibody is a bispecific antibody. In certain embodiments, the antibody is multivalent. In other embodiments, the antibody is capable of binding at least three antigens. In some embodiments, the antibody is capable of binding at least five antigens.

In another aspect, provided herein is an antibody that binds to TRGV9, wherein the antibody comprises: (i) a VH comprising a VH CDR1 having an amino acid sequence of SEQ ID NO:127, a VH CDR2 having an amino acid sequence of SEQ ID NO:128, and a VH CDR3 having an amino acid sequence of SEQ ID NO: 129; and (ii) a VL comprising a VL CDR1 having an amino acid sequence of SEQ ID NO:130, a VL CDR2 having an amino acid sequence of SEQ ID NO:131, and a VL CDR3 having an amino acid sequence of SEQ ID NO:132. In some embodiments, the antibody comprises a VH having an amino acid sequence of SEQ ID NO:133. In some embodiments, the antibody comprises a VL having an amino acid sequence of SEQ ID NO:134. In some embodiments, the antibody comprises a VH having an amino acid sequence of SEQ ID NO:133, and a VL having an amino acid sequence of SEQ ID NO:134. In some embodiments, the antibody specifically binds TRGV9. In other embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody. In some embodiments, the antibody is a bispecific antibody. In certain embodiments, the antibody is multivalent. In other embodiments, the antibody is capable of binding at least three antigens. In some embodiments, the antibody is capable of binding at least five antigens.

Also provided is a nucleic acid encoding an antibody that binds to a TRGV9 provided herein. Also provided is a vector comprising a nucleic acid encoding an antibody that binds to a TRGV9 provided herein. Also provided is a host cell comprising a vector comprising a nucleic acid encoding an antibody that binds to a TRGV9 provided herein. Also provided is a kit comprising the vector comprising a nucleic acid encoding an antibody that binds to a TRGV9 provided herein, and packaging for the same.

Also provided is a pharmaceutical composition comprising an antibody that binds to a TRGV9 provided herein, and a pharmaceutically acceptable carrier. Also provided is a method of producing the pharmaceutical composition, comprising combining the antibody with a pharmaceutically acceptable carrier to obtain the pharmaceutical composition.

Also provided is a method of activating a γδ T cell expressing TRGV9, comprising contacting the γδ T cell with an antibody that binds to a TRGV9 provided herein. In some embodiments, the contacting results in an increase in CD69, CD25, and/or Granzyme B expression, as compared to a control γδ T cell expressing TRGV9. Also provided is a method of inactivating a γδ T cell expressing TRGV9, comprising contacting the γδ T cell with an antibody that binds to a TRGV9 provided herein. Also provided is a method of blocking activation a γδ T cell expressing TRGV9, comprising contacting the γδ T cell with an antibody that binds to a TRGV9 provided herein. Also provided is a method of modulating the activity of a γδ T cell expressing TRGV9, comprising contacting the γδ T cell with an antibody that binds to a TRGV9 provided herein.

In another aspect, provided herein is a bispecific antibody comprising: (a) a first binding domain that binds to TRGV9, and (b) a second binding domain that binds to a second target that is not TRGV9. In certain embodiments, the first binding domain of the bispecific antibody specifically binds TRGV9. In some embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:3; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In some embodiments, the first binding domain comprises a VH having an amino acid sequence of SEQ ID NO:7. In some embodiments, the first binding domain comprises a VL having an amino acid sequence of SEQ ID NO:8. In some embodiments, the first binding domain comprises a VH having an amino acid sequence of SEQ ID NO:7, and a VL having an amino acid sequence of SEQ ID NO:8. In certain embodiments, the first binding domain of the bispecific antibody specifically binds TRGV9. In some embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:31; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In some embodiments, the first binding domain comprises a VH having an amino acid sequence of SEQ ID NO:34. In some embodiments, the first binding domain comprises a VL having an amino acid sequence of SEQ ID NO:8. In some embodiments, the first binding domain comprises a VH having an amino acid sequence of SEQ ID NO:34, and a VL having an amino acid sequence of SEQ ID NO:8. In certain embodiments, the first binding domain of the bispecific antibody specifically binds TRGV9. In some embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:32; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In some embodiments, the first binding domain comprises a VH having an amino acid sequence of SEQ ID NO:35. In some embodiments, the first binding domain comprises a VL having an amino acid sequence of SEQ ID NO:8. In some embodiments, the first binding domain comprises a VH having an amino acid sequence of SEQ ID NO:35, and a VL having an amino acid sequence of SEQ ID NO:8. In certain embodiments, the first binding domain of the bispecific antibody specifically binds TRGV9. In some embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:33; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In some embodiments, the first binding domain comprises a VH having an amino acid sequence of SEQ ID NO:36. In some embodiments, the first binding domain comprises a VL having an amino acid sequence of SEQ ID NO:8. In some embodiments, the first binding domain comprises a VH having an amino acid sequence of SEQ ID NO:36, and a VL having an amino acid sequence of SEQ ID NO:8. In certain embodiments, the first binding domain of the bispecific antibody specifically binds TRGV9. In some embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:1, a VH CDR2 having an amino acid sequence of SEQ ID NO:76, and a VH CDR3 having an amino acid sequence of SEQ ID NO:3; and (ii) a VL comprising a VL CDR1 having an amino acid sequence of SEQ ID NO:77, a VL CDR2 having an amino acid sequence of SEQ ID NO:5, and a VL CDR3 having an amino acid sequence of SEQ ID NO:6. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:60, a VH CDR2 having an amino acid sequence of SEQ ID NO:61, and a VH CDR3 having an amino acid sequence of SEQ ID NO:62; and (ii) a VL comprising a VL CDR1 having an amino acid sequence of SEQ ID NO:63, a VL CDR2 having an amino acid sequence of SEQ ID NO:64, and a VL CDR3 having an amino acid sequence of SEQ ID NO:6. In some embodiments, the first binding domain comprises a VH having an amino acid sequence of SEQ ID NO:65. In some embodiments, the first binding domain comprises a VL having an amino acid sequence of SEQ ID NO:66. In some embodiments, the first binding domain comprises a VH having an amino acid sequence of SEQ ID NO:65, and a VL having an amino acid sequence of SEQ ID NO:66. In some embodiments, the first binding domain comprises a VH having an amino acid sequence of SEQ ID NO:67. In some embodiments, the first binding domain comprises a VL having an amino acid sequence of SEQ ID NO:68. In some embodiments, the first binding domain a VH having an amino acid sequence of SEQ ID NO:67, and a VL having an amino acid sequence of SEQ ID NO:68. In certain embodiments, the first binding domain of the bispecific antibody specifically binds TRGV9. In some embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:89, a VH CDR2 having an amino acid sequence of SEQ ID NO:90, and a VH CDR3 having an amino acid sequence of SEQ ID NO:91; and (ii) a VL comprising a VL CDR1 having an amino acid sequence of SEQ ID NO:92, a VL CDR2 having an amino acid sequence of SEQ ID NO:93, and a VL CDR3 having an amino acid sequence of SEQ ID NO:94. In some embodiments, the first binding domain comprises a VH having an amino acid sequence of SEQ ID NO:95. In some embodiments, the first binding domain comprises a VL having an amino acid sequence of SEQ ID NO:96. In some embodiments, the first binding domain comprises a VH having an amino acid sequence of SEQ ID NO:95, and a VL having an amino acid sequence of SEQ ID NO:96. In certain embodiments, the first binding domain of the bispecific antibody specifically binds TRGV9. In some embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:98, a VH CDR2 having an amino acid sequence of SEQ ID NO:99, and a VH CDR3 having an amino acid sequence of SEQ ID NO:100, and (ii) a VL comprising a VL CDR1 having an amino acid sequence of SEQ ID NO:101, a VL CDR2 having an amino acid sequence of SEQ ID NO:102, and a VL CDR3 having an amino acid sequence of SEQ ID NO:103. In some embodiments, the first binding domain comprises a VH having an amino acid sequence of SEQ ID NO:104. In some embodiments, the first binding domain comprises a VL having an amino acid sequence of SEQ ID NO:105. In some embodiments, the first binding domain comprises a VH having an amino acid sequence of SEQ ID NO:104, and a VL having an amino acid sequence of SEQ ID NO:105. In certain embodiments, the first binding domain of the bispecific antibody specifically binds TRGV9. In some embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:107, a VH CDR2 having an amino acid sequence of SEQ ID NO:108, and a VH CDR3 having an amino acid sequence of SEQ ID NO:109, and (ii) a VL comprising a VL CDR1 having an amino acid sequence of SEQ ID NO:110, a VL CDR2 having an amino acid sequence of SEQ ID NO:111, and a VL CDR3 having an amino acid sequence of SEQ ID NO:112. In some embodiments, the first binding domain comprises a VH having an amino acid sequence of SEQ ID NO:113. In some embodiments, the first binding domain comprises a VL having an amino acid sequence of SEQ ID NO:114. In some embodiments, the first binding domain comprises a VH having an amino acid sequence of SEQ ID NO:113, and a VL having an amino acid sequence of SEQ ID NO:114. In certain embodiments, the first binding domain of the bispecific antibody specifically binds TRGV9. In some embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:117, a VH CDR2 having an amino acid sequence of SEQ ID NO:118, and a VH CDR3 having an amino acid sequence of SEQ ID NO:119, and (ii) a VL comprising a VL CDR1 having an amino acid sequence of SEQ ID NO:120, a VL CDR2 having an amino acid sequence of SEQ ID NO:121, and a VL CDR3 having an amino acid sequence of SEQ ID NO:122. In some embodiments, the first binding domain comprises a VH having an amino acid sequence of SEQ ID NO:123. In some embodiments, the first binding domain comprises a VL having an amino acid sequence of SEQ ID NO:124. In some embodiments, the first binding domain comprises a VH having an amino acid sequence of SEQ ID NO:123, and a VL having an amino acid sequence of SEQ ID NO:124. In certain embodiments, the first binding domain of the bispecific antibody specifically binds TRGV9. In some embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:127, a VH CDR2 having an amino acid sequence of SEQ ID NO:128, and a VH CDR3 having an amino acid sequence of SEQ ID NO:129, and (ii) a VL comprising a VL CDR1 having an amino acid sequence of SEQ ID NO:130, a VL CDR2 having an amino acid sequence of SEQ ID NO:131, and a VL CDR3 having an amino acid sequence of SEQ ID NO:132. In some embodiments, the first binding domain comprises a VH having an amino acid sequence of SEQ ID NO:133. In some embodiments, the first binding domain comprises a VL having an amino acid sequence of SEQ ID NO:134. In some embodiments, the first binding domain comprises a VH having an amino acid sequence of SEQ ID NO:133, and a VL having an amino acid sequence of SEQ ID NO:134. In certain embodiments, the first binding domain of the bispecific antibody specifically binds TRGV9. In some embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to a cancer antigen present on the surface of a cancer cell. In some embodiments, the antigen on the surface of the cancer cell is a tumor-specific antigen, a tumor associated antigen, or a neoantigen. In certain embodiments, the first binding domain of the bispecific antibody specifically binds TRGV9. In some embodiments, the TRGV9 is present on the surface of a γδ T cell. In some embodiments, the cancer cell is killed when the bispecific antibody binds to the TRGV9 on the surface of the γδ T cell and the antigen on the surface of the cancer cell. In some embodiments, the first binding domain is humanized, the second binding domain is humanized, or both the first binding domain and the second binding domain are humanized. In some embodiments, the bispecific antibody is an IgG antibody. In some embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to CD123. In certain embodiments, the first binding domain of the bispecific antibody specifically binds TRGV9. In some embodiments, the TRGV9 is present on the surface of a γδ T cell. In some embodiments, the CD123 is on the surface of a cell. In certain embodiments, the TRGV9 is present on the surface of a γδ T cell, and the CD123 is on the surface of a cell. In some embodiments, the cell having the CD123 on the surface is killed when the bispecific antibody binds to the TRGV9 on the surface of the γδ T cell and the CD123 on the surface of the cell. In some embodiments, the CD123 is on the surface of a cancer cell. In certain embodiments, the TRGV9 is present on the surface of a γδ T cell, and the CD123 is on the surface of a cancer cell. In some embodiments, the cancer cell is killed when the bispecific antibody binds to the TRGV9 on the surface of the γδ T cell and the CD123 on the surface of the cell. In some embodiments, the first binding domain is humanized, the second binding domain is humanized, or both the first binding domain and the second binding domain are humanized. In some embodiments, the bispecific antibody is an IgG antibody. In some embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to CD123, wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In some embodiments, the second binding domain comprises a VH having an amino acid sequence of SEQ ID NO:15. In some embodiments, the second binding domain comprises a VL having an amino acid sequence of SEQ ID NO:16. In some embodiments, the second binding domain comprises a VH having an amino acid sequence of SEQ ID NO:15, and a VL having an amino acid sequence of SEQ ID NO:16. In some embodiments, the CD123 is on the surface of a cell. In certain embodiments, the TRGV9 is present on the surface of a γδ T cell, and the CD123 is on the surface of a cell. In some embodiments, the cell having the CD123 on the surface is killed when the bispecific antibody binds to the TRGV9 on the surface of the γδ T cell and the CD123 on the surface of the cell. In some embodiments, the CD123 is on the surface of a cancer cell. In certain embodiments, the TRGV9 is present on the surface of a γδ T cell, and the CD123 is on the surface of a cancer cell. In some embodiments, the cancer cell is killed when the bispecific antibody binds to the TRGV9 on the surface of the γδ T cell and the CD123 on the surface of the cell. In some embodiments, the first binding domain is humanized, the second binding domain is humanized, or both the first binding domain and the second binding domain are humanized. In some embodiments, the bispecific antibody is an IgG antibody. In some embodiments, the IgG antibody is an IgG1, IgG2, IgG3, or IgG4 antibody.

In some embodiments of the various bispecific antibodies provided herein, the first binding domain that binds to TRGV9 comprises a VH CDR1, VH CDR2, VH CDR3, VL CDR1, VL CDR2 and VL CDR3 having amino acid sequences, as provided herein. In some embodiments, the first binding domain that binds to TRGV9 comprises a VH CDR1, VH CDR2 and VH CDR3 of a VH domain having an amino acid sequence, as provided herein. In some embodiments, the first binding domain that binds to TRGV9 comprises a VL CDR1, VL CDR2 and VL CDR3 of a VL domain having an amino acid sequence, as provided herein. In some embodiments, the first binding domain that binds to TRGV9 comprises a VH CDR1, VH CDR2 and VH CDR3 of a VH domain having an amino acid sequence, as provided herein; and a VL CDR1, VL CDR2 and VL CDR3 of a VL domain having an amino acid sequence, as provided herein. In some embodiments, the first binding domain that binds to TRGV9 comprises a VH domain having an amino acid sequence, as provided herein. In some embodiments, the first binding domain that binds to TRGV9 comprises a VL domain having an amino acid sequence, as provided herein. In some embodiments, the first binding domain that binds to TRGV9 comprises a VH domain having an amino acid sequence, as provided herein; and a VL domain having an amino acid sequence, as provided herein.

Also provided is a nucleic acid encoding a bispecific antibody comprising: (a) a first binding domain that binds to TRGV9, and (b) a second binding domain that binds to a second target that is not TRGV9, as provided herein. Also provided is a vector comprising a nucleic acid encoding a bispecific antibody that binds to a TRGV9 provided herein. Also provided is a host cell comprising a vector comprising a nucleic acid encoding a bispecific antibody that binds to a TRGV9 provided herein. Also provided is a kit comprising the vector comprising a nucleic acid encoding a bispecific antibody that binds to a TRGV9 provided herein, and packaging for the same.

In another aspect, provided herein is a pharmaceutical composition comprising a comprising: (a) a first binding domain that binds to TRGV9, and (b) a second binding domain that binds to a second target that is not TRGV9, and a pharmaceutically acceptable carrier. Any of the bispecific antibodies provided herein are contemplated in the pharmaceutical compositions. In certain embodiments, the second binding domain binds to CD123.

In another aspect, provided herein is a method of directing a γδ T cell expressing TRGV9 to a cancer cell, the method comprising contacting the γδ T cell with a bispecific antibody provided herein. In some embodiments, the contacting directs the γδ T cell to the cancer cell.

In another aspect, provided herein is a method of inhibiting growth or proliferation of cancer cells expressing a cancer antigen on the cell surface, the method comprising contacting the cancer cells with a bispecific antibody provided herein. In some embodiments, contacting the cancer cells with the pharmaceutical composition inhibits growth or proliferation of the cancer cells. In some embodiments, the cancer cells are in the presence of a γδ T cell expressing TRGV9 while in contact with the bispecific antibody.

In another aspect, provided herein is a method for eliminating cancer cells in a subject, comprising administering an effective amount of a bispecific antibody, as provided herein, to the subject. In some embodiments, the subject is a subject in need thereof. In some embodiments, the subject is a human.

In another aspect, provided herein is a method of activating a γδ T cell expressing TRGV9, comprising contacting the γδ T cell with the bispecific antibody, as provided herein.

Provided herein are isolated TRGV9 bispecific antibodies or antigen binding fragments thereof, the isolated TRGV9 bispecific antibody or antigen binding fragment thereof comprising:
    a. a first heavy chain (HC1);
    b. a second heavy chain (HC2);
    c. a first light chain (LC1); and
    d. a second light chain (LC2),
wherein HC1 is associated with LC1 and HC2 is associated with LC2, and wherein HC1 comprises a heavy chain complementarity determining region 1 (HCDR1), HCDR2, and HCDR3 comprising the amino acid sequences of:
    i. SEQ ID NO:1, SEQ ID NO:2, and SEQ ID NO:3, respectively,
    ii. SEQ ID NO:1, SEQ ID NO:2, and SEQ ID NO:31, respectively,
    iii. SEQ ID NO:1, SEQ ID NO:2, and SEQ ID NO:32, respectively, or
    iv. SEQ ID NO:1, SEQ ID NO:2, and SEQ ID NO:33, respectively,
and LC1 comprises a light chain complementarity determining region 1 (LCDR1), LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen. In one embodiment, the isolated TRGV9 bispecific antibody or antigen binding fragment thereof comprises an HC1 comprising an amino acid sequence having at least 95% identity to an amino acid sequence selected from SEQ ID NO:7, SEQ ID NO:34, SEQ ID NO:35, or SEQ ID NO:36, and LC1 comprises an amino acid sequence having at least 95% identity to the amino acid sequence of SEQ ID NO:8. In another embodiment, the isolated TRGV9 bispecific antibody or antigen binding fragment thereof comprises an HC1 comprising the amino acid sequence selected from SEQ ID NO:7, SEQ ID NO:34, SEQ ID NO:35, or SEQ ID NO:36, and LC1 comprises the amino acid sequence of SEQ ID NO:8.

Also provided herein are isolated TRGV9 bispecific antibodies or antigen binding fragments thereof, the isolated TRGV9 bispecific antibody or antigen binding fragment thereof comprising: (a) a HC1; (b) a HC2; (c) a LC1; and (d) a LC2, wherein HC1 is associated with LC1 and HC2 is associated with LC2, and wherein HC1 is associated with LC1 and HC2 is associated with LC2, and wherein HC1 comprises a HCDR1, HCDR2, and HCDR3 comprising the amino acid sequences of: SEQ ID NO:1, SEQ ID NO:2, and SEQ ID NO:3, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen, and wherein HC2 and LC2 form a binding site for a second antigen. In one embodiment, the isolated TRGV9 bispecific antibody or antigen binding fragment thereof comprises an HC1 comprising an amino acid sequence having at least 95% identity to an amino acid sequence of SEQ ID NO:7, and LC1 comprises an amino acid sequence having at least 95% identity to the amino acid sequence of SEQ ID NO:8. In another embodiment, the isolated TRGV9 bispecific antibody or antigen binding fragment thereof comprises an HC1 comprising the amino acid sequence of SEQ ID NO:7, and LC1 comprises the amino acid sequence of SEQ ID NO:8.

Also provided herein are isolated TRGV9 bispecific antibodies or antigen binding fragments thereof, the isolated TRGV9 bispecific antibody or antigen binding fragment thereof comprising: (a) a HC1; (b) a HC2; (c) a LC1; and (d)

a LC2, wherein HC1 is associated with LC1 and HC2 is associated with LC2, and wherein HC1 is associated with LC1 and HC2 is associated with LC2, and wherein HC1 comprises a HCDR1, HCDR2, and HCDR3 comprising the amino acid sequences of: SEQ ID NO:1, SEQ ID NO:2, and SEQ ID NO:31, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen, and wherein HC2 and LC2 form a binding site for a second antigen. In one embodiment, the isolated TRGV9 bispecific antibody or antigen binding fragment thereof comprises an HC1 comprising an amino acid sequence having at least 95% identity to an amino acid sequence of SEQ ID NO:34, and LC1 comprises an amino acid sequence having at least 95% identity to the amino acid sequence of SEQ ID NO:8. In another embodiment, the isolated TRGV9 bispecific antibody or antigen binding fragment thereof comprises an HC1 comprising the amino acid sequence of SEQ ID NO:34, and LC1 comprises the amino acid sequence of SEQ ID NO:8.

Also provided herein are isolated TRGV9 bispecific antibodies or antigen binding fragments thereof, the isolated TRGV9 bispecific antibody or antigen binding fragment thereof comprising: (a) a HC1; (b) a HC2; (c) a LC1; and (d) a LC2, wherein HC1 is associated with LC1 and HC2 is associated with LC2, and wherein HC1 is associated with LC1 and HC2 is associated with LC2, and wherein HC1 comprises a HCDR1, HCDR2, and HCDR3 comprising the amino acid sequences of: SEQ ID NO:1, SEQ ID NO:2, and SEQ ID NO:32, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen, and wherein HC2 and LC2 form a binding site for a second antigen. In one embodiment, the isolated TRGV9 bispecific antibody or antigen binding fragment thereof comprises an HC1 comprising an amino acid sequence having at least 95% identity to an amino acid sequence of SEQ ID NO:35, and LC1 comprises an amino acid sequence having at least 95% identity to the amino acid sequence of SEQ ID NO:8. In another embodiment, the isolated TRGV9 bispecific antibody or antigen binding fragment thereof comprises an HC1 comprising the amino acid sequence of SEQ ID NO:35, and LC1 comprises the amino acid sequence of SEQ ID NO:8.

Also provided herein are isolated TRGV9 bispecific antibodies or antigen binding fragments thereof, the isolated TRGV9 bispecific antibody or antigen binding fragment thereof comprising: (a) a HC1; (b) a HC2; (c) a LC1; and (d) a LC2, wherein HC1 is associated with LC1 and HC2 is associated with LC2, and wherein HC1 is associated with LC1 and HC2 is associated with LC2, and wherein HC1 comprises a HCDR1, HCDR2, and HCDR3 comprising the amino acid sequences of: SEQ ID NO:1, SEQ ID NO:2, and SEQ ID NO:33, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen, and wherein HC2 and LC2 form a binding site for a second antigen. In one embodiment, the isolated TRGV9 bispecific antibody or antigen binding fragment thereof comprises an HC1 comprising an amino acid sequence having at least 95% identity to an amino acid sequence of SEQ ID NO:36, and LC1 comprises an amino acid sequence having at least 95% identity to the amino acid sequence of SEQ ID NO:8. In another embodiment, the isolated TRGV9 bispecific antibody or antigen binding fragment thereof comprises an HC1 comprising the amino acid sequence of SEQ ID NO:36, and LC1 comprises the amino acid sequence of SEQ ID NO:8.

Also provided herein are isolated TRGV9 bispecific antibodies or antigen binding fragments thereof, the isolated TRGV9 bispecific antibody or antigen binding fragment thereof comprising: (a) a HC1; (b) a HC2; (c) a LC1; and (d) a LC2, wherein HC1 is associated with LC1 and HC2 is associated with LC2, and wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:76, and SEQ ID NO:3, respectively, and LC1 comprises a LCDR1, LCDR2, and LCDR3 comprising the amino acid sequences of SEQ ID NO:77, SEQ ID NO:5, and SEQ ID NO:6, respectively, to form a binding site for a first antigen, and wherein HC2 and LC2 form a binding site for a second antigen. In one embodiment, the isolated TRGV9 bispecific antibody or antigen binding fragment thereof comprises an HC1 comprising an amino acid sequence having at least 95% identity to an amino acid sequence of SEQ ID NO:65, and LC1 comprises an amino acid sequence having at least 95% identity to the amino acid sequence of SEQ ID NO:66. In another embodiment, the isolated TRGV9 bispecific antibody or antigen binding fragment thereof comprises an HC1 comprising the amino acid sequence of SEQ ID NO:65, and LC1 comprises the amino acid sequence of SEQ ID NO:66. In one embodiment, the isolated TRGV9 bispecific antibody or antigen binding fragment thereof comprises an HC1 comprising an amino acid sequence having at least 95% identity to an amino acid sequence of SEQ ID NO:67, and LC1 comprises an amino acid sequence having at least 95% identity to the amino acid sequence of SEQ ID NO:68. In another embodiment, the isolated TRGV9 bispecific antibody or antigen binding fragment thereof comprises an HC1 comprising the amino acid sequence of SEQ ID NO:67, and LC1 comprises the amino acid sequence of SEQ ID NO:68.

Also provided herein are isolated TRGV9 bispecific antibodies or antigen binding fragments thereof, the isolated TRGV9 bispecific antibody or antigen binding fragment thereof comprising: (a) a HC1; (b) a HC2; (c) a LC1; and (d) a LC2, wherein HC1 is associated with LC1 and HC2 is associated with LC2, and wherein HC1 is associated with LC1 and HC2 is associated with LC2, and wherein HC1 comprises a HCDR1, HCDR2, and HCDR3 comprising the amino acid sequences of SEQ ID NO:60, SEQ ID NO:61, and SEQ ID NO:62, respectively, and LC1 comprises a LCDR1, LCDR2, and LCDR3 comprising the amino acid sequences of SEQ ID NO:63, SEQ ID NO:64, and SEQ ID NO:6, respectively, to form a binding site for a first antigen, and wherein HC2 and LC2 form a binding site for a second antigen. In one embodiment, the isolated TRGV9 bispecific antibody or antigen binding fragment thereof comprises an HC1 comprising an amino acid sequence having at least 95% identity to an amino acid sequence of SEQ ID NO:65, and LC1 comprises an amino acid sequence having at least 95% identity to the amino acid sequence of SEQ ID NO:66. In another embodiment, the isolated TRGV9 bispecific antibody or antigen binding fragment thereof comprises an HC1 comprising the amino acid sequence of SEQ ID NO:65, and LC1 comprises the amino acid sequence of SEQ ID NO:66. In one embodiment, the isolated TRGV9 bispecific antibody or antigen binding fragment thereof comprises an HC1 comprising an amino acid sequence having at least 95% identity to an amino acid sequence of SEQ ID NO:67, and LC1 comprises an amino acid sequence having at least 95% identity to the amino acid sequence of SEQ ID NO:68. In another embodiment, the isolated TRGV9 bispecific antibody or antigen binding fragment thereof comprises an HC1 comprising the amino acid sequence of SEQ ID NO:67, and LC1 comprises the amino acid sequence of SEQ ID NO:68.

Also provided herein are isolated TRGV9 bispecific antibodies or antigen binding fragments thereof, the isolated TRGV9 bispecific antibody or antigen binding fragment thereof comprising: (a) a HC1; (b) a HC2; (c) a LC1; and (d) a LC2, wherein HC1 is associated with LC1 and HC2 is associated with LC2, and wherein HC1 is associated with LC1 and HC2 is associated with LC2, and wherein HC1 comprises a HCDR1, HCDR2, and HCDR3 comprising the amino acid sequences of SEQ ID NO:89, SEQ ID NO:90, and SEQ ID NO:91, respectively, and LC1 comprises a LCDR1, LCDR2, and LCDR3 comprising the amino acid sequences of SEQ ID NO:92, SEQ ID NO:93, and SEQ ID NO:94, respectively, to form a binding site for a first antigen, and wherein HC2 and LC2 form a binding site for a second antigen. In one embodiment, the isolated TRGV9 bispecific antibody or antigen binding fragment thereof comprises an HC1 comprising an amino acid sequence having at least 95% identity to an amino acid sequence of SEQ ID NO:95, and LC1 comprises an amino acid sequence having at least 95% identity to the amino acid sequence of SEQ ID NO:96. In another embodiment, the isolated TRGV9 bispecific antibody or antigen binding fragment thereof comprises an HC1 comprising the amino acid sequence of SEQ ID NO:95, and LC1 comprises the amino acid sequence of SEQ ID NO:96.

Also provided herein are isolated TRGV9 bispecific antibodies or antigen binding fragments thereof, the isolated TRGV9 bispecific antibody or antigen binding fragment thereof comprising: (a) a HC1; (b) a HC2; (c) a LC1; and (d) a LC2, wherein HC1 is associated with LC1 and HC2 is associated with LC2, and wherein HC1 is associated with LC1 and HC2 is associated with LC2, and wherein HC1 comprises a HCDR1, HCDR2, and HCDR3 comprising the amino acid sequences of SEQ ID NO:98, SEQ ID NO:99, and SEQ ID NO:100, respectively, and LC1 comprises a LCDR1, LCDR2, and LCDR3 comprising the amino acid sequences of SEQ ID NO:101, SEQ ID NO:102, and SEQ ID NO:103, respectively, to form a binding site for a first antigen, and wherein HC2 and LC2 form a binding site for a second antigen. In one embodiment, the isolated TRGV9 bispecific antibody or antigen binding fragment thereof comprises an HC1 comprising an amino acid sequence having at least 95% identity to an amino acid sequence of SEQ ID NO:104, and LC1 comprises an amino acid sequence having at least 95% identity to the amino acid sequence of SEQ ID NO:105. In another embodiment, the isolated TRGV9 bispecific antibody or antigen binding fragment thereof comprises an HC1 comprising the amino acid sequence of SEQ ID NO:104, and LC1 comprises the amino acid sequence of SEQ ID NO:105.

Also provided herein are isolated TRGV9 bispecific antibodies or antigen binding fragments thereof, the isolated TRGV9 bispecific antibody or antigen binding fragment thereof comprising: (a) a HC1; (b) a HC2; (c) a LC1; and (d) a LC2, wherein HC1 is associated with LC1 and HC2 is associated with LC2, and wherein HC1 is associated with LC1 and HC2 is associated with LC2, and wherein HC1 comprises a HCDR1, HCDR2, and HCDR3 comprising the amino acid sequences of SEQ ID NO:107, SEQ ID NO:108, and SEQ ID NO:109, respectively, and LC1 comprises a LCDR1, LCDR2, and LCDR3 comprising the amino acid sequences of SEQ ID NO:110, SEQ ID NO:111, and SEQ ID NO:112, respectively, to form a binding site for a first antigen, and wherein HC2 and LC2 form a binding site for a second antigen. In one embodiment, the isolated TRGV9 bispecific antibody or antigen binding fragment thereof comprises an HC1 comprising an amino acid sequence having at least 95% identity to an amino acid sequence of SEQ ID NO:113, and LC1 comprises an amino acid sequence having at least 95% identity to the amino acid sequence of SEQ ID NO:114. In another embodiment, the isolated TRGV9 bispecific antibody or antigen binding fragment thereof comprises an HC1 comprising the amino acid sequence of SEQ ID NO:113, and LC1 comprises the amino acid sequence of SEQ ID NO:114.

Also provided herein are isolated TRGV9 bispecific antibodies or antigen binding fragments thereof, the isolated TRGV9 bispecific antibody or antigen binding fragment thereof comprising: (a) a HC1; (b) a HC2; (c) a LC1; and (d) a LC2, wherein HC1 is associated with LC1 and HC2 is associated with LC2, and wherein HC1 is associated with LC1 and HC2 is associated with LC2, and wherein HC1 comprises a HCDR1, HCDR2, and HCDR3 comprising the amino acid sequences of SEQ ID NO:117, SEQ ID NO:118, and SEQ ID NO:119, respectively, and LC1 comprises a LCDR1, LCDR2, and LCDR3 comprising the amino acid sequences of SEQ ID NO:120, SEQ ID NO:121, and SEQ ID NO:122, respectively, to form a binding site for a first antigen, and wherein HC2 and LC2 form a binding site for a second antigen. In one embodiment, the isolated TRGV9 bispecific antibody or antigen binding fragment thereof comprises an HC1 comprising an amino acid sequence having at least 95% identity to an amino acid sequence of SEQ ID NO:123, and LC1 comprises an amino acid sequence having at least 95% identity to the amino acid sequence of SEQ ID NO:124. In another embodiment, the isolated TRGV9 bispecific antibody or antigen binding fragment thereof comprises an HC1 comprising the amino acid sequence of SEQ ID NO:123, and LC1 comprises the amino acid sequence of SEQ ID NO:124.

Also provided herein are isolated TRGV9 bispecific antibodies or antigen binding fragments thereof, the isolated TRGV9 bispecific antibody or antigen binding fragment thereof comprising: (a) a HC1; (b) a HC2; (c) a LC1; and (d) a LC2, wherein HC1 is associated with LC1 and HC2 is associated with LC2, and wherein HC1 is associated with LC1 and HC2 is associated with LC2, and wherein HC1 comprises a HCDR1, HCDR2, and HCDR3 comprising the amino acid sequences of SEQ ID NO:127, SEQ ID NO:128, and SEQ ID NO:129, respectively, and LC1 comprises a LCDR1, LCDR2, and LCDR3 comprising the amino acid sequences of SEQ ID NO:130, SEQ ID NO:131, and SEQ ID NO:132, respectively, to form a binding site for a first antigen, and wherein HC2 and LC2 form a binding site for a second antigen. In one embodiment, the isolated TRGV9 bispecific antibody or antigen binding fragment thereof comprises an HC1 comprising an amino acid sequence having at least 95% identity to an amino acid sequence of SEQ ID NO:133, and LC1 comprises an amino acid sequence having at least 95% identity to the amino acid sequence of SEQ ID NO:134. In another embodiment, the isolated TRGV9 bispecific antibody or antigen binding fragment thereof comprises an HC1 comprising the amino acid sequence of SEQ ID NO:133, and LC1 comprises the amino acid sequence of SEQ ID NO:134.

In another embodiment, the binding site for a first antigen binds to TRGV9 on a γδ T cell.

In another embodiment, the binding site for a second antigen binds to a cancer antigen present on the surface of a cancer cell.

In another embodiment, the bispecific antibody binds to TRGV9 present on the surface of the $\gamma\delta$ T cell and the binding of the cancer antigen present on the surface of the cancer cell results in the killing of the cancer cell.

In another embodiment, TRGV9 bispecific antibody comprises a humanized HC1 and a humanized LC1.

In another embodiment, the HC2 and LC2 of the TRGV9 antibody bind to CD123.

In another embodiment the bispecific antibody or antigen binding fragment thereof is an IgG1, an IgG2, an IgG3, or an IgG4 isotype.

In a specific embodiment, the bispecific antibody or antigen binding fragment thereof is an IgG4 isotype.

In another embodiment, the TRGV9 bispecific antibody or antigen binding fragment thereof induces $\gamma\delta$ T cell dependent cytotoxicity of a cancer cell in vitro with an $EC_{50}$ of less than about 500 pM.

In another embodiment, the TRGV9 bispecific antibody or antigen binding fragment thereof induces $\gamma\delta$ T cell dependent cytotoxicity of a cancer cell in vitro with an $EC_{50}$ of less than about 300 pM.

In another embodiment, the TRGV9 bispecific antibody or antigen binding fragment thereof induces $\gamma\delta$ T cell dependent cytotoxicity of a cancer cell in vitro with an $EC_{50}$ of less than about 160 pM.

In one embodiment, the $EC_{50}$ is assessed with a mixture of $\gamma\delta$ T effector cells and Kasumi3 AML target cells.

In another embodiment, effector cell to target cell ratio is about 0.01 to 1 to about 5 to 1.

In yet another embodiment, the effector cell to target cell ratio is about 0.1 to 1 to about 2 to 1.

In a specific embodiment, the effector cell to target cell ratio is about 1:1.

In another embodiment, the TRGV9 bispecific antibody or antigen binding fragment thereof is multivalent.

In another embodiment, the TRGV9 bispecific antibody or antigen binding fragment thereof is capable of binding at least three antigens.

In another embodiment, the TRGV9 bispecific antibody or antigen binding fragment thereof is capable of binding at least five antigens.

Also provided are isolated $\gamma\delta$ T cell bispecific antibodies or antigen binding fragments thereof, the isolated $\gamma\delta$ T cell bispecific antibody or antigen binding fragment thereof comprising:

a. a HC1;
b. a HC2;
c. a LC1; and
d. a LC2, wherein HC1 is associated with LC1 and HC2 is associated with LC2, wherein HC1 and LC1 form a binding site for a first antigen on a $\gamma\delta$ T cell, and wherein HC2 and LC2 form a binding site for a second antigen.

Also provided herein are bispecific antibodies comprising: a first means capable of specifically binding a T cell receptor gamma chain; and a second means capable of specifically binding a target molecule that is not a T cell receptor gamma chain.

Also provided are processes for making a molecule capable of specifically binding to more than one target molecule, the molecule comprising: a step for performing a function of obtaining an oligopeptide or polypeptide capable of binding to a T cell receptor gamma chain; a step for performing a function of obtaining an oligopeptide or polypeptide capable of binding to a target; and a step for performing a function of providing a molecule capable of specifically binding to a T cell receptor gamma chain and a target molecule.

In one embodiment, the step in the process for performing a function of obtaining an oligopeptide or polypeptide capable of binding to a target is repeated n times and further comprising n steps for performing a function of providing a molecule capable of specifically binding to a T cell receptor gamma chain and n number of target molecules, wherein n is at least 2.

Provided herein are isolated anti-TRGV9/anti-CD123 bispecific antibodies or antigen binding fragments thereof comprising:

a. a HC1;
b. a HC2;
c. a LC1; and
d. a LC2, wherein HC1 is associated with LC1 and HC2 is associated with LC2, and wherein HC1 comprises a HCDR1, HCDR2, and HCDR3 comprising the amino acid sequences of:

i. SEQ ID NO:1, SEQ ID NO:2, and SEQ ID NO:3, respectively, ii. SEQ ID NO:1, SEQ ID NO:2, and SEQ ID NO:31, respectively, iii. SEQ ID NO:1, SEQ ID NO:2, and SEQ ID NO:32, respectively, or iv. SEQ ID NO:1, SEQ ID NO:2, and SEQ ID NO:33, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen that specifically binds V$\gamma$9, and wherein HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In one embodiment, the isolated anti-TRGV9/anti-CD123 bispecific antibody or antigen binding fragment comprises an HC1 comprising an amino acid sequence having at least 95% identity to an amino acid sequence selected from SEQ ID NO:7, SEQ ID NO:34, SEQ ID NO:35, or SEQ ID NO:36, and LC1 comprises an amino acid sequence having at least 95% identity to the amino acid sequence of SEQ ID NO:8. In another embodiment, the isolated anti-TRGV9/anti-CD123 bispecific antibody or antigen binding fragment comprises an HC1 comprising the amino acid sequence selected from SEQ ID NO:7, SEQ ID NO:34, SEQ ID NO:35, or SEQ ID NO:36, and LC1 comprises the amino acid sequence of SEQ ID NO:8. In another embodiment, the isolated anti-TRGV9/anti-CD123 bispecific antibody or antigen binding fragment comprises an HC2 comprising an amino acid sequence having at least 95% identity to the amino acid sequence of SEQ ID NO:15 and LC2 comprises an amino acid sequence having at least 95% identity to the amino acid sequence of SEQ ID NO:16. In another embodiment, the isolated anti-TRGV9/anti-CD123 bispecific antibody or antigen binding fragment comprises an HC2 comprising the amino acid sequence of SEQ ID NO:15 and LC2 comprises the amino acid sequence of SEQ ID NO:16.

Also provided herein are isolated anti-TRGV9/anti-CD123 bispecific antibodies or antigen binding fragments thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:3, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen that specifically binds Vγ9, and wherein HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:7, and LC1 comprises an amino acid sequence having at least 95% identity to the amino acid sequence of SEQ ID NO:8. In another embodiment, the isolated anti-TRGV9/anti-CD123 bispecific antibody or antigen binding fragment comprises an HC1 comprising the amino acid sequence of SEQ ID NO:7, and LC1 comprises the amino acid sequence of SEQ ID NO:8. In another embodiment, the isolated anti-TRGV9/anti-CD123 bispecific antibody or antigen binding fragment comprises an HC2 comprising an amino acid sequence having at least 95% identity to the amino acid sequence of SEQ ID NO:15 and LC2 comprises an amino acid sequence having at least 95% identity to the amino acid sequence of SEQ ID NO:16. In another embodiment, the isolated anti-TRGV9/anti-CD123 bispecific antibody or antigen binding fragment comprises an HC2 comprising the amino acid sequence of SEQ ID NO:15 and LC2 comprises the amino acid sequence of SEQ ID NO:16.

Also provided herein are isolated anti-TRGV9/anti-CD123 bispecific antibodies or antigen binding fragments thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:31, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen that specifically binds Vγ9, and wherein HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:34, and LC1 comprises an amino acid sequence having at least 95% identity to the amino acid sequence of SEQ ID NO:8. In another embodiment, the isolated anti-TRGV9/anti-CD123 bispecific antibody or antigen binding fragment comprises an HC1 comprising the amino acid sequence of SEQ ID NO:34, and LC1 comprises the amino acid sequence of SEQ ID NO:8. In another embodiment, the isolated anti-TRGV9/anti-CD123 bispecific antibody or antigen binding fragment comprises an HC2 comprising an amino acid sequence having at least 95% identity to the amino acid sequence of SEQ ID NO:15 and LC2 comprises an amino acid sequence having at least 95% identity to the amino acid sequence of SEQ ID NO:16. In another embodiment, the isolated anti-TRGV9/anti-CD123 bispecific antibody or antigen binding fragment comprises an HC2 comprising the amino acid sequence of SEQ ID NO:15 and LC2 comprises the amino acid sequence of SEQ ID NO:16.

Also provided herein are isolated anti-TRGV9/anti-CD123 bispecific antibodies or antigen binding fragments thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:32, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen that specifically binds Vγ9, and wherein HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:35, and LC1 comprises an amino acid sequence having at least 95% identity to the amino acid sequence of SEQ ID NO:8. In another embodiment, the isolated anti-TRGV9/anti-CD123 bispecific antibody or antigen binding fragment comprises an HC1 comprising the amino acid sequence of SEQ ID NO:35, and LC1 comprises the amino acid sequence of SEQ ID NO:8. In another embodiment, the isolated anti-TRGV9/anti-CD123 bispecific antibody or antigen binding fragment comprises an HC2 comprising an amino acid sequence having at least 95% identity to the amino acid sequence of SEQ ID NO:15 and LC2 comprises an amino acid sequence having at least 95% identity to the amino acid sequence of SEQ ID NO:16. In another embodiment, the isolated anti-TRGV9/anti-CD123 bispecific antibody or antigen binding fragment comprises an HC2 comprising the amino acid sequence of SEQ ID NO:15 and LC2 comprises the amino acid sequence of SEQ ID NO:16.

Also provided herein are isolated anti-TRGV9/anti-CD123 bispecific antibodies or antigen binding fragments thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:33, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen that specifically binds Vγ9, and wherein HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:36, and LC1 comprises an amino acid sequence having at least 95% identity to the amino acid sequence of SEQ ID NO:8. In another embodiment, the isolated anti-TRGV9/ anti-CD123 bispecific antibody or antigen binding fragment comprises an HC1 comprising the amino acid sequence of SEQ ID NO:36, and LC1 comprises the amino acid sequence of SEQ ID NO:8. In another embodiment, the isolated anti-TRGV9/anti-CD123 bispecific antibody or antigen binding fragment comprises an HC2 comprising an amino acid sequence having at least 95% identity to the amino acid sequence of SEQ ID NO:15 and LC2 comprises an amino acid sequence having at least 95% identity to the amino acid sequence of SEQ ID NO:16. In another embodiment, the isolated anti-TRGV9/anti-CD123 bispecific antibody or antigen binding fragment comprises an HC2 comprising the amino acid sequence of SEQ ID NO:15 and LC2 comprises the amino acid sequence of SEQ ID NO:16.

Also provided herein are isolated anti-TRGV9/anti-CD123 bispecific antibodies or antigen binding fragments thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:76, and SEQ ID NO:3, respectively, and LC1 comprises a LCDR1, LCDR2, and LCDR3 comprising the amino acid sequences of SEQ ID NO:77, SEQ ID NO:5, and SEQ ID NO:6, respectively, to form a binding site for a first antigen that specifically binds Vγ9, and wherein HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:65, and LC1 comprises an amino acid sequence having at least 95% identity to the amino acid sequence of SEQ ID NO:66. In another embodiment, the isolated anti-TRGV9/ anti-CD123 bispecific antibody or antigen binding fragment comprises an HC1 comprising the amino acid sequence of SEQ ID NO:65, and LC1 comprises the amino acid sequence of SEQ ID NO:66. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:67, and LC1 comprises an amino acid sequence having at least 95% identity to the amino acid sequence of SEQ ID NO:68. In another embodiment, the isolated anti-TRGV9/anti-CD123 bispecific antibody or antigen binding fragment comprises an HC1 comprising the amino acid sequence of SEQ ID NO:67, and LC1 comprises the amino acid sequence of SEQ ID NO:68. In another embodiment, the isolated anti-TRGV9/anti-CD123 bispecific antibody or antigen binding fragment comprises an HC2 comprising an amino acid sequence having at least 95% identity to the amino acid sequence of SEQ ID NO:15 and LC2 comprises an amino acid sequence having at least 95% identity to the amino acid sequence of SEQ ID NO:16. In another embodiment, the isolated anti-TRGV9/anti-CD123 bispecific antibody or antigen binding fragment comprises an HC2 comprising the amino acid sequence of SEQ ID NO:15 and LC2 comprises the amino acid sequence of SEQ ID NO:16.

Also provided herein are isolated anti-TRGV9/anti-CD123 bispecific antibodies or antigen binding fragments thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:60, SEQ ID NO:61, and SEQ ID NO:62, respectively, and LC1 comprises a LCDR1, LCDR2, and LCDR3 comprising the amino acid sequences of SEQ ID NO:63, SEQ ID NO:64, and SEQ ID NO:65, respectively, to form a binding site for a first antigen that specifically binds Vγ9, and wherein HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO: 12, SEQ ID NO:13, and SEQ ID NO:14, respectively, to form a binding site for a second antigen that specifically binds CD123. In one embodiment, the isolated anti-TRGV9/ anti-CD123 bispecific antibody or antigen binding fragment comprises an HC1 comprising an amino acid sequence having at least 95% identity to an amino acid sequence selected of SEQ ID NO:65, and LC1 comprises an amino acid sequence having at least 95% identity to the amino acid sequence of SEQ ID NO:66. In another embodiment, the isolated anti-TRGV9/anti-CD123 bispecific antibody or antigen binding fragment comprises an HC1 comprising the amino acid sequence of SEQ ID NO:65, and LC1 comprises the amino acid sequence of SEQ ID NO:66. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:67, and LC1 comprises an amino acid sequence having at least 95% identity to the amino acid sequence of SEQ ID NO:68. In another embodiment, the isolated anti-TRGV9/anti-CD123 bispecific antibody or antigen binding fragment comprises an HC1 comprising the amino acid sequence of SEQ ID NO:67, and LC1 comprises the amino acid sequence of SEQ ID NO:68. In another embodiment, the isolated anti-TRGV9/anti-CD123 bispecific antibody or antigen binding fragment comprises an HC2 comprising an amino acid sequence having at least 95% identity to the amino acid sequence of SEQ ID NO:15 and LC2 comprises an amino acid sequence having at least 95% identity to the amino acid sequence of SEQ ID NO:16. In another embodiment, the isolated anti-TRGV9/anti-CD123 bispecific antibody or antigen binding fragment comprises an HC2 comprising the amino acid sequence of SEQ ID NO:15 and LC2 comprises the amino acid sequence of SEQ ID NO:16.

Also provided herein are isolated anti-TRGV9/anti-CD123 bispecific antibodies or antigen binding fragments thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:89, SEQ ID NO:90, and SEQ ID NO:91, respectively, and LC1 comprises a LCDR1, LCDR2, and LCDR3 comprising the amino acid sequences of SEQ ID NO:92, SEQ ID NO:93, and SEQ ID NO:94, respectively, to form a binding site for a first antigen that specifically binds Vγ9, and wherein HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:95, and LC1 comprises an amino acid sequence having at least 95% identity to the amino acid sequence of SEQ ID NO:96. In another embodiment, the isolated anti-TRGV9/anti-CD123 bispecific antibody or antigen binding fragment comprises an HC1 comprising the amino acid sequence of SEQ ID NO:95, and LC1 comprises the amino acid sequence of SEQ ID NO:96. In another embodiment, the isolated anti-TRGV9/anti-CD123 bispecific antibody or antigen binding fragment comprises an HC2 comprising an amino acid sequence having at least 95% identity to the amino acid sequence of SEQ ID NO:15 and LC2 comprises an amino acid sequence having at least 95% identity to the amino acid sequence of SEQ ID NO:16. In another embodiment, the isolated anti-TRGV9/anti-CD123 bispecific antibody or antigen binding fragment comprises an HC2 comprising the amino acid sequence of SEQ ID NO:15 and LC2 comprises the amino acid sequence of SEQ ID NO:16.

Also provided herein are isolated anti-TRGV9/anti-CD123 bispecific antibodies or antigen binding fragments thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:98, SEQ ID NO:99, and SEQ ID NO:100, respectively, and LC1 comprises a LCDR1, LCDR2, and LCDR3 comprising the amino acid sequences of SEQ ID NO:101, SEQ ID NO:102, and SEQ ID NO:103, respectively, to form a binding site for a first antigen that specifically binds Vγ9, and wherein HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:104, and LC1 comprises an amino acid sequence having at least 95% identity to the amino acid sequence of SEQ ID NO:105. In another embodiment, the isolated anti-TRGV9/anti-CD123 bispecific antibody or antigen binding fragment comprises an HC1 comprising the amino acid sequence of SEQ ID NO:104, and LC1 comprises the amino acid sequence of SEQ ID NO:105. In another embodiment, the isolated anti-TRGV9/anti-CD123 bispecific antibody or antigen binding fragment comprises an HC2 comprising an amino acid sequence having at least 95% identity to the amino acid sequence of SEQ ID NO:15 and LC2 comprises an amino acid sequence having at least 95% identity to the amino acid sequence of SEQ ID NO:16. In another embodiment, the isolated anti-TRGV9/anti-CD123 bispecific antibody or antigen binding fragment comprises an HC2 comprising the amino acid sequence of SEQ ID NO:15 and LC2 comprises the amino acid sequence of SEQ ID NO:16.

Also provided herein are isolated anti-TRGV9/anti-CD123 bispecific antibodies or antigen binding fragments thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:107, SEQ ID NO:108, and SEQ ID NO:109, respectively, and LC1 comprises a LCDR1, LCDR2, and LCDR3 comprising the amino acid sequences of SEQ ID NO:110, SEQ ID NO:111, and SEQ ID NO:112, respectively, to form a binding site for a first antigen that specifically binds Vγ9, and wherein HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO: 12, SEQ ID NO:13, and SEQ ID NO:14, respectively, to form a binding site for a second antigen that specifically binds CD123. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:113, and LC1 comprises an amino acid sequence having at least 95% identity to the amino acid sequence of SEQ ID NO:114. In another embodiment, the isolated anti-TRGV9/anti-CD123 bispecific antibody or antigen binding fragment comprises an HC1 comprising the amino acid sequence of SEQ ID NO:113, and LC1 comprises the amino acid sequence of SEQ ID NO:114. In another embodiment, the isolated anti-TRGV9/anti-CD123 bispecific antibody or antigen binding fragment comprises an HC2 comprising an amino acid sequence having at least 95% identity to the amino acid sequence of SEQ ID NO:15 and LC2 comprises an amino acid sequence having at least 95% identity to the amino acid sequence of SEQ ID NO:16. In another embodiment, the isolated anti-TRGV9/anti-CD123 bispecific antibody or antigen binding fragment comprises an HC2 comprising the amino acid sequence of SEQ ID NO:15 and LC2 comprises the amino acid sequence of SEQ ID NO:16.

Also provided herein are isolated anti-TRGV9/anti-CD123 bispecific antibodies or antigen binding fragments thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO: 117, SEQ ID NO: 118, and SEQ ID NO: 119, respectively, and LC1 comprises a LCDR1, LCDR2, and LCDR3 comprising the amino acid sequences of SEQ ID NO:120, SEQ ID NO:121, and SEQ ID NO:122, respectively, to form a binding site for a first antigen that specifically binds Vγ9, and wherein HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:123, and LC1 comprises an amino acid sequence having at least 95% identity to the amino acid sequence of SEQ ID NO:124. In another embodiment, the isolated anti-TRGV9/anti-CD123 bispecific antibody or antigen binding fragment comprises an HC1 comprising the amino acid sequence of SEQ ID NO:123, and LC1 comprises the amino acid sequence of SEQ ID NO:124. In another embodiment, the isolated anti-TRGV9/anti-CD123 bispecific antibody or antigen binding fragment comprises an HC2 comprising an amino acid sequence having at least 95% identity to the amino acid sequence of SEQ ID NO:15 and LC2 comprises an amino acid sequence having at least 95% identity to the amino acid sequence of SEQ ID NO:16. In another embodiment, the isolated anti-TRGV9/anti-CD123 bispecific antibody or antigen binding fragment comprises an HC2 comprising the amino acid sequence of SEQ ID NO:15 and LC2 comprises the amino acid sequence of SEQ ID NO:16.

Also provided herein are isolated anti-TRGV9/anti-CD123 bispecific antibodies or antigen binding fragments thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:127, SEQ ID NO:128, and SEQ ID NO:129, respectively, and LC1 comprises a LCDR1, LCDR2, and LCDR3 comprising the amino acid sequences of SEQ ID NO:130, SEQ ID NO:131, and SEQ ID NO:132, respectively, to form a binding site for a first antigen that specifically binds Vγ9, and wherein HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:133, and LC1 comprises an amino acid sequence having at least 95% identity to the amino acid sequence of SEQ ID NO:134. In another embodiment, the isolated anti-TRGV9/anti-CD123 bispecific antibody or antigen binding fragment comprises an HC1 comprising the amino acid sequence of SEQ ID NO:133, and LC1 comprises the amino acid sequence of SEQ ID NO:134. In another embodiment, the isolated anti-TRGV9/anti-CD123 bispecific antibody or antigen binding fragment comprises an HC2 comprising an amino acid sequence having at least 95% identity to the amino acid sequence of SEQ ID NO:15 and LC2 comprises an amino acid sequence having at least 95% identity to the amino acid sequence of SEQ ID NO:16. In another embodiment, the isolated anti-TRGV9/anti-CD123 bispecific antibody or antigen binding fragment comprises an HC2 comprising the amino acid sequence of SEQ ID NO:15 and LC2 comprises the amino acid sequence of SEQ ID NO:16.

In another embodiment, the TRGV9 is on the surface of a γδ T cell.

In another embodiment, the CD123 is on the surface of a tumor cell or a CD34+ stem cell.

In another embodiment, the binding of the bispecific antibody to TRGV9 present on the surface of the γδ T cell and the binding of the CD123 on the surface of the cancer cell results in the killing of the cancer cell.

In another embodiment, the isolated anti-TRGV9/anti-CD123 bispecific antibody or antigen binding fragment thereof comprises a humanized HC1 and a humanized LC1.

In another embodiment, the isolated anti-TRGV9/anti-CD123 bispecific antibody or antigen binding fragment comprises a humanized HC2 and a humanized LC2.

In another embodiment, the isolated anti-TRGV9/anti-CD123 bispecific antibody or antigen binding fragment thereof is an IgG1, an IgG2, an IgG3, or an IgG4 isotype. In a specific embodiment, the bispecific antibody is an IgG4 isotype.

In another embodiment, the isolated anti-TRGV9/anti-CD123 bispecific antibody or antigen binding fragment thereof induces γδ T cell dependent cytotoxicity of a cancer cell in vitro with an $EC_{50}$ of less than about 500 pM.

In another embodiment, the isolated anti-TRGV9/anti-CD123 bispecific antibody or antigen binding fragment thereof induces γδ T cell dependent cytotoxicity of a cancer cell in vitro with an $EC_{50}$ of less than about 300 pM.

In another embodiment, the isolated anti-TRGV9/anti-CD123 bispecific antibody or antigen binding fragment thereof induces γδ T cell dependent cytotoxicity of a cancer cell in vitro with an $EC_{50}$ of less than about 160 pM.

In one embodiment, the $EC_{50}$ is assessed with a mixture of γδ T effector cells and Kasumi3 AML target cells.

In another embodiment, the effector cell to target cell ratio is about 0.01 to 1 to about 5 to 1.

In yet another embodiment, the effector cell to target cell ratio is about 0.1 to 1 to about 2 to 1.

In a specific embodiment, the effector cell to target cell ratio is about 1:1.

Also provided are methods of making the isolated anti-TRGV9/anti-CD123 bispecific antibody or antigen binding fragment provided herein, the method comprising culturing a cell comprising a nucleic acid encoding the anti-TRGV9/anti-CD123 bispecific antibody or antigen binding fragment thereof under conditions to produce the bispecific antibody or antigen binding fragment thereof and recovering the bispecific antibody or antigen binding fragment thereof.

In another aspect, provided herein are isolated TRGV9 bispecific antibodies or antigen epitope binding fragments thereof, wherein the isolated TRGV9 bispecific antibodies or antigen epitope binding fragments thereof comprise a binding site for a first antigen and a binding site for a second antigen, wherein the binding site for the first antigen binds a TRGV9 epitope on a γδ T cell and the binding site for the second antigen binds an epitope of the second antigen on a surface of a target cell, and the binding of the TRGV9 epitope on the γδ T cell and the binding of the second antigen epitope on the target cell results in the killing of the target cell.

In one embodiment, the TRGV9 bispecific antibodies or antigen binding fragments comprise:
   a. a HC1;
   b. a HC2;
   c. a LC1; and
   d. a LC2,
wherein HC1 is associated with LC1 and HC2 is associated with LC2, and wherein HC1 comprises a HCDR1, HCDR2, and HCDR3 comprising the amino acid sequences of:
   i. SEQ ID NO:1, SEQ ID NO:2, and SEQ ID NO:3, respectively,
   ii. SEQ ID NO:1, SEQ ID NO:2, and SEQ ID NO:31, respectively,
   iii. SEQ ID NO:1, SEQ ID NO:2, and SEQ ID NO:32, respectively, or
   iv. SEQ ID NO:1, SEQ ID NO:2, and SEQ ID NO:33, respectively,
and LC1 comprises a LCDR1, LCDR2, and LCDR2 comprising the amino acid sequences of SEQ ID NO:4, SEQ ID NO:5, and SEQ ID NO:6, respectively, to form the binding site for the first antigen, and wherein HC2 and LC2 form the binding site for the second antigen epitope. In another embodiment, the TRGV9 bispecific antibodies or antigen binding fragments comprise an HC1 comprising an amino acid sequence having at least 95% identity to an amino acid sequence selected from SEQ ID NO: 7, SEQ ID NO:34, SEQ ID NO:35, or SEQ ID NO:36, and LC1 comprises an amino acid sequence having at least 95% identity to the amino acid sequence of SEQ ID NO:8. In another embodiment, the TRGV9 bispecific antibodies or antigen binding fragments comprise an HC1 comprising the amino acid sequence selected from SEQ ID NO:7, SEQ ID NO:34, SEQ ID NO:35, or SEQ ID NO:36, and LC1 comprises the amino acid sequence of SEQ ID NO:8.

In one embodiment, the TRGV9 bispecific antibodies or antigen binding fragments comprise: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:3, respectively, and LC1 comprises a LCDR1, LCDR2, and LCDR2 comprising the amino acid sequences of SEQ ID NO:4, SEQ ID NO:5, and SEQ ID NO:6, respectively, to form the binding site for the first antigen, and wherein HC2 and LC2 form the binding site for the second antigen epitope. In another embodiment, the TRGV9 bispecific antibodies or antigen binding fragments comprise an HC1 comprising an amino acid sequence having at least 95% identity to an amino acid sequence of SEQ ID NO:7, and LC1 comprises an amino acid sequence having at least 95% identity to the amino acid sequence of SEQ ID NO:8. In another embodiment, the TRGV9 bispecific antibodies or antigen binding fragments comprise an HC1 comprising the amino acid sequence of SEQ ID NO:7, and LC1 comprises the amino acid sequence of SEQ ID NO:8.

In one embodiment, the TRGV9 bispecific antibodies or antigen binding fragments comprise: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:31, respectively, and LC1 comprises a LCDR1, LCDR2, and LCDR2 comprising the amino acid sequences of SEQ ID NO:4, SEQ ID NO:5, and SEQ ID NO:6, respectively, to form the binding site for the first antigen, and wherein HC2 and LC2 form the binding site for the second antigen epitope. In another embodiment, the TRGV9 bispecific antibodies or antigen binding fragments comprise an HC1 comprising an amino acid sequence having at least 95% identity to an amino acid sequence of SEQ ID NO:34, and LC1 comprises an amino acid sequence having at least 95% identity to the amino acid sequence of SEQ ID NO:8. In another embodiment, the TRGV9 bispecific antibodies or antigen binding fragments comprise an HC1 comprising the amino acid sequence of SEQ ID NO:34, and LC1 comprises the amino acid sequence of SEQ ID NO:8.

In one embodiment, the TRGV9 bispecific antibodies or antigen binding fragments comprise: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:32, respectively, and LC1 comprises a LCDR1, LCDR2, and LCDR2 comprising the amino acid sequences of SEQ ID NO:4, SEQ ID NO:5, and SEQ ID NO:6, respectively, to form the binding site for the first antigen, and wherein HC2 and LC2 form the binding site for the second antigen epitope. In another embodiment, the TRGV9 bispecific antibodies or antigen binding fragments comprise an HC1 comprising an amino acid sequence having at least 95% identity to an amino acid sequence of SEQ ID NO:35, and LC1 comprises an amino acid sequence having at least 95% identity to the amino acid sequence of SEQ ID NO:8. In another embodiment, the TRGV9 bispecific antibodies or antigen binding fragments comprise an HC1 comprising the amino acid sequence of SEQ ID NO:35, and LC1 comprises the amino acid sequence of SEQ ID NO:8.

In one embodiment, the TRGV9 bispecific antibodies or antigen binding fragments comprise: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:33, respectively, and LC1 comprises a LCDR1, LCDR2, and LCDR2 comprising the amino acid sequences of SEQ ID NO:4, SEQ ID NO:5, and SEQ ID NO:6, respectively, to form the binding site for the first antigen, and wherein HC2 and LC2 form the binding site for the second antigen epitope. In another embodiment, the TRGV9 bispecific antibodies or antigen binding fragments comprise an HC1 comprising an amino acid sequence having at least 95% identity to an amino acid sequence of SEQ ID NO:36, and LC1 comprises an amino acid sequence having at least 95% identity to the amino acid sequence of SEQ ID NO:8. In another embodiment, the TRGV9 bispecific antibodies or antigen binding fragments comprise an HC1 comprising the amino acid sequence of SEQ ID NO:36, and LC1 comprises the amino acid sequence of SEQ ID NO:8.

In one embodiment, the TRGV9 bispecific antibodies or antigen binding fragments comprise: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:76, and SEQ ID NO:3, respectively, and LC1 comprises a LCDR1, LCDR2, and LCDR2 comprising the amino acid sequences of SEQ ID NO:77, SEQ ID NO:5, and SEQ ID NO:6, respectively, to form the binding site for the first antigen, and wherein HC2 and LC2 form the binding site for the second antigen epitope. In another embodiment, the TRGV9 bispecific antibodies or antigen binding fragments comprise an HC1 comprising an amino acid sequence having at least 95% identity to an amino acid sequence of SEQ ID NO:65, and LC1 comprises an amino acid sequence having at least 95% identity to the amino acid sequence of SEQ ID NO:66. In another embodiment, the TRGV9 bispecific antibodies or antigen binding fragments comprise an HC1 comprising the amino acid sequence of SEQ ID NO:65, and LC1 comprises the amino acid sequence of SEQ ID NO:66. In another embodiment, the TRGV9 bispecific antibodies or antigen binding fragments comprise an HC1 comprising an amino acid sequence having at least 95% identity to an amino acid sequence of SEQ ID NO:67, and LC1 comprises an amino acid sequence having at least 95% identity to the amino acid sequence of SEQ ID NO:68. In another embodiment, the TRGV9 bispecific antibodies or antigen binding fragments comprise an HC1 comprising the amino acid sequence of SEQ ID NO:67, and LC1 comprises the amino acid sequence of SEQ ID NO:68.

In one embodiment, the TRGV9 bispecific antibodies or antigen binding fragments comprise: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:60, SEQ ID NO:61, and SEQ ID NO:62, respectively, and LC1 comprises a LCDR1, LCDR2, and LCDR2 comprising the amino acid sequences of SEQ ID NO:63, SEQ ID NO:64, and SEQ ID NO:6, respectively, to form the binding site for the first antigen, and wherein HC2 and LC2 form the binding site for the second antigen epitope. In another embodiment, the TRGV9 bispecific antibodies or antigen binding fragments comprise an HC1 comprising an amino acid sequence having at least 95% identity to an amino acid sequence of SEQ ID NO:65, and LC1 comprises an amino acid sequence having at least 95% identity to the amino acid sequence of SEQ ID NO:66. In another embodiment, the TRGV9 bispecific antibodies or antigen binding fragments comprise an HC1 comprising the amino acid sequence of SEQ ID NO:65, and LC1 comprises the amino acid sequence of SEQ ID NO:66. In another embodiment, the TRGV9 bispecific antibodies or antigen binding fragments comprise an HC1 comprising an amino acid sequence having at least 95% identity to an amino acid sequence of SEQ ID NO:67, and LC1 comprises an amino acid sequence having at least 95% identity to the amino acid sequence of SEQ ID NO:68. In another embodiment, the TRGV9 bispecific antibodies or antigen binding fragments comprise an HC1 comprising the amino acid sequence of SEQ ID NO:67, and LC1 comprises the amino acid sequence of SEQ ID NO:68.

In one embodiment, the TRGV9 bispecific antibodies or antigen binding fragments comprise: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:89, SEQ ID NO:90, and SEQ ID NO:91, respectively, and LC1 comprises a LCDR1, LCDR2, and LCDR2 comprising the amino acid sequences of SEQ ID NO:92, SEQ ID NO:93, and SEQ ID NO:94, respectively, to form the binding site for the first antigen, and wherein HC2 and LC2 form the binding site for the second antigen epitope. In another embodiment, the TRGV9 bispecific antibodies or antigen binding fragments comprise an HC1 comprising an amino acid sequence having at least 95% identity to an amino acid sequence of SEQ ID NO:95, and LC1 comprises an amino acid sequence having at least 95% identity to the amino acid sequence of SEQ ID NO:96. In another embodiment, the TRGV9 bispecific antibodies or antigen binding fragments comprise an HC1 comprising the amino acid sequence of SEQ ID NO:95, and LC1 comprises the amino acid sequence of SEQ ID NO:96.

In one embodiment, the TRGV9 bispecific antibodies or antigen binding fragments comprise: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:98, SEQ ID NO:99, and SEQ ID NO:100, respectively, and LC1 comprises a LCDR1, LCDR2, and LCDR2 comprising the amino acid sequences of SEQ ID NO:101, SEQ ID NO:102, and SEQ ID NO:103, respectively, to form the binding site for the first antigen, and wherein HC2 and LC2 form the binding site for the second antigen epitope. In another embodiment, the TRGV9 bispecific antibodies or antigen binding fragments comprise an HC1 comprising an amino acid sequence having at least 95% identity to an amino acid sequence of SEQ ID NO:104, and LC1 comprises an amino acid sequence having at least 95% identity to the amino acid sequence of SEQ ID NO:105. In another embodiment, the TRGV9 bispecific antibodies or antigen binding fragments comprise an HC1 comprising the amino acid sequence of SEQ ID NO:104, and LC1 comprises the amino acid sequence of SEQ ID NO:105.

In one embodiment, the TRGV9 bispecific antibodies or antigen binding fragments comprise: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:107, SEQ ID NO:108, and SEQ ID NO:109, respectively, and LC1 comprises a LCDR1, LCDR2, and LCDR2 comprising the amino acid sequences of SEQ ID NO:110, SEQ ID NO:111, and SEQ ID NO:112, respectively, to form the binding site for the first antigen, and wherein HC2 and LC2 form the binding site for the second antigen epitope. In another embodiment, the TRGV9 bispecific antibodies or antigen binding fragments comprise an HC1 comprising an amino acid sequence having at least 95% identity to an amino acid sequence of SEQ ID NO:113, and LC1 comprises an amino acid sequence having at least 95% identity to the amino acid sequence of SEQ ID NO:114. In another embodiment, the TRGV9 bispecific antibodies or antigen binding fragments comprise an HC1 comprising the amino acid sequence of SEQ ID NO:113, and LC1 comprises the amino acid sequence of SEQ ID NO:114.

In one embodiment, the TRGV9 bispecific antibodies or antigen binding fragments comprise: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:117, SEQ ID NO:118, and SEQ ID NO:119, respectively, and LC1 comprises a LCDR1, LCDR2, and LCDR2 comprising the amino acid sequences of SEQ ID NO:120, SEQ ID NO:121, and SEQ ID NO:122, respectively, to form the binding site for the first antigen, and wherein HC2 and LC2 form the binding site for the second antigen epitope. In another embodiment, the TRGV9 bispecific antibodies or antigen binding fragments comprise an HC1 comprising an amino acid sequence having at least 95% identity to an amino acid sequence of SEQ ID NO:123, and LC1 comprises an amino acid sequence having at least 95% identity to the amino acid sequence of SEQ ID NO:124. In another embodiment, the TRGV9 bispecific antibodies or antigen binding fragments comprise an HC1 comprising the amino acid sequence of SEQ ID NO:123, and LC1 comprises the amino acid sequence of SEQ ID NO:124.

In one embodiment, the TRGV9 bispecific antibodies or antigen binding fragments comprise: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:127, SEQ ID NO:128, and SEQ ID NO:129, respectively, and LC1 comprises a LCDR1, LCDR2, and LCDR2 comprising the amino acid sequences of SEQ ID NO:130, SEQ ID NO:131, and SEQ ID NO:132, respectively, to form the binding site for the first antigen, and wherein HC2 and LC2 form the binding site for the second antigen epitope. In another embodiment, the TRGV9 bispecific antibodies or antigen binding fragments comprise an HC1 comprising an amino acid sequence having at least 95% identity to an amino acid sequence of SEQ ID NO:133, and LC1 comprises an amino acid sequence having at least 95% identity to the amino acid sequence of SEQ ID NO:134. In another embodiment, the TRGV9 bispecific antibodies or antigen binding fragments comprise an HC1 comprising the amino acid sequence of SEQ ID NO:133, and LC1 comprises the amino acid sequence of SEQ ID NO:134.

In another embodiment, the TRGV9 bispecific antibodies or antigen binding fragments comprise a humanized HC1 and a humanized LC.

In another embodiment, the TRGV9 bispecific antibodies or antigen binding fragments bind to a CD123 epitope.

In another embodiment, the TRGV9 bispecific antibodies or antigen binding fragments comprise and HC2 comprising an amino acid sequence having at least 95% identity to the amino acid sequence of SEQ ID NO:15 and LC2 comprises an amino acid sequence having at least 95% identity to the amino acid sequence of SEQ ID NO:16.

In another embodiment, the TRGV9 bispecific antibodies or antigen binding fragments comprise an HC2 comprising the amino acid sequence of SEQ ID NO:15 and LC2 comprises the amino acid sequence of SEQ ID NO:16.

In another embodiment, the TRGV9 bispecific antibodies or antigen binding fragments thereof are an IgG1, an IgG2, an IgG3, or an IgG4 isotype. In a specific embodiment, the bispecific antibodies or antigen binding fragments thereof fragment thereof are an IgG4 isotype.

In another embodiment, the TRGV9 bispecific antibodies or antigen binding fragments thereof induce $\gamma\delta$ T cell dependent cytotoxicity of a cancer cell in vitro with an $EC_{50}$ of less than about 500 pM.

In another embodiment, the TRGV9 bispecific antibodies or antigen binding fragments thereof induce $\gamma\delta$ T cell dependent cytotoxicity of a cancer cell in vitro with an $EC_{50}$ of less than about 300 pM.

In another embodiment, the TRGV9 bispecific antibodies or antigen binding fragments thereof induce $\gamma\delta$ T cell dependent cytotoxicity of a cancer cell in vitro with an $EC_{50}$ of less than about 160 pM.

In one embodiment, the $EC_{50}$ is assessed with a mixture of $\gamma\delta$ T effector cells and Kasumi3 AML target cells.

In another embodiment, the effector cell to target cell ratio is about 0.01 to 1 to about 5 to 1. In another embodiment, the effector cell to target cell ratio is about 0.1 to 1 to about 2 to 1. In a specific embodiment, the effector cell to target cell ratio is about 1:1.

Also provided are isolated $\gamma\delta$ T cell bispecific antibodies or antigen binding fragments thereof, wherein the isolated $\gamma\delta$ T cell bispecific antibody or antigen binding fragment thereof comprises a binding site for a first antigen epitope and a binding site for a second antigen epitope, wherein the binding site for the first antigen epitope binds a first antigen on a $\gamma\delta$ T cell and the binding site for the second antigen epitope binds the second antigen epitope on a surface of a target cell, and the binding of the first antigen epitope on the $\gamma\delta$ T cell and the binding of the second antigen epitope on the target cell results in the killing of the target cell.

In another aspect, provided herein are isolated nucleic acids encoding a TRGV9 bispecific antibody or antigen binding fragment thereof, the isolated TRGV9 bispecific antibody or antigen binding fragment thereof comprising:

a. a HC1;

b. a HC2;

c. a LC1; and d. a LC2, wherein HC1 is associated with LC1 and HC2 is associated with LC2, and wherein HC1 comprises a HCDR1, HCDR2, and HCDR3 comprising the amino acid sequences of:

i. SEQ ID NO:1, SEQ ID NO:2, and SEQ ID NO:3, respectively, ii. SEQ ID NO:1, SEQ ID NO:2, and SEQ ID NO:31, respectively, iii. SEQ ID NO:1, SEQ ID NO:2, and SEQ ID NO:32, respectively, or iv. SEQ ID NO:1, SEQ ID NO:2, and SEQ ID NO:33, respectively, and LC1 comprises a LCDR1, LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen. In one embodiment, the isolated nucleic acid encodes a TRGV9 bispecific antibody comprising an HC1 comprising an amino acid sequence having at least 95% identity to an amino acid sequence selected from SEQ ID NO:7, SEQ ID NO:34, SEQ ID NO:35, or SEQ ID NO:36, and LC1 comprises an amino acid sequence having at least 95% identity to the amino acid sequence of SEQ ID NO:8. In another embodiment, the isolated nucleic acid encodes a TRGV9 bispecific antibody comprising an HC1 comprising the amino acid sequence selected from SEQ ID NO:7, SEQ ID NO:34, SEQ ID NO:35, or SEQ ID NO:36, and LC1 comprises the amino acid sequence of SEQ ID NO: 8.

In another aspect, provided herein are isolated nucleic acids encoding a TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:3, respectively, and LC1 comprises a LCDR1, LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen. In one embodiment, the isolated nucleic acid encodes a TRGV9 bispecific antibody comprising an HC1 comprising an amino acid sequence having at least 95% identity to an amino acid sequence of SEQ ID NO:7, and LC1 comprises an amino acid sequence having at least 95% identity to the amino acid sequence of SEQ ID NO:8. In another embodiment, the isolated nucleic acid encodes a TRGV9 bispecific antibody comprising an HC1 comprising the amino acid sequence of SEQ ID NO:7, and LC1 comprises the amino acid sequence of SEQ ID NO:8.

In another aspect, provided herein are isolated nucleic acids encoding a TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:31, respectively, and LC1 comprises a LCDR1, LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen. In one embodiment, the isolated nucleic acid encodes a TRGV9 bispecific antibody comprising an HC1 comprising an amino acid sequence having at least 95% identity to an amino acid sequence of SEQ ID NO:34, and LC1 comprises an amino acid sequence having at least 95% identity to the amino acid sequence of SEQ ID NO:8. In another embodiment, the isolated nucleic acid encodes a TRGV9 bispecific antibody comprising an HC1 comprising the amino acid sequence of SEQ ID NO:34, and LC1 comprises the amino acid sequence of SEQ ID NO:8.

In another aspect, provided herein are isolated nucleic acids encoding a TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:32, respectively, and LC1 comprises a LCDR1, LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen. In one embodiment, the isolated nucleic acid encodes a TRGV9 bispecific antibody comprising an HC1 comprising an amino acid sequence having at least 95% identity to an amino acid sequence of SEQ ID NO:35, and LC1 comprises an amino acid sequence having at least 95% identity to the amino acid sequence of SEQ ID NO:8. In another embodiment, the isolated nucleic acid encodes a TRGV9 bispecific antibody comprising an HC1 comprising the amino acid sequence of SEQ ID NO:35, and LC1 comprises the amino acid sequence of SEQ ID NO:8.

In another aspect, provided herein are isolated nucleic acids encoding a TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:33, respectively, and LC1 comprises a LCDR1, LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen. In one embodiment, the isolated nucleic acid encodes a TRGV9 bispecific antibody comprising an HC1 comprising an amino acid sequence having at least 95% identity to an amino acid sequence of SEQ ID NO:36, and LC1 comprises an amino acid sequence having at least 95% identity to the amino acid sequence of SEQ ID NO:8. In another embodiment, the isolated nucleic acid encodes a TRGV9 bispecific antibody comprising an HC1 comprising the amino acid sequence of SEQ ID NO:36, and LC1 comprises the amino acid sequence of SEQ ID NO:8.

In another aspect, provided herein are isolated nucleic acids encoding a TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:76, and SEQ ID NO:3, respectively, and LC1 comprises a LCDR1, LCDR2, and LCDR2 comprising the amino acid sequences of SEQ ID NO:77, SEQ ID NO:5, and SEQ ID NO:6, respectively, to form a binding site for a first antigen, and wherein HC2 and LC2 form a binding site for a second antigen. In one embodiment, the isolated nucleic acid encodes a TRGV9 bispecific antibody comprising an HC1 comprising an amino acid sequence having at least 95% identity to an amino acid sequence of SEQ ID NO:65, and LC1 comprises an amino acid sequence having at least 95% identity to the amino acid sequence of SEQ ID NO:66. In another embodiment, the isolated nucleic acid encodes a TRGV9 bispecific antibody comprising an HC1 comprising the amino acid sequence of SEQ ID NO:65, and LC1 comprises the amino acid sequence of SEQ ID NO:66. In one embodiment, the isolated nucleic acid encodes a TRGV9 bispecific antibody comprising an HC1 comprising an amino acid sequence having at least 95% identity to an amino acid sequence of SEQ ID NO:67, and LC1 comprises an amino acid sequence having at least 95% identity to the amino acid sequence of SEQ ID NO:68. In another embodiment, the isolated nucleic acid encodes a TRGV9 bispecific antibody comprising an HC1 comprising the amino acid sequence of SEQ ID NO:67, and LC1 comprises the amino acid sequence of SEQ ID NO:68.

In another aspect, provided herein are isolated nucleic acids encoding a TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:60, SEQ ID NO:61, and SEQ ID NO:62, respectively, and LC1 comprises a LCDR1, LCDR2, and LCDR2 comprising the amino acid sequences of SEQ ID NO:63, SEQ ID NO:64, and SEQ ID NO:6, respectively, to form a binding site for a first antigen, and wherein HC2 and LC2 form a binding site for a second antigen. In one embodiment, the isolated nucleic acid encodes a TRGV9 bispecific antibody comprising an HC1 comprising an amino acid sequence having at least 95% identity to an amino acid sequence of SEQ ID NO:65, and LC1 comprises an amino acid sequence having at least 95% identity to the amino acid sequence of SEQ ID NO:66. In another embodiment, the isolated nucleic acid encodes a TRGV9 bispecific antibody comprising an HC1 comprising the amino acid sequence of SEQ ID NO:65, and LC1 comprises the amino acid sequence of SEQ ID NO:66. In one embodiment, the isolated nucleic acid encodes a TRGV9 bispecific antibody comprising an HC1 comprising an amino acid sequence having at least 95% identity to an amino acid sequence of SEQ ID NO:67, and LC1 comprises an amino acid sequence having at least 95% identity to the amino acid sequence of SEQ ID NO:68. In another embodiment, the isolated nucleic acid encodes a TRGV9 bispecific antibody comprising an HC1 comprising the amino acid sequence of SEQ ID NO:67, and LC1 comprises the amino acid sequence of SEQ ID NO:68.

In another aspect, provided herein are isolated nucleic acids encoding a TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:89, SEQ ID NO:90, and SEQ ID NO:91, respectively, and LC1 comprises a LCDR1, LCDR2, and LCDR2 comprising the amino acid sequences of SEQ ID NO:92, SEQ ID NO:93, and SEQ ID NO:94, respectively, to form a binding site for a first antigen, and wherein HC2 and LC2 form a binding site for a second antigen. In one embodiment, the isolated nucleic acid encodes a TRGV9 bispecific antibody comprising an HC1 comprising an amino acid sequence having at least 95% identity to an amino acid sequence of SEQ ID NO:95, and LC1 comprises an amino acid sequence having at least 95% identity to the amino acid sequence of SEQ ID NO:96. In another embodiment, the isolated nucleic acid encodes a TRGV9 bispecific antibody comprising an HC1 comprising the amino acid sequence of SEQ ID NO:95, and LC1 comprises the amino acid sequence of SEQ ID NO:96.

In another aspect, provided herein are isolated nucleic acids encoding a TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:98, SEQ ID NO:99, and SEQ ID NO:100, respectively, and LC1 comprises a LCDR1, LCDR2, and LCDR2 comprising the amino acid sequences of SEQ ID NO:101, SEQ ID NO: 102, and SEQ ID NO:103, respectively, to form a binding site for a first antigen, and wherein HC2 and LC2 form a binding site for a second antigen. In one embodiment, the isolated nucleic acid encodes a TRGV9 bispecific antibody comprising an HC1 comprising an amino acid sequence having at least 95% identity to an amino acid sequence of SEQ ID NO:104, and LC1 comprises an amino acid sequence having at least 95% identity to the amino acid sequence of SEQ ID NO:105. In another embodiment, the isolated nucleic acid encodes a TRGV9 bispecific antibody comprising an HC1 comprising the amino acid sequence of SEQ ID NO:104, and LC1 comprises the amino acid sequence of SEQ ID NO:105.

In another aspect, provided herein are isolated nucleic acids encoding a TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:107, SEQ ID NO:108, and SEQ ID NO:109, respectively, and LC1 comprises a LCDR1, LCDR2, and LCDR2 comprising the amino acid sequences of SEQ ID NO:110, SEQ ID NO:111, and SEQ ID NO:112, respectively, to form a binding site for a first antigen, and wherein HC2 and LC2 form a binding site for a second antigen. In one embodiment, the isolated nucleic acid encodes a TRGV9 bispecific antibody comprising an HC1 comprising an amino acid sequence having at least 95% identity to an amino acid sequence of SEQ ID NO:113, and LC1 comprises an amino acid sequence having at least 95% identity to the amino acid sequence of SEQ ID NO:114. In another embodiment, the isolated nucleic acid encodes a TRGV9 bispecific antibody comprising an HC1 comprising the amino acid sequence of SEQ ID NO:113, and LC1 comprises the amino acid sequence of SEQ ID NO:114.

In another aspect, provided herein are isolated nucleic acids encoding a TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:117, SEQ ID NO:118, and SEQ ID NO:119, respectively, and LC1 comprises a LCDR1, LCDR2, and LCDR2 comprising the amino acid sequences of SEQ ID NO:120, SEQ ID NO:121, and SEQ ID NO:122, respectively, to form a binding site for a first antigen, and wherein HC2 and LC2 form a binding site for a second antigen. In one embodiment, the isolated nucleic acid encodes a TRGV9 bispecific antibody comprising an HC1 comprising an amino acid sequence having at least 95% identity to an amino acid sequence of SEQ ID NO:123, and LC1 comprises an amino acid sequence having at least 95% identity to the amino acid sequence of SEQ ID NO:124. In another embodiment, the isolated nucleic acid encodes a TRGV9 bispecific antibody comprising an HC1 comprising the amino acid sequence of SEQ ID NO:123, and LC1 comprises the amino acid sequence of SEQ ID NO:124.

In another aspect, provided herein are isolated nucleic acids encoding a TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:127, SEQ ID NO:128, and SEQ ID NO:129, respectively, and LC1 comprises a LCDR1, LCDR2, and LCDR2 comprising the amino acid sequences of SEQ ID NO:130, SEQ ID NO:131, and SEQ ID NO:132, respectively, to form a binding site for a first antigen, and wherein HC2 and LC2 form a binding site for a second antigen. In one embodiment, the isolated nucleic acid encodes a TRGV9 bispecific antibody comprising an HC1 comprising an amino acid sequence having at least 95% identity to an amino acid sequence of SEQ ID NO:133, and LC1 comprises an amino acid sequence having at least 95% identity to the amino acid sequence of SEQ ID NO:134. In another embodiment, the isolated nucleic acid encodes a TRGV9 bispecific antibody comprising an HC1 comprising the amino acid sequence of SEQ ID NO:133, and LC1 comprises the amino acid sequence of SEQ ID NO:134.

In another embodiment, the isolated nucleic acid encodes a TRGV9 bispecific antibody comprising a binding site comprising a first antigen that binds to TRGV9 on a γδ T cell.

In another embodiment, the isolated nucleic acid encodes a TRGV9 bispecific antibody comprising a binding site for a second antigen that binds to a cancer antigen present on the surface of a cancer cell.

In another embodiment, the isolated nucleic acid encodes a TRGV9 bispecific antibody, wherein the binding of the bispecific antibody to TRGV9 present on the surface of the γδ T cell and the binding of the cancer antigen present on the surface of the cancer cell results in the killing of the cancer cell.

In another embodiment, the isolated nucleic acid encodes a TRGV9 bispecific antibody, wherein HC1 and LC1 are humanized.

In another embodiment, the isolated nucleic acid encodes a TRGV9 bispecific antibody, wherein HC2 and LC2 bind to CD123.

In another embodiment, the isolated nucleic acid encodes a TRGV9 bispecific antibody, wherein the bispecific antibody or antigen binding fragment thereof is an IgG1, an IgG2, an IgG3, or an IgG4 isotype.

In a specific embodiment, the bispecific antibody or antigen binding fragment thereof is an IgG4 isotype.

In another embodiment, the isolated nucleic acid encodes a TRGV9 bispecific antibody, wherein the bispecific antibody or antigen binding fragment thereof induces γδ T cell dependent cytotoxicity of a cancer cell in vitro with an $EC_{50}$ of less than about 500 pM.

In another embodiment, the isolated nucleic acid encodes a TRGV9 bispecific antibody, wherein the bispecific antibody or antigen binding fragment thereof induces $\gamma\delta$ T cell dependent cytotoxicity of a cancer cell in vitro with an $EC_{50}$ of less than about 300 pM.

In another embodiment, the isolated nucleic acid encodes a TRGV9 bispecific antibody, wherein the bispecific antibody or antigen binding fragment thereof induces $\gamma\delta$ T cell dependent cytotoxicity of a cancer cell in vitro with an $EC_{50}$ of less than about 160 pM.

In another embodiment, the isolated nucleic acid encodes a TRGV9 bispecific antibody, wherein the $EC_{50}$ is assessed with a mixture of $\gamma\delta$ T effector cells and Kasumi3 AML target cells.

In another embodiment, the isolated nucleic acid encodes a TRGV9 bispecific antibody, wherein the effector cell to target cell ratio is about 0.01 to 1 to about 5 to 1. In one embodiment, the effector cell to target cell ratio is about 0.1 to 1 to about 2 to 1. In yet another embodiment, the effector cell to target cell ratio is about 1:1.

In another embodiment, the isolated nucleic acid encodes a TRGV9 bispecific antibody, wherein the bispecific antibody or antigen binding fragment thereof is multivalent.

In another embodiment, the isolated nucleic acid encodes a TRGV9 bispecific antibody, wherein the bispecific antibody or antigen binding fragment thereof is capable of binding at least three antigens.

In another embodiment, the isolated nucleic acid encodes a TRGV9 bispecific antibody, wherein the bispecific antibody or antigen binding fragment thereof is capable of binding at least five antigens.

Also provided are vectors comprising the isolated nucleic acids provided herein.

Also provided are host cells comprising the vectors provided herein.

Also provided are kits comprising the vectors provided herein and packaging for the same.

Provided herein are pharmaceutical compositions comprising: (A) an isolated TRGV9 bispecific antibody or antigen binding fragment thereof, the isolated TRGV9 bispecific antibody or antigen binding fragment thereof comprising:

a. a HC1;

b. a HC2;

c. a LC1; and d. a LC2, wherein HC1 is associated with LC1 and HC2 is associated with LC2, and wherein HC1 comprises a HCDR1, HCDR2, and HCDR3 comprising the amino acid sequences of:

i. SEQ ID NO:1, SEQ ID NO:2, and SEQ ID NO:3, respectively, ii. SEQ ID NO:1, SEQ ID NO:2, and SEQ ID NO:31, respectively, iii. SEQ ID NO:1, SEQ ID NO:2, and SEQ ID NO:32, respectively, or iv. SEQ ID NO:1, SEQ ID NO:2, and SEQ ID NO:33, respectively, and LC1 comprises a LCDR1, LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen;

and (B) a pharmaceutically acceptable carrier. In one embodiment, the pharmaceutical composition comprises a bispecific antibody comprising an HC1 comprising an amino acid sequence having at least 95% identity to an amino acid sequence selected from SEQ ID NO:7, SEQ ID NO:34, SEQ ID NO:35, or SEQ ID NO:36, and an LC1 comprising an amino acid sequence having at least 95% identity to the amino acid sequence of SEQ ID NO:8. In another embodiment, the pharmaceutical composition comprises a bispecific antibody comprising an HC1 comprising the amino acid sequence selected from SEQ ID NO:7, SEQ ID NO:34, SEQ ID NO:35, or SEQ ID NO:36, and an LC1 comprising the amino acid sequence of SEQ ID NO:8.

Also provided herein are pharmaceutical compositions comprising: (A) an isolated TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:3, respectively; and LC1 comprises a LCDR1, LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen; and (B) a pharmaceutically acceptable carrier. In one embodiment, the pharmaceutical composition comprises a bispecific antibody comprising an HC1 comprising an amino acid sequence having at least 95% identity to an amino acid sequence of SEQ ID NO:7, and an LC1 comprising an amino acid sequence having at least 95% identity to the amino acid sequence of SEQ ID NO:8. In another embodiment, the pharmaceutical composition comprises a bispecific antibody comprising an HC1 comprising the amino acid sequence of SEQ ID NO:7, and an LC1 comprising the amino acid sequence of SEQ ID NO:8.

Also provided herein are pharmaceutical compositions comprising: (A) an isolated TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:31, respectively; and LC1 comprises a LCDR1, LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen; and (B) a pharmaceutically acceptable carrier. In one embodiment, the pharmaceutical composition comprises a bispecific antibody comprising an HC1 comprising an amino acid sequence having at least 95% identity to an amino acid sequence of SEQ ID NO:34, and an LC1 comprising an amino acid sequence having at least 95% identity to the amino acid sequence of SEQ ID NO:8. In another embodiment, the pharmaceutical composition comprises a bispecific antibody comprising an HC1 comprising the amino acid sequence of SEQ ID NO:34, and an LC1 comprising the amino acid sequence of SEQ ID NO:8.

Also provided herein are pharmaceutical compositions comprising: (A) an isolated TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:32, respectively; and LC1 comprises a LCDR1, LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen; and (B) a pharmaceutically acceptable carrier. In one embodiment, the pharmaceutical composition comprises a bispecific antibody comprising an HC1 comprising an amino acid sequence having at least 95% identity to an amino acid sequence of SEQ ID NO:35, and an LC1 comprising an amino acid sequence having at least 95% identity to the amino acid sequence of SEQ ID NO:8. In another embodiment, the pharmaceutical composition comprises a bispecific antibody comprising an HC1 comprising the amino acid sequence of SEQ ID NO:35, and an LC1 comprising the amino acid sequence of SEQ ID NO:8.

Also provided herein are pharmaceutical compositions comprising: (A) an isolated TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:33, respectively; and LC1 comprises a LCDR1, LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen; and (B) a pharmaceutically acceptable carrier. In one embodiment, the pharmaceutical composition comprises a bispecific antibody comprising an HC1 comprising an amino acid sequence having at least 95% identity to an amino acid sequence of SEQ ID NO:36, and an LC1 comprising an amino acid sequence having at least 95% identity to the amino acid sequence of SEQ ID NO:8. In another embodiment, the pharmaceutical composition comprises a bispecific antibody comprising an HC1 comprising the amino acid sequence of SEQ ID NO:36, and an LC1 comprising the amino acid sequence of SEQ ID NO:8.

Also provided herein are pharmaceutical compositions comprising: (A) an isolated TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:76, and SEQ ID NO:3, respectively; and LC1 comprises a LCDR1, LCDR2, and LCDR2 comprising the amino acid sequences of SEQ ID NO:77, SEQ ID NO:5, and SEQ ID NO:6, respectively, to form a binding site for a first antigen, and wherein HC2 and LC2 form a binding site for a second antigen; and (B) a pharmaceutically acceptable carrier. In one embodiment, the pharmaceutical composition comprises a bispecific antibody comprising an HC1 comprising an amino acid sequence having at least 95% identity to an amino acid sequence of SEQ ID NO:65, and an LC1 comprising an amino acid sequence having at least 95% identity to the amino acid sequence of SEQ ID NO:66. In another embodiment, the pharmaceutical composition comprises a bispecific antibody comprising an HC1 comprising the amino acid sequence of SEQ ID NO:65, and an LC1 comprising the amino acid sequence of SEQ ID NO:66. In one embodiment, the pharmaceutical composition comprises a bispecific antibody comprising an HC1 comprising an amino acid sequence having at least 95% identity to an amino acid sequence of SEQ ID NO:67, and an LC1 comprising an amino acid sequence having at least 95% identity to the amino acid sequence of SEQ ID NO:68. In another embodiment, the pharmaceutical composition comprises a bispecific antibody comprising an HC1 comprising the amino acid sequence of SEQ ID NO:67, and an LC1 comprising the amino acid sequence of SEQ ID NO:68.

Also provided herein are pharmaceutical compositions comprising: (A) an isolated TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:60, SEQ ID NO:61, and SEQ ID NO:62, respectively; and LC1 comprises a LCDR1, LCDR2, and LCDR2 comprising the amino acid sequences of SEQ ID NO:63, SEQ ID NO:64, and SEQ ID NO:6, respectively, to form a binding site for a first antigen, and wherein HC2 and LC2 form a binding site for a second antigen; and (B) a pharmaceutically acceptable carrier. In one embodiment, the pharmaceutical composition comprises a bispecific antibody comprising an HC1 comprising an amino acid sequence having at least 95% identity to an amino acid sequence of SEQ ID NO:65, and an LC1 comprising an amino acid sequence having at least 95% identity to the amino acid sequence of SEQ ID NO:66. In another embodiment, the pharmaceutical composition comprises a bispecific antibody comprising an HC1 comprising the amino acid sequence of SEQ ID NO:65, and an LC1 comprising the amino acid sequence of SEQ ID NO:66. In one embodiment, the pharmaceutical composition comprises a bispecific antibody comprising an HC1 comprising an amino acid sequence having at least 95% identity to an amino acid sequence of SEQ ID NO:67, and an LC1 comprising an amino acid sequence having at least 95% identity to the amino acid sequence of SEQ ID NO:68. In another embodiment, the pharmaceutical composition comprises a bispecific antibody comprising an HC1 comprising the amino acid sequence of SEQ ID NO:67, and an LC1 comprising the amino acid sequence of SEQ ID NO:68.

Also provided herein are pharmaceutical compositions comprising: (A) an isolated TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:89, SEQ ID NO:90, and SEQ ID NO:91, respectively; and LC1 comprises a LCDR1, LCDR2, and LCDR2 comprising the amino acid sequences of SEQ ID NO:92, SEQ ID NO:93, and SEQ ID NO:94, respectively, to form a binding site for a first antigen, and wherein HC2 and LC2 form a binding site for a second antigen; and (B) a pharmaceutically acceptable carrier. In one embodiment, the pharmaceutical composition comprises a bispecific antibody comprising an HC1 comprising an amino acid sequence having at least 95% identity to an amino acid sequence of SEQ ID NO:95, and an LC1 comprising an amino acid sequence having at least 95% identity to the amino acid sequence of SEQ ID NO:96. In another embodiment, the pharmaceutical composition comprises a bispecific antibody comprising an HC1 comprising the amino acid sequence of SEQ ID NO:95, and an LC1 comprising the amino acid sequence of SEQ ID NO:96.

Also provided herein are pharmaceutical compositions comprising: (A) an isolated TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2;

wherein HC1 is associated with LC1 and HC2 is associated with LC2, and wherein HC1 comprises a HCDR1, HCDR2, and HCDR3 comprising the amino acid sequences of SEQ ID NO:98, SEQ ID NO:99, and SEQ ID NO:100, respectively; and LC1 comprises a LCDR1, LCDR2, and LCDR2 comprising the amino acid sequences of SEQ ID NO:101, SEQ ID NO: 102, and SEQ ID NO:103, respectively, to form a binding site for a first antigen, and wherein HC2 and LC2 form a binding site for a second antigen; and (B) a pharmaceutically acceptable carrier. In one embodiment, the pharmaceutical composition comprises a bispecific antibody comprising an HC1 comprising an amino acid sequence having at least 95% identity to an amino acid sequence of SEQ ID NO:104, and an LC1 comprising an amino acid sequence having at least 95% identity to the amino acid sequence of SEQ ID NO:105. In another embodiment, the pharmaceutical composition comprises a bispecific antibody comprising an HC1 comprising the amino acid sequence of SEQ ID NO:104, and an LC1 comprising the amino acid sequence of SEQ ID NO:105.

Also provided herein are pharmaceutical compositions comprising: (A) an isolated TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:107, SEQ ID NO:108, and SEQ ID NO:109, respectively; and LC1 comprises a LCDR1, LCDR2, and LCDR2 comprising the amino acid sequences of SEQ ID NO:110, SEQ ID NO:111, and SEQ ID NO:112, respectively, to form a binding site for a first antigen, and wherein HC2 and LC2 form a binding site for a second antigen; and (B) a pharmaceutically acceptable carrier. In one embodiment, the pharmaceutical composition comprises a bispecific antibody comprising an HC1 comprising an amino acid sequence having at least 95% identity to an amino acid sequence of SEQ ID NO:113, and an LC1 comprising an amino acid sequence having at least 95% identity to the amino acid sequence of SEQ ID NO:114. In another embodiment, the pharmaceutical composition comprises a bispecific antibody comprising an HC1 comprising the amino acid sequence of SEQ ID NO:113, and an LC1 comprising the amino acid sequence of SEQ ID NO:114.

Also provided herein are pharmaceutical compositions comprising: (A) an isolated TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:117, SEQ ID NO:118, and SEQ ID NO:119, respectively; and LC1 comprises a LCDR1, LCDR2, and LCDR2 comprising the amino acid sequences of SEQ ID NO:120, SEQ ID NO:121, and SEQ ID NO:122, respectively, to form a binding site for a first antigen, and wherein HC2 and LC2 form a binding site for a second antigen; and (B) a pharmaceutically acceptable carrier. In one embodiment, the pharmaceutical composition comprises a bispecific antibody comprising an HC1 comprising an amino acid sequence having at least 95% identity to an amino acid sequence of SEQ ID NO:123, and an LC1 comprising an amino acid sequence having at least 95% identity to the amino acid sequence of SEQ ID NO:124. In another embodiment, the pharmaceutical composition comprises a bispecific antibody comprising an HC1 comprising the amino acid sequence of SEQ ID NO:123, and an LC1 comprising the amino acid sequence of SEQ ID NO:124.

Also provided herein are pharmaceutical compositions comprising: (A) an isolated TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:127, SEQ ID NO:128, and SEQ ID NO:129, respectively; and LC1 comprises a LCDR1, LCDR2, and LCDR2 comprising the amino acid sequences of SEQ ID NO:130, SEQ ID NO:131, and SEQ ID NO:132, respectively, to form a binding site for a first antigen, and wherein HC2 and LC2 form a binding site for a second antigen; and (B) a pharmaceutically acceptable carrier. In one embodiment, the pharmaceutical composition comprises a bispecific antibody comprising an HC1 comprising an amino acid sequence having at least 95% identity to an amino acid sequence of SEQ ID NO:133, and an LC1 comprising an amino acid sequence having at least 95% identity to the amino acid sequence of SEQ ID NO:134. In another embodiment, the pharmaceutical composition comprises a bispecific antibody comprising an HC1 comprising the amino acid sequence of SEQ ID NO:133, and an LC1 comprising the amino acid sequence of SEQ ID NO:134.

In another embodiment, the pharmaceutical composition comprises a bispecific antibody comprising a binding site for a first antigen binds to TRGV9 on a γδ T cell.

In another embodiment, the pharmaceutical composition comprises a bispecific antibody, wherein the binding site for a second antigen binds to a cancer antigen present on the surface of a cancer cell.

In another embodiment, the pharmaceutical composition comprises a bispecific antibody, wherein the binding of the bispecific antibody to TRGV9 present on the surface of the γδ T cell and the binding of the cancer antigen present on the surface of the cancer cell results in the killing of the cancer cell.

In another embodiment, the pharmaceutical composition comprises a bispecific antibody, wherein HC1 and LC1 are humanized.

In another embodiment, the pharmaceutical composition comprises a bispecific antibody, wherein HC2 and LC2 bind to CD123.

In another embodiment, the pharmaceutical composition comprises a bispecific antibody, wherein the bispecific antibody or antigen binding fragment thereof is an IgG1, an IgG2, an IgG3, or an IgG4 isotype.

Also provided are methods of directing a Vγ9-expressing γδ T cell to a cancer cell, the method comprising contacting a Vγ9-expressing γδ T cell with the pharmaceutical compositions provided herein, wherein contacting the Vγ9-expressing γδ T cell with the pharmaceutical composition directs the Vγ9-expressing γδ T cell to a cancer cell.

Also provided are methods of inhibiting growth or proliferation of cancer cells expressing a cancer antigen on the cell surface, the method comprising contacting the cancer cells with the pharmaceutical compositions provided herein, wherein contacting the cancer cells with the pharmaceutical composition inhibits growth or proliferation of the cancer cells.

In one embodiment, the cancer cell is in the presence of a Vγ9-expressing γδ T cell while in contact with anti-TRGV9 bispecific antibody or antigen binding fragment thereof.

Also provided are methods for treating a cancer in a subject in need thereof, the method comprising:

a. identifying a subject in need of cancer treatment; and b. administering to the subject in need thereof the pharmaceutical compositions provided herein, wherein administering the pharmaceutical composition to the subject in need thereof treats the cancer in the subject.

Also provided are methods of activating a Vγ9-expressing γδ T cell, the method comprising contacting the Vγ9-expressing γδ T cell with the pharmaceutical composition provided herein, wherein contacting the Vγ9-expressing γδ T cell with the pharmaceutical composition results in an increase in CD69, CD25, and/or Granzyme B expression as compared to a control Vγ9-expressing γδ T cell.

Also provided are methods of producing the pharmaceutical composition provided herein, the method comprising combining the bispecific antibody or antigen binding fragment thereof with a pharmaceutically acceptable carrier to obtain the pharmaceutical composition.

BRIEF DESCRIPTION OF THE DRAWINGS

The foregoing summary, as well as the following detailed description of certain embodiments of the present application, will be better understood when read in conjunction with the appended drawings. It should be understood, however, that the application is not limited to the precise embodiments shown in the drawings.

FIG. 3A shows a schematic depiction of gates used to describe the differentiation of γδ T cells (left). Representative FACS-dot plots show the differentiation profile of Vγ9+ γδ T cells from fresh PBMCs (left) and PBMCs cultured ex vivo with Zoledronic acid+IL-2+IL-15 for 14 days (right). Numbers in quadrants mirror the frequency (mean±SEM) of the respective population among fresh and activated Vγ9+ γδ T cells. Represented data is mean (±SEM) of five donors (n=5) from a single experiment. FIG. 3B shows numbers in representative dot plots mirroring the frequency (mean±SEM) of Vγ9+ γδ T cells positive for respective activation marker either from fresh PBMCs (upper row) or PBMCs cultured with Zoledronic acid+IL-2+IL-15 for 14 days (lower row). Represented data is mean (±SEM) of seven donors (n=7) for CD62L, CD69, CD44 expression data from two independent experiments. n=5 donors for NKG2D and 2 donors for CD45RO and CD71 expression data respectively from a single experiment. FIG. 3C shows numbers above gates in dot plots depicting the frequency (mean±SEM) of Vγ9+ γδ T cells positive for respective inhibitory receptor surface expression either from fresh PBMCs (upper row) or PBMCs cultured with Zoledronic acid+TL-2+IL-15 for day 14 days (lower row). Data shown here is mean (±SEM) of five donors (n=5) for PD1, CTLA4, TIGIT and LAG3 surface expression and seven donors (n=7) for 2B4 and TIM3 surface expression data from two independent experiments. FIG. 3D shows representative FACS dot plots demonstrating the frequency (mean±SEM) of Vγ9+ γ6 T cells expressing intracellular Granzyme B (left column) and Perforin (right column) from fresh PBMCs (upper row) and PBMCs cultured ex vivo with Zoledronic acid+IL-2+IL-15 for 14 days (lower row). Depicted data is mean (±SEM) of four (n=4) and seven (n=7) donors for Granzyme B and Perforin data respectively from two independent experiments. FIG. 3E shows bars representing the mean (±SEM) concentration (pg/mL) of cytokine in the cell culture supernatant on day 0 and day 14 of PBMCs culture with Zoledronic acid+TL-2+IL-15. Represented data is mean (±SEM) of four wells (n=4) from a single donor.

Figure 15:
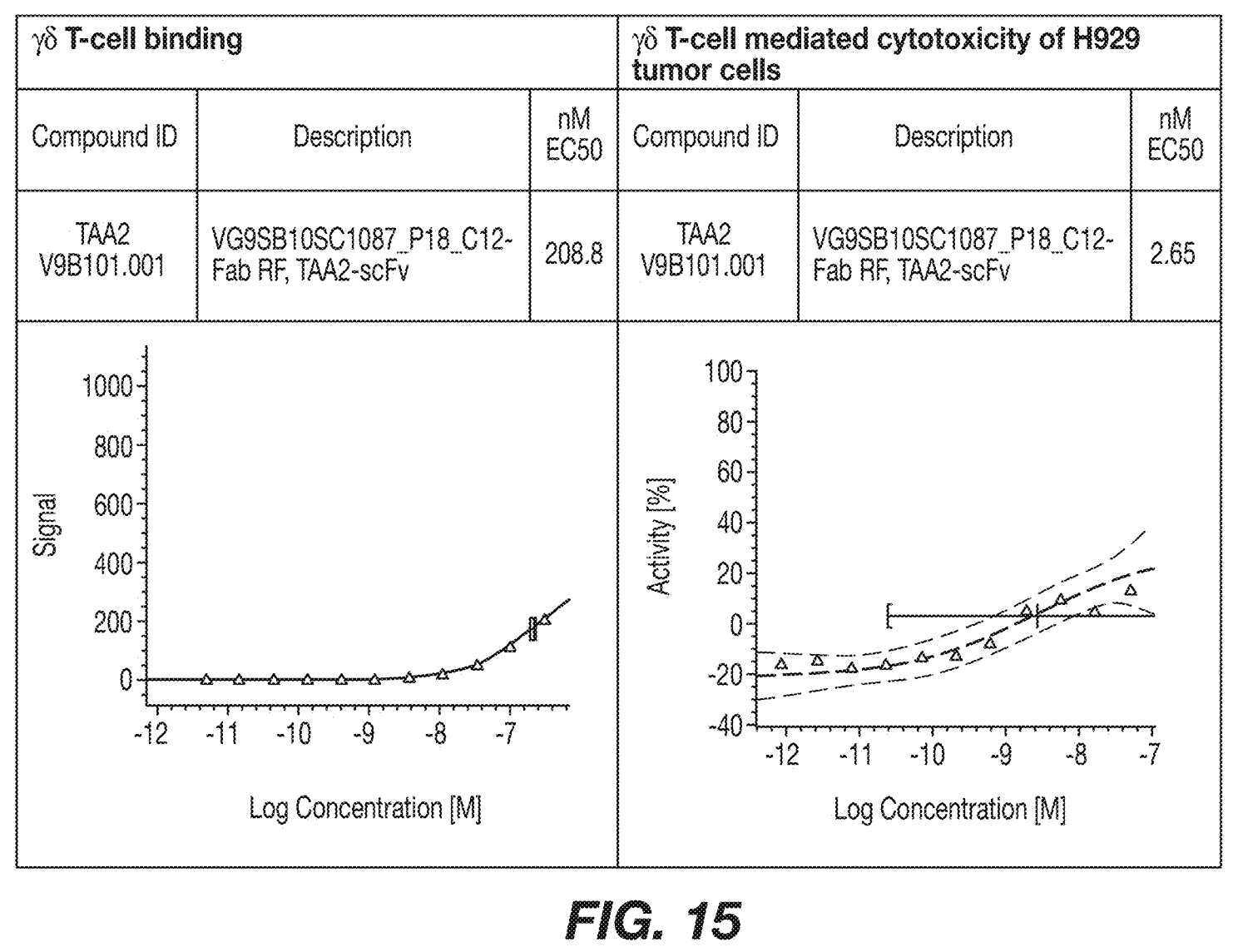

FIG. 15 shows that the anti-TRGV9/anti-TAA2 bispecific antibody (VG9SB10SC1087_P18_C12-Fab RF, TAA2-scFv (TAA2V9B101.001)) binds γδ T cells (left panel) and mediates γδ T cell cytotoxicity against TAA2 expressing H929 cells in vitro (right panel). $EC_{50}$ values were calculated as described in methods. Representative data shown here are from a single experiment.

DETAILED DESCRIPTION

Figure 1:
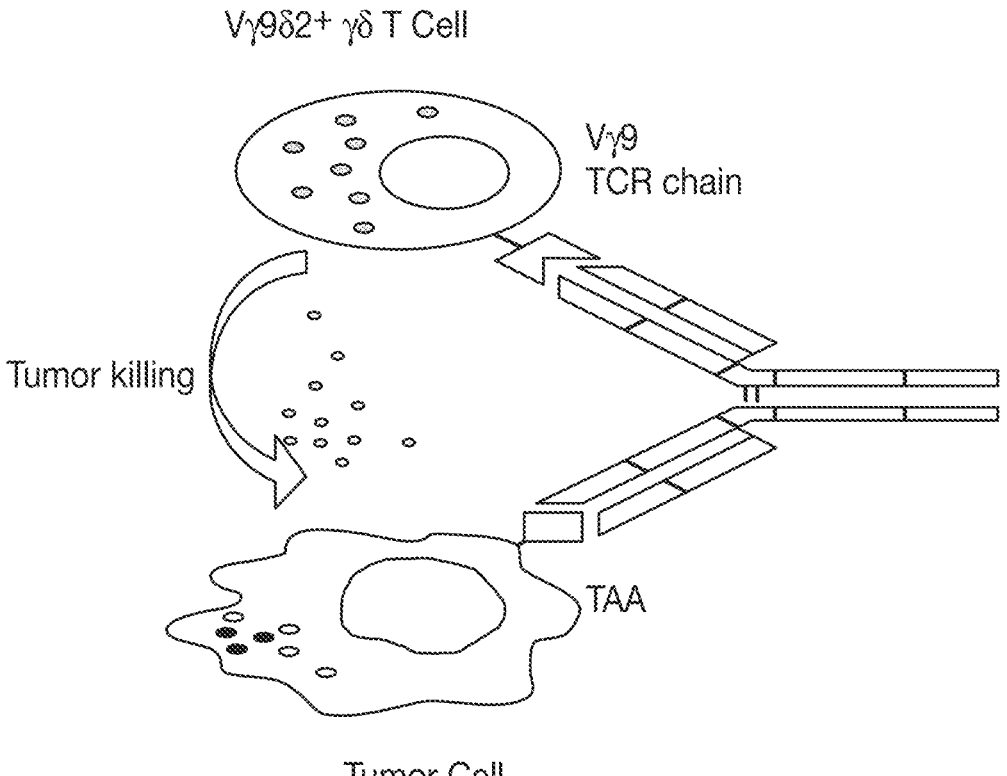
FIG. 1 shows a schematic demonstrating the binding of an anti-TRGV9/anti-tumor associated antigen (TAA) bispecific antibody to recruit γδ T cells to a cancer cell and to induce cancer cell death.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

As used herein, "subject" means any animal, such as a mammal, such as a human. The term "mammal" as used herein, encompasses any mammal. Examples of mammals include, but are not limited to, cows, horses, sheep, pigs, cats, dogs, mice, rats, rabbits, guinea pigs, monkeys, humans, etc., or such as a human.

It should also be understood that the terms "about," "approximately," "generally," "substantially," and like terms, used herein when referring to a dimension or characteristic of a component, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., anti-TRGV9/anti-cancer-associated antigen bispecific antibodies and polynucleotides that encode them, anti-TRGV9/anti-CD123 bispecific antibodies and polynucleotides that encode them, TRGV9 polypeptides and TRGV9 polynucleotides that encode them, CD123 polypeptides and CD123 polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1997) Nucleic Acids Res. 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, less than about 0.01, or less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

As used herein, the term "polynucleotide," synonymously referred to as "nucleic acid molecule," "nucleotides" or "nucleic acids," refers to any polyribonucleotide or polydeoxyribonucleotide, which can be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

As used herein, the term "vector" is a replicon in which another nucleic acid segment can be operably inserted so as to bring about the replication or expression of the segment.

As used herein, the term "host cell" refers to a cell comprising a nucleic acid molecule provided herein. The "host cell" can be any type of cell, e.g., a primary cell, a cell in culture, or a cell from a cell line. In one embodiment, a "host cell" is a cell transfected with a nucleic acid molecule provided herein. In another embodiment, a "host cell" is a progeny or potential progeny of such a transfected cell. A progeny of a cell may or may not be identical to the parent cell, e.g., due to mutations or environmental influences that can occur in succeeding generations or integration of the nucleic acid molecule into the host cell genome.

The term "expression" as used herein, refers to the biosynthesis of a gene product. The term encompasses the transcription of a gene into RNA. The term also encompasses translation of RNA into one or more polypeptides, and further encompasses all naturally occurring post-transcriptional and post-translational modifications. The expressed bispecific antibody can be within the cytoplasm of a host cell, into the extracellular milieu such as the growth medium of a cell culture or anchored to the cell membrane.

As used herein, the terms "peptide," "polypeptide," or "protein" can refer to a molecule comprised of amino acids and can be recognized as a protein by those of skill in the art. The conventional one-letter or three-letter code for amino acid residues is used herein. The terms "peptide," "polypep-tide," and "protein" can be used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phos-phorylation, or any other manipulation or modification, such as conjugation with a labeling component. Also included within the definition are, for example, polypeptides contain-ing one or more analogs of an amino acid (including, for example, unnatural amino acids, etc.), as well as other modifications known in the art.

The peptide sequences described herein are written according to the usual convention whereby the N-terminal region of the peptide is on the left and the C-terminal region is on the right. Although isomeric forms of the amino acids are known, it is the L-form of the amino acid that is represented unless otherwise expressly indicated.

Antibodies

Provided herein are anti-TRGV9 antibodies or antigen-binding fragments thereof, nucleic acids and expression vectors encoding the antibodies, recombinant cells contain-ing the vectors, and compositions comprising the antibodies. Also provided herein are anti-TRGV9 bispecific antibodies or antigen-binding fragments thereof, nucleic acids and expression vectors encoding the bispecific antibodies, recombinant cells containing the vectors, and compositions comprising the bispecific antibodies. Also provided herein are anti-TRGV9/anti-CD123 bispecific antibodies or anti-gen-binding fragments thereof, nucleic acids and expression vectors encoding the bispecific antibodies, recombinant cells containing the vectors, and compositions comprising the bispecific antibodies. Methods of making the antibodies, and methods of using the antibodies to treat diseases, including cancer, are also provided. The antibodies disclosed herein possess one or more desirable functional properties, includ-ing but not limited to high-affinity binding to TRGV9 and/or high affinity binding to CD123, high specificity to TRGV9 and/or high specificity to CD123, and the ability to treat or prevent cancer when administered alone or in combination with other anti-cancer therapies.

As used herein, the term "antibody" is used in a broad sense and includes immunoglobulin or antibody molecules including human, humanized, composite and chimeric anti-bodies and antibody fragments that are monoclonal or polyclonal. In general, antibodies are proteins or peptide chains that exhibit binding specificity to a specific antigen. Antibody structures are well known. Immunoglobulins can be assigned to five major classes (i.e., IgA, IgD, IgE, IgG and IgM), depending on the heavy chain constant domain amino acid sequence. IgA and IgG are further sub-classified as the isotypes IgA1, IgA2, IgG1, IgG2, IgG3 and IgG4. Accordingly, the antibodies provided herein can be of any of the five major classes or corresponding sub-classes. In certain embodiments, the antibodies provided herein are IgG1. In some embodiments, the antibodies provided herein are IgG2. In some embodiments, the antibodies provided herein are IgG3. In some embodiments, the antibodies provided herein are IgG4. Antibody light chains of verte-brate species can be assigned to one of two clearly distinct types, namely kappa and lambda, based on the amino acid sequences of their constant domains. Accordingly, the anti-bodies provided herein can contain a kappa or lambda light chain constant domain. According to particular embodi-ments, the antibodies provided herein include heavy and/or light chain constant regions from rat or human antibodies.

In addition to the heavy and light constant domains, antibodies contain an antigen-binding region that is made up of a light chain variable region and a heavy chain variable region, each of which contains three domains (i.e., comple-mentarity determining regions 1-3; CDR1, CDR2, and CDR3). A "CDR" refers to one of three hypervariable regions (HCDR1, HCDR2 or HCDR3) within the non-framework region of the immunoglobulin (Ig or antibody) VH β-sheet framework, or one of three hypervariable regions (LCDR1, LCDR2 or LCDR3) within the non-frame-work region of the antibody VL β-sheet framework. Accord-ingly, CDRs are variable region sequences interspersed within the framework region sequences. CDR regions are well known to those skilled in the art and have been defined by, for example, Kabat as the regions of most hypervari-ability within the antibody variable (V) domains (Kabat et al., *J. Biol. Chem.* 252:6609-6616 (1977); Kabat, *Adv. Prot. Chem.* 32:1-75 (1978)). CDR region sequences also have been defined structurally by Chothia as those residues that are not part of the conserved β-sheet framework, and thus are able to adapt different conformations (Chothia and Lesk, *J. Mol. Biol.* 196:901-917 (1987)). Both terminologies are well recognized in the art. CDR region sequences have also been defined by AbM, Contact and IMGT. Exemplary CDR region sequences are illustrated herein, for example, in the Sequence Listing, and tables provided in the Examples below. The positions of CDRs within a canonical antibody variable region have been determined by comparison of numerous structures (Al-Lazikani et al., *J. Mol. Biol.* 273: 927-948 (1997); Morea et al., *Methods* 20:267-279 (2000)). Because the number of residues within a hypervariable region varies in different antibodies, additional residues relative to the canonical positions are conventionally num-bered with a, b, c and so forth next to the residue number in the canonical variable region numbering scheme (Al-Lazi-kani et al., supra (1997)). Such nomenclature is similarly well known to those skilled in the art.

The light chain variable region CDR1 domain is inter-changeably referred to herein as LCDR1 or VL CDR1. The light chain variable region CDR2 domain is interchangeably referred to herein as LCDR2 or VL CDR2. The light chain variable region CDR3 domain is interchangeably referred to herein as LCDR3 or VL CDR3. The heavy chain variable region CDR1 domain is interchangeably referred to herein as HCDR1 or VH CDR1. The heavy chain variable region CDR2 domain is interchangeably referred to herein as HCDR2 or VH CDR2. The heavy chain variable region CDR1 domain is interchangeably referred to herein as HCDR3 or VH CDR3.

The term "hypervariable region", such as a VH or VL, when used herein refers to the regions of an antibody variable region that are hypervariable in sequence and/or form structurally defined loops. Generally, antibodies com-prise six hypervariable regions; three in the VH (HCDR1, HCDR2, HCDR3), and three in the VL (LCDR1, LCDR2, LCDR3). A number of hypervariable region delineations are in use and are encompassed herein. The "Kabat" CDRs are based on sequence variability and are the most commonly used (see, e.g., Kabat et al., *Sequences of Proteins of Immunological Interest,* 5th Ed. Public Health Service, National Institutes of Health, Bethesda, MD. (1991)). "Chothia" refers instead to the location of the structural loops (see, e.g., Chothia and Lesk, *J. Mol. Biol.* 196:901-917 (1987)). The end of the Chothia CDR-HCDR1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The "AbM" hypervariable regions represent a compromise between the Kabat CDRs and Chothia structural loops, and are used by Oxford Molecular's AbM antibody modeling software (see, e.g., Martin, in *Antibody Engineering*, Vol. 2, Chapter 3, Springer Verlag). "Contact" hypervariable regions are based on an analysis of the available complex crystal structures.

Recently, a universal numbering system has been developed and widely adopted, ImMunoGeneTics (IMGT) Information System® (Lafranc et al., *Dev. Comp. Immunol.* 27(1):55-77 (2003)). IMGT is an integrated information system specializing in immunoglobulins (IG), T cell receptors (TR) and major histocompatibility complex (MHC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues and are readily identified. This information can be used in grafting and replacement of CDR residues from immunoglobulins of one species into an acceptor framework from, typically, a human antibody. An additional numbering system (AHon) has been developed by Honegger and Plückthun, *J. Mol. Biol.* 309: 657-670 (2001). Correspondence between the numbering system, including, for example, the Kabat numbering and the IMGT unique numbering system, is well known to one skilled in the art (see, e.g., Kabat, supra; Chothia and Lesk, supra; Martin, supra; Lefranc et al., supra). An Exemplary system, shown herein, combines Kabat and Chothia.

|  | Exemplary | IMGT | Kabat | AbM | Chothia | Contact |
|---|---|---|---|---|---|---|
| $V_H$ CDR1 | 26-35 | 27-38 | 31-35 | 26-35 | 26-32 | 30-35 |
| $V_H$ CDR2 | 50-65 | 56-65 | 50-65 | 50-58 | 53-55 | 47-58 |
| $V_H$ CDR3 | 95-102 | 105-117 | 95-102 | 95-102 | 96-101 | 93-101 |
| $V_L$ CDR1 | 24-34 | 27-38 | 24-34 | 24-34 | 26-32 | 30-36 |
| $V_L$ CDR2 | 50-56 | 56-65 | 50-56 | 50-56 | 50-52 | 46-55 |
| $V_L$ CDR3 | 89-97 | 105-117 | 89-97 | 89-97 | 91-96 | 89-96 |

Hypervariable regions may comprise "extended hypervariable regions" as follows: 24-36 or 24-34 (LCDR1), 46-56 or 50-56 (LCDR2) and 89-97 or 89-96 (LCDR3) in the VL and 26-35 or 26-35A (HCDR1), 50-65 or 49-65 (HCDR2) and 93-102, 94-102, or 95-102 (HCDR3) in the VH. CDR sequences, reflecting each of the above numbering schemes, are provided herein, including in the Sequence Listing.

The term "constant region" or "constant domain" refers to a carboxy terminal portion of the light and heavy chain which is not directly involved in binding of the antibody to antigen but exhibits various effector function, such as interaction with the Fc receptor. The terms refer to the portion of an immunoglobulin molecule having a more conserved amino acid sequence relative to the other portion of the immunoglobulin, the variable region, which contains the antigen binding site. The constant region may contain the CH1, CH2 and CH3 regions of the heavy chain and the CL region of the light chain.

The term "framework" or "FR" residues are those variable region residues flanking the CDRs. FR residues are present, for example, in chimeric, humanized, human, domain antibodies, diabodies, linear antibodies, and bispecific antibodies. FR residues are those variable domain residues other than the hypervariable region residues or CDR residues.

As used herein, the term an "isolated antibody" refers to an antibody which is substantially free of other antibodies having different antigenic specificities (e.g., an isolated antibody that specifically binds to TRGV9 is substantially free of antibodies that do not bind to Vγ9; an isolated antibody that specifically binds to CD123 is substantially free of antibodies that do not bind to CD123). In addition, an isolated antibody is substantially free of other cellular material and/or chemicals.

As used herein, the term "monoclonal antibody" refers to an antibody obtained from a population of substantially homogeneous antibodies, i.e., the individual antibodies comprising the population are identical except for possible naturally occurring mutations that can be present in minor amounts. The monoclonal antibodies provided herein can be made by the hybridoma method, phage display technology, single lymphocyte gene cloning technology, or by recombinant DNA methods. For example, the monoclonal antibodies can be produced by a hybridoma which includes a B cell obtained from a transgenic nonhuman animal, such as a transgenic mouse or rat, having a genome comprising a human heavy chain transgene and a light chain transgene.

As used herein, the term "antigen-binding fragment" refers to an antibody fragment such as, for example, a diabody, a Fab, a Fab', a F(ab')2, an Fv fragment, a disulfide stabilized Fv fragment (dsFv), a $(dsFv)_2$, a bispecific dsFv (dsFv-dsFv'), a disulfide stabilized diabody (ds diabody), a single-chain antibody molecule (scFv), a single domain antibody (sdAb) an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment of the heavy chain. According to other particular embodiments, the antigen-binding fragment comprises Fab and F(ab').

As used herein, the term "single-chain antibody" refers to a conventional single-chain antibody in the field, which comprises a heavy chain variable region and a light chain variable region connected by a short peptide of about 15 to about 20 amino acids. As used herein, the term "single domain antibody" refers to a conventional single domain antibody in the field, which comprises a heavy chain variable region and a heavy chain constant region or which comprises only a heavy chain variable region.

As used herein, the term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide.

As used herein, the term "humanized antibody" refers to a non-human antibody that is modified to increase the sequence homology to that of a human antibody, such that the antigen-binding properties of the antibody are retained, but its antigenicity in the human body is reduced.

As used herein, the term "chimeric antibody" refers to an antibody wherein the amino acid sequence of the immunoglobulin molecule is derived from two or more species. The variable region of both the light and heavy chains often corresponds to the variable region of an antibody derived from one species of mammal (e.g., mouse, rat, rabbit, etc.) having the desired specificity, affinity, and capability, while the constant regions correspond to the sequences of an antibody derived from another species of mammal (e.g., human) to avoid eliciting an immune response in that species.

As used herein, the term "multispecific antibody" refers to an antibody that comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes do not overlap or do not substantially overlap. In an embodiment, the first and second epitopes are on different antigens, e.g., the different proteins (or different subunits of a multimeric protein). In an embodiment, a multispecific antibody comprises a third, fourth, or fifth immunoglobulin variable domain. In an embodiment, a multispecific antibody is a bispecific antibody molecule, a trispecific antibody molecule, or a tetraspecific antibody molecule.

As used herein, the term "bispecific antibody" refers to a multispecific antibody that binds no more than two epitopes or two antigens. A bispecific antibody is characterized by a first immunoglobulin variable domain sequence which has binding specificity for a first epitope (e.g., an epitope on a TRGV9 antigen) and a second immunoglobulin variable domain sequence that has binding specificity for a second epitope (e.g., an epitope on a tumor-associated antigen (e.g., a CD123 antigen)). In an embodiment, the first and second epitopes are on different antigens, e.g., the different proteins (or different subunits of a multimeric protein). In an embodiment, a bispecific antibody comprises a heavy chain variable domain sequence and a light chain variable domain sequence which have binding specificity for a first epitope and a heavy chain variable domain sequence and a light chain variable domain sequence which have binding specificity for a second epitope. In an embodiment, a bispecific antibody comprises a half antibody, or fragment thereof, having binding specificity for a first epitope and a half antibody, or fragment thereof, having binding specificity for a second epitope. In an embodiment, a bispecific antibody comprises a scFv, or fragment thereof, having binding specificity for a first epitope, and a scFv, or fragment thereof, having binding specificity for a second epitope. In an embodiment, the first epitope is located on TRGV9 and the second epitope is located on CD123. In an embodiment, the first epitope is located on TRGV9 and the second epitope is located on PD-1, PD-L1, CTLA-4, EGFR, HER-2, CD19, CD20, CD3 and/or other cancer associated immune suppressors or surface antigens.

The term "half antibody" as used herein refers to one immunoglobulin heavy chain associated with one immunoglobulin light chain. An exemplary half-antibody is depicted in SEQ ID NO:17. One skilled in the art will readily appreciate that a half-antibody can encompass a fragment thereof and can also have an antigen binding domain consisting of a single variable domain, e.g., originating from a camelidae.

As used herein, the term "TRGV9" refers to a polypeptide capable of forming a T cell receptor when expressed on the surface of γδ T cells. TRGV9-expressing γδ T cells are among the first T cells to develop in the human fetus and are the predominant γδ T cell subset in healthy adult peripheral blood cells. The term "TRGV9" includes any TRGV9 variant, isoform, and species homolog, which is naturally expressed by cells (including T cells) or can be expressed on cells transfected with genes or cDNA encoding the polypeptide. Unless noted, the TRGV9, in specific embodiments, is a human TRGV9. A human TRGV9 amino acid sequence is provided by GenBank Accession Number NG_001336.2.

The term "CD123" refers to a molecule that is found on cells which helps transmit the signal of interleukin-3, a soluble cytokine that is important in the immune system. CD123 can also be referred to as the "interleukin-3 receptor." The receptor belongs to the type I cytokine receptor family and is a heterodimer with a unique alpha chain paired with the common beta subunit (beta c or CD131). The CD123 receptor can be found on pluripotent progenitor cells and can induce tyrosine phosphorylation within the cell and promote proliferation and differentiation within hematopoietic cell lines. CD123 can also be expressed in acute myeloid leukemia (AML) subtypes. The term "CD123" includes any CD123 variant, isoform, and species homolog, which is naturally expressed by cells (including T cells) or can be expressed on cells transfected with genes or cDNA encoding those polypeptides, unless noted, in specific embodiments the "CD123" is a human CD123. A human CD123 amino acid sequence is provided by GenBank Accession Number AY789109.1.

As used herein, an antibody that "specifically binds to TRGV9" refers to an antibody that binds to a TRGV9, such as a human TRGV9, with a KD of $1\times10^{-7}$ M or less, such as $1\times10^{-8}$ M or less, $5\times10^{-9}$ M or less, $1\times10^{-9}$ M or less, $5\times10^{-10}$ M or less, or $1\times10^{-10}$ M or less. The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antibody can be determined by using surface plasmon resonance, such as by using a biosensor system, e.g., a Biacore® system, or by using bio-layer interferometry technology, such as an Octet RED96 system.

As used herein, an antigen binding domain or antigen binding fragment that "specifically binds to a tumor-associated antigen" refers to an antigen binding domain or antigen binding fragment that binds a tumor-associated antigen, with a KD of $1\times10^{-7}$ M or less, such as $1\times10^{-8}$ M or less, $5\times10^{-9}$ M or less, $1\times10^{-9}$ M or less, $5\times10^{-10}$ M or less, or $1\times10^{-10}$ M or less.

The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antigen binding domain or antigen binding fragment can be determined by using surface plasmon resonance, such as by using a biosensor system, e.g., a Biacore® system, or by using bio-layer interferometry technology, such as an Octet RED96 system.

As used herein, an antibody that "specifically binds to CD123" refers to an antibody that binds to a CD123, such as a human CD123, with a KD of $1\times10^{-7}$ M or less, such as $1\times10^{-8}$ M or less, $5\times10^{-9}$ M or less, $1\times10^{-9}$ M or less, $5\times10^{-10}$ M or less, or $1\times10^{-10}$ M or less. The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antibody can be determined by using surface plasmon resonance, such as by using a biosensor system, e.g., a Biacore® system, or by using bio-layer interferometry technology, such as an Octet RED96 system.

The smaller the value of the KD of an antibody, the higher affinity that the antibody binds to a target antigen.

In one aspect, provided herein is an antibody that binds to TRGV9. In some embodiments, the antibody comprises a heavy chain variable region and a light chain variable region. In a some embodiments, the TRGV9 antibody is not a single domain antibody or nanobody. In some embodiments, the TRGV1 antibody is a humanized antibody.

In certain embodiments, provided herein is an anti-TRGV9 antibody comprising a VH region, VL region, VH CDR1, VH CDR2, VH CDR3, VL CDR1, VL CDR2, and/or VL CDR3 of any one of the antibodies described herein. In some embodiments, provided herein is an anti-TRGV9 antibody comprising a VH region of any one of the antibodies described herein. In some embodiments, provided herein is an anti-TRGV9 antibody comprising a VL region of any one of the antibodies described herein. In some embodiments, provided herein is an anti-TRGV9 antibody comprising a VH region of any one of the antibodies described herein, and a VL region of any one of the antibodies described herein. In some embodiments, provided herein is an anti-TRGV9 antibody comprising a VH CDR1, VH CDR2, and VH CDR3 of any one of the antibodies described herein. In some embodiments, provided herein is an anti-TRGV9 antibody comprising a VL CDR1, VL CDR2, and VL CDR3 of any one of the antibodies described herein. In some embodiments, provided herein is an anti-TRGV9 antibody comprising a VH CDR1, VH CDR2, and VH CDR3 of any one of the antibodies described herein; and a VL CDR1, VL CDR2, and VL CDR3 of any one of the antibodies described herein. Representative VH and VL amino acid sequences, including VH CDR1, VH CDR2, VH CDR3, VL CDR1, VL CDR2 and VL CDR3 amino acid sequences, of TRGV9 antibodies provided herein are provided in the Sequence Listing, as well as Tables 1-31.

In certain embodiments, provided herein is an anti-TRGV9 bispecific antibody comprising a binding domain that binds to TRGV9 having a VH region, VL region, VH CDR1, VH CDR2, VH CDR3, VL CDR1, VL CDR2, and/or VL CDR3 of any one of the antibodies described herein. In some embodiments, provided herein is an anti-TRGV9 bispecific antibody comprising a binding domain that binds to TRGV9 having a VH region of any one of the antibodies described herein. In some embodiments, provided herein is an anti-TRGV9 bispecific antibody comprising a binding domain that binds to TRGV9 having a VL region of any one of the antibodies described herein. In some embodiments, provided herein is an anti-TRGV9 bispecific antibody comprising a binding domain that binds to TRGV9 having a VH region of any one of the antibodies described herein, and a VL region of any one of the antibodies described herein. In some embodiments, provided herein is an anti-TRGV9 bispecific antibody comprising a binding domain that binds to TRGV9 having a VH CDR1, VH CDR2, and VH CDR3 of any one of the antibodies described. In some embodiments, provided herein is an anti-TRGV9 bispecific antibody comprising a binding domain that binds to TRGV9 having a VL CDR1, VL CDR2, and VL CDR3 of any one of the antibodies described herein. In some embodiments, provided herein is an anti-TRGV9 bispecific antibody comprising a binding domain that binds to TRGV9 having a VH CDR1, VH CDR2, and VH CDR3 of any one of the antibodies described herein; and a VL CDR1, VL CDR2, and VL CDR3 of any one of the antibodies described herein.

In certain embodiments, the anti-TRGV9 antibody is a bispecific antibody. In some embodiments, the anti-TRGV9 bispecific antibody further comprises a second binding domain that binds to CD123 having a VH region, VL region, VH CDR1, VH CDR2, VH CDR3, VL CDR1, VL CDR2, and/or VL CDR3 of an anti-CD123 antibody provided herein. In some embodiments, the anti-TRGV9 bispecific antibody further comprises a second binding domain that binds to CD123 having a VH region of an anti-CD123 antibody provided herein. In some embodiments, the anti-TRGV9 bispecific antibody further comprises a second binding domain that binds to CD123 having a VL region of an anti-CD123 antibody provided herein. In some embodiments, the anti-TRGV9 bispecific antibody further comprises a second binding domain that binds to CD123 having a VH region of an anti-CD123 antibody provided herein, and a VL region of an anti-CD123 antibody provided herein. In some embodiments, the anti-TRGV9 bispecific antibody further comprises a second binding domain that binds to CD123 having a VH CDR1, VH CDR2, and VH CDR3 of an anti-CD123 antibody provided herein. In some embodiments, the anti-TRGV9 bispecific antibody further comprises a second binding domain that binds to CD123 having a VL CDR1, VL CDR2, and VL CDR3 of an anti-CD123 antibody provided herein. In some embodiments, the anti-TRGV9 bispecific antibody further comprises a second binding domain that binds to CD123 having a VH CDR1, VH CDR2, and VH CDR3 of an anti-CD123 antibody provided herein, and a VL CDR1, VL CDR2, and VL CDR3 of an anti-CD123 antibody provided herein.

In certain embodiments, provided is an anti-TRGV9 antibody that is an intact antibody. In other embodiments, provided is an anti-TRGV9 antibody is an antigen binding fragment of the anti-TRGV9 antibody. In some embodiments, the antigen binding fragment of the anti-TRGV9 antibody is a functional fragment. In some embodiments, the antigen binding fragment is a diabody. In some embodiments, the antigen binding fragment is a Fab. In some embodiments, the antigen binding fragment is a Fab'. In some embodiments, the antigen binding fragment is a F(ab')2. In some embodiments, the antigen binding fragment is a Fv fragment. In some embodiments, the antigen binding fragment is a disulfide stabilized Fv fragment (dsFv). In some embodiments, the antigen binding fragment is a (dsFv)$_2$. In some embodiments, the antigen binding fragment is a bispecific dsFv (dsFv-dsFv'). In some embodiments, the antigen binding fragment is a disulfide stabilized diabody (ds diabody). In some embodiments, the antigen binding fragment is a single-chain antibody molecule (scFv). In some embodiments, the antigen binding fragment is a single domain antibody (sdAb). In some embodiments, the antigen binding fragment is an scFv dimer (bivalent diabody). In some embodiments, the antigen binding fragment is a multispecific antibody formed from a portion of an antibody comprising one or more CDRs. In some embodiments, the antigen binding fragment is a camelized single domain antibody. In some embodiments, the antigen binding fragment is a nanobody. In some embodiments, the antigen binding fragment is a domain antibody. In some embodiments, the antigen binding fragment is a bivalent domain antibody. In some embodiments, the antigen binding fragment is an antibody fragment that binds to an antigen but does not comprise a complete antibody structure.

In specific embodiments, the anti-TRGV9 antibody comprises a VH region and a VL region. In some embodiments, the anti-TRGV9 antibody is not a single chain antibody. In some embodiments, the anti-TRGV9 antibody is not a single domain antibody. In some embodiments, the anti-TRGV9 antibody is not a nanobody. In certain embodiments, the anti-TRGV9 antibody is not a VHH antibody. In certain embodiments, the anti-TRGV9 antibody is not a llama antibody. In some embodiments, the anti-TRGV9 bispecific antibody does not comprise a single chain antibody. In some embodiments, the anti-TRGV9 bispecific antibody does not comprise a single domain antibody. In certain embodiments, the anti-TRGV9 bispecific antibody does not comprise a nanobody. In certain embodiments, the anti-TRGV9 bispecific antibody does not comprise a VHH antibody. In certain embodiments, the anti-TRGV9 bispecific antibody does not comprise a llama antibody. In some embodiments, the anti-TRGV9 antibody is a multispecific antibody. In other embodiments, the anti-TRGV9 antibody is a bispecific antibody. In certain embodiments, the multispecific antibody comprises an antigen binding fragment of an anti-TRGV9 antibody provided herein. In other embodiments, the bispecific antibody comprises an antigen binding fragment of an anti-TRGV9 antibody provided herein. In some embodiments, the anti-TRGV9 antibody is an agonistic antibody. In certain embodiments, the anti-TRGV9 antibody activates $\gamma\delta$ T cells. In other embodiments, the anti-TRGV9 antibody is an antagonistic antibody. In certain embodiments, the anti-TRGV9 antibody inactivates $\gamma\delta$ T cells. In some embodiments, the anti-TRGV9 antibody blocks activation of $\gamma\delta$ T cells. In some embodiments, the anti-TRGV9 antibody modulates the activity of $\gamma\delta$ T cells. In some embodiments, the anti-TRGV9 antibody neither activates or inactivates the activity of $\gamma\delta$ T cells. In specific embodiments, the $\gamma\delta$ T cells are human $\gamma\delta$ T cells. In specific embodiments, provided is a bispecific antibody comprising a TRGV9 antibody provided herein in a knob-in-hole format. In some embodiments, an anti-TRGV9 antibody provided herein may be comprised in a bispecific antibody. In some embodiments, an anti-TRGV9 bispecific antibody provided herein may be comprised in a multispecific antibody. In certain embodiments, a bispecific antibody provided herein comprises a first binding domain comprising an anti-TRGV9 antibody provided herein that binds to a first TRGV9 epitope, and a second binding domain comprising an anti-TRGV9 antibody provided herein that binds to a second TRGV9 epitope, wherein the first TRGV9 epitope and the second TRGV9 epitope are not the same. In a specific embodiment, a TRGV9 antibody, or antigen binding fragment thereof, provided herein specifically binds to TRGV9. In certain embodiments, a TRGV9 antibody, or antigen binding fragment thereof, provided herein does not bind to an epitope of V$\delta$2.

In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:34; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is an antibody that binds to TRGV9, wherein the antibody comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:31; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In another aspect, provided herein is an antibody that binds to TRGV9, wherein the antibody comprises: (i) a VH comprising a VH CDR1 having an amino acid sequence of SEQ ID NO:196, a VH CDR2 having an amino acid sequence of SEQ ID NO:197, and a VH CDR3 having an amino acid sequence of SEQ ID NO:198; and (ii) a VL comprising a VL CDR1 having an amino acid sequence of SEQ ID NO:199, a VL CDR2 having an amino acid sequence of SEQ ID NO:200, and a VL CDR3 having an amino acid sequence of SEQ ID NO:201. In another aspect, provided herein is an antibody that binds to TRGV9, wherein the antibody comprises: (i) a VH comprising a VH CDR1 having an amino acid sequence of SEQ ID NO:202, a VH CDR2 having an amino acid sequence of SEQ ID NO:203, and a VH CDR3 having an amino acid sequence of SEQ ID NO:204; and (ii) a VL comprising a VL CDR1 having an amino acid sequence of SEQ ID NO:205, a VL CDR2 having an amino acid sequence of SEQ ID NO:206, and a VL CDR3 having an amino acid sequence of SEQ ID NO:207. In another aspect, provided herein is an antibody that binds to TRGV9, wherein the antibody comprises: (i) a VH comprising a VH CDR1 having an amino acid sequence of SEQ ID NO:208, a VH CDR2 having an amino acid sequence of SEQ ID NO:209, and a VH CDR3 having an amino acid sequence of SEQ ID NO:210; and (ii) a VL comprising a VL CDR1 having an amino acid sequence of SEQ ID NO:211, a VL CDR2 having an amino acid sequence of SEQ ID NO:212, and a VL CDR3 having an amino acid sequence of SEQ ID NO:213. In another aspect, provided herein is an antibody that binds to TRGV9, wherein the antibody comprises: (i) a VH comprising a VH CDR1 having an amino acid sequence of SEQ ID NO:214, a VH CDR2 having an amino acid sequence of SEQ ID NO:215, and a VH CDR3 having an amino acid sequence of SEQ ID NO:216; and (ii) a VL comprising a VL CDR1 having an amino acid sequence of SEQ ID NO:217, a VL CDR2 having an amino acid sequence of SEQ ID NO:218, and a VL CDR3 having an amino acid sequence of SEQ ID NO:219. In another aspect, provided herein is an antibody that binds to TRGV9, wherein the antibody comprises: (i) a VH comprising a VH CDR1 having an amino acid sequence of SEQ ID NO:214, a VH CDR2 having an amino acid sequence of SEQ ID NO:702, and a VH CDR3 having an amino acid sequence of SEQ ID NO:703; and (ii) a VL comprising a VL CDR1 having an amino acid sequence of SEQ ID NO:217, a VL CDR2 having an amino acid sequence of SEQ ID NO:218, and a VL CDR3 having an amino acid sequence of SEQ ID NO:219. In another aspect, provided herein is an antibody that binds to TRGV9, wherein the antibody comprises: (i) a VH comprising a VH CDR1 having an amino acid sequence of SEQ ID NO:220, a VH CDR2 having an amino acid sequence of SEQ ID NO:221, and a VH CDR3 having an amino acid sequence of SEQ ID NO:222; and (ii) a VL comprising a VL CDR1 having an amino acid sequence of SEQ ID NO:223, a VL CDR2 having an amino acid sequence of SEQ ID NO:224, and a VL CDR3 having an amino acid sequence of SEQ ID NO:225. In another aspect, provided herein is an antibody that binds to TRGV9, wherein the antibody comprises: (i) a VH comprising a VH CDR1 having an amino acid sequence of SEQ ID NO:226, a VH CDR2 having an amino acid sequence of SEQ ID NO:227, and a VH CDR3 having an amino acid sequence of SEQ ID NO:228; and (ii) a VL comprising a VL CDR1 having an amino acid sequence of SEQ ID NO:229, a VL CDR2 having an amino acid sequence of SEQ ID NO:230, and a VL CDR3 having an amino acid sequence of SEQ ID NO:231. In some embodiments, the antibody comprises a VH having an amino acid sequence of SEQ ID NO:34. In some embodiments, the antibody comprises a VL having an amino acid sequence of SEQ ID NO:8. In some embodiments, the antibody comprises a VH having an amino acid sequence of SEQ ID NO:34, and a VL having an amino acid sequence of SEQ ID NO:8. In some embodiments, the antibody comprises a VH comprising an amino acid sequence having at least 95% identity to the amino acid sequence of SEQ ID NO:34. In some embodiments, the antibody comprises a VL comprising an amino acid sequence having at least 95% identity to the amino acid sequence of SEQ ID NO:8. In some embodiments, the antibody comprises a VH comprising an amino acid sequence having at least 95% identity to the amino acid sequence of SEQ ID NO:34, and a VL comprising an amino acid sequence having at least 95% identity to the amino acid sequence of SEQ ID NO:8.

In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:35; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is an antibody that binds to TRGV9, wherein the antibody comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:32; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In another aspect, provided herein is an antibody that binds to TRGV9, wherein the antibody comprises: (i) a VH comprising a VH CDR1 having an amino acid sequence of SEQ ID NO:232, a VH CDR2 having an amino acid sequence of SEQ ID NO:233, and a VH CDR3 having an amino acid sequence of SEQ ID NO:234; and (ii) a VL comprising a VL CDR1 having an amino acid sequence of SEQ ID NO:235, a VL CDR2 having an amino acid sequence of SEQ ID NO:236, and a VL CDR3 having an amino acid sequence of SEQ ID NO:237. In another aspect, provided herein is an antibody that binds to TRGV9, wherein the antibody comprises: (i) a VH comprising a VH CDR1 having an amino acid sequence of SEQ ID NO:238, a VH CDR2 having an amino acid sequence of SEQ ID NO:239, and a VH CDR3 having an amino acid sequence of SEQ ID NO:240; and (ii) a VL comprising a VL CDR1 having an amino acid sequence of SEQ ID NO:241, a VL CDR2 having an amino acid sequence of SEQ ID NO:242, and a VL CDR3 having an amino acid sequence of SEQ ID NO:243. In another aspect, provided herein is an antibody that binds to TRGV9, wherein the antibody comprises: (i) a VH comprising a VH CDR1 having an amino acid sequence of SEQ ID NO:244, a VH CDR2 having an amino acid sequence of SEQ ID NO:245, and a VH CDR3 having an amino acid sequence of SEQ ID NO:246; and (ii) a VL comprising a VL CDR1 having an amino acid sequence of SEQ ID NO:247, a VL CDR2 having an amino acid sequence of SEQ ID NO:248, and a VL CDR3 having an amino acid sequence of SEQ ID NO:249. In another aspect, provided herein is an antibody that binds to TRGV9, wherein the antibody comprises: (i) a VH comprising a VH CDR1 having an amino acid sequence of SEQ ID NO:250, a VH CDR2 having an amino acid sequence of SEQ ID NO:251, and a VH CDR3 having an amino acid sequence of SEQ ID NO:252; and (ii) a VL comprising a VL CDR1 having an amino acid sequence of SEQ ID NO:253, a VL CDR2 having an amino acid sequence of SEQ ID NO:254, and a VL CDR3 having an amino acid sequence of SEQ ID NO:255. In another aspect, provided herein is an antibody that binds to TRGV9, wherein the antibody comprises: (i) a VH comprising a VH CDR1 having an amino acid sequence of SEQ ID NO:250, a VH CDR2 having an amino acid sequence of SEQ ID NO:704, and a VH CDR3 having an amino acid sequence of SEQ ID NO:705; and (ii) a VL comprising a VL CDR1 having an amino acid sequence of SEQ ID NO:253, a VL CDR2 having an amino acid sequence of SEQ ID NO:254, and a VL CDR3 having an amino acid sequence of SEQ ID NO:255. In another aspect, provided herein is an antibody that binds to TRGV9, wherein the antibody comprises: (i) a VH comprising a VH CDR1 having an amino acid sequence of SEQ ID NO:256, a VH CDR2 having an amino acid sequence of SEQ ID NO:257, and a VH CDR3 having an amino acid sequence of SEQ ID NO:258; and (ii) a VL comprising a VL CDR1 having an amino acid sequence of SEQ ID NO:259, a VL CDR2 having an amino acid sequence of SEQ ID NO:260, and a VL CDR3 having an amino acid sequence of SEQ ID NO:261. In another aspect, provided herein is an antibody that binds to TRGV9, wherein the antibody comprises: (i) a VH comprising a VH CDR1 having an amino acid sequence of SEQ ID NO:262, a VH CDR2 having an amino acid sequence of SEQ ID NO:263, and a VH CDR3 having an amino acid sequence of SEQ ID NO:264; and (ii) a VL comprising a VL CDR1 having an amino acid sequence of SEQ ID NO:265, a VL CDR2 having an amino acid sequence of SEQ ID NO:266, and a VL CDR3 having an amino acid sequence of SEQ ID NO:267. In some embodiments, the antibody comprises a VH having an amino acid sequence of SEQ ID NO:35. In some embodiments, the antibody comprises a VL having an amino acid sequence of SEQ ID NO:8. In some embodiments, the antibody comprises a VH having an amino acid sequence of SEQ ID NO:35, and a VL having an amino acid sequence of SEQ ID NO:8. In some embodiments, the antibody comprises a VH comprising an amino acid sequence having at least 95% identity to the amino acid sequence of SEQ ID NO:35. In some embodiments, the antibody comprises a VL comprising an amino acid sequence having at least 95% identity to the amino acid sequence of SEQ ID NO:8. In some embodiments, the antibody comprises a VH comprising an amino acid sequence having at least 95% identity to the amino acid sequence of SEQ ID NO:35, and a VL comprising an amino acid sequence having at least 95% identity to the amino acid sequence of SEQ ID NO:8.

In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:36; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is an antibody that binds to TRGV9, wherein the antibody comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:33; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In another aspect, provided herein is an antibody that binds to TRGV9, wherein the antibody comprises: (i) a VH comprising a VH CDR1 having an amino acid sequence of SEQ ID NO:268, a VH CDR2 having an amino acid sequence of SEQ ID NO:269, and a VH CDR3 having an amino acid sequence of SEQ ID NO:270; and (ii) a VL comprising a VL CDR1 having an amino acid sequence of SEQ ID NO:271, a VL CDR2 having an amino acid sequence of SEQ ID NO:272, and a VL CDR3 having an amino acid sequence of SEQ ID NO:273. In another aspect, provided herein is an antibody that binds to TRGV9, wherein the antibody comprises: (i) a VH comprising a VH CDR1 having an amino acid sequence of SEQ ID NO:274, a VH CDR2 having an amino acid sequence of SEQ ID NO:275, and a VH CDR3 having an amino acid sequence of SEQ ID NO:276; and (ii) a VL comprising a VL CDR1 having an amino acid sequence of SEQ ID NO:277, a VL CDR2 having an amino acid sequence of SEQ ID NO:278, and a VL CDR3 having an amino acid sequence of SEQ ID NO:279. In another aspect, provided herein is an antibody that binds to TRGV9, wherein the antibody comprises: (i) a VH comprising a VH CDR1 having an amino acid sequence of SEQ ID NO:280, a VH CDR2 having an amino acid sequence of SEQ ID NO:281, and a VH CDR3 having an amino acid sequence of SEQ ID NO:282; and (ii) a VL comprising a VL CDR1 having an amino acid sequence of SEQ ID NO:283, a VL CDR2 having an amino acid sequence of SEQ ID NO:284, and a VL CDR3 having an amino acid sequence of SEQ ID NO:285. In another aspect, provided herein is an antibody that binds to TRGV9, wherein the antibody comprises: (i) a VH comprising a VH CDR1 having an amino acid sequence of SEQ ID NO:286, a VH CDR2 having an amino acid sequence of SEQ ID NO:287, and a VH CDR3 having an amino acid sequence of SEQ ID NO:288; and (ii) a VL comprising a VL CDR1 having an amino acid sequence of SEQ ID NO:289, a VL CDR2 having an amino acid sequence of SEQ ID NO:290, and a VL CDR3 having an amino acid sequence of SEQ ID NO:291. In another aspect, provided herein is an antibody that binds to TRGV9, wherein the antibody comprises: (i) a VH comprising a VH CDR1 having an amino acid sequence of SEQ ID NO:286, a VH CDR2 having an amino acid sequence of SEQ ID NO:706, and a VH CDR3 having an amino acid sequence of SEQ ID NO:707; and (ii) a VL comprising a VL CDR1 having an amino acid sequence of SEQ ID NO:289, a VL CDR2 having an amino acid sequence of SEQ ID NO:290, and a VL CDR3 having an amino acid sequence of SEQ ID NO:291. In another aspect, provided herein is an antibody that binds to TRGV9, wherein the antibody comprises: (i) a VH comprising a VH CDR1 having an amino acid sequence of SEQ ID NO:292, a VH CDR2 having an amino acid sequence of SEQ ID NO:293, and a VH CDR3 having an amino acid sequence of SEQ ID NO:294; and (ii) a VL comprising a VL CDR1 having an amino acid sequence of SEQ ID NO:295, a VL CDR2 having an amino acid sequence of SEQ ID NO:296, and a VL CDR3 having an amino acid sequence of SEQ ID NO:297. In another aspect, provided herein is an antibody that binds to TRGV9, wherein the antibody comprises: (i) a VH comprising a VH CDR1 having an amino acid sequence of SEQ ID NO:298, a VH CDR2 having an amino acid sequence of SEQ ID NO:299, and a VH CDR3 having an amino acid sequence of SEQ ID NO:300; and (ii) a VL comprising a VL CDR1 having an amino acid sequence of SEQ ID NO:301, a VL CDR2 having an amino acid sequence of SEQ ID NO:302, and a VL CDR3 having an amino acid sequence of SEQ ID NO:303. In some embodiments, the antibody comprises a VH having an amino acid sequence of SEQ ID NO:36. In some embodiments, the antibody comprises a VL having an amino acid sequence of SEQ ID NO:8. In some embodiments, the antibody comprises a VH having an amino acid sequence of SEQ ID NO:36, and a VL having an amino acid sequence of SEQ ID NO:8. In some embodiments, the antibody comprises a VH comprising an amino acid sequence having at least 95% identity to the amino acid sequence of SEQ ID NO:36. In some embodiments, the antibody comprises a VL comprising an amino acid sequence having at least 95% identity to the amino acid sequence of SEQ ID NO:8. In some embodiments, the antibody comprises a VH comprising an amino acid sequence having at least 95% identity to the amino acid sequence of SEQ ID NO:36, and a VL comprising an amino acid sequence having at least 95% identity to the amino acid sequence of SEQ ID NO:8.

In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:65; and (ii) a VL comprising a VL CDR1, a VL CDR2, and a VL CDR3 having amino acid sequences of the VL CDR1, VL CDR2, and VL CDR3, respectively, of SEQ ID NO:66. In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:67; and (ii) a VL comprising a VL CDR1, a VL CDR2, and a VL CDR3 having amino acid sequences of the VL CDR1, VL CDR2, and VL CDR3, respectively, of SEQ ID NO:68. In another aspect, provided herein is an antibody that binds to TRGV9, wherein the antibody comprises: (i) a VH comprising a VH CDR1 having an amino acid sequence of SEQ ID NO:1, a VH CDR2 having an amino acid sequence of SEQ ID NO:76, and a VH CDR3 having an amino acid sequence of SEQ ID NO:3; and (ii) a VL comprising a VL CDR1 having an amino acid sequence of SEQ ID NO:77, a VL CDR2 having an amino acid sequence of SEQ ID NO:5, and a VL CDR3 having an amino acid sequence of SEQ ID NO:6. In another aspect, provided herein is an antibody that binds to TRGV9, wherein the antibody comprises: (i) a VH comprising a VH CDR1 having an amino acid sequence of SEQ ID NO:60, a VH CDR2 having an amino acid sequence of SEQ ID NO:61, and a VH CDR3 having an amino acid sequence of SEQ ID NO:62; and (ii) a VL comprising a VL CDR1 having an amino acid sequence of SEQ ID NO:63, a VL CDR2 having an amino acid sequence of SEQ ID NO:64, and a VL CDR3 having an amino acid sequence of SEQ ID NO:6. In another aspect, provided herein is an antibody that binds to TRGV9, wherein the antibody comprises: (i) a VH comprising a VH CDR1 having an amino acid sequence of SEQ ID NO:304, a VH CDR2 having an amino acid sequence of SEQ ID NO:305, and a VH CDR3 having an amino acid sequence of SEQ ID NO:306; and (ii) a VL comprising a VL CDR1 having an amino acid sequence of SEQ ID NO:307, a VL CDR2 having an amino acid sequence of SEQ ID NO:308, and a VL CDR3 having an amino acid sequence of SEQ ID NO:309. In another aspect, provided herein is an antibody that binds to TRGV9, wherein the antibody comprises: (i) a VH comprising a VH CDR1 having an amino acid sequence of SEQ ID NO:310, a VH CDR2 having an amino acid sequence of SEQ ID NO:311, and a VH CDR3 having an amino acid sequence of SEQ ID NO:312; and (ii) a VL comprising a VL CDR1 having an amino acid sequence of SEQ ID NO:313, a VL CDR2 having an amino acid sequence of SEQ ID NO:314, and a VL CDR3 having an amino acid sequence of SEQ ID NO:315. In another aspect, provided herein is an antibody that binds to TRGV9, wherein the antibody comprises: (i) a VH comprising a VH CDR1 having an amino acid sequence of SEQ ID NO:316, a VH CDR2 having an amino acid sequence of SEQ ID NO:317, and a VH CDR3 having an amino acid sequence of SEQ ID NO:318; and (ii) a VL comprising a VL CDR1 having an amino acid sequence of SEQ ID NO:319, a VL CDR2 having an amino acid sequence of SEQ ID NO:320, and a VL CDR3 having an amino acid sequence of SEQ ID NO:321. In another aspect, provided herein is an antibody that binds to TRGV9, wherein the antibody comprises: (i) a VH comprising a VH CDR1 having an amino acid sequence of SEQ ID NO:322, a VH CDR2 having an amino acid sequence of SEQ ID NO:323, and a VH CDR3 having an amino acid sequence of SEQ ID NO:324; and (ii) a VL comprising a VL CDR1 having an amino acid sequence of SEQ ID NO:325, a VL CDR2 having an amino acid sequence of SEQ ID NO:326, and a VL CDR3 having an amino acid sequence of SEQ ID NO:327. In another aspect, provided herein is an antibody that binds to TRGV9, wherein the antibody comprises: (i) a VH comprising a VH CDR1 having an amino acid sequence of SEQ ID NO:322, a VH CDR2 having an amino acid sequence of SEQ ID NO:708, and a VH CDR3 having an amino acid sequence of SEQ ID NO:709; and (ii) a VL comprising a VL CDR1 having an amino acid sequence of SEQ ID NO:325, a VL CDR2 having an amino acid sequence of SEQ ID NO:326, and a VL CDR3 having an amino acid sequence of SEQ ID NO:327. In another aspect, provided herein is an antibody that binds to TRGV9, wherein the antibody comprises: (i) a VH comprising a VH CDR1 having an amino acid sequence of SEQ ID NO:328, a VH CDR2 having an amino acid sequence of SEQ ID NO:329, and a VH CDR3 having an amino acid sequence of SEQ ID NO:330; and (ii) a VL comprising a VL CDR1 having an amino acid sequence of SEQ ID NO:331, a VL CDR2 having an amino acid sequence of SEQ ID NO:332, and a VL CDR3 having an amino acid sequence of SEQ ID NO:333. In another aspect, provided herein is an antibody that binds to TRGV9, wherein the antibody comprises: (i) a VH comprising a VH CDR1 having an amino acid sequence of SEQ ID NO:334, a VH CDR2 having an amino acid sequence of SEQ ID NO:335, and a VH CDR3 having an amino acid sequence of SEQ ID NO:336; and (ii) a VL comprising a VL CDR1 having an amino acid sequence of SEQ ID NO:337, a VL CDR2 having an amino acid sequence of SEQ ID NO:338, and a VL CDR3 having an amino acid sequence of SEQ ID NO:339. In another aspect, provided herein is an antibody that binds to TRGV9, wherein the antibody comprises: (i) a VH comprising a VH CDR1 having an amino acid sequence of SEQ ID NO:340, a VH CDR2 having an amino acid sequence of SEQ ID NO:341, and a VH CDR3 having an amino acid sequence of SEQ ID NO:342; and (ii) a VL comprising a VL CDR1 having an amino acid sequence of SEQ ID NO:343, a VL CDR2 having an amino acid sequence of SEQ ID NO:344, and a VL CDR3 having an amino acid sequence of SEQ ID NO:345. In another aspect, provided herein is an antibody that binds to TRGV9, wherein the antibody comprises: (i) a VH comprising a VH CDR1 having an amino acid sequence of SEQ ID NO:346, a VH CDR2 having an amino acid sequence of SEQ ID NO:347, and a VH CDR3 having an amino acid sequence of SEQ ID NO:348; and (ii) a VL comprising a VL CDR1 having an amino acid sequence of SEQ ID NO:349, a VL CDR2 having an amino acid sequence of SEQ ID NO:350, and a VL CDR3 having an amino acid sequence of SEQ ID NO:351. In another aspect, provided herein is an antibody that binds to TRGV9, wherein the antibody comprises: (i) a VH comprising a VH CDR1 having an amino acid sequence of SEQ ID NO:352, a VH CDR2 having an amino acid sequence of SEQ ID NO:353, and a VH CDR3 having an amino acid sequence of SEQ ID NO:354; and (ii) a VL comprising a VL CDR1 having an amino acid sequence of SEQ ID NO:355, a VL CDR2 having an amino acid sequence of SEQ ID NO:356, and a VL CDR3 having an amino acid sequence of SEQ ID NO:357. In another aspect, provided herein is an antibody that binds to TRGV9, wherein the antibody comprises: (i) a VH comprising a VH CDR1 having an amino acid sequence of SEQ ID NO:358, a VH CDR2 having an amino acid sequence of SEQ ID NO:359, and a VH CDR3 having an amino acid sequence of SEQ ID NO:360; and (ii) a VL comprising a VL CDR1 having an amino acid sequence of SEQ ID NO:361, a VL CDR2 having an amino acid sequence of SEQ ID NO:362, and a VL CDR3 having an amino acid sequence of SEQ ID NO:363. In another aspect, provided herein is an antibody that binds to TRGV9, wherein the antibody comprises: (i) a VH comprising a VH CDR1 having an amino acid sequence of SEQ ID NO:358, a VH CDR2 having an amino acid sequence of SEQ ID NO:710, and a VH CDR3 having an amino acid sequence of SEQ ID NO:711; and (ii) a VL comprising a VL CDR1 having an amino acid sequence of SEQ ID NO:361, a VL CDR2 having an amino acid sequence of SEQ ID NO:362, and a VL CDR3 having an amino acid sequence of SEQ ID NO:363. In another aspect, provided herein is an antibody that binds to TRGV9, wherein the antibody comprises: (i) a VH comprising a VH CDR1 having an amino acid sequence of SEQ ID NO:364, a VH CDR2 having an amino acid sequence of SEQ ID NO:365, and a VH CDR3 having an amino acid sequence of SEQ ID NO:366; and (ii) a VL comprising a VL CDR1 having an amino acid sequence of SEQ ID NO:367, a VL CDR2 having an amino acid sequence of SEQ ID NO:368, and a VL CDR3 having an amino acid sequence of SEQ ID NO:369. In another aspect, provided herein is an antibody that binds to TRGV9, wherein the antibody comprises: (i) a VH comprising a VH CDR1 having an amino acid sequence of SEQ ID NO:370, a VH CDR2 having an amino acid sequence of SEQ ID NO:371, and a VH CDR3 having an amino acid sequence of SEQ ID NO:372; and (ii) a VL comprising a VL CDR1 having an amino acid sequence of SEQ ID NO:373, a VL CDR2 having an amino acid sequence of SEQ ID NO:374, and a VL CDR3 having an amino acid sequence of SEQ ID NO:375. In some embodiments, the antibody comprises a VH having an amino acid sequence of SEQ ID NO:65. In some embodiments, the antibody comprises a VL having an amino acid sequence of SEQ ID NO:66. In some embodiments, the antibody comprises a VH having an amino acid sequence of SEQ ID NO:65, and a VL having an amino acid sequence of SEQ ID NO:66. In some embodiments, the antibody comprises a VH having an amino acid sequence of SEQ ID NO:67. In some embodiments, the antibody comprises a VL having an amino acid sequence of SEQ ID NO:68. In some embodiments, the antibody comprises a VH having an amino acid sequence of SEQ ID NO:67, and a VL having an amino acid sequence of SEQ ID NO:68. In some embodiments, the antibody comprises a heavy chain having an amino acid sequence of SEQ ID NO:71. In some embodiments, the antibody comprises a light chain having an amino acid sequence of SEQ ID NO:72. In some embodiments, the antibody comprises a heavy chain having an amino acid sequence of SEQ ID NO:71, and a light chain having an amino acid sequence of SEQ ID NO:72. In some embodiments, the antibody comprises an amino acid sequence of SEQ ID NO:70. In some embodiments, the antibody comprises a heavy chain having an amino acid sequence of SEQ ID NO:74. In some embodiments, the antibody comprises a light chain having an amino acid sequence of SEQ ID NO:75. In some embodiments, the antibody comprises a heavy chain having an amino acid sequence of SEQ ID NO:74, and a light chain having an amino acid sequence of SEQ ID NO:75. In some embodiments, the antibody comprises an amino acid sequence of SEQ ID NO:73. In some embodiments, the antibody comprises a VH comprising an amino acid sequence having at least 95% identity to the amino acid sequence of SEQ ID NO:65. In some embodiments, the antibody comprises a VL comprising an amino acid sequence having at least 95% identity to the amino acid sequence of SEQ ID NO:66. In some embodiments, the antibody comprises a VH comprising an amino acid sequence having at least 95% identity to the amino acid sequence of SEQ ID NO:65, and a VL comprising an amino acid sequence having at least 95% identity to the amino acid sequence of SEQ ID NO:66. In some embodiments, the antibody comprises a VH comprising an amino acid sequence having at least 95% identity to the amino acid sequence of SEQ ID NO:67. In some embodiments, the antibody comprises a VL comprising an amino acid sequence having at least 95% identity to the amino acid sequence of SEQ ID NO:68. In some embodiments, the antibody comprises a VH comprising an amino acid sequence having at least 95% identity to the amino acid sequence of SEQ ID NO:67, and a VL comprising an amino acid sequence having at least 95% identity to the amino acid sequence of SEQ ID NO:68. In some embodiments, the antibody comprises a heavy chain comprising an amino acid sequence having at least 95% identity to the amino acid sequence of SEQ ID NO:71. In some embodiments, the antibody comprises a light chain comprising an amino acid sequence having at least 95% identity to the amino acid sequence of SEQ ID NO:72. In some embodiments, the antibody comprises a heavy chain comprising an amino acid sequence having at least 95% identity to the amino acid sequence of SEQ ID NO:71, and a light chain comprising an amino acid sequence having at least 95% identity to the amino acid sequence of SEQ ID NO:72. In some embodiments, the antibody comprises an amino acid sequence of SEQ ID NO:70. In some embodiments, the antibody comprises a heavy chain comprising an amino acid sequence having at least 95% identity to the amino acid sequence of SEQ ID NO:74. In some embodiments, the antibody comprises a light chain comprising an amino acid sequence having at least 95% identity to the amino acid sequence of SEQ ID NO:75. In some embodiments, the antibody comprises a heavy chain comprising an amino acid sequence having at least 95% identity to the amino acid sequence of SEQ ID NO:74, and a light chain comprising an amino acid sequence having at least 95% identity to the amino acid sequence of SEQ ID NO:75. In some embodiments, the antibody comprises an amino acid sequence of SEQ ID NO:73.

In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:104; and (ii) a VL comprising a VL CDR1, a VL CDR2, and a VL CDR3 having amino acid sequences of the VL CDR1, VL CDR2, and VL CDR3, respectively, of SEQ ID NO:105. In another aspect, provided herein is an antibody that binds to TRGV9, wherein the antibody comprises: (i) a VH comprising a VH CDR1 having an amino acid sequence of SEQ ID NO:98, a VH CDR2 having an amino acid sequence of SEQ ID NO:99, and a VH CDR3 having an amino acid sequence of SEQ ID NO:100; and (ii) a VL comprising a VL CDR1 having an amino acid sequence of SEQ ID NO:101, a VL CDR2 having an amino acid sequence of SEQ ID NO:102, and a VL CDR3 having an amino acid sequence of SEQ ID NO:103. In another aspect, provided herein is an antibody that binds to TRGV9, wherein the antibody comprises: (i) a VH comprising a VH CDR1 having an amino acid sequence of SEQ ID NO:412, a VH CDR2 having an amino acid sequence of SEQ ID NO:413, and a VH CDR3 having an amino acid sequence of SEQ ID NO:414; and (ii) a VL comprising a VL CDR1 having an amino acid sequence of SEQ ID NO:415, a VL CDR2 having an amino acid sequence of SEQ ID NO:416, and a VL CDR3 having an amino acid sequence of SEQ ID NO:417. In another aspect, provided herein is an antibody that binds to TRGV9, wherein the antibody comprises: (i) a VH comprising a VH CDR1 having an amino acid sequence of SEQ ID NO:418, a VH CDR2 having an amino acid sequence of SEQ ID NO:419, and a VH CDR3 having an amino acid sequence of SEQ ID NO:420; and (ii) a VL comprising a VL CDR1 having an amino acid sequence of SEQ ID NO:421, a VL CDR2 having an amino acid sequence of SEQ ID NO:422, and a VL CDR3 having an amino acid sequence of SEQ ID NO:423. In another aspect, provided herein is an antibody that binds to TRGV9, wherein the antibody comprises: (i) a VH comprising a VH CDR1 having an amino acid sequence of SEQ ID NO:424, a VH CDR2 having an amino acid sequence of SEQ ID NO:425, and a VH CDR3 having an amino acid sequence of SEQ ID NO:426; and (ii) a VL comprising a VL CDR1 having an amino acid sequence of SEQ ID NO:427, a VL CDR2 having an amino acid sequence of SEQ ID NO:428, and a VL CDR3 having an amino acid sequence of SEQ ID NO:429. In another aspect, provided herein is an antibody that binds to TRGV9, wherein the antibody comprises: (i) a VH comprising a VH CDR1 having an amino acid sequence of SEQ ID NO:430, a VH CDR2 having an amino acid sequence of SEQ ID NO:431, and a VH CDR3 having an amino acid sequence of SEQ ID NO:432; and (ii) a VL comprising a VL CDR1 having an amino acid sequence of SEQ ID NO:433, a VL CDR2 having an amino acid sequence of SEQ ID NO:434, and a VL CDR3 having an amino acid sequence of SEQ ID NO:435. In another aspect, provided herein is an antibody that binds to TRGV9, wherein the antibody comprises: (i) a VH comprising a VH CDR1 having an amino acid sequence of SEQ ID NO:430, a VH CDR2 having an amino acid sequence of SEQ ID NO:714, and a VH CDR3 having an amino acid sequence of SEQ ID NO:715; and (ii) a VL comprising a VL CDR1 having an amino acid sequence of SEQ ID NO:433, a VL CDR2 having an amino acid sequence of SEQ ID NO:434, and a VL CDR3 having an amino acid sequence of SEQ ID NO:435. In another aspect, provided herein is an antibody that binds to TRGV9, wherein the antibody comprises: (i) a VH comprising a VH CDR1 having an amino acid sequence of SEQ ID NO:436, a VH CDR2 having an amino acid sequence of SEQ ID NO:437, and a VH CDR3 having an amino acid sequence of SEQ ID NO:438; and (ii) a VL comprising a VL CDR1 having an amino acid sequence of SEQ ID NO:439, a VL CDR2 having an amino acid sequence of SEQ ID NO:440, and a VL CDR3 having an amino acid sequence of SEQ ID NO:441. In another aspect, provided herein is an antibody that binds to TRGV9, wherein the antibody comprises: (i) a VH comprising a VH CDR1 having an amino acid sequence of SEQ ID NO:442, a VH CDR2 having an amino acid sequence of SEQ ID NO:443, and a VH CDR3 having an amino acid sequence of SEQ ID NO:444; and (ii) a VL comprising a VL CDR1 having an amino acid sequence of SEQ ID NO:445, a VL CDR2 having an amino acid sequence of SEQ ID NO:446, and a VL CDR3 having an amino acid sequence of SEQ ID NO:447. In some embodiments, the antibody comprises a VH having an amino acid sequence of SEQ ID NO:104. In some embodiments, the antibody comprises a VL having an amino acid sequence of SEQ ID NO:105. In some embodiments, the antibody comprises a VH having an amino acid sequence of SEQ ID NO:104, and a VL having an amino acid sequence of SEQ ID NO:105. In some embodiments, the antibody comprises an amino acid sequence of SEQ ID NO:106. In some embodiments, the antibody comprises a VH comprising an amino acid sequence having at least 95% identity to the amino acid sequence of SEQ ID NO:104. In some embodiments, the antibody comprises a VL comprising an amino acid sequence having at least 95% identity to the amino acid sequence of SEQ ID NO:105. In some embodiments, the antibody comprises a VH comprising an amino acid sequence having at least 95% identity to the amino acid sequence of SEQ ID NO:104, and a VL comprising an amino acid sequence having at least 95% identity to the amino acid sequence of SEQ ID NO:105. In some embodiments, the antibody comprises an amino acid sequence of SEQ ID NO:106.

In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:113; and (ii) a VL comprising a VL CDR1, a VL CDR2, and a VL CDR3 having amino acid sequences of the VL CDR1, VL CDR2, and VL CDR3, respectively, of SEQ ID NO:114. In another aspect, provided herein is an antibody that binds to TRGV9, wherein the antibody comprises: (i) a VH comprising a VH CDR1 having an amino acid sequence of SEQ ID NO:107, a VH CDR2 having an amino acid sequence of SEQ ID NO:108, and a VH CDR3 having an amino acid sequence of SEQ ID NO:109; and (ii) a VL comprising a VL CDR1 having an amino acid sequence of SEQ ID NO:110, a VL CDR2 having an amino acid sequence of SEQ ID NO:111, and a VL CDR3 having an amino acid sequence of SEQ ID NO:112. In another aspect, provided herein is an antibody that binds to TRGV9, wherein the antibody comprises: (i) a VH comprising a VH CDR1 having an amino acid sequence of SEQ ID NO:448, a VH CDR2 having an amino acid sequence of SEQ ID NO:449, and a VH CDR3 having an amino acid sequence of SEQ ID NO:450; and (ii) a VL comprising a VL CDR1 having an amino acid sequence of SEQ ID NO:451, a VL CDR2 having an amino acid sequence of SEQ ID NO:452, and a VL CDR3 having an amino acid sequence of SEQ ID NO:453. In another aspect, provided herein is an antibody that binds to TRGV9, wherein the antibody comprises: (i) a VH comprising a VH CDR1 having an amino acid sequence of SEQ ID NO:454, a VH CDR2 having an amino acid sequence of SEQ ID NO:455, and a VH CDR3 having an amino acid sequence of SEQ ID NO:456; and (ii) a VL comprising a VL CDR1 having an amino acid sequence of SEQ ID NO:457, a VL CDR2 having an amino acid sequence of SEQ ID NO:458, and a VL CDR3 having an amino acid sequence of SEQ ID NO:459. In another aspect, provided herein is an antibody that binds to TRGV9, wherein the antibody comprises: (i) a VH comprising a VH CDR1 having an amino acid sequence of SEQ ID NO:460, a VH CDR2 having an amino acid sequence of SEQ ID NO:461, and a VH CDR3 having an amino acid sequence of SEQ ID NO:462; and (ii) a VL comprising a VL CDR1 having an amino acid sequence of SEQ ID NO:463, a VL CDR2 having an amino acid sequence of SEQ ID NO:464, and a VL CDR3 having an amino acid sequence of SEQ ID NO:465. In another aspect, provided herein is an antibody that binds to TRGV9, wherein the antibody comprises: (i) a VH comprising a VH CDR1 having an amino acid sequence of SEQ ID NO:466, a VH CDR2 having an amino acid sequence of SEQ ID NO:467, and a VH CDR3 having an amino acid sequence of SEQ ID NO:468; and (ii) a VL comprising a VL CDR1 having an amino acid sequence of SEQ ID NO:469, a VL CDR2 having an amino acid sequence of SEQ ID NO:470, and a VL CDR3 having an amino acid sequence of SEQ ID NO:471. In another aspect, provided herein is an antibody that binds to TRGV9, wherein the antibody comprises: (i) a VH comprising a VH CDR1 having an amino acid sequence of SEQ ID NO:466, a VH CDR2 having an amino acid sequence of SEQ ID NO:716, and a VH CDR3 having an amino acid sequence of SEQ ID NO:717; and (ii) a VL comprising a VL CDR1 having an amino acid sequence of SEQ ID NO:469, a VL CDR2 having an amino acid sequence of SEQ ID NO:470, and a VL CDR3 having an amino acid sequence of SEQ ID NO:471. In another aspect, provided herein is an antibody that binds to TRGV9, wherein the antibody comprises: (i) a VH comprising a VH CDR1 having an amino acid sequence of SEQ ID NO:472, a VH CDR2 having an amino acid sequence of SEQ ID NO:473, and a VH CDR3 having an amino acid sequence of SEQ ID NO:474; and (ii) a VL comprising a VL CDR1 having an amino acid sequence of SEQ ID NO:475, a VL CDR2 having an amino acid sequence of SEQ ID NO:476, and a VL CDR3 having an amino acid sequence of SEQ ID NO:477. In another aspect, provided herein is an antibody that binds to TRGV9, wherein the antibody comprises: (i) a VH comprising a VH CDR1 having an amino acid sequence of SEQ ID NO:478, a VH CDR2 having an amino acid sequence of SEQ ID NO:479, and a VH CDR3 having an amino acid sequence of SEQ ID NO:480; and (ii) a VL comprising a VL CDR1 having an amino acid sequence of SEQ ID NO:481, a VL CDR2 having an amino acid sequence of SEQ ID NO:482, and a VL CDR3 having an amino acid sequence of SEQ ID NO:483. In some embodiments, the antibody comprises a VH having an amino acid sequence of SEQ ID NO:113. In some embodiments, the antibody comprises a VL having an amino acid sequence of SEQ ID NO:114. In some embodiments, the antibody comprises a VH having an amino acid sequence of SEQ ID NO:113, and a VL having an amino acid sequence of SEQ ID NO:114. In some embodiments, the antibody comprises a heavy chain having an amino acid sequence of SEQ ID NO:115. In some embodiments, the antibody comprises a light chain having an amino acid sequence of SEQ ID NO:116. In some embodiments, the antibody comprises a heavy chain having an amino acid sequence of SEQ ID NO:115, and a light chain having an amino acid sequence of SEQ ID NO:116. In some embodiments, the antibody comprises a VH comprising an amino acid sequence having at least 95% identity to the amino acid sequence of SEQ ID NO:113. In some embodiments, the antibody comprises a VL comprising an amino acid sequence having at least 95% identity to the amino acid sequence of SEQ ID NO:114. In some embodiments, the antibody comprises a VH comprising an amino acid sequence having at least 95% identity to the amino acid sequence of SEQ ID NO:113, and a VL comprising an amino acid sequence having at least 95% identity to the amino acid sequence of SEQ ID NO:114. In some embodiments, the antibody comprises a heavy chain comprising an amino acid sequence having at least 95% identity to the amino acid sequence of SEQ ID NO:115. In some embodiments, the antibody comprises a light chain comprising an amino acid sequence having at least 95% identity to the amino acid sequence of SEQ ID NO:116. In some embodiments, the antibody comprises a heavy chain comprising an amino acid sequence having at least 95% identity to the amino acid sequence of SEQ ID NO:115, and a light chain comprising an amino acid sequence having at least 95% identity to the amino acid sequence of SEQ ID NO:116.

In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:123; and (ii) a VL comprising a VL CDR1, a VL CDR2, and a VL CDR3 having amino acid sequences of the VL CDR1, VL CDR2, and VL CDR3, respectively, of SEQ ID NO:124. In another aspect, provided herein is an antibody that binds to TRGV9, wherein the antibody comprises: (i) a VH comprising a VH CDR1 having an amino acid sequence of SEQ ID NO:117, a VH CDR2 having an amino acid sequence of SEQ ID NO:118, and a VH CDR3 having an amino acid sequence of SEQ ID NO:119; and (ii) a VL comprising a VL CDR1 having an amino acid sequence of SEQ ID NO:120, a VL CDR2 having an amino acid sequence of SEQ ID NO:121, and a VL CDR3 having an amino acid sequence of SEQ ID NO:122. In another aspect, provided herein is an antibody that binds to TRGV9, wherein the antibody comprises: (i) a VH comprising a VH CDR1 having an amino acid sequence of SEQ ID NO:484, a VH CDR2 having an amino acid sequence of SEQ ID NO:485, and a VH CDR3 having an amino acid sequence of SEQ ID NO:486; and (ii) a VL comprising a VL CDR1 having an amino acid sequence of SEQ ID NO:487, a VL CDR2 having an amino acid sequence of SEQ ID NO:488, and a VL CDR3 having an amino acid sequence of SEQ ID NO:489. In another aspect, provided herein is an antibody that binds to TRGV9, wherein the antibody comprises: (i) a VH comprising a VH CDR1 having an amino acid sequence of SEQ ID NO:490, a VH CDR2 having an amino acid sequence of SEQ ID NO:491, and a VH CDR3 having an amino acid sequence of SEQ ID NO:492; and (ii) a VL comprising a VL CDR1 having an amino acid sequence of SEQ ID NO:493, a VL CDR2 having an amino acid sequence of SEQ ID NO:494, and a VL CDR3 having an amino acid sequence of SEQ ID NO:495. In another aspect, provided herein is an antibody that binds to TRGV9, wherein the antibody comprises: (i) a VH comprising a VH CDR1 having an amino acid sequence of SEQ ID NO:496, a VH CDR2 having an amino acid sequence of SEQ ID NO:497, and a VH CDR3 having an amino acid sequence of SEQ ID NO:498; and (ii) a VL comprising a VL CDR1 having an amino acid sequence of SEQ ID NO:499, a VL CDR2 having an amino acid sequence of SEQ ID NO:500, and a VL CDR3 having an amino acid sequence of SEQ ID NO:501. In another aspect, provided herein is an antibody that binds to TRGV9, wherein the antibody comprises: (i) a VH comprising a VH CDR1 having an amino acid sequence of SEQ ID NO:502, a VH CDR2 having an amino acid sequence of SEQ ID NO:503, and a VH CDR3 having an amino acid sequence of SEQ ID NO:504; and (ii) a VL comprising a VL CDR1 having an amino acid sequence of SEQ ID NO:505, a VL CDR2 having an amino acid sequence of SEQ ID NO:506, and a VL CDR3 having an amino acid sequence of SEQ ID NO:507. In another aspect, provided herein is an antibody that binds to TRGV9, wherein the antibody comprises: (i) a VH comprising a VH CDR1 having an amino acid sequence of SEQ ID NO:502, a VH CDR2 having an amino acid sequence of SEQ ID NO:718, and a VH CDR3 having an amino acid sequence of SEQ ID NO:719; and (ii) a VL comprising a VL CDR1 having an amino acid sequence of SEQ ID NO:505, a VL CDR2 having an amino acid sequence of SEQ ID NO:506, and a VL CDR3 having an amino acid sequence of SEQ ID NO:507. In another aspect, provided herein is an antibody that binds to TRGV9, wherein the antibody comprises: (i) a VH comprising a VH CDR1 having an amino acid sequence of SEQ ID NO:508, a VH CDR2 having an amino acid sequence of SEQ ID NO:509, and a VH CDR3 having an amino acid sequence of SEQ ID NO:510; and (ii) a VL comprising a VL CDR1 having an amino acid sequence of SEQ ID NO:511, a VL CDR2 having an amino acid sequence of SEQ ID NO:512, and a VL CDR3 having an amino acid sequence of SEQ ID NO:513. In another aspect, provided herein is an antibody that binds to TRGV9, wherein the antibody comprises: (i) a VH comprising a VH CDR1 having an amino acid sequence of SEQ ID NO:514, a VH CDR2 having an amino acid sequence of SEQ ID NO:515, and a VH CDR3 having an amino acid sequence of SEQ ID NO:516; and (ii) a VL comprising a VL CDR1 having an amino acid sequence of SEQ ID NO:517, a VL CDR2 having an amino acid sequence of SEQ ID NO:518, and a VL CDR3 having an amino acid sequence of SEQ ID NO:519. In some embodiments, the antibody comprises a VH having an amino acid sequence of SEQ ID NO:123. In some embodiments, the antibody comprises a VL having an amino acid sequence of SEQ ID NO:124. In some embodiments, the antibody comprises a VH having an amino acid sequence of SEQ ID NO:123, and a VL having an amino acid sequence of SEQ ID NO:124. In some embodiments, the antibody comprises a heavy chain having an amino acid sequence of SEQ ID NO:125. In some embodiments, the antibody comprises a light chain having an amino acid sequence of SEQ ID NO:126. In some embodiments, the antibody comprises a heavy chain having an amino acid sequence of SEQ ID NO:125, and a light chain having an amino acid sequence of SEQ ID NO:126. In some embodiments, the antibody comprises a VH comprising an amino acid sequence having at least 95% identity to the amino acid sequence of SEQ ID NO:123. In some embodiments, the antibody comprises a VL comprising an amino acid sequence having at least 95% identity to the amino acid sequence of SEQ ID NO:124. In some embodiments, the antibody comprises a VH comprising an amino acid sequence having at least 95% identity to the amino acid sequence of SEQ ID NO:123, and a VL comprising an amino acid sequence having at least 95% identity to the amino acid sequence of SEQ ID NO:124. In some embodiments, the antibody comprises a heavy chain comprising an amino acid sequence having at least 95% identity to the amino acid sequence of SEQ ID NO:125. In some embodiments, the antibody comprises a light chain comprising an amino acid sequence having at least 95% identity to the amino acid sequence of SEQ ID NO:126. In some embodiments, the antibody comprises a heavy chain comprising an amino acid sequence having at least 95% identity to the amino acid sequence of SEQ ID NO:125, and a light chain comprising an amino acid sequence having at least 95% identity to the amino acid sequence of SEQ ID NO:126.

In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:133; and (ii) a VL comprising a VL CDR1, a VL CDR2, and a VL CDR3 having amino acid sequences of the VL CDR1, VL CDR2, and VL CDR3, respectively, of SEQ ID NO:134. In another aspect, provided herein is an antibody that binds to TRGV9, wherein the antibody comprises: (i) a VH comprising a VH CDR1 having an amino acid sequence of SEQ ID NO:127, a VH CDR2 having an amino acid sequence of SEQ ID NO:128, and a VH CDR3 having an amino acid sequence of SEQ ID NO:129; and (ii) a VL comprising a VL CDR1 having an amino acid sequence of SEQ ID NO:130, a VL CDR2 having an amino acid sequence of SEQ ID NO:131, and a VL CDR3 having an amino acid sequence of SEQ ID NO:132. In another aspect, provided herein is an antibody that binds to TRGV9, wherein the antibody comprises: (i) a VH comprising a VH CDR1 having an amino acid sequence of SEQ ID NO:520, a VH CDR2 having an amino acid sequence of SEQ ID NO:521, and a VH CDR3 having an amino acid sequence of SEQ ID NO:522; and (ii) a VL comprising a VL CDR1 having an amino acid sequence of SEQ ID NO:523, a VL CDR2 having an amino acid sequence of SEQ ID NO:524, and a VL CDR3 having an amino acid sequence of SEQ ID NO:525. In another aspect, provided herein is an antibody that binds to TRGV9, wherein the antibody comprises: (i) a VH comprising a VH CDR1 having an amino acid sequence of SEQ ID NO:526, a VH CDR2 having an amino acid sequence of SEQ ID NO:527, and a VH CDR3 having an amino acid sequence of SEQ ID NO:528; and (ii) a VL comprising a VL CDR1 having an amino acid sequence of SEQ ID NO:529, a VL CDR2 having an amino acid sequence of SEQ ID NO:530, and a VL CDR3 having an amino acid sequence of SEQ ID NO:531. In another aspect, provided herein is an antibody that binds to TRGV9, wherein the antibody comprises: (i) a VH comprising a VH CDR1 having an amino acid sequence of SEQ ID NO:532, a VH CDR2 having an amino acid sequence of SEQ ID NO:533, and a VH CDR3 having an amino acid sequence of SEQ ID NO:534; and (ii) a VL comprising a VL CDR1 having an amino acid sequence of SEQ ID NO:535, a VL CDR2 having an amino acid sequence of SEQ ID NO:536, and a VL CDR3 having an amino acid sequence of SEQ ID NO:537. In another aspect, provided herein is an antibody that binds to TRGV9, wherein the antibody comprises: (i) a VH comprising a VH CDR1 having an amino acid sequence of SEQ ID NO:538, a VH CDR2 having an amino acid sequence of SEQ ID NO:539, and a VH CDR3 having an amino acid sequence of SEQ ID NO:540; and (ii) a VL comprising a VL CDR1 having an amino acid sequence of SEQ ID NO:541, a VL CDR2 having an amino acid sequence of SEQ ID NO:542, and a VL CDR3 having an amino acid sequence of SEQ ID NO:543. In another aspect, provided herein is an antibody that binds to TRGV9, wherein the antibody comprises: (i) a VH comprising a VH CDR1 having an amino acid sequence of SEQ ID NO:538, a VH CDR2 having an amino acid sequence of SEQ ID NO:720, and a VH CDR3 having an amino acid sequence of SEQ ID NO:721; and (ii) a VL comprising a VL CDR1 having an amino acid sequence of SEQ ID NO:541, a VL CDR2 having an amino acid sequence of SEQ ID NO:542, and a VL CDR3 having an amino acid sequence of SEQ ID NO:543. In another aspect, provided herein is an antibody that binds to TRGV9, wherein the antibody comprises: (i) a VH comprising a VH CDR1 having an amino acid sequence of SEQ ID NO:544, a VH CDR2 having an amino acid sequence of SEQ ID NO:545, and a VH CDR3 having an amino acid sequence of SEQ ID NO:546; and (ii) a VL comprising a VL CDR1 having an amino acid sequence of SEQ ID NO:547, a VL CDR2 having an amino acid sequence of SEQ ID NO:548, and a VL CDR3 having an amino acid sequence of SEQ ID NO:549. In another aspect, provided herein is an antibody that binds to TRGV9, wherein the antibody comprises: (i) a VH comprising a VH CDR1 having an amino acid sequence of SEQ ID NO:550, a VH CDR2 having an amino acid sequence of SEQ ID NO:551, and a VH CDR3 having an amino acid sequence of SEQ ID NO:552; and (ii) a VL comprising a VL CDR1 having an amino acid sequence of SEQ ID NO:553, a VL CDR2 having an amino acid sequence of SEQ ID NO:554, and a VL CDR3 having an amino acid sequence of SEQ ID NO:555. In some embodiments, the antibody comprises a VH having an amino acid sequence of SEQ ID NO:133. In some embodiments, the antibody comprises a VL having an amino acid sequence of SEQ ID NO:134. In some embodiments, the antibody comprises a VH having an amino acid sequence of SEQ ID NO:133, and a VL having an amino acid sequence of SEQ ID NO:134. In some embodiments, the antibody comprises a heavy chain having an amino acid sequence of SEQ ID NO:135. In some embodiments, the antibody comprises a light chain having an amino acid sequence of SEQ ID NO:136. In some embodiments, the antibody comprises a heavy chain having an amino acid sequence of SEQ ID NO:135, and a light chain having an amino acid sequence of SEQ ID NO:136. In some embodiments, the antibody comprises a VH comprising an amino acid sequence having at least 95% identity to the amino acid sequence of SEQ ID NO:133. In some embodiments, the antibody comprises a VL comprising an amino acid sequence having at least 95% identity to the amino acid sequence of SEQ ID NO:134. In some embodiments, the antibody comprises a VH comprising an amino acid sequence having at least 95% identity to the amino acid sequence of SEQ ID NO:133, and a VL comprising an amino acid sequence having at least 95% identity to the amino acid sequence of SEQ ID NO:134. In some embodiments, the antibody comprises a heavy chain comprising an amino acid sequence having at least 95% identity to the amino acid sequence of SEQ ID NO:135. In some embodiments, the antibody comprises a light chain comprising an amino acid sequence having at least 95% identity to the amino acid sequence of SEQ ID NO:136. In some embodiments, the antibody comprises a heavy chain comprising an amino acid sequence having at least 95% identity to the amino acid sequence of SEQ ID NO:135, and a light chain comprising an amino acid sequence having at least 95% identity to the amino acid sequence of SEQ ID NO:136.

In some embodiments, the anti-TRGV9 antibody is not a single chain antibody. In some embodiments, the anti-TRGV9 antibody is not a single domain antibody. In some embodiments, the anti-TRGV9 antibody is not a nanobody. In certain embodiments, the anti-TRGV9 antibody is not a VHH antibody. In certain embodiments, the anti-TRGV9 antibody is not a llama antibody.

In some embodiments, an anti-TRGV9 antibody provided herein does not comprise a VH CDR1, VH CDR2, and VH CDR3 having the amino acid sequence of SEQ ID NOs:730, 731, and 732, respectively. In some embodiments, an anti-TRGV9 antibody provided herein does not comprise a VH CDR1, VH CDR2, and VH CDR3 having the amino acid sequence of SEQ ID NOs:733, 734, and 735, respectively. In some embodiments, an anti-TRGV9 antibody provided herein does not comprise a VH CDR1, VH CDR2, and VH CDR3 having the amino acid sequence of SEQ ID NOs:736, 737, and 738, respectively. In some embodiments, an anti-TRGV9 antibody provided herein does not comprise a VH CDR1, VH CDR2, and VH CDR3 having the amino acid sequence of SEQ ID NOs:739, 740, and 741, respectively. In some embodiments, an anti-TRGV9 antibody provided herein does not comprise a VH CDR1, VH CDR2, and VH CDR3 having the amino acid sequence of SEQ ID NOs:742, 743, and 744, respectively. In some embodiments, an anti-TRGV9 antibody provided herein does not comprise a VH CDR1, VH CDR2, and VH CDR3 having the amino acid sequence of SEQ ID NOs:745, 746, and 747, respectively. In some embodiments, an anti-TRGV9 antibody provided herein does not comprise a VH CDR1, VH CDR2, and VH CDR3 having the amino acid sequence of SEQ ID NOs:748, 749, and 750, respectively. In some embodiments, an anti-TRGV9 antibody provided herein does not comprise a VH domain having the amino acid sequence of SEQ ID NO:751. In some embodiments, an anti-TRGV9 antibody provided herein does not comprise a VH domain having the amino acid sequence of SEQ ID NO:752. In some embodiments, an anti-TRGV9 antibody provided herein does not comprise a VH domain having the amino acid sequence of SEQ ID NO:753. In some embodiments, an anti-TRGV9 antibody provided herein does not comprise a VH domain having the amino acid sequence of SEQ ID NO:754. In some embodiments, an anti-TRGV9 antibody provided herein does not comprise a VH domain having the amino acid sequence of SEQ ID NO:755. In some embodiments, an anti-TRGV9 antibody provided herein does not comprise a VH domain having the amino acid sequence of SEQ ID NO:756. In some embodiments, an anti-TRGV9 antibody provided herein does not comprise a VH domain having the amino acid sequence of SEQ ID NO:757.

In another aspect, provided herein is an anti-TRGV9 antibody, comprising a VH domain comprising a VH CDR3 having the amino acid sequence of APNxGzYTbDF (SEQ ID NO:758), wherein x is Y or M, z is M or D, and b is I or L. In another aspect, provided herein is an anti-TRGV9 antibody, comprising a VH domain comprising the amino acid sequence of SEQ ID NO:758. In another aspect, provided herein is an anti-TRGV9 antibody, comprising a VH domain comprising a VH CDR1 having the amino acid sequence of GxTFzz, wherein x is F, D or G, and z is S or N. In another aspect, provided herein is an anti-TRGV9 antibody, comprising a VH domain comprising the amino acid sequence of SEQ ID NO:761. In another aspect, provided herein is an anti-TRGV9 antibody, comprising a VL domain comprising a VL CDR1 having the amino acid sequence of RxSQSz (SEQ ID NO:762), wherein x is A or S, and z is V or L. In another aspect, provided herein is an anti-TRGV9 antibody, comprising a VL domain comprising the amino acid sequence of SEQ ID NO:761.

In another aspect, provided herein is an antibody that binds to TRGV9, wherein the antibody comprises: (i) a VH comprising a VH CDR1, a VH CDR2, and a VH CDR3; and (ii) a VL comprising a VL CDR1, a VL CDR2, and a VL CDR3. In some embodiments, the VH CDR1 comprises a first polar amino acid. In some embodiments, the VH CDR1 comprises a last polar uncharged amino acid. In some embodiments, the VH CDR1 comprises at least one tyrosine. In some embodiments, the VH CDR1 comprises at least 20% hydrophobic amino acids. In some embodiments, the VH CDR1 comprises at least two hydrophobic amino acids. In some embodiments, the VH CDR1 comprises at least about 40% hydrophobic amino acids. In some embodiments, the VH CDR1 comprises the VH CDR1 comprises a first polar amino acid, a last polar uncharged amino acid, at least one tyrosine, at least 20% hydrophobic amino acids, at least two hydrophobic amino acids, and at least about 40% hydrophobic amino acids. Any combination of two or more of the above-mentioned VH CDR1 structural features are also contemplated. In some embodiments, the VH CDR2 comprises a polar amino acid at residue 13. In some embodiments, the VH CDR2 comprises a hydrophobic at amino acid position 15. In some embodiments, the VH CDR2 comprises a phenylalanine (F) or leucine (L) at position 15. In some embodiments, the VH CDR2 comprises a polar amino acid at position 14. In some embodiments, the VH CDR2 comprises a lysine (K) or serine (S) at position 14. In some embodiments, the VH CDR2 comprises a hydrophobic amino acid at position 2. In some embodiments, the VH CDR2 comprises a hydrophobic amino acid at position 3. In some embodiments, the VH CDR2 comprises and a polar penultimate amino acid. In some embodiments, the VH CDR2 comprises a polar amino acid at residue 13, a hydrophobic at amino acid position 15, a phenylalanine (F) or leucine (L) at position 15, a polar amino acid at position 14, a lysine (K) or serine (S) at position 14, a hydrophobic amino acid at position 2 or 3, and a polar penultimate amino acid. Any combination of two or more of the above-mentioned VH CDR2 structural features are also contemplated. In some embodiments, the VH CDR3 does not comprise a polar charged amino acid at position 3. In some embodiments, the VH CDR3 comprises a hydrophobic or polar charged amino acid at position 7. In some embodiments, the VH CDR3 comprises a polar uncharged or hydrophobic amino acid at position 6. In some embodiments, the VH CDR3 comprises no polar charged amino acid at position 3, a hydrophobic or polar charged amino acid at position 7, and a polar uncharged or hydrophobic amino acid at position 6. Any combination of two or more of the above-mentioned VH CDR3 structural features are also contemplated. In some embodiments, the VL CDR1 comprises a polar amino acid at position 4. In some embodiments, the VL CDR1 comprises a first amino acid that is polar charged. In some embodiments, the VL CDR1 comprises a polar uncharged or hydrophobic amino acid at position 2. In some embodiments, the VL CDR1 comprises a serine at position 3. In some embodiments, the VL CDR1 comprises a polar amino acid at position 5. In some embodiments, the VL CDR1 comprises a hydrophobic amino acid at position 6. In some embodiments, the VL CDR1 comprises a polar amino acid at position 4, a first amino acid that is polar charged, a polar uncharged or hydrophobic amino acid at position 2, a serine at position 3, a polar amino acid at position 5, and a hydrophobic amino acid at position 6. Any combination of two or more of the above-mentioned VL CDR1 structural features are also contemplated. In some embodiments, the VL CDR2 comprises a polar amino acid at position 7. In some embodiments, the VL CDR2 comprises a polar charged or hydrophobic amino acid at position 6. In some embodiments, the VL CDR2 comprises a polar charged amino acid at position 3. In some embodiments, the VL CDR2 comprises a polar uncharged amino acid at position 4. In some embodiments, the VL CDR2 comprises a hydrophobic amino acid at position 2. In some embodiments, the VL CDR2 comprises a polar amino acid at position 7, a polar charged or hydrophobic amino acid at position 6, a polar charged amino acid at position 3, a polar uncharged amino acid at position 4, and a hydrophobic amino acid at position 2. Any combination of two or more of the above-mentioned VL CDR2 structural features are also contemplated. In some embodiments, the VL CDR3 comprises a hydrophobic terminal amino acid. In some embodiments, the VL CDR3 comprises a terminal tyrosine. In some embodiments, the VL CDR3 comprises a polar uncharged amino acid at position 5. In some embodiments, the VL CDR3 comprises a polar amino acid at position 2. In some embodiments, the VL CDR3 comprises a polar uncharged or hydrophobic amino acid at position 1. In some embodiments, the VL CDR3 comprises a hydrophobic amino acid at position 3. In some embodiments, the VL CDR3 comprises a hydrophylic or polar uncharged amino acid at position 6. In some embodiments, the VL CDR3 comprises no polar or hydrophobic amino acid at position 7. In some embodiments, the VL CDR3 comprises a hydrophobic terminal amino acid, a terminal tyrosine, a polar uncharged amino acid at position 5, a polar amino acid at position 2, a polar uncharged or hydrophobic amino acid at position 1, a hydrophobic amino acid at position 3, a hydrophylic or polar uncharged amino acid at position 6, and no polar or hydrophobic amino acid at position 7. Any combination of two or more of the above-mentioned VL CDR3 structural features are also contemplated. In specific embodiments, residue position numbering is according to Exemplary numbering.

In some embodiments, the anti-TRGV9 antibody is a multispecific antibody. In other embodiments, the anti-TRGV9 antibody is a bispecific antibody. In certain embodiments, the multispecific antibody comprises an antigen binding fragment of an anti-TRGV9 antibody provided herein. In some embodiments, the multispecific antibody comprises a first binding domain that binds to a first TRGV9 epitope and a second domain that binds to a second TRGV9 epitope, wherein the first TRGV9 epitope and the second TRGV9 epitope are different. In certain embodiments, the multispecific antibody further comprises a third binding domain that binds to a target that is not TRGV9.

In another aspect, provided herein is a bispecific antibody comprising: (a) a first binding domain that binds to TRGV9, and (b) a second binding domain that binds to a second target that is not TRGV9.

In some embodiments, the bispecific antibody comprises heavy chain variable regions and light chain variable region. In some embodiments, the first binding domain comprises a heavy chain variable region and a light chain variable region. In some embodiments, the second binding domain comprises a heavy chain variable region and a light chain variable region. In some embodiments, the first binding domain comprises a heavy chain variable region and a light chain variable region, and the second binding domain comprises a heavy chain variable region and a light chain variable region. In a some embodiments, the TRGV9 antibody is not a single domain antibody or nanobody.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:7; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:3; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:160, a VH CDR2 having an amino acid sequence of SEQ ID NO:161, and a VH CDR3 having an amino acid sequence of SEQ ID NO:162; and (ii) a VL comprising a VL CDR1 having an amino acid sequence of SEQ ID NO:163, a VL CDR2 having an amino acid sequence of SEQ ID NO:164, and a VL CDR3 having an amino acid sequence of SEQ ID NO:165. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:166, a VH CDR2 having an amino acid sequence of SEQ ID NO:167, and a VH CDR3 having an amino acid sequence of SEQ ID NO:168; and (ii) a VL comprising a VL CDR1 having an amino acid sequence of SEQ ID NO:169, a VL CDR2 having an amino acid sequence of SEQ ID NO:170, and a VL CDR3 having an amino acid sequence of SEQ ID NO:171. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:172, a VH CDR2 having an amino acid sequence of SEQ ID NO:173, and a VH CDR3 having an amino acid sequence of SEQ ID NO:174; and (ii) a VL comprising a VL CDR1 having an amino acid sequence of SEQ ID NO:175, a VL CDR2 having an amino acid sequence of SEQ ID NO:176, and a VL CDR3 having an amino acid sequence of SEQ ID NO:177. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:178, a VH CDR2 having an amino acid sequence of SEQ ID NO:179, and a VH CDR3 having an amino acid sequence of SEQ ID NO:180; and (ii) a VL comprising a VL CDR1 having an amino acid sequence of SEQ ID NO:181, a VL CDR2 having an amino acid sequence of SEQ ID NO:182, and a VL CDR3 having an amino acid sequence of SEQ ID NO:183. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:178, a VH CDR2 having an amino acid sequence of SEQ ID NO:700, and a VH CDR3 having an amino acid sequence of SEQ ID NO:701; and (ii) a VL comprising a VL CDR1 having an amino acid sequence of SEQ ID NO:181, a VL CDR2 having an amino acid sequence of SEQ ID NO:182, and a VL CDR3 having an amino acid sequence of SEQ ID NO:183. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:184, a VH CDR2 having an amino acid sequence of SEQ ID NO:185, and a VH CDR3 having an amino acid sequence of SEQ ID NO:186; and (ii) a VL comprising a VL CDR1 having an amino acid sequence of SEQ ID NO:187, a VL CDR2 having an amino acid sequence of SEQ ID NO:188, and a VL CDR3 having an amino acid sequence of SEQ ID NO:189. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:190, a VH CDR2 having an amino acid sequence of SEQ ID NO:191, and a VH CDR3 having an amino acid sequence of SEQ ID NO:192; and (ii) a VL comprising a VL CDR1 having an amino acid sequence of SEQ ID NO:193, a VL CDR2 having an amino acid sequence of SEQ ID NO:194, and a VL CDR3 having an amino acid sequence of SEQ ID NO:195. In some embodiments, the first binding domain comprises a VH having an amino acid sequence of SEQ ID NO:7. In some embodiments, the first binding domain comprises a VL having an amino acid sequence of SEQ ID NO:8. In some embodiments, the first binding domain comprises a VH having an amino acid sequence of SEQ ID NO:7, and a VL having an amino acid sequence of SEQ ID NO:8. In some embodiments, the first binding domain comprises a heavy chain having an amino acid sequence of SEQ ID NO:23. In some embodiments, the first binding domain comprises a light chain having an amino acid sequence of SEQ ID NO:24. In some embodiments, the first binding domain comprises a heavy chain having an amino acid sequence of SEQ ID NO:23, and a light chain having an amino acid sequence of SEQ ID NO:24. In some embodiments, the first binding domain comprises an amino acid sequence of SEQ ID NO:17. In some embodiments, the first binding domain comprises a heavy chain having an amino acid sequence of SEQ ID NO:69. In some embodiments, the first binding domain comprises a light chain having an amino acid sequence of SEQ ID NO:24. In some embodiments, the first binding domain comprises a heavy chain having an amino acid sequence of SEQ ID NO:69, and a light chain having an amino acid sequence of SEQ ID NO:24. In some embodiments, the first binding domain comprises a VH comprising an amino acid sequence having at least 95% identity to the amino acid sequence of SEQ ID NO:7. In some embodiments, the first binding domain comprises a VL comprising an amino acid sequence having at least 95% identity to the amino acid sequence of SEQ ID NO:8. In some embodiments, the first binding domain comprises a VH comprising an amino acid sequence having at least 95% identity to the amino acid sequence of SEQ ID NO:7, and a VL comprising an amino acid sequence having at least 95% identity to the amino acid sequence of SEQ ID NO:8. In some embodiments, the first binding domain comprises a heavy chain comprising an amino acid sequence having at least 95% identity to the amino acid sequence of SEQ ID NO:23. In some embodiments, the first binding domain comprises a light chain comprising an amino acid sequence having at least 95% identity to the amino acid sequence of SEQ ID NO:24. In some embodiments, the first binding domain comprises a heavy chain comprising an amino acid sequence having at least 95% identity to the amino acid sequence of SEQ ID NO:23, and a light chain comprising an amino acid sequence having at least 95% identity to the amino acid sequence of SEQ ID NO:24. In some embodiments, the first binding domain comprises an amino acid sequence of SEQ ID NO:17. In some embodiments, the first binding domain comprises a heavy chain comprising an amino acid sequence having at least 95% identity to the amino acid sequence of SEQ ID NO:69. In some embodiments, the first binding domain comprises a light chain comprising an amino acid sequence having at least 95% identity to the amino acid sequence of SEQ ID NO:24. In some embodiments, the first binding domain comprises a heavy chain comprising an amino acid sequence having at least 95% identity to the amino acid sequence of SEQ ID NO:69, and a light chain comprising an amino acid sequence having at least 95% identity to the amino acid sequence of SEQ ID NO:24.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:34; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:31; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:196, a VH CDR2 having an amino acid sequence of SEQ ID NO:197, and a VH CDR3 having an amino acid sequence of SEQ ID NO:198; and (ii) a VL comprising a VL CDR1 having an amino acid sequence of SEQ ID NO:199, a VL CDR2 having an amino acid sequence of SEQ ID NO:200, and a VL CDR3 having an amino acid sequence of SEQ ID NO:201. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:202, a VH CDR2 having an amino acid sequence of SEQ ID NO:203, and a VH CDR3 having an amino acid sequence of SEQ ID NO:204; and (ii) a VL comprising a VL CDR1 having an amino acid sequence of SEQ ID NO:205, a VL CDR2 having an amino acid sequence of SEQ ID NO:206, and a VL CDR3 having an amino acid sequence of SEQ ID NO:207. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:208, a VH CDR2 having an amino acid sequence of SEQ ID NO:209, and a VH CDR3 having an amino acid sequence of SEQ ID NO:210; and (ii) a VL comprising a VL CDR1 having an amino acid sequence of SEQ ID NO:211, a VL CDR2 having an amino acid sequence of SEQ ID NO:212, and a VL CDR3 having an amino acid sequence of SEQ ID NO:213. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:214, a VH CDR2 having an amino acid sequence of SEQ ID NO:215, and a VH CDR3 having an amino acid sequence of SEQ ID NO:216; and (ii) a VL comprising a VL CDR1 having an amino acid sequence of SEQ ID NO:217, a VL CDR2 having an amino acid sequence of SEQ ID NO:218, and a VL CDR3 having an amino acid sequence of SEQ ID NO:219. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:214, a VH CDR2 having an amino acid sequence of SEQ ID NO:702, and a VH CDR3 having an amino acid sequence of SEQ ID NO:703; and (ii) a VL comprising a VL CDR1 having an amino acid sequence of SEQ ID NO:217, a VL CDR2 having an amino acid sequence of SEQ ID NO:218, and a VL CDR3 having an amino acid sequence of SEQ ID NO:219. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:220, a VH CDR2 having an amino acid sequence of SEQ ID NO:221, and a VH CDR3 having an amino acid sequence of SEQ ID NO:222; and (ii) a VL comprising a VL CDR1 having an amino acid sequence of SEQ ID NO:223, a VL CDR2 having an amino acid sequence of SEQ ID NO:224, and a VL CDR3 having an amino acid sequence of SEQ ID NO:225. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:226, a VH CDR2 having an amino sequence of SEQ ID NO:227, and a VH CDR3 having an amino acid sequence of SEQ ID NO:228; and (ii) a VL comprising a VL CDR1 having an amino acid sequence of SEQ ID NO:229, a VL CDR2 having an amino acid sequence of SEQ ID NO:230, and a VL CDR3 having an amino acid sequence of SEQ ID NO:231. In some embodiments, the first binding domain comprises a VH having an amino acid sequence of SEQ ID NO:34. In some embodiments, the first binding domain comprises a VL having an amino acid sequence of SEQ ID NO:8. In some embodiments, the first binding domain comprises a VH having an amino acid sequence of SEQ ID NO:34, and a VL having an amino acid sequence of SEQ ID NO:8. In some embodiments, the first binding domain comprises a VH comprising an amino acid sequence having at least 95% identity to the amino acid sequence of SEQ ID NO:34. In some embodiments, the first binding domain comprises a VL comprising an amino acid sequence having at least 95% identity to the amino acid sequence of SEQ ID NO:8. In some embodiments, the first binding domain comprises a VH comprising an amino acid sequence having at least 95% identity to the amino acid sequence of SEQ ID NO:34, and a VL comprising an amino acid sequence having at least 95% identity to the amino acid sequence of SEQ ID NO:8.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:35; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:32; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:232, a VH CDR2 having an amino acid sequence of SEQ ID NO:233, and a VH CDR3 having an amino acid sequence of SEQ ID NO:234; and (ii) a VL comprising a VL CDR1 having an amino acid sequence of SEQ ID NO:235, a VL CDR2 having an amino acid sequence of SEQ ID NO:236, and a VL CDR3 having an amino acid sequence of SEQ ID NO:237. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:238, a VH CDR2 having an amino acid sequence of SEQ ID NO:239, and a VH CDR3 having an amino acid sequence of SEQ ID NO:240; and (ii) a VL comprising a VL CDR1 having an amino acid sequence of SEQ ID NO:241, a VL CDR2 having an amino acid sequence of SEQ ID NO:242, and a VL CDR3 having an amino acid sequence of SEQ ID NO:243. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:244, a VH CDR2 having an amino acid sequence of SEQ ID NO:245, and a VH CDR3 having an amino acid sequence of SEQ ID NO:246; and (ii) a VL comprising a VL CDR1 having an amino acid sequence of SEQ ID NO:247, a VL CDR2 having an amino acid sequence of SEQ ID NO:248, and a VL CDR3 having an amino acid sequence of SEQ ID NO:249. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:250, a VH CDR2 having an amino acid sequence of SEQ ID NO:251, and a VH CDR3 having an amino acid sequence of SEQ ID NO:252; and (ii) a VL comprising a VL CDR1 having an amino acid sequence of SEQ ID NO:253, a VL CDR2 having an amino acid sequence of SEQ ID NO:254, and a VL CDR3 having an amino acid sequence of SEQ ID NO:255. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:250, a VH CDR2 having an amino acid sequence of SEQ ID NO:704, and a VH CDR3 having an amino acid sequence of SEQ ID NO:705; and (ii) a VL comprising a VL CDR1 having an amino acid sequence of SEQ ID NO:253, a VL CDR2 having an amino acid sequence of SEQ ID NO:254, and a VL CDR3 having an amino acid sequence of SEQ ID NO:255. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:256, a VH CDR2 having an amino acid sequence of SEQ ID NO:257, and a VH CDR3 having an amino acid sequence of SEQ ID NO:258; and (ii) a VL comprising a VL CDR1 having an amino acid sequence of SEQ ID NO:259, a VL CDR2 having an amino acid sequence of SEQ ID NO:260, and a VL CDR3 having an amino acid sequence of SEQ ID NO:261. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:262, a VH CDR2 having an amino acid sequence of SEQ ID NO:263, and a VH CDR3 having an amino acid sequence of SEQ ID NO:264; and (ii) a VL comprising a VL CDR1 having an amino acid sequence of SEQ ID NO:265, a VL CDR2 having an amino acid sequence of SEQ ID NO:266, and a VL CDR3 having an amino acid sequence of SEQ ID NO:267. In some embodiments, the first binding domain comprises a VH having an amino acid sequence of SEQ ID NO:35. In some embodiments, the first binding domain comprises a VL having an amino acid sequence of SEQ ID NO:8. In some embodiments, the first binding domain comprises a VH having an amino acid sequence of SEQ ID NO:35, and a VL having an amino acid sequence of SEQ ID NO:8. In some embodiments, the first binding domain comprises a VH comprising an amino acid sequence having at least 95% identity to the amino acid sequence of SEQ ID NO:35. In some embodiments, the first binding domain comprises a VL comprising an amino acid sequence having at least 95% identity to the amino acid sequence of SEQ ID NO:8. In some embodiments, the first binding domain comprises a VH comprising an amino acid sequence having at least 95% identity to the amino acid sequence of SEQ ID NO:35, and a VL comprising an amino acid sequence having at least 95% identity to the amino acid sequence of SEQ ID NO:8.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:36; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:33; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:268, a VH CDR2 having an amino acid sequence of SEQ ID NO:269, and a VH CDR3 having an amino acid sequence of SEQ ID NO:270; and (ii) a VL comprising a VL CDR1 having an amino acid sequence of SEQ ID NO:271, a VL CDR2 having an amino acid sequence of SEQ ID NO:272, and a VL CDR3 having an amino acid sequence of SEQ ID NO:273. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:274, a VH CDR2 having an amino acid sequence of SEQ ID NO:275, and a VH CDR3 having an amino acid sequence of SEQ ID NO:276; and (ii) a VL comprising a VL CDR1 having an amino acid sequence of SEQ ID NO:277, a VL CDR2 having an amino acid sequence of SEQ ID NO:278, and a VL CDR3 having an amino acid sequence of SEQ ID NO:279. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:280, a VH CDR2 having an amino acid sequence of SEQ ID NO:281, and a VH CDR3 having an amino acid sequence of SEQ ID NO:282; and (ii) a VL comprising a VL CDR1 having an amino acid sequence of SEQ ID NO:283, a VL CDR2 having an amino acid sequence of SEQ ID NO:284, and a VL CDR3 having an amino acid sequence of SEQ ID NO:285. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:286, a VH CDR2 having an amino acid sequence of SEQ ID NO:287, and a VH CDR3 having an amino acid sequence of SEQ ID NO:288; and (ii) a VL comprising a VL CDR1 having an amino acid sequence of SEQ ID NO:289, a VL CDR2 having an amino acid sequence of SEQ ID NO:290, and a VL CDR3 having an amino acid sequence of SEQ ID NO:291. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:286, a VH CDR2 having an amino acid sequence of SEQ ID NO:706, and a VH CDR3 having an amino acid sequence of SEQ ID NO:707; and (ii) a VL comprising a VL CDR1 having an amino acid sequence of SEQ ID NO:289, a VL CDR2 having an amino acid sequence of SEQ ID NO:290, and a VL CDR3 having an amino acid sequence of SEQ ID NO:291. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:292, a VH CDR2 having an amino acid sequence of SEQ ID NO:293, and a VH CDR3 having an amino acid sequence of SEQ ID NO:294; and (ii) a VL comprising a VL CDR1 having an amino acid sequence of SEQ ID NO:295, a VL CDR2 having an amino acid sequence of SEQ ID NO:296, and a VL CDR3 having an amino acid sequence of SEQ ID NO:297. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:298, a VH CDR2 having an amino acid sequence of SEQ ID NO:299, and a VH CDR3 having an amino acid sequence of SEQ ID NO:300; and (ii) a VL comprising a VL CDR1 having an amino acid sequence of SEQ ID NO:301, a VL CDR2 having an amino acid sequence of SEQ ID NO:302, and a VL CDR3 having an amino acid sequence of SEQ ID NO:303. In some embodiments, the first binding domain comprises a VH having an amino acid sequence of SEQ ID NO:36. In some embodiments, the first binding domain comprises a VL having an amino acid sequence of SEQ ID NO:8. In some embodiments, the first binding domain comprises a VH having an amino acid sequence of SEQ ID NO:36, and a VL having an amino acid sequence of SEQ ID NO:8. In some embodiments, the first binding domain comprises a VH comprising an amino acid sequence having at least 95% identity to the amino acid sequence of SEQ ID NO:36. In some embodiments, the first binding domain comprises a VL comprising an amino acid sequence having at least 95% identity to the amino acid sequence of SEQ ID NO:8. In some embodiments, the first binding domain comprises a VH comprising an amino acid sequence having at least 95% identity to the amino acid sequence of SEQ ID NO:36, and a VL comprising an amino acid sequence having at least 95% identity to the amino acid sequence of SEQ ID NO:8.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:65; and (ii) a VL comprising a VL CDR1, a VL CDR2, and a VL CDR3 having amino acid sequences of the VL CDR1, VL CDR2, and VL CDR3, respectively, of SEQ ID NO:66. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:67; and (ii) a VL comprising a VL CDR1, a VL CDR2, and a VL CDR3 having amino acid sequences of the VL CDR1, VL CDR2, and VL CDR3, respectively, of SEQ ID NO:68. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:1, a VH CDR2 having an amino acid sequence of SEQ ID NO:76, and a VH CDR3 having an amino acid sequence of SEQ ID NO:3; and (ii) a VL comprising a VL CDR1 having an amino acid sequence of SEQ ID NO:77, a VL CDR2 having an amino acid sequence of SEQ ID NO:5, and a VL CDR3 having an amino acid sequence of SEQ ID NO:6. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:60, a VH CDR2 having an amino acid sequence of SEQ ID NO:61, and a VH CDR3 having an amino acid sequence of SEQ ID NO:62; and (ii) a VL comprising a VL CDR1 having an amino acid sequence of SEQ ID NO:63, a VL CDR2 having an amino acid sequence of SEQ ID NO:64, and a VL CDR3 having an amino acid sequence of SEQ ID NO:6. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:304, a VH CDR2 having an amino acid sequence of SEQ ID NO:305, and a VH CDR3 having an amino acid sequence of SEQ ID NO:306; and (ii) a VL comprising a VL CDR1 having an amino acid sequence of SEQ ID NO:307, a VL CDR2 having an amino acid sequence of SEQ ID NO:308, and a VL CDR3 having an amino acid sequence of SEQ ID NO:309. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:310, a VH CDR2 having an amino acid sequence of SEQ ID NO:311, and a VH CDR3 having an amino acid sequence of SEQ ID NO:312; and (ii) a VL comprising a VL CDR1 having an amino acid sequence of SEQ ID NO:313, a VL CDR2 having an amino acid sequence of SEQ ID NO:314, a VL CDR3 having an amino acid sequence of SEQ ID NO:315. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:316, a VH CDR2 having an amino acid sequence of SEQ ID NO:317, and a VH CDR3 having an amino acid sequence of SEQ ID NO:318; and (ii) a VL comprising a VL CDR1 having an amino acid sequence of SEQ ID NO:319, a VL CDR2 having an amino acid sequence of SEQ ID NO:320, and a VL CDR3 having an amino acid sequence of SEQ ID NO:321. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:322, a VH CDR2 having an amino acid sequence of SEQ ID NO:323, and a VH CDR3 having an amino acid sequence of SEQ ID NO:324; and (ii) a VL comprising a VL CDR1 having an amino acid sequence of SEQ ID NO:325, a VL CDR2 having an amino acid sequence of SEQ ID NO:326, and a VL CDR3 having an amino acid sequence of SEQ ID NO:327. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:322, a VH CDR2 having an amino acid sequence of SEQ ID NO:708, and a VH CDR3 having an amino acid sequence of SEQ ID NO:709; and (ii) a VL comprising a VL CDR1 having an amino acid sequence of SEQ ID NO:325, a VL CDR2 having an amino acid sequence of SEQ ID NO:326, and a VL CDR3 having an amino acid sequence of SEQ ID NO:327. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:328, a VH CDR2 having an amino acid sequence of SEQ ID NO:329, and a VH CDR3 having an amino acid sequence of SEQ ID NO:330; and (ii) a VL comprising a VL CDR1 having an amino acid sequence of SEQ ID NO:331, a VL CDR2 having an amino acid sequence of SEQ ID NO:332, and a VL CDR3 having an amino acid sequence of SEQ ID NO:333. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:334, a VH CDR2 having an amino acid sequence of SEQ ID NO:335, and a VH CDR3 having an amino acid sequence of SEQ ID NO:336; and (ii) a VL comprising a VL CDR1 having an amino acid sequence of SEQ ID NO:337, a VL CDR2 having an amino acid sequence of SEQ ID NO:338, and a VL CDR3 having an amino acid sequence of SEQ ID NO:339. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:340, a VH CDR2 having an amino acid sequence of SEQ ID NO:341, and a VH CDR3 having an amino acid sequence of SEQ ID NO:342; and (ii) a VL comprising a VL CDR1 having an amino acid sequence of SEQ ID NO:343, a VL CDR2 having an amino acid sequence of SEQ ID NO:344, and a VL CDR3 having an amino acid sequence of SEQ ID NO:345. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:346, a VH CDR2 having an amino acid sequence of SEQ ID NO:347, and a VH CDR3 having an amino acid sequence of SEQ ID NO:348; and (ii) a VL comprising a VL CDR1 having an amino acid sequence of SEQ ID NO:349, a VL CDR2 having an amino acid sequence of SEQ ID NO:350, and a VL CDR3 having an amino acid sequence of SEQ ID NO:351. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:352, a VH CDR2 having an amino acid sequence of SEQ ID NO:353, and a VH CDR3 having an amino acid sequence of SEQ ID NO:354; and (ii) a VL comprising a VL CDR1 having an amino acid sequence of SEQ ID NO:355, a VL CDR2 having an amino acid sequence of SEQ ID NO:356, and a VL CDR3 having an amino acid sequence of SEQ ID NO:357. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:358, a VH CDR2 having an amino acid sequence of SEQ ID NO:359, and a VH CDR3 having an amino acid sequence of SEQ ID NO:360; and (ii) a VL comprising a VL CDR1 having an amino acid sequence of SEQ ID NO:361, a VL CDR2 having an amino acid sequence of SEQ ID NO:362, and a VL CDR3 having an amino acid sequence of SEQ ID NO:363. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:358, a VH CDR2 having an amino acid sequence of SEQ ID NO:710, and a VH CDR3 having an amino acid sequence of SEQ ID NO:711; and (ii) a VL comprising a VL CDR1 having an amino acid sequence of SEQ ID NO:361, a VL CDR2 having an amino acid sequence of SEQ ID NO:362, and a VL CDR3 having an amino acid sequence of SEQ ID NO:363. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:364, a VH CDR2 having an amino acid sequence of SEQ ID NO:365, and a VH CDR3 having an amino acid sequence of SEQ ID NO:366; and (ii) a VL comprising a VL CDR1 having an amino acid sequence of SEQ ID NO:367, a VL CDR2 having an amino acid sequence of SEQ ID NO:368, and a VL CDR3 having an amino acid sequence of SEQ ID NO:369. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:370, a VH CDR2 having an amino acid sequence of SEQ ID NO:371, and a VH CDR3 having an amino acid sequence of SEQ ID NO:372; and (ii) a VL comprising a VL CDR1 having an amino acid sequence of SEQ ID NO:373, a VL CDR2 having an amino acid sequence of SEQ ID NO:374, and a VL CDR3 having an amino acid sequence of SEQ ID NO:375. In some embodiments, the first binding domain comprises a VH having an amino acid sequence of SEQ ID NO:65. In some embodiments, the first binding domain comprises a VL having an amino acid sequence of SEQ ID NO:66. In some embodiments, the first binding domain comprises a VH having an amino acid sequence of SEQ ID NO:65, and a VL having an amino acid sequence of SEQ ID NO:66. In some embodiments, the first binding domain comprises a VH having an amino acid sequence of SEQ ID NO:67. In some embodiments, the first binding domain comprises a VL having an amino acid sequence of SEQ ID NO:68. In some embodiments, the first binding domain a VH having an amino acid sequence of SEQ ID NO:67, and a VL having an amino acid sequence of SEQ ID NO:68. In some embodiments, the first binding domain comprises a heavy chain having an amino acid sequence of SEQ ID NO:71. In some embodiments, the first binding domain comprises a light chain having an amino acid sequence of SEQ ID NO:72. In some embodiments, the first binding domain comprises a heavy chain having an amino acid sequence of SEQ ID NO:71, and a light chain having an amino acid sequence of SEQ ID NO:72. In some embodiments, the first binding domain comprises an amino acid sequence of SEQ ID NO:70. In some embodiments, the first binding domain comprises a heavy chain having an amino acid sequence of SEQ ID NO:74. In some embodiments, the first binding domain comprises a light chain having an amino acid sequence of SEQ ID NO:75. In some embodiments, the first binding domain comprises a heavy chain having an amino acid sequence of SEQ ID NO:74, and a light chain having an amino acid sequence of SEQ ID NO:75. In some embodiments, the first binding domain comprises an amino acid sequence of SEQ ID NO:73. In some embodiments, the first binding domain comprises a VH comprising an amino acid sequence having at least 95% identity to the amino acid sequence of SEQ ID NO:65. In some embodiments, the first binding domain comprises a VL comprising an amino acid sequence having at least 95% identity to the amino acid sequence of SEQ ID NO:66. In some embodiments, the first binding domain comprises a VH comprising an amino acid sequence having at least 95% identity to the amino acid sequence of SEQ ID NO:65, and a VL comprising an amino acid sequence having at least 95% identity to the amino acid sequence of SEQ ID NO:66. In some embodiments, the first binding domain comprises a VH comprising an amino acid sequence having at least 95% identity to the amino acid sequence of SEQ ID NO:67. In some embodiments, the first binding domain comprises a VL comprising an amino acid sequence having at least 95% identity to the amino acid sequence of SEQ ID NO:68. In some embodiments, the first binding domain a VH comprising an amino acid sequence having at least 95% identity to the amino acid sequence of SEQ ID NO:67, and a VL comprising an amino acid sequence having at least 95% identity to the amino acid sequence of SEQ ID NO:68. In some embodiments, the first binding domain comprises a heavy chain comprising an amino acid sequence having at least 95% identity to the amino acid sequence of SEQ ID NO:71. In some embodiments, the first binding domain comprises a light chain comprising an amino acid sequence having at least 95% identity to the amino acid sequence of SEQ ID NO:72. In some embodiments, the first binding domain comprises a heavy chain comprising an amino acid sequence having at least 95% identity to the amino acid sequence of SEQ ID NO:71, and a light chain comprising an amino acid sequence having at least 95% identity to the amino acid sequence of SEQ ID NO:72. In some embodiments, the first binding domain comprises an amino acid sequence having at least 95% identity to an amino acid sequence of SEQ ID NO:70. In some embodiments, the first binding domain comprises a heavy chain comprising an amino acid sequence having at least 95% identity to the amino acid sequence of SEQ ID NO:74. In some embodiments, the first binding domain comprises a light chain comprising an amino acid sequence having at least 95% identity to the amino acid sequence of SEQ ID NO:75. In some embodiments, the first binding domain comprises a heavy chain comprising an amino acid sequence having at least 95% identity to the amino acid sequence of SEQ ID NO:74, and a light chain comprising an amino acid sequence having at least 95% identity to the amino acid sequence of SEQ ID NO:75. In some embodiments, the first binding domain comprises an amino acid sequence having at least 95% identity to an amino acid sequence of SEQ ID NO:73.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:95; and (ii) a VL comprising a VL CDR1, a VL CDR2, and a VL CDR3 having amino acid sequences of the VL CDR1, VL CDR2, and VL CDR3, respectively, of SEQ ID NO:96. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:89, a VH CDR2 having an amino acid sequence of SEQ ID NO:90, and a VH CDR3 having an amino acid sequence of SEQ ID NO:91; and (ii) a VL comprising a VL CDR1 having an amino acid sequence of SEQ ID NO:92, a VL CDR2 having an amino acid sequence of SEQ ID NO:93, and a VL CDR3 having an amino acid sequence of SEQ ID NO:94. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:376, a VH CDR2 having an amino acid sequence of SEQ ID NO:377, and a VH CDR3 having an amino acid sequence of SEQ ID NO:378; and (ii) a VL comprising a VL CDR1 having an amino acid sequence of SEQ ID NO:379, a VL CDR2 having an amino acid sequence of SEQ ID NO:380, and a VL CDR3 having an amino acid sequence of SEQ ID NO:381. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:382, a VH CDR2 having an amino acid sequence of SEQ ID NO:383, and a VH CDR3 having an amino acid sequence of SEQ ID NO:384; and (ii) a VL comprising a VL CDR1 having an amino acid sequence of SEQ ID NO:385, a VL CDR2 having an amino acid sequence of SEQ ID NO:386, and a VL CDR3 having an amino acid sequence of SEQ ID NO:387. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:388, a VH CDR2 having an amino acid sequence of SEQ ID NO:389, and a VH CDR3 having an amino acid sequence of SEQ ID NO:390; and (ii) a VL comprising a VL CDR1 having an amino acid sequence of SEQ ID NO:391, a VL CDR2 having an amino acid sequence of SEQ ID NO:392, and a VL CDR3 having an amino acid sequence of SEQ ID NO:393. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:394, a VH CDR2 having an amino acid sequence of SEQ ID NO:395, and a VH CDR3 having an amino acid sequence of SEQ ID NO:396; and (ii) a VL comprising a VL CDR1 having an amino acid sequence of SEQ ID NO:397, a VL CDR2 having an amino acid sequence of SEQ ID NO:398, and a VL CDR3 having an amino acid sequence of SEQ ID NO:399. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:394, a VH CDR2 having an amino acid sequence of SEQ ID NO:712, and a VH CDR3 having an amino acid sequence of SEQ ID NO:713; and (ii) a VL comprising a VL CDR1 having an amino acid sequence of SEQ ID NO:397, a VL CDR2 having an amino acid sequence of SEQ ID NO:398, and a VL CDR3 having an amino acid sequence of SEQ ID NO:399. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:400, a VH CDR2 having an amino acid sequence of SEQ ID NO:401, and a VH CDR3 having an amino acid sequence of SEQ ID NO:402; and (ii) a VL comprising a VL CDR1 having an amino acid sequence of SEQ ID NO:403, a VL CDR2 having an amino acid sequence of SEQ ID NO:404, and a VL CDR3 having an amino acid sequence of SEQ ID NO:405. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:406, a VH CDR2 having an amino acid sequence of SEQ ID NO:407, and a VH CDR3 having an amino acid sequence of SEQ ID NO:408; and (ii) a VL comprising a VL CDR1 having an amino acid sequence of SEQ ID NO:409, a VL CDR2 having an amino acid sequence of SEQ ID NO:410, and a VL CDR3 having an amino acid sequence of SEQ ID NO:411. In some embodiments, the first binding domain comprises a VH having an amino acid sequence of SEQ ID NO:95. In some embodiments, the first binding domain comprises a VL having an amino acid sequence of SEQ ID NO:96. In some embodiments, the first binding domain comprises a VH having an amino acid sequence of SEQ ID NO:95, and a VL having an amino acid sequence of SEQ ID NO:96. In some embodiments, the first binding domain comprises an amino acid sequence of SEQ ID NO:97. In some embodiments, the first binding domain comprises a VH comprising an amino acid sequence having at least 95% identity to the amino acid sequence of SEQ ID NO:95. In some embodiments, the first binding domain comprises a VL comprising an amino acid sequence having at least 95% identity to the amino acid sequence of SEQ ID NO:96. In some embodiments, the first binding domain comprises a VH comprising an amino acid sequence having at least 95% identity to the amino acid sequence of SEQ ID NO:95, and a VL comprising an amino acid sequence having at least 95% identity to the amino acid sequence of SEQ ID NO:96. In some embodiments, the first binding domain comprises an amino acid sequence having at least 95% identity to an amino acid sequence of SEQ ID NO:97.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:104; and (ii) a VL comprising a VL CDR1, a VL CDR2, and a VL CDR3 having amino acid sequences of the VL CDR1, VL CDR2, and VL CDR3, respectively, of SEQ ID NO:105. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:98, a VH CDR2 having an amino acid sequence of SEQ ID NO:99, and a VH CDR3 having an amino acid sequence of SEQ ID NO:100, and (ii) a VL comprising a VL CDR1 having an amino acid sequence of SEQ ID NO:101, a VL CDR2 having an amino acid sequence of SEQ ID NO:102, and a VL CDR3 having an amino acid sequence of SEQ ID NO:103. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:412, a VH CDR2 having an amino acid sequence of SEQ ID NO:413, and a VH CDR3 having an amino acid sequence of SEQ ID NO:414; and (ii) a VL comprising a VL CDR1 having an amino acid sequence of SEQ ID NO:415, a VL CDR2 having an amino acid sequence of SEQ ID NO:416, and a VL CDR3 having an amino acid sequence of SEQ ID NO:417. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:418, a VH CDR2 having an amino acid sequence of SEQ ID NO:419, and a VH CDR3 having an amino acid sequence of SEQ ID NO:420; and (ii) a VL comprising a VL CDR1 having an amino acid sequence of SEQ ID NO:421, a VL CDR2 having an amino acid sequence of SEQ ID NO:422, and a VL CDR3 having an amino acid sequence of SEQ ID NO:423. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:424, a VH CDR2 having an amino acid sequence of SEQ ID NO:425, and a VH CDR3 having an amino acid sequence of SEQ ID NO:426; and (ii) a VL comprising a VL CDR1 having an amino acid sequence of SEQ ID NO:427, a VL CDR2 having an amino acid sequence of SEQ ID NO:428, and a VL CDR3 having an amino acid sequence of SEQ ID NO:429. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:430, a VH CDR2 having an amino acid sequence of SEQ ID NO:431, and a VH CDR3 having an amino acid sequence of SEQ ID NO:432; and (ii) a VL comprising a VL CDR1 having an amino acid sequence of SEQ ID NO:433, a VL CDR2 having an amino acid sequence of SEQ ID NO:434, and a VL CDR3 having an amino acid sequence of SEQ ID NO:435. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:430, a VH CDR2 having an amino acid sequence of SEQ ID NO:714, and a VH CDR3 having an amino acid sequence of SEQ ID NO:715; and (ii) a VL comprising a VL CDR1 having an amino acid sequence of SEQ ID NO:433, a VL CDR2 having an amino acid sequence of SEQ ID NO:434, and a VL CDR3 having an amino acid sequence of SEQ ID NO:435. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:436, a VH CDR2 having an amino acid sequence of SEQ ID NO:437, and a VH CDR3 having an amino acid sequence of SEQ ID NO:438; and (ii) a VL comprising a VL CDR1 having an amino acid sequence of SEQ ID NO:439, a VL CDR2 having an amino acid sequence of SEQ ID NO:440, and a VL CDR3 having an amino acid sequence of SEQ ID NO:441. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:442, a VH CDR2 having an amino acid sequence of SEQ ID NO:443, and a VH CDR3 having an amino acid sequence of SEQ ID NO:444; and (ii) a VL comprising a VL CDR1 having an amino acid sequence of SEQ ID NO:445, a VL CDR2 having an amino acid sequence of SEQ ID NO:446, and a VL CDR3 having an amino acid sequence of SEQ ID NO:447. In some embodiments, the first binding domain comprises a VH having an amino acid sequence of SEQ ID NO:104. In some embodiments, the first binding domain comprises a VL having an amino acid sequence of SEQ ID NO:105. In some embodiments, the first binding domain comprises a VH having an amino acid sequence of SEQ ID NO:104, and a VL having an amino acid sequence of SEQ ID NO:105. In some embodiments, the first binding domain comprises an amino acid sequence of SEQ ID NO:106. In some embodiments, the first binding domain comprises a VH comprising an amino acid sequence having at least 95% identity to the amino acid sequence of SEQ ID NO:104. In some embodiments, the first binding domain comprises a VL comprising an amino acid sequence having at least 95% identity to the amino acid sequence of SEQ ID NO:105. In some embodiments, the first binding domain comprises a VH comprising an amino acid sequence having at least 95% identity to the amino acid sequence of SEQ ID NO:104, and a VL comprising an amino acid sequence having at least 95% identity to the amino acid sequence of SEQ ID NO:105. In some embodiments, the first binding domain comprises an amino acid sequence having at least 95% identity to an amino acid sequence of SEQ ID NO:106.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:113; and (ii) a VL comprising a VL CDR1, a VL CDR2, and a VL CDR3 having amino acid sequences of the VL CDR1, VL CDR2, and VL CDR3, respectively, of SEQ ID NO:114. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:107, a VH CDR2 having an amino acid sequence of SEQ ID NO:108, and a VH CDR3 having an amino acid sequence of SEQ ID NO:109, and (ii) a VL comprising a VL CDR1 having an amino acid sequence of SEQ ID NO:110, a VL CDR2 having an amino acid sequence of SEQ ID NO:111, and a VL CDR3 having an amino acid sequence of SEQ ID NO:112. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:448, a VH CDR2 having an amino acid sequence of SEQ ID NO:449, and a VH CDR3 having an amino acid sequence of SEQ ID NO:450; and (ii) a VL comprising a VL CDR1 having an amino acid sequence of SEQ ID NO:451, a VL CDR2 having an amino acid sequence of SEQ ID NO:452, and a VL CDR3 having an amino acid sequence of SEQ ID NO:453. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:454, a VH CDR2 having an amino acid sequence of SEQ ID NO:455, and a VH CDR3 having an amino acid sequence of SEQ ID NO:456; and (ii) a VL comprising a VL CDR1 having an amino acid sequence of SEQ ID NO:457, a VL CDR2 having an amino acid sequence of SEQ ID NO:458, and a VL CDR3 having an amino acid sequence of SEQ ID NO:459. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:460, a VH CDR2 having an amino acid sequence of SEQ ID NO:461, and a VH CDR3 having an amino acid sequence of SEQ ID NO:462; and (ii) a VL comprising a VL CDR1 having an amino acid sequence of SEQ ID NO:463, a VL CDR2 having an amino acid sequence of SEQ ID NO:464, and a VL CDR3 having an amino acid sequence of SEQ ID NO:465. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:466, a VH CDR2 having an amino acid sequence of SEQ ID NO:467, and a VH CDR3 having an amino acid sequence of SEQ ID NO:468; and (ii) a VL comprising a VL CDR1 having an amino acid sequence of SEQ ID NO:469, a VL CDR2 having an amino acid sequence of SEQ ID NO:470, and a VL CDR3 having an amino acid sequence of SEQ ID NO:471. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:466, a VH CDR2 having an amino acid sequence of SEQ ID NO:716, and a VH CDR3 having an amino acid sequence of SEQ ID NO:717; and (ii) a VL comprising a VL CDR1 having an amino acid sequence of SEQ ID NO:469, a VL CDR2 having an amino acid sequence of SEQ ID NO:470, and a VL CDR3 having an amino acid sequence of SEQ ID NO:471. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:472, a VH CDR2 having an amino acid sequence of SEQ ID NO:473, and a VH CDR3 having an amino acid sequence of SEQ ID NO:474; and (ii) a VL comprising a VL CDR1 having an amino acid sequence of SEQ ID NO:475, a VL CDR2 having an amino acid sequence of SEQ ID NO:476, and a VL CDR3 having an amino acid sequence of SEQ ID NO:477. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:478, a VH CDR2 having an amino acid sequence of SEQ ID NO:479, and a VH CDR3 having an amino acid sequence of SEQ ID NO:480; and (ii) a VL comprising a VL CDR1 having an amino acid sequence of SEQ ID NO:481, a VL CDR2 having an amino acid sequence of SEQ ID NO:482, and a VL CDR3 having an amino acid sequence of SEQ ID NO:483. In some embodiments, the first binding domain comprises a VH having an amino acid sequence of SEQ ID NO:113. In some embodiments, the first binding domain comprises a VL having an amino acid sequence of SEQ ID NO:114. In some embodiments, the first binding domain comprises a VH having an amino acid sequence of SEQ ID NO:113, and a VL having an amino acid sequence of SEQ ID NO:114. In some embodiments, the first binding domain comprises a heavy chain having an amino acid sequence of SEQ ID NO:115. In some embodiments, the first binding domain comprises a light chain having an amino acid sequence of SEQ ID NO:116. In some embodiments, the first binding domain comprises a heavy chain having an amino acid sequence of SEQ ID NO:115, and a light chain having an amino acid sequence of SEQ ID NO:116. In some embodiments, the first binding domain comprises a VH comprising an amino acid sequence having at least 95% identity to the amino acid sequence of SEQ ID NO:113. In some embodiments, the first binding domain comprises a VL comprising an amino acid sequence having at least 95% identity to the amino acid sequence of SEQ ID NO:114. In some embodiments, the first binding domain comprises a VH comprising an amino acid sequence having at least 95% identity to the amino acid sequence of SEQ ID NO:113, and a VL comprising an amino acid sequence having at least 95% identity to the amino acid sequence of SEQ ID NO:114. In some embodiments, the first binding domain comprises a heavy chain comprising an amino acid sequence having at least 95% identity to the amino acid sequence of SEQ ID NO:115. In some embodiments, the first binding domain comprises a light chain comprising an amino acid sequence having at least 95% identity to the amino acid sequence of SEQ ID NO:116. In some embodiments, the first binding domain comprises a heavy chain comprising an amino acid sequence having at least 95% identity to the amino acid sequence of SEQ ID NO:115, and a light chain comprising an amino acid sequence having at least 95% identity to the amino acid sequence of SEQ ID NO:116.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:123; and (ii) a VL comprising a VL CDR1, a VL CDR2, and a VL CDR3 having amino acid sequences of the VL CDR1, VL CDR2, and VL CDR3, respectively, of SEQ ID NO:124. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:117, a VH CDR2 having an amino acid sequence of SEQ ID NO:118, and a VH CDR3 having an amino acid sequence of SEQ ID NO:119, and (ii) a VL comprising a VL CDR1 having an amino acid sequence of SEQ ID NO:120, a VL CDR2 having an amino acid sequence of SEQ ID NO:121, and a VL CDR3 having an amino acid sequence of SEQ ID NO:122. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:484, a VH CDR2 having an amino acid sequence of SEQ ID NO:485, and a VH CDR3 having an amino acid sequence of SEQ ID NO:486; and (ii) a VL comprising a VL CDR1 having an amino acid sequence of SEQ ID NO:487, a VL CDR2 having an amino acid sequence of SEQ ID NO:488, and a VL CDR3 having an amino acid sequence of SEQ ID NO:489. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:490, a VH CDR2 having an amino acid sequence of SEQ ID NO:491, and a VH CDR3 having an amino acid sequence of SEQ ID NO:492; and (ii) a VL comprising a VL CDR1 having an amino acid sequence of SEQ ID NO:493, a VL CDR2 having an amino acid sequence of SEQ ID NO:494, and a VL CDR3 having an amino acid sequence of SEQ ID NO:495. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:496, a VH CDR2 having an amino acid sequence of SEQ ID NO:497, and a VH CDR3 having an amino acid sequence of SEQ ID NO:498; and (ii) a VL comprising a VL CDR1 having an amino acid sequence of SEQ ID NO:499, a VL CDR2 having an amino acid sequence of SEQ ID NO:500, and a VL CDR3 having an amino acid sequence of SEQ ID NO:501. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:502, a VH CDR2 having an amino acid sequence of SEQ ID NO:503, and a VH CDR3 having an amino acid sequence of SEQ ID NO:504; and (ii) a VL comprising a VL CDR1 having an amino acid sequence of SEQ ID NO:505, a VL CDR2 having an amino acid sequence of SEQ ID NO:506, and a VL CDR3 having an amino acid sequence of SEQ ID NO:507. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:502, a VH CDR2 having an amino acid sequence of SEQ ID NO:718, and a VH CDR3 having an amino acid sequence of SEQ ID NO:719; and (ii) a VL comprising a VL CDR1 having an amino acid sequence of SEQ ID NO:505, a VL CDR2 having an amino acid sequence of SEQ ID NO:506, and a VL CDR3 having an amino acid sequence of SEQ ID NO:507. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:508, a VH CDR2 having an amino acid sequence of SEQ ID NO:509, and a VH CDR3 having an amino acid sequence of SEQ ID NO:510; and (ii) a VL comprising a VL CDR1 having an amino acid sequence of SEQ ID NO:511, a VL CDR2 having an amino acid sequence of SEQ ID NO:512, and a VL CDR3 having an amino acid sequence of SEQ ID NO:513. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:514, a VH CDR2 having an amino acid sequence of SEQ ID NO:515, and a VH CDR3 having an amino acid sequence of SEQ ID NO:516; and (ii) a VL comprising a VL CDR1 having an amino acid sequence of SEQ ID NO:517, a VL CDR2 having an amino acid sequence of SEQ ID NO:518, and a VL CDR3 having an amino acid sequence of SEQ ID NO:519. In some embodiments, the first binding domain comprises a VH having an amino acid sequence of SEQ ID NO:123. In some embodiments, the first binding domain comprises a VL having an amino acid sequence of SEQ ID NO:124. In some embodiments, the first binding domain comprises a VH having an amino acid sequence of SEQ ID NO:123, and a VL having an amino acid sequence of SEQ ID NO:124. In some embodiments, the first binding domain comprises a heavy chain having an amino acid sequence of SEQ ID NO:125. In some embodiments, the first binding domain comprises a light chain having an amino acid sequence of SEQ ID NO:126. In some embodiments, the first binding domain comprises a heavy chain having an amino acid sequence of SEQ ID NO:125, and a light chain having an amino acid sequence of SEQ ID NO:126. In some embodiments, the first binding domain comprises a VH comprising an amino acid sequence having at least 95% identity to the amino acid sequence of SEQ ID NO:123. In some embodiments, the first binding domain comprises a VL comprising an amino acid sequence having at least 95% identity to the amino acid sequence of SEQ ID NO:124. In some embodiments, the first binding domain comprises a VH comprising an amino acid sequence having at least 95% identity to the amino acid sequence of SEQ ID NO:123, and a VL comprising an amino acid sequence having at least 95% identity to the amino acid sequence of SEQ ID NO:124. In some embodiments, the first binding domain comprises a heavy chain comprising an amino acid sequence having at least 95% identity to the amino acid sequence of SEQ ID NO:125. In some embodiments, the first binding domain comprises a light chain comprising an amino acid sequence having at least 95% identity to the amino acid sequence of SEQ ID NO:126. In some embodiments, the first binding domain comprises a heavy chain comprising an amino acid sequence having at least 95% identity to the amino acid sequence of SEQ ID NO:125, and a light chain comprising an amino acid sequence having at least 95% identity to the amino acid sequence of SEQ ID NO:126.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:133; and (ii) a VL comprising a VL CDR1, a VL CDR2, and a VL CDR3 having amino acid sequences of the VL CDR1, VL CDR2, and VL CDR3, respectively, of SEQ ID NO:134. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:127, a VH CDR2 having an amino acid sequence of SEQ ID NO:128, and a VH CDR3 having an amino acid sequence of SEQ ID NO:129, and (ii) a VL comprising a VL CDR1 having an amino acid sequence of SEQ ID NO:130, a VL CDR2 having an amino acid sequence of SEQ ID NO:131, and a VL CDR3 having an amino acid sequence of SEQ ID NO:132. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:520, a VH CDR2 having an amino acid sequence of SEQ ID NO:521, and a VH CDR3 having an amino acid sequence of SEQ ID NO:522; and (ii) a VL comprising a VL CDR1 having an amino acid sequence of SEQ ID NO:523, a VL CDR2 having an amino acid sequence of SEQ ID NO:524, and a VL CDR3 having an amino acid sequence of SEQ ID NO:525. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:526, a VH CDR2 having an amino acid sequence of SEQ ID NO:527, and a VH CDR3 having an amino acid sequence of SEQ ID NO:528; and (ii) a VL comprising a VL CDR1 having an amino acid sequence of SEQ ID NO:529, a VL CDR2 having an amino acid sequence of SEQ ID NO:530, and a VL CDR3 having an amino acid sequence of SEQ ID NO:531. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:532, a VH CDR2 having an amino acid sequence of SEQ ID NO:533, and a VH CDR3 having an amino acid sequence of SEQ ID NO:534; and (ii) a VL comprising a VL CDR1 having an amino acid sequence of SEQ ID NO:535, a VL CDR2 having an amino acid sequence of SEQ ID NO:536, and a VL CDR3 having an amino acid sequence of SEQ ID NO:537. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:538, a VH CDR2 having an amino acid sequence of SEQ ID NO:539, and a VH CDR3 having an amino acid sequence of SEQ ID NO:540; and (ii) a VL comprising a VL CDR1 having an amino acid sequence of SEQ ID NO:541, a VL CDR2 having an amino acid sequence of SEQ ID NO:542, and a VL CDR3 having an amino acid sequence of SEQ ID NO:543. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:538, a VH CDR2 having an amino acid sequence of SEQ ID NO:720, and a VH CDR3 having an amino acid sequence of SEQ ID NO:721; and (ii) a VL comprising a VL CDR1 having an amino acid sequence of SEQ ID NO:541, a VL CDR2 having an amino acid sequence of SEQ ID NO:542, and a VL CDR3 having an amino acid sequence of SEQ ID NO:543. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:544, a VH CDR2 having an amino acid sequence of SEQ ID NO:545, and a VH CDR3 having an amino acid sequence of SEQ ID NO:546; and (ii) a VL comprising a VL CDR1 having an amino acid sequence of SEQ ID NO:547, a VL CDR2 having an amino acid sequence of SEQ ID NO:548, and a VL CDR3 having an amino acid sequence of SEQ ID NO:549. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:550, a VH CDR2 having an amino acid sequence of SEQ ID NO:551, and a VH CDR3 having an amino acid sequence of SEQ ID NO:552; and (ii) a VL comprising a VL CDR1 having an amino acid sequence of SEQ ID NO:553, a VL CDR2 having an amino acid sequence of SEQ ID NO:554, and a VL CDR3 having an amino acid sequence of SEQ ID NO:555. In some embodiments, the first binding domain comprises a VH having an amino acid sequence of SEQ ID NO:133. In some embodiments, the first binding domain comprises a VL having an amino acid sequence of SEQ ID NO:134. In some embodiments, the first binding domain comprises a VH having an amino acid sequence of SEQ ID NO:133, and a VL having an amino acid sequence of SEQ ID NO:134. In some embodiments, the first binding domain comprises a heavy chain having an amino acid sequence of SEQ ID NO:135. In some embodiments, the first binding domain comprises a light chain having an amino acid sequence of SEQ ID NO:136. In some embodiments, the first binding domain comprises a heavy chain having an amino acid sequence of SEQ ID NO:135, and a light chain having an amino acid sequence of SEQ ID NO:136. In some embodiments, the first binding domain comprises a VH comprising an amino acid sequence having at least 95% identity to the amino acid sequence of SEQ ID NO:133. In some embodiments, the first binding domain comprises a VL comprising an amino acid sequence having at least 95% identity to the amino acid sequence of SEQ ID NO:134. In some embodiments, the first binding domain comprises a VH comprising an amino acid sequence having at least 95% identity to the amino acid sequence of SEQ ID NO:133, and a VL comprising an amino acid sequence having at least 95% identity to the amino acid sequence of SEQ ID NO:134. In some embodiments, the first binding domain comprises a heavy chain comprising an amino acid sequence having at least 95% identity to the amino acid sequence of SEQ ID NO:135. In some embodiments, the first binding domain comprises a light chain comprising an amino acid sequence having at least 95% identity to the amino acid sequence of SEQ ID NO:136. In some embodiments, the first binding domain comprises a heavy chain comprising an amino acid sequence having at least 95% identity to the amino acid sequence of SEQ ID NO:135, and a light chain comprising an amino acid sequence having at least 95% identity to the amino acid sequence of SEQ ID NO:136.

In another aspect, provided herein is a bispecific antibody comprising: (a) a first binding domain that binds to TRGV9, and (b) a second binding domain that binds to a cancer antigen present on the surface of a cancer cell. In some embodiments, the antigen on the surface of the cancer cell is a tumor-specific antigen. In some embodiments, the antigen on the surface of the cancer cell is a tumor associated antigen. In some embodiments, the antigen on the surface of the cancer cell is a neoantigen. In certain embodiments, the first binding domain of the bispecific antibody specifically binds TRGV9. In some embodiments, the TRGV9 is present on the surface of a γδ T cell. In some embodiments, the cancer cell is killed when the bispecific antibody binds to the TRGV9 on the surface of the γδ T cell and the antigen on the surface of the cancer cell. Bispecific antibodies comprising any of the TRGV9 antibodies provided herein as the first binding domain are contemplated, in certain embodiments.

In another aspect, provided herein is a bispecific antibody comprising: (a) a first binding domain that binds to TRGV9, and (b) a second binding domain that binds to CD123. In certain embodiments, the first binding domain of the bispecific antibody specifically binds TRGV9. In some embodiments, the TRGV9 is present on the surface of a γδ T cell. In some embodiments, the CD123 is on the surface of a cell. In certain embodiments, the TRGV9 is present on the surface of a γδ T cell, and the CD123 is on the surface of a cell. In some embodiments, the cell having the CD123 on the surface is killed when the bispecific antibody binds to the TRGV9 on the surface of the γδ T cell and the CD123 on the surface of the cell. In some embodiments, the CD123 is on the surface of a cancer cell. In certain embodiments, the TRGV9 is present on the surface of a γδ T cell, and the CD123 is on the surface of a cancer cell. In some embodiments, the cancer cell is killed when the bispecific antibody binds to the TRGV9 on the surface of the γδ T cell and the CD123 on the surface of the cell. Bispecific antibodies comprising any of the TRGV9 antibodies provided herein as the first binding domain are contemplated, in certain embodiments. In addition, bispecific antibodies comprising any of the TRGV9 antibodies provided herein as the first binding domain, and a second binding domain that binds to CD123 are also contemplated in certain embodiments.

In another aspect, provided herein is a bispecific antibody comprising: (a) a first binding domain that binds to TRGV9, and (b) a second binding domain that binds to CD123, wherein the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In another aspect, provided herein is a bispecific antibody comprising: (a) a first binding domain that binds to TRGV9, and (b) a second binding domain that binds to CD123, wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In another aspect, provided herein is a bispecific antibody comprising: (a) a first binding domain that binds to TRGV9, and (b) a second binding domain that binds to CD123, wherein the second binding domain comprises: (i) a VH comprising a VH CDR1 having an amino acid sequence of SEQ ID NO:556, a VH CDR2 having an amino acid sequence of SEQ ID NO:557, and a VH CDR3 having an amino acid sequence of SEQ ID NO:558; and (ii) a VL comprising a VL CDR1 having an amino acid sequence of SEQ ID NO:559, a VL CDR2 having an amino acid sequence of SEQ ID NO:560, and a VL CDR3 having an amino acid sequence of SEQ ID NO:561. In another aspect, provided herein is a bispecific antibody comprising: (a) a first binding domain that binds to TRGV9, and (b) a second binding domain that binds to CD123, wherein the second binding domain comprises: (i) a VH comprising a VH CDR1 having an amino acid sequence of SEQ ID NO:562, a VH CDR2 having an amino acid sequence of SEQ ID NO:563, and a VH CDR3 having an amino acid sequence of SEQ ID NO:564; and (ii) a VL comprising a VL CDR1 having an amino acid sequence of SEQ ID NO:565, a VL CDR2 having an amino acid sequence of SEQ ID NO:566, and a VL CDR3 having an amino acid sequence of SEQ ID NO:567. In another aspect, provided herein is a bispecific antibody comprising: (a) a first binding domain that binds to TRGV9, and (b) a second binding domain that binds to CD123, wherein the second binding domain comprises: (i) a VH comprising a VH CDR1 having an amino acid sequence of SEQ ID NO:568, a VH CDR2 having an amino acid sequence of SEQ ID NO:569, and a VH CDR3 having an amino acid sequence of SEQ ID NO:570; and (ii) a VL comprising a VL CDR1 having an amino acid sequence of SEQ ID NO:571, a VL CDR2 having an amino acid sequence of SEQ ID NO:572, and a VL CDR3 having an amino acid sequence of SEQ ID NO:573. In another aspect, provided herein is a bispecific antibody comprising: (a) a first binding domain that binds to TRGV9, and (b) a second binding domain that binds to CD123, wherein the second binding domain comprises: (i) a VH comprising a VH CDR1 having an amino acid sequence of SEQ ID NO:574, a VH CDR2 having an amino acid sequence of SEQ ID NO:575, and a VH CDR3 having an amino acid sequence of SEQ ID NO:576; and (ii) a VL comprising a VL CDR1 having an amino acid sequence of SEQ ID NO:577, a VL CDR2 having an amino acid sequence of SEQ ID NO:578, and a VL CDR3 having an amino acid sequence of SEQ ID NO:579. In another aspect, provided herein is a bispecific antibody comprising: (a) a first binding domain that binds to TRGV9, and (b) a second binding domain that binds to CD123, wherein the second binding domain comprises: (i) a VH comprising a VH CDR1 having an amino acid sequence of SEQ ID NO:574, a VH CDR2 having an amino acid sequence of SEQ ID NO:722, and a VH CDR3 having an amino acid sequence of SEQ ID NO:723; and (ii) a VL comprising a VL CDR1 having an amino acid sequence of SEQ ID NO:577, a VL CDR2 having an amino acid sequence of SEQ ID NO:578, and a VL CDR3 having an amino acid sequence of SEQ ID NO:579. In another aspect, provided herein is a bispecific antibody comprising: (a) a first binding domain that binds to TRGV9, and (b) a second binding domain that binds to CD123, wherein the second binding domain comprises: (i) a VH comprising a VH CDR1 having an amino acid sequence of SEQ ID NO:580, a VH CDR2 having an amino acid sequence of SEQ ID NO:581, and a VH CDR3 having an amino acid sequence of SEQ ID NO:582; and (ii) a VL comprising a VL CDR1 having an amino acid sequence of SEQ ID NO:583, a VL CDR2 having an amino acid sequence of SEQ ID NO:584, and a VL CDR3 having an amino acid sequence of SEQ ID NO:585. In another aspect, provided herein is a bispecific antibody comprising: (a) a first binding domain that binds to TRGV9, and (b) a second binding domain that binds to CD123, wherein the second binding domain comprises: (i) a VH comprising a VH CDR1 having an amino acid sequence of SEQ ID NO:586, a VH CDR2 having an amino acid sequence of SEQ ID NO:587, and a VH CDR3 having an amino acid sequence of SEQ ID NO:588; and (ii) a VL comprising a VL CDR1 having an amino acid sequence of SEQ ID NO:589, a VL CDR2 having an amino acid sequence of SEQ ID NO:590, and a VL CDR3 having an amino acid sequence of SEQ ID NO:591. In some embodiments, the second binding domain comprises a VH having an amino acid sequence of SEQ ID NO:15. In some embodiments, the second binding domain comprises a VL having an amino acid sequence of SEQ ID NO:16. In some embodiments, the second binding domain comprises a VH having an amino acid sequence of SEQ ID NO:15, and a VL having an amino acid sequence of SEQ ID NO:16. In some embodiments, the second binding domain comprises a heavy chain having an amino acid sequence of SEQ ID NO:25. In some embodiments, the second binding domain comprises a light chain having an amino acid sequence of SEQ ID NO:26. In some embodiments, the second binding domain comprises a heavy chain having an amino acid sequence of SEQ ID NO:25, and a light chain having an amino acid sequence of SEQ ID NO:26. In some embodiments, the second binding domain comprises an amino acid sequence of SEQ ID NO:18. In some embodiments, the second binding domain comprises a VH comprising an amino acid sequence having at least 95% identity to the amino acid sequence of SEQ ID NO:15. In some embodiments, the second binding domain comprises a VL comprising an amino acid sequence having at least 95% identity to the amino acid sequence of SEQ ID NO:16. In some embodiments, the second binding domain comprises a VH comprising an amino acid sequence having at least 95% identity to the amino acid sequence of SEQ ID NO:15, and a VL comprising an amino acid sequence having at least 95% identity to the amino acid sequence of SEQ ID NO:16. In some embodiments, the second binding domain comprises a heavy chain comprising an amino acid sequence having at least 95% identity to the amino acid sequence of SEQ ID NO:25. In some embodiments, the second binding domain comprises a light chain comprising an amino acid sequence having at least 95% identity to the amino acid sequence of SEQ ID NO:26. In some embodiments, the second binding domain comprises a heavy chain comprising an amino acid sequence having at least 95% identity to the amino acid sequence of SEQ ID NO:25, and a light chain comprising an amino acid sequence having at least 95% identity to the amino acid sequence of SEQ ID NO:26. In some embodiments, the second binding domain comprises an amino acid sequence having at least 95% identity to an amino acid sequence of SEQ ID NO:18.

In another aspect, provided herein is a bispecific antibody comprising: (a) a first binding domain that binds to TRGV9, and (b) a second binding domain that binds to CD123, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:7; and (ii) a VL comprising a VL CDR1, a VL CDR2, and a VL CDR3 having amino acid sequences of the VL CDR1, VL CDR2, and VL CDR3, respectively, of SEQ ID NO:8; and wherein the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In another aspect, provided herein is a bispecific antibody comprising: (a) a first binding domain that binds to TRGV9, and (b) a second binding domain that binds to CD123, wherein the first binding domain comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:3; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6; and wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In some embodiments, the first binding domain comprises a VH having an amino acid sequence of SEQ ID NO:7. In some embodiments, the first binding domain comprises a VL having an amino acid sequence of SEQ ID NO:8. In some embodiments, the first binding domain comprises a VH having an amino acid sequence of SEQ ID NO:7, and a VL having an amino acid sequence of SEQ ID NO:8. In some embodiments, the first binding domain comprises a heavy chain having an amino acid sequence of SEQ ID NO:23. In some embodiments, the first binding domain comprises a light chain having an amino acid sequence of SEQ ID NO:24. In some embodiments, the first binding domain comprises a heavy chain having an amino acid sequence of SEQ ID NO:23, and a light chain having an amino acid sequence of SEQ ID NO:24. In some embodiments, the first binding domain comprises an amino acid sequence of SEQ ID NO:17. In some embodiments, the first binding domain comprises a heavy chain having an amino acid sequence of SEQ ID NO:69. In some embodiments, the first binding domain comprises a light chain having an amino acid sequence of SEQ ID NO:24. In some embodiments, the first binding domain comprises a heavy chain having an amino acid sequence of SEQ ID NO:69, and a light chain having an amino acid sequence of SEQ ID NO:24.

In some embodiments, the second binding domain comprises a VH having an amino acid sequence of SEQ ID NO:15. In some embodiments, the second binding domain comprises a VL having an amino acid sequence of SEQ ID NO:16. In some embodiments, the second binding domain comprises a VH having an amino acid sequence of SEQ ID NO:15, and a VL having an amino acid sequence of SEQ ID NO:16. In some embodiments, the second binding domain comprises a heavy chain having an amino acid sequence of SEQ ID NO:25. In some embodiments, the second binding domain comprises a light chain having an amino acid sequence of SEQ ID NO:26. In some embodiments, the second binding domain comprises a heavy chain having an amino acid sequence of SEQ ID NO:25, and a light chain having an amino acid sequence of SEQ ID NO:26. In some embodiments, the second binding domain comprises an amino acid sequence of SEQ ID NO:18. In some embodiments, the first binding domain comprises a VH comprising an amino acid sequence having at least 95% identity to the amino acid sequence of SEQ ID NO:7. In some embodiments, the first binding domain comprises a VL comprising an amino acid sequence having at least 95% identity to the amino acid sequence of SEQ ID NO:8. In some embodiments, the first binding domain comprises a VH comprising an amino acid sequence having at least 95% identity to the amino acid sequence of SEQ ID NO:7, and a VL comprising an amino acid sequence having at least 95% identity to the amino acid sequence of SEQ ID NO:8. In some embodiments, the first binding domain comprises a heavy chain comprising an amino acid sequence having at least 95% identity to the amino acid sequence of SEQ ID NO:23. In some embodiments, the first binding domain comprises a light chain comprising an amino acid sequence having at least 95% identity to the amino acid sequence of SEQ ID NO:24. In some embodiments, the first binding domain comprises a heavy chain comprising an amino acid sequence having at least 95% identity to the amino acid sequence of SEQ ID NO:23, and a light chain comprising an amino acid sequence having at least 95% identity to the amino acid sequence of SEQ ID NO:24. In some embodiments, the first binding domain comprises an amino acid sequence of SEQ ID NO:17. In some embodiments, the first binding domain comprises a heavy chain comprising an amino acid sequence having at least 95% identity to the amino acid sequence of SEQ ID NO:69. In some embodiments, the first binding domain comprises a light chain comprising an amino acid sequence having at least 95% identity to the amino acid sequence of SEQ ID NO:24. In some embodiments, the first binding domain comprises a heavy chain comprising an amino acid sequence having at least 95% identity to the amino acid sequence of SEQ ID NO:69, and a light chain comprising an amino acid sequence having at least 95% identity to the amino acid sequence of SEQ ID NO:24. In some embodiments, the second binding domain comprises a VH comprising an amino acid sequence having at least 95% identity to the amino acid sequence of SEQ ID NO:15. In some embodiments, the second binding domain comprises a VL comprising an amino acid sequence having at least 95% identity to the amino acid sequence of SEQ ID NO:16. In some embodiments, the second binding domain comprises a VH comprising an amino acid sequence having at least 95% identity to the amino acid sequence of SEQ ID NO:15, and a VL comprising an amino acid sequence having at least 95% identity to the amino acid sequence of SEQ ID NO:16. In some embodiments, the second binding domain comprises a heavy chain comprising an amino acid sequence having at least 95% identity to the amino acid sequence of SEQ ID NO:25. In some embodiments, the second binding domain comprises a light chain comprising an amino acid sequence having at least 95% identity to the amino acid sequence of SEQ ID NO:26. In some embodiments, the second binding domain comprises a heavy chain comprising an amino acid sequence having at least 95% identity to the amino acid sequence of SEQ ID NO:25, and a light chain comprising an amino acid sequence having at least 95% identity to the amino acid sequence of SEQ ID NO:26. In some embodiments, the second binding domain comprises an amino acid sequence of SEQ ID NO:18.

In another aspect, provided herein is a bispecific antibody comprising: (a) a first binding domain that binds to TRGV9, and (b) a second binding domain that binds to CD123, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:34; and (ii) a VL comprising a VL CDR1, a VL CDR2, and a VL CDR3 having amino acid sequences of the VL CDR1, VL CDR2, and VL CDR3, respectively, of SEQ ID NO:8; and wherein the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In another aspect, provided herein is a bispecific antibody comprising: (a) a first binding domain that binds to TRGV9, and (b) a second binding domain that binds to CD123, wherein the first binding domain comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:31; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6; and wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In some embodiments, the first binding domain comprises a VH having an amino acid sequence of SEQ ID NO:34. In some embodiments, the first binding domain comprises a VL having an amino acid sequence of SEQ ID NO:8. In some embodiments, the first binding domain comprises a VH having an amino acid sequence of SEQ ID NO:34, and a VL having an amino acid sequence of SEQ ID NO:8. In some embodiments, the second binding domain comprises a VH having an amino acid sequence of SEQ ID NO:15. In some embodiments, the second binding domain comprises a VL having an amino acid sequence of SEQ ID NO:16. In some embodiments, the second binding domain comprises a VH having an amino acid sequence of SEQ ID NO:15, and a VL having an amino acid sequence of SEQ ID NO:16. In some embodiments, the second binding domain comprises a heavy chain having an amino acid sequence of SEQ ID NO:25. In some embodiments, the second binding domain comprises a light chain having an amino acid sequence of SEQ ID NO:26. In some embodiments, the second binding domain comprises a heavy chain having an amino acid sequence of SEQ ID NO:25, and a light chain having an amino acid sequence of SEQ ID NO:26. In some embodiments, the second binding domain comprises an amino acid sequence of SEQ ID NO:18. In some embodiments, the first binding domain comprises a VH comprising an amino acid sequence having at least 95% identity to the amino acid sequence of SEQ ID NO:34. In some embodiments, the first binding domain comprises a VL comprising an amino acid sequence having at least 95% identity to the amino acid sequence of SEQ ID NO:8. In some embodiments, the first binding domain comprises a VH comprising an amino acid sequence having at least 95% identity to the amino acid sequence of SEQ ID NO:34, and a VL comprising an amino acid sequence having at least 95% identity to the amino acid sequence of SEQ ID NO:8. In some embodiments, the second binding domain comprises a VH comprising an amino acid sequence having at least 95% identity to the amino acid sequence of SEQ ID NO:15. In some embodiments, the second binding domain comprises a VL comprising an amino acid sequence having at least 95% identity to the amino acid sequence of SEQ ID NO:16. In some embodiments, the second binding domain comprises a VH comprising an amino acid sequence having at least 95% identity to the amino acid sequence of SEQ ID NO:15, and a VL comprising an amino acid sequence having at least 95% identity to the amino acid sequence of SEQ ID NO:16. In some embodiments, the second binding domain comprises a heavy chain comprising an amino acid sequence having at least 95% identity to the amino acid sequence of SEQ ID NO:25. In some embodiments, the second binding domain comprises a light chain comprising an amino acid sequence having at least 95% identity to the amino acid sequence of SEQ ID NO:26. In some embodiments, the second binding domain comprises a heavy chain comprising an amino acid sequence having at least 95% identity to the amino acid sequence of SEQ ID NO:25, and a light chain comprising an amino acid sequence having at least 95% identity to the amino acid sequence of SEQ ID NO:26. In some embodiments, the second binding domain comprises an amino acid sequence of SEQ ID NO:18.

In another aspect, provided herein is a bispecific antibody comprising: (a) a first binding domain that binds to TRGV9, and (b) a second binding domain that binds to CD123, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:35; and (ii) a VL comprising a VL CDR1, a VL CDR2, and a VL CDR3 having amino acid sequences of the VL CDR1, VL CDR2, and VL CDR3, respectively, of SEQ ID NO:8; and wherein the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In another aspect, provided herein is a bispecific antibody comprising: (a) a first binding domain that binds to TRGV9, and (b) a second binding domain that binds to CD123, wherein the first binding domain comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:32; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6; and wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In some embodiments, the first binding domain comprises a VH having an amino acid sequence of SEQ ID NO:35. In some embodiments, the first binding domain comprises a VL having an amino acid sequence of SEQ ID NO:8. In some embodiments, the first binding domain comprises a VH having an amino acid sequence of SEQ ID NO:35, and a VL having an amino acid sequence of SEQ ID NO:8. In some embodiments, the second binding domain comprises a VH having an amino acid sequence of SEQ ID NO:15. In some embodiments, the second binding domain comprises a VL having an amino acid sequence of SEQ ID NO:16. In some embodiments, the second binding domain comprises a VH having an amino acid sequence of SEQ ID NO:15, and a VL having an amino acid sequence of SEQ ID NO:16. In some embodiments, the second binding domain comprises a heavy chain having an amino acid sequence of SEQ ID NO:25. In some embodiments, the second binding domain comprises a light chain having an amino acid sequence of SEQ ID NO:26. In some embodiments, the second binding domain comprises a heavy chain having an amino acid sequence of SEQ ID NO:25, and a light chain having an amino acid sequence of SEQ ID NO:26. In some embodiments, the second binding domain comprises an amino acid sequence of SEQ ID NO:18. In some embodiments, the first binding domain comprises a VH comprising an amino acid sequence having at least 95% identity to the amino acid sequence of SEQ ID NO:35. In some embodiments, the first binding domain comprises a VL comprising an amino acid sequence having at least 95% identity to the amino acid sequence of SEQ ID NO:8. In some embodiments, the first binding domain comprises a VH comprising an amino acid sequence having at least 95% identity to the amino acid sequence of SEQ ID NO:35, and a VL comprising an amino acid sequence having at least 95% identity to the amino acid sequence of SEQ ID NO:8. In some embodiments, the second binding domain comprises a VH comprising an amino acid sequence having at least 95% identity to the amino acid sequence of SEQ ID NO:15. In some embodiments, the second binding domain comprises a VL comprising an amino acid sequence having at least 95% identity to the amino acid sequence of SEQ ID NO:16. In some embodiments, the second binding domain comprises a VH comprising an amino acid sequence having at least 95% identity to the amino acid sequence of SEQ ID NO:15, and a VL comprising an amino acid sequence having at least 95% identity to the amino acid sequence of SEQ ID NO:16. In some embodiments, the second binding domain comprises a heavy chain comprising an amino acid sequence having at least 95% identity to the amino acid sequence of SEQ ID NO:25. In some embodiments, the second binding domain comprises a light chain comprising an amino acid sequence having at least 95% identity to the amino acid sequence of SEQ ID NO:26. In some embodiments, the second binding domain comprises a heavy chain comprising an amino acid sequence having at least 95% identity to the amino acid sequence of SEQ ID NO:25, and a light chain comprising an amino acid sequence having at least 95% identity to the amino acid sequence of SEQ ID NO:26. In some embodiments, the second binding domain comprises an amino acid sequence of SEQ ID NO:18.

In another aspect, provided herein is a bispecific antibody comprising: (a) a first binding domain that binds to TRGV9, and (b) a second binding domain that binds to CD123, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:36; and (ii) a VL comprising a VL CDR1, a VL CDR2, and a VL CDR3 having amino acid sequences of the VL CDR1, VL CDR2, and VL CDR3, respectively, of SEQ ID NO:8; and wherein the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In another aspect, provided herein is a bispecific antibody comprising: (a) a first binding domain that binds to TRGV9, and (b) a second binding domain that binds to CD123, wherein the first binding domain comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:33; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6; and wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In some embodiments, the first binding domain comprises a VH having an amino acid sequence of SEQ ID NO:36. In some embodiments, the first binding domain comprises a VL having an amino acid sequence of SEQ ID NO:8. In some embodiments, the first binding domain comprises a VH having an amino acid sequence of SEQ ID NO:36, and a VL having an amino acid sequence of SEQ ID NO:8. In some embodiments, the second binding domain comprises a VH having an amino acid sequence of SEQ ID NO:15. In some embodiments, the second binding domain comprises a VL having an amino acid sequence of SEQ ID NO:16. In some embodiments, the second binding domain comprises a VH having an amino acid sequence of SEQ ID NO:15, and a VL having an amino acid sequence of SEQ ID NO:16. In some embodiments, the second binding domain comprises a heavy chain having an amino acid sequence of SEQ ID NO:25. In some embodiments, the second binding domain comprises a light chain having an amino acid sequence of SEQ ID NO:26. In some embodiments, the second binding domain comprises a heavy chain having an amino acid sequence of SEQ ID NO:25, and a light chain having an amino acid sequence of SEQ ID NO:26. In some embodiments, the second binding domain comprises an amino acid sequence of SEQ ID NO:18. In some embodiments, the first binding domain comprises a VH comprising an amino acid sequence having at least 95% identity to the amino acid sequence of SEQ ID NO:36. In some embodiments, the first binding domain comprises a VL comprising an amino acid sequence having at least 95% identity to the amino acid sequence of SEQ ID NO:8. In some embodiments, the first binding domain comprises a VH comprising an amino acid sequence having at least 95% identity to the amino acid sequence of SEQ ID NO:36, and a VL comprising an amino acid sequence having at least 95% identity to the amino acid sequence of SEQ ID NO:8. In some embodiments, the second binding domain comprises a VH comprising an amino acid sequence having at least 95% identity to the amino acid sequence of SEQ ID NO:15. In some embodiments, the second binding domain comprises a VL comprising an amino acid sequence having at least 95% identity to the amino acid sequence of SEQ ID NO:16. In some embodiments, the second binding domain comprises a VH comprising an amino acid sequence having at least 95% identity to the amino acid sequence of SEQ ID NO:15, and a VL comprising an amino acid sequence having at least 95% identity to the amino acid sequence of SEQ ID NO:16. In some embodiments, the second binding domain comprises a heavy chain comprising an amino acid sequence having at least 95% identity to the amino acid sequence of SEQ ID NO:25. In some embodiments, the second binding domain comprises a light chain comprising an amino acid sequence having at least 95% identity to the amino acid sequence of SEQ ID NO:26. In some embodiments, the second binding domain comprises a heavy chain comprising an amino acid sequence having at least 95% identity to the amino acid sequence of SEQ ID NO:25, and a light chain comprising an amino acid sequence having at least 95% identity to the amino acid sequence of SEQ ID NO:26. In some embodiments, the second binding domain comprises an amino acid sequence of SEQ ID NO:18.

In another aspect, provided herein is a bispecific antibody comprising: (a) a first binding domain that binds to TRGV9, and (b) a second binding domain that binds to CD123, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:65; and (ii) a VL comprising a VL CDR1, a VL CDR2, and a VL CDR3 having amino acid sequences of the VL CDR1, VL CDR2, and VL CDR3, respectively, of SEQ ID NO:66; and wherein the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In another aspect, provided herein is a bispecific antibody comprising: (a) a first binding domain that binds to TRGV9, and (b) a second binding domain that binds to CD123, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:67; and (ii) a VL comprising a VL CDR1, a VL CDR2, and a VL CDR3 having amino acid sequences of the VL CDR1, VL CDR2, and VL CDR3, respectively, of SEQ ID NO:68; and wherein the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In another aspect, provided herein is a bispecific antibody comprising: (a) a first binding domain that binds to TRGV9, and (b) a second binding domain that binds to CD123, wherein the first binding domain comprises: (i) a VH comprising a VH CDR1 having an amino acid sequence of SEQ ID NO:1, a VH CDR2 having an amino acid sequence of SEQ ID NO:76, and a VH CDR3 having an amino acid sequence of SEQ ID NO:3; and (ii) a VL comprising a VL CDR1 having an amino acid sequence of SEQ ID NO:77, a VL CDR2 having an amino acid sequence of SEQ ID NO:5, and a VL CDR3 having an amino acid sequence of SEQ ID NO:6; and wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In another aspect, provided herein is a bispecific antibody comprising: (a) a first binding domain that binds to TRGV9, and (b) a second binding domain that binds to CD123, wherein the first binding domain comprises: (i) a VH comprising a VH CDR1 having an amino acid sequence of SEQ ID NO:60, a VH CDR2 having an amino acid sequence of SEQ ID NO:61, and a VH CDR3 having an amino acid sequence of SEQ ID NO:62; and (ii) a VL comprising a VL CDR1 having an amino acid sequence of SEQ ID NO:63, a VL CDR2 having an amino acid sequence of SEQ ID NO:64, and a VL CDR3 having an amino acid sequence of SEQ ID NO:6; and wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In some embodiments, the first binding domain comprises a VH having an amino acid sequence of SEQ ID NO:65. In some embodiments, the first binding domain comprises a VL having an amino acid sequence of SEQ ID NO:66. In some embodiments, the first binding domain comprises a VH having an amino acid sequence of SEQ ID NO:65, and a VL having an amino acid sequence of SEQ ID NO:66. In some embodiments, the first binding domain comprises a VH having an amino acid sequence of SEQ ID NO:67. In some embodiments, the first binding domain comprises a VL having an amino acid sequence of SEQ ID NO:68. In some embodiments, the first binding domain a VH having an amino acid sequence of SEQ ID NO:67, and a VL having an amino acid sequence of SEQ ID NO:68. In some embodiments, the first binding domain comprises a heavy chain having an amino acid sequence of SEQ ID NO:71. In some embodiments, the first binding domain comprises a light chain having an amino acid sequence of SEQ ID NO:72. In some embodiments, the first binding domain comprises a heavy chain having an amino acid sequence of SEQ ID NO:71, and a light chain having an amino acid sequence of SEQ ID NO:72. In some embodiments, the first binding domain comprises an amino acid sequence of SEQ ID NO:70. In some embodiments, the first binding domain comprises a heavy chain having an amino acid sequence of SEQ ID NO:74. In some embodiments, the first binding domain comprises a light chain having an amino acid sequence of SEQ ID NO:75. In some embodiments, the first binding domain comprises a heavy chain having an amino acid sequence of SEQ ID NO:74, and a light chain having an amino acid sequence of SEQ ID NO:75. In some embodiments, the first binding domain comprises an amino acid sequence of SEQ ID NO:73. In some embodiments, the second binding domain comprises a VH having an amino acid sequence of SEQ ID NO:15. In some embodiments, the second binding domain comprises a VL having an amino acid sequence of SEQ ID NO:16. In some embodiments, the second binding domain comprises a VH having an amino acid sequence of SEQ ID NO:15, and a VL having an amino acid sequence of SEQ ID NO:16. In some embodiments, the second binding domain comprises a heavy chain having an amino acid sequence of SEQ ID NO:25. In some embodiments, the second binding domain comprises a light chain having an amino acid sequence of SEQ ID NO:26. In some embodiments, the second binding domain comprises a heavy chain having an amino acid sequence of SEQ ID NO:25, and a light chain having an amino acid sequence of SEQ ID NO:26. In some embodiments, the second binding domain comprises an amino acid sequence of SEQ ID NO:18. In some embodiments, the first binding domain comprises a VH comprising an amino acid sequence having at least 95% identity to the amino acid sequence of SEQ ID NO:65. In some embodiments, the first binding domain comprises a VL comprising an amino acid sequence having at least 95% identity to the amino acid sequence of SEQ ID NO:66. In some embodiments, the first binding domain comprises a VH comprising an amino acid sequence having at least 95% identity to the amino acid sequence of SEQ ID NO:65, and a VL comprising an amino acid sequence having at least 95% identity to the amino acid sequence of SEQ ID NO:66. In some embodiments, the first binding domain comprises a VH comprising an amino acid sequence having at least 95% identity to the amino acid sequence of SEQ ID NO:67. In some embodiments, the first binding domain comprises a VL comprising an amino acid sequence having at least 95% identity to the amino acid sequence of SEQ ID NO:68. In some embodiments, the first binding domain a VH comprising an amino acid sequence having at least 95% identity to the amino acid sequence of SEQ ID NO:67, and a VL comprising an amino acid sequence having at least 95% identity to the amino acid sequence of SEQ ID NO:68. In some embodiments, the first binding domain comprises a heavy chain comprising an amino acid sequence having at least 95% identity to the amino acid sequence of SEQ ID NO:71. In some embodiments, the first binding domain comprises a light chain comprising an amino acid sequence having at least 95% identity to the amino acid sequence of SEQ ID NO:72. In some embodiments, the first binding domain comprises a heavy chain comprising an amino acid sequence having at least 95% identity to the amino acid sequence of SEQ ID NO:71, and a light chain comprising an amino acid sequence having at least 95% identity to the amino acid sequence of SEQ ID NO:72. In some embodiments, the first binding domain comprises an amino acid sequence of SEQ ID NO:70. In some embodiments, the first binding domain comprises a heavy chain comprising an amino acid sequence having at least 95% identity to the amino acid sequence of SEQ ID NO:74. In some embodiments, the first binding domain comprises a light chain comprising an amino acid sequence having at least 95% identity to the amino acid sequence of SEQ ID NO:75. In some embodiments, the first binding domain comprises a heavy chain comprising an amino acid sequence having at least 95% identity to the amino acid sequence of SEQ ID NO:74, and a light chain comprising an amino acid sequence having at least 95% identity to the amino acid sequence of SEQ ID NO:75. In some embodiments, the first binding domain comprises an amino acid sequence of SEQ ID NO:73. In some embodiments, the second binding domain comprises a VH comprising an amino acid sequence having at least 95% identity to the amino acid sequence of SEQ ID NO:15. In some embodiments, the second binding domain comprises a VL comprising an amino acid sequence having at least 95% identity to the amino acid sequence of SEQ ID NO:16. In some embodiments, the second binding domain comprises a VH comprising an amino acid sequence having at least 95% identity to the amino acid sequence of SEQ ID NO:15, and a VL comprising an amino acid sequence having at least 95% identity to the amino acid sequence of SEQ ID NO:16. In some embodiments, the second binding domain comprises a heavy chain comprising an amino acid sequence having at least 95% identity to the amino acid sequence of SEQ ID NO:25. In some embodiments, the second binding domain comprises a light chain comprising an amino acid sequence having at least 95% identity to the amino acid sequence of SEQ ID NO:26. In some embodiments, the second binding domain comprises a heavy chain comprising an amino acid sequence having at least 95% identity to the amino acid sequence of SEQ ID NO:25, and a light chain comprising an amino acid sequence having at least 95% identity to the amino acid sequence of SEQ ID NO:26. In some embodiments, the second binding domain comprises an amino acid sequence of SEQ ID NO:18.

In another aspect, provided herein is a bispecific antibody comprising: (a) a first binding domain that binds to TRGV9, and (b) a second binding domain that binds to CD123, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:95; and (ii) a VL comprising a VL CDR1, a VL CDR2, and a VL CDR3 having amino acid sequences of the VL CDR1, VL CDR2, and VL CDR3, respectively, of SEQ ID NO:96; and wherein the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In another aspect, provided herein is a bispecific antibody comprising: (a) a first binding domain that binds to TRGV9, and (b) a second binding domain that binds to CD123, wherein the first binding domain comprises: (i) a VH comprising a VH CDR1 having an amino acid sequence of SEQ ID NO:89, a VH CDR2 having an amino acid sequence of SEQ ID NO:90, and a VH CDR3 having an amino acid sequence of SEQ ID NO:91; and (ii) a VL comprising a VL CDR1 having an amino acid sequence of SEQ ID NO:92, a VL CDR2 having an amino acid sequence of SEQ ID NO:93, and a VL CDR3 having an amino acid sequence of SEQ ID NO:94; and wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In some embodiments, the first binding domain comprises a VH having an amino acid sequence of SEQ ID NO:95. In some embodiments, the first binding domain comprises a VL having an amino acid sequence of SEQ ID NO:96. In some embodiments, the first binding domain comprises a VH having an amino acid sequence of SEQ ID NO:95, and a VL having an amino acid sequence of SEQ ID NO:96. In some embodiments, the first binding domain comprises an amino acid sequence of SEQ ID NO:97. In some embodiments, the second binding domain comprises a VH having an amino acid sequence of SEQ ID NO:15. In some embodiments, the second binding domain comprises a VL having an amino acid sequence of SEQ ID NO:16. In some embodiments, the second binding domain comprises a VH having an amino acid sequence of SEQ ID NO:15, and a VL having an amino acid sequence of SEQ ID NO:16. In some embodiments, the second binding domain comprises a heavy chain having an amino acid sequence of SEQ ID NO:25. In some embodiments, the second binding domain comprises a light chain having an amino acid sequence of SEQ ID NO:26. In some embodiments, the second binding domain comprises a heavy chain having an amino acid sequence of SEQ ID NO:25, and a light chain having an amino acid sequence of SEQ ID NO:26. In some embodiments, the second binding domain comprises an amino acid sequence of SEQ ID NO:18. In some embodiments, the first binding domain comprises a VH comprising an amino acid sequence having at least 95% identity to the amino acid sequence of SEQ ID NO:95. In some embodiments, the first binding domain comprises a VL comprising an amino acid sequence having at least 95% identity to the amino acid sequence of SEQ ID NO:96. In some embodiments, the first binding domain comprises a VH comprising an amino acid sequence having at least 95% identity to the amino acid sequence of SEQ ID NO:95, and a VL comprising an amino acid sequence having at least 95% identity to the amino acid sequence of SEQ ID NO:96. In some embodiments, the first binding domain comprises an amino acid sequence of SEQ ID NO:97. In some embodiments, the second binding domain comprises a VH comprising an amino acid sequence having at least 95% identity to the amino acid sequence of SEQ ID NO:15. In some embodiments, the second binding domain comprises a VL comprising an amino acid sequence having at least 95% identity to the amino acid sequence of SEQ ID NO:16. In some embodiments, the second binding domain comprises a VH comprising an amino acid sequence having at least 95% identity to the amino acid sequence of SEQ ID NO:15, and a VL comprising an amino acid sequence having at least 95% identity to the amino acid sequence of SEQ ID NO:16. In some embodiments, the second binding domain comprises a heavy chain comprising an amino acid sequence having at least 95% identity to the amino acid sequence of SEQ ID NO:25. In some embodiments, the second binding domain comprises a light chain comprising an amino acid sequence having at least 95% identity to the amino acid sequence of SEQ ID NO:26. In some embodiments, the second binding domain comprises a heavy chain comprising an amino acid sequence having at least 95% identity to the amino acid sequence of SEQ ID NO:25, and a light chain comprising an amino acid sequence having at least 95% identity to the amino acid sequence of SEQ ID NO:26. In some embodiments, the second binding domain comprises an amino acid sequence of SEQ ID NO:18.

In another aspect, provided herein is a bispecific antibody comprising: (a) a first binding domain that binds to TRGV9, and (b) a second binding domain that binds to CD123, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:104; and (ii) a VL comprising a VL CDR1, a VL CDR2, and a VL CDR3 having amino acid sequences of the VL CDR1, VL CDR2, and VL CDR3, respectively, of SEQ ID NO:105; and wherein the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In another aspect, provided herein is a bispecific antibody comprising: (a) a first binding domain that binds to TRGV9, and (b) a second binding domain that binds to CD123, wherein the first binding domain comprises: (i) a VH comprising a VH CDR1 having an amino acid sequence of SEQ ID NO:98, a VH CDR2 having an amino acid sequence of SEQ ID NO:99, and a VH CDR3 having an amino acid sequence of SEQ ID NO:100, and (ii) a VL comprising a VL CDR1 having an amino acid sequence of SEQ ID NO:101, a VL CDR2 having an amino acid sequence of SEQ ID NO:102, and a VL CDR3 having an amino acid sequence of SEQ ID NO:103; and wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In some embodiments, the first binding domain comprises a VH having an amino acid sequence of SEQ ID NO:104. In some embodiments, the first binding domain comprises a VL having an amino acid sequence of SEQ ID NO:105. In some embodiments, the first binding domain comprises a VH having an amino acid sequence of SEQ ID NO:104, and a VL having an amino acid sequence of SEQ ID NO:105. In some embodiments, the first binding domain comprises an amino acid sequence of SEQ ID NO:106. In some embodiments, the second binding domain comprises a VH having an amino acid sequence of SEQ ID NO:15. In some embodiments, the second binding domain comprises a VL having an amino acid sequence of SEQ ID NO:16. In some embodiments, the second binding domain comprises a VH having an amino acid sequence of SEQ ID NO:15, and a VL having an amino acid sequence of SEQ ID NO:16. In some embodiments, the second binding domain comprises a heavy chain having an amino acid sequence of SEQ ID NO:25. In some embodiments, the second binding domain comprises a light chain having an amino acid sequence of SEQ ID NO:26. In some embodiments, the second binding domain comprises a heavy chain having an amino acid sequence of SEQ ID NO:25, and a light chain having an amino acid sequence of SEQ ID NO:26. In some embodiments, the second binding domain comprises an amino acid sequence of SEQ ID NO:18. In some embodiments, the first binding domain comprises a VH comprising an amino acid sequence having at least 95% identity to the amino acid sequence of SEQ ID NO:104. In some embodiments, the first binding domain comprises a VL comprising an amino acid sequence having at least 95% identity to the amino acid sequence of SEQ ID NO:105. In some embodiments, the first binding domain comprises a VH comprising an amino acid sequence having at least 95% identity to the amino acid sequence of SEQ ID NO:104, and a VL comprising an amino acid sequence having at least 95% identity to the amino acid sequence of SEQ ID NO:105. In some embodiments, the first binding domain comprises an amino acid sequence of SEQ ID NO:106. In some embodiments, the second binding domain comprises a VH comprising an amino acid sequence having at least 95% identity to the amino acid sequence of SEQ ID NO:15. In some embodiments, the second binding domain comprises a VL comprising an amino acid sequence having at least 95% identity to the amino acid sequence of SEQ ID NO:16. In some embodiments, the second binding domain comprises a VH comprising an amino acid sequence having at least 95% identity to the amino acid sequence of SEQ ID NO:15, and a VL comprising an amino acid sequence having at least 95% identity to the amino acid sequence of SEQ ID NO:16. In some embodiments, the second binding domain comprises a heavy chain comprising an amino acid sequence having at least 95% identity to the amino acid sequence of SEQ ID NO:25. In some embodiments, the second binding domain comprises a light chain comprising an amino acid sequence having at least 95% identity to the amino acid sequence of SEQ ID NO:26. In some embodiments, the second binding domain comprises a heavy chain comprising an amino acid sequence having at least 95% identity to the amino acid sequence of SEQ ID NO:25, and a light chain comprising an amino acid sequence having at least 95% identity to the amino acid sequence of SEQ ID NO:26. In some embodiments, the second binding domain comprises an amino acid sequence of SEQ ID NO:18.

In another aspect, provided herein is a bispecific antibody comprising: (a) a first binding domain that binds to TRGV9, and (b) a second binding domain that binds to CD123, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:113; and (ii) a VL comprising a VL CDR1, a VL CDR2, and a VL CDR3 having amino acid sequences of the VL CDR1, VL CDR2, and VL CDR3, respectively, of SEQ ID NO:114; and wherein the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In another aspect, provided herein is a bispecific antibody comprising: (a) a first binding domain that binds to TRGV9, and (b) a second binding domain that binds to CD123, wherein the first binding domain comprises: (i) a VH comprising a VH CDR1 having an amino acid sequence of SEQ ID NO:107, a VH CDR2 having an amino acid sequence of SEQ ID NO:108, and a VH CDR3 having an amino acid sequence of SEQ ID NO:109, and (ii) a VL comprising a VL CDR1 having an amino acid sequence of SEQ ID NO:110, a VL CDR2 having an amino acid sequence of SEQ ID NO:111, and a VL CDR3 having an amino acid sequence of SEQ ID NO:112; and wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In some embodiments, the first binding domain comprises a VH having an amino acid sequence of SEQ ID NO:113. In some embodiments, the first binding domain comprises a VL having an amino acid sequence of SEQ ID NO:114. In some embodiments, the first binding domain comprises a VH having an amino acid sequence of SEQ ID NO:113, and a VL having an amino acid sequence of SEQ ID NO:114. In some embodiments, the first binding domain comprises a heavy chain having an amino acid sequence of SEQ ID NO:115. In some embodiments, the first binding domain comprises a light chain having an amino acid sequence of SEQ ID NO:116. In some embodiments, the first binding domain comprises a heavy chain having an amino acid sequence of SEQ ID NO:115, and a light chain having an amino acid sequence of SEQ ID NO:116. In some embodiments, the second binding domain comprises a VH having an amino acid sequence of SEQ ID NO:15. In some embodiments, the second binding domain comprises a VL having an amino acid sequence of SEQ ID NO:16. In some embodiments, the second binding domain comprises a VH having an amino acid sequence of SEQ ID NO:15, and a VL having an amino acid sequence of SEQ ID NO:16. In some embodiments, the second binding domain comprises a heavy chain having an amino acid sequence of SEQ ID NO:25. In some embodiments, the second binding domain comprises a light chain having an amino acid sequence of SEQ ID NO:26. In some embodiments, the second binding domain comprises a heavy chain having an amino acid sequence of SEQ ID NO:25, and a light chain having an amino acid sequence of SEQ ID NO:26. In some embodiments, the second binding domain comprises an amino acid sequence of SEQ ID NO:18. In some embodiments, the first binding domain comprises a VH comprising an amino acid sequence having at least 95% identity to the amino acid sequence of SEQ ID NO:113. In some embodiments, the first binding domain comprises a VL comprising an amino acid sequence having at least 95% identity to the amino acid sequence of SEQ ID NO:114. In some embodiments, the first binding domain comprises a VH comprising an amino acid sequence having at least 95% identity to the amino acid sequence of SEQ ID NO:113, and a VL comprising an amino acid sequence having at least 95% identity to the amino acid sequence of SEQ ID NO:114. In some embodiments, the first binding domain comprises a heavy chain comprising an amino acid sequence having at least 95% identity to the amino acid sequence of SEQ ID NO:115. In some embodiments, the first binding domain comprises a light chain comprising an amino acid sequence having at least 95% identity to the amino acid sequence of SEQ ID NO:116. In some embodiments, the first binding domain comprises a heavy chain comprising an amino acid sequence having at least 95% identity to the amino acid sequence of SEQ ID NO:115, and a light chain comprising an amino acid sequence having at least 95% identity to the amino acid sequence of SEQ ID NO:116. In some embodiments, the second binding domain comprises a VH comprising an amino acid sequence having at least 95% identity to the amino acid sequence of SEQ ID NO:15. In some embodiments, the second binding domain comprises a VL comprising an amino acid sequence having at least 95% identity to the amino acid sequence of SEQ ID NO:16. In some embodiments, the second binding domain comprises a VH comprising an amino acid sequence having at least 95% identity to the amino acid sequence of SEQ ID NO:15, and a VL comprising an amino acid sequence having at least 95% identity to the amino acid sequence of SEQ ID NO:16. In some embodiments, the second binding domain comprises a heavy chain comprising an amino acid sequence having at least 95% identity to the amino acid sequence of SEQ ID NO:25. In some embodiments, the second binding domain comprises a light chain comprising an amino acid sequence having at least 95% identity to the amino acid sequence of SEQ ID NO:26. In some embodiments, the second binding domain comprises a heavy chain comprising an amino acid sequence having at least 95% identity to the amino acid sequence of SEQ ID NO:25, and a light chain comprising an amino acid sequence having at least 95% identity to the amino acid sequence of SEQ ID NO:26. In some embodiments, the second binding domain comprises an amino acid sequence of SEQ ID NO:18.

In another aspect, provided herein is a bispecific antibody comprising: (a) a first binding domain that binds to TRGV9, and (b) a second binding domain that binds to CD123, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:123; and (ii) a VL comprising a VL CDR1, a VL CDR2, and a VL CDR3 having amino acid sequences of the VL CDR1, VL CDR2, and VL CDR3, respectively, of SEQ ID NO:124; and wherein the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In another aspect, provided herein is a bispecific antibody comprising: (a) a first binding domain that binds to TRGV9, and (b) a second binding domain that binds to CD123, wherein the first binding domain comprises: (i) a VH comprising a VH CDR1 having an amino acid sequence of SEQ ID NO:117, a VH CDR2 having an amino acid sequence of SEQ ID NO:118, and a VH CDR3 having an amino acid sequence of SEQ ID NO:119, and (ii) a VL comprising a VL CDR1 having an amino acid sequence of SEQ ID NO:120, a VL CDR2 having an amino acid sequence of SEQ ID NO:121, and a VL CDR3 having an amino acid sequence of SEQ ID NO:122. In some embodiments, the first binding domain comprises a VH having an amino acid sequence of SEQ ID NO:123; and wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In some embodiments, the first binding domain comprises a VL having an amino acid sequence of SEQ ID NO:124. In some embodiments, the first binding domain comprises a VH having an amino acid sequence of SEQ ID NO:123, and a VL having an amino acid sequence of SEQ ID NO:124. In some embodiments, the first binding domain comprises a heavy chain having an amino acid sequence of SEQ ID NO:125. In some embodiments, the first binding domain comprises a light chain having an amino acid sequence of SEQ ID NO:126. In some embodiments, the first binding domain comprises a heavy chain having an amino acid sequence of SEQ ID NO:125, and a light chain having an amino acid sequence of SEQ ID NO:126. In some embodiments, the second binding domain comprises a VH having an amino acid sequence of SEQ ID NO:15. In some embodiments, the second binding domain comprises a VL having an amino acid sequence of SEQ ID NO:16. In some embodiments, the second binding domain comprises a VH having an amino acid sequence of SEQ ID NO:15, and a VL having an amino acid sequence of SEQ ID NO:16. In some embodiments, the second binding domain comprises a heavy chain having an amino acid sequence of SEQ ID NO:25. In some embodiments, the second binding domain comprises a light chain having an amino acid sequence of SEQ ID NO:26. In some embodiments, the second binding domain comprises a heavy chain having an amino acid sequence of SEQ ID NO:25, and a light chain having an amino acid sequence of SEQ ID NO:26. In some embodiments, the second binding domain comprises an amino acid sequence of SEQ ID NO:18. In some embodiments, the first binding domain comprises a VL comprising an amino acid sequence having at least 95% identity to the amino acid sequence of SEQ ID NO:124. In some embodiments, the first binding domain comprises a VH comprising an amino acid sequence having at least 95% identity to the amino acid sequence of SEQ ID NO:123, and a VL comprising an amino acid sequence having at least 95% identity to the amino acid sequence of SEQ ID NO:124. In some embodiments, the first binding domain comprises a heavy chain comprising an amino acid sequence having at least 95% identity to the amino acid sequence of SEQ ID NO:125. In some embodiments, the first binding domain comprises a light chain comprising an amino acid sequence having at least 95% identity to the amino acid sequence of SEQ ID NO:126. In some embodiments, the first binding domain comprises a heavy chain comprising an amino acid sequence having at least 95% identity to the amino acid sequence of SEQ ID NO:125, and a light chain comprising an amino acid sequence having at least 95% identity to the amino acid sequence of SEQ ID NO:126. In some embodiments, the second binding domain comprises a VH comprising an amino acid sequence having at least 95% identity to the amino acid sequence of SEQ ID NO:15. In some embodiments, the second binding domain comprises a VL comprising an amino acid sequence having at least 95% identity to the amino acid sequence of SEQ ID NO:16. In some embodiments, the second binding domain comprises a VH comprising an amino acid sequence having at least 95% identity to the amino acid sequence of SEQ ID NO:15, and a VL comprising an amino acid sequence having at least 95% identity to the amino acid sequence of SEQ ID NO:16.

In some embodiments, the second binding domain comprises a heavy chain comprising an amino acid sequence having at least 95% identity to the amino acid sequence of SEQ ID NO:25. In some embodiments, the second binding domain comprises a light chain comprising an amino acid sequence having at least 95% identity to the amino acid sequence of SEQ ID NO:26. In some embodiments, the second binding domain comprises a heavy chain comprising an amino acid sequence having at least 95% identity to the amino acid sequence of SEQ ID NO:25, and a light chain comprising an amino acid sequence having at least 95% identity to the amino acid sequence of SEQ ID NO:26. In some embodiments, the second binding domain comprises an amino acid sequence of SEQ ID NO:18.

In another aspect, provided herein is a bispecific antibody comprising: (a) a first binding domain that binds to TRGV9, and (b) a second binding domain that binds to CD123, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:133; and (ii) a VL comprising a VL CDR1, a VL CDR2, and a VL CDR3 having amino acid sequences of the VL CDR1, VL CDR2, and VL CDR3, respectively, of SEQ ID NO:134; and wherein the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In another aspect, provided herein is a bispecific antibody comprising: (a) a first binding domain that binds to TRGV9, and (b) a second binding domain that binds to CD123, wherein the first binding domain comprises: (i) a VH comprising a VH CDR1 having an amino acid sequence of SEQ ID NO:127, a VH CDR2 having an amino acid sequence of SEQ ID NO:128, and a VH CDR3 having an amino acid sequence of SEQ ID NO:129, and (ii) a VL comprising a VL CDR1 having an amino acid sequence of SEQ ID NO:130, a VL CDR2 having an amino acid sequence of SEQ ID NO:131, and a VL CDR3 having an amino acid sequence of SEQ ID NO:132. In some embodiments, the first binding domain comprises a VH having an amino acid sequence of SEQ ID NO:133; and wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In some embodiments, the first binding domain comprises a VL having an amino acid sequence of SEQ ID NO:134. In some embodiments, the first binding domain comprises a VH having an amino acid sequence of SEQ ID NO:133, and a VL having an amino acid sequence of SEQ ID NO:134. In some embodiments, the first binding domain comprises a heavy chain having an amino acid sequence of SEQ ID NO:135. In some embodiments, the first binding domain comprises a light chain having an amino acid sequence of SEQ ID NO:136. In some embodiments, the first binding domain comprises a heavy chain having an amino acid sequence of SEQ ID NO:135, and a light chain having an amino acid sequence of SEQ ID NO:136. In some embodiments, the second binding domain comprises a VH having an amino acid sequence of SEQ ID NO:15. In some embodiments, the second binding domain comprises a VL having an amino acid sequence of SEQ ID NO:16. In some embodiments, the second binding domain comprises a VH having an amino acid sequence of SEQ ID NO:15, and a VL having an amino acid sequence of SEQ ID NO:16. In some embodiments, the second binding domain comprises a heavy chain having an amino acid sequence of SEQ ID NO:25. In some embodiments, the second binding domain comprises a light chain having an amino acid sequence of SEQ ID NO:26. In some embodiments, the second binding domain comprises a heavy chain having an amino acid sequence of SEQ ID NO:25, and a light chain having an amino acid sequence of SEQ ID NO:26. In some embodiments, the second binding domain comprises an amino acid sequence of SEQ ID NO:18. In some embodiments, the first binding domain comprises a VL comprising an amino acid sequence having at least 95% identity to the amino acid sequence of SEQ ID NO:134. In some embodiments, the first binding domain comprises a VH comprising an amino acid sequence having at least 95% identity to the amino acid sequence of SEQ ID NO:133, and a VL comprising an amino acid sequence having at least 95% identity to the amino acid sequence of SEQ ID NO:134. In some embodiments, the first binding domain comprises a heavy chain comprising an amino acid sequence having at least 95% identity to the amino acid sequence of SEQ ID NO:135. In some embodiments, the first binding domain comprises a light chain comprising an amino acid sequence having at least 95% identity to the amino acid sequence of SEQ ID NO:136. In some embodiments, the first binding domain comprises a heavy chain comprising an amino acid sequence having at least 95% identity to the amino acid sequence of SEQ ID NO:135, and a light chain comprising an amino acid sequence having at least 95% identity to the amino acid sequence of SEQ ID NO:136. In some embodiments, the second binding domain comprises a VH comprising an amino acid sequence having at least 95% identity to the amino acid sequence of SEQ ID NO:15. In some embodiments, the second binding domain comprises a VL comprising an amino acid sequence having at least 95% identity to the amino acid sequence of SEQ ID NO:16. In some embodiments, the second binding domain comprises a VH comprising an amino acid sequence having at least 95% identity to the amino acid sequence of SEQ ID NO:15, and a VL comprising an amino acid sequence having at least 95% identity to the amino acid sequence of SEQ ID NO:16. In some embodiments, the second binding domain comprises a heavy chain comprising an amino acid sequence having at least 95% identity to the amino acid sequence of SEQ ID NO:25. In some embodiments, the second binding domain comprises a light chain comprising an amino acid sequence having at least 95% identity to the amino acid sequence of SEQ ID NO:26. In some embodiments, the second binding domain comprises a heavy chain comprising an amino acid sequence having at least 95% identity to the amino acid sequence of SEQ ID NO:25, and a light chain comprising an amino acid sequence having at least 95% identity to the amino acid sequence of SEQ ID NO:26. In some embodiments, the second binding domain comprises an amino acid sequence of SEQ ID NO:18.

In another aspect, provided herein is a bispecific antibody comprising: (a) a first binding domain that binds to TRGV9, and (b) a second binding domain that binds to CD123. In some embodiments, the first binding domain that binds to TRGV9 comprises: (i) a VH comprising a VH CDR1 having an amino acid sequence of SEQ ID NO:160, a VH CDR2 having an amino acid sequence of SEQ ID NO:161, and a VH CDR3 having an amino acid sequence of SEQ ID NO:162; and (ii) a VL comprising a VL CDR1 having an amino acid sequence of SEQ ID NO:163, a VL CDR2 having an amino acid sequence of SEQ ID NO:164, and a VL CDR3 having an amino acid sequence of SEQ ID NO:165. In some embodiments, the first binding domain that binds to TRGV9 comprises: (i) a VH comprising a VH CDR1 having an amino acid sequence of SEQ ID NO:166, a VH CDR2 having an amino acid sequence of SEQ ID NO:167, and a VH CDR3 having an amino acid sequence of SEQ ID NO:168; and (ii) a VL comprising a VL CDR1 having an amino acid sequence of SEQ ID NO:169, a VL CDR2 having an amino acid sequence of SEQ ID NO:170, and a VL CDR3 having an amino acid sequence of SEQ ID NO:171. In some embodiments, the first binding domain that binds to TRGV9 comprises: (i) a VH comprising a VH CDR1 having an amino acid sequence of SEQ ID NO:172, a VH CDR2 having an amino acid sequence of SEQ ID NO:173, and a VH CDR3 having an amino acid sequence of SEQ ID NO:174; and (ii) a VL comprising a VL CDR1 having an amino acid sequence of SEQ ID NO:175, a VL CDR2 having an amino acid sequence of SEQ ID NO:176, and a VL CDR3 having an amino acid sequence of SEQ ID NO:177. In some embodiments, the first binding domain that binds to TRGV9 comprises: (i) a VH comprising a VH CDR1 having an amino acid sequence of SEQ ID NO:178, a VH CDR2 having an amino acid sequence of SEQ ID NO:179, and a VH CDR3 having an amino acid sequence of SEQ ID NO:180; and (ii) a VL comprising a VL CDR1 having an amino acid sequence of SEQ ID NO:181, a VL CDR2 having an amino acid sequence of SEQ ID NO:182, and a VL CDR3 having an amino acid sequence of SEQ ID NO:183. In some embodiments, the first binding domain that binds to TRGV9 comprises: (i) a VH comprising a VH CDR1 having an amino acid sequence of SEQ ID NO:178, a VH CDR2 having an amino acid sequence of SEQ ID NO:700, and a VH CDR3 having an amino acid sequence of SEQ ID NO:701; and (ii) a VL comprising a VL CDR1 having an amino acid sequence of SEQ ID NO:181, a VL CDR2 having an amino acid sequence of SEQ ID NO:182, and a VL CDR3 having an amino acid sequence of SEQ ID NO:183. In some embodiments, the first binding domain that binds to TRGV9 comprises: (i) a VH comprising a VH CDR1 having an amino acid sequence of SEQ ID NO:184, a VH CDR2 having an amino acid sequence of SEQ ID NO:185, and a VH CDR3 having an amino acid sequence of SEQ ID NO:186; and (ii) a VL comprising a VL CDR1 having an amino acid sequence of SEQ ID NO:187, a VL CDR2 having an amino acid sequence of SEQ ID NO:188, and a VL CDR3 having an amino acid sequence of SEQ ID NO:189. In some embodiments, the first binding domain that binds to TRGV9 comprises: (i) a VH comprising a VH CDR1 having an amino acid sequence of SEQ ID NO:190, a VH CDR2 having an amino acid sequence of SEQ ID NO:191, and a VH CDR3 having an amino acid sequence of SEQ ID NO:192; and (ii) a VL comprising a VL CDR1 having an amino acid sequence of SEQ ID NO:193, a VL CDR2 having an amino acid sequence of SEQ ID NO:194, and a VL CDR3 having an amino acid sequence of SEQ ID NO:195. In some embodiments, the first binding domain that binds to TRGV9 comprises: (i) a VH comprising a VH CDR1 having an amino acid sequence of SEQ ID NO:196, a VH CDR2 having an amino acid sequence of SEQ ID NO:197, and a VH CDR3 having an amino acid sequence of SEQ ID NO:198; and (ii) a VL comprising a VL CDR1 having an amino acid sequence of SEQ ID NO:199, a VL CDR2 having an amino acid sequence of SEQ ID NO:200, and a VL CDR3 having an amino acid sequence of SEQ ID NO:201. In some embodiments, the first binding domain that binds to TRGV9 comprises: (i) a VH comprising a VH CDR1 having an amino acid sequence of SEQ ID NO:202, a VH CDR2 having an amino acid sequence of SEQ ID NO:203, and a VH CDR3 having an amino acid sequence of SEQ ID NO:204; and (ii) a VL comprising a VL CDR1 having an amino acid sequence of SEQ ID NO:205, a VL CDR2 having an amino acid sequence of SEQ ID NO:206, and a VL CDR3 having an amino acid sequence of SEQ ID NO:207. In some embodiments, the first binding domain that binds to TRGV9 comprises: (i) a VH comprising a VH CDR1 having an amino acid sequence of SEQ ID NO:208, a VH CDR2 having an amino acid sequence of SEQ ID NO:209, and a VH CDR3 having an amino acid sequence of SEQ ID NO:210; and (ii) a VL comprising a VL CDR1 having an amino acid sequence of SEQ ID NO:211, a VL CDR2 having an amino acid sequence of SEQ ID NO:212, and a VL CDR3 having an amino acid sequence of SEQ ID NO:213. In some embodiments, the first binding domain that binds to TRGV9 comprises: (i) a VH comprising a VH CDR1 having an amino acid sequence of SEQ ID NO:214, a VH CDR2 having an amino acid sequence of SEQ ID NO:215, and a VH CDR3 having an amino acid sequence of SEQ ID NO:216; and (ii) a VL comprising a VL CDR1 having an amino acid sequence of SEQ ID NO:217, a VL CDR2 having an amino acid sequence of SEQ ID NO:218, and a VL CDR3 having an amino acid sequence of SEQ ID NO:219. In some embodiments, the first binding domain that binds to TRGV9 comprises: (i) a VH comprising a VH CDR1 having an amino acid sequence of SEQ ID NO:214, a VH CDR2 having an amino acid sequence of SEQ ID NO:702, and a VH CDR3 having an amino acid sequence of SEQ ID NO:703; and (ii) a VL comprising a VL CDR1 having an amino acid sequence of SEQ ID NO:217, a VL CDR2 having an amino acid sequence of SEQ ID NO:218, and a VL CDR3 having an amino acid sequence of SEQ ID NO:219. In some embodiments, the first binding domain that binds to TRGV9 comprises: (i) a VH comprising a VH CDR1 having an amino acid sequence of SEQ ID NO:220, a VH CDR2 having an amino acid sequence of SEQ ID NO:221, and a VH CDR3 having an amino acid sequence of SEQ ID NO:222; and (ii) a VL comprising a VL CDR1 having an amino acid sequence of SEQ ID NO:223, a VL CDR2 having an amino acid sequence of SEQ ID NO:224, and a VL CDR3 having an amino acid sequence of SEQ ID NO:225. In some embodiments, the first binding domain that binds to TRGV9 comprises: (i) a VH comprising a VH CDR1 having an amino acid sequence of SEQ ID NO:226, a VH CDR2 having an amino acid sequence of SEQ ID NO:227, and a VH CDR3 having an amino acid sequence of SEQ ID NO:228; and (ii) a VL comprising a VL CDR1 having an amino acid sequence of SEQ ID NO:229, a VL CDR2 having an amino acid sequence of SEQ ID NO:230, and a VL CDR3 having an amino acid sequence of SEQ ID NO:231. In some embodiments, the first binding domain that binds to TRGV9 comprises: (i) a VH comprising a VH CDR1 having an amino acid sequence of SEQ ID NO:232, a VH CDR2 having an amino acid sequence of SEQ ID NO:233, and a VH CDR3 having an amino acid sequence of SEQ ID NO:234; and (ii) a VL comprising a VL CDR1 having an amino acid sequence of SEQ ID NO:235, a VL CDR2 having an amino acid sequence of SEQ ID NO:236, and a VL CDR3 having an amino acid sequence of SEQ ID NO:237. In some embodiments, the first binding domain that binds to TRGV9 comprises: (i) a VH comprising a VH CDR1 having an amino acid sequence of SEQ ID NO:238, a VH CDR2 having an amino acid sequence of SEQ ID NO:239, and a VH CDR3 having an amino acid sequence of SEQ ID NO:240; and (ii) a VL comprising a VL CDR1 having an amino acid sequence of SEQ ID NO:241, a VL CDR2 having an amino acid sequence of SEQ ID NO:242, and a VL CDR3 having an amino acid sequence of SEQ ID NO:243. In some embodiments, the first binding domain that binds to TRGV9 comprises: (i) a VH comprising a VH CDR1 having an amino acid sequence of SEQ ID NO:244, a VH CDR2 having an amino acid sequence of SEQ ID NO:245, and a VH CDR3 having an amino acid sequence of SEQ ID NO:246; and (ii) a VL comprising a VL CDR1 having an amino acid sequence of SEQ ID NO:247, a VL CDR2 having an amino acid sequence of SEQ ID NO:248, and a VL CDR3 having an amino acid sequence of SEQ ID NO:249. In some embodiments, the first binding domain that binds to TRGV9 comprises: (i) a VH comprising a VH CDR1 having an amino acid sequence of SEQ ID NO:250, a VH CDR2 having an amino acid sequence of SEQ ID NO:251, and a VH CDR3 having an amino acid sequence of SEQ ID NO:252; and (ii) a VL comprising a VL CDR1 having an amino acid sequence of SEQ ID NO:253, a VL CDR2 having an amino acid sequence of SEQ ID NO:254, and a VL CDR3 having an amino acid sequence of SEQ ID NO:255. In some embodiments, the first binding domain that binds to TRGV9 comprises: (i) a VH comprising a VH CDR1 having an amino acid sequence of SEQ ID NO:250, a VH CDR2 having an amino acid sequence of SEQ ID NO:704, and a VH CDR3 having an amino acid sequence of SEQ ID NO:705; and (ii) a VL comprising a VL CDR1 having an amino acid sequence of SEQ ID NO:253, a VL CDR2 having an amino acid sequence of SEQ ID NO:254, and a VL CDR3 having an amino acid sequence of SEQ ID NO:255. In some embodiments, the first binding domain that binds to TRGV9 comprises: (i) a VH comprising a VH CDR1 having an amino acid sequence of SEQ ID NO:256, a VH CDR2 having an amino acid sequence of SEQ ID NO:257, and a VH CDR3 having an amino acid sequence of SEQ ID NO:258; and (ii) a VL comprising a VL CDR1 having an amino acid sequence of SEQ ID NO:259, a VL CDR2 having an amino acid sequence of SEQ ID NO:260, and a VL CDR3 having an amino acid sequence of SEQ ID NO:261. In some embodiments, the first binding domain that binds to TRGV9 comprises: (i) a VH comprising a VH CDR1 having an amino acid sequence of SEQ ID NO:262, a VH CDR2 having an amino acid sequence of SEQ ID NO:263, and a VH CDR3 having an amino acid sequence of SEQ ID NO:264; and (ii) a VL comprising a VL CDR1 having an amino acid sequence of SEQ ID NO:265, a VL CDR2 having an amino acid sequence of SEQ ID NO:266, and a VL CDR3 having an amino acid sequence of SEQ ID NO:267. In some embodiments, the first binding domain that binds to TRGV9 comprises: (i) a VH comprising a VH CDR1 having an amino acid sequence of SEQ ID NO:268, a VH CDR2 having an amino acid sequence of SEQ ID NO:269, and a VH CDR3 having an amino acid sequence of SEQ ID NO:270; and (ii) a VL comprising a VL CDR1 having an amino acid sequence of SEQ ID NO:271, a VL CDR2 having an amino acid sequence of SEQ ID NO:272, and a VL CDR3 having an amino acid sequence of SEQ ID NO:273. In some embodiments, the first binding domain that binds to TRGV9 comprises: (i) a VH comprising a VH CDR1 having an amino acid sequence of SEQ ID NO:274, a VH CDR2 having an amino acid sequence of SEQ ID NO:275, and a VH CDR3 having an amino acid sequence of SEQ ID NO:276; and (ii) a VL comprising a VL CDR1 having an amino acid sequence of SEQ ID NO:277, a VL CDR2 having an amino acid sequence of SEQ ID NO:278, and a VL CDR3 having an amino acid sequence of SEQ ID NO:279. In some embodiments, the first binding domain that binds to TRGV9 comprises: (i) a VH comprising a VH CDR1 having an amino acid sequence of SEQ ID NO:280, a VH CDR2 having an amino acid sequence of SEQ ID NO:281, and a VH CDR3 having an amino acid sequence of SEQ ID NO:282; and (ii) a VL comprising a VL CDR1 having an amino acid sequence of SEQ ID NO:283, a VL CDR2 having an amino acid sequence of SEQ ID NO:284, and a VL CDR3 having an amino acid sequence of SEQ ID NO:285. In some embodiments, the first binding domain that binds to TRGV9 comprises: (i) a VH comprising a VH CDR1 having an amino acid sequence of SEQ ID NO:286, a VH CDR2 having an amino acid sequence of SEQ ID NO:287, and a VH CDR3 having an amino acid sequence of SEQ ID NO:288; and (ii) a VL comprising a VL CDR1 having an amino acid sequence of SEQ ID NO:289, a VL CDR2 having an amino acid sequence of SEQ ID NO:290, and a VL CDR3 having an amino acid sequence of SEQ ID NO:291. In some embodiments, the first binding domain that binds to TRGV9 comprises: (i) a VH comprising a VH CDR1 having an amino acid sequence of SEQ ID NO:286, a VH CDR2 having an amino acid sequence of SEQ ID NO:706, and a VH CDR3 having an amino acid sequence of SEQ ID NO:707; and (ii) a VL comprising a VL CDR1 having an amino acid sequence of SEQ ID NO:289, a VL CDR2 having an amino acid sequence of SEQ ID NO:290, and a VL CDR3 having an amino acid sequence of SEQ ID NO:291. In some embodiments, the first binding domain that binds to TRGV9 comprises: (i) a VH comprising a VH CDR1 having an amino acid sequence of SEQ ID NO:292, a VH CDR2 having an amino acid sequence of SEQ ID NO:293, and a VH CDR3 having an amino acid sequence of SEQ ID NO:294; and (ii) a VL comprising a VL CDR1 having an amino acid sequence of SEQ ID NO:295, a VL CDR2 having an amino acid sequence of SEQ ID NO:296, and a VL CDR3 having an amino acid sequence of SEQ ID NO:297. In some embodiments, the first binding domain that binds to TRGV9 comprises: (i) a VH comprising a VH CDR1 having an amino acid sequence of SEQ ID NO:298, a VH CDR2 having an amino acid sequence of SEQ ID NO:299, and a VH CDR3 having an amino acid sequence of SEQ ID NO:300; and (ii) a VL comprising a VL CDR1 having an amino acid sequence of SEQ ID NO:301, a VL CDR2 having an amino acid sequence of SEQ ID NO:302, and a VL CDR3 having an amino acid sequence of SEQ ID NO:303. In some embodiments, the first binding domain that binds to TRGV9 comprises: (i) a VH comprising a VH CDR1 having an amino acid sequence of SEQ ID NO:304, a VH CDR2 having an amino acid sequence of SEQ ID NO:305, and a VH CDR3 having an amino acid sequence of SEQ ID NO:306; and (ii) a VL comprising a VL CDR1 having an amino acid sequence of SEQ ID NO:307, a VL CDR2 having an amino acid sequence of SEQ ID NO:308, and a VL CDR3 having an amino acid sequence of SEQ ID NO:309. In some embodiments, the first binding domain that binds to TRGV9 comprises: (i) a VH comprising a VH CDR1 having an amino acid sequence of SEQ ID NO:310, a VH CDR2 having an amino acid sequence of SEQ ID NO:311, and a VH CDR3 having an amino acid sequence of SEQ ID NO:312; and (ii) a VL comprising a VL CDR1 having an amino acid sequence of SEQ ID NO:313, a VL CDR2 having an amino acid sequence of SEQ ID NO:314, and a VL CDR3 having an amino acid sequence of SEQ ID NO:315. In some embodiments, the first binding domain that binds to TRGV9 comprises: (i) a VH comprising a VH CDR1 having an amino acid sequence of SEQ ID NO:316, a VH CDR2 having an amino acid sequence of SEQ ID NO:317, and a VH CDR3 having an amino acid sequence of SEQ ID NO:318; and (ii) a VL comprising a VL CDR1 having an amino acid sequence of SEQ ID NO:319, a VL CDR2 having an amino acid sequence of SEQ ID NO:320, and a VL CDR3 having an amino acid sequence of SEQ ID NO:321. In some embodiments, the first binding domain that binds to TRGV9 comprises: (i) a VH comprising a VH CDR1 having an amino acid sequence of SEQ ID NO:322, a VH CDR2 having an amino acid sequence of SEQ ID NO:323, and a VH CDR3 having an amino acid sequence of SEQ ID NO:324; and (ii) a VL comprising a VL CDR1 having an amino acid sequence of SEQ ID NO:325, a VL CDR2 having an amino acid sequence of SEQ ID NO:326, and a VL CDR3 having an amino acid sequence of SEQ ID NO:327. In some embodiments, the first binding domain that binds to TRGV9 comprises: (i) a VH comprising a VH CDR1 having an amino acid sequence of SEQ ID NO:322, a VH CDR2 having an amino acid sequence of SEQ ID NO:708, and a VH CDR3 having an amino acid sequence of SEQ ID NO:709; and (ii) a VL comprising a VL CDR1 having an amino acid sequence of SEQ ID NO:325, a VL CDR2 having an amino acid sequence of SEQ ID NO:326, and a VL CDR3 having an amino acid sequence of SEQ ID NO:327. In some embodiments, the first binding domain that binds to TRGV9 comprises: (i) a VH comprising a VH CDR1 having an amino acid sequence of SEQ ID NO:328, a VH CDR2 having an amino acid sequence of SEQ ID NO:329, and a VH CDR3 having an amino acid sequence of SEQ ID NO:330; and (ii) a VL comprising a VL CDR1 having an amino acid sequence of SEQ ID NO:331, a VL CDR2 having an amino acid sequence of SEQ ID NO:332, and a VL CDR3 having an amino acid sequence of SEQ ID NO:333. In some embodiments, the first binding domain that binds to TRGV9 comprises: (i) a VH comprising a VH CDR1 having an amino acid sequence of SEQ ID NO:334, a VH CDR2 having an amino acid sequence of SEQ ID NO:335, and a VH CDR3 having an amino acid sequence of SEQ ID NO:336; and (ii) a VL comprising a VL CDR1 having an amino acid sequence of SEQ ID NO:337, a VL CDR2 having an amino acid sequence of SEQ ID NO:338, and a VL CDR3 having an amino acid sequence of SEQ ID NO:339. In some embodiments, the first binding domain that binds to TRGV9 comprises: (i) a VH comprising a VH CDR1 having an amino acid sequence of SEQ ID NO:340, a VH CDR2 having an amino acid sequence of SEQ ID NO:341, and a VH CDR3 having an amino acid sequence of SEQ ID NO:342; and (ii) a VL comprising a VL CDR1 having an amino acid sequence of SEQ ID NO:343, a VL CDR2 having an amino acid sequence of SEQ ID NO:344, and a VL CDR3 having an amino acid sequence of SEQ ID NO:345. In some embodiments, the first binding domain that binds to TRGV9 comprises: (i) a VH comprising a VH CDR1 having an amino acid sequence of SEQ ID NO:346, a VH CDR2 having an amino acid sequence of SEQ ID NO:347, and a VH CDR3 having an amino acid sequence of SEQ ID NO:348; and (ii) a VL comprising a VL CDR1 having an amino acid sequence of SEQ ID NO:349, a VL CDR2 having an amino acid sequence of SEQ ID NO:350, and a VL CDR3 having an amino acid sequence of SEQ ID NO:351. In some embodiments, the first binding domain that binds to TRGV9 comprises: (i) a VH comprising a VH CDR1 having an amino acid sequence of SEQ ID NO:352, a VH CDR2 having an amino acid sequence of SEQ ID NO:353, and a VH CDR3 having an amino acid sequence of SEQ ID NO:354; and (ii) a VL comprising a VL CDR1 having an amino acid sequence of SEQ ID NO:355, a VL CDR2 having an amino acid sequence of SEQ ID NO:356, and a VL CDR3 having an amino acid sequence of SEQ ID NO:357. In some embodiments, the first binding domain that binds to TRGV9 comprises: (i) a VH comprising a VH CDR1 having an amino acid sequence of SEQ ID NO:358, a VH CDR2 having an amino acid sequence of SEQ ID NO:359, and a VH CDR3 having an amino acid sequence of SEQ ID NO:360; and (ii) a VL comprising a VL CDR1 having an amino acid sequence of SEQ ID NO:361, a VL CDR2 having an amino acid sequence of SEQ ID NO:362, and a VL CDR3 having an amino acid sequence of SEQ ID NO:363. In some embodiments, the first binding domain that binds to TRGV9 comprises: (i) a VH comprising a VH CDR1 having an amino acid sequence of SEQ ID NO:358, a VH CDR2 having an amino acid sequence of SEQ ID NO:710, and a VH CDR3 having an amino acid sequence of SEQ ID NO:711; and (ii) a VL comprising a VL CDR1 having an amino acid sequence of SEQ ID NO:361, a VL CDR2 having an amino acid sequence of SEQ ID NO:362, and a VL CDR3 having an amino acid sequence of SEQ ID NO:363. In some embodiments, the first binding domain that binds to TRGV9 comprises: (i) a VH comprising a VH CDR1 having an amino acid sequence of SEQ ID NO:364, a VH CDR2 having an amino acid sequence of SEQ ID NO:365, and a VH CDR3 having an amino acid sequence of SEQ ID NO:366; and (ii) a VL comprising a VL CDR1 having an amino acid sequence of SEQ ID NO:367, a VL CDR2 having an amino acid sequence of SEQ ID NO:368, and a VL CDR3 having an amino acid sequence of SEQ ID NO:369. In some embodiments, the first binding domain that binds to TRGV9 comprises: (i) a VH comprising a VH CDR1 having an amino acid sequence of SEQ ID NO:370, a VH CDR2 having an amino acid sequence of SEQ ID NO:371, and a VH CDR3 having an amino acid sequence of SEQ ID NO:372; and (ii) a VL comprising a VL CDR1 having an amino acid sequence of SEQ ID NO:373, a VL CDR2 having an amino acid sequence of SEQ ID NO:374, and a VL CDR3 having an amino acid sequence of SEQ ID NO:375. In some embodiments, the first binding domain that binds to TRGV9 comprises: (i) a VH comprising a VH CDR1 having an amino acid sequence of SEQ ID NO:376, a VH CDR2 having an amino acid sequence of SEQ ID NO:377, and a VH CDR3 having an amino acid sequence of SEQ ID NO:378; and (ii) a VL comprising a VL CDR1 having an amino acid sequence of SEQ ID NO:379, a VL CDR2 having an amino acid sequence of SEQ ID NO:380, and a VL CDR3 having an amino acid sequence of SEQ ID NO:381. In some embodiments, the first binding domain that binds to TRGV9 comprises: (i) a VH comprising a VH CDR1 having an amino acid sequence of SEQ ID NO:382, a VH CDR2 having an amino acid sequence of SEQ ID NO:383, and a VH CDR3 having an amino acid sequence of SEQ ID NO:384; and (ii) a VL comprising a VL CDR1 having an amino acid sequence of SEQ ID NO:385, a VL CDR2 having an amino acid sequence of SEQ ID NO:386, and a VL CDR3 having an amino acid sequence of SEQ ID NO:387. In some embodiments, the first binding domain that binds to TRGV9 comprises: (i) a VH comprising a VH CDR1 having an amino acid sequence of SEQ ID NO:388, a VH CDR2 having an amino acid sequence of SEQ ID NO:389, and a VH CDR3 having an amino acid sequence of SEQ ID NO:390; and (ii) a VL comprising a VL CDR1 having an amino acid sequence of SEQ ID NO:391, a VL CDR2 having an amino acid sequence of SEQ ID NO:392, and a VL CDR3 having an amino acid sequence of SEQ ID NO:393. In some embodiments, the first binding domain that binds to TRGV9 comprises: (i) a VH comprising a VH CDR1 having an amino acid sequence of SEQ ID NO:394, a VH CDR2 having an amino acid sequence of SEQ ID NO:395, and a VH CDR3 having an amino acid sequence of SEQ ID NO:396; and (ii) a VL comprising a VL CDR1 having an amino acid sequence of SEQ ID NO:397, a VL CDR2 having an amino acid sequence of SEQ ID NO:398, and a VL CDR3 having an amino acid sequence of SEQ ID NO:399. In some embodiments, the first binding domain that binds to TRGV9 comprises: (i) a VH comprising a VH CDR1 having an amino acid sequence of SEQ ID NO:394, a VH CDR2 having an amino acid sequence of SEQ ID NO:712, and a VH CDR3 having an amino acid sequence of SEQ ID NO:713; and (ii) a VL comprising a VL CDR1 having an amino acid sequence of SEQ ID NO:397, a VL CDR2 having an amino acid sequence of SEQ ID NO:398, and a VL CDR3 having an amino acid sequence of SEQ ID NO:399. In some embodiments, the first binding domain that binds to TRGV9 comprises: (i) a VH comprising a VH CDR1 having an amino acid sequence of SEQ ID NO:400, a VH CDR2 having an amino acid sequence of SEQ ID NO:401, and a VH CDR3 having an amino acid sequence of SEQ ID NO:402; and (ii) a VL comprising a VL CDR1 having an amino acid sequence of SEQ ID NO:403, a VL CDR2 having an amino acid sequence of SEQ ID NO:404, and a VL CDR3 having an amino acid sequence of SEQ ID NO:405. In some embodiments, the first binding domain that binds to TRGV9 comprises: (i) a VH comprising a VH CDR1 having an amino acid sequence of SEQ ID NO:406, a VH CDR2 having an amino acid sequence of SEQ ID NO:407, and a VH CDR3 having an amino acid sequence of SEQ ID NO:408; and (ii) a VL comprising a VL CDR1 having an amino acid sequence of SEQ ID NO:409, a VL CDR2 having an amino acid sequence of SEQ ID NO:410, and a VL CDR3 having an amino acid sequence of SEQ ID NO:411. In some embodiments, the first binding domain that binds to TRGV9 comprises: (i) a VH comprising a VH CDR1 having an amino acid sequence of SEQ ID NO:412, a VH CDR2 having an amino acid sequence of SEQ ID NO:413, and a VH CDR3 having an amino acid sequence of SEQ ID NO:414; and (ii) a VL comprising a VL CDR1 having an amino acid sequence of SEQ ID NO:415, a VL CDR2 having an amino acid sequence of SEQ ID NO:416, and a VL CDR3 having an amino acid sequence of SEQ ID NO:417. In some embodiments, the first binding domain that binds to TRGV9 comprises: (i) a VH comprising a VH CDR1 having an amino acid sequence of SEQ ID NO:418, a VH CDR2 having an amino acid sequence of SEQ ID NO:419, and a VH CDR3 having an amino acid sequence of SEQ ID NO:420; and (ii) a VL comprising a VL CDR1 having an amino acid sequence of SEQ ID NO:421, a VL CDR2 having an amino acid sequence of SEQ ID NO:422, and a VL CDR3 having an amino acid sequence of SEQ ID NO:423. In some embodiments, the first binding domain that binds to TRGV9 comprises: (i) a VH comprising a VH CDR1 having an amino acid sequence of SEQ ID NO:424, a VH CDR2 having an amino acid sequence of SEQ ID NO:425, and a VH CDR3 having an amino acid sequence of SEQ ID NO:426; and (ii) a VL comprising a VL CDR1 having an amino acid sequence of SEQ ID NO:427, a VL CDR2 having an amino acid sequence of SEQ ID NO:428, and a VL CDR3 having an amino acid sequence of SEQ ID NO:429. In some embodiments, the first binding domain that binds to TRGV9 comprises: (i) a VH comprising a VH CDR1 having an amino acid sequence of SEQ ID NO:430, a VH CDR2 having an amino acid sequence of SEQ ID NO:431, and a VH CDR3 having an amino acid sequence of SEQ ID NO:432; and (ii) a VL comprising a VL CDR1 having an amino acid sequence of SEQ ID NO:433, a VL CDR2 having an amino acid sequence of SEQ ID NO:434, and a VL CDR3 having an amino acid sequence of SEQ ID NO:435. In some embodiments, the first binding domain that binds to TRGV9 comprises: (i) a VH comprising a VH CDR1 having an amino acid sequence of SEQ ID NO:430, a VH CDR2 having an amino acid sequence of SEQ ID NO:714, and a VH CDR3 having an amino acid sequence of SEQ ID NO:715; and (ii) a VL comprising a VL CDR1 having an amino acid sequence of SEQ ID NO:433, a VL CDR2 having an amino acid sequence of SEQ ID NO:434, and a VL CDR3 having an amino acid sequence of SEQ ID NO:435. In some embodiments, the first binding domain that binds to TRGV9 comprises: (i) a VH comprising a VH CDR1 having an amino acid sequence of SEQ ID NO:436, a VH CDR2 having an amino acid sequence of SEQ ID NO:437, and a VH CDR3 having an amino acid sequence of SEQ ID NO:438; and (ii) a VL comprising a VL CDR1 having an amino acid sequence of SEQ ID NO:439, a VL CDR2 having an amino acid sequence of SEQ ID NO:440, and a VL CDR3 having an amino acid sequence of SEQ ID NO:441. In some embodiments, the first binding domain that binds to TRGV9 comprises: (i) a VH comprising a VH CDR1 having an amino acid sequence of SEQ ID NO:442, a VH CDR2 having an amino acid sequence of SEQ ID NO:443, and a VH CDR3 having an amino acid sequence of SEQ ID NO:444; and (ii) a VL comprising a VL CDR1 having an amino acid sequence of SEQ ID NO:445, a VL CDR2 having an amino acid sequence of SEQ ID NO:446, and a VL CDR3 having an amino acid sequence of SEQ ID NO:447. In some embodiments, the first binding domain that binds to TRGV9 comprises: (i) a VH comprising a VH CDR1 having an amino acid sequence of SEQ ID NO:448, a VH CDR2 having an amino acid sequence of SEQ ID NO:449, and a VH CDR3 having an amino acid sequence of SEQ ID NO:450; and (ii) a VL comprising a VL CDR1 having an amino acid sequence of SEQ ID NO:451, a VL CDR2 having an amino acid sequence of SEQ ID NO:452, and a VL CDR3 having an amino acid sequence of SEQ ID NO:453. In some embodiments, the first binding domain that binds to TRGV9 comprises: (i) a VH comprising a VH CDR1 having an amino acid sequence of SEQ ID NO:454, a VH CDR2 having an amino acid sequence of SEQ ID NO:455, and a VH CDR3 having an amino acid sequence of SEQ ID NO:456; and (ii) a VL comprising a VL CDR1 having an amino acid sequence of SEQ ID NO:457, a VL CDR2 having an amino acid sequence of SEQ ID NO:458, and a VL CDR3 having an amino acid sequence of SEQ ID NO:459. In some embodiments, the first binding domain that binds to TRGV9 comprises: (i) a VH comprising a VH CDR1 having an amino acid sequence of SEQ ID NO:460, a VH CDR2 having an amino acid sequence of SEQ ID NO:461, and a VH CDR3 having an amino acid sequence of SEQ ID NO:462; and (ii) a VL comprising a VL CDR1 having an amino acid sequence of SEQ ID NO:463, a VL CDR2 having an amino acid sequence of SEQ ID NO:464, and a VL CDR3 having an amino acid sequence of SEQ ID NO:465. In some embodiments, the first binding domain that binds to TRGV9 comprises: (i) a VH comprising a VH CDR1 having an amino acid sequence of SEQ ID NO:466, a VH CDR2 having an amino acid sequence of SEQ ID NO:467, and a VH CDR3 having an amino acid sequence of SEQ ID NO:468; and (ii) a VL comprising a VL CDR1 having an amino acid sequence of SEQ ID NO:469, a VL CDR2 having an amino acid sequence of SEQ ID NO:470, and a VL CDR3 having an amino acid sequence of SEQ ID NO:471. In some embodiments, the first binding domain that binds to TRGV9 comprises: (i) a VH comprising a VH CDR1 having an amino acid sequence of SEQ ID NO:466, a VH CDR2 having an amino acid sequence of SEQ ID NO:716, and a VH CDR3 having an amino acid sequence of SEQ ID NO:717; and (ii) a VL comprising a VL CDR1 having an amino acid sequence of SEQ ID NO:469, a VL CDR2 having an amino acid sequence of SEQ ID NO:470, and a VL CDR3 having an amino acid sequence of SEQ ID NO:471. In some embodiments, the first binding domain that binds to TRGV9 comprises: (i) a VH comprising a VH CDR1 having an amino acid sequence of SEQ ID NO:472, a VH CDR2 having an amino acid sequence of SEQ ID NO:473, and a VH CDR3 having an amino acid sequence of SEQ ID NO:474; and (ii) a VL comprising a VL CDR1 having an amino acid sequence of SEQ ID NO:475, a VL CDR2 having an amino acid sequence of SEQ ID NO:476, and a VL CDR3 having an amino acid sequence of SEQ ID NO:477. In some embodiments, the first binding domain that binds to TRGV9 comprises: (i) a VH comprising a VH CDR1 having an amino acid sequence of SEQ ID NO:478, a VH CDR2 having an amino acid sequence of SEQ ID NO:479, and a VH CDR3 having an amino acid sequence of SEQ ID NO:480; and (ii) a VL comprising a VL CDR1 having an amino acid sequence of SEQ ID NO:481, a VL CDR2 having an amino acid sequence of SEQ ID NO:482, and a VL CDR3 having an amino acid sequence of SEQ ID NO:483. In some embodiments, the first binding domain that binds to TRGV9 comprises: (i) a VH comprising a VH CDR1 having an amino acid sequence of SEQ ID NO:484, a VH CDR2 having an amino acid sequence of SEQ ID NO:485, and a VH CDR3 having an amino acid sequence of SEQ ID NO:486; and (ii) a VL comprising a VL CDR1 having an amino acid sequence of SEQ ID NO:487, a VL CDR2 having an amino acid sequence of SEQ ID NO:488, and a VL CDR3 having an amino acid sequence of SEQ ID NO:489. In some embodiments, the first binding domain that binds to TRGV9 comprises: (i) a VH comprising a VH CDR1 having an amino acid sequence of SEQ ID NO:490, a VH CDR2 having an amino acid sequence of SEQ ID NO:491, and a VH CDR3 having an amino acid sequence of SEQ ID NO:492; and (ii) a VL comprising a VL CDR1 having an amino acid sequence of SEQ ID NO:493, a VL CDR2 having an amino acid sequence of SEQ ID NO:494, and a VL CDR3 having an amino acid sequence of SEQ ID NO:495. In some embodiments, the first binding domain that binds to TRGV9 comprises: (i) a VH comprising a VH CDR1 having an amino acid sequence of SEQ ID NO:496, a VH CDR2 having an amino acid sequence of SEQ ID NO:497, and a VH CDR3 having an amino acid sequence of SEQ ID NO:498; and (ii) a VL comprising a VL CDR1 having an amino acid sequence of SEQ ID NO:499, a VL CDR2 having an amino acid sequence of SEQ ID NO:500, and a VL CDR3 having an amino acid sequence of SEQ ID NO:501. In some embodiments, the first binding domain that binds to TRGV9 comprises: (i) a VH comprising a VH CDR1 having an amino acid sequence of SEQ ID NO:502, a VH CDR2 having an amino acid sequence of SEQ ID NO:503, and a VH CDR3 having an amino acid sequence of SEQ ID NO:504; and (ii) a VL comprising a VL CDR1 having an amino acid sequence of SEQ ID NO:505, a VL CDR2 having an amino acid sequence of SEQ ID NO:506, and a VL CDR3 having an amino acid sequence of SEQ ID NO:507. In some embodiments, the first binding domain that binds to TRGV9 comprises: (i) a VH comprising a VH CDR1 having an amino acid sequence of SEQ ID NO:502, a VH CDR2 having an amino acid sequence of SEQ ID NO:718, and a VH CDR3 having an amino acid sequence of SEQ ID NO:719; and (ii) a VL comprising a VL CDR1 having an amino acid sequence of SEQ ID NO:505, a VL CDR2 having an amino acid sequence of SEQ ID NO:506, and a VL CDR3 having an amino acid sequence of SEQ ID NO:507. In some embodiments, the first binding domain that binds to TRGV9 comprises: (i) a VH comprising a VH CDR1 having an amino acid sequence of SEQ ID NO:508, a VH CDR2 having an amino acid sequence of SEQ ID NO:509, and a VH CDR3 having an amino acid sequence of SEQ ID NO:510; and (ii) a VL comprising a VL CDR1 having an amino acid sequence of SEQ ID NO:511, a VL CDR2 having an amino acid sequence of SEQ ID NO:512, and a VL CDR3 having an amino acid sequence of SEQ ID NO:513. In some embodiments, the first binding domain that binds to TRGV9 comprises: (i) a VH comprising a VH CDR1 having an amino acid sequence of SEQ ID NO:514, a VH CDR2 having an amino acid sequence of SEQ ID NO:515, and a VH CDR3 having an amino acid sequence of SEQ ID NO:516; and (ii) a VL comprising a VL CDR1 having an amino acid sequence of SEQ ID NO:517, a VL CDR2 having an amino acid sequence of SEQ ID NO:518, and a VL CDR3 having an amino acid sequence of SEQ ID NO:519. In some embodiments, the first binding domain that binds to TRGV9 comprises: (i) a VH comprising a VH CDR1 having an amino acid sequence of SEQ ID NO:520, a VH CDR2 having an amino acid sequence of SEQ ID NO:521, and a VH CDR3 having an amino acid sequence of SEQ ID NO:522; and (ii) a VL comprising a VL CDR1 having an amino acid sequence of SEQ ID NO:523, a VL CDR2 having an amino acid sequence of SEQ ID NO:524, and a VL CDR3 having an amino acid sequence of SEQ ID NO:525. In some embodiments, the first binding domain that binds to TRGV9 comprises: (i) a VH comprising a VH CDR1 having an amino acid sequence of SEQ ID NO:526, a VH CDR2 having an amino acid sequence of SEQ ID NO:527, and a VH CDR3 having an amino acid sequence of SEQ ID NO:528; and (ii) a VL comprising a VL CDR1 having an amino acid sequence of SEQ ID NO:529, a VL CDR2 having an amino acid sequence of SEQ ID NO:530, and a VL CDR3 having an amino acid sequence of SEQ ID NO:531. In some embodiments, the first binding domain that binds to TRGV9 comprises: (i) a VH comprising a VH CDR1 having an amino acid sequence of SEQ ID NO:532, a VH CDR2 having an amino acid sequence of SEQ ID NO:533, and a VH CDR3 having an amino acid sequence of SEQ ID NO:534; and (ii) a VL comprising a VL CDR1 having an amino acid sequence of SEQ ID NO:535, a VL CDR2 having an amino acid sequence of SEQ ID NO:536, and a VL CDR3 having an amino acid sequence of SEQ ID NO:537. In some embodiments, the first binding domain that binds to TRGV9 comprises: (i) a VH comprising a VH CDR1 having an amino acid sequence of SEQ ID NO:538, a VH CDR2 having an amino acid sequence of SEQ ID NO:539, and a VH CDR3 having an amino acid sequence of SEQ ID NO:540; and (ii) a VL comprising a VL CDR1 having an amino acid sequence of SEQ ID NO:541, a VL CDR2 having an amino acid sequence of SEQ ID NO:542, and a VL CDR3 having an amino acid sequence of SEQ ID NO:543. In some embodiments, the first binding domain that binds to TRGV9 comprises: (i) a VH comprising a VH CDR1 having an amino acid sequence of SEQ ID NO:538, a VH CDR2 having an amino acid sequence of SEQ ID NO:720, and a VH CDR3 having an amino acid sequence of SEQ ID NO:721; and (ii) a VL comprising a VL CDR1 having an amino acid sequence of SEQ ID NO:541, a VL CDR2 having an amino acid sequence of SEQ ID NO:542, and a VL CDR3 having an amino acid sequence of SEQ ID NO:543. In some embodiments, the first binding domain that binds to TRGV9 comprises: (i) a VH comprising a VH CDR1 having an amino acid sequence of SEQ ID NO:544, a VH CDR2 having an amino acid sequence of SEQ ID NO:545, and a VH CDR3 having an amino acid sequence of SEQ ID NO:546; and (ii) a VL comprising a VL CDR1 having an amino acid sequence of SEQ ID NO:547, a VL CDR2 having an amino acid sequence of SEQ ID NO:548, and a VL CDR3 having an amino acid sequence of SEQ ID NO:549. In some embodiments, the first binding domain that binds to TRGV9 comprises: (i) a VH comprising a VH CDR1 having an amino acid sequence of SEQ ID NO:550, a VH CDR2 having an amino acid sequence of SEQ ID NO:551, and a VH CDR3 having an amino acid sequence of SEQ ID NO:552; and (ii) a VL comprising a VL CDR1 having an amino acid sequence of SEQ ID NO:553, a VL CDR2 having an amino acid sequence of SEQ ID NO:554, and a VL CDR3 having an amino acid sequence of SEQ ID NO:555. In some embodiments, the second binding domain that binds CD123 comprises: (i) a VH comprising a VH CDR1 having an amino acid sequence of SEQ ID NO:556, a VH CDR2 having an amino acid sequence of SEQ ID NO:557, and a VH CDR3 having an amino acid sequence of SEQ ID NO:558; and (ii) a VL comprising a VL CDR1 having an amino acid sequence of SEQ ID NO:559, a VL CDR2 having an amino acid sequence of SEQ ID NO:560, and a VL CDR3 having an amino acid sequence of SEQ ID NO:561. In some embodiments, the second binding domain that binds CD123 comprises: (i) a VH comprising a VH CDR1 having an amino acid sequence of SEQ ID NO:562, a VH CDR2 having an amino acid sequence of SEQ ID NO:563, and a VH CDR3 having an amino acid sequence of SEQ ID NO:564; and (ii) a VL comprising a VL CDR1 having an amino acid sequence of SEQ ID NO:565, a VL CDR2 having an amino acid sequence of SEQ ID NO:566, and a VL CDR3 having an amino acid sequence of SEQ ID NO:567. In some embodiments, the second binding domain that binds CD123 comprises: (i) a VH comprising a VH CDR1 having an amino acid sequence of SEQ ID NO:568, a VH CDR2 having an amino acid sequence of SEQ ID NO:569, and a VH CDR3 having an amino acid sequence of SEQ ID NO:570; and (ii) a VL comprising a VL CDR1 having an amino acid sequence of SEQ ID NO:571, a VL CDR2 having an amino acid sequence of SEQ ID NO:572, and a VL CDR3 having an amino acid sequence of SEQ ID NO:573. In some embodiments, the second binding domain that binds CD123 comprises: (i) a VH comprising a VH CDR1 having an amino acid sequence of SEQ ID NO:574, a VH CDR2 having an amino acid sequence of SEQ ID NO:575, and a VH CDR3 having an amino acid sequence of SEQ ID NO:576; and (ii) a VL comprising a VL CDR1 having an amino acid sequence of SEQ ID NO:577, a VL CDR2 having an amino acid sequence of SEQ ID NO:578, and a VL CDR3 having an amino acid sequence of SEQ ID NO:579. In some embodiments, the second binding domain that binds CD123 comprises: (i) a VH comprising a VH CDR1 having an amino acid sequence of SEQ ID NO:574, a VH CDR2 having an amino acid sequence of SEQ ID NO:722, and a VH CDR3 having an amino acid sequence of SEQ ID NO:723; and (ii) a VL comprising a VL CDR1 having an amino acid sequence of SEQ ID NO:577, a VL CDR2 having an amino acid sequence of SEQ ID NO:578, and a VL CDR3 having an amino acid sequence of SEQ ID NO:579. In some embodiments, the second binding domain that binds CD123 comprises: (i) a VH comprising a VH CDR1 having an amino acid sequence of SEQ ID NO:580, a VH CDR2 having an amino acid sequence of SEQ ID NO:581, and a VH CDR3 having an amino acid sequence of SEQ ID NO:582; and (ii) a VL comprising a VL CDR1 having an amino acid sequence of SEQ ID NO:583, a VL CDR2 having an amino acid sequence of SEQ ID NO:584, and a VL CDR3 having an amino acid sequence of SEQ ID NO:585. In some embodiments, the second binding domain that binds CD123 comprises: (i) a VH comprising a VH CDR1 having an amino acid sequence of SEQ ID NO:586, a VH CDR2 having an amino acid sequence of SEQ ID NO:587, and a VH CDR3 having an amino acid sequence of SEQ ID NO:588; and (ii) a VL comprising a VL CDR1 having an amino acid sequence of SEQ ID NO:589, a VL CDR2 having an amino acid sequence of SEQ ID NO:590, and a VL CDR3 having an amino acid sequence of SEQ ID NO:591.

In some embodiments, the VH CDR1, VH CDR2, VH CDR3, VL CDR1, VL CDR2, and VL CDR3 sequences are according to the Kabat numbering system. In some embodiments, the VH CDR1, VH CDR2, VH CDR3, VL CDR1, VL CDR2, and VL CDR3 sequences are according to the Chothia numbering system. In some embodiments, the VH CDR1, VH CDR2, VH CDR3, VL CDR1, VL CDR2, and VL CDR3 sequences are according to the Exemplary numbering system. In some embodiments, the VH CDR1, VH CDR2, VH CDR3, VL CDR1, VL CDR2, and VL CDR3 sequences are according to the Contact numbering system. In some embodiments, the VH CDR1, VH CDR2, VH CDR3, VL CDR1, VL CDR2, and VL CDR3 sequences are according to the IMGT numbering system. In some embodiments, the VH CDR1, VH CDR2, VH CDR3, VL CDR1, VL CDR2, and VL CDR3 sequences are according to the AbM numbering system.

In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:7; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:34; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:35; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:36; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:65; and (ii) a VL comprising a VL CDR1, a VL CDR2, and a VL CDR3 having amino acid sequences of the VL CDR1, VL CDR2, and VL CDR3, respectively, of SEQ ID NO:66. In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:67; and (ii) a VL comprising a VL CDR1, a VL CDR2, and a VL CDR3 having amino acid sequences of the VL CDR1, VL CDR2, and VL CDR3, respectively, of SEQ ID NO:68. In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:95; and (ii) a VL comprising a VL CDR1, a VL CDR2, and a VL CDR3 having amino acid sequences of the VL CDR1, VL CDR2, and VL CDR3, respectively, of SEQ ID NO:96. In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:104; and (ii) a VL comprising a VL CDR1, a VL CDR2, and a VL CDR3 having amino acid sequences of the VL CDR1, VL CDR2, and VL CDR3, respectively, of SEQ ID NO:105. In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:113; and (ii) a VL comprising a VL CDR1, a VL CDR2, and a VL CDR3 having amino acid sequences of the VL CDR1, VL CDR2, and VL CDR3, respectively, of SEQ ID NO:114. In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:123; and (ii) a VL comprising a VL CDR1, a VL CDR2, and a VL CDR3 having amino acid sequences of the VL CDR1, VL CDR2, and VL CDR3, respectively, of SEQ ID NO:124. In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:133; and (ii) a VL comprising a VL CDR1, a VL CDR2, and a VL CDR3 having amino acid sequences of the VL CDR1, VL CDR2, and VL CDR3, respectively, of SEQ ID NO:134. In some embodiments, the VH CDR1, VH CDR2, VH CDR3, VL CDR1, VL CDR2, and VL CDR3 sequences are according to the Kabat numbering system. In some embodiments, the VH CDR1, VH CDR2, VH CDR3, VL CDR1, VL CDR2, and VL CDR3 sequences are according to the Chothia numbering system. In some embodiments, the VH CDR1, VH CDR2, VH CDR3, VL CDR1, VL CDR2, and VL CDR3 sequences are according to the Exemplary numbering system. In some embodiments, the VH CDR1, VH CDR2, VH CDR3, VL CDR1, VL CDR2, and VL CDR3 sequences are according to the Contact numbering system. In some embodiments, the VH CDR1, VH CDR2, VH CDR3, VL CDR1, VL CDR2, and VL CDR3 sequences are according to the IMGT numbering system. In some embodiments, the VH CDR1, VH CDR2, VH CDR3, VL CDR1, VL CDR2, and VL CDR3 sequences are according to the AbM numbering system.

In another aspect, provided herein is a bispecific antibody having a first binding domain that binds to TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:7; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is a bispecific antibody having a first binding domain that binds to TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:34; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is a bispecific antibody having a first binding domain that binds to TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:35; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is a bispecific antibody having a first binding domain that binds to TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:36; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is a bispecific antibody having a first binding domain that binds to TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:65; and (ii) a VL comprising a VL CDR1, a VL CDR2, and a VL CDR3 having amino acid sequences of the VL CDR1, VL CDR2, and VL CDR3, respectively, of SEQ ID NO:66. In another aspect, provided herein is a bispecific antibody having a first binding domain that binds to TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:67; and (ii) a VL comprising a VL CDR1, a VL CDR2, and a VL CDR3 having amino acid sequences of the VL CDR1, VL CDR2, and VL CDR3, respectively, of SEQ ID NO:68. In another aspect, provided herein is a bispecific antibody having a first binding domain that binds to TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:95; and (ii) a VL comprising a VL CDR1, a VL CDR2, and a VL CDR3 having amino acid sequences of the VL CDR1, VL CDR2, and VL CDR3, respectively, of SEQ ID NO:96. In another aspect, provided herein is a bispecific antibody having a first binding domain that binds to TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:104; and (ii) a VL comprising a VL CDR1, a VL CDR2, and a VL CDR3 having amino acid sequences of the VL CDR1, VL CDR2, and VL CDR3, respectively, of SEQ ID NO:105. In another aspect, provided herein is a bispecific antibody having a first binding domain that binds to TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:113; and (ii) a VL comprising a VL CDR1, a VL CDR2, and a VL CDR3 having amino acid sequences of the VL CDR1, VL CDR2, and VL CDR3, respectively, of SEQ ID NO:114. In another aspect, provided herein is a bispecific antibody having a first binding domain that binds to TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:123; and (ii) a VL comprising a VL CDR1, a VL CDR2, and a VL CDR3 having amino acid sequences of the VL CDR1, VL CDR2, and VL CDR3, respectively, of SEQ ID NO:124. In another aspect, provided herein is a bispecific antibody having a first binding domain that binds to TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:133; and (ii) a VL comprising a VL CDR1, a VL CDR2, and a VL CDR3 having amino acid sequences of the VL CDR1, VL CDR2, and VL CDR3, respectively, of SEQ ID NO:134. In certain embodiments, the bispecific antibody comprises a second binding domain that binds to tumor associated antigen. In certain embodiments, the bispecific antibody comprises a second binding domain that binds to CD123. In some embodiments, the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In some embodiments, the VH CDR1, VH CDR2, VH CDR3, VL CDR1, VL CDR2, and VL CDR3 sequences are according to the Kabat numbering system. In some embodiments, the VH CDR1, VH CDR2, VH CDR3, VL CDR1, VL CDR2, and VL CDR3 sequences are according to the Chothia numbering system. In some embodiments, the VH CDR1, VH CDR2, VH CDR3, VL CDR1, VL CDR2, and VL CDR3 sequences are according to the Exemplary numbering system. In some embodiments, the VH CDR1, VH CDR2, VH CDR3, VL CDR1, VL CDR2, and VL CDR3 sequences are according to the Contact numbering system. In some embodiments, the VH CDR1, VH CDR2, VH CDR3, VL CDR1, VL CDR2, and VL CDR3 sequences are according to the IMGT numbering system. In some embodiments, the VH CDR1, VH CDR2, VH CDR3, VL CDR1, VL CDR2, and VL CDR3 sequences are according to the AbM numbering system.

According to a particular aspect, provided herein is an isolated TRGV9 antibody or antigen-binding fragment thereof comprising (a) a first heavy chain (HC1); (b) a second heavy chain (HC2); (c) a first light chain (LC1); and (d) a second light chain (LC2). The HC1 can be associated with the LC1 and the HC2 can be associated with LC2. The HC1 can comprise a heavy chain complementarity determining region 1 (HCDR1), HCDR2, and HCDR3 comprising the amino acid sequences of:
  i. SEQ ID NO:1, SEQ ID NO:2, and SEQ ID NO:3, respectively,
  ii. SEQ ID NO:1, SEQ ID NO:2, and SEQ ID NO:31, respectively,
  iii. SEQ ID NO:1, SEQ ID NO:2, and SEQ ID NO:32, respectively, or
  iv. SEQ ID NO:1, SEQ ID NO:2, and SEQ ID NO:33, respectively,
and LC1 can comprise a light chain complementarity determining region 1 (LCDR1), LCDR2, and LCDR3 comprising the amino acid sequences of SEQ ID NO:4, SEQ ID NO:5, and SEQ ID NO:6, respectively. The HC1 and LC1 form a binding site for a first antigen, and the HC2 and LC2 form a binding site for a second antigen. The binding site for a first antigen can, for example, bind a TRGV9 on a γδ T cell. The binding site for a second antigen can, for example, bind a cancer antigen present on the surface of a cancer cell. The binding of the TRGV9 bispecific antibody to TRGV9 present on the surface of the γδ T cell, and the binding of the tumor associated antigen present on the surface of the cancer cell can, for example, result in the killing of the cancer cell.

According to another particular aspect, provided herein is an isolated TRGV9 antibody or antigen-binding fragment thereof comprising (a) a HC1; (b) a HC2; (c) a LC1; and (d) a LC2. The HC1 can be associated with the LC1 and the HC2 can be associated with LC2. In some embodiments, the HC1 comprises a HCDR1, HCDR2, and HCDR3 comprising the amino acid sequences of SEQ ID NO:1, SEQ ID NO:2, and SEQ ID NO:3, and LC1 comprises a LCDR1, LCDR2, and LCDR3 comprising the amino acid sequences of SEQ ID NO:4, SEQ ID NO:5, and SEQ ID NO:6, respectively. In some embodiments, the HC1 comprises a HCDR1, HCDR2, and HCDR3 comprising the amino acid sequences of SEQ ID NO:1, SEQ ID NO:2, and SEQ ID NO:31, and LC1 comprises a LCDR1, LCDR2, and LCDR3 comprising the amino acid sequences of SEQ ID NO:4, SEQ ID NO:5, and SEQ ID NO:6, respectively. In some embodiments, the HC1 comprises a HCDR1, HCDR2, and HCDR3 comprising the amino acid sequences of SEQ ID NO:1, SEQ ID NO:2, and SEQ ID NO:32, and LC1 comprises a LCDR1, LCDR2, and LCDR3 comprising the amino acid sequences of SEQ ID NO:4, SEQ ID NO:5, and SEQ ID NO:6, respectively. In some embodiments, the HC1 comprises a HCDR1, HCDR2, and HCDR3 comprising the amino acid sequences of SEQ ID NO:1, SEQ ID NO:2, and SEQ ID NO:33, and LC1 comprises a LCDR1, LCDR2, and LCDR3 comprising the amino acid sequences of SEQ ID NO:4, SEQ ID NO:5, and SEQ ID NO:6, respectively. In some embodiments, the HC1 comprises a HCDR1, HCDR2, and HCDR3 comprising the amino acid sequences of SEQ ID NO:1, SEQ ID NO:76, and SEQ ID NO:3, respectively, and LC1 comprises a LCDR1, LCDR2, and LCDR3 comprising the amino acid sequences of SEQ ID NO:77, SEQ ID NO:5, and SEQ ID NO:6, respectively. In some embodiments, the HC1 comprises a HCDR1, HCDR2, and HCDR3 comprising the amino acid sequences of SEQ ID NO:60, SEQ ID NO:61, and SEQ ID NO:62, respectively, and LC1 comprises a LCDR1, LCDR2, and LCDR3 comprising the amino acid sequences of SEQ ID NO:63, SEQ ID NO:64, and SEQ ID NO:6, respectively. In some embodiments, the HC1 comprises a HCDR1, HCDR2, and HCDR3 comprising the amino acid sequences of SEQ ID NO:89, SEQ ID NO:90, and SEQ ID NO:91, respectively, and LC1 comprises a LCDR1, LCDR2, and LCDR3 comprising the amino acid sequences of SEQ ID NO:92, SEQ ID NO:93, and SEQ ID NO:94, respectively. In some embodiments, the HC1 comprises a HCDR1, HCDR2, and HCDR3 comprising the amino acid sequences of SEQ ID NO:98, SEQ ID NO:99, and SEQ ID NO:100, respectively, and LC1 comprises a LCDR1, LCDR2, and LCDR3 comprising the amino acid sequences of SEQ ID NO:101, SEQ ID NO:102, and SEQ ID NO:103, respectively. In some embodiments, the HC1 comprises a HCDR1, HCDR2, and HCDR3 comprising the amino acid sequences of SEQ ID NO:107, SEQ ID NO:108, and SEQ ID NO:109, respectively, and LC1 comprises a LCDR1, LCDR2, and LCDR3 comprising the amino acid sequences of SEQ ID NO:110, SEQ ID NO:111, and SEQ ID NO:112, respectively. In some embodiments, the HC1 comprises a HCDR1, HCDR2, and HCDR3 comprising the amino acid sequences of SEQ ID NO:117, SEQ ID NO:118, and SEQ ID NO:119, respectively, and LC1 comprises a LCDR1, LCDR2, and LCDR3 comprising the amino acid sequences of SEQ ID NO:120, SEQ ID NO:121, and SEQ ID NO:122, respectively. In some embodiments, the HC1 comprises a HCDR1, HCDR2, and HCDR3 comprising the amino acid sequences of SEQ ID NO:127, SEQ ID NO:128, and SEQ ID NO:129, respectively, and LC1 comprises a LCDR1, LCDR2, and LCDR3 comprising the amino acid sequences of SEQ ID NO:130, SEQ ID NO:131, and SEQ ID NO:132, respectively. In some embodiments, the HC1 comprises a HCDR1, HCDR2, and HCDR3 comprising the amino acid sequences of SEQ ID NO:160, SEQ ID NO:161, and SEQ ID NO:162, respectively, and LC1 comprises a LCDR1, LCDR2, and LCDR3 comprising the amino acid sequences of SEQ ID NO:163, SEQ ID NO:164, and SEQ ID NO:165, respectively. In some embodiments, the HC1 comprises a HCDR1, HCDR2, and HCDR3 comprising the amino acid sequences of SEQ ID NO:166, SEQ ID NO: 167, and SEQ ID NO:168, respectively, and LC1 comprises a LCDR1, LCDR2, and LCDR3 comprising the amino acid sequences of SEQ ID NO:169, SEQ ID NO:170, and SEQ ID NO:171, respectively. In some embodiments, the HC1 comprises a HCDR1, HCDR2, and HCDR3 comprising the amino acid sequences of SEQ ID NO:172, SEQ ID NO: 173, and SEQ ID NO:174, respectively, and LC1 comprises a LCDR1, LCDR2, and LCDR3 comprising the amino acid sequences of SEQ ID NO:175, SEQ ID NO:176, and SEQ ID NO:177, respectively. In some embodiments, the HC1 comprises a HCDR1, HCDR2, and HCDR3 comprising the amino acid sequences of SEQ ID NO:178, SEQ ID NO: 179, and SEQ ID NO:180, respectively, and LC1 comprises a LCDR1, LCDR2, and LCDR3 comprising the amino acid sequences of SEQ ID NO:181, SEQ ID NO:182, and SEQ ID NO:183, respectively. In some embodiments, the HC1 comprises a HCDR1, HCDR2, and HCDR3 comprising the amino acid sequences of SEQ ID NO:178, SEQ ID NO:700, and SEQ ID NO:701, respectively, and LC1 comprises a LCDR1, LCDR2, and LCDR3 comprising the amino acid sequences of SEQ ID NO:181, SEQ ID NO:182, and SEQ ID NO:183, respectively. In some embodiments, the HC1 comprises a HCDR1, HCDR2, and HCDR3 comprising the amino acid sequences of SEQ ID NO:184, SEQ ID NO: 185, and SEQ ID NO:186, respectively, and LC1 comprises a LCDR1, LCDR2, and LCDR3 comprising the amino acid sequences of SEQ ID NO:187, SEQ ID NO:188, and SEQ ID NO:189, respectively. In some embodiments, the HC1 comprises a HCDR1, HCDR2, and HCDR3 comprising the amino acid sequences of SEQ ID NO:190, SEQ ID NO:191, and SEQ ID NO:192, respectively, and LC1 comprises a LCDR1, LCDR2, and LCDR3 comprising the amino acid sequences of SEQ ID NO:193, SEQ ID NO:194, and SEQ ID NO:195, respectively. In some embodiments, the HC1 comprises a HCDR1, HCDR2, and HCDR3 comprising the amino acid sequences of SEQ ID NO:196, SEQ ID NO: 197, and SEQ ID NO:198, respectively, and LC1 comprises a LCDR1, LCDR2, and LCDR3 comprising the amino acid sequences of SEQ ID NO:199, SEQ ID NO:200, and SEQ ID NO:201, respectively. In some embodiments, the HC1 comprises a HCDR1, HCDR2, and HCDR3 comprising the amino acid sequences of SEQ ID NO:202, SEQ ID NO:203, and SEQ ID NO:204, respectively, and LC1 comprises a LCDR1, LCDR2, and LCDR3 comprising the amino acid sequences of SEQ ID NO:205, SEQ ID NO:206, and SEQ ID NO:207, respectively. In some embodiments, the HC1 comprises a HCDR1, HCDR2, and HCDR3 comprising the amino acid sequences of SEQ ID NO:208, SEQ ID NO:209, and SEQ ID NO:210, respectively, and LC1 comprises a LCDR1, LCDR2, and LCDR3 comprising the amino acid sequences of SEQ ID NO:211, SEQ ID NO:212, and SEQ ID NO:213, respectively. In some embodiments, the HC1 comprises a HCDR1, HCDR2, and HCDR3 comprising the amino acid sequences of SEQ ID NO:214, SEQ ID NO:215, and SEQ ID NO:216, respectively, and LC1 comprises a LCDR1, LCDR2, and LCDR3 comprising the amino acid sequences of SEQ ID NO:217, SEQ ID NO:218, and SEQ ID NO:219, respectively. In some embodiments, the HC1 comprises a HCDR1, HCDR2, and HCDR3 comprising the amino acid sequences of SEQ ID NO:214, SEQ ID NO:702, and SEQ ID NO:703, respectively, and LC1 comprises a LCDR1, LCDR2, and LCDR3 comprising the amino acid sequences of SEQ ID NO:217, SEQ ID NO:218, and SEQ ID NO:219, respectively. In some embodiments, the HC1 comprises a HCDR1, HCDR2, and HCDR3 comprising the amino acid sequences of SEQ ID NO:220, SEQ ID NO:221, and SEQ ID NO:222, respectively, and LC1 comprises a LCDR1, LCDR2, and LCDR3 comprising the amino acid sequences of SEQ ID NO:223, SEQ ID NO:224, and SEQ ID NO:225, respectively. In some embodiments, the HC1 comprises a HCDR1, HCDR2, and HCDR3 comprising the amino acid sequences of SEQ ID NO:226, SEQ ID NO:227, and SEQ ID NO:228, respectively, and LC1 comprises a LCDR1, LCDR2, and LCDR3 comprising the amino acid sequences of SEQ ID NO:229, SEQ ID NO:230, and SEQ ID NO:231, respectively. In some embodiments, the HC1 comprises a HCDR1, HCDR2, and HCDR3 comprising the amino acid sequences of SEQ ID NO:232, SEQ ID NO:233, and SEQ ID NO:234, respectively, and LC1 comprises a LCDR1, LCDR2, and LCDR3 comprising the amino acid sequences of SEQ ID NO:235, SEQ ID NO:236, and SEQ ID NO:237, respectively. In some embodiments, the HC1 comprises a HCDR1, HCDR2, and HCDR3 comprising the amino acid sequences of SEQ ID NO:238, SEQ ID NO:239, and SEQ ID NO:240, respectively, and LC1 comprises a LCDR1, LCDR2, and LCDR3 comprising the amino acid sequences of SEQ ID NO:241, SEQ ID NO:242, and SEQ ID NO:243, respectively. In some embodiments, the HC1 comprises a HCDR1, HCDR2, and HCDR3 comprising the amino acid sequences of SEQ ID NO:244, SEQ ID NO:245, and SEQ ID NO:246, respectively, and LC1 comprises a LCDR1, LCDR2, and LCDR3 comprising the amino acid sequences of SEQ ID NO:247, SEQ ID NO:248, and SEQ ID NO:249, respectively. In some embodiments, the HC1 comprises a HCDR1, HCDR2, and HCDR3 comprising the amino acid sequences of SEQ ID NO:250, SEQ ID NO:251, and SEQ ID NO:252, respectively, and LC1 comprises a LCDR1, LCDR2, and LCDR3 comprising the amino acid sequences of SEQ ID NO:253, SEQ ID NO:254, and SEQ ID NO:255, respectively. In some embodiments, the HC1 comprises a HCDR1, HCDR2, and HCDR3 comprising the amino acid sequences of SEQ ID NO:250, SEQ ID NO:704, and SEQ ID NO:705, respectively, and LC1 comprises a LCDR1, LCDR2, and LCDR3 comprising the amino acid sequences of SEQ ID NO:253, SEQ ID NO:254, and SEQ ID NO:255, respectively. In some embodiments, the HC1 comprises a HCDR1, HCDR2, and HCDR3 comprising the amino acid sequences of SEQ ID NO:256, SEQ ID NO:257, and SEQ ID NO:258, respectively, and LC1 comprises a LCDR1, LCDR2, and LCDR3 comprising the amino acid sequences of SEQ ID NO:259, SEQ ID NO:260, and SEQ ID NO:261, respectively. In some embodiments, the HC1 comprises a HCDR1, HCDR2, and HCDR3 comprising the amino acid sequences of SEQ ID NO:262, SEQ ID NO:263, and SEQ ID NO:264, respectively, and LC1 comprises a LCDR1, LCDR2, and LCDR3 comprising the amino acid sequences of SEQ ID NO:265, SEQ ID NO:266, and SEQ ID NO:267, respectively. In some embodiments, the HC1 comprises a HCDR1, HCDR2, and HCDR3 comprising the amino acid sequences of SEQ ID NO:268, SEQ ID NO:269, and SEQ ID NO:270, respectively, and LC1 comprises a LCDR1, LCDR2, and LCDR3 comprising the amino acid sequences of SEQ ID NO:271, SEQ ID NO:272, and SEQ ID NO:273, respectively. In some embodiments, the HC1 comprises a HCDR1, HCDR2, and HCDR3 comprising the amino acid sequences of SEQ ID NO:274, SEQ ID NO:275, and SEQ ID NO:276, respectively, and LC1 comprises a LCDR1, LCDR2, and LCDR3 comprising the amino acid sequences of SEQ ID NO:277, SEQ ID NO:278, and SEQ ID NO:279, respectively. In some embodiments, the HC1 comprises a HCDR1, HCDR2, and HCDR3 comprising the amino acid sequences of SEQ ID NO:280, SEQ ID NO:281, and SEQ ID NO:282, respectively, and LC1 comprises a LCDR1, LCDR2, and LCDR3 comprising the amino acid sequences of SEQ ID NO:283, SEQ ID NO:284, and SEQ ID NO:285, respectively. In some embodiments, the HC1 comprises a HCDR1, HCDR2, and HCDR3 comprising the amino acid sequences of SEQ ID NO:286, SEQ ID NO:287, and SEQ ID NO:288, respectively, and LC1 comprises a LCDR1, LCDR2, and LCDR3 comprising the amino acid sequences of SEQ ID NO:289, SEQ ID NO:290, and SEQ ID NO:291, respectively. In some embodiments, the HC1 comprises a HCDR1, HCDR2, and HCDR3 comprising the amino acid sequences of SEQ ID NO:286, SEQ ID NO:706, and SEQ ID NO:707, respectively, and LC1 comprises a LCDR1, LCDR2, and LCDR3 comprising the amino acid sequences of SEQ ID NO:289, SEQ ID NO:290, and SEQ ID NO:291, respectively. In some embodiments, the HC1 comprises a HCDR1, HCDR2, and HCDR3 comprising the amino acid sequences of SEQ ID NO:292, SEQ ID NO:293, and SEQ ID NO:294, respectively, and LC1 comprises a LCDR1, LCDR2, and LCDR3 comprising the amino acid sequences of SEQ ID NO:295, SEQ ID NO:296, and SEQ ID NO:297, respectively. In some embodiments, the HC1 comprises a HCDR1, HCDR2, and HCDR3 comprising the amino acid sequences of SEQ ID NO:298, SEQ ID NO:299, and SEQ ID NO:300, respectively, and LC1 comprises a LCDR1, LCDR2, and LCDR3 comprising the amino acid sequences of SEQ ID NO:301, SEQ ID NO:302, and SEQ ID NO:303, respectively. In some embodiments, the HC1 comprises a HCDR1, HCDR2, and HCDR3 comprising the amino acid sequences of SEQ ID NO:304, SEQ ID NO:305, and SEQ ID NO:306, respectively, and LC1 comprises a LCDR1, LCDR2, and LCDR3 comprising the amino acid sequences of SEQ ID NO:307, SEQ ID NO:308, and SEQ ID NO:309, respectively. In some embodiments, the HC1 comprises a HCDR1, HCDR2, and HCDR3 comprising the amino acid sequences of SEQ ID NO:310, SEQ ID NO:311, and SEQ ID NO:312, respectively, and LC1 comprises a LCDR1, LCDR2, and LCDR3 comprising the amino acid sequences of SEQ ID NO:313, SEQ ID NO:314, and SEQ ID NO:315, respectively. In some embodiments, the HC1 comprises a HCDR1, HCDR2, and HCDR3 comprising the amino acid sequences of SEQ ID NO:316, SEQ ID NO:317, and SEQ ID NO:318, respectively, and LC1 comprises a LCDR1, LCDR2, and LCDR3 comprising the amino acid sequences of SEQ ID NO:319, SEQ ID NO:320, and SEQ ID NO:321, respectively. In some embodiments, the HC1 comprises a HCDR1, HCDR2, and HCDR3 comprising the amino acid sequences of SEQ ID NO:322, SEQ ID NO:323, and SEQ ID NO:324, respectively, and LC1 comprises a LCDR1, LCDR2, and LCDR3 comprising the amino acid sequences of SEQ ID NO:325, SEQ ID NO:326, and SEQ ID NO:327, respectively. In some embodiments, the HC1 comprises a HCDR1, HCDR2, and HCDR3 comprising the amino acid sequences of SEQ ID NO:322, SEQ ID NO:708, and SEQ ID NO:709, respectively, and LC1 comprises a LCDR1, LCDR2, and LCDR3 comprising the amino acid sequences of SEQ ID NO:325, SEQ ID NO:326, and SEQ ID NO:327, respectively. In some embodiments, the HC1 comprises a HCDR1, HCDR2, and HCDR3 comprising the amino acid sequences of SEQ ID NO:328, SEQ ID NO:329, and SEQ ID NO:330, respectively, and LC1 comprises a LCDR1, LCDR2, and LCDR3 comprising the amino acid sequences of SEQ ID NO:331, SEQ ID NO:332, and SEQ ID NO:333, respectively. In some embodiments, the HC1 comprises a HCDR1, HCDR2, and HCDR3 comprising the amino acid sequences of SEQ ID NO:334, SEQ ID NO:335, and SEQ ID NO:336, respectively, and LC1 comprises a LCDR1, LCDR2, and LCDR3 comprising the amino acid sequences of SEQ ID NO:337, SEQ ID NO:338, and SEQ ID NO:339, respectively. In some embodiments, the HC1 comprises a HCDR1, HCDR2, and HCDR3 comprising the amino acid sequences of SEQ ID NO:340, SEQ ID NO:341, and SEQ ID NO:342, respectively, and LC1 comprises a LCDR1, LCDR2, and LCDR3 comprising the amino acid sequences of SEQ ID NO:343, SEQ ID NO:344, and SEQ ID NO:345, respectively. In some embodiments, the HC1 comprises a HCDR1, HCDR2, and HCDR3 comprising the amino acid sequences of SEQ ID NO:346, SEQ ID NO:347, and SEQ ID NO:348, respectively, and LC1 comprises a LCDR1, LCDR2, and LCDR3 comprising the amino acid sequences of SEQ ID NO:349, SEQ ID NO:350, and SEQ ID NO:351, respectively. In some embodiments, the HC1 comprises a HCDR1, HCDR2, and HCDR3 comprising the amino acid sequences of SEQ ID NO:352, SEQ ID NO:353, and SEQ ID NO:354, respectively, and LC1 comprises a LCDR1, LCDR2, and LCDR3 comprising the amino acid sequences of SEQ ID NO:355, SEQ ID NO:356, and SEQ ID NO:357, respectively. In some embodiments, the HC1 comprises a HCDR1, HCDR2, and HCDR3 comprising the amino acid sequences of SEQ ID NO:358, SEQ ID NO:359, and SEQ ID NO:360, respectively, and LC1 comprises a LCDR1, LCDR2, and LCDR3 comprising the amino acid sequences of SEQ ID NO:361, SEQ ID NO:362, and SEQ ID NO:363, respectively. In some embodiments, the HC1 comprises a HCDR1, HCDR2, and HCDR3 comprising the amino acid sequences of SEQ ID NO:358, SEQ ID NO:710, and SEQ ID NO:711, respectively, and LC1 comprises a LCDR1, LCDR2, and LCDR3 comprising the amino acid sequences of SEQ ID NO:361, SEQ ID NO:362, and SEQ ID NO:363, respectively. In some embodiments, the HC1 comprises a HCDR1, HCDR2, and HCDR3 comprising the amino acid sequences of SEQ ID NO:364, SEQ ID NO:365, and SEQ ID NO:366, respectively, and LC1 comprises a LCDR1, LCDR2, and LCDR3 comprising the amino acid sequences of SEQ ID NO:367, SEQ ID NO:368, and SEQ ID NO:369, respectively. In some embodiments, the HC1 comprises a HCDR1, HCDR2, and HCDR3 comprising the amino acid sequences of SEQ ID NO:370, SEQ ID NO:371, and SEQ ID NO:372, respectively, and LC1 comprises a LCDR1, LCDR2, and LCDR3 comprising the amino acid sequences of SEQ ID NO:373, SEQ ID NO:374, and SEQ ID NO:375, respectively. In some embodiments, the HC1 comprises a HCDR1, HCDR2, and HCDR3 comprising the amino acid sequences of SEQ ID NO:376, SEQ ID NO:377, and SEQ ID NO:378, respectively, and LC1 comprises a LCDR1, LCDR2, and LCDR3 comprising the amino acid sequences of SEQ ID NO:379, SEQ ID NO:380, and SEQ ID NO:381, respectively. In some embodiments, the HC1 comprises a HCDR1, HCDR2, and HCDR3 comprising the amino acid sequences of SEQ ID NO:382, SEQ ID NO:383, and SEQ ID NO:384, respectively, and LC1 comprises a LCDR1, LCDR2, and LCDR3 comprising the amino acid sequences of SEQ ID NO:385, SEQ ID NO:386, and SEQ ID NO:387, respectively. In some embodiments, the HC1 comprises a HCDR1, HCDR2, and HCDR3 comprising the amino acid sequences of SEQ ID NO:388, SEQ ID NO:389, and SEQ ID NO:390, respectively, and LC1 comprises a LCDR1, LCDR2, and LCDR3 comprising the amino acid sequences of SEQ ID NO:391, SEQ ID NO:392, and SEQ ID NO:393, respectively. In some embodiments, the HC1 comprises a HCDR1, HCDR2, and HCDR3 comprising the amino acid sequences of SEQ ID NO:394, SEQ ID NO:395, and SEQ ID NO:396, respectively, and LC1 comprises a LCDR1, LCDR2, and LCDR3 comprising the amino acid sequences of SEQ ID NO:397, SEQ ID NO:398, and SEQ ID NO:399, respectively. In some embodiments, the HC1 comprises a HCDR1, HCDR2, and HCDR3 comprising the amino acid sequences of SEQ ID NO:394, SEQ ID NO:712, and SEQ ID NO:713, respectively, and LC1 comprises a LCDR1, LCDR2, and LCDR3 comprising the amino acid sequences of SEQ ID NO:397, SEQ ID NO:398, and SEQ ID NO:399, respectively. In some embodiments, the HC1 comprises a HCDR1, HCDR2, and HCDR3 comprising the amino acid sequences of SEQ ID NO:400, SEQ ID NO:401, and SEQ ID NO:402, respectively, and LC1 comprises a LCDR1, LCDR2, and LCDR3 comprising the amino acid sequences of SEQ ID NO:403, SEQ ID NO:404, and SEQ ID NO:405, respectively. In some embodiments, the HC1 comprises a HCDR1, HCDR2, and HCDR3 comprising the amino acid sequences of SEQ ID NO:406, SEQ ID NO:407, and SEQ ID NO:408, respectively, and LC1 comprises a LCDR1, LCDR2, and LCDR3 comprising the amino acid sequences of SEQ ID NO:409, SEQ ID NO:410, and SEQ ID NO:411, respectively. In some embodiments, the HC1 comprises a HCDR1, HCDR2, and HCDR3 comprising the amino acid sequences of SEQ ID NO:412, SEQ ID NO:413, and SEQ ID NO:414, respectively, and LC1 comprises a LCDR1, LCDR2, and LCDR3 comprising the amino acid sequences of SEQ ID NO:415, SEQ ID NO:416, and SEQ ID NO:417, respectively. In some embodiments, the HC1 comprises a HCDR1, HCDR2, and HCDR3 comprising the amino acid sequences of SEQ ID NO:418, SEQ ID NO:419, and SEQ ID NO:420, respectively, and LC1 comprises a LCDR1, LCDR2, and LCDR3 comprising the amino acid sequences of SEQ ID NO:421, SEQ ID NO:422, and SEQ ID NO:423, respectively. In some embodiments, the HC1 comprises a HCDR1, HCDR2, and HCDR3 comprising the amino acid sequences of SEQ ID NO:424, SEQ ID NO:425, and SEQ ID NO:426, respectively, and LC1 comprises a LCDR1, LCDR2, and LCDR3 comprising the amino acid sequences of SEQ ID NO:427, SEQ ID NO:428, and SEQ ID NO:429, respectively. In some embodiments, the HC1 comprises a HCDR1, HCDR2, and HCDR3 comprising the amino acid sequences of SEQ ID NO:430, SEQ ID NO:431, and SEQ ID NO:432, respectively, and LC1 comprises a LCDR1, LCDR2, and LCDR3 comprising the amino acid sequences of SEQ ID NO:433, SEQ ID NO:434, and SEQ ID NO:435, respectively. In some embodiments, the HC1 comprises a HCDR1, HCDR2, and HCDR3 comprising the amino acid sequences of SEQ ID NO:430, SEQ ID NO:714, and SEQ ID NO:715, respectively, and LC1 comprises a LCDR1, LCDR2, and LCDR3 comprising the amino acid sequences of SEQ ID NO:433, SEQ ID NO:434, and SEQ ID NO:435, respectively. In some embodiments, the HC1 comprises a HCDR1, HCDR2, and HCDR3 comprising the amino acid sequences of SEQ ID NO:436, SEQ ID NO:437, and SEQ ID NO:438, respectively, and LC1 comprises a LCDR1, LCDR2, and LCDR3 comprising the amino acid sequences of SEQ ID NO:439, SEQ ID NO:440, and SEQ ID NO:441, respectively. In some embodiments, the HC1 comprises a HCDR1, HCDR2, and HCDR3 comprising the amino acid sequences of SEQ ID NO:442, SEQ ID NO:443, and SEQ ID NO:444, respectively, and LC1 comprises a LCDR1, LCDR2, and LCDR3 comprising the amino acid sequences of SEQ ID NO:445, SEQ ID NO:446, and SEQ ID NO:447, respectively. In some embodiments, the HC1 comprises a HCDR1, HCDR2, and HCDR3 comprising the amino acid sequences of SEQ ID NO:448, SEQ ID NO:449, and SEQ ID NO:450, respectively, and LC1 comprises a LCDR1, LCDR2, and LCDR3 comprising the amino acid sequences of SEQ ID NO:451, SEQ ID NO:452, and SEQ ID NO:453, respectively. In some embodiments, the HC1 comprises a HCDR1, HCDR2, and HCDR3 comprising the amino acid sequences of SEQ ID NO:454, SEQ ID NO:455, and SEQ ID NO:456, respectively, and LC1 comprises a LCDR1, LCDR2, and LCDR3 comprising the amino acid sequences of SEQ ID NO:457, SEQ ID NO:458, and SEQ ID NO:459, respectively. In some embodiments, the HC1 comprises a HCDR1, HCDR2, and HCDR3 comprising the amino acid sequences of SEQ ID NO:460, SEQ ID NO:461, and SEQ ID NO:462, respectively, and LC1 comprises a LCDR1, LCDR2, and LCDR3 comprising the amino acid sequences of SEQ ID NO:463, SEQ ID NO:464, and SEQ ID NO:465, respectively. In some embodiments, the HC1 comprises a HCDR1, HCDR2, and HCDR3 comprising the amino acid sequences of SEQ ID NO:466, SEQ ID NO:467, and SEQ ID NO:468, respectively, and LC1 comprises a LCDR1, LCDR2, and LCDR3 comprising the amino acid sequences of SEQ ID NO:469, SEQ ID NO:470, and SEQ ID NO:471, respectively. In some embodiments, the HC1 comprises a HCDR1, HCDR2, and HCDR3 comprising the amino acid sequences of SEQ ID NO:466, SEQ ID NO:716, and SEQ ID NO:717, respectively, and LC1 comprises a LCDR1, LCDR2, and LCDR3 comprising the amino acid sequences of SEQ ID NO:469, SEQ ID NO:470, and SEQ ID NO:471, respectively. In some embodiments, the HC1 comprises a HCDR1, HCDR2, and HCDR3 comprising the amino acid sequences of SEQ ID NO:472, SEQ ID NO:473, and SEQ ID NO:474, respectively, and LC1 comprises a LCDR1, LCDR2, and LCDR3 comprising the amino acid sequences of SEQ ID NO:475, SEQ ID NO:476, and SEQ ID NO:477, respectively. In some embodiments, the HC1 comprises a HCDR1, HCDR2, and HCDR3 comprising the amino acid sequences of SEQ ID NO:478, SEQ ID NO:479, and SEQ ID NO:480, respectively, and LC1 comprises a LCDR1, LCDR2, and LCDR3 comprising the amino acid sequences of SEQ ID NO:481, SEQ ID NO:482, and SEQ ID NO:483, respectively. In some embodiments, the HC1 comprises a HCDR1, HCDR2, and HCDR3 comprising the amino acid sequences of SEQ ID NO:484, SEQ ID NO:485, and SEQ ID NO:486, respectively, and LC1 comprises a LCDR1, LCDR2, and LCDR3 comprising the amino acid sequences of SEQ ID NO:487, SEQ ID NO:488, and SEQ ID NO:489, respectively. In some embodiments, the HC1 comprises a HCDR1, HCDR2, and HCDR3 comprising the amino acid sequences of SEQ ID NO:490, SEQ ID NO:491, and SEQ ID NO:492, respectively, and LC1 comprises a LCDR1, LCDR2, and LCDR3 comprising the amino acid sequences of SEQ ID NO:493, SEQ ID NO:494, and SEQ ID NO:495, respectively. In some embodiments, the HC1 comprises a HCDR1, HCDR2, and HCDR3 comprising the amino acid sequences of SEQ ID NO:496, SEQ ID NO:497, and SEQ ID NO:498, respectively, and LC1 comprises a LCDR1, LCDR2, and LCDR3 comprising the amino acid sequences of SEQ ID NO:499, SEQ ID NO:500, and SEQ ID NO:501, respectively. In some embodiments, the HC1 comprises a HCDR1, HCDR2, and HCDR3 comprising the amino acid sequences of SEQ ID NO:502, SEQ ID NO:503, and SEQ ID NO:504, respectively, and LC1 comprises a LCDR1, LCDR2, and LCDR3 comprising the amino acid sequences of SEQ ID NO:505, SEQ ID NO:506, and SEQ ID NO:507, respectively. In some embodiments, the HC1 comprises a HCDR1, HCDR2, and HCDR3 comprising the amino acid sequences of SEQ ID NO:502, SEQ ID NO:718, and SEQ ID NO:719, respectively, and LC1 comprises a LCDR1, LCDR2, and LCDR3 comprising the amino acid sequences of SEQ ID NO:505, SEQ ID NO:506, and SEQ ID NO:507, respectively. In some embodiments, the HC1 comprises a HCDR1, HCDR2, and HCDR3 comprising the amino acid sequences of SEQ ID NO:508, SEQ ID NO:509, and SEQ ID NO:510, respectively, and LC1 comprises a LCDR1, LCDR2, and LCDR3 comprising the amino acid sequences of SEQ ID NO:511, SEQ ID NO:512, and SEQ ID NO:513, respectively. In some embodiments, the HC1 comprises a HCDR1, HCDR2, and HCDR3 comprising the amino acid sequences of SEQ ID NO:514, SEQ ID NO:515, and SEQ ID NO:516, respectively, and LC1 comprises a LCDR1, LCDR2, and LCDR3 comprising the amino acid sequences of SEQ ID NO:517, SEQ ID NO:518, and SEQ ID NO:519, respectively. In some embodiments, the HC1 comprises a HCDR1, HCDR2, and HCDR3 comprising the amino acid sequences of SEQ ID NO:520, SEQ ID NO:521, and SEQ ID NO:522, respectively, and LC1 comprises a LCDR1, LCDR2, and LCDR3 comprising the amino acid sequences of SEQ ID NO:523, SEQ ID NO:524, and SEQ ID NO:525, respectively. In some embodiments, the HC1 comprises a HCDR1, HCDR2, and HCDR3 comprising the amino acid sequences of SEQ ID NO:526, SEQ ID NO:527, and SEQ ID NO:528, respectively, and LC1 comprises a LCDR1, LCDR2, and LCDR3 comprising the amino acid sequences of SEQ ID NO:529, SEQ ID NO:530, and SEQ ID NO:531, respectively. In some embodiments, the HC1 comprises a HCDR1, HCDR2, and HCDR3 comprising the amino acid sequences of SEQ ID NO:532, SEQ ID NO:533, and SEQ ID NO:534, respectively, and LC1 comprises a LCDR1, LCDR2, and LCDR3 comprising the amino acid sequences of SEQ ID NO:535, SEQ ID NO:536, and SEQ ID NO:537, respectively. In some embodiments, the HC1 comprises a HCDR1, HCDR2, and HCDR3 comprising the amino acid sequences of SEQ ID NO:538, SEQ ID NO:539, and SEQ ID NO:540, respectively, and LC1 comprises a LCDR1, LCDR2, and LCDR3 comprising the amino acid sequences of SEQ ID NO:541, SEQ ID NO:542, and SEQ ID NO:543, respectively. In some embodiments, the HC1 comprises a HCDR1, HCDR2, and HCDR3 comprising the amino acid sequences of SEQ ID NO:532, SEQ ID NO:533, and SEQ ID NO:534, respectively, and LC1 comprises a LCDR1, LCDR2, and LCDR3 comprising the amino acid sequences of SEQ ID NO:535, SEQ ID NO:536, and SEQ ID NO:537, respectively. In some embodiments, the HC1 comprises a HCDR1, HCDR2, and HCDR3 comprising the amino acid sequences of SEQ ID NO:538, SEQ ID NO:720, and SEQ ID NO:721, respectively, and LC1 comprises a LCDR1, LCDR2, and LCDR3 comprising the amino acid sequences of SEQ ID NO:541, SEQ ID NO:542, and SEQ ID NO:543, respectively. In some embodiments, the HC1 comprises a HCDR1, HCDR2, and HCDR3 comprising the amino acid sequences of SEQ ID NO:544, SEQ ID NO:545, and SEQ ID NO:546, respectively, and LC1 comprises a LCDR1, LCDR2, and LCDR3 comprising the amino acid sequences of SEQ ID NO:547, SEQ ID NO:548, and SEQ ID NO:549, respectively. In some embodiments, the HC1 comprises a HCDR1, HCDR2, and HCDR3 comprising the amino acid sequences of SEQ ID NO:550, SEQ ID NO:551, and SEQ ID NO:552, respectively, and LC1 comprises a LCDR1, LCDR2, and LCDR3 comprising the amino acid sequences of SEQ ID NO:553, SEQ ID NO:554, and SEQ ID NO:555, respectively. In specific embodiments, the HC1 and LC1 form a binding site for a first antigen, and the HC2 and LC2 form a binding site for a second antigen. In some embodiments, HC1 is associated with LC1 and HC2 is associated with LC2. In some embodiments, HC1 and LC1 form a binding site for a first antigen that specifically binds TRGV9. The binding site for a first antigen can, for example, bind a TRGV9 on a γδ T cell. The binding site for a second antigen can, for example, bind a cancer antigen present on the surface of a cancer cell. In some embodiments, the cancer antigen is CD123. The binding of the TRGV9 bispecific antibody to TRGV9 present on the surface of the γδ T cell, and the binding of the tumor associated antigen present on the surface of the cancer cell can, for example, result in the killing of the cancer cell.

In certain embodiments, the first binding domain of the bispecific antibody specifically binds TRGV9. In some embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody.

Also provided herein are anti-TRGV9/anti-CD123 bispecific antibodies or antigen-binding fragments thereof comprising an anti-TRGV9 antibody or an antigen-binding fragment thereof and an anti-CD123 antibody or antigen-binding fragment thereof. In certain embodiments the anti-TRGV9/anti-CD123 bispecific antibody or antigen binding fragment thereof comprises (a) a HC1; (b) a HC2; (c) a LC1; and a LC2. In some embodiments, HC1 is associated with LC1 and HC2 is associated with LC2. HC1 can, for example, comprise a HCDR1, HCDR2, and HCDR3 comprising the amino acid sequences of:

i. SEQ ID NO:1, SEQ ID NO:2, and SEQ ID NO:3, respectively, ii. SEQ ID NO:1, SEQ ID NO:2, and SEQ ID NO:31, respectively, iii. SEQ ID NO:1, SEQ ID NO:2, and SEQ ID NO:32, respectively, or iv. SEQ ID NO:1, SEQ ID NO:2, and SEQ ID NO:33, respectively, and LC1 can, for example, comprise a LCDR1, LCDR2, and LCDR3 comprising the amino acid sequences of SEQ ID NO:4, SEQ ID NO:5, and SEQ ID NO:6, respectively, to form a binding site for a first antigen that specifically binds TRGV9. HC2 can, for example, comprise a HCDR1, HCDR2, and HCDR3 comprising the amino acid sequences of SEQ ID NO:9, SEQ ID NO:10, and SEQ ID NO:11, respectively, and LC2 can, for example, comprise a LCDR1, LCDR2, and LCDR3 comprising the amino acid sequences of SEQ ID NO: 12, SEQ ID NO:13, and SEQ ID NO:14, respectively, to form a binding site for a second antigen that specifically binds CD123. In certain embodiments, the HC1 comprises the amino acid sequence of SEQ ID NO:7, SEQ ID NO:34, SEQ ID NO:35, or SEQ ID NO:36, and LC1 comprises the amino acid sequence of SEQ ID NO:8, and the HC2 comprises the amino acid sequence of SEQ ID NO:15 and LC2 comprises the amino acid sequence of SEQ ID NO:16. In certain embodiments, the TRGV9 is on the surface of a γδ T cell. In certain embodiments, the CD123 is on the surface of a cancer cell (e.g., a leukemia cell).

Also provided herein are anti-TRGV9/anti-CD123 bispecific antibodies or antigen-binding fragments thereof comprising an anti-TRGV9 antibody or an antigen-binding fragment thereof and an anti-CD123 antibody or antigen-binding fragment thereof. In certain embodiments the anti-TRGV9/anti-CD123 bispecific antibody or antigen binding fragment thereof comprises (a) a HC1; (b) a HC2; (c) a LC1; and a LC2. In some embodiments, HC1 is associated with LC1 and HC2 is associated with LC2. In some embodiments, HC1 comprises a HCDR1, HCDR2, and HCDR3 comprising the amino acid sequences of SEQ ID NO:1, SEQ ID NO:2, and SEQ ID NO:3, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen that specifically binds TRGV9. In some embodiments, HC1 comprises a HCDR1, HCDR2, and HCDR3 comprising the amino acid sequences of SEQ ID NO:1, SEQ ID NO:2, and SEQ ID NO:31, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen that specifically binds TRGV9. In some embodiments, HC1 comprises a HCDR1, HCDR2, and HCDR3 comprising the amino acid sequences of SEQ ID NO:1, SEQ ID NO:2, and SEQ ID NO:32, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen that specifically binds TRGV9. In some embodiments, HC1 comprises a HCDR1, HCDR2, and HCDR3 comprising the amino acid sequences of SEQ ID NO:1, SEQ ID NO:2, and SEQ ID NO:33, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen that specifically binds TRGV9. In some embodiments, HC1 comprises a HCDR1, HCDR2, and HCDR3 comprising the amino acid sequences of SEQ ID NO:1, SEQ ID NO:76, and SEQ ID NO:3, respectively, and LC1 comprises a LCDR1, LCDR2, and LCDR3 comprising the amino acid sequences of SEQ ID NO:77, SEQ ID NO:5, and SEQ ID NO:6, respectively, to form a binding site for a first antigen that specifically binds TRGV9. In some embodiments, HC1 comprises a HCDR1, HCDR2, and HCDR3 comprising the amino acid sequences of SEQ ID NO:60, SEQ ID NO:61, and SEQ ID NO:62, respectively, and LC1 comprises a LCDR1, LCDR2, and LCDR3 comprising the amino acid sequences of SEQ ID NO:63, SEQ ID NO:64, and SEQ ID NO:6, respectively, to form a binding site for a first antigen that specifically binds TRGV9. In some embodiments, the HC1 comprises a HCDR1, HCDR2, and HCDR3 comprising the amino acid sequences of SEQ ID NO:89, SEQ ID NO:90, and SEQ ID NO:91, respectively, and LC1 comprises a LCDR1, LCDR2, and LCDR3 comprising the amino acid sequences of SEQ ID NO:92, SEQ ID NO:93, and SEQ ID NO:94, respectively, to form a binding site for a first antigen that specifically binds TRGV9. In some embodiments, the HC1 comprises a HCDR1, HCDR2, and HCDR3 comprising the amino acid sequences of SEQ ID NO:98, SEQ ID NO:99, and SEQ ID NO:100, respectively, and LC1 comprises a LCDR1, LCDR2, and LCDR3 comprising the amino acid sequences of SEQ ID NO:101, SEQ ID NO:102, and SEQ ID NO:103, respectively, to form a binding site for a first antigen that specifically binds TRGV9. In some embodiments, the HC1 comprises a HCDR1, HCDR2, and HCDR3 comprising the amino acid sequences of SEQ ID NO:107, SEQ ID NO:108, and SEQ ID NO:109, respectively, and LC1 comprises a LCDR1, LCDR2, and LCDR3 comprising the amino acid sequences of SEQ ID NO:110, SEQ ID NO:111, and SEQ ID NO:112, respectively, to form a binding site for a first antigen that specifically binds TRGV9. In some embodiments, the HC1 comprises a HCDR1, HCDR2, and HCDR3 comprising the amino acid sequences of SEQ ID NO:117, SEQ ID NO:118, and SEQ ID NO:119, respectively, and LC1 comprises a LCDR1, LCDR2, and LCDR3 comprising the amino acid sequences of SEQ ID NO:120, SEQ ID NO:121, and SEQ ID NO:122, respectively, to form a binding site for a first antigen that specifically binds TRGV9. In some embodiments, the HC1 comprises a HCDR1, HCDR2, and HCDR3 comprising the amino acid sequences of SEQ ID NO:127, SEQ ID NO:128, and SEQ ID NO:129, respectively, and LC1 comprises a LCDR1, LCDR2, and LCDR3 comprising the amino acid sequences of SEQ ID NO:130, SEQ ID NO:131, and SEQ ID NO:132, respectively, to form a binding site for a first antigen that specifically binds TRGV9. In some embodiments, the HC1 comprises a HCDR1, HCDR2, and HCDR3 comprising the amino acid sequences of SEQ ID NO:160, SEQ ID NO:161, and SEQ ID NO:162, respectively, and LC1 comprises a LCDR1, LCDR2, and LCDR3 comprising the amino acid sequences of SEQ ID NO:163, SEQ ID NO:164, and SEQ ID NO:165, respectively, to form a binding site for a first antigen that specifically binds TRGV9. In some embodiments, the HC1 comprises a HCDR1, HCDR2, and HCDR3 comprising the amino acid sequences of SEQ ID NO:166, SEQ ID NO:167, and SEQ ID NO:168, respectively, and LC1 comprises a LCDR1, LCDR2, and LCDR3 comprising the amino acid sequences of SEQ ID NO:169, SEQ ID NO:170, and SEQ ID NO:171, respectively, to form a binding site for a first antigen that specifically binds TRGV9. In some embodiments, the HC1 comprises a HCDR1, HCDR2, and HCDR3 comprising the amino acid sequences of SEQ ID NO:172, SEQ ID NO:173, and SEQ ID NO:174, respectively, and LC1 comprises a LCDR1, LCDR2, and LCDR3 comprising the amino acid sequences of SEQ ID NO:175, SEQ ID NO:176, and SEQ ID NO:177, respectively, to form a binding site for a first antigen that specifically binds TRGV9. In some embodiments, the HC1 comprises a HCDR1, HCDR2, and HCDR3 comprising the amino acid sequences of SEQ ID NO:178, SEQ ID NO:179, and SEQ ID NO:180, respectively, and LC1 comprises a LCDR1, LCDR2, and LCDR3 comprising the amino acid sequences of SEQ ID NO:181, SEQ ID NO:182, and SEQ ID NO:183, respectively, to form a binding site for a first antigen that specifically binds TRGV9. In some embodiments, the HC1 comprises a HCDR1, HCDR2, and HCDR3 comprising the amino acid sequences of SEQ ID NO:178, SEQ ID NO:700, and SEQ ID NO:701, respectively, and LC1 comprises a LCDR1, LCDR2, and LCDR3 comprising the amino acid sequences of SEQ ID NO:181, SEQ ID NO:182, and SEQ ID NO:183, respectively, to form a binding site for a first antigen that specifically binds TRGV9. In some embodiments, the HC1 comprises a HCDR1, HCDR2, and HCDR3 comprising the amino acid sequences of SEQ ID NO:184, SEQ ID NO:185, and SEQ ID NO:186, respectively, and LC1 comprises a LCDR1, LCDR2, and LCDR3 comprising the amino acid sequences of SEQ ID NO:187, SEQ ID NO:188, and SEQ ID NO:189, respectively, to form a binding site for a first antigen that specifically binds TRGV9. In some embodiments, the HC1 comprises a HCDR1, HCDR2, and HCDR3 comprising the amino acid sequences of SEQ ID NO:190, SEQ ID NO:191, and SEQ ID NO:192, respectively, and LC1 comprises a LCDR1, LCDR2, and LCDR3 comprising the amino acid sequences of SEQ ID NO:193, SEQ ID NO:194, and SEQ ID NO:195, respectively, to form a binding site for a first antigen that specifically binds TRGV9. In some embodiments, the HC1 comprises a HCDR1, HCDR2, and HCDR3 comprising the amino acid sequences of SEQ ID NO:196, SEQ ID NO:197, and SEQ ID NO:198, respectively, and LC1 comprises a LCDR1, LCDR2, and LCDR3 comprising the amino acid sequences of SEQ ID NO:199, SEQ ID NO:200, and SEQ ID NO:201, respectively, to form a binding site for a first antigen that specifically binds TRGV9. In some embodiments, the HC1 comprises a HCDR1, HCDR2, and HCDR3 comprising the amino acid sequences of SEQ ID NO:202, SEQ ID NO:203, and SEQ ID NO:204, respectively, and LC1 comprises a LCDR1, LCDR2, and LCDR3 comprising the amino acid sequences of SEQ ID NO:205, SEQ ID NO:206, and SEQ ID NO:207, respectively, to form a binding site for a first antigen that specifically binds TRGV9. In some embodiments, the HC1 comprises a HCDR1, HCDR2, and HCDR3 comprising the amino acid sequences of SEQ ID NO:208, SEQ ID NO:209, and SEQ ID NO:210, respectively, and LC1 comprises a LCDR1, LCDR2, and LCDR3 comprising the amino acid sequences of SEQ ID NO:211, SEQ ID NO:212, and SEQ ID NO:213, respectively, to form a binding site for a first antigen that specifically binds TRGV9. In some embodiments, the HC1 comprises a HCDR1, HCDR2, and HCDR3 comprising the amino acid sequences of SEQ ID NO:214, SEQ ID NO:215, and SEQ ID NO:216, respectively, and LC1 comprises a LCDR1, LCDR2, and LCDR3 comprising the amino acid sequences of SEQ ID NO:217, SEQ ID NO:218, and SEQ ID NO:219, respectively, to form a binding site for a first antigen that specifically binds TRGV9. In some embodiments, the HC1 comprises a HCDR1, HCDR2, and HCDR3 comprising the amino acid sequences of SEQ ID NO:214, SEQ ID NO:702, and SEQ ID NO:703, respectively, and LC1 comprises a LCDR1, LCDR2, and LCDR3 comprising the amino acid sequences of SEQ ID NO:217, SEQ ID NO:218, and SEQ ID NO:219, respectively, to form a binding site for a first antigen that specifically binds TRGV9. In some embodiments, the HC1 comprises a HCDR1, HCDR2, and HCDR3 comprising the amino acid sequences of SEQ ID NO:220, SEQ ID NO:221, and SEQ ID NO:222, respectively, and LC1 comprises a LCDR1, LCDR2, and LCDR3 comprising the amino acid sequences of SEQ ID NO:223, SEQ ID NO:224, and SEQ ID NO:225, respectively, to form a binding site for a first antigen that specifically binds TRGV9. In some embodiments, the HC1 comprises a HCDR1, HCDR2, and HCDR3 comprising the amino acid sequences of SEQ ID NO:226, SEQ ID NO:227, and SEQ ID NO:228, respectively, and LC1 comprises a LCDR1, LCDR2, and LCDR3 comprising the amino acid sequences of SEQ ID NO:229, SEQ ID NO:230, and SEQ ID NO:231, respectively, to form a binding site for a first antigen that specifically binds TRGV9. In some embodiments, the HC1 comprises a HCDR1, HCDR2, and HCDR3 comprising the amino acid sequences of SEQ ID NO:232, SEQ ID NO:233, and SEQ ID NO:234, respectively, and LC1 comprises a LCDR1, LCDR2, and LCDR3 comprising the amino acid sequences of SEQ ID NO:235, SEQ ID NO:236, and SEQ ID NO:237, respectively, to form a binding site for a first antigen that specifically binds TRGV9. In some embodiments, the HC1 comprises a HCDR1, HCDR2, and HCDR3 comprising the amino acid sequences of SEQ ID NO:238, SEQ ID NO:239, and SEQ ID NO:240, respectively, and LC1 comprises a LCDR1, LCDR2, and LCDR3 comprising the amino acid sequences of SEQ ID NO:241, SEQ ID NO:242, and SEQ ID NO:243, respectively, to form a binding site for a first antigen that specifically binds TRGV9. In some embodiments, the HC1 comprises a HCDR1, HCDR2, and HCDR3 comprising the amino acid sequences of SEQ ID NO:244, SEQ ID NO:245, and SEQ ID NO:246, respectively, and LC1 comprises a LCDR1, LCDR2, and LCDR3 comprising the amino acid sequences of SEQ ID NO:247, SEQ ID NO:248, and SEQ ID NO:249, respectively, to form a binding site for a first antigen that specifically binds TRGV9. In some embodiments, the HC1 comprises a HCDR1, HCDR2, and HCDR3 comprising the amino acid sequences of SEQ ID NO:250, SEQ ID NO:251, and SEQ ID NO:252, respectively, and LC1 comprises a LCDR1, LCDR2, and LCDR3 comprising the amino acid sequences of SEQ ID NO:253, SEQ ID NO:254, and SEQ ID NO:255, respectively, to form a binding site for a first antigen that specifically binds TRGV9. In some embodiments, the HC1 comprises a HCDR1, HCDR2, and HCDR3 comprising the amino acid sequences of SEQ ID NO:250, SEQ ID NO:704, and SEQ ID NO:705, respectively, and LC1 comprises a LCDR1, LCDR2, and LCDR3 comprising the amino acid sequences of SEQ ID NO:253, SEQ ID NO:254, and SEQ ID NO:255, respectively, to form a binding site for a first antigen that specifically binds TRGV9. In some embodiments, the HC1 comprises a HCDR1, HCDR2, and HCDR3 comprising the amino acid sequences of SEQ ID NO:256, SEQ ID NO:257, and SEQ ID NO:258, respectively, and LC1 comprises a LCDR1, LCDR2, and LCDR3 comprising the amino acid sequences of SEQ ID NO:259, SEQ ID NO:260, and SEQ ID NO:261, respectively, to form a binding site for a first antigen that specifically binds TRGV9. In some embodiments, the HC1 comprises a HCDR1, HCDR2, and HCDR3 comprising the amino acid sequences of SEQ ID NO:262, SEQ ID NO:263, and SEQ ID NO:264, respectively, and LC1 comprises a LCDR1, LCDR2, and LCDR3 comprising the amino acid sequences of SEQ ID NO:265, SEQ ID NO:266, and SEQ ID NO:267, respectively, to form a binding site for a first antigen that specifically binds TRGV9. In some embodiments, the HC1 comprises a HCDR1, HCDR2, and HCDR3 comprising the amino acid sequences of SEQ ID NO:268, SEQ ID NO:269, and SEQ ID NO:270, respectively, and LC1 comprises a LCDR1, LCDR2, and LCDR3 comprising the amino acid sequences of SEQ ID NO:271, SEQ ID NO:272, and SEQ ID NO:273, respectively, to form a binding site for a first antigen that specifically binds TRGV9. In some embodiments, the HC1 comprises a HCDR1, HCDR2, and HCDR3 comprising the amino acid sequences of SEQ ID NO:274, SEQ ID NO:275, and SEQ ID NO:276, respectively, and LC1 comprises a LCDR1, LCDR2, and LCDR3 comprising the amino acid sequences of SEQ ID NO:277, SEQ ID NO:278, and SEQ ID NO:279, respectively, to form a binding site for a first antigen that specifically binds TRGV9. In some embodiments, the HC1 comprises a HCDR1, HCDR2, and HCDR3 comprising the amino acid sequences of SEQ ID NO:280, SEQ ID NO:281, and SEQ ID NO:282, respectively, and LC1 comprises a LCDR1, LCDR2, and LCDR3 comprising the amino acid sequences of SEQ ID NO:283, SEQ ID NO:284, and SEQ ID NO:285, respectively, to form a binding site for a first antigen that specifically binds TRGV9. In some embodiments, the HC1 comprises a HCDR1, HCDR2, and HCDR3 comprising the amino acid sequences of SEQ ID NO:286, SEQ ID NO:287, and SEQ ID NO:288, respectively, and LC1 comprises a LCDR1, LCDR2, and LCDR3 comprising the amino acid sequences of SEQ ID NO:289, SEQ ID NO:290, and SEQ ID NO:291, respectively, to form a binding site for a first antigen that specifically binds TRGV9. In some embodiments, the HC1 comprises a HCDR1, HCDR2, and HCDR3 comprising the amino acid sequences of SEQ ID NO:286, SEQ ID NO:706, and SEQ ID NO:707, respectively, and LC1 comprises a LCDR1, LCDR2, and LCDR3 comprising the amino acid sequences of SEQ ID NO:289, SEQ ID NO:290, and SEQ ID NO:291, respectively, to form a binding site for a first antigen that specifically binds TRGV9. In some embodiments, the HC1 comprises a HCDR1, HCDR2, and HCDR3 comprising the amino acid sequences of SEQ ID NO:292, SEQ ID NO:293, and SEQ ID NO:294, respectively, and LC1 comprises a LCDR1, LCDR2, and LCDR3 comprising the amino acid sequences of SEQ ID NO:295, SEQ ID NO:296, and SEQ ID NO:297, respectively, to form a binding site for a first antigen that specifically binds TRGV9. In some embodiments, the HC1 comprises a HCDR1, HCDR2, and HCDR3 comprising the amino acid sequences of SEQ ID NO:298, SEQ ID NO:299, and SEQ ID NO:300, respectively, and LC1 comprises a LCDR1, LCDR2, and LCDR3 comprising the amino acid sequences of SEQ ID NO:301, SEQ ID NO:302, and SEQ ID NO:303, respectively, to form a binding site for a first antigen that specifically binds TRGV9. In some embodiments, the HC1 comprises a HCDR1, HCDR2, and HCDR3 comprising the amino acid sequences of SEQ ID NO:304, SEQ ID NO:305, and SEQ ID NO:306, respectively, and LC1 comprises a LCDR1, LCDR2, and LCDR3 comprising the amino acid sequences of SEQ ID NO:307, SEQ ID NO:308, and SEQ ID NO:309, respectively, to form a binding site for a first antigen that specifically binds TRGV9. In some embodiments, the HC1 comprises a HCDR1, HCDR2, and HCDR3 comprising the amino acid sequences of SEQ ID NO:310, SEQ ID NO:311, and SEQ ID NO:312, respectively, and LC1 comprises a LCDR1, LCDR2, and LCDR3 comprising the amino acid sequences of SEQ ID NO:313, SEQ ID NO:314, and SEQ ID NO:315, respectively, to form a binding site for a first antigen that specifically binds TRGV9. In some embodiments, the HC1 comprises a HCDR1, HCDR2, and HCDR3 comprising the amino acid sequences of SEQ ID NO:316, SEQ ID NO:317, and SEQ ID NO:318, respectively, and LC1 comprises a LCDR1, LCDR2, and LCDR3 comprising the amino acid sequences of SEQ ID NO:319, SEQ ID NO:320, and SEQ ID NO:321, respectively, to form a binding site for a first antigen that specifically binds TRGV9. In some embodiments, the HC1 comprises a HCDR1, HCDR2, and HCDR3 comprising the amino acid sequences of SEQ ID NO:322, SEQ ID NO:323, and SEQ ID NO:324, respectively, and LC1 comprises a LCDR1, LCDR2, and LCDR3 comprising the amino acid sequences of SEQ ID NO:325, SEQ ID NO:326, and SEQ ID NO:327, respectively, to form a binding site for a first antigen that specifically binds TRGV9. In some embodiments, the HC1 comprises a HCDR1, HCDR2, and HCDR3 comprising the amino acid sequences of SEQ ID NO:322, SEQ ID NO:708, and SEQ ID NO:709, respectively, and LC1 comprises a LCDR1, LCDR2, and LCDR3 comprising the amino acid sequences of SEQ ID NO:325, SEQ ID NO:326, and SEQ ID NO:327, respectively, to form a binding site for a first antigen that specifically binds TRGV9. In some embodiments, the HC1 comprises a HCDR1, HCDR2, and HCDR3 comprising the amino acid sequences of SEQ ID NO:328, SEQ ID NO:329, and SEQ ID NO:330, respectively, and LC1 comprises a LCDR1, LCDR2, and LCDR3 comprising the amino acid sequences of SEQ ID NO:331, SEQ ID NO:332, and SEQ ID NO:333, respectively, to form a binding site for a first antigen that specifically binds TRGV9. In some embodiments, the HC1 comprises a HCDR1, HCDR2, and HCDR3 comprising the amino acid sequences of SEQ ID NO:334, SEQ ID NO:335, and SEQ ID NO:336, respectively, and LC1 comprises a LCDR1, LCDR2, and LCDR3 comprising the amino acid sequences of SEQ ID NO:337, SEQ ID NO:338, and SEQ ID NO:339, respectively, to form a binding site for a first antigen that specifically binds TRGV9. In some embodiments, the HC1 comprises a HCDR1, HCDR2, and HCDR3 comprising the amino acid sequences of SEQ ID NO:340, SEQ ID NO:341, and SEQ ID NO:342, respectively, and LC1 comprises a LCDR1, LCDR2, and LCDR3 comprising the amino acid sequences of SEQ ID NO:343, SEQ ID NO:344, and SEQ ID NO:345, respectively, to form a binding site for a first antigen that specifically binds TRGV9. In some embodiments, the HC1 comprises a HCDR1, HCDR2, and HCDR3 comprising the amino acid sequences of SEQ ID NO:346, SEQ ID NO:347, and SEQ ID NO:348, respectively, and LC1 comprises a LCDR1, LCDR2, and LCDR3 comprising the amino acid sequences of SEQ ID NO:349, SEQ ID NO:350, and SEQ ID NO:351, respectively, to form a binding site for a first antigen that specifically binds TRGV9. In some embodiments, the HC1 comprises a HCDR1, HCDR2, and HCDR3 comprising the amino acid sequences of SEQ ID NO:352, SEQ ID NO:353, and SEQ ID NO:354, respectively, and LC1 comprises a LCDR1, LCDR2, and LCDR3 comprising the amino acid sequences of SEQ ID NO:355, SEQ ID NO:356, and SEQ ID NO:357, respectively, to form a binding site for a first antigen that specifically binds TRGV9. In some embodiments, the HC1 comprises a HCDR1, HCDR2, and HCDR3 comprising the amino acid sequences of SEQ ID NO:358, SEQ ID NO:359, and SEQ ID NO:360, respectively, and LC1 comprises a LCDR1, LCDR2, and LCDR3 comprising the amino acid sequences of SEQ ID NO:361, SEQ ID NO:362, and SEQ ID NO:363, respectively, to form a binding site for a first antigen that specifically binds TRGV9. In some embodiments, the HC1 comprises a HCDR1, HCDR2, and HCDR3 comprising the amino acid sequences of SEQ ID NO:358, SEQ ID NO:710, and SEQ ID NO:711, respectively, and LC1 comprises a LCDR1, LCDR2, and LCDR3 comprising the amino acid sequences of SEQ ID NO:361, SEQ ID NO:362, and SEQ ID NO:363, respectively, to form a binding site for a first antigen that specifically binds TRGV9. In some embodiments, the HC1 comprises a HCDR1, HCDR2, and HCDR3 comprising the amino acid sequences of SEQ ID NO:364, SEQ ID NO:365, and SEQ ID NO:366, respectively, and LC1 comprises a LCDR1, LCDR2, and LCDR3 comprising the amino acid sequences of SEQ ID NO:367, SEQ ID NO:368, and SEQ ID NO:369, respectively, to form a binding site for a first antigen that specifically binds TRGV9. In some embodiments, the HC1 comprises a HCDR1, HCDR2, and HCDR3 comprising the amino acid sequences of SEQ ID NO:370, SEQ ID NO:371, and SEQ ID NO:372, respectively, and LC1 comprises a LCDR1, LCDR2, and LCDR3 comprising the amino acid sequences of SEQ ID NO:373, SEQ ID NO:374, and SEQ ID NO:375, respectively, to form a binding site for a first antigen that specifically binds TRGV9. In some embodiments, the HC1 comprises a HCDR1, HCDR2, and HCDR3 comprising the amino acid sequences of SEQ ID NO:376, SEQ ID NO:377, and SEQ ID NO:378, respectively, and LC1 comprises a LCDR1, LCDR2, and LCDR3 comprising the amino acid sequences of SEQ ID NO:379, SEQ ID NO:380, and SEQ ID NO:381, respectively, to form a binding site for a first antigen that specifically binds TRGV9. In some embodiments, the HC1 comprises a HCDR1, HCDR2, and HCDR3 comprising the amino acid sequences of SEQ ID NO:382, SEQ ID NO:383, and SEQ ID NO:384, respectively, and LC1 comprises a LCDR1, LCDR2, and LCDR3 comprising the amino acid sequences of SEQ ID NO:385, SEQ ID NO:386, and SEQ ID NO:387, respectively, to form a binding site for a first antigen that specifically binds TRGV9. In some embodiments, the HC1 comprises a HCDR1, HCDR2, and HCDR3 comprising the amino acid sequences of SEQ ID NO:388, SEQ ID NO:389, and SEQ ID NO:390, respectively, and LC1 comprises a LCDR1, LCDR2, and LCDR3 comprising the amino acid sequences of SEQ ID NO:391, SEQ ID NO:392, and SEQ ID NO:393, respectively, to form a binding site for a first antigen that specifically binds TRGV9. In some embodiments, the HC1 comprises a HCDR1, HCDR2, and HCDR3 comprising the amino acid sequences of SEQ ID NO:394, SEQ ID NO:395, and SEQ ID NO:396, respectively, and LC1 comprises a LCDR1, LCDR2, and LCDR3 comprising the amino acid sequences of SEQ ID NO:397, SEQ ID NO:398, and SEQ ID NO:399, respectively, to form a binding site for a first antigen that specifically binds TRGV9. In some embodiments, the HC1 comprises a HCDR1, HCDR2, and HCDR3 comprising the amino acid sequences of SEQ ID NO:394, SEQ ID NO:712, and SEQ ID NO:713, respectively, and LC1 comprises a LCDR1, LCDR2, and LCDR3 comprising the amino acid sequences of SEQ ID NO:397, SEQ ID NO:398, and SEQ ID NO:399, respectively, to form a binding site for a first antigen that specifically binds TRGV9. In some embodiments, the HC1 comprises a HCDR1, HCDR2, and HCDR3 comprising the amino acid sequences of SEQ ID NO:400, SEQ ID NO:401, and SEQ ID NO:402, respectively, and LC1 comprises a LCDR1, LCDR2, and LCDR3 comprising the amino acid sequences of SEQ ID NO:403, SEQ ID NO:404, and SEQ ID NO:405, respectively, to form a binding site for a first antigen that specifically binds TRGV9. In some embodiments, the HC1 comprises a HCDR1, HCDR2, and HCDR3 comprising the amino acid sequences of SEQ ID NO:406, SEQ ID NO:407, and SEQ ID NO:408, respectively, and LC1 comprises a LCDR1, LCDR2, and LCDR3 comprising the amino acid sequences of SEQ ID NO:409, SEQ ID NO:410, and SEQ ID NO:411, respectively, to form a binding site for a first antigen that specifically binds TRGV9. In some embodiments, the HC1 comprises a HCDR1, HCDR2, and HCDR3 comprising the amino acid sequences of SEQ ID NO:412, SEQ ID NO:413, and SEQ ID NO:414, respectively, and LC1 comprises a LCDR1, LCDR2, and LCDR3 comprising the amino acid sequences of SEQ ID NO:415, SEQ ID NO:416, and SEQ ID NO:417, respectively, to form a binding site for a first antigen that specifically binds TRGV9. In some embodiments, the HC1 comprises a HCDR1, HCDR2, and HCDR3 comprising the amino acid sequences of SEQ ID NO:418, SEQ ID NO:419, and SEQ ID NO:420, respectively, and LC1 comprises a LCDR1, LCDR2, and LCDR3 comprising the amino acid sequences of SEQ ID NO:421, SEQ ID NO:422, and SEQ ID NO:423, respectively, to form a binding site for a first antigen that specifically binds TRGV9. In some embodiments, the HC1 comprises a HCDR1, HCDR2, and HCDR3 comprising the amino acid sequences of SEQ ID NO:424, SEQ ID NO:425, and SEQ ID NO:426, respectively, and LC1 comprises a LCDR1, LCDR2, and LCDR3 comprising the amino acid sequences of SEQ ID NO:427, SEQ ID NO:428, and SEQ ID NO:429, respectively, to form a binding site for a first antigen that specifically binds TRGV9. In some embodiments, the HC1 comprises a HCDR1, HCDR2, and HCDR3 comprising the amino acid sequences of SEQ ID NO:430, SEQ ID NO:431, and SEQ ID NO:432, respectively, and LC1 comprises a LCDR1, LCDR2, and LCDR3 comprising the amino acid sequences of SEQ ID NO:433, SEQ ID NO:434, and SEQ ID NO:435, respectively, to form a binding site for a first antigen that specifically binds TRGV9. In some embodiments, the HC1 comprises a HCDR1, HCDR2, and HCDR3 comprising the amino acid sequences of SEQ ID NO:430, SEQ ID NO:714, and SEQ ID NO:715, respectively, and LC1 comprises a LCDR1, LCDR2, and LCDR3 comprising the amino acid sequences of SEQ ID NO:433, SEQ ID NO:434, and SEQ ID NO:435, respectively, to form a binding site for a first antigen that specifically binds TRGV9. In some embodiments, the HC1 comprises a HCDR1, HCDR2, and HCDR3 comprising the amino acid sequences of SEQ ID NO:436, SEQ ID NO:437, and SEQ ID NO:438, respectively, and LC1 comprises a LCDR1, LCDR2, and LCDR3 comprising the amino acid sequences of SEQ ID NO:439, SEQ ID NO:440, and SEQ ID NO:441, respectively, to form a binding site for a first antigen that specifically binds TRGV9. In some embodiments, the HC1 comprises a HCDR1, HCDR2, and HCDR3 comprising the amino acid sequences of SEQ ID NO:442, SEQ ID NO:443, and SEQ ID NO:444, respectively, and LC1 comprises a LCDR1, LCDR2, and LCDR3 comprising the amino acid sequences of SEQ ID NO:445, SEQ ID NO:446, and SEQ ID NO:447, respectively, to form a binding site for a first antigen that specifically binds TRGV9. In some embodiments, the HC1 comprises a HCDR1, HCDR2, and HCDR3 comprising the amino acid sequences of SEQ ID NO:448, SEQ ID NO:449, and SEQ ID NO:450, respectively, and LC1 comprises a LCDR1, LCDR2, and LCDR3 comprising the amino acid sequences of SEQ ID NO:451, SEQ ID NO:452, and SEQ ID NO:453, respectively, to form a binding site for a first antigen that specifically binds TRGV9. In some embodiments, the HC1 comprises a HCDR1, HCDR2, and HCDR3 comprising the amino acid sequences of SEQ ID NO:454, SEQ ID NO:455, and SEQ ID NO:456, respectively, and LC1 comprises a LCDR1, LCDR2, and LCDR3 comprising the amino acid sequences of SEQ ID NO:457, SEQ ID NO:458, and SEQ ID NO:459, respectively, to form a binding site for a first antigen that specifically binds TRGV9. In some embodiments, the HC1 comprises a HCDR1, HCDR2, and HCDR3 comprising the amino acid sequences of SEQ ID NO:460, SEQ ID NO:461, and SEQ ID NO:462, respectively, and LC1 comprises a LCDR1, LCDR2, and LCDR3 comprising the amino acid sequences of SEQ ID NO:463, SEQ ID NO:464, and SEQ ID NO:465, respectively, to form a binding site for a first antigen that specifically binds TRGV9. In some embodiments, the HC1 comprises a HCDR1, HCDR2, and HCDR3 comprising the amino acid sequences of SEQ ID NO:466, SEQ ID NO:467, and SEQ ID NO:468, respectively, and LC1 comprises a LCDR1, LCDR2, and LCDR3 comprising the amino acid sequences of SEQ ID NO:469, SEQ ID NO:470, and SEQ ID NO:471, respectively, to form a binding site for a first antigen that specifically binds TRGV9. In some embodiments, the HC1 comprises a HCDR1, HCDR2, and HCDR3 comprising the amino acid sequences of SEQ ID NO:466, SEQ ID NO:716, and SEQ ID NO:717, respectively, and LC1 comprises a LCDR1, LCDR2, and LCDR3 comprising the amino acid sequences of SEQ ID NO:469, SEQ ID NO:470, and SEQ ID NO:471, respectively, to form a binding site for a first antigen that specifically binds TRGV9. In some embodiments, the HC1 comprises a HCDR1, HCDR2, and HCDR3 comprising the amino acid sequences of SEQ ID NO:472, SEQ ID NO:473, and SEQ ID NO:474, respectively, and LC1 comprises a LCDR1, LCDR2, and LCDR3 comprising the amino acid sequences of SEQ ID NO:475, SEQ ID NO:476, and SEQ ID NO:477, respectively, to form a binding site for a first antigen that specifically binds TRGV9. In some embodiments, the HC1 comprises a HCDR1, HCDR2, and HCDR3 comprising the amino acid sequences of SEQ ID NO:478, SEQ ID NO:479, and SEQ ID NO:480, respectively, and LC1 comprises a LCDR1, LCDR2, and LCDR3 comprising the amino acid sequences of SEQ ID NO:481, SEQ ID NO:482, and SEQ ID NO:483, respectively, to form a binding site for a first antigen that specifically binds TRGV9. In some embodiments, the HC1 comprises a HCDR1, HCDR2, and HCDR3 comprising the amino acid sequences of SEQ ID NO:484, SEQ ID NO:485, and SEQ ID NO:486, respectively, and LC1 comprises a LCDR1, LCDR2, and LCDR3 comprising the amino acid sequences of SEQ ID NO:487, SEQ ID NO:488, and SEQ ID NO:489, respectively, to form a binding site for a first antigen that specifically binds TRGV9. In some embodiments, the HC1 comprises a HCDR1, HCDR2, and HCDR3 comprising the amino acid sequences of SEQ ID NO:490, SEQ ID NO:491, and SEQ ID NO:492, respectively, and LC1 comprises a LCDR1, LCDR2, and LCDR3 comprising the amino acid sequences of SEQ ID NO:493, SEQ ID NO:494, and SEQ ID NO:495, respectively, to form a binding site for a first antigen that specifically binds TRGV9. In some embodiments, the HC1 comprises a HCDR1, HCDR2, and HCDR3 comprising the amino acid sequences of SEQ ID NO:496, SEQ ID NO:497, and SEQ ID NO:498, respectively, and LC1 comprises a LCDR1, LCDR2, and LCDR3 comprising the amino acid sequences of SEQ ID NO:499, SEQ ID NO:500, and SEQ ID NO:501, respectively, to form a binding site for a first antigen that specifically binds TRGV9. In some embodiments, the HC1 comprises a HCDR1, HCDR2, and HCDR3 comprising the amino acid sequences of SEQ ID NO:502, SEQ ID NO:503, and SEQ ID NO:504, respectively, and LC1 comprises a LCDR1, LCDR2, and LCDR3 comprising the amino acid sequences of SEQ ID NO:505, SEQ ID NO:506, and SEQ ID NO:507, respectively, to form a binding site for a first antigen that specifically binds TRGV9. In some embodiments, the HC1 comprises a HCDR1, HCDR2, and HCDR3 comprising the amino acid sequences of SEQ ID NO:502, SEQ ID NO:718, and SEQ ID NO:719, respectively, and LC1 comprises a LCDR1, LCDR2, and LCDR3 comprising the amino acid sequences of SEQ ID NO:505, SEQ ID NO:506, and SEQ ID NO:507, respectively, to form a binding site for a first antigen that specifically binds TRGV9. In some embodiments, the HC1 comprises a HCDR1, HCDR2, and HCDR3 comprising the amino acid sequences of SEQ ID NO:508, SEQ ID NO:509, and SEQ ID NO:510, respectively, and LC1 comprises a LCDR1, LCDR2, and LCDR3 comprising the amino acid sequences of SEQ ID NO:511, SEQ ID NO:512, and SEQ ID NO:513, respectively, to form a binding site for a first antigen that specifically binds TRGV9. In some embodiments, the HC1 comprises a HCDR1, HCDR2, and HCDR3 comprising the amino acid sequences of SEQ ID NO:514, SEQ ID NO:515, and SEQ ID NO:516, respectively, and LC1 comprises a LCDR1, LCDR2, and LCDR3 comprising the amino acid sequences of SEQ ID NO:517, SEQ ID NO:518, and SEQ ID NO:519, respectively, to form a binding site for a first antigen that specifically binds TRGV9. In some embodiments, the HC1 comprises a HCDR1, HCDR2, and HCDR3 comprising the amino acid sequences of SEQ ID NO: 520, SEQ ID NO:521, and SEQ ID NO:522, respectively, and LC1 comprises a LCDR1, LCDR2, and LCDR3 comprising the amino acid sequences of SEQ ID NO:523, SEQ ID NO:524, and SEQ ID NO:525, respectively, to form a binding site for a first antigen that specifically binds TRGV9. In some embodiments, the HC1 comprises a HCDR1, HCDR2, and HCDR3 comprising the amino acid sequences of SEQ ID NO:526, SEQ ID NO:527, and SEQ ID NO:528, respectively, and LC1 comprises a LCDR1, LCDR2, and LCDR3 comprising the amino acid sequences of SEQ ID NO:529, SEQ ID NO:530, and SEQ ID NO:531, respectively, to form a binding site for a first antigen that specifically binds TRGV9. In some embodiments, the HC1 comprises a HCDR1, HCDR2, and HCDR3 comprising the amino acid sequences of SEQ ID NO:532, SEQ ID NO:533, and SEQ ID NO:534, respectively, and LC1 comprises a LCDR1, LCDR2, and LCDR3 comprising the amino acid sequences of SEQ ID NO:535, SEQ ID NO:536, and SEQ ID NO:537, respectively, to form a binding site for a first antigen that specifically binds TRGV9. In some embodiments, the HC1 comprises a HCDR1, HCDR2, and HCDR3 comprising the amino acid sequences of SEQ ID NO:538, SEQ ID NO:539, and SEQ ID NO:540, respectively, and LC1 comprises a LCDR1, LCDR2, and LCDR3 comprising the amino acid sequences of SEQ ID NO:541, SEQ ID NO:542, and SEQ ID NO:543, respectively, to form a binding site for a first antigen that specifically binds TRGV9. In some embodiments, the HC1 comprises a HCDR1, HCDR2, and HCDR3 comprising the amino acid sequences of SEQ ID NO:538, SEQ ID NO:720, and SEQ ID NO:721, respectively, and LC1 comprises a LCDR1, LCDR2, and LCDR3 comprising the amino acid sequences of SEQ ID NO:541, SEQ ID NO:542, and SEQ ID NO:543, respectively, to form a binding site for a first antigen that specifically binds TRGV9. In some embodiments, the HC1 comprises a HCDR1, HCDR2, and HCDR3 comprising the amino acid sequences of SEQ ID NO:544, SEQ ID NO:545, and SEQ ID NO:546, respectively, and LC1 comprises a LCDR1, LCDR2, and LCDR3 comprising the amino acid sequences of SEQ ID NO:547, SEQ ID NO:548, and SEQ ID NO:549, respectively, to form a binding site for a first antigen that specifically binds TRGV9. In some embodiments, the HC1 comprises a HCDR1, HCDR2, and HCDR3 comprising the amino acid sequences of SEQ ID NO:550, SEQ ID NO:551, and SEQ ID NO:552, respectively, and LC1 comprises a LCDR1, LCDR2, and LCDR3 comprising the amino acid sequences of SEQ ID NO:553, SEQ ID NO:554, and SEQ ID NO:555, respectively, to form a binding site for a first antigen that specifically binds TRGV9. The HC2 can, for example, comprise a HCDR1, HCDR2, and HCDR3 comprising the amino acid sequences of SEQ ID NO:9, SEQ ID NO:10, and SEQ ID NO:11, respectively, and LC2 can, for example, comprise a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In some embodiments, the HC2 comprises a HCDR1, HCDR2, and HCDR3 comprising the amino acid sequence of SEQ ID NO:556, SEQ ID NO:557, and SEQ ID NO:558, respectively, and a LCDR1, LCDR2, and LCDR3 comprising the amino acid sequence of SEQ ID NO:559, SEQ ID NO:560, and SEQ ID NO:561, respectively, to form a binding site for a second antigen that specifically binds CD123. In some embodiments, the HC2 comprises a HCDR1, HCDR2, and HCDR3 comprising the amino acid sequence of SEQ ID NO:562, SEQ ID NO:563, and SEQ ID NO:564, respectively, and a LCDR1, LCDR2, and LCDR3 comprising the amino acid sequence of SEQ ID NO:565, SEQ ID NO:566, and SEQ ID NO:567, respectively, to form a binding site for a second antigen that specifically binds CD123. In some embodiments, the HC2 comprises a HCDR1, HCDR2, and HCDR3 comprising the amino acid sequence of SEQ ID NO:568, SEQ ID NO:569, and SEQ ID NO:570, respectively, and a LCDR1, LCDR2, and LCDR3 comprising the amino acid sequence of SEQ ID NO:571, SEQ ID NO:572, and SEQ ID NO:573, respectively, to form a binding site for a second antigen that specifically binds CD123. In some embodiments, the HC2 comprises a HCDR1, HCDR2, and HCDR3 comprising the amino acid sequence of SEQ ID NO:574, SEQ ID NO:575, and SEQ ID NO:576, respectively, and a LCDR1, LCDR2, and LCDR3 comprising the amino acid sequence of SEQ ID NO:577, SEQ ID NO:578, and SEQ ID NO:579, respectively, to form a binding site for a second antigen that specifically binds CD123. In some embodiments, the HC2 comprises a HCDR1, HCDR2, and HCDR3 comprising the amino acid sequence of SEQ ID NO:574, SEQ ID NO:722, and SEQ ID NO:723, respectively, and a LCDR1, LCDR2, and LCDR3 comprising the amino acid sequence of SEQ ID NO:577, SEQ ID NO:578, and SEQ ID NO:579, respectively, to form a binding site for a second antigen that specifically binds CD123. In some embodiments, the HC2 comprises a HCDR1, HCDR2, and HCDR3 comprising the amino acid sequence of SEQ ID NO:580, SEQ ID NO:581, and SEQ ID NO:582, respectively, and a LCDR1, LCDR2, and LCDR3 comprising the amino acid sequence of SEQ ID NO:583, SEQ ID NO:584, and SEQ ID NO:585, respectively, to form a binding site for a second antigen that specifically binds CD123. In some embodiments, the HC2 comprises a HCDR1, HCDR2, and HCDR3 comprising the amino acid sequence of SEQ ID NO:586, SEQ ID NO:587, and SEQ ID NO:588; and (ii) a VL comprising a VL CDR1 having an amino acid sequence of SEQ ID NO:589, SEQ ID NO:590, and SEQ ID NO:591, respectively, to form a binding site for a second antigen that specifically binds CD123. In certain embodiments, the HC1 comprises the amino acid sequence of SEQ ID NO:7, SEQ ID NO:34, SEQ ID NO:35, or SEQ ID NO:36, and LC1 comprises the amino acid sequence of SEQ ID NO:8, and the HC2 comprises the amino acid sequence of SEQ ID NO:15 and LC2 comprises the amino acid sequence of SEQ ID NO:16. In certain embodiments, the HC1 comprises the amino acid sequence of SEQ ID NO:7, and LC1 comprises the amino acid sequence of SEQ ID NO:8, and the HC2 comprises the amino acid sequence of SEQ ID NO:15 and LC2 comprises the amino acid sequence of SEQ ID NO:16. In certain embodiments, the HC1 comprises the amino acid sequence of SEQ ID NO:34, and LC1 comprises the amino acid sequence of SEQ ID NO:8, and the HC2 comprises the amino acid sequence of SEQ ID NO:15 and LC2 comprises the amino acid sequence of SEQ ID NO:16. In certain embodiments, the HC1 comprises the amino acid sequence of SEQ ID NO:35, and LC1 comprises the amino acid sequence of SEQ ID NO:8, and the HC2 comprises the amino acid sequence of SEQ ID NO:15 and LC2 comprises the amino acid sequence of SEQ ID NO:16. In certain embodiments, the HC1 comprises the amino acid sequence of SEQ ID NO:36, and LC1 comprises the amino acid sequence of SEQ ID NO:8, and the HC2 comprises the amino acid sequence of SEQ ID NO:15 and LC2 comprises the amino acid sequence of SEQ ID NO:16. In certain embodiments, the HC1 comprises the amino acid sequence of SEQ ID NO:65, and LC1 comprises the amino acid sequence of SEQ ID NO:66, and the HC2 comprises the amino acid sequence of SEQ ID NO:15 and LC2 comprises the amino acid sequence of SEQ ID NO:16. In certain embodiments, the HC1 comprises the amino acid sequence of SEQ ID NO:67, and LC1 comprises the amino acid sequence of SEQ ID NO:68, and the HC2 comprises the amino acid sequence of SEQ ID NO:15 and LC2 comprises the amino acid sequence of SEQ ID NO:16. In certain embodiments, the HC1 comprises the amino acid sequence of SEQ ID NO:95, and LC1 comprises the amino acid sequence of SEQ ID NO:96, and the HC2 comprises the amino acid sequence of SEQ ID NO:15 and LC2 comprises the amino acid sequence of SEQ ID NO:16. In certain embodiments, the HC1 comprises the amino acid sequence of SEQ ID NO:104, and LC1 comprises the amino acid sequence of SEQ ID NO:105, and the HC2 comprises the amino acid sequence of SEQ ID NO:15 and LC2 comprises the amino acid sequence of SEQ ID NO:16. In certain embodiments, the HC1 comprises the amino acid sequence of SEQ ID NO:113, and LC1 comprises the amino acid sequence of SEQ ID NO:114, and the HC2 comprises the amino acid sequence of SEQ ID NO:15 and LC2 comprises the amino acid sequence of SEQ ID NO:16. In certain embodiments, the HC1 comprises the amino acid sequence of SEQ ID NO:123, and LC1 comprises the amino acid sequence of SEQ ID NO:124, and the HC2 comprises the amino acid sequence of SEQ ID NO:15 and LC2 comprises the amino acid sequence of SEQ ID NO:16. In certain embodiments, the HC1 comprises the amino acid sequence of SEQ ID NO:133, and LC1 comprises the amino acid sequence of SEQ ID NO:134, and the HC2 comprises the amino acid sequence of SEQ ID NO:15 and LC2 comprises the amino acid sequence of SEQ ID NO:16. In certain embodiments, the TRGV9 is on the surface of a γδ T cell. In certain embodiments, the CD123 is on the surface of a cancer cell (e.g., a leukemia cell).

In some embodiments, the antibody specifically binds TRGV9. In other embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody. In some embodiments, the antibody is a bispecific antibody. In certain embodiments, the antibody is multivalent. In other embodiments, the antibody is capable of binding at least three antigens. In some embodiments, the antibody is capable of binding at least five antigens.

In some embodiments, the bispecific antibody provided herein is a diabody, a cross-body, or a bispecific antibody obtained via a controlled Fab arm exchange as those described herein.

In some embodiments, the bispecific antibodies include IgG-like molecules with complementary CH3 domains to force heterodimerization; recombinant IgG-like dual targeting molecules, wherein the two sides of the molecule each contain the Fab fragment or part of the Fab fragment of at least two different antibodies; IgG fusion molecules, wherein full length IgG antibodies are fused to an extra Fab fragment or parts of Fab fragment; Fc fusion molecules, wherein single chain Fv molecules or stabilized diabodies are fused to heavy-chain constant-domains, Fc-regions or parts thereof; Fab fusion molecules, wherein different Fab-fragments are fused together; ScFv- and diabody-based and heavy chain antibodies (e.g., domain antibodies, nanobodies) In some embodiments, different single chain Fv molecules or different diabodies or different heavy-chain antibodies (e.g. domain antibodies, nanobodies) are fused to each other or to another protein or carrier molecule.

In some embodiments, IgG-like molecules with complementary CH3 domains molecules include the Triomab/Quadroma (Trion Pharma/Fresenius Biotech), the Knobs-into-Holes (Genentech), CrossMAbs (Roche) and the electrostatically-matched (Amgen), the LUZ-Y (Genentech), the Strand Exchange Engineered Domain body (SEEDbody) (EMD Serono), the Biclonic (Merus) and the DuoBody (Genmab A/S).

In some embodiments, recombinant IgG-like dual targeting molecules include Dual Targeting (DT)-Ig (GSK/Domantis), Two-in-one Antibody (Genentech), Cross-linked Mabs (Karmanos Cancer Center), mAb2 (F-Star) and CovX-body (CovX/Pfizer).

In some embodiments, IgG fusion molecules include Dual Variable Domain (DVD)-Ig (Abbott), IgG-like Bispecific (InnClone/Eli Lilly), Ts2Ab (MedImmune/AZ) and BsAb (Zymogenetics), HERCULES (Biogen Idec) and TvAb (Roche).

In some embodiments, Fc fusion molecules can include ScFv/Fc Fusions (Academic Institution), SCORPION (Emergent BioSolutions/Trubion, Zymogenetics/BMS), Dual Affinity Retargeting Technology (Fc-DART) (Macro-Genics) and Dual(ScFv)$_2$-Fab (National Research Center for Antibody Medicine-China).

In some embodiments, Fab fusion bispecific antibodies include F(ab)$_2$ (Medarex/AMGEN), Dual-Action or Bis-Fab (Genentech), Dock-and-Lock (DNL) (ImmunoMedics), Bivalent Bispecific (Biotecnol) and Fab-Fv (UCB-Celltech). ScFv-, diabody-based, and domain antibodies, include but are not limited to, Bispecific T Cell Engager (BiTE) (Micromet), Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), dual targeting heavy chain only domain antibodies.

Full length bispecific antibodies provided herein can be generated for example using Fab arm exchange (or half molecule exchange) between two mono specific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy-chain disulfide bonds in the hinge regions of the parent mono specific antibodies are reduced. The resulting free cysteines of one of the parent monospecific antibodies form an inter heavy-chain disulfide bond with cysteine residues of a second parent mono specific antibody molecule and simultaneously CH3 domains of the parent antibodies release and reform by dissociation-association. The CH3 domains of the Fab arms can be engineered to favor heterodimerization over homodimerization. The resulting product is a bispecific antibody having two Fab arms or half molecules which each binding a distinct epitope, i.e. an epitope on TRGV9 and an epitope on a tumor antigen.

"Homodimerization" as used herein refers to an interaction of two heavy chains having identical CH3 amino acid sequences. "Homodimer" as used herein refers to an antibody having two heavy chains with identical CH3 amino acid sequences.

"Heterodimerization" as used herein refers to an interaction of two heavy chains having non-identical CH3 amino acid sequences. "Heterodimer" as used herein refers to an antibody having two heavy chains with non-identical CH3 amino acid sequences.

The "knob-in-hole" strategy (see, e.g., PCT Publ. No. WO2006/028936) can be used to generate full length bispecific antibodies. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob." Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S_L368A_Y407V.

Other strategies such as promoting heavy chain heterodimerization using electrostatic interactions by substituting positively charged residues at one CH3 surface and negatively charged residues at a second CH3 surface can be used, as described in US Pat. Publ. No. US2010/0015133; US Pat. Publ. No. US2009/0182127; US Pat. Publ. No. US2010/028637; or US Pat. Publ. No. US2011/0123532. In other strategies, heterodimerization can be promoted by the following substitutions (expressed as modified position in the first CH3 domain of the first heavy chain/modified position in the second CH3 domain of the second heavy chain): L351Y_F405AY407V/T394W, T366I_K392M_T394W/F405A_Y407V, T366L_K392M T394W/F405A Y407V, L351Y_Y407A/T366A_K409F, L351Y_Y407A/T366V K409F Y407A/T366A_K409F, or T350V_L351Y_F405A Y407V/T350V_T366L_K392L_T394W as described in U.S. Pat. Publ. No. US2012/0149876 or U.S. Pat. Publ. No. US2013/0195849.

In addition to methods described above, bispecific antibodies provided herein can be generated in vitro in a cell-free environment by introducing asymmetrical mutations in the CH3 regions of two mono specific homodimeric antibodies and forming the bispecific heterodimeric antibody from two parent monospecific homodimeric antibodies in reducing conditions to allow disulfide bond isomerization according to methods described in PCT Pat. Publ. No. WO2011/131746. In the methods, the first monospecific bivalent antibody (e.g., anti-CD33 antibody) and the second monospecific bivalent antibody (e.g., anti-CD3 antibody) are engineered to have certain substitutions at the CH3 domain that promotes heterodimer stability; the antibodies are incubated together under reducing conditions sufficient to allow the cysteines in the hinge region to undergo disulfide bond isomerization; thereby generating the bispecific antibody by Fab arm exchange. The incubation conditions can optionally be restored to non-reducing conditions. Exemplary reducing agents that can be used are 2-mercaptoethylamine (2-MEA), dithiothreitol (DTT), dithioerythritol (DTE), glutathione, tris (2-carboxyethyl) phosphine (TCEP), L-cysteine and beta-mercaptoethanol, or a reducing agent selected from the group consisting of: 2-mercaptoethylamine, dithiothreitol and tris (2-carboxyethyl) phosphine. For example, incubation for at least 90 min at a temperature of at least 20° C. in the presence of at least 25 mM 2-MEA or in the presence of at least 0.5 mM dithiothreitol at a pH from 5-8, for example at pH of 7.0 or at pH of 7.4 can be used.

In some embodiments, the anti-TRGV9 antibody is a multispecific antibody. In other embodiments, the anti-TRGV9 antibody is a bispecific antibody. In other embodiments, the bispecific antibody comprises an antigen binding fragment of an anti-TRGV9 antibody provided herein.

In some embodiments, the anti-TRGV9 bispecific antibody does not comprise a single chain antibody. In some embodiments, the anti-TRGV9 bispecific antibody does not comprise a single domain antibody. In certain embodiments, the anti-TRGV9 bispecific antibody does not comprise a nanobody. In certain embodiments, the anti-TRGV9 bispecific antibody does not comprise a VHH antibody. In certain embodiments, the anti-TRGV9 bispecific antibody does not comprise a llama antibody.

Also provided herein is a bispecific antibody comprising an anti-TRGV9 antibody or antigen-binding fragment thereof, and an anti-CD123 antibody or antigen-binding fragment thereof. In certain embodiments, the bispecific antibody comprises an anti-TRGV9 antibody, and an anti-CD123 antibody. In certain embodiments, the bispecific antibody comprises an antigen binding fragment of an anti-TRGV9 antibody, and an anti-CD123 antibody. In certain embodiments, the bispecific antibody comprises an anti-TRGV9 antibody, and an antigen-binding fragment of an anti-CD123 antibody. In certain embodiments, the bispecific antibody comprises an antigen-binding fragment of an anti-TRGV9 antibody, and an antigen binding fragment of an anti-CD123 antibody.

In some embodiments, an anti-TRGV9 bispecific antibody provided herein does not comprise a VH CDR1, VH CDR2, and VH CDR3 having the amino acid sequence of SEQ ID NOs:730, 731, and 732, respectively. In some embodiments, an anti-TRGV9 bispecific antibody provided herein does not comprise a VH CDR1, VH CDR2, and VH CDR3 having the amino acid sequence of SEQ ID NOs:733, 734, and 735, respectively. In some embodiments, an anti-TRGV9 bispecific antibody provided herein does not comprise a VH CDR1, VH CDR2, and VH CDR3 having the amino acid sequence of SEQ ID NOs:736, 737, and 738, respectively. In some embodiments, an anti-TRGV9 bispecific antibody provided herein does not comprise a VH CDR1, VH CDR2, and VH CDR3 having the amino acid sequence of SEQ ID NOs:739, 740, and 741, respectively. In some embodiments, an anti-TRGV9 bispecific antibody provided herein does not comprise a VH CDR1, VH CDR2, and VH CDR3 having the amino acid sequence of SEQ ID NOs:742, 743, and 744, respectively. In some embodiments, an anti-TRGV9 bispecific antibody provided herein does not comprise a VH CDR1, VH CDR2, and VH CDR3 having the amino acid sequence of SEQ ID NOs:745, 746, and 747, respectively. In some embodiments, an anti-TRGV9 bispecific antibody provided herein does not comprise a VH CDR1, VH CDR2, and VH CDR3 having the amino acid sequence of SEQ ID NOs:748, 749, and 750, respectively. In some embodiments, an anti-TRGV9 bispecific antibody provided herein does not comprise a VH domain having the amino acid sequence of SEQ ID NO:751. In some embodiments, an anti-TRGV9 bispecific antibody provided herein does not comprise a VH domain having the amino acid sequence of SEQ ID NO:752. In some embodiments, an anti-TRGV9 bispecific antibody provided herein does not comprise a VH domain having the amino acid sequence of SEQ ID NO:753. In some embodiments, an anti-TRGV9 bispecific antibody provided herein does not comprise a VH domain having the amino acid sequence of SEQ ID NO:754. In some embodiments, an anti-TRGV9 bispecific antibody provided herein does not comprise a VH domain having the amino acid sequence of SEQ ID NO:755. In some embodiments, an anti-TRGV9 bispecific antibody provided herein does not comprise a VH domain having the amino acid sequence of SEQ ID NO:756. In some embodiments, an anti-TRGV9 bispecific antibody provided herein does not comprise a VH domain having the amino acid sequence of SEQ ID NO:757.

In certain embodiments, the anti-TRGV9 antibody or antigen-binding fragment thereof comprises a HCDR1, HCDR2, HCDR3, a LCDR1, LCDR2, and LCDR3, having the polypeptide sequence of:

i. SEQ ID NOs:1, 2, 3, 4, 5, and 6, respectively;
ii. SEQ ID NOs:1, 2, 31, 4, 5, and 6, respectively;
iii. SEQ ID NOs:1, 2, 32, 4, 5, and 6, respectively; or
iv. SEQ ID NOs:1, 2, 33, 4, 5, and 6, respectively;

and the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively.

In certain embodiments, the anti-TRGV9 antibody or antigen-binding fragment thereof comprises a HCDR1, HCDR2, HCDR3, a LCDR1, LCDR2, and LCDR3, having the polypeptide sequence of SEQ ID NOs:1, 2, 3, 4, 5, and 6, respectively; and the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively. In certain embodiments, the anti-TRGV9 antibody or antigen-binding fragment thereof comprises a HCDR1, HCDR2, HCDR3, a LCDR1, LCDR2, and LCDR3, having the polypeptide sequence of SEQ ID NOs:1, 2, 31, 4, 5, and 6, respectively; and the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively. In certain embodiments, the anti-TRGV9 antibody or antigen-binding fragment thereof comprises a HCDR1, HCDR2, HCDR3, a LCDR1, LCDR2, and LCDR3, having the polypeptide sequence of SEQ ID NOs:1, 2, 32, 4, 5, and 6, respectively; and the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively. In certain embodiments, the anti-TRGV9 antibody or antigen-binding fragment thereof comprises a HCDR1, HCDR2, HCDR3, a LCDR1, LCDR2, and LCDR3, having the polypeptide sequence of SEQ ID NOs:1, 2, 33, 4, 5, and 6, respectively; and the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively. In certain embodiments, the anti-TRGV9 antibody or antigen-binding fragment thereof comprises a HCDR1, HCDR2, HCDR3, a LCDR1, LCDR2, and LCDR3, having the polypeptide sequence of SEQ ID NOs:1, 76, 3, 77, 5, and 6, respectively; and the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively. In certain embodiments, the anti-TRGV9 antibody or antigen-binding fragment thereof comprises a HCDR1, HCDR2, HCDR3, a LCDR1, LCDR2, and LCDR3, having the polypeptide sequence of SEQ ID NOs:60, 61, 62, 63, 64, and 6, respectively; and the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively. In certain embodiments, the anti-TRGV9 antibody or antigen-binding fragment thereof comprises a HCDR1, HCDR2, HCDR3, a LCDR1, LCDR2, and LCDR3, having the polypeptide sequence of SEQ ID NOs:89, 90, 91, 92, 93, and 94, respectively; and the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively. In certain embodiments, the anti-TRGV9 antibody or antigen-binding fragment thereof comprises a HCDR1, HCDR2, HCDR3, a LCDR1, LCDR2, and LCDR3, having the polypeptide sequence of SEQ ID NOs:98, 99, 100, 101, 102, and 103, respectively; and the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively. In certain embodiments, the anti-TRGV9 antibody or antigen-binding fragment thereof comprises a HCDR1, HCDR2, HCDR3, a LCDR1, LCDR2, and LCDR3, having the polypeptide sequence of SEQ ID NOs: 107, 108, 109, 110, 111, and 112, respectively; and the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively. In certain embodiments, the anti-TRGV9 antibody or antigen-binding fragment thereof comprises a HCDR1, HCDR2, HCDR3, a LCDR1, LCDR2, and LCDR3, having the polypeptide sequence of SEQ ID NOs:117, 118, 119, 120, 121, and 122, respectively; and the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively. In certain embodiments, the anti-TRGV9 antibody or antigen-binding fragment thereof comprises a HCDR1, HCDR2, HCDR3, a LCDR1, LCDR2, and LCDR3, having the polypeptide sequence of SEQ ID NOs: 127, 128, 129, 130, 131, and 132, respectively; and the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively.

In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:160, 161, 162, 163, 164, and 165, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:166, 167, 168, 169, 170, and 171, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:172, 173, 174, 175, 176, and 177, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs: 178, 179, 180, 181, 182, and 183, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:178, 700, 701, 181, 182, and 183, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:184, 185, 186, 187, 188, and 189, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:190, 191, 192, 193, 194, and 195, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:196, 197, 198, 199, 200, and 201, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:202, 203, 204, 205, 206, and 207, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:208, 209, 210, 211, 212, and 213, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:214, 215, 216, 217, 218, and 219, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:214, 702, 703, 217, 218, and 219, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:220, 221, 222, 223, 224, and 225, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:226, 227, 228, 229, 230, and 231, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:232, 233, 234, 235, 236, and 237, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:238, 239, 240, 241, 242, and 243, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:244, 245, 246, 247, 248, and 249, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:250, 251, 252, 253, 254, and 255, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:250, 704, 705, 253, 254, and 255, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:256, 257, 258, 259, 260, and 261, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:262, 263, 264, 265, 266, and 267, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:268, 269, 270, 271, 272, and 273, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:274, 275, 276, 277, 278, and 279, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:280, 281, 282, 283, 284, and 285, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:286, 287, 288, 289, 290, and 291, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:286, 706, 707, 289, 290, and 291, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:292, 293, 294, 295, 296, and 297, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:298, 299, 300, 301, 302, and 303, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:304, 305, 306, 307, 308, and 309, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:310, 311, 312, 313, 314, and 315, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:316, 317, 318, 319, 320, and 321, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:322, 323, 324, 325, 326, and 327, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:322, 708, 709, 325, 326, and 327, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:328, 329, 330, 331, 332, and 333, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:334, 335, 336, 337, 338, and 339, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:340, 341, 342, 343, 344, and 345, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:346, 347, 348, 349, 350, and 351, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:352, 353, 354, 355, 356, and 357, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:358, 359, 360, 361, 362, and 363, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:358, 710, 711, 361, 362, and 363, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:364, 365, 366, 367, 368, and 369, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:370, 371, 372, 373, 374, and 375, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:376, 377, 378, 379, 380, and 381, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:382, 383, 384, 385, 386, and 387, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:388, 389, 390, 391, 392, and 393, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:394, 395, 396, 397, 398, and 399, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:394, 712, 713, 397, 398, and 399, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:400, 401, 402, 403, 404, and 405, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:406, 407, 408, 409, 410, and 411, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:412, 413, 414, 415, 416, and 417, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:418, 419, 420, 421, 422, and 423, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:424, 425, 426, 427, 428, and 429, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:430, 431, 432, 433, 434, and 435, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:430, 714, 715, 433, 434, and 435, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:436, 437, 438, 439, 440, and 441, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:442, 443, 444, 445, 446, and 447, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:448, 449, 450, 451, 452, and 453, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:454, 455, 456, 457, 458, and 459, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:460, 461, 462, 463, 464, and 465, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:466, 467, 468, 469, 470, and 471, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:466, 716, 717, 469, 470, and 471, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:472, 473, 474, 475, 476, and 477, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:478, 479, 480, 481, 482, and 483, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:484, 485, 486, 487, 488, and 489, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:490, 491, 492, 493, 494, and 495, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:496, 497, 498, 499, 500, and 501, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:502, 503, 504, 505, 506, and 507, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:502, 718, 719, 505, 506, and 507, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:508, 509, 510, 511, 512, and 513, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:514, 515, 516, 517, 518, and 519, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:520, 521, 522, 523, 524, and 525, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:526, 527, 528, 529, 530, and 531, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:532, 533, 534, 535, 536, and 537, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:538, 539, 540, 541, 542, and 543, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:538, 720, 721, 541, 542, and 543, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:544, 545, 546, 547, 548, and 549, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:550, 551, 552, 553, 554, and 555, respectively.

In some embodiments, the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively. In some embodiments, the anti-CD123 antibody or antigen-binding fragment thereof comprises a HCDR1, HCDR2, HCDR3, LCDR1, LCDR2, and LCDR3, having the polypeptide sequence of SEQ ID NOs:556, 557, 558, 559, 560, and 561, respectively. In some embodiments, the anti-CD123 antibody or antigen-binding fragment thereof comprises a HCDR1, HCDR2, HCDR3, LCDR1, LCDR2, and LCDR3, having the polypeptide sequence of SEQ ID NOs:562, 563, 564, 565, 566, and 567, respectively. In some embodiments, the anti-CD123 antibody or antigen-binding fragment thereof comprises a HCDR1, HCDR2, HCDR3, LCDR1, LCDR2, and LCDR3, having the polypeptide sequence of SEQ ID NOs:568, 569, 570, 571, 572, and 573, respectively. In some embodiments, the anti-CD123 antibody or antigen-binding fragment thereof comprises a HCDR1, HCDR2, HCDR3, LCDR1, LCDR2, and LCDR3, having the polypeptide sequence of SEQ ID NOs: 574, 575, 576, 577, 578, and 579, respectively. In some embodiments, the anti-CD123 antibody or antigen-binding fragment thereof comprises a HCDR1, HCDR2, HCDR3, LCDR1, LCDR2, and LCDR3, having the polypeptide sequence of SEQ ID NOs:574, 722, 723, 577, 578, and 579, respectively. In some embodiments, the anti-CD123 antibody or antigen-binding fragment thereof comprises a HCDR1, HCDR2, HCDR3, LCDR1, LCDR2, and LCDR3, having the polypeptide sequence of SEQ ID NOs:580, 581, 582, 583, 584, and 585, respectively. In some embodiments, the anti-CD123 antibody or antigen-binding fragment thereof comprises a HCDR1, HCDR2, HCDR3, LCDR1, LCDR2, and LCDR3, having the polypeptide sequence of SEQ ID NOs:586, 587, 588, 589, 590, and 591, respectively.

In certain embodiments, the bispecific antibody comprises any of the anti-TRGV9 antibodies provided herein. In some embodiments, the bispecific antibody comprises an antigen binding fragment of any of the anti-TRGV9 antibodies provided herein. In certain embodiments, the bispecific antibody comprises any of the anti-CD123 antibodies provided herein. In some embodiments, the bispecific antibody comprises an antigen binding fragment of any of the anti-CD123 antibodies provided herein. In other embodiments, the bispecific antibody comprises any of the anti-TRGV9 antibodies provided herein, and any of the CD123 antibodies provided herein. In some embodiments, the bispecific antibody comprises any of the anti-TRGV9 antibodies provided herein, and an antigen binding fragment of any of the CD123 antibodies provided herein. In other embodiments, the bispecific antibody comprises an antigen binding fragment any of the anti-TRGV9 antibodies provided herein, and any of the CD123 antibodies provided herein. In yet other embodiments, the bispecific antibody comprises an antigen binding fragment of any of the anti-TRGV9 antibodies provided herein, and an antigen binding fragment of any of the CD123 antibodies provided herein.

According to another particular aspect, provided herein is an isolated anti-TRGV9/anti-CD123 bispecific antibody or antigen-binding fragment thereof that induces antibody-dependent cell-mediated cytotoxicity (ADCC). The bispecific antibody or antigen-binding fragment thereof can, for example, induce ADCC in vitro.

In certain embodiments, the bispecific antibody or antigen-binding fragment thereof induces $\gamma\delta$ T cell dependent cytotoxicity of a cancer cell in vitro with an $EC_{50}$ of less than about 160 pM, when assessed in vitro at an effector to target cell ratio of 1:1. In one such embodiment, the bispecific antibody is an isolated anti-TRGV9/anti-CD123 bispecific antibody or antigen-binding fragment thereof that exhibits an $EC_{50}$ of less than about 160 pM, when assessed in vitro with a mixture of $\gamma\delta$ T effector cells and Kasumi3 AML target cells, where such cells are present in an effector to target cell ratio of about 1:1 and the bispecific antibody or antigen-binding fragment thereof is present at a concentration of about 30 ng/mL.

In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein, HC1 comprises a HCDR1, HCDR2, and HCDR3 comprising the amino acid sequences of (i) SEQ ID NO:1, SEQ ID NO:2, and SEQ ID NO:3, respectively, (ii) SEQ ID NO:1, SEQ ID NO:2, and SEQ ID NO:31, respectively, (iii) SEQ ID NO:1, SEQ ID NO:2, and SEQ ID NO:32, respectively, or (iv) SEQ ID NO:1, SEQ ID NO:2, and SEQ ID NO:33, respectively, and LC1 comprises a LCDR1, LCDR2, and LCDR3 comprising the amino acid sequences of SEQ ID NO:4, SEQ ID NO:5, and SEQ ID NO:6, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein, HC1 comprises a HCDR1, HCDR2, and HCDR3 comprising the amino acid sequences of SEQ ID NO:1, SEQ ID NO:2, and SEQ ID NO:3, respectively, and LC1 comprises a LCDR1, LCDR2, and LCDR3 comprising the amino acid sequences of SEQ ID NO:4, SEQ ID NO:5, and SEQ ID NO:6, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:31, respectively, and LC1 comprises a LCDR1, LCDR2, and LCDR3 comprising the amino acid sequences of SEQ ID NO:4, SEQ ID NO:5, and SEQ ID NO:6, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:32, respectively, and LC1 comprises a LCDR1, LCDR2, and LCDR3 comprising the amino acid sequences of SEQ ID NO:4, SEQ ID NO:5, and SEQ ID NO:6, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:33, respectively, and LC1 comprises a LCDR1, LCDR2, and LCDR3 comprising the amino acid sequences of SEQ ID NO:4, SEQ ID NO:5, and SEQ ID NO:6, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:76, and SEQ ID NO:3, respectively, and LC1 comprises a LCDR1, LCDR2, and LCDR3 comprising the amino acid sequences of SEQ ID NO:77, SEQ ID NO:5, and SEQ ID NO:6, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:60, SEQ ID NO:61, and SEQ ID NO:62, respectively, and LC1 comprises a LCDR1, LCDR2, and LCDR3 comprising the amino acid sequences of SEQ ID NO:63, SEQ ID NO:64, and SEQ ID NO:6, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:89, SEQ ID NO:90, and SEQ ID NO:91, respectively, and LC1 comprises a LCDR1, LCDR2, and LCDR3 comprising the amino acid sequences of SEQ ID NO:92, SEQ ID NO:93, and SEQ ID NO:94, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:98, SEQ ID NO:99, and SEQ ID NO:100, respectively, and LC1 comprises a LCDR1, LCDR2, and LCDR3 comprising the amino acid sequences of SEQ ID NO:101, SEQ ID NO: 102, and SEQ ID NO:103, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:107, SEQ ID NO:108, and SEQ ID NO:109, respectively, and LC1 comprises a LCDR1, LCDR2, and LCDR3 comprising the amino acid sequences of SEQ ID NO:110, SEQ ID NO:111, and SEQ ID NO:112, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:117, SEQ ID NO:118, and SEQ ID NO:119, respectively, and LC1 comprises a LCDR1, LCDR2, and LCDR3 comprising the amino acid sequences of SEQ ID NO:120, SEQ ID NO:121, and SEQ ID NO:122, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:127, SEQ ID NO:128, and SEQ ID NO:129, respectively, and LC1 comprises a LCDR1, LCDR2, and LCDR3 comprising the amino acid sequences of SEQ ID NO:130, SEQ ID NO:131, and SEQ ID NO:132, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:160, SEQ ID NO:161, and SEQ ID NO:162, respectively, and LC1 comprises a LCDR1, LCDR2, and LCDR3 comprising the amino acid sequences of SEQ ID NO:163, SEQ ID NO: 164, and SEQ ID NO:165, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:166, SEQ ID NO:167, and SEQ ID NO:168, respectively, and LC1 comprises a LCDR1, LCDR2, and LCDR3 comprising the amino acid sequences of SEQ ID NO:169, SEQ ID NO: 170, and SEQ ID NO:171, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:172, SEQ ID NO:173, and SEQ ID NO:174, respectively, and LC1 comprises a LCDR1, LCDR2, and LCDR3 comprising the amino acid sequences of SEQ ID NO:175, SEQ ID NO: 176, and SEQ ID NO:177, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:178, SEQ ID NO:179, and SEQ ID NO:180, respectively, and LC1 comprises a LCDR1, LCDR2, and LCDR3 comprising the amino acid sequences of SEQ ID NO:181, SEQ ID NO: 182, and SEQ ID NO:183, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:178, SEQ ID NO:700, and SEQ ID NO:701, respectively, and LC1 comprises a LCDR1, LCDR2, and LCDR3 comprising the amino acid sequences of SEQ ID NO:181, SEQ ID NO: 182, and SEQ ID NO:183, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:184, SEQ ID NO:185, and SEQ ID NO:186, respectively, and LC1 comprises a LCDR1, LCDR2, and LCDR3 comprising the amino acid sequences of SEQ ID NO:187, SEQ ID NO: 188, and SEQ ID NO:189, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:190, SEQ ID NO:191, and SEQ ID NO:192, respectively, and LC1 comprises a LCDR1, LCDR2, and LCDR3 comprising the amino acid sequences of SEQ ID NO:193, SEQ ID NO: 194, and SEQ ID NO:195, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:196, SEQ ID NO:197, and SEQ ID NO:198, respectively, and LC1 comprises a LCDR1, LCDR2, and LCDR3 comprising the amino acid sequences of SEQ ID NO:199, SEQ ID NO:200, and SEQ ID NO:201, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:202, SEQ ID NO:203, and SEQ ID NO:204, respectively, and LC1 comprises a LCDR1, LCDR2, and LCDR3 comprising the amino acid sequences of SEQ ID NO:205, SEQ ID NO:206, and SEQ ID NO:207, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:208, SEQ ID NO:209, and SEQ ID NO:210, respectively, and LC1 comprises a LCDR1, LCDR2, and LCDR3 comprising the amino acid sequences of SEQ ID NO:211, SEQ ID NO:212, and SEQ ID NO:213, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:214, SEQ ID NO:215, and SEQ ID NO:216, respectively, and LC1 comprises a LCDR1, LCDR2, and LCDR3 comprising the amino acid sequences of SEQ ID NO:217, SEQ ID NO:218, and SEQ ID NO:219, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:214, SEQ ID NO:702, and SEQ ID NO:703, respectively, and LC1 comprises a LCDR1, LCDR2, and LCDR3 comprising the amino acid sequences of SEQ ID NO:217, SEQ ID NO:218, and SEQ ID NO:219, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:220, SEQ ID NO:221, and SEQ ID NO:222, respectively, and LC1 comprises a LCDR1, LCDR2, and LCDR3 comprising the amino acid sequences of SEQ ID NO:223, SEQ ID NO:224, and SEQ ID NO:225, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:226, SEQ ID NO:227, and SEQ ID NO:228, respectively, and LC1 comprises a LCDR1, LCDR2, and LCDR3 comprising the amino acid sequences of SEQ ID NO:229, SEQ ID NO:230, and SEQ ID NO:231, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:232, SEQ ID NO:233, and SEQ ID NO:234, respectively, and LC1 comprises a LCDR1, LCDR2, and LCDR3 comprising the amino acid sequences of SEQ ID NO:235, SEQ ID NO:236, and SEQ ID NO:237, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:238, SEQ ID NO:239, and SEQ ID NO:240, respectively, and LC1 comprises a LCDR1, LCDR2, and LCDR3 comprising the amino acid sequences of SEQ ID NO:241, SEQ ID NO:242, and SEQ ID NO:243, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:244, SEQ ID NO:245, and SEQ ID NO:246, respectively, and LC1 comprises a LCDR1, LCDR2, and LCDR3 comprising the amino acid sequences of SEQ ID NO:247, SEQ ID NO:248, and SEQ ID NO:249, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:250, SEQ ID NO:251, and SEQ ID NO:252, respectively, and LC1 comprises a LCDR1, LCDR2, and LCDR3 comprising the amino acid sequences of SEQ ID NO:253, SEQ ID NO:254, and SEQ ID NO:255, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:250, SEQ ID NO:704, and SEQ ID NO:705, respectively, and LC1 comprises a LCDR1, LCDR2, and LCDR3 comprising the amino acid sequences of SEQ ID NO:253, SEQ ID NO:254, and SEQ ID NO:255, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:256, SEQ ID NO:257, and SEQ ID NO:258, respectively, and LC1 comprises a LCDR1, LCDR2, and LCDR3 comprising the amino acid sequences of SEQ ID NO:259, SEQ ID NO:260, and SEQ ID NO:261, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:262, SEQ ID NO:263, and SEQ ID NO:264, respectively, and LC1 comprises a LCDR1, LCDR2, and LCDR3 comprising the amino acid sequences of SEQ ID NO:265, SEQ ID NO:266, and SEQ ID NO:267, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:268, SEQ ID NO:269, and SEQ ID NO:270, respectively, and LC1 comprises a LCDR1, LCDR2, and LCDR3 comprising the amino acid sequences of SEQ ID NO:271, SEQ ID NO:272, and SEQ ID NO:273, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:274, SEQ ID NO:275, and SEQ ID NO:276, respectively, and LC1 comprises a LCDR1, LCDR2, and LCDR3 comprising the amino acid sequences of SEQ ID NO:277, SEQ ID NO:278, and SEQ ID NO:279, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:280, SEQ ID NO:281, and SEQ ID NO:282, respectively, and LC1 comprises a LCDR1, LCDR2, and LCDR3 comprising the amino acid sequences of SEQ ID NO:283, SEQ ID NO:284, and SEQ ID NO:285, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:286, SEQ ID NO:287, and SEQ ID NO:288, respectively, and LC1 comprises a LCDR1, LCDR2, and LCDR3 comprising the amino acid sequences of SEQ ID NO:289, SEQ ID NO:290, and SEQ ID NO:291, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:286, SEQ ID NO:706, and SEQ ID NO:707, respectively, and LC1 comprises a LCDR1, LCDR2, and LCDR3 comprising the amino acid sequences of SEQ ID NO:289, SEQ ID NO:290, and SEQ ID NO:291, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:292, SEQ ID NO:293, and SEQ ID NO:294, respectively, and LC1 comprises a LCDR1, LCDR2, and LCDR3 comprising the amino acid sequences of SEQ ID NO:295, SEQ ID NO:296, and SEQ ID NO:297, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:298, SEQ ID NO:299, and SEQ ID NO:300, respectively, and LC1 comprises a LCDR1, LCDR2, and LCDR3 comprising the amino acid sequences of SEQ ID NO:301, SEQ ID NO:302, and SEQ ID NO:303, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:304, SEQ ID NO:305, and SEQ ID NO:306, respectively, and LC1 comprises a LCDR1, LCDR2, and LCDR3 comprising the amino acid sequences of SEQ ID NO:307, SEQ ID NO:308, and SEQ ID NO:309, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:310, SEQ ID NO:311, and SEQ ID NO:312, respectively, and LC1 comprises a LCDR1, LCDR2, and LCDR3 comprising the amino acid sequences of SEQ ID NO:313, SEQ ID NO:314, and SEQ ID NO:315, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:316, SEQ ID NO:317, and SEQ ID NO:318, respectively, and LC1 comprises a LCDR1, LCDR2, and LCDR3 comprising the amino acid sequences of SEQ ID NO:319, SEQ ID NO:320, and SEQ ID NO:321, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:322, SEQ ID NO:323, and SEQ ID NO:324, respectively, and LC1 comprises a LCDR1, LCDR2, and LCDR3 comprising the amino acid sequences of SEQ ID NO:325, SEQ ID NO:326, and SEQ ID NO:327, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:322, SEQ ID NO:708, and SEQ ID NO:709, respectively, and LC1 comprises a LCDR1, LCDR2, and LCDR3 comprising the amino acid sequences of SEQ ID NO:325, SEQ ID NO:326, and SEQ ID NO:327, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:328, SEQ ID NO:329, and SEQ ID NO:330, respectively, and LC1 comprises a LCDR1, LCDR2, and LCDR3 comprising the amino acid sequences of SEQ ID NO:331, SEQ ID NO:332, and SEQ ID NO:333, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:334, SEQ ID NO:335, and SEQ ID NO:336, respectively, and LC1 comprises a LCDR1, LCDR2, and LCDR3 comprising the amino acid sequences of SEQ ID NO:337, SEQ ID NO:338, and SEQ ID NO:339, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:340, SEQ ID NO:341, and SEQ ID NO:342, respectively, and LC1 comprises a LCDR1, LCDR2, and LCDR3 comprising the amino acid sequences of SEQ ID NO:343, SEQ ID NO:344, and SEQ ID NO:345, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:346, SEQ ID NO:347, and SEQ ID NO:348, respectively, and LC1 comprises a LCDR1, LCDR2, and LCDR3 comprising the amino acid sequences of SEQ ID NO:349, SEQ ID NO:350, and SEQ ID NO:351, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:352, SEQ ID NO:353, and SEQ ID NO:354, respectively, and LC1 comprises a LCDR1, LCDR2, and LCDR3 comprising the amino acid sequences of SEQ ID NO:355, SEQ ID NO:356, and SEQ ID NO:357, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:358, SEQ ID NO:359, and SEQ ID NO:360, respectively, and LC1 comprises a LCDR1, LCDR2, and LCDR3 comprising the amino acid sequences of SEQ ID NO:361, SEQ ID NO:362, and SEQ ID NO:363, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:358, SEQ ID NO:710, and SEQ ID NO:711, respectively, and LC1 comprises a LCDR1, LCDR2, and LCDR3 comprising the amino acid sequences of SEQ ID NO:361, SEQ ID NO:362, and SEQ ID NO:363, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:364, SEQ ID NO:365, and SEQ ID NO:366, respectively, and LC1 comprises a LCDR1, LCDR2, and LCDR3 comprising the amino acid sequences of SEQ ID NO:367, SEQ ID NO:368, and SEQ ID NO:369, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:370, SEQ ID NO:371, and SEQ ID NO:372, respectively, and LC1 comprises a LCDR1, LCDR2, and LCDR3 comprising the amino acid sequences of SEQ ID NO:373, SEQ ID NO:374, and SEQ ID NO:375, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:376, SEQ ID NO:377, and SEQ ID NO:378, respectively, and LC1 comprises a LCDR1, LCDR2, and LCDR3 comprising the amino acid sequences of SEQ ID NO:379, SEQ ID NO:380, and SEQ ID NO:381, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:382, SEQ ID NO:383, and SEQ ID NO:384, respectively, and LC1 comprises a LCDR1, LCDR2, and LCDR3 comprising the amino acid sequences of SEQ ID NO:385, SEQ ID NO:386, and SEQ ID NO:387, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:388, SEQ ID NO:389, and SEQ ID NO:390, respectively, and LC1 comprises a LCDR1, LCDR2, and LCDR3 comprising the amino acid sequences of SEQ ID NO:391, SEQ ID NO:392, and SEQ ID NO:393, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:394, SEQ ID NO:395, and SEQ ID NO:396, respectively, and LC1 comprises a LCDR1, LCDR2, and LCDR3 comprising the amino acid sequences of SEQ ID NO:397, SEQ ID NO:398, and SEQ ID NO:399, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:394, SEQ ID NO:712, and SEQ ID NO:713, respectively, and LC1 comprises a LCDR1, LCDR2, and LCDR3 comprising the amino acid sequences of SEQ ID NO:397, SEQ ID NO:398, and SEQ ID NO:399, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:400, SEQ ID NO:401, and SEQ ID NO:402, respectively, and LC1 comprises a LCDR1, LCDR2, and LCDR3 comprising the amino acid sequences of SEQ ID NO:403, SEQ ID NO:404, and SEQ ID NO:405, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:406, SEQ ID NO:407, and SEQ ID NO:408, respectively, and LC1 comprises a LCDR1, LCDR2, and LCDR3 comprising the amino acid sequences of SEQ ID NO:409, SEQ ID NO:410, and SEQ ID NO:411, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:412, SEQ ID NO:413, and SEQ ID NO:414, respectively, and LC1 comprises a LCDR1, LCDR2, and LCDR3 comprising the amino acid sequences of SEQ ID NO:415, SEQ ID NO:416, and SEQ ID NO:417, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2;

(c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:418, SEQ ID NO:419, and SEQ ID NO:420, respectively, and LC1 comprises a LCDR1, LCDR2, and LCDR3 comprising the amino acid sequences of SEQ ID NO:421, SEQ ID NO:422, and SEQ ID NO:423, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:424, SEQ ID NO:425, and SEQ ID NO:426, respectively, and LC1 comprises a LCDR1, LCDR2, and LCDR3 comprising the amino acid sequences of SEQ ID NO:427, SEQ ID NO:428, and SEQ ID NO:429, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:430, SEQ ID NO:431, and SEQ ID NO:432, respectively, and LC1 comprises a LCDR1, LCDR2, and LCDR3 comprising the amino acid sequences of SEQ ID NO:433, SEQ ID NO:434, and SEQ ID NO:435, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:430, SEQ ID NO:714, and SEQ ID NO:715, respectively, and LC1 comprises a LCDR1, LCDR2, and LCDR3 comprising the amino acid sequences of SEQ ID NO:433, SEQ ID NO:434, and SEQ ID NO:435, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:436, SEQ ID NO:437, and SEQ ID NO:438, respectively, and LC1 comprises a LCDR1, LCDR2, and LCDR3 comprising the amino acid sequences of SEQ ID NO:439, SEQ ID NO:440, and SEQ ID NO:441, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:442, SEQ ID NO:443, and SEQ ID NO:444, respectively, and LC1 comprises a LCDR1, LCDR2, and LCDR3 comprising the amino acid sequences of SEQ ID NO:445, SEQ ID NO:446, and SEQ ID NO:447, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:448, SEQ ID NO:449, and SEQ ID NO:450, respectively, and LC1 comprises a LCDR1, LCDR2, and LCDR3 comprising the amino acid sequences of SEQ ID NO:451, SEQ ID NO:452, and SEQ ID NO:453, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:454, SEQ ID NO:455, and SEQ ID NO:456, respectively, and LC1 comprises a LCDR1, LCDR2, and LCDR3 comprising the amino acid sequences of SEQ ID NO:457, SEQ ID NO:458, and SEQ ID NO:459, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:460, SEQ ID NO:461, and SEQ ID NO:462, respectively, and LC1 comprises a LCDR1, LCDR2, and LCDR3 comprising the amino acid sequences of SEQ ID NO:463, SEQ ID NO:464, and SEQ ID NO:465, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:466, SEQ ID NO:467, and SEQ ID NO:468, respectively, and LC1 comprises a LCDR1, LCDR2, and LCDR3 comprising the amino acid sequences of SEQ ID NO:469, SEQ ID NO:470, and SEQ ID NO:471, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:466, SEQ ID NO:716, and SEQ ID NO:717, respectively, and LC1 comprises a LCDR1, LCDR2, and LCDR3 comprising the amino acid sequences of SEQ ID NO:469, SEQ ID NO:470, and SEQ ID NO:471, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:472, SEQ ID NO:473, and SEQ ID NO:474, respectively, and LC1 comprises a LCDR1, LCDR2, and LCDR3 comprising the amino acid sequences of SEQ ID NO:475, SEQ ID NO:476, and SEQ ID NO:477, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:478, SEQ ID NO:479, and SEQ ID NO:480, respectively, and LC1 comprises a LCDR1, LCDR2, and LCDR3 comprising the amino acid sequences of SEQ ID NO:481, SEQ ID NO:482, and SEQ ID NO:483, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:484, SEQ ID NO:485, and SEQ ID NO:486, respectively, and LC1 comprises a LCDR1, LCDR2, and LCDR3 comprising the amino acid sequences of SEQ ID NO:487, SEQ ID NO:488, and SEQ ID NO:489, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:490, SEQ ID NO:491, and SEQ ID NO:492, respectively, and LC1 comprises a LCDR1, LCDR2, and LCDR3 comprising the amino acid sequences of SEQ ID NO:493, SEQ ID NO:494, and SEQ ID NO:495, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:496, SEQ ID NO:497, and SEQ ID NO:498, respectively, and LC1 comprises a LCDR1, LCDR2, and LCDR3 comprising the amino acid sequences of SEQ ID NO:499, SEQ ID NO:500, and SEQ ID NO:501, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:502, SEQ ID NO:503, and SEQ ID NO:504, respectively, and LC1 comprises a LCDR1, LCDR2, and LCDR3 comprising the amino acid sequences of SEQ ID NO:505, SEQ ID NO:506, and SEQ ID NO:507, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:502, SEQ ID NO:503, and SEQ ID NO:719, respectively, and LC1 comprises a LCDR1, LCDR2, and LCDR3 comprising the amino acid sequences of SEQ ID NO:505, SEQ ID NO:506, and SEQ ID NO:507, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:508, SEQ ID NO:509, and SEQ ID NO:510, respectively, and LC1 comprises a LCDR1, LCDR2, and LCDR3 comprising the amino acid sequences of SEQ ID NO:511, SEQ ID NO:512, and SEQ ID NO:513, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:514, SEQ ID NO:515, and SEQ ID NO:516, respectively, and LC1 comprises a LCDR1, LCDR2, and LCDR3 comprising the amino acid sequences of SEQ ID NO:517, SEQ ID NO:518, and SEQ ID NO:519, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:520, SEQ ID NO:521, and SEQ ID NO:522, respectively, and LC1 comprises a LCDR1, LCDR2, and LCDR3 comprising the amino acid sequences of SEQ ID NO:523, SEQ ID NO:524, and SEQ ID NO:525, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:526, SEQ ID NO:527, and SEQ ID NO:528, respectively, and LC1 comprises a LCDR1, LCDR2, and LCDR3 comprising the amino acid sequences of SEQ ID NO:529, SEQ ID NO:530, and SEQ ID NO:531, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:532, SEQ ID NO:533, and SEQ ID NO:534, respectively, and LC1 comprises a LCDR1, LCDR2, and LCDR3 comprising the amino acid sequences of SEQ ID NO:535, SEQ ID NO:536, and SEQ ID NO:537, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:538, SEQ ID NO:539, and SEQ ID NO:540, respectively, and LC1 comprises a LCDR1, LCDR2, and LCDR3 comprising the amino acid sequences of SEQ ID NO:541, SEQ ID NO:542, and SEQ ID NO:543, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:538, SEQ ID NO:720, and SEQ ID NO:721, respectively, and LC1 comprises a LCDR1, LCDR2, and LCDR3 comprising the amino acid sequences of SEQ ID NO:541, SEQ ID NO:542, and SEQ ID NO:543, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:544, SEQ ID NO:545, and SEQ ID NO:546, respectively, and LC1 comprises a LCDR1, LCDR2, and LCDR3 comprising the amino acid sequences of SEQ ID NO:547, SEQ ID NO:548, and SEQ ID NO:549, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:550, SEQ ID NO:551, and SEQ ID NO:552, respectively, and LC1 comprises a LCDR1, LCDR2, and LCDR3 comprising the amino acid sequences of SEQ ID NO:553, SEQ ID NO:554, and SEQ ID NO:555, respectively, to form a first antigen-binding site that specifically binds TRGV9. In some embodiments, HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14 respectively, to form a second antigen-binding site that specifically binds CD123, wherein the anti-TRGV9/anti-CD123 bispecific antibody or antigen-binding fragment thereof exhibits an EC$_{50}$ of less than about 160 pM, when assessed in vitro with a mixture of γδ T effector cells and Kasumi3 AML target cells, where such cells are present in an effector to target cell ratio of about 1:1 and the bispecific antibody or antigen-binding fragment thereof is present at a concentration of about 30 ng/mL. In some embodiments, HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14 respectively, to form a second antigen-binding site that specifically binds CD123. In some embodiments, the HC2 comprises a HCDR1, HCDR2, and HCDR3 comprising the amino acid sequence of SEQ ID NO:556, SEQ ID NO:557, and SEQ ID NO:558, respectively, and a LCDR1, LCDR2, and LCDR3 comprising the amino acid sequence of SEQ ID NO:559, SEQ ID NO:560, and SEQ ID NO:561, respectively, to form a second antigen-binding site that specifically binds CD123. In some embodiments, the HC2 comprises a HCDR1, HCDR2, and HCDR3 comprising the amino acid sequence of SEQ ID NO:562, SEQ ID NO:563, and SEQ ID NO:564, respectively, and a LCDR1, LCDR2, and LCDR3 comprising the amino acid sequence of SEQ ID NO:565, SEQ ID NO:566, and SEQ ID NO:567, respectively, to form a second antigen-binding site that specifically binds CD123. In some embodiments, the HC2 comprises a HCDR1, HCDR2, and HCDR3 comprising the amino acid sequence of SEQ ID NO:568, SEQ ID NO:569, and SEQ ID NO:570, respectively, and a LCDR1, LCDR2, and LCDR3 comprising the amino acid sequence of SEQ ID NO:571, SEQ ID NO:572, and SEQ ID NO:573, respectively, to form a second antigen-binding site that specifically binds CD123. In some embodiments, the HC2 comprises a HCDR1, HCDR2, and HCDR3 comprising the amino acid sequence of SEQ ID NO:574, SEQ ID NO:575, and SEQ ID NO:576, respectively, and a LCDR1, LCDR2, and LCDR3 comprising the amino acid sequence of SEQ ID NO:577, SEQ ID NO:578, and SEQ ID NO:579, respectively, to form a second antigen-binding site that specifically binds CD123. In some embodiments, the HC2 comprises a HCDR1, HCDR2, and HCDR3 comprising the amino acid sequence of SEQ ID NO:574, SEQ ID NO:722, and SEQ ID NO:723, respectively, and a LCDR1, LCDR2, and LCDR3 comprising the amino acid sequence of SEQ ID NO:577, SEQ ID NO:578, and SEQ ID NO:579, respectively, to form a second antigen-binding site that specifically binds CD123. In some embodiments, the HC2 comprises a HCDR1, HCDR2, and HCDR3 comprising the amino acid sequence of SEQ ID NO:580, SEQ ID NO:581, and SEQ ID NO:582, respectively, and a LCDR1, LCDR2, and LCDR3 comprising the amino acid sequence of SEQ ID NO:583, SEQ ID NO:584, and SEQ ID NO:585, respectively, to form a second antigen-binding site that specifically binds CD123. In some embodiments, the HC2 comprises a HCDR1, HCDR2, and HCDR3 comprising the amino acid sequence of SEQ ID NO:586, SEQ ID NO:587, and SEQ ID NO:588; and (ii) a VL comprising a VL CDR1 having an amino acid sequence of SEQ ID NO:589, SEQ ID NO:590, and SEQ ID NO:591, respectively, to form a second antigen-binding site that specifically binds CD123. In certain embodiments, the anti-TRGV9/anti-CD123 bispecific antibody or antigen-binding fragment thereof exhibits an EC$_{50}$ of less than about 160 pM, when assessed in vitro with a mixture of γδ T effector cells and Kasumi3 AML target cells, where such cells are present in an effector to target cell ratio of about 1:1 and the bispecific antibody or antigen-binding fragment thereof is present at a concentration of about 30 ng/mL.

In certain embodiments, the EC$_{50}$ is less than about 1000 pM, less than about 900 pM, less than about 800 pM, less than about 700 pM, less than about 600 pM, less than about 500 pM, less than about 400 pM, less than about 300 pM, less than about 200 pM, less than about 190 pM, less than about 180 pM, less than about 170 pM, less than about 160 pM, less than about 150 pM, less than about 140 pM, less than about 130 pM, less than about 120 pM, less than about 110 pM, less than about 100 pM, less than about 90 pM, less than about 80 pM, less than about 70 pM, less than about 60 pM, less than about 50 pM, less than about 40 pM, less than about 30 pM, less than about 20 pM, or less than about 10 pM.

In certain embodiments, the effector to target cell ratio can, for example, be 0.01:1, 0.02:1, 0.03:1, 0.04:1, 0.05:1, 0.06:1, 0.07:1, 0.08:1, 0.09:1, 1:1, 2:1, 3:1, 4:1, 5:1, 6:1, 7:1, 8:1, 9:1, or 10:1.

In certain embodiments, the concentration of the bispecific antibody or antigen-binding fragment thereof is about 0.000005 ng/mL, about 0.00005 ng/mL, about 0.0005, about 0.005 ng/mL, about 0.01 ng/mL, about 0.02 ng/mL, about 0.03 ng/mL, about 0.04 ng/mL, about 0.05 ng/mL, about 0.06 ng/mL, about 0.07 ng/mL, about 0.08 ng/mL, about 0.09 ng/mL, about 0.1 ng/mL, about 0.5 ng/mL, about 1.0 ng/mL, about 10 ng/mL, about 20 ng/mL about, about 30 ng/mL about 40 ng/mL, about 50 ng/mL, about 60 ng/mL, about 70 ng/mL, about 80 ng/mL, about 90 ng/mL, about 100 ng/mL, or about 1000 ng/mL.

In some embodiments described herein, immune effector properties of the anti-TRGV9/anti-CD123 bispecific antibodies can be enhanced or silenced through Fc modifications by techniques known to those skilled in the art. For example, Fc effector functions such as Clq binding, complement dependent cytotoxicity (CDC), antibody-dependent cell-mediated cytotoxicity (ADCC), antibody-dependent cell-mediated phagocytosis (ADCP), down regulation of cell surface receptors (e.g., B cell receptor; BCR), etc. can be provided and/or controlled by modifying residues in the Fc responsible for these activities.

"Antibody-dependent cell-mediated cytotoxicity" or "ADCC" refers to a cell-mediated reaction in which non-specific cytotoxic cells that express Fc receptors (FcRs) (e.g. Natural Killer (NK) cells, neutrophils, and macrophages) recognize bound antibody on a target cell and subsequently cause lysis of the target cell.

The ability of antibodies to induce ADCC can be enhanced by engineering their oligosaccharide component. Human IgG1 or IgG3 are N-glycosylated at Asn297 with the majority of the glycans in the well-known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved FcγRIIIa binding without altering antigen binding or CDC activity. Such Abs can be achieved using different methods reported to lead to the successful expression of relatively high defucosylated antibodies bearing the biantennary complex-type of Fc oligosaccharides such as control of culture osmolality (Konno et al., Cytotechnology 64:249-65, 2012), application of a variant CHO line Lec13 as the host cell line (Shields et al., J Biol Chem 277:26733-26740, 2002), application of a variant CHO line EB66 as the host cell line (Olivier et al., MAbs; 2(4), 2010; Epub ahead of print; PMID:20562582), application of a rat hybridoma cell line YB2/0 as the host cell line (Shinkawa et al., J Biol Chem 278:3466-3473, 2003), introduction of small interfering RNA specifically against the α-1,6-fucosyltrasferase (FUT8) gene (Mori et al., Biotechnol Bioeng 88:901-908, 2004), or coexpression of 0-1,4-N-acetylglucosaminyltransferase III and golgi α-mannosidase II or a potent alpha-mannosidase I inhibitor, kifunensine (Ferrara et al., J Biol Chem 281:5032-5036, 2006, Ferrara et al., Biotechnol Bioeng 93:851-861, 2006; Xhou et al., Biotechnol Bioeng 99:652-65, 2008).

In some embodiments described herein, ADCC elicited by the anti-TRGV9/anti-CD123 bispecific antibodies can also be enhanced by certain substitutions in the antibody Fc. Exemplary substitutions are for example substitutions at amino acid positions 256, 290, 298, 312, 356, 330, 333, 334, 360, 378 or 430 (residue numbering according to the EU index) as described in U.S. Pat. No. 6,737,056.

According to another particular aspect, provided herein is an isolated anti-TRGV9/anti-CD123 bispecific antibody or antigen-binding fragment thereof. In some embodiments, the anti-TRGV9/anti-CD123 bispecific antibody or antigen-binding fragment thereof is chimeric.

According to another particular aspect, provided herein is an isolated anti-TRGV9/anti-CD123 bispecific antibody or antigen-binding fragment thereof. In some embodiments, the anti-TRGV9/anti-CD123 bispecific antibody or antigen-binding fragment thereof is human or humanized.

Also provided is a nucleic acid encoding an antibody that binds to a TRGV9 provided herein. Also provided is a vector comprising a nucleic acid encoding an antibody that binds to a TRGV9 provided herein. Also provided is a host cell comprising a vector comprising a nucleic acid encoding an antibody that binds to a TRGV9 provided herein. Also provided is a kit comprising the vector comprising a nucleic acid encoding an antibody that binds to a TRGV9 provided herein, and packaging for the same.

Also provided is a nucleic acid encoding a bispecific antibody comprising: (a) a first binding domain that binds to TRGV9, and (b) a second binding domain that binds to a second target that is not TRGV9, as provided herein. Also provided is a vector comprising a nucleic acid encoding a bispecific antibody that binds to a TRGV9 provided herein. Also provided is a host cell comprising a vector comprising a nucleic acid encoding a bispecific antibody that binds to a TRGV9 provided herein. Also provided is a kit comprising the vector comprising a nucleic acid encoding a bispecific antibody that binds to a TRGV9 provided herein, and packaging for the same.

In another general aspect, provided is an isolated nucleic acid encoding an antibody or antigen-binding fragment thereof provided herein. In some embodiments, the antibody is a TRGV9 antibody provided herein. In certain embodiments, the antibody is a monoclonal antibody. In another general aspect, provided is an isolated nucleic acid encoding a bispecific antibody or antigen-binding fragment thereof provided herein. In some embodiments, the antibody is a TRGV bispecific antibody provided herein. It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding monoclonal antibodies and/or bispecific antibodies provided herein can be altered without changing the amino acid sequences of the proteins.

In another general aspect, provided is a vector comprising an isolated nucleic acid encoding an antibody or antigen-binding fragment thereof provided herein. In some embodiments, the antibody is a TRGV antibody provided herein. In certain embodiments, the antibody is a monoclonal antibody. In some embodiments, the antibody is a TRGV bispecific antibody provided herein. In another general aspect, provided is a vector comprising an isolated nucleic acid encoding a bispecific antibody or antigen-binding fragment thereof provided herein. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible or repressible promoter. A number of expression vectors capable of delivering nucleic acids to a cell are known in the art and can be used herein for production of an antibody or antigen-binding fragment thereof in the cell. Conventional cloning techniques or artificial gene synthesis can be used to generate a recombinant expression vector according to certain embodiments. Such techniques are well known to those skilled in the art in view of the present disclosure.

In another general aspect, provided is a host cell comprising an isolated nucleic acid encoding an antibody or antigen-binding fragment thereof provided herein. In some embodiments, the antibody is a TRGV antibody provided herein. In certain embodiments, the antibody is a monoclonal antibody. In some embodiments, the antibody is a TRGV bispecific antibody provided herein. Any host cell known to those skilled in the art in view of the present disclosure can be used for recombinant expression of antibodies or antigen-binding fragments thereof provided herein. In some embodiments, the host cells are *E. coli* TG1 or BL21 cells (for expression of, e.g., an scFv or Fab antibody), CHO-DG44 or CHO-K1 cells or HEK293 cells (for expression of, e.g., a full-length IgG antibody). According to particular embodiments, the recombinant expression vector is transformed into host cells by conventional methods such as chemical transfection, heat shock, or electroporation, where it is stably integrated into the host cell genome such that the recombinant nucleic acid is effectively expressed.

In another general aspect, provided is a method of producing an antibody or antigen-binding fragment thereof disclosed herein. The methods comprise culturing a cell comprising a nucleic acid encoding the antibody or antigen-binding fragment thereof under conditions to produce an antibody or antigen-binding fragment thereof disclosed herein and recovering the antibody or antigen-binding fragment thereof from the cell or cell culture (e.g., from the supernatant). Expressed antibodies or antigen-binding fragments thereof can be harvested from the cells and purified according to conventional techniques known in the art and as described herein.

In another general aspect, provided is a method of producing a bispecific antibody or antigen-binding fragment thereof disclosed herein. The methods comprise culturing a cell comprising a nucleic acid encoding the bispecific antibody or antigen-binding fragment thereof under conditions to produce a bispecific antibody or antigen-binding fragment thereof disclosed herein and recovering the antibody or antigen-binding fragment thereof from the cell or cell culture (e.g., from the supernatant). Expressed antibodies or antigen-binding fragments thereof can be harvested from the cells and purified according to conventional techniques known in the art and as described herein.

Pharmaceutical Compositions

In another general aspect, provided is a pharmaceutical composition comprising an isolated bispecific antibody or antigen-binding fragment thereof provided herein and a pharmaceutically acceptable carrier. Also provided is a pharmaceutical composition comprising an antibody that binds to a TRGV9 provided herein, and a pharmaceutically acceptable carrier. Also provided is a method of producing the pharmaceutical composition, comprising combining the antibody with a pharmaceutically acceptable carrier to obtain the pharmaceutical composition. In another aspect, provided herein is a pharmaceutical composition comprising a comprising: (a) a first binding domain that binds to TRGV9, and (b) a second binding domain that binds to a second target that is not TRGV9, and a pharmaceutically acceptable carrier. Any of the bispecific antibodies provided herein are contemplated in the pharmaceutical compositions. In certain embodiments, the second binding domain binds to CD123. The term "pharmaceutical composition" as used herein means a product comprising an antibody provided herein together with a pharmaceutically acceptable carrier. Antibodies provided herein and compositions comprising them are also useful in the manufacture of a medicament for therapeutic applications mentioned herein.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness or biological activity of a composition provided herein. According to particular embodiments, in view of the present disclosure, any pharmaceutically acceptable carrier suitable for use in an antibody pharmaceutical composition can be used herein.

The formulation of pharmaceutically active ingredients with pharmaceutically acceptable carriers is known in the art, e.g., *Remington: The Science and Practice of Pharmacy* (e.g. 21st edition (2005), and any later editions). Non-limiting examples of additional ingredients include: buffers, diluents, solvents, tonicity regulating agents, preservatives, stabilizers, and chelating agents. One or more pharmaceutically acceptable carriers can be used in formulating the pharmaceutical compositions provided herein.

In one embodiment, the pharmaceutical composition is a liquid formulation. One example of a liquid formulation is an aqueous formulation, i.e., a formulation comprising water. The liquid formulation can comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In one embodiment, the pharmaceutical composition can be formulated as an injectable which can be injected, for example, via an injection device (e.g., a syringe or an infusion pump). The injection can be delivered subcutaneously, intramuscularly, intraperitoneally, intravitreally, or intravenously, for example.

In another embodiment, the pharmaceutical composition is a solid formulation, e.g., a freeze-dried or spray-dried composition, which can be used as is, or whereto the physician or the patient adds solvents, and/or diluents prior to use. Solid dosage forms can include tablets, such as compressed tablets, and/or coated tablets, and capsules (e.g., hard or soft gelatin capsules). The pharmaceutical composition can also be in the form of sachets, dragees, powders, granules, lozenges, or powders for reconstitution, for example.

The dosage forms can be immediate release, in which case they can comprise a water-soluble or dispersible carrier, or they can be delayed release, sustained release, or modified release, in which case they can comprise water-insoluble polymers that regulate the rate of dissolution of the dosage form in the gastrointestinal tract or under the skin.

In other embodiments, the pharmaceutical composition can be delivered intranasally, intrabuccally, or sublingually.

The pH in an aqueous formulation can be between pH 3 and pH 10. In one embodiment, the pH of the formulation is from about 7.0 to about 9.5. In another embodiment, the pH of the formulation is from about 3.0 to about 7.0.

In another embodiment, the pharmaceutical composition comprises a buffer. Non-limiting examples of buffers include: arginine, aspartic acid, bicine, citrate, disodium hydrogen phosphate, fumaric acid, glycine, glycylglycine, histidine, lysine, maleic acid, malic acid, sodium acetate, sodium carbonate, sodium dihydrogen phosphate, sodium phosphate, succinate, tartaric acid, tricine, and tris(hydroxymethyl)-aminomethane, and mixtures thereof. The buffer can be present individually or in the aggregate, in a concentration from about 0.01 mg/ml to about 50 mg/ml, for example from about 0.1 mg/ml to about 20 mg/ml. Pharmaceutical compositions comprising each one of these specific buffers constitute alternative embodiments.

In another embodiment, the pharmaceutical composition comprises a preservative. Non-limiting examples of preservatives include: benzethonium chloride, benzoic acid, benzyl alcohol, bronopol, butyl 4-hydroxybenzoate, chlorobutanol, chlorocresol, chlorohexidine, chlorphenesin, o-cresol, m-cresol, p-cresol, ethyl 4-hydroxybenzoate, imidurea, methyl 4-hydroxybenzoate, phenol, 2-phenoxyethanol, 2-phenylethanol, propyl 4-hydroxybenzoate, sodium dehydroacetate, thiomerosal, and mixtures thereof. The preservative can be present individually or in the aggregate, in a concentration from about 0.01 mg/ml to about 50 mg/ml, for example from about 0.1 mg/ml to about 20 mg/ml. Pharmaceutical compositions comprising each one of these specific preservatives constitute alternative embodiments.

In another embodiment, the pharmaceutical composition comprises an isotonic agent. Non-limiting examples of isotonic agents include a salt (such as sodium chloride), an amino acid (such as glycine, histidine, arginine, lysine, isoleucine, aspartic acid, tryptophan, and threonine), an alditol (such as glycerol, 1,2-propanediol propyleneglycol), 1,3-propanediol, and 1,3-butanediol), polyethyleneglycol (e.g. PEG400), and mixtures thereof. Another example of an isotonic agent includes a sugar. Non-limiting examples of sugars can include mono-, di-, or polysaccharides, or watersoluble glucans, including for example fructose, glucose, mannose, sorbose, xylose, maltose, lactose, sucrose, trehalose, dextran, pullulan, dextrin, cyclodextrin, alpha and beta-HPCD, soluble starch, hydroxyethyl starch, and sodium carboxymethyl-cellulose. Another example of an isotonic agent is a sugar alcohol. In some embodiments, the term "sugar alcohol" is defined as a C(4-8) hydrocarbon having at least one —OH group. Non-limiting examples of sugar alcohols include mannitol, sorbitol, inositol, galactitol, dulcitol, xylitol, and arabitol. The isotonic agent can be present individually or in the aggregate, in a concentration from about 0.01 mg/ml to about 50 mg/ml, for example from about 0.1 mg/ml to about 20 mg/ml. Pharmaceutical compositions comprising each one of these specific isotonic agents constitute alternative embodiments.

In another embodiment, the pharmaceutical composition comprises a chelating agent. Non-limiting examples of chelating agents include citric acid, aspartic acid, salts of ethylenediaminetetraacetic acid (EDTA), and mixtures thereof. The chelating agent can be present individually or in the aggregate, in a concentration from about 0.01 mg/ml to about 50 mg/ml, for example from about 0.1 mg/ml to about 20 mg/ml. Pharmaceutical compositions comprising each one of these specific chelating agents constitute alternative embodiments.

In another embodiment, the pharmaceutical composition comprises a stabilizer. Non-limiting examples of stabilizers include one or more aggregation inhibitors, one or more oxidation inhibitors, one or more surfactants, and/or one or more protease inhibitors.

In another embodiment, the pharmaceutical composition comprises a stabilizer. In some embodiments, said stabilizer is carboxy-/hydroxycellulose and derivates thereof (such as HPC, HPC-SL, HPC-L and HPMC), cyclodextrins, 2-methylthioethanol, polyethylene glycol (such as PEG 3350), polyvinyl alcohol (PVA), polyvinyl pyrrolidone, salts (such as sodium chloride), sulphur-containing substances such as monothioglycerol), or thioglycolic acid. The stabilizer can be present individually or in the aggregate, in a concentration from about 0.01 mg/ml to about 50 mg/ml, for example from about 0.1 mg/ml to about 20 mg/ml. Pharmaceutical compositions comprising each one of these specific stabilizers constitute alternative embodiments.

In further embodiments, the pharmaceutical composition comprises one or more surfactants, such as a surfactant, at least one surfactant, or two different surfactants. The term "surfactant" refers to any molecules or ions that are comprised of a water-soluble (hydrophilic) part, and a fat-soluble (lipophilic) part. The surfactant can, for example, be selected from the group consisting of anionic surfactants, cationic surfactants, nonionic surfactants, and/or zwitterionic surfactants. The surfactant can be present individually or in the aggregate, in a concentration from about 0.1 mg/ml to about 20 mg/ml. Pharmaceutical compositions comprising each one of these specific surfactants constitute alternative embodiments.

In a further embodiment, the pharmaceutical composition comprises one or more protease inhibitors, such as, e.g., EDTA, and/or benzamidine hydrochloric acid (HC1). The protease inhibitor can be present individually or in the aggregate, in a concentration from about 0.1 mg/ml to about 20 mg/ml. Pharmaceutical compositions comprising each one of these specific protease inhibitors constitute alternative embodiments.

In another general aspect, provided is a method of producing a pharmaceutical composition comprising a bispecific antibody or antigen-binding fragment thereof provided herein, comprising combining a bispecific antibody or antigen-binding fragment thereof with a pharmaceutically acceptable carrier to obtain the pharmaceutical composition.

Methods of Use

In one general aspect, provided is a method of activating a γδ T cell expressing TRGV9, comprising contacting the γδ T cell with an antibody that binds to a TRGV9 provided herein. In another aspect, provided herein is a method of activating a γδ T cell expressing TRGV9, comprising contacting the γδ T cell with the bispecific antibody, as provided herein. In some embodiments, the contacting results in an increase in CD69, CD25, and/or Granzyme B expression, as compared to a control γδ T cell expressing TRGV9.

In another general aspect, provided is a method of inactivating a γδ T cell expressing TRGV9, comprising contacting the γδ T cell with an antibody that binds to a TRGV9 provided herein. In another aspect, provided herein is a method of inactivating a γδ T cell expressing TRGV9, comprising contacting the γδ T cell with the bispecific antibody, as provided herein.

In another general aspect, provided is a method of blocking activation of a γδ T cell expressing TRGV9, comprising contacting the γδ T cell with an antibody that binds to a TRGV9 provided herein. In another aspect, provided herein is a method of blocking activation of a γδ T cell expressing TRGV9, comprising contacting the γδ T cell with the bispecific antibody, as provided herein.

In another general aspect, provided is a method of modulating the activation of a γδ T cell expressing TRGV9, comprising contacting the γδ T cell with an antibody that binds to a TRGV9 provided herein. In another aspect, provided herein is a method of modulating the activation of a γδ T cell expressing TRGV9, comprising contacting the γδ T cell with the bispecific antibody, as provided herein.

In another aspect, provided herein is a method of directing a γδ T cell expressing TRGV9 to a cancer cell, the method comprising contacting the γδ T cell with a bispecific antibody provided herein. In some embodiments, the contacting directs the γδ T cell to the cancer cell.

In another general aspect, provided is a method of targeting CD123 on the surface of a cancer cell, the method comprising exposing the cancer cell to an anti-TRGV9/anti-CD123 bispecific antibody or antigen binding fragment thereof or a pharmaceutical composition provided herein.

The functional activity of bispecific antibodies and antigen-binding fragments thereof that bind TRGV9 and/or CD123 can be characterized by methods known in the art and as described herein. Methods for characterizing antibodies and antigen-binding fragments thereof that bind TRGV9 and/or CD123 include, but are not limited to, affinity and specificity assays including Biacore, ELISA, and OctetRed analysis; binding assays to detect the binding of antibodies to CD123 on cancer cells by FACS; binding assays to detect the binding of antibodies to TRGV9 on γδ T cells. According to particular embodiments, the methods for characterizing antibodies and antigen-binding fragments thereof that bind TRGV9 and/or CD123 include those described below.

In another general aspect, provided herein is a method of directing Vγ9-expressing γδ T cells to a cancer cell. The methods comprise contacting the Vγ9-expressing γδ T cell with an anti-TRGV9/anti-CD123 bispecific antibody or antigen binding fragment thereof. In some embodiments, the anti-TRGV9/anti-CD123 bispecific antibody or antigen binding fragment thereof directs the Vγ9-expressing γδ T cell to a cancer cell having CD123 on its surface.

In another general aspect, provided herein is a method for inhibiting growth or proliferation of cancer cells. The methods comprise contacting the Vγ9-expressing γδ T cells with an anti-TRGV9/anti-CD123 bispecific antibody or antigen binding fragment thereof. In some embodiments, contacting the cancer cells with the anti-TRGV9/anti-CD123 bispecific antibody or antigen binding fragment thereof composition inhibits the growth or proliferation of the cancer cells.

In another aspect, provided herein is a method of inhibiting growth or proliferation of cancer cells expressing a cancer antigen on the cell surface, the method comprising contacting the cancer cells with a bispecific antibody provided herein. In some embodiments, contacting the cancer cells with the pharmaceutical composition inhibits growth or proliferation of the cancer cells. In some embodiments, the cancer cells are in the presence of a γδ T cell expressing TRGV9 while in contact with the bispecific antibody.

In another aspect, provided herein is a method for eliminating cancer cells in a subject, comprising administering an effective amount of a bispecific antibody, as provided herein, to the subject. In another general aspect, provided is a method of treating a cancer in a subject in need thereof, comprising administering to the subject an isolated bispecific antibody or antigen binding fragment thereof that specifically binds TRGV9 and a tumor-associated antigen presented on the surface of a tumor cell (e.g., CD123) or a pharmaceutical composition disclosed herein. The cancer can, for example, be a CD123-expressing cancer. The cancer can, for example, be a CD123-expressing cancer. The cancer can, for example, be a hematologic cancer. The hematologic cancer can, for example, be a leukemia, a lymphoma, and a myeloma. The leukemia can be an acute myeloid leukemia (AML) or an acute lymphocytic leukemia (ALL). In some embodiments, the subject is a human. In some embodiments, the subject is a subject in need thereof.

According to certain embodiments, the pharmaceutical composition comprises an effective amount of an anti-TRGV9/anti-CD123 bispecific antibody or antigen-binding fragment thereof. As used herein, the term "effective amount" refers to an amount of an active ingredient or component that elicits the desired biological or medicinal response in a subject.

According to particular embodiments, an effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

The effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

According to particular embodiments, the compositions described herein are formulated to be suitable for the intended route of administration to a subject. For example, the compositions described herein can be formulated to be suitable for intravenous, subcutaneous, or intramuscular administration.

As used herein, the terms "treat," "treating," and "treatment" are all intended to refer to an amelioration or reversal of at least one measurable physical parameter related to a cancer, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition, such as a tumor or a cancer. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat,"

"treating," and "treatment" refer to elimination of the disease, disorder, or condition in the subject.

According to particular embodiments, provided are compositions used in the treatment of a cancer. For cancer therapy, the compositions can be used in combination with another treatment including, but not limited to, a chemotherapy, an anti-CD20 mAb, an anti-TIM-3 mAb, an anti-CTLA-4 antibody, an anti-PD-L1 antibody, an anti-PD-1 antibody, a PD-1/PD-L1 therapy, IDO, an anti-OX40 antibody, an anti-GITR antibody, an anti-CD40 antibody, an anti-CD38 antibody, cytokines, oncolytic viruses, TLR agonists, STING agonist, other immuno-oncology drugs, an antiangiogenic agent, a radiation therapy, an antibody-drug conjugate (ADC), a targeted therapy, or other anticancer drugs.

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

Anti-TRGV9 antibodies provided herein may also be used as agents to detect Vγ9-expressing cells. Thus, in another methods, provided is a method of detecting a cell expressing Vγ9, comprising contacting a cell with a TRGV9 antibody provided herein. In certain embodiments, the detecting is by ELISA. In some embodiments, the detecting is by FACS analysis. Also provided are kits comprising a TRGV9 antibody provided herein, and instructions for use.

EMBODIMENTS

This invention provides the following non-limiting embodiments.

In one set of embodiments, provided are:

1. An antibody that binds to T Cell Receptor Gamma Variable 9 (TRGV9).

2. The antibody of embodiment 1, wherein the antibody comprises:
   (i) a VH comprising a VH complementarity determining region (CDR) 1 having an amino acid sequence of SEQ ID NO:1, a VH CDR2 having an amino acid sequence of SEQ ID NO:2, and a VH CDR3 having an amino acid sequence of SEQ ID NO:31; and
   (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6.

3. The antibody of embodiment 2, wherein the antibody comprises a VH having an amino acid sequence of SEQ ID NO:34.

4. The antibody of embodiment 2, wherein the antibody comprises a VL having an amino acid sequence of SEQ ID NO:8.

5. The antibody of embodiment 2, wherein the antibody comprises a VH having an amino acid sequence of SEQ ID NO:34, and a VL having an amino acid sequence of SEQ ID NO:8.

6. The antibody of embodiment 1, wherein the antibody comprises:
   (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:32; and
   (ii) a VL comprising a VL CDR1 having an amino acid sequence of SEQ ID NO:4, a VL CDR2 having an amino acid sequence of SEQ ID NO: 5, and a VL CDR3 having an amino acid sequence of SEQ ID NO:6.

7. The antibody of embodiment 6, wherein the antibody comprises a VH having an amino acid sequence of SEQ ID NO:35.

8. The antibody of embodiment 6, wherein the antibody comprises a VL having an amino acid sequence of SEQ ID NO:8.

9. The antibody of embodiment 6, wherein the antibody comprises a VH having an amino acid sequence of SEQ ID NO:35, and a VL having an amino acid sequence of SEQ ID NO:8.

10. The antibody of embodiment 1, wherein the antibody comprises:
    (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:33; and
    (ii) a VL comprising a VL CDR1 having an amino acid sequence of SEQ ID NO:4, a VL CDR2 having an amino acid sequence of SEQ ID NO: 5, and a VL CDR3 having an amino acid sequence of SEQ ID NO:6.

11. The antibody of embodiment 10, wherein the antibody comprises a VH having an amino acid sequence of SEQ ID NO:36.

12. The antibody of embodiment 10, wherein the antibody comprises a VL having an amino acid sequence of SEQ ID NO:8.

13. The antibody of embodiment 10, wherein the antibody comprises a VH having an amino acid sequence of SEQ ID NO:36, and a VL having an amino acid sequence of SEQ ID NO:8.

14. The antibody of embodiment 1, wherein the antibody comprises:
    (i) a VH comprising a VH CDR1 having an amino acid sequence of SEQ ID NO:1, a VH CDR2 having an amino acid sequence of SEQ ID NO: 76, and a VH CDR3 having an amino acid sequence of SEQ ID NO:3; and
    (ii) a VL comprising a VL CDR1 having an amino acid sequence of SEQ ID NO:77, a VL CDR2 having an amino acid sequence of SEQ ID NO: 5, and a VL CDR3 having an amino acid sequence of SEQ ID NO:6.

15. The antibody of embodiment 1, wherein the antibody comprises:
    (i) a VH comprising a VH CDR1 having an amino acid sequence of SEQ ID NO:60, a VH CDR2 having an amino acid sequence of SEQ ID NO:61, and a VH CDR3 having an amino acid sequence of SEQ ID NO:62; and
    (ii) a VL comprising a VL CDR1 having an amino acid sequence of SEQ ID NO:63, a VL CDR2 having an amino acid sequence of SEQ ID NO:64, and a VL CDR3 having an amino acid sequence of SEQ ID NO:6.

16. The antibody of embodiment 14 or 15, wherein the antibody comprises a VH having an amino acid sequence of SEQ ID NO:65.

17. The antibody of embodiment 14 or 15, wherein the antibody comprises a VL having an amino acid sequence of SEQ ID NO:66.

18. The antibody of embodiment 14 or 15, wherein the antibody comprises a VH having an amino acid sequence of SEQ ID NO:65, and a VL having an amino acid sequence of SEQ ID NO:66.

19. The antibody of embodiment 14 or 15, wherein the antibody comprises a VH having an amino acid sequence of SEQ ID NO:67.

20. The antibody of embodiment 14 or 15, wherein the antibody comprises a VL having an amino acid sequence of SEQ ID NO:68.

21. The antibody of embodiment 14 or 15, wherein the antibody comprises a VH having an amino acid sequence of SEQ ID NO:67, and a VL having an amino acid sequence of SEQ ID NO:68.

22. The antibody of embodiment 1, wherein the antibody comprises:
   (i) a VH comprising a VH CDR1 having an amino acid sequence of SEQ ID NO:98, a VH CDR2 having an amino acid sequence of SEQ ID NO:99, and a VH CDR3 having an amino acid sequence of SEQ ID NO:100; and
   (ii) a VL comprising a VL CDR1 having an amino acid sequence of SEQ ID NO:101, a VL CDR2 having an amino acid sequence of SEQ ID NO: 102, and a VL CDR3 having an amino acid sequence of SEQ ID NO: 103.

23. The antibody of embodiment 22, wherein the antibody comprises a VH having an amino acid sequence of SEQ ID NO:104.

24. The antibody of embodiment 22, wherein the antibody comprises a VL having an amino acid sequence of SEQ ID NO:105.

25. The antibody of embodiment 22, wherein the antibody comprises a VH having an amino acid sequence of SEQ ID NO:104, and a VL having an amino acid sequence of SEQ ID NO:105.

26. The antibody of embodiment 1, wherein the antibody comprises:
   (i) a VH comprising a VH CDR1 having an amino acid sequence of SEQ ID NO:107, a VH CDR2 having an amino acid sequence of SEQ ID NO:108, and a VH CDR3 having an amino acid sequence of SEQ ID NO:109; and
   (ii) a VL comprising a VL CDR1 having an amino acid sequence of SEQ ID NO:110, a VL CDR2 having an amino acid sequence of SEQ ID NO:111, and a VL CDR3 having an amino acid sequence of SEQ ID NO: 112.

27. The antibody of embodiment 26, wherein the antibody comprises a VH having an amino acid sequence of SEQ ID NO:113.

28. The antibody of embodiment 26, wherein the antibody comprises a VL having an amino acid sequence of SEQ ID NO:114.

29. The antibody of embodiment 26, wherein the antibody comprises a VH having an amino acid sequence of SEQ ID NO:113, and a VL having an amino acid sequence of SEQ ID NO:114.

30. The antibody of embodiment 1, wherein the antibody comprises:
   (i) a VH comprising a VH CDR1 having an amino acid sequence of SEQ ID NO:117, a VH CDR2 having an amino acid sequence of SEQ ID NO:118, and a VH CDR3 having an amino acid sequence of SEQ ID NO:119; and
   (ii) a VL comprising a VL CDR1 having an amino acid sequence of SEQ ID NO:120, a VL CDR2 having an amino acid sequence of SEQ ID NO:121, and a VL CDR3 having an amino acid sequence of SEQ ID NO: 122.

31. The antibody of embodiment 30, wherein the antibody comprises a VH having an amino acid sequence of SEQ ID NO:123.

32. The antibody of embodiment 30, wherein the antibody comprises a VL having an amino acid sequence of SEQ ID NO:124.

33. The antibody of embodiment 30, wherein the antibody comprises a VH having an amino acid sequence of SEQ ID NO:123, and a VL having an amino acid sequence of SEQ ID NO:124.

34. The antibody of embodiment 1, wherein the antibody comprises:
   (i) a VH comprising a VH CDR1 having an amino acid sequence of SEQ ID NO:127, a VH CDR2 having an amino acid sequence of SEQ ID NO:128, and a VH CDR3 having an amino acid sequence of SEQ ID NO:129; and
   (ii) a VL comprising a VL CDR1 having an amino acid sequence of SEQ ID NO:130, a VL CDR2 having an amino acid sequence of SEQ ID NO:131, and a VL CDR3 having an amino acid sequence of SEQ ID NO: 132.

35. The antibody of embodiment 34, wherein the antibody comprises a VH having an amino acid sequence of SEQ ID NO:133.

36. The antibody of embodiment 34, wherein the antibody comprises a VL having an amino acid sequence of SEQ ID NO:134.

37. The antibody of embodiment 34, wherein the antibody comprises a VH having an amino acid sequence of SEQ ID NO:133, and a VL having an amino acid sequence of SEQ ID NO:134.

38. The antibody of any one of embodiments 1 to 37, wherein the TRGV9 is present on the surface of a γδ T cell.

39. The antibody of any one of embodiments 1 to 38, wherein the antibody is a humanized antibody.

40. The antibody of any one of embodiments 1 to 39, wherein the antibody is an IgG antibody.

41. The antibody of embodiment 40, wherein the IgG antibody is an IgG1, IgG2, IgG3, or IgG4 antibody.

42. The antibody of any one of embodiments 1 to 41, wherein the antibody is multivalent.

43. The antibody of embodiment 42, wherein the antibody is capable of binding at least three antigens.

44. The antibody of embodiment 42, wherein the antibody is capable of binding at least five antigens.

45. A nucleic acid encoding the antibody of any one of embodiments 1 to 44.

46. A vector comprising the nucleic acid of embodiment 45.

47. A host cell comprising the vector of embodiment 45.

48. A kit comprising the vector of embodiment 45 and packaging for the same.

49. A pharmaceutical composition comprising the antibody of any one of embodiments 1 to 44, and a pharmaceutically acceptable carrier.

50. A method of producing the pharmaceutical composition of embodiment 49, comprising combining the antibody with a pharmaceutically acceptable carrier to obtain the pharmaceutical composition.

51. A method of activating a γδ T cell expressing TRGV9, comprising contacting the γδ T cell with the antibody of any one of embodiments 1 to 44.

52. The method of embodiment 51, wherein the contacting results in an increase in CD69, CD25, and/or Granzyme B expression, as compared to a control γδ T cell expressing TRGV9.

53. A bispecific antibody comprising:
   (a) a first binding domain that binds to TRGV9, and
   (b) a second binding domain that binds to a second target that is not TRGV9.

54. The bispecific antibody of embodiment 53, wherein the first binding domain comprises:
   (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:3; and
   (ii) a VL comprising a VL CDR1 having an amino acid sequence of SEQ ID NO:4, a VL CDR2 having an amino acid sequence of SEQ ID NO: 5, and a VL CDR3 having an amino acid sequence of SEQ ID NO:6.

55. The bispecific antibody of embodiment 54, wherein the first binding domain comprises a VH having an amino acid sequence of SEQ ID NO:7.

56. The bispecific antibody of embodiment 54, wherein the first binding domain comprises a VL having an amino acid sequence of SEQ ID NO:8.

57. The bispecific antibody of embodiment 54, wherein the first binding domain comprises a VH having an amino acid sequence of SEQ ID NO:7, and a VL having an amino acid sequence of SEQ ID NO:8.

58. The bispecific antibody of embodiment 53, wherein the first binding domain comprises:
   (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:31; and
   (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6.

59. The bispecific antibody of embodiment 58, wherein the first binding domain comprises a VH having an amino acid sequence of SEQ ID NO:34.

60. The bispecific antibody of embodiment 58, wherein the first binding domain comprises a VL having an amino acid sequence of SEQ ID NO:8.

61. The bispecific antibody of embodiment 58, wherein the first binding domain comprises a VH having an amino acid sequence of SEQ ID NO:34, and a VL having an amino acid sequence of SEQ ID NO:8.

62. The bispecific antibody of embodiment 53, wherein the first binding domain comprises:
   (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:32; and
   (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6.

63. The bispecific antibody of embodiment 62, wherein the first binding domain comprises a VH having an amino acid sequence of SEQ ID NO:35.

64. The bispecific antibody of embodiment 62, wherein the first binding domain comprises a VL having an amino acid sequence of SEQ ID NO:8.

65. The bispecific antibody of embodiment 62, wherein the first binding domain comprises a VH having an amino acid sequence of SEQ ID NO:35, and a VL having an amino acid sequence of SEQ ID NO:8.

66. The bispecific antibody of embodiment 53, wherein the first binding domain comprises:
   (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:33; and
   (ii) a VL comprising a VL CDR1 having an amino acid sequence of SEQ ID NO:4, a VL CDR2 having an amino acid sequence of SEQ ID NO: 5, and a VL CDR3 having an amino acid sequence of SEQ ID NO:6.

67. The bispecific antibody of embodiment 66, wherein the first binding domain comprises a VH having an amino acid sequence of SEQ ID NO:36.

68. The bispecific antibody of embodiment 66, wherein the first binding domain comprises a VL having an amino acid sequence of SEQ ID NO:8.

69. The bispecific antibody of embodiment 66, wherein the first binding domain comprises a VH having an amino acid sequence of SEQ ID NO:36, and a VL having an amino acid sequence of SEQ ID NO:8.

70. The bispecific antibody of embodiment 53, wherein the first binding domain comprises:
   (i) a VH comprising a VH CDR1 having an amino acid sequence of SEQ ID NO:1, a VH CDR2 having an amino acid sequence of SEQ ID NO: 76, and a VH CDR3 having an amino acid sequence of SEQ ID NO:3; and
   (ii) a VL comprising a VL CDR1 having an amino acid sequence of SEQ ID NO:77, a VL CDR2 having an amino acid sequence of SEQ ID NO: 5, and a VL CDR3 having an amino acid sequence of SEQ ID NO:6.

71. The bispecific antibody of embodiment 53, wherein the first binding domain comprises:
   (i) a VH comprising a VH CDR1 having an amino acid sequence of SEQ ID NO:60, a VH CDR2 having an amino acid sequence of SEQ ID NO:61, and a VH CDR3 having an amino acid sequence of SEQ ID NO:62; and
   (ii) a VL comprising a VL CDR1 having an amino acid sequence of SEQ ID NO:63, a VL CDR2 having an amino acid sequence of SEQ ID NO:64, and a VL CDR3 having an amino acid sequence of SEQ ID NO:6.

72. The bispecific antibody of embodiment 70 or 71, wherein the first binding domain comprises a VH having an amino acid sequence of SEQ ID NO:65.

73. The bispecific antibody of embodiment 70 or 71, wherein the first binding domain comprises a VL having an amino acid sequence of SEQ ID NO:66.

74. The bispecific antibody of embodiment 70 or 71, wherein the first binding domain comprises a VH having an amino acid sequence of SEQ ID NO:65, and a VL having an amino acid sequence of SEQ ID NO:66.

75. The bispecific antibody of embodiment 70 or 71, wherein the first binding domain comprises a VH having an amino acid sequence of SEQ ID NO:67.

76. The bispecific antibody of embodiment 70 or 71, wherein the first binding domain comprises a VL having an amino acid sequence of SEQ ID NO:68.

77. The bispecific antibody of embodiment 70 or 71, wherein the first binding domain a VH having an amino acid sequence of SEQ ID NO:67, and a VL having an amino acid sequence of SEQ ID NO:68.

78. The bispecific antibody of embodiment 53, wherein the first binding domain comprises:
   (i) a VH comprising a VH CDR1 having an amino acid sequence of SEQ ID NO:89, a VH CDR2 having an amino acid sequence of SEQ ID NO:90, and a VH CDR3 having an amino acid sequence of SEQ ID NO:91; and
   (ii) a VL comprising a VL CDR1 having an amino acid sequence of SEQ ID NO:92, a VL CDR2 having an amino acid sequence of SEQ ID NO:93, and a VL CDR3 having an amino acid sequence of SEQ ID NO:94.

79. The bispecific antibody of embodiment 78, wherein the first binding domain comprises a VH having an amino acid sequence of SEQ ID NO:95.

80. The bispecific antibody of embodiment 78, wherein the first binding domain comprises a VL having an amino acid sequence of SEQ ID NO:96.

81. The bispecific antibody of embodiment 78, wherein the first binding domain comprises a VH having an amino acid sequence of SEQ ID NO:95, and a VL having an amino acid sequence of SEQ ID NO:96.

82. The bispecific antibody of embodiment 53, wherein the first binding domain comprises:
   (i) a VH comprising a VH CDR1 having an amino acid sequence of SEQ ID NO:98, a VH CDR2 having an amino acid sequence of SEQ ID NO:99, and a VH CDR3 having an amino acid sequence of SEQ ID NO:100, and
   (ii) a VL comprising a VL CDR1 having an amino acid sequence of SEQ ID NO:101, a VL CDR2 having an amino acid sequence of SEQ ID NO:102, and a VL CDR3 having an amino acid sequence of SEQ ID NO: 103.

83. The bispecific antibody of embodiment 82, wherein the first binding domain comprises a VH having an amino acid sequence of SEQ ID NO:104.

84. The bispecific antibody of embodiment 82, wherein the first binding domain comprises a VL having an amino acid sequence of SEQ ID NO:105.

85. The bispecific antibody of embodiment 82, wherein the first binding domain comprises a VH having an amino acid sequence of SEQ ID NO:104, and a VL having an amino acid sequence of SEQ ID NO:105.

86. The bispecific antibody of embodiment 53, wherein the first binding domain comprises:
   (i) a VH comprising a VH CDR1 having an amino acid sequence of SEQ ID NO:107, a VH CDR2 having an amino acid sequence of SEQ ID NO:108, and a VH CDR3 having an amino acid sequence of SEQ ID NO:109, and
   (ii) a VL comprising a VL CDR1 having an amino acid sequence of SEQ ID NO:110, a VL CDR2 having an amino acid sequence of SEQ ID NO:111, and a VL CDR3 having an amino acid sequence of SEQ ID NO: 112.

87. The bispecific antibody of embodiment 86, wherein the first binding domain comprises a VH having an amino acid sequence of SEQ ID NO:113.

88. The bispecific antibody of embodiment 86, wherein the first binding domain comprises a VL having an amino acid sequence of SEQ ID NO: 114.

89. The bispecific antibody of embodiment 86, wherein the first binding domain comprises a VH having an amino acid sequence of SEQ ID NO:113, and a VL having an amino acid sequence of SEQ ID NO:114.

90. The bispecific antibody of embodiment 53, wherein the first binding domain comprises:
   (i) a VH comprising a VH CDR1 having an amino acid sequence of SEQ ID NO:117, a VH CDR2 having an amino acid sequence of SEQ ID NO:118, and a VH CDR3 having an amino acid sequence of SEQ ID NO:119, and
   (ii) a VL comprising a VL CDR1 having an amino acid sequence of SEQ ID NO:120, a VL CDR2 having an amino acid sequence of SEQ ID NO:121, and a VL CDR3 having an amino acid sequence of SEQ ID NO: 122.

91. The bispecific antibody of embodiment 90, wherein the first binding domain comprises a VH having an amino acid sequence of SEQ ID NO:123.

92. The bispecific antibody of embodiment 90, wherein the first binding domain comprises a VL having an amino acid sequence of SEQ ID NO:124.

93. The bispecific antibody of embodiment 90, wherein the first binding domain comprises a VH having an amino acid sequence of SEQ ID NO:123, and a VL having an amino acid sequence of SEQ ID NO:124.

94. The bispecific antibody of embodiment 53, wherein the first binding domain comprises:
   (i) a VH comprising a VH CDR1 having an amino acid sequence of SEQ ID NO:127, a VH CDR2 having an amino acid sequence of SEQ ID NO:128, and a VH CDR3 having an amino acid sequence of SEQ ID NO:129, and
   (ii) a VL comprising a VL CDR1 having an amino acid sequence of SEQ ID NO:130, a VL CDR2 having an amino acid sequence of SEQ ID NO:131, and a VL CDR3 having an amino acid sequence of SEQ ID NO: 132.

95. The bispecific antibody of embodiment 94, wherein the first binding domain comprises a VH having an amino acid sequence of SEQ ID NO:133.

96. The bispecific antibody of embodiment 94, wherein the first binding domain comprises a VL having an amino acid sequence of SEQ ID NO:134.

97. The bispecific antibody of embodiment 94, wherein the first binding domain comprises a VH having an amino acid sequence of SEQ ID NO:133, and a VL having an amino acid sequence of SEQ ID NO:134.

98. The bispecific antibody of any one of embodiments 53 to 97, wherein the second target is a cancer antigen present on the surface of a cancer cell.

99. The bispecific antibody of embodiment 98, wherein the antigen on the surface of the cancer cell is a tumor-specific antigen, a tumor associated antigen, or a neoantigen.

100. The bispecific antibody of any one of embodiments 53 to 99, wherein the second target is CD123.

101. The bispecific antibody of embodiment 100, wherein the second binding domain comprises:
   (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO: 14.

102. The bispecific antibody of embodiment 101, wherein the second binding domain comprises a VH having an amino acid sequence of SEQ ID NO:15.

103. The bispecific antibody of embodiment 101, wherein the second binding domain comprises a VL having an amino acid sequence of SEQ ID NO:16.

104. The bispecific antibody of embodiment 101, wherein the second binding domain comprises a VH having an amino acid sequence of SEQ ID NO:15, and a VL having an amino acid sequence of SEQ ID NO:16.

105. The bispecific antibody of any one of embodiments 53 to 104, wherein the TRGV9 is present on the surface of a γδ T cell.

106. The bispecific antibody of any one of embodiments 53 to 104, wherein the TRGV9 is present on the surface of a γδ T cell, and the second target is a cancer antigen expressed on the surface of the cancer cell.

107. The bispecific antibody of embodiment 106, wherein the cancer cell is killed when the bispecific antibody binds to the TRGV9 on the surface of the γδ T cell and the antigen on the surface of the cancer cell.

108. The bispecific antibody of any one of embodiments 53 to 107, wherein the first binding domain is humanized, the second binding domain is humanized, or both the first binding domain and the second binding domain are humanized.

109. The bispecific antibody of any one of embodiments 53 to 108, wherein the bispecific antibody is an IgG antibody.

110. The bispecific antibody of embodiment 109, wherein the IgG antibody is an IgG1, IgG2, IgG3, or IgG4 antibody.

111. A pharmaceutical composition comprising the bispecific antibody of any one of embodiments 53 to 110, and a pharmaceutically acceptable carrier.

112. A method of directing a γδ T cell expressing TRGV9 to a cancer cell, the method comprising contacting the γδ T cell with the bispecific antibody of any one of embodiments 53 to 110, wherein the contacting directs the γδ T cell to the cancer cell.

113. A method of inhibiting growth or proliferation of cancer cells expressing a cancer antigen on the cell surface, the method comprising contacting the cancer cells with the bispecific antibody of any one of embodiments 53 to 110, wherein contacting the cancer cells with the pharmaceutical composition inhibits growth or proliferation of the cancer cells.

114. The method of embodiment 113, wherein the cancer cells are in the presence of a γδ T cell expressing TRGV9 while in contact with the bispecific antibody.

115. A method for eliminating cancer cells in a subject, comprising administering an effective amount of the bispecific antibody of any one of embodiments 53 to 110 to the subject.

116. The method of embodiment 115, wherein the subject is a subject in need thereof.

117. The method of embodiments 115 or 116, wherein the subject is a human.

118. A method of activating a γδ T cell expressing TRGV9, comprising contacting the γδ T cell with the bispecific antibody of any one of embodiments 53 to 110.

In another set of embodiments, provided are:

1. An isolated TRGV9 bispecific antibody or antigen binding fragment thereof, the isolated TRGV9 bispecific antibody or antigen binding fragment thereof comprising:
a. a first heavy chain (HC1);
b. a second heavy chain (HC2);
c. a first light chain (LC1); and
d. a second light chain (LC2),
wherein HC1 is associated with LC1 and HC2 is associated with LC2, and
wherein HC1 comprises a heavy chain complementarity determining region 1 (HCDR1), HCDR2, and HCDR3 comprising the amino acid sequences of:
i. SEQ ID NO:1, SEQ ID NO:2, and SEQ ID NO:3, respectively,
ii. SEQ ID NO:1, SEQ ID NO:2, and SEQ ID NO:31, respectively,
iii. SEQ ID NO:1, SEQ ID NO:2, and SEQ ID NO:32, respectively, or
iv. SEQ ID NO:1, SEQ ID NO:2, and SEQ ID NO:33, respectively,
and LC1 comprises a light chain complementarity determining region 1 (LCDR1), LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen.

2. The isolated TRGV9 bispecific antibody or antigen binding fragment thereof of embodiment 1, wherein HC1 comprises an amino acid sequence having at least 95% identity to an amino acid sequence selected from SEQ ID NO:7, SEQ ID NO:34, SEQ ID NO:35, or SEQ ID NO:36, and LC1 comprises an amino acid sequence having at least 95% identity to the amino acid sequence of SEQ ID NO:8.

3. The isolated TRGV9 bispecific antibody or antigen binding fragment thereof of embodiment 2, wherein HC1 comprises the amino acid sequence selected from SEQ ID NO:7, SEQ ID NO:34, SEQ ID NO:35, or SEQ ID NO:36, and LC1 comprises the amino acid sequence of SEQ ID NO:8.

4. The isolated TRGV9 bispecific antibody or antigen binding fragment thereof any one of embodiments 1 to 3, wherein the binding site for a first antigen binds to TRGV9 on a γδ T cell.

5. The isolated TRGV9 bispecific antibody or antigen binding fragment thereof any one of embodiments 1 to 4, wherein the binding site for a second antigen binds to a cancer antigen present on the surface of a cancer cell.

6. The isolated TRGV9 bispecific antibody or antigen binding fragment of embodiment 5, wherein the binding of the bispecific antibody to TRGV9 present on the surface of the γδ T cell and the binding of the cancer antigen present on the surface of the cancer cell results in the killing of the cancer cell.

7. The isolated TRGV9 bispecific antibody or antigen binding fragment of any one of embodiments 1 to 6, wherein HC1 and LC1 are humanized.

8. The isolated TRGV9 bispecific antibody or antigen binding fragment thereof any one of embodiments 1 to 7, wherein HC2 and LC2 bind to CD123.

9. The isolated TRGV9 bispecific antibody or antigen binding fragment thereof any one of embodiments 1 to 8, wherein the bispecific antibody or antigen binding fragment thereof is an IgG1, an IgG2, an IgG3, or an IgG4 isotype.

10. The isolated TRGV9 bispecific antibody or antigen binding fragment thereof any one of embodiments 1 to 9, wherein the bispecific antibody or antigen binding fragment thereof is an IgG4 isotype.

11. The isolated TRGV9 bispecific antibody or antigen binding fragment thereof any one of embodiments 1 to 10, wherein the bispecific antibody or antigen binding fragment thereof induces γδ T cell dependent cytotoxicity of a cancer cell in vitro with an $EC_{50}$ of less than about 500 pM.

12. The isolated TRGV9 bispecific antibody or antigen binding fragment thereof of embodiment 11, wherein the bispecific antibody or antigen binding fragment thereof induces γδ T cell dependent cytotoxicity of a cancer cell in vitro with an $EC_{50}$ of less than about 300 pM.

13. The isolated TRGV9 bispecific antibody or antigen binding fragment thereof of embodiment 11, wherein the bispecific antibody or antigen binding fragment thereof induces γδ T cell dependent cytotoxicity of a cancer cell in vitro with an $EC_{50}$ of less than about 160 pM.

14. The isolated TRGV9 bispecific antibody or antigen binding fragment thereof any one of embodiments 11 to 13, wherein the $EC_{50}$ is assessed with a mixture of γδ T effector cells and Kasumi3 AML target cells.

15. The isolated TRGV9 bispecific antibody or antigen binding fragment thereof of embodiment 14, wherein the effector cell to target cell ratio is about 0.01 to 1 to about 5 to 1.

16. The isolated TRGV9 bispecific antibody or antigen binding fragment thereof of embodiment 15, wherein the effector cell to target cell ratio is about 0.1 to 1 to about 2 to 1.

17. The isolated TRGV9 bispecific antibody or antigen binding fragment thereof of embodiment 16, wherein the effector cell to target cell ratio is about 1:1.

18. The isolated TRGV9 bispecific antibody or antigen binding fragment thereof any one of embodiments 1 to 17, wherein the bispecific antibody or antigen binding fragment thereof is multivalent.

19. The isolated TRGV9 bispecific antibody or antigen binding fragment thereof of embodiment 18, wherein the bispecific antibody or antigen binding fragment thereof is capable of binding at least three antigens.

20. The isolated TRGV9 bispecific antibody or antigen binding fragment thereof of embodiment 18, wherein the bispecific antibody or antigen binding fragment thereof is capable of binding at least five antigens.

21. An isolated γδ T cell bispecific antibody or antigen binding fragment thereof, the isolated γδ T cell bispecific antibody or antigen binding fragment thereof comprising:
a. a first heavy chain (HC1);
b. a second heavy chain (HC2);
c. a first light chain (LC1); and
d. a second light chain (LC2),
wherein HC1 is associated with LC1 and HC2 is associated with LC2,
wherein HC1 and LC1 form a binding site for a first antigen on a γδ T cell, and
wherein HC2 and LC2 form a binding site for a second antigen.

22. A bispecific antibody comprising: a first means capable of specifically binding a T cell receptor gamma chain; and a second means capable of specifically binding a target molecule that is not a T cell receptor gamma chain.

23. A process for making a molecule capable of specifically binding to more than one target molecule, the molecule comprising: a step for performing a function of obtaining an oligopeptide or polypeptide capable of binding to a T cell receptor gamma chain; a step for performing a function of obtaining an oligopeptide or polypeptide capable of binding to a target; and a step for performing a function of providing a molecule capable of specifically binding to a T cell receptor gamma chain and a target molecule.

24. The process of embodiment 23, wherein the step for performing a function of obtaining an oligopeptide or polypeptide capable of binding to a target is repeated n times and further comprising n steps for performing a function of providing a molecule capable of specifically binding to a T cell receptor gamma chain and n number of target molecules, wherein n is at least 2.

In another set of embodiments, provided are:

1. An isolated anti-TRGV9/anti-CD123 bispecific antibody or antigen binding fragment thereof comprising:
a. a first heavy chain (HC1);
b. a second heavy chain (HC2)
c. a first light chain (LC1); and
d. a second light chain (LC2),
wherein HC1 is associated with LC1 and HC2 is associated with LC2, and
wherein HC1 comprises a heavy chain complementarity determining region 1 (HCDR1), HCDR2, and HCDR3 comprising the amino acid sequences of:
i. SEQ ID NO:1, SEQ ID NO:2, and SEQ ID NO:3, respectively,
ii. SEQ ID NO:1, SEQ ID NO:2, and SEQ ID NO:31, respectively,
iii. SEQ ID NO:1, SEQ ID NO:2, and SEQ ID NO:32, respectively, or
iv. SEQ ID NO:1, SEQ ID NO:2, and SEQ ID NO:33, respectively,
and LC1 comprises a light chain complementarity determining region 1 (LCDR1), LCDR2, and LCDR3 comprising the amino acid sequences of SEQ ID NO:4, SEQ ID NO:5, and SEQ ID NO:6, respectively, to form a binding site for a first antigen that specifically binds Vγ9, and wherein HC2 comprises a heavy chain complementarity determining region 1 (HCDR1), HCDR2, and HCDR3 comprising the amino acid sequences of SEQ ID NO:9, SEQ ID NO:10, and SEQ ID NO:11, respectively, and LC2 comprises a light chain complementarity determining region 1 (LCDR1), LCDR2, and LCDR3 comprising the amino acid sequences of SEQ ID NO: 12, SEQ ID NO:13, and SEQ ID NO:14, respectively, to form a binding site for a second antigen that specifically binds CD123.

2. The isolated anti-TRGV9/anti-CD123 bispecific antibody or antigen binding fragment thereof of embodiment 1, wherein HC1 comprises an amino acid sequence having at least 95% identity to an amino acid sequence selected from SEQ ID NO:7, SEQ ID NO:34, SEQ ID NO:35, or SEQ ID NO:36, and LC1 comprises an amino acid sequence having at least 95% identity to the amino acid sequence of SEQ ID NO:8.

3. The isolated anti-TRGV9/anti-CD123 bispecific antibody or antigen binding fragment thereof of embodiment 2, wherein HC1 comprises the amino acid sequence selected from SEQ ID NO:7, SEQ ID NO:34, SEQ ID NO:35, or SEQ ID NO:36, and LC1 comprises the amino acid sequence of SEQ ID NO:8.

4. The isolated anti-TRGV9/anti-CD123 bispecific antibody or antigen binding fragment thereof any one of embodiments 1 to 3, wherein HC2 comprises an amino acid sequence having at least 95% identity to the amino acid sequence of SEQ ID NO:15 and LC2 comprises an amino acid sequence having at least 95% identity to the amino acid sequence of SEQ ID NO:16.

5. The isolated anti-TRGV9/anti-CD123 bispecific antibody or antigen binding fragment thereof of embodiment 4, wherein HC2 comprises the amino acid sequence of SEQ ID NO:15 and LC2 comprises the amino acid sequence of SEQ ID NO:16.

6. The isolated anti-TRGV9/anti-CD123 bispecific antibody or antigen binding fragment thereof any one of embodiments 1 to 5, wherein the TRGV9 is on the surface of a γδ T cell.

7. The isolated anti-TRGV9/anti-CD123 bispecific antibody or antigen binding fragment thereof any one of embodiments 1 to 6, wherein the CD123 is on the surface of a tumor cell or a CD34+ stem cell.

8. The isolated anti-TRGV9/anti-CD123 bispecific antibody or antigen binding fragment thereof any one of embodiments 1 to 7, wherein the binding of the bispecific antibody to TRGV9 present on the surface of the γδ T cell and the binding of the CD123 on the surface of the cancer cell results in the killing of the cancer cell.

9. The isolated anti-TRGV9/anti-CD123 bispecific antibody or antigen binding fragment thereof any one of embodiments 1 to 8, wherein HC1 and LC1 are humanized.

10. The isolated anti-TRGV9/anti-CD123 bispecific antibody or antigen binding fragment thereof any one of embodiments 1 to 9, wherein HC2 and LC2 are humanized.

11. The isolated anti-TRGV9/anti-CD123 bispecific antibody or antigen binding fragment thereof any one of embodiments 1 to 10, wherein the bispecific antibody or antigen binding fragment thereof is an IgG1, an IgG2, an IgG3, or an IgG4 isotype.

12. The isolated anti-TRGV9/anti-CD123 bispecific antibody or antigen binding fragment thereof any one of embodiments 1 to 11, wherein the bispecific antibody or antigen binding fragment thereof is an IgG4 isotype.

13. The isolated anti-TRGV9/anti-CD123 bispecific antibody or antigen binding fragment thereof any one of embodiments 1 to 12, wherein the bispecific antibody or antigen binding fragment thereof induces γδ T cell dependent cytotoxicity of a cancer cell in vitro with an $EC_{50}$ of less than about 500 pM.

14. The isolated anti-TRGV9/anti-CD123 bispecific antibody or antigen binding fragment thereof of embodiment 13, wherein the bispecific antibody or antigen binding fragment thereof induces γδ T cell dependent cytotoxicity of a cancer cell in vitro with an $EC_{50}$ of less than about 300 pM.

15. The isolated anti-TRGV9/anti-CD123 bispecific antibody or antigen binding fragment thereof of embodiment 13, wherein the bispecific antibody or antigen binding fragment thereof induces γδ T cell dependent cytotoxicity of a cancer cell in vitro with an $EC_{50}$ of less than about 160 pM.

16. The isolated anti-TRGV9/anti-CD123 bispecific antibody or antigen binding fragment thereof any one of embodiments 13 to 15, wherein the $EC_{50}$ is assessed with a mixture of γδ T effector cells and Kasumi3 AML target cells.

17. The isolated anti-TRGV9/anti-CD123 bispecific antibody or antigen binding fragment thereof of embodiment 16, wherein the effector cell to target cell ratio is about 0.01 to 1 to about 5 to 1.

18. The isolated anti-TRGV9/anti-CD123 bispecific antibody or antigen binding fragment thereof of embodiment 17, wherein the effector cell to target cell ratio is about 0.1 to 1 to about 2 to 1.

19. The isolated anti-TRGV9/anti-CD123 bispecific antibody or antigen binding fragment thereof of embodiment 18, wherein the effector cell to target cell ratio is about 1:1.

20. A method of making the isolated anti-TRGV9/anti-CD123 bispecific antibody or antigen binding fragment thereof any one of embodiments 1 to 19, the method comprising culturing a cell comprising a nucleic acid encoding the anti-TRGV9/anti-CD123 bispecific antibody or antigen binding fragment thereof under conditions to produce the bispecific antibody or antigen binding fragment thereof and recovering the bispecific antibody or antigen binding fragment thereof.

In another set of embodiments, provided are:

1. An isolated TRGV9 bispecific antibody or antigen epitope binding fragment thereof, wherein the isolated TRGV9 bispecific antibody or antigen epitope binding fragment thereof comprises a binding site for a first antigen and a binding site for a second antigen, wherein the binding site for the first antigen binds a TRGV9 epitope on a γδ T cell and the binding site for the second antigen binds an epitope of the second antigen on a surface of a target cell, and the binding of the TRGV9 epitope on the γδ T cell and the binding of the second antigen epitope on the target cell results in the killing of the target cell.

2. The isolated TRGV9 bispecific antibody or antigen binding fragment thereof, wherein the isolated TRGV9 bispecific antibody or antigen binding fragment thereof comprises:
   a. a first heavy chain (HC1);
   b. a second heavy chain (HC2);
   c. a first light chain (LC1); and
   d. a second light chain (LC2),
   wherein HC1 is associated with LC1 and HC2 is associated with LC2, and
   wherein HC1 comprises a heavy chain complementarity determining region 1 (HCDR1), HCDR2, and HCDR3 comprising the amino acid sequences of:
   i. SEQ ID NO:1, SEQ ID NO:2, and SEQ ID NO:3, respectively,
   ii. SEQ ID NO:1, SEQ ID NO:2, and SEQ ID NO:31, respectively,
   iii. SEQ ID NO:1, SEQ ID NO:2, and SEQ ID NO:32, respectively, or
   iv. SEQ ID NO:1, SEQ ID NO:2, and SEQ ID NO:33, respectively,
   and LC1 comprises a light chain complementarity determining region 1 (LCDR1), LCDR2, and LCDR2 comprising the amino acid sequences of SEQ ID NO:4, SEQ ID NO:5, and SEQ ID NO:6, respectively, to form the binding site for the first antigen, and wherein HC2 and LC2 form the binding site for the second antigen epitope.

3. The isolated TRGV9 bispecific antibody or antigen binding fragment thereof of embodiment 2, wherein HC1 comprises an amino acid sequence having at least 95% identity to an amino acid sequence selected from SEQ ID NO:7, SEQ ID NO:34, SEQ ID NO:35, or SEQ ID NO:36, and LC1 comprises an amino acid sequence having at least 95% identity to the amino acid sequence of SEQ ID NO:8.

4. The isolated TRGV9 bispecific antibody or antigen binding fragment thereof of embodiment 3, wherein HC1 comprises the amino acid sequence selected from SEQ ID NO:7, SEQ ID NO:34, SEQ ID NO:35, or SEQ ID NO:36, and LC1 comprises the amino acid sequence of SEQ ID NO:8.

5. The isolated TRGV9 bispecific antibody or antigen binding fragment of any one of embodiments 2 to 4, wherein HC1 and LC1 are humanized.

6. The isolated TRGV9 bispecific antibody or antigen binding fragment thereof any one of embodiments 2 to 5, wherein HC2 and LC2 bind to a CD123 epitope.

7. The isolated TRGV9 bispecific antibody or antigen binding fragment thereof of embodiment 6, wherein HC2 comprises an amino acid sequence having at least 95% identity to the amino acid sequence of SEQ ID NO:15 and LC2 comprises an amino acid sequence having at least 95% identity to the amino acid sequence of SEQ ID NO:16.

8. The isolated TRGV9 bispecific antibody or antigen binding fragment thereof of embodiment 7, wherein HC2 comprises the amino acid sequence of SEQ ID NO:15 and LC2 comprises the amino acid sequence of SEQ ID NO:16.

9. The isolated TRGV9 bispecific antibody or antigen binding fragment thereof any one of embodiments 1 to 8, wherein the bispecific antibody or antigen binding fragment thereof is an IgG1, an IgG2, an IgG3, or an IgG4 isotype.

10. The isolated TRGV9 bispecific antibody or antigen binding fragment thereof any one of embodiments 1 to 9, wherein the bispecific antibody or antigen binding fragment thereof is an IgG4 isotype.

11. The isolated TRGV9 bispecific antibody or antigen binding fragment thereof any one of embodiments 1 to 10, wherein the bispecific antibody or antigen binding fragment thereof induces $\gamma\delta$ T cell dependent cytotoxicity of a cancer cell in vitro with an $EC_{50}$ of less than about 500 pM.

12. The isolated TRGV9 bispecific antibody or antigen binding fragment thereof of embodiment 11, wherein the bispecific antibody or antigen binding fragment thereof induces $\gamma\delta$ T cell dependent cytotoxicity of a cancer cell in vitro with an $EC_{50}$ of less than about 300 pM.

13. The isolated TRGV9 bispecific antibody or antigen binding fragment thereof of embodiment 12, wherein the bispecific antibody or antigen binding fragment thereof induces $\gamma\delta$ T cell dependent cytotoxicity of a cancer cell in vitro with an $EC_{50}$ of less than about 160 pM.

14. The isolated TRGV9 bispecific antibody or antigen binding fragment thereof any one of embodiments 11 to 13, wherein the $EC_{50}$ is assessed with a mixture of $\gamma\delta$ T effector cells and Kasumi3 AML target cells.

15. The isolated TRGV9 bispecific antibody or antigen binding fragment thereof of embodiment 14, wherein the effector cell to target cell ratio is about 0.01 to 1 to about 5 to 1.

16. The isolated TRGV9 bispecific antibody or antigen binding fragment thereof of embodiment 15, wherein the effector cell to target cell ratio is about 0.1 to 1 to about 2 to 1.

17. The isolated TRGV9 bispecific antibody or antigen binding fragment thereof of embodiment 16, wherein the effector cell to target cell ratio is about 1:1.

18. An isolated $\gamma\delta$ T cell bispecific antibody or antigen binding fragment thereof, wherein the isolated $\gamma\delta$ T cell bispecific antibody or antigen binding fragment thereof comprises a binding site for a first antigen epitope and a binding site for a second antigen epitope, wherein the binding site for the first antigen epitope binds a first antigen on a $\gamma\delta$ T cell and the binding site for the second antigen epitope binds the second antigen epitope on a surface of a target cell, and the binding of the first antigen epitope on the $\gamma\delta$ T cell and the binding of the second antigen epitope on the target cell results in the killing of the target cell.

In another set of embodiments, provided are:

1. An isolated nucleic acid encoding a TRGV9 bispecific antibody or antigen binding fragment thereof, the isolated TRGV9 bispecific antibody or antigen binding fragment thereof comprising:
   a. a first heavy chain (HC1);
   b. a second heavy chain (HC2);
   c. a first light chain (LC1); and
   d. a second light chain (LC2),
   wherein HC1 is associated with LC1 and HC2 is associated with LC2, and
   wherein HC1 comprises a heavy chain complementarity determining region 1 (HCDR1), HCDR2, and HCDR3 comprising the amino acid sequences of:
   i. SEQ ID NO:1, SEQ ID NO:2, and SEQ ID NO:3, respectively,
   ii. SEQ ID NO:1, SEQ ID NO:2, and SEQ ID NO:31, respectively,
   iii. SEQ ID NO:1, SEQ ID NO:2, and SEQ ID NO:32, respectively, or
   iv. SEQ ID NO:1, SEQ ID NO:2, and SEQ ID NO:33, respectively,
   and LC1 comprises a light chain complementarity determining region 1 (LCDR1), LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen.

2. The isolated nucleic acid of embodiment 1, wherein HC1 comprises an amino acid sequence having at least 95% identity to an amino acid sequence selected from SEQ ID NO:7, SEQ ID NO:34, SEQ ID NO:35, or SEQ ID NO:36, and LC1 comprises an amino acid sequence having at least 95% identity to the amino acid sequence of SEQ ID NO:8.

3. The isolated nucleic acid of embodiment 2, wherein HC1 comprises the amino acid sequence selected from SEQ ID NO:7, SEQ ID NO:34, SEQ ID NO:35, or SEQ ID NO:36, and LC1 comprises the amino acid sequence of SEQ ID NO:8.

4. The isolated nucleic acid of any one of embodiments 1 to 3, wherein the binding site for a first antigen binds to TRGV9 on a $\gamma\delta$ T cell.

5. The isolated nucleic acid of any one of embodiments 1 to 4, wherein the binding site for a second antigen binds to a cancer antigen present on the surface of a cancer cell.

6. The isolated nucleic acid of embodiment 5, wherein the binding of the bispecific antibody to TRGV9 present on the surface of the $\gamma\delta$ T cell and the binding of the cancer antigen present on the surface of the cancer cell results in the killing of the cancer cell.

7. The isolated nucleic acid of any one of embodiments 1 to 6, wherein HC1 and LC1 are humanized.

8. The isolated nucleic acid of any one of embodiments 1 to 7, wherein HC2 and LC2 bind to CD123.

9. The isolated nucleic acid of any one of embodiments 1 to 8, wherein the bispecific antibody or antigen binding fragment thereof is an IgG1, an IgG2, an IgG3, or an IgG4 isotype.

10. The isolated nucleic acid of any one of embodiments 1 to 9, wherein the bispecific antibody or antigen binding fragment thereof is an IgG4 isotype.

11. The isolated nucleic acid of any one of embodiments 1 to 10, wherein the bispecific antibody or antigen binding fragment thereof induces γδ T cell dependent cytotoxicity of a cancer cell in vitro with an $EC_{50}$ of less than about 500 pM.

12. The isolated nucleic acid of embodiment 11, wherein the bispecific antibody or antigen binding fragment thereof induces γδ T cell dependent cytotoxicity of a cancer cell in vitro with an $EC_{50}$ of less than about 300 pM.

13. The isolated nucleic acid of embodiment 11, wherein the bispecific antibody or antigen binding fragment thereof induces γδ T cell dependent cytotoxicity of a cancer cell in vitro with an $EC_{50}$ of less than about 160 pM.

14. The isolated nucleic acid of any one of embodiments 11 to 13, wherein the $EC_{50}$ is assessed with a mixture of γδ T effector cells and Kasumi3 AML target cells.

15. The isolated nucleic acid of embodiment 14, wherein the effector cell to target cell ratio is about 0.01 to 1 to about 5 to 1.

16. The isolated nucleic acid of embodiment 15, wherein the effector cell to target cell ratio is about 0.1 to 1 to about 2 to 1.

17. The isolated nucleic acid of embodiment 16, wherein the effector cell to target cell ratio is about 1:1.

18. The isolated nucleic acid of any one of embodiments 1 to 17, wherein the bispecific antibody or antigen binding fragment thereof is multivalent.

19. The isolated nucleic acid of embodiment 18, wherein the bispecific antibody or antigen binding fragment thereof is capable of binding at least three antigens.

20. The isolated nucleic acid of embodiment 18, wherein the bispecific antibody or antigen binding fragment thereof is capable of binding at least five antigens.

21. A vector comprising the isolated nucleic acid of any one of embodiments 1 to 20.

22. A host cell comprising the vector of embodiment 21.

23. A kit comprising the vector of embodiment 21 and packaging for the same.

In another set of embodiments, provided are:

1. A pharmaceutical composition comprising an isolated TRGV9 bispecific antibody or antigen binding fragment thereof, the isolated TRGV9 bispecific antibody or antigen binding fragment thereof comprising:
a. a first heavy chain (HC1);
b. a second heavy chain (HC2);
c. a first light chain (LC1); and
d. a second light chain (LC2),
wherein HC1 is associated with LC1 and HC2 is associated with LC2, and
wherein HC1 comprises a heavy chain complementarity determining region 1 (HCDR1), HCDR2, and HCDR3 comprising the amino acid sequences of:
i. SEQ ID NO:1, SEQ ID NO:2, and SEQ ID NO:3, respectively,
ii. SEQ ID NO:1, SEQ ID NO:2, and SEQ ID NO:31, respectively,
iii. SEQ ID NO:1, SEQ ID NO:2, and SEQ ID NO:32, respectively, or
iv. SEQ ID NO:1, SEQ ID NO:2, and SEQ ID NO:33, respectively,
and LC1 comprises a light chain complementarity determining region 1 (LCDR1), LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen,
and a pharmaceutically acceptable carrier.

2. The pharmaceutical composition of embodiment 1, wherein HC1 comprises an amino acid sequence having at least 95% identity to an amino acid sequence selected from SEQ ID NO:7, SEQ ID NO:34, SEQ ID NO:35, or SEQ ID NO:36, and LC1 comprises an amino acid sequence having at least 95% identity to the amino acid sequence of SEQ ID NO:8.

3. The pharmaceutical composition of embodiment 2, wherein HC1 comprises the amino acid sequence selected from SEQ ID NO:7, SEQ ID NO:34, SEQ ID NO:35, or SEQ ID NO:36, and LC1 comprises the amino acid sequence of SEQ ID NO: 8.

4. The pharmaceutical composition of any one of embodiments 1 to 3, wherein the binding site for a first antigen binds to TRGV9 on a γδ T cell.

5. The pharmaceutical composition of any one of embodiments 1 to 4, wherein the binding site for a second antigen binds to a cancer antigen present on the surface of a cancer cell.

6. The pharmaceutical composition of embodiment 5, wherein the binding of the bispecific antibody to TRGV9 present on the surface of the γδ T cell and the binding of the cancer antigen present on the surface of the cancer cell results in the killing of the cancer cell.

7. The pharmaceutical composition of any one of embodiments 1 to 6, wherein HC1 and LC1 are humanized.

8. The pharmaceutical composition of any one of embodiments 1 to 7, wherein HC2 and LC2 bind to CD123.

9. The pharmaceutical composition of any one of embodiments 1 to 8, wherein the bispecific antibody or antigen binding fragment thereof is an IgG1, an IgG2, an IgG3, or an IgG4 isotype.

10. A method of directing a Vγ9-expressing γδ T cell to a cancer cell, the method comprising contacting a Vγ9-expressing γδ T cell with the pharmaceutical composition of any one of embodiments 1 to 9, wherein contacting the Vγ9-expressing γδ T cell with the pharmaceutical composition directs the Vγ9-expressing γδ T cell to a cancer cell.

11. A method of inhibiting growth or proliferation of cancer cells expressing a cancer antigen on the cell surface, the method comprising contacting the cancer cells with the pharmaceutical composition of any one of embodiments 1 to 9, wherein contacting the cancer cells with the pharmaceutical composition inhibits growth or proliferation of the cancer cells.

12. The method of embodiment 11, wherein the cancer cell is in the presence of a Vγ9-expressing γδ T cell while in contact with anti-TRGV9 bispecific antibody or antigen binding fragment thereof.

13. A method for treating a cancer in a subject in need thereof, the method comprising:
a. identifying a subject in need of cancer treatment; and
b. administering to the subject in need thereof the pharmaceutical composition of any one of embodiments 1 to 9,
wherein administering the pharmaceutical composition to the subject in need thereof treats the cancer in the subject.

14. A method of activating a Vγ9-expressing γδ T cell, the method comprising contacting the Vγ9-expressing γδ T cell with the pharmaceutical composition of any one of embodiments 1 to 9, wherein contacting the Vγ9-expressing γδ T cell with the pharmaceutical composition results in an increase in CD69, CD25, and/or Granzyme B expression as compared to a control Vγ9-expressing γδ T cell.

15. A method of producing the pharmaceutical composition of any one of embodiments 1 to 9, the method comprising combining the bispecific antibody or antigen binding fragment thereof with a pharmaceutically acceptable carrier to obtain the pharmaceutical composition.

Provided in the Examples herein are exemplary multispecific (bispecific) antibodies that bind to TRGV9 and CD123 (also known as IL3RA). CD123 is expressed on a variety of cell types in various tissues, including adipose tissue, adrenal gland, appendix, bone marrow, breast, bronchus, caudate, cerebellum, cerebral cortex, cervix, uterine, colon, duodenum, endometrium, epididymis, esophagus, fallopian tube, gallbladder, heart muscle, hippocampus, kidney, liver, lung, lymph node, nasopharynx, oral mucosa, ovary, pancreas, parathyroid gland, placenta, prostate, rectum, salivary gland, seminal vesicle, skeletal muscle, skin, small intestine, smooth muscle, soft tissue, spleen, stomach, testis, thyroid gland, tonsil, urinary bladder, and vagina (see, e.g., proteinatlas.org). Thus, these Examples are illustrative of exemplary bispecific antibodies that can effectively target a wide variety of cells and tissues in a subject.

In some embodiments, provided herein is a bispecific antibody comprising: (a) a first binding domain that binds to a TRGV9 antigen, and (b) a second binding domain that binds to a second target antigen. In some embodiments, provided herein is a bispecific antibody comprising: (a) a first binding domain that specifically binds to a TRGV9 antigen, and (b) a second binding domain that specifically binds to a second target antigen. In some embodiments, provided herein is a bispecific antibody comprising: (a) a first binding domain that binds to a first epitope on a TRGV9 antigen, and (b) a second binding domain that binds to a second epitope on a second target antigen. In some embodiments, provided herein is a bispecific antibody comprising: (a) a first binding domain that specifically binds to a first epitope on a TRGV9 antigen, and (b) a second binding domain that specifically binds to a second epitope on a second target antigen. In certain embodiments, the second target antigen is a cancer antigen on the surface of a cancer cell. In certain embodiments, the second target antigen is CD123.

Exemplary binding agents that bind to TRGV9, as well as exemplary binding agents that bind to CD123 are provided elsewhere herein, for example in the Examples, as well as in Tables 1-31.

Particular embodiments of this invention are described herein. Upon reading the foregoing description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. A number of embodiments of the invention have been described. Nevertheless, it will be understood that various modifications may be made without departing from the spirit and scope of the invention. Accordingly, the descriptions in the Examples section are intended to illustrate but not limit the scope of invention described in the claims.

EXAMPLES

Example 1: Production of Multispecific Antibodies that Bind γδ T Cells 1.1: Production of Mabs that Bind γδ T Cell Antigens Antigens or portions of antigens specific for γδ T cells are used to immunize an animal (e.g., a mouse or a rabbit). To generate the γδ T cell monoclonal antibodies, peripheral blood mononuclear cells are isolated from the whole blood of the immunized animal, and antigen specific B cells are grown. B cells secreting reactive antibodies for the γδ T cell antigens are identified by an antigen-binding ELISA screening of the B cell culture supernatants. High binding ELISA plates are coated with the γδ T cell antigen overnight. The ELISA plates are blocked, and diluted B cell culture supernatants are added to the plates. The plates are incubated at room temperature and following incubation, a secondary antibody specific for recognizing the γδ T cell antigen antibody is added to the plate to determine if the γδ T cell antigen antibody bound the γδ T cell antigen. Binding of the antibody is determined by reaction of a substrate on the secondary antibody.

After the identification of monoclonal antibodies that are capable of binding γδ T cell antigens, the variable regions of the heavy and light chains of the γδ T cell antibody are sequenced. Constructs are created for the expression of the heavy and light chain of the γδ T cell antibody. The constructs are transfected into a host cell to express the heavy and light chains, and the γδ T cell antibody is isolated from the supernatant.

1.2: Production of γδ T Cell Bispecific Antibodies

The variable region sequence of the γδ T cell monoclonal antibody and a second monoclonal antibody capable of binding a target antigen on a target cell of interest are used to generate a bispecific antibody to be tested for γδ T cell re-directed killing of the target cells. Target antigens of interest can be selected from, but not limited, antigens described in Zhang et al., Nucleic Acids Research 47(D1): D721-D728 (2019). γδ T cell bispecific antibodies are produced as full-length antibodies in the knob-into-hole format as human IgG4, as previously described (Atwell et al., J. Mol. Biol. 270:26-35 (1997)). Nucleic acid sequences encoding variable regions are sub-cloned into custom mammalian expression vectors containing the constant region of IgG4 expression cassettes using standard PCR restriction enzyme based cloning techniques. The bispecific antibodies are expressed by transient transfection in Chinese hamster ovary cell line. The antibodies are initially purified by MAB SELECT SURE Protein A column (GE Healthcare, Piscataway, New Jersey) (Brown, Bottomley et al. Biochem Soc Trans. 1998 August; 26(3):S249). The column is equilibrated with Phosphate Buffer Saline (PBS), pH 7.2 and is loaded with fermentation supernatant at a flow rate of 2 mL/min. After loading, the column is washed with PBS (4 column volumes (CV)) followed by elution in 30 mM sodium acetate, pH 3.5. Fractions containing protein peaks as monitored by absorbance at 280 nm in Akta Explorer (GE healthcare) are pooled together and are neutralized to pH 5.0 by adding 1% of 3M sodium acetate, pH 9.0. As a polishing step, the antibodies are purified on a preparative size exclusion chromatography (SEC) using a SUPERDEX 200 column (GE healthcare). The integrity of sample is assessed by endotoxin measurement and SDS polyacrylamide gel electrophoresis under reducing and non-reducing conditions. The final protein concentrations are determined.

1.3: Production of Anti-TRGV9 Bispecific Antibodies

Variable region sequences of exemplary anti-TRGV9 monoclonal antibodies are provided below in Table 1 and Table 2.

al., J. Mol. Biol. 270:26-35 (1997)). Nucleic acid sequences encoding variable regions are sub-cloned into custom mammalian expression vectors containing the constant region of IgG4 expression cassettes using standard PCR restriction enzyme based cloning techniques. The bispecific antibodies are expressed by transient transfection in Chinese hamster ovary cell line. The antibodies are initially purified by MAB SELECT SURE Protein A column (GE Healthcare, Piscataway, New Jersey) (Brown, Bottomley et al. Biochem Soc

TABLE 1

Anti-TRGV9 mAb CDR Sequences

| Antibody | VH CDR1 | VH CDR2 | VH CDR3 | VL CDR1 | VL CDR2 | VL CDR3 |
|---|---|---|---|---|---|---|
| TRGV9Ab_1 (LP7A5_1) | DHYIN (SEQ ID NO: 1) | QIYPGDGNT YYNQKFKG (SEQ ID NO: 2) | NYGDYTIDF (SEQ ID NO: 3) | KSSQSLLYS SNQKNYLA (SEQ ID NO: 4) | WASTRES (SEQ ID NO: 5) | QQYYRYHT (SEQ ID NO: 6) |
| TRGV9Ab_2 (LP7A5_2) | DHYIN (SEQ ID NO: 1) | QIYPGDGNT YYNQKFKG (SEQ ID NO: 2) | NMGMYTIDF (SEQ ID NO: 31) | KSSQSLLYS SNQKNYLA (SEQ ID NO: 4) | WASTRES (SEQ ID NO: 5) | QQYYRYHT (SEQ ID NO: 6) |
| TRGV9Ab_3 (LP7A5_3) | DHYIN (SEQ ID NO: 1) | QIYPGDGNT YYNQKFKG (SEQ ID NO: 2) | NMGMYTLDF (SEQ ID NO: 32) | KSSQSLLYS SNQKNYLA (SEQ ID NO: 4) | WASTRES (SEQ ID NO: 5) | QQYYRYHT (SEQ ID NO: 6) |
| TRGV9Ab_4 (LP7A5_4) | DHYIN (SEQ ID NO: 1) | QIYPGDGNT YYNQKFKG (SEQ ID NO: 2) | NYGDYTLDF (SEQ ID NO: 33) | KSSQSLLYS SNQKNYLA (SEQ ID NO: 4) | WASTRES (SEQ ID NO: 5) | QQYYRYHT (SEQ ID NO: 6) |

TABLE 2

Anti-TRGV9 mAb VH and VL Domain Sequences

| Antibody | VH | VL |
|---|---|---|
| TRGV9Ab_1 (LP7A5_1) | EVQLQQSGAELARPGASVKLSCKASGFTFTDHY INWVKQRTGQGLEWIGQIYPGDGNTYYNQKFKG KATLTADKSSSTAYMQLSSLTSEDSAVYFCAP NYGDYTIDFWGQGTSVTVSS (SEQ ID NO: 7) | DIVMSQSPSSLAVSVGEKVTMSCKSSQSLLYSSN QKNYLAWYQQKPGQSPKLLIYWASTRESGVPDRF TGSGSGTDFTLTISSVKAEDLAVYYCQQYYRY HTFGTGTKLEIK (SEQ ID NO: 8) |
| TRGV9Ab_2 (LP7A5_2) | EVQLQQSGAELARPGASVKLSCKASGFTFTDHY INWVKQRTGQGLEWIGQIYPGDGNTYYNQKFKG KATLTADKSSSTAYMQLSSLTSEDSAVYFCAP NMGMYTIDFWGQGTSVTVSS (SEQ ID NO: 34) | DIVMSQSPSSLAVSVGEKVTMSCKSSQSLLYSSN QKNYLAWYQQKPGQSPKLLIYWASTRESGVPDRF TGSGSGTDFTLTISSVKAEDLAVYYCQQYYRY HTFGTGTKLEIK (SEQ ID NO: 8) |
| TRGV9Ab_3 (LP7A5_3) | EVQLQQSGAELARPGASVKLSCKASGFTFTDHY INWVKQRTGQGLEWIGQIYPGDGNTYYNQKFKG KATLTADKSSSTAYMQLSSLTSEDSAVYFCAP NMGMYTLDFWGQGTSVTVSS (SEQ ID NO: 35) | DIVMSQSPSSLAVSVGEKVTMSCKSSQSLLYSSN QKNYLAWYQQKPGQSPKLLIYWASTRESGVPDRF TGSGSGTDFTLTISSVKAEDLAVYYCQQYYRY HTFGTGTKLEIK (SEQ ID NO: 8) |
| TRGV9Ab_4 (LP7A5_4) | EVQLQQSGAELARPGASVKLSCKASGFTFTDHY INWVKQRTGQGLEWIGQIYPGDGNTYYNQKFKG KATLTADKSSSTAYMQLSSLTSEDSAVYFCAP NYGDYTLDFWGQGTSVTVSS (SEQ ID NO: 36) | DIVMSQSPSSLAVSVGEKVTMSCKSSQSLLYSSN QKNYLAWYQQKPGQSPKLLIYWASTRESGVPDRF TGSGSGTDFTLTISSVKAEDLAVYYCQQYYRY HTFGTGTKLEIK (SEQ ID NO: 8) |

Variable region sequences of an anti-TRGV9 monoclonal antibody and a second monoclonal antibody capable of binding a target antigen on a target cell of interest are used to generate a bispecific antibody to be tested for γδ T cell re-directed killing of the target cells. Target antigens of interest can be selected from, but not limited to, antigens described in Zhang et al., Nucleic Acids Research 47(D1): D721-D728 (2019). Anti-TRGV9 bispecific antibodies are produced as full-length antibodies in the knob-into-hole format as human IgG4, as previously described (Atwell et Trans. 1998 August; 26(3):S249). The column is equilibrated with Phosphate Buffer Saline (PBS), pH 7.2 and is loaded with fermentation supernatant at a flow rate of 2 mL/min. After loading, the column is washed with PBS (4 column volumes (CV)) followed by elution in 30 mM sodium acetate, pH 3.5. Fractions containing protein peaks as monitored by Absorbance at 280 nm in Akta Explorer (GE healthcare) are pooled together and are neutralized to pH 5.0 by adding 1% of 3M sodium acetate, pH 9.0. As a polishing step, the antibodies are purified on a preparative size exclusion chromatography (SEC) using a SUPERDEX 200 column (GE healthcare). The integrity of sample is assessed by endotoxin measurement and SDS polyacrylamide gel electrophoresis under reducing and non-reducing conditions. The final protein concentrations are determined.

Example 2—Bispecific Antibodies that Bind TRGV9 and a Cancer Antigen

Examples 2.1-2.4 are based on the premise that γδ T cells, which mainly express heterodimers of TRGV9 and Vδ2 chains demonstrate potent anti-tumor functions. These cells express TCR-TRGV9 and the majority, if not all, of these cells exhibit efficient cytotoxicity of tumor target cells. This ability is then harnessed using bispecific antibodies constructed such that one arm binds to the TRGV9 structure and the other arm binds to a tumor-associated antigen expressed by the tumor cells. Thus, the bispecific antibody bridges the effector and target cells together-resulting in tumor cell killing. This mechanism of action is described in the schematic outlined in FIG. 1.

The subsequent examples can be divided into the following categories: (1) Generation and characterization of bispecific antibodies capable of binding to the TRGV9 arm expressed on γδ T cells and a cancer antigen (e.g., CD123) on cancer cells (Examples 2.1, 2.2, and 2.3.); and (2) Evidence for bispecific antibody-enabled target cell killing by γδ T cells expanded in vitro (Example 2.4).

Example 2.1: Production of Anti-TRGV9 Mab

The mouse IgG1 anti-human T cell receptor TRGV9 clone 7A5 was sourced commercially. Sample preparation and LC/MSMS analysis were performed by Lake Pharma. (San Carlos, CA). The sample was reduced and alkylated, divided into seven aliquots, and proteolytically digested with Trypsin/LysC, Chymotrypsin, LysC, Pepsin, and AspN, Elastase, and Proteinase K enzymes. Resulting peptides were desalted using a ZIPTIP C18 Pipette Tips and separated on-line using reverse phase chromatography. Mass spectrometry was performed on THERMO Q-EXACTIVE spectrometer using HCD fragmentation. MS data sets were analyzed using PEAKS software by matching de novo sequence tags to an IMGT-based antibody sequences database. Gaps in the sequence were assigned using Contig sequence assembly of de novo identified peptides. All CDRs and hyper-mutations were confirmed by inspecting the MS/MS spectra The sequences obtained are shown in Tables 3-7.

TABLE 4

CDR Sequences of anti-TRGV9 mAb.

| Antibody | HCDR1 | SEQ ID NO: | HCDR2 | SEQ ID NO: | HCDR3 | SEQ ID NO: |
|---|---|---|---|---|---|---|
| LP7A5_2 | DHYIN | 1 | QIYPGDGNT YYNQKFKG | 2 | NMGMYTIDF | 31 |

| Antibody | LCDR1 | SEQ ID NO: | LCDR2 | SEQ ID NO: | LCDR3 | SEQ ID NO: |
|---|---|---|---|---|---|---|
| LP7A5_2 | KSSQSLLYS SNQKNYLA | 4 | WASTRES | 5 | QQYYRYHT | 6 |

TABLE 5

CDR Sequences of anti-TRGV9 mAb.

| Antibody | HCDR1 | SEQ ID NO: | HCDR2 | SEQ ID NO: | HCDR3 | SEQ ID NO: |
|---|---|---|---|---|---|---|
| LP7A5_3 | DHYIN | 1 | QIYPGDGNT YYNQKFKG | 2 | NMGMYTLDF | 32 |

| Antibody | LCDR1 | SEQ ID NO: | LCDR2 | SEQ ID NO: | LCDR3 | SEQ ID NO: |
|---|---|---|---|---|---|---|
| LP7A5_3 | KSSQSLLYS SNQKNYLA | 4 | WASTRES | 5 | QQYYRYHT | 6 |

TABLE 6

CDR Sequences of anti-TRGV9 mAb.

| Antibody | HCDR1 | SEQ ID NO: | HCDR2 | SEQ ID NO: | HCDR3 | SEQ ID NO: |
|---|---|---|---|---|---|---|
| LP7A5_4 | DHYIN | 1 | QIYPGDGNT YYNQKFKG | 2 | NYGDYTLDF | 33 |

| Antibody | LCDR1 | SEQ ID NO: | LCDR2 | SEQ ID NO: | LCDR3 | SEQ ID NO: |
|---|---|---|---|---|---|---|
| LP7A5_4 | KSSQSLLYS SNQKNYLA | 4 | WASTRES | 5 | QQYYRYHT | 6 |

TABLE 3

CDR Sequences of anti-TRGV9 mAb.

| Antibody | HCDR1 | SEQ ID NO: | HCDR2 | SEQ ID NO: | HCDR3 | SEQ ID NO: |
|---|---|---|---|---|---|---|
| LP7A5_1 | DHYIN | 1 | QIYPGDGNT YYNQKFKG | 2 | NYGDYTIDF | 3 |

| Antibody | LCDR1 | SEQ ID NO: | LCDR2 | SEQ ID NO: | LCDR3 | SEQ ID NO: |
|---|---|---|---|---|---|---|
| LP7A5_1 | KSSQSLLYS SNQKNYLA | 4 | WASTRES | 5 | QQYYRYHT | 6 |

TABLE 7

Heavy chain and light chain sequences
of anti-TRGV9 mAb.

| mAb | Heavy Chain Amino Acid Sequence | SEQ ID NO: |
|---|---|---|
| LP7A5_1 | EVQLQQSGAELARPGASVKLSCKASGFTFTDHY INWVKQRTGQGLEWIGQIYPGDGNTYYNQKFKG KATLTADKSSSTAYMQLSSLTSEDSAVYFCAPN YGDYTIDFWGQGTSVTVSS | 7 |
| LP7A5_2 | EVQLQQSGAELARPGASVKLSCKASGFTFTDHY INWVKQRTGQGLEWIGQIYPGDGNTYYNQKFKG KATLTADKSSSTAYMQLSSLTSEDSAVYFCAPN MGMYTIDFWGQGTSVTVSS | 34 |
| LP7A5_3 | EVQLQQSGAELARPGASVKLSCKASGFTFTDHY INWVKQRTGQGLEWIGQIYPGDGNTYYNQKFKG KATLTADKSSSTAYMQLSSLTSEDSAVYFCAPN MGMYTLDFWGQGTSVTVSS | 35 |
| LP7A5_4 | EVQLQQSGAELARPGASVKLSCKASGFTFTDHY INWVKQRTGQGLEWIGQIYPGDGNTYYNQKFKG KATLTADKSSSTAYMQLSSLTSEDSAVYFCAPN YGDYTLDFWGQGTSVTVSS | 36 |

| | Light Chain Amino Acid Sequence | SEQ ID NO: |
|---|---|---|
| LP7A5_1 | DIVMSQSPSSLAVSVGEKVTMSCKSSQSLLYSS NQKNYLAWYQQKPGQSPKLLIYWASTRESGVPD RFTGSGSGTDFTLTISSVKAEDLAVYYCQQYYR YHTFGTGTKLEIK | 8 |

Example 2.2: Preparation of Anti-TRGV9/Anti-CD123 Bispecific Antibodies

The variable region sequence of LP7A5 (anti-TRGV9) and I3RB217 (anti-CD123 antibody) (HCDRs and LCDRs in Table 8, HC and LC in Table 9) were used to generate a bispecific antibody to be tested for T cell re-directed killing of acute myeloid leukemia (AML) cells. VG1 (anti-TRGV9 x CD123) and VG3 (anti-TRGV9 x Null) bispecific antibodies were produced as full-length antibodies in the knob-into-hole format as human IgG4, as previously described (Atwell et al. J. Mol. Biol. 270: 26-35, 1997). Nucleic acid sequences encoding variable regions were sub-cloned into a custom mammalian expression vectors containing constant region of IgG4 expression cassettes using standard PCR restriction enzyme based cloning techniques. The bispecific antibodies were expressed by transient transfection in Chinese hamster ovary cell line. The antibodies were initially purified by MAB SELECT SURE Protein A column (GE Healthcare, Piscataway, New Jersey) (Brown, Bottomley et al. Biochem Soc Trans. 1998 August; 26(3):S249). The column was equilibrated with Phosphate Buffer Saline (PBS), pH 7.2 and loaded with fermentation supernatant at a flow rate of 2 mL/min. After loading, the column was washed with PBS (4 column volumes (CV)) followed by elution in 30 mM sodium acetate, pH 3.5. Fractions containing protein peaks as monitored by Absorbance at 280 nm in AKTA EXPLORER (GE healthcare) were pooled together and were neutralized to pH 5.0 by adding 1% of 3M sodium acetate, pH 9.0. As a polishing step, the antibodies were purified on a preparative size exclusion chromatography (SEC) using a SUPERDEX 200 column (GE healthcare). The integrity of sample was assessed by endotoxin measurement and SDS polyacrylamide gel electrophoresis under reducing and non-reducing conditions. The final protein concentrations were 1.0 mg/ml for anti-TRGV9/anti-CD123 and 1.0 mg/mL for anti-TRGV9/Null. The final EU levels of anti-TRGV9/anti-CD123 and anti-TRGV9/Null based on these were <3.0 EU/mg.

TABLE 8

CDR Sequences of anti-CD123 mAb.

| Antibody | HCDR1 | SEQ ID NO: | HCDR2 | SEQ ID NO: | HCDR3 | SEQ ID NO: |
|---|---|---|---|---|---|---|
| I3RB217 | SYWIS | 9 | IIDPSDSDT RYSPSFQG | 10 | GDGSTDLDY | 11 |

| Antibody | LCDR1 | SEQ ID NO: | LCDR2 | SEQ ID NO: | LCDR3 | SEQ ID NO: |
|---|---|---|---|---|---|---|
| I3RB217 | RASQSV SSSYL | 12 | GASSRAT | 13 | QQDYGFPWT | 14 |

TABLE 9

Heavy chain and light chain sequences of anti-CD123 mAb.

| mAb ID | Heavy Chain Amino Acid Sequence | SEQ ID NO: |
|---|---|---|
| I3RB217 | EVQLVQSGAEVKKPGESLKISCKGSGYSFTS YWISWVRQMPGKGLEWMGIIDPSDSDTRYSP SFQGQVTISADKSISTAYLQWSSLKASDTAM YYCARGDGSTDLDYWGQGTLVTVSS | 15 |

TABLE 9-continued

Heavy chain and light chain sequences of anti-CD123 mAb.

| mAb ID | Light Chain Amino Acid Sequence | SEQ ID NO: |
|---|---|---|
| I3RB217 | EIVLTQSPGTLSLSPGERATLSCRASQSVSS SYLAWYQQKPGQAPRLLIYGASSRATGIPDR FSGSGSGTDFTLTISRLEPEDFAVYYCQQDY GFPWTFGQGTKVEIK | 16 |

TABLE 10

Sequences of half antibodies expressed in CHO cells.

| mAb ID | 'Knob' arm and 'hole' arm amino acid sequence | SEQ ID NO: |
|---|---|---|
| VG1 (ANTI-TRGV9 half antibody) | MAWVWTLLFLMAAAQSIQADIVMSQSPSSLAVSVGEKVTMSCKSSQSLLYS SNQKNYLAWYQQKPGQSPKLLIYWASTRESGVPDRFTGSGSGTDFTLTISSV KAEDLAVYYCQQYYRYHTFGTGTKLEIKRTVAAPSVFIFPPSDEQLKSGTAS VVCLLNNFYPREAKVQWKVDNALQSGNSQESVTEQDSKDSTYSLSSTLTLS KADYEKHKVYACEVTHQGLSSPVTKSFNRGECGGSEGKSSGSGSESKSTEG KSSGSGSESKSTGGSEVQLQQSGAELARPGASVKLSCKASGFTFTDHYINWV KQRTGQGLEWIGQIYPGDGNTYYNQKFKGKATLTADKSSSTAYMQLSSLTS EDSAVYFCAPNYGDYTIDFWGQGTSVTVSSASTKGPSVFPLAPCSRSTSEST AALGCLVKDYFPEPVTVSWNSGALTSGVHTFPAVLQSSGLYSLSSVVTVPSS SLGTKTYTCNVDHKPSNTKVDKRVESKYGPPCPPCPAPEAAGGPSVFLFPPK PKDTLMISRTPEVTCVVVDVSQEDPEVQFNWYVDGVEVHNAKTKPREEQF NSTYRVVSVLTVLHQDWLNGKEYKCKVSNKGLPSSIEKTISKAKGQPREPQ VYTLPPSQEEMTKNQVSLSCAVKGFYPSDIAVEWESNGQPENNYKTTPPVL DSDGSFFLVSRLTVDKSRWQEGNVFSCSVMHEALHNRFTQKSLSLSLGK | 17 |
| VG1 (anti-CD123 half Ab) | MAWVWTLLFLMAAAQSIQAEIVLTQSPGTLSLSPGERATLSCRASQSVSSSY LAWYQQKPGQAPRLLIYGASSRATGIPDRFSGSGSGTDFTLTISRLEPEDFAV YYCQQDYGFPWTFGQGTKVEIKRTVAAPSVFIFPPSDEQLKSGTASVVCLLN NFYPREAKVQWKVDNALQSGNSQESVTEQDSKDSTYSLSSTLTLSKADYEK HKVYACEVTHQGLSSPVTKSFNRGECGGSEGKSSGSGSESKSTEGKSSGSGS ESKSTGGSEVQLVQSGAEVKKPGESLKISCKGSGYSFTSYWISWVRQMPGK GLEWMGIIDPSDSDTRYSPSFQGQVTISADKSISTAYLQWSSLKASDTAMYY CARGDGSTDLDYWGQGTLVTVSSASTKGPSVFPLAPCSRSTSESTAALGCLV KDYFPEPVTVSWNSGALTSGVHTFPAVLQSSGLYSLSSVVTVPSSSLGTKTY TCNVDHKPSNTKVDKRVESKYGPPCPPCPAPEAAGGPSVFLFPPKPKDTLMI SRTPEVTCVVVDVSQEDPEVQFNWYVDGVEVHNAKTKPREEQFNSTYRVV SVLTVLHQDWLNGKEYKCKVSNKGLPSSIEKTISKAKGQPREPQVYTLPPSQ EEMTKNQVSLWCLVKGFYPSDIAVEWESNGQPENNYKTTPPVLDSD GSFFL YSRLTVDKSRWQEGNVFSCSVMHEALHNHYTQKSLSLSLGK | 18 |
| VG3 (B23B49 Null half Ab) | MAWVWTLLFLMAAAQSIQAEIVLTQSPGTLSLSPGERATLSCRASQSVSSSY LAWYQQKPGQAPRLLIYGASSRATGIPDRFSGSGSGTDFTLTISRLEPEDFAV YYCQQDYGFPWTFGQGTKVEIKRTVAAPSVFIFPPSDEQLKSGTASVVCLLN NFYPREAKVQWKVDNALQSGNSQESVTEQDSKDSTYSLSSTLTLSKADYEK HKVYACEVTHQGLSSPVTKSFNRGECGGSEGKSSGSGSESKSTEGKSSGSGS ESKSTGGSEVQLVQSGAEVKKPGESLKISCKGSGYSFTSYWISWVRQMPGK GLEWMGIIDPSDSDTRYSPSFQGQVTISADKSISTAYLQWSSLKASDTAMYY CARGDGSTDLDYWGQGTLVTVSSASTKGPSVFPLAPCSRSTSESTAALGCLV KDYFPEPVTVSWNSGALTSGVHTFPAVLQSSGLYSLSSVVTVPSSSLGTKTY TCNVDHKPSNTKVDKRVESKYGPPCPPCPAPEAAGGPSVFLFPPKPKDTLMI SRTPEVTCVVVDVSQEDPEVQFNWYVDGVEVHNAKTKPREEQFNSTYRVV SVLTVLHQDWLNGKEYKCKVSNKGLPSSIEKTISKAKGQPREPQVYTLPPSQ EEMTKNQVSLWCLVKGFYPSDIAVEWESNGQPENNYKTTPPVLDSDGSFFL YSRLTVDKSRWQEGNVFSCSVMHEALHNHYTQKSLSLSLGK | 19 |

Half Antibody DNA sequence

| mAb ID | | SEQ ID NO: |
|---|---|---|
| VG1 (ANTI-TRGV9 half Ab) | ATGGCCTGGGTGTGGACCCTGCTGTTCCTGATGGCCGCCGCCCAGAGCAT CCAGGCCGACATCGTGATGAGCCAGAGCCCAAGCAGCCTGGCCGTGAGC GTGGGCGAGAAGGTGACCATGAGCTGCAAGAGCAGCCAGAGCCTGCTGT ACAGCAGCAACCAGAAGAACTACCTGGCCTGGTACCAGCAGAAGCCCAG GCCAGAGCCCAAAGCTGCTGATCTACTGGGCCAGCACCCGCGAGAGCGG CGTGCCAGACCGCTTCACCGGCAGCGGCAGCGGCACCGACTTCACCCTG ACCATCAGCAGCGTGAAGGCCGAGGACCTGGCCGTGTACTACTGCCAGC AGTACTACCGCTACCACACCTTCGGCACCGGCACCAAGCTGGAGATCAA GCGCACCGTGGCCGCCCCCAGCGTGTTCATCTTCCCACCAAGCGACGAG CAGCTGAAGAGCGGCACCGCCAGCGTGGTGTGCCTGCTGAACAACTTCT | 20 |

TABLE 10-continued

Sequences of half antibodies expressed in CHO cells.

ACCCACGCGAGGCCAAGGTGCAGTGGAAGGTGGACAACGCCCTGCAGA
GCGGCAACAGCCAGGAGAGCGTGACCGAGCAGGACAGCAAGGACAGCA
CCTACAGCCTGAGCAGCACCCTGACCCTGAGCAAGGCCGACTACGAGAA
GCACAAGGTGTACGCCTGCGAGGTGACCCACCAGGGCCTGAGCAGCCCA
GTGACCAAGAGCTTCAACCGCGGCGAGTGCggcggcagcgagggcaaga
gcagcggcagcggcagcgagagcaagagcaccgagggcaagagcagcgg
cagcggcagcgagagcaagagcaccggcggca
gcGAGGTGCAGCTGCAGCAGAGCGGCGCCGAGCTGGCCCGCCCAGGCGC
CAGCGTGAAGCTGAGCTGCAAGGCCAGCGGCTTCACCTTCACCGACCAC
TACATCAACTGGGTGAAGCAGCGCACCGGCCAGGGCCTGGAGTGGATCG
GCCAGATCTACCCAGGCGACGGCAACACCTACTACAACCAGAAGTTCAA
GGGCAAGGCCACCCTGACCGCCGACAAGAGCAGCAGCACCGCCTACATG
CAGCTGAGCAGCCTGACCAGCGAGGACAGCGCCGTGTACTTCTGCGCCC
CAAACTACGGCGACTACACCATCGACTTCTGGGGCCAGGGCACCAGCGT
GACCGTGAGCAGCGCCAGCACCAAGGGCCCAAGCGTGTTCCCACTGGCC
CCATGCAGCCGCAGCACCAGCGAGAGCACCGCCGCCCTGGGCTGCCTGG
TGAAGGACTACTTCCCAGAGCCAGTGACCGTGAGCTGGAACAGCGGCGC
CCTGACCAGCGGCGTGCACACCTTCCCAGCCGTGCTGCAGAGCAGCGGC
CTGTACAGCCTGAGCAGCGTGGTGACCGTGCCAAGCAGCAGCCTGGGCA
CCAAGACCTACACCTGCAACGTGGACCACAAGCCAAGCAACACCAAGGT
GGACAAGCGCGTGGAGAGCAAGTACGGCCCACCATGCCCACCATGCCCA
GCCCCAGAGGCCGCCGGCGGCCCAAGCGTGTTCCTGTTCCCACCAAAGC
CAAAGGACACCCTGATGATCAGCCGCACCCCAGAGGTGACCTGCGTGGT
GGTGGACGTGAGCCAGGAGGACCCAGAGGTGCAGTTCAACTGGTACGTG
GACGGCGTGGAGGTGCACAACGCCAAGACCAAGCCACGCGAGGAGCAG
TTCAACAGCACCTACCGCGTGGTGAGCGTGCTGACCGTGCTGCACCAGG
ACTGGCTGAACGGCAAGGAGTACAAGTGCAAGGTGAGCAACAAGGGCC
TGCCAAGCAGCATCGAGAAGACCATCAGCAAGGCCAAGGGCCAGCCAC
GCGAGCCACAGGTGTACACCCTGCCACCAAGCCAGGAGGAGATGACCA
AGAACCAGGTGAGCCTGTGGTGCCTGGTGAAGGGCTTCTACCCAAGCGA
CATCGCCGTGGAGTGGGAGAGCAACGGCCAGCCAGAGAACAACTACAA
GACCACCCCACCAGTGCTGGACAGCGACGGCAGCTTCTTCCTGTACAGC
CGCCTGACCGTGGACAAGAGCCGCTGGCAGGAGGGCAACGTGTTCAGCT
GCAGCGTGATGCACGAGGCCCTGCACAACCACTACACCCAGAAGAGCCT
GAGCCTGAGCCTGGGCAAG VG1
(anti-
CD123
half Ab)

ATGGCCTGGGTGTGGACCCTGCTGTTCCTGATGGCCGCCGCCCAGAGCAT 21
CCAGGCCGAGATCGTGCTGACCCAGAGCCCAGGCACCCTGAGCCTGAGC
CCAGGCGAGCGCGCCACCCTGAGCTGCCGCGCCAGCCAGAGCGTGAGCA
GCAGCTACCTGGCCTGGTACCAGCAGAAGCCAGGCCAGGCCCCACGCCT
GCTGATCTACGGCGCCAGCAGCCGCGCCACCGGCATCCCAGACCGCTTC
AGCGGCAGCGGCAGCGGCACCGACTTCACCCTGACCATCAGCCGCCTGG
AGCCAGAGGACTTCGCCGTGTACTACTGCCAGCAGGACTACGGCTTCCC
ATGGACCTTCGGCCAGGGCACCAAGGTGGAGATCAAGCGCACCGTGGCC
GCCCCAAGCGTGTTCATCTTCCCACCAAGCGACGAGCAGCTGAAGAGCG
GCACCGCCAGCGTGGTGTGCCTGCTGAACAACTTCTACCCACGCGAGGC
CAAGGTGCAGTGGAAGGTGGACAACGCCCTGCAGAGCGGCAACAGCCA
GGAGAGCGTGACCGAGCAGGACAGCAAGGACAGCACCTACAGCCTGAG
CAGCACCCTGACCCTGAGCAAGGCCGACTACGAGAAGCACAAGGTGTAC
GCCTGCGAGGTGACCCACCAGGGCCTGAGCAGCCCAGTGACCAAGAGCT
TCAACCGCGGCGAGTGCggcggcagcgagggcaagagcagcggcagcgg
cagcgagagcaagagcaccgagggcaagagcagcggcagcggcagcgag
agcaagagcaccggcggcagcGAGGTGCAGCT
GGTGCAGAGCGGCGCCGAGGTGAAGAAGCCAGGCGAGAGCCTGAAGAT
CAGCTGCAAGGGCAGCGGCTACAGCTTCACCAGCTACTGGATCAGCTGG
GTGCGCCAGATGCCAGGCAAGGGCCTGGAGTGGATGGGCATCATCGACC
CAAGCGACAGCGACACCCGCTACAGCCCAAGCTTCCAGGGCCAGGTGAC
CATCAGCGCCGACAAGAGCATCAGCACCGCCTACCTGCAGTGGAGCAGC
CTGAAGGCCAGCGACACCGCCATGTACTACTGCGCCCGCGGCGACGGCA
GCACCGACCTGGACTACTGGGGCCAGGGCACCCTGGTGACCGTGAGCAG
CGCCAGCACCAAGGGCCCAAGCGTGTTCCCACTGGCCCCATGCAGCCGC
AGCACCAGCGAGAGCACCGCCGCCCTGGGCTGCCTGGTGAAGGACTACT
TCCCAGAGCCAGTGACCGTGAGCTGGAACAGCGGCGCCCTGACCAGCGG
CGTGCACACCTTCCCAGCCGTGCTGCAGAGCAGCGGCCTGTACAGCCTG
AGCAGCGTGGTGACCGTGCCAAGCAGCAGCCTGGGCACCAAGACCTACA
CCTGCAACGTGGACCACAAGCCAAGCAACACCAAGGTGGACAAGCGCG
TGGAGAGCAAGTACGGCCCACCATGCCCACCATGCCCAGCCCCAGAGGC
CGCCGGCGGCCCAAGCGTGTTCCTGTTCCCACCAAAGCCAAAGGACACC
CTGATGATCAGCCGCACCCCAGAGGTGACCTGCGTGGTGGTGGACGTGA
GCCAGGAGGACCCAGAGGTGCAGTTCAACTGGTACGTGGACGGCGTGGA
GGTGCACAACGCCAAGACCAAGCCACGCGAGGAGCAGTTCAACAGCAC
CTACCGCGTGGTGAGCGTGCTGACCGTGCTGCACCAGGACTGGCTGAAC
GGCAAGGAGTACAAGTGCAAGGTGAGCAACAAGGGCCTGCCAAGCAGC
ATCGAGAAGACCATCAGCAAGGCCAAGGGCCAGCCACGCGAGCCACAG
GTGTACACCCTGCCACCAAGCCAGGAGGAGATGACCAAGAACCAGGTG
AGCCTGTGGTGCCTGGTGAAGGGCTTCTACCCAAGCGACATCGCCGTGG
AGTGGGAGAGCAACGGCCAGCCAGAGAACAACTACAAGACCACCCCAC
CAGTGCTGGACAGCGACGGCAGCTTCTTCCTGTACAGCCGCCTGACCGT TABLE 10-continued

| Sequences of half antibodies expressed in CHO cells. |
|---|

|  | GGACAAGAGCCGCTGGCAGGAGGGCAACGTGTTCAGCTGCAGCGTGATG CACGAGGCCCTGCACAACCACTACACCCAGAAGAGCCTGAGCCTGAGCC TGGGCAAG |  |
| VG3 (Null half Ab) | ATGGCCTGGGTGTGGACCCTGCTGTTCCTGATGGCCGCCGCCCAGAGCAT CCAGGCCGACATCGTGATGACCCAGAGCCCAGACAGCCTGGCCGTGAGC CTGGGCGAGCGCGCCACCATCAACTGCCGCGCCAGCCAGAGCGTGGACT ACAACGGCATCAGCTACATGCACTGGTACCAGCAGAAGCCAGGCCAGCC ACCAAAGCTGCTGATCTACGCCGCCAGCAACCCAGAGAGCGGCGTGCCA GACCGCTTCAGCGGCAGCGGCAGCGGCACCGACTTCACCCTGACCATCA GCAGCCTGCAGGCCGAGGACGTGGCCGTGTACTACTGCCAGCAGATCAT CGAGGACCCATGGACCTTCGGCCAGGGCACCAAGGTGGAGATCAAGCGC ACCGTGGCCGCCCCAAGCGTGTTCATCTTCCCACCAAGCGACGAGCAGC TGAAGAGCGGCACCGCCAGCGTGGTGTGCCTGCTGAACAACTTCTACCC ACGCGAGGCCAAGGTGCAGTGGAAGGTGGACAACGCCCTGCAGAGCGG CAACAGCCAGGAGAGCGTGACCGAGCAGGACAGCAAGGACAGCACCTA CAGCCTGAGCAGCACCCTGACCCTGAGCAAGGCCGACTACGAGAAGCAC AAGGTGTACGCCTGCGAGGTGACCCACCAGGGCCTGAGCAGCCCAGTGA CCAAGAGCTTCAACCGCGGCGAGTGCGGCGGCAGCGAGGGCAAGAGCA GCGGCAGCGGCAGCGAGAGCAAGAGCACCGAGGGCAAGAGCAGCGGCA GCGGCAGCGAGAGCAAGAGCACCGGCGGCAGCCAGATCACCCTGAAGG AGAGCGGCCCCAACCCTGGTGAAGCCAACCCAGACCCTGACCCTGACCTG CACCTTCAGCGGCTTCAGCCTGAGCACCAGCGGCATGGGCGTGAGCTGG ATCCGCCAGCCACCAGGCAAGGCCCTGGAGTGGCTGGCCCACATCTACT GGGACGACGACAAGCGCTACAACCCAAGCCTGAAGAGCCGCCTGACCAT CACCAAGGACACCAGCAAGAACCAGGTGGTGCTGACCATGACCAACATG GACCCAGTGGACACCGCCACCTACTACTGCGCCCGCCTGTACGGCTTCAC CTACGGCTTCGCCTACTGGGGCCAGGGCACCCTGGTGACCGTGAGCAGC GCCAGCACCAAGGGCCCAAGCGTGTTCCCACTGGCCCCCATGCAGCCGCA GCACCAGCGAGAGCACCGCCGCCCTGGGCTGCCTGGTGAAGGACTACTT CCCAGAGCCAGTGACCGTGAGCTGGAACAGCGGCGCCCTGACCAGCGGC GTGCACACCTTCCCAGCCGTGCTGCAGAGCAGCGGCCTGTACAGCCTGA GCAGCGTGGTGACCGTGCCAAGCAGCAGCCTGGGCACCAAGACCTACAC CTGCAACGTGGACCACAAGCCAAGCAACACCAAGGTGGACAAGCGCGT GGGAGAGCAAGTACGGCCCCACCATGCCCACCATGCCCAGCCCCAGAGGCC GCCGGCGGCCCAAGCGTGTTCCTGTTCCCACCAAAGCCAAAGGACACCC TGATGATCAGCCGCACCCCAGAGGTGACCTGCGTGGTGGTGGACGTGAG CCAGGAGGACCCAGAGGTGCAGTTCAACTGGTACGTGGACGGCGTGGAG GTGCACAACGCCAAGACCAAGCCACGCGAGGAGCAGTTCAACAGCACCT ACCGCGTGGTGAGCGTGCTGACCGTGCTGCACCAGGACTGGCTGAACGG CAAGGAGTACAAGTGCAAGGTGAGCAACAAGGGCCTGCCAAGCAGCAT CGAGAAGACCATCAGCAAGGCCAAGGGCCAGCCACGCGAGCCACAGGT GTACACCCTGCCACCAAGCCAGGAGGAGATGACCAAGAACCAGGTGAG CCTGTGGTGCCTGGTGAAGGGCTTCTACCCAAGCGACATCGCCGTGGAG TGGGAGAGCAACGGCCAGCCAGAGAACAACTACAAGACCACCCCACCA GTGCTGGACAGCGACGGCAGCTTCTTCCTGTACAGCCGCCTGACCGTGG ACAAGAGCCGCTGGCAGGAGGGCAACGTGTTCAGCTGCAGCGTGATGCA CGAGGCCCTGCACAACCACTACACCCAGAAGAGCCTGAGCCTGAGCCTG GGCAAG | 22 |

TABLE 11

| Heavy and Light Chain Sequences for TRGV9 bispecific antibodies |
|---|

| Bispecific Antibody |  | Amino Acid Sequence |
|---|---|---|
| VG1 (ANTI-TRGV9/anti-CD123) | Heavy chain VG1 (SEQ ID NO: 23) | 1 EVQLQQSGAELARPGASVKLSCKASGFTFTDHYINWVKQRT GQGLEWIGQIYPGDGNTYYNQKFKGKATLTADKSSSTAYM QLSSLTSEDSAVYFCAPNYGDYTIDFWGQGTSVTVSSASTK GPSVFPLAPCSRSTSESTAALGCLVKDYFPEPVTVSWNSGAL TSGVHTFPAVLQSSGLYSLSSVVTVPSSSLGTKTYTCNVDHK PSNTKVDKRVESKYGPPCPPCPAPEAAGGPSVFLFPPKPKDT LMISRTPEVTCVVVDVSQEDPEVQFNWYVDGVEVHNAKTK PREEQFNSTYRVVSVLTVLHQDWLNGKEYKCKVSNKGLPS SIEKTISKAKGQPREPQVYTLPPSQEEMTKNQVSLSCAVKGF YPSDIAVEWESNGQPENNYKTTPPVLDSDGSFFLVSRLTVD KSRWQEGNVFSCSVMHEALHNRFTQKSLSLSLGK |
|  | Light Chain VG1 (SEQ ID NO: 24) | 1 DIVMSQSPSSLAVSVGEKVTMSCKSSQSLLYSSNQKNYLAW YQQKPGQSPKLLIYWASTRESGVPDRFTGSGSGTDFTLTISS VKAEDLAVYYCQQYYRYHTFGTGTKLEIKRTVAAPSVFIFP PSDEQLKSGTASVVCLLNNFYPREAKVQWKVDNALQSGNS QESVTEQDSKDSTYSLSSTLTLSKADYEKHKVYACEVTHQG LSSPVTKSFNRGEC |

TABLE 11-continued

Heavy and Light Chain Sequences for TRGV9 bispecific antibodies

| Bispecific Antibody | | Amino Acid Sequence |
|---|---|---|
| | Heavy chain 2 VG1 (SEQ ID NO: 25) | EVQLVQSGAEVKKPGESLKISCKGSGYSFTSYWISWVRQMP GKGLEWMGIIDPSDSDTRYSPSFQGQVTISADKSISTAYLQW SSLKASDTAMYYCARGDGSTDLDYWGQGTLVTVSSASTKG PSVFPLAPCSRSTSESTAALGCLVKDYFPEPVTVSWNSGALT SGVHTFPAVLQSSGLYSLSSVVTVPSSSLGTKTYTCNVDHKP SNTKVDKRVESKYGPPCPPCPAPEAAGGPSVFLFPPKPKDTL MISRTPEVTCVVVDVSQEDPEVQFNWYVDGVEVHNAKTKP REEQFNSTYRVVSVLTVLHQDWLNGKEYKCKVSNKGLPSSI EKTISKAKGQPREPQVYTLPPSQEEMTKNQVSLWCLVKGFY PSDIAVEWESNGQPENNYKTTPPVLDSDGSFFLYSRLTVDKS RWQEGNVFSCSVMHEALHNHYTQKSLSLSLGK |
| | Light Chain 2 VG1 (SEQ ID NO: 26) | EIVLTQSPGTLSLSPGERATLSCRASQSVSSSYLAWYQQKPG QAPRLLIYGASSRATGIPDRFSGSGSGTDFTLTISRLEPEDFA VYYCQQDYGFPWTFGQGTKVEIKRTVAAPSVFIFPPSDEQL KSGTASVVCLLNNFYPREAKVQWKVDNALQSGNSQESVTE QDSKDSTYSLSSTLTLSKADYEKHKVYACEVTHQGLSSPVT KSFNRGEC |
| ANTI-TRGV9 x Null | Heavy chain 1 VG3 (SEQ ID NO: 27) | QVQLQESGPGLVKPSETLSLTCTVSGYSITSGYFWNWIRQPP GKGLEWIGYISYDGSNNYNPSLKSRVTISRDTSKNQFSLKLS SVTAADTAVYYCASPSPGTGYAVDYWGQGTLVTVSSASTK GPSVFPLAPCSRSTSESTAALGCLVKDYFPEPVTVSWNSGAL TSGVHTFPAVLQSSGLYSLSSVVTVPSSSLGTKTYTCNVDHK PSNTKVDKRVESKYGPPCPPCPAPEAAGGPSVFLFPPKPKDT LMISRTPEVTCVVVDVSQEDPEVQFNWYVDGVEVHNAKTK PREEQFNSTYRVVSVLTVLHQDWLNGKEYKCKVSNKGLPS SIEKTISKAKGQPREPQVYTLPPSQEEMTKNQVSLSCAVKGF YPSDIAVEWESNGQPENNYKTTPPVLDSDGSFFLVSRLTVD KSRWQEGNVFSCSVMHEALHNRFTQKSLSLSLGK |
| | Light Chain 1 VG3 (SEQ ID NO: 28) | DIQMTQSPSSLSASVGDRVTITCRSSQSLVHSNGNTYLHWY QQKPGKAPKFLIYKVSNRFSGVPSRFSGSGSGTDFTLTISSLQ PEDFATYYCSQSTHVPFTFGQGTKLEIKRTVAAPSVFIFPPSD EQLKSGTASVVCLLNNFYPREAKVQWKVDNALQSGNSQES VTEQDSKDSTYSLSSTLTLSKADYEKHKVYACEVTHQGLSS PVTKSFNRGEC |
| | Heavy chain 2 VG3 (SEQ ID NO: 29) | QITLKESGPTLVKPTQTLTLTCTFSGFSLSTSGMGVSWIRQPP GKALEWLAHIYWDDDKRYNPSLKSRLTITKDTSKNQVVLT MTNMDPVDTATYYCARLYGFTYGFAYWGQGTLVTVSSAS TKGPSVFPLAPCSRSTSESTAALGCLVKDYFPEPVTVSWNSG ALTSGVHTFPAVLQSSGLYSLSSVVTVPSSSLGTKTYTCNVD HKPSNTKVDKRVESKYGPPCPPCPAPEAAGGPSVFLFPPKPK DTLMISRTPEVTCVVVDVSQEDPEVQFNWYVDGVEVHNAK TKPREEQFNSTYRVVSVLTVLHQDWLNGKEYKCKVSNKGL PSSIEKTISKAKGQPREPQVYTLPPSQEEMTKNQVSLWCLVK GFYPSDIAVEWESNGQPENNYKTTPPVLDSDGSFFLYSRLTV DKSRWQEGNVFSCSVMHEALHNHYTQKSLSLSLGK |
| | Light Chain 2 VG3 (SEQ ID NO: 30) | DIVMTQSPDSLAVSLGERATINCRASQSVDYNGISYMHWYQ QKPGQPPKLLIYAASNPESGVPDRFSGSGSGTDFTLTISSLQA EDVAVYYCQQIIEDPWTFGQGTKVEIKRTVAAPSVFIFPPSD EQLKSGTASVVCLLNNFYPREAKVQWKVDNALQSGNSQES VTEQDSKDSTYSLSSTLTLSKADYEKHKVYACEVTHQGLSS PVTKSFNRGEC |

Example 2.3: Characterization of Vγ9+ (γδ) T Cells and Pan T Cells

Zoledronic acid selectively expands Vγ9+ γδ T cells from whole PBMCs. PBMCs were isolated from whole fresh PBMCs using EASYSEP Human γδ T cell isolation kit (Stem cell Technologies; Vancouver, CA) according to manufacturer instructions. Isolated PBMCs were cultured in RPMI-10 (RPMI supplemented with 10% FBS, 1× Pen/ Strep) medium with recombinant human IL-2 (rhIL-2) to a final concentration of 1000 IU/mL and recombinant human IL-15 (rhIL-15) to a final concentration of 10 ng/mL and Zoledronic acid to a final concentration of 5 pM. for 14 days.

Figure 2:
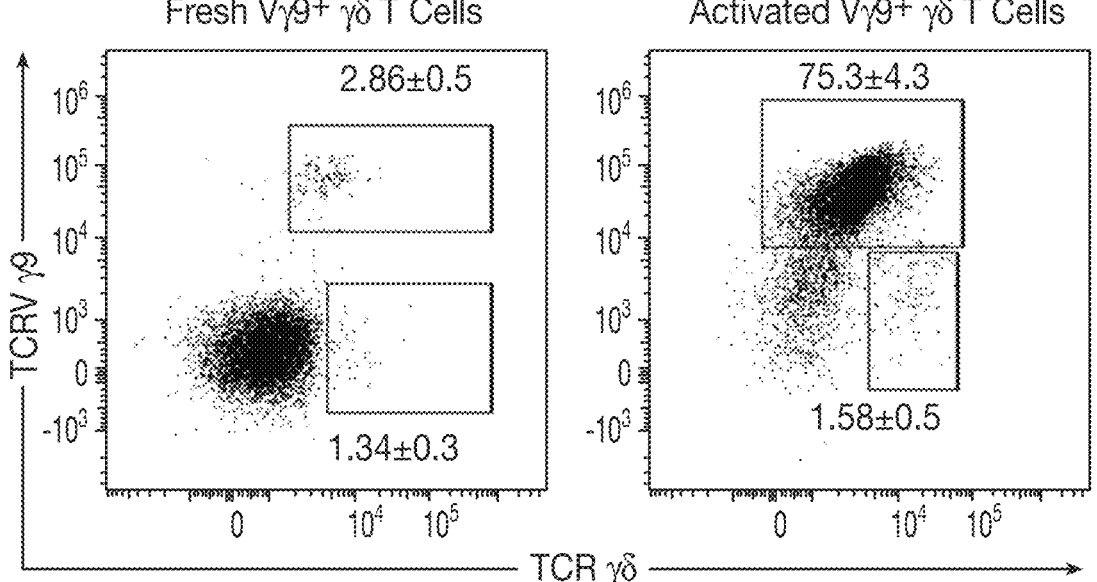
FIG. 2 shows a graph demonstrating that Zoledronic acid selectively expands Vγ9Vδ2 T cells from whole peripheral blood mononuclear cells (PBMCs).

Numbers in representative dot plots show the frequency (mean±SEM) of Vγ9+ and Vγ9− TCR γδ T cells among total PBMCs on day 0 (left) and day 14 of PBMCs cultured with Zoledronic acid+IL-2+IL-15 (right). Represented data is mean (±SEM) of five donors (n=5) from a single experiment (FIG. 2).

Figure 3A:
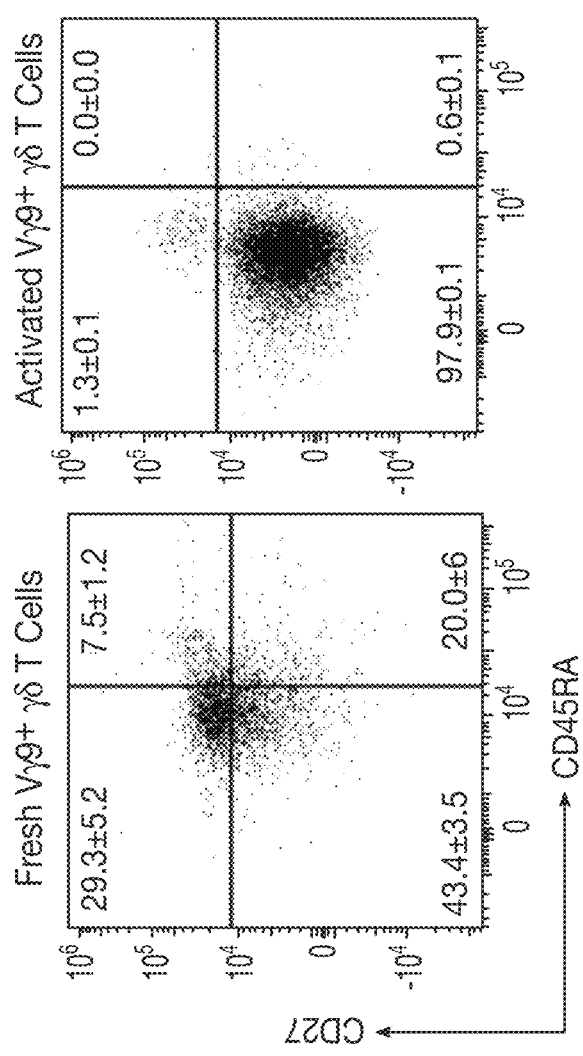
FIGS. 3A-3E show phenotypic characterization of Vγ9+ γδ T cells.
Figure 3A:
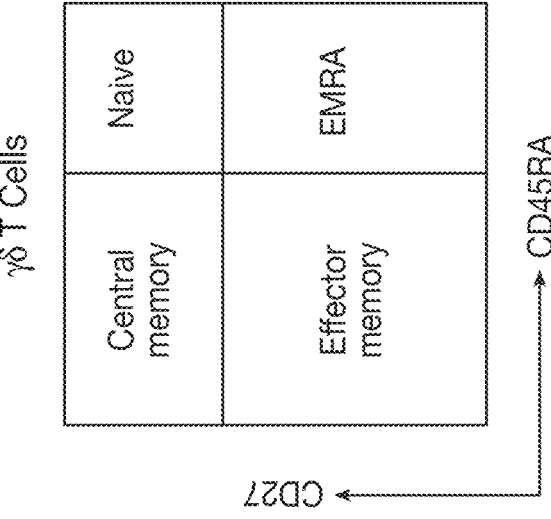
Figure 3B:
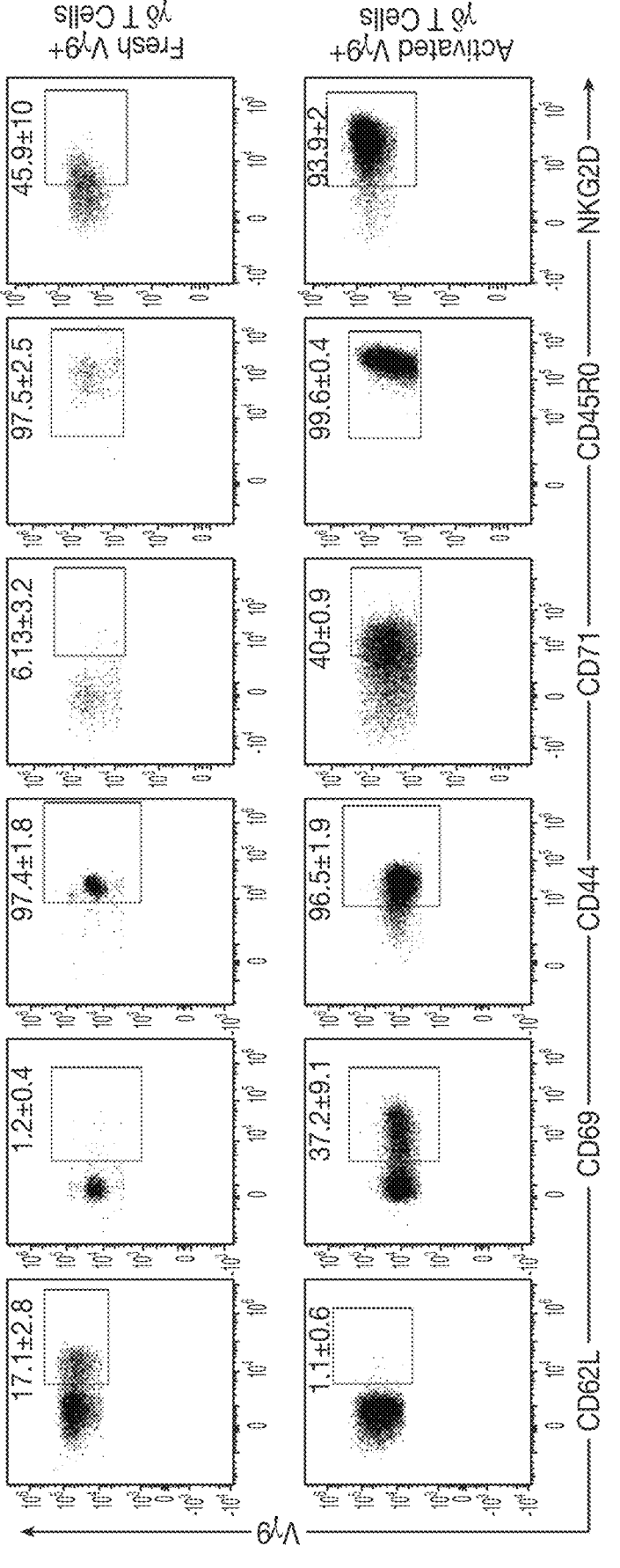
Figure 3C:
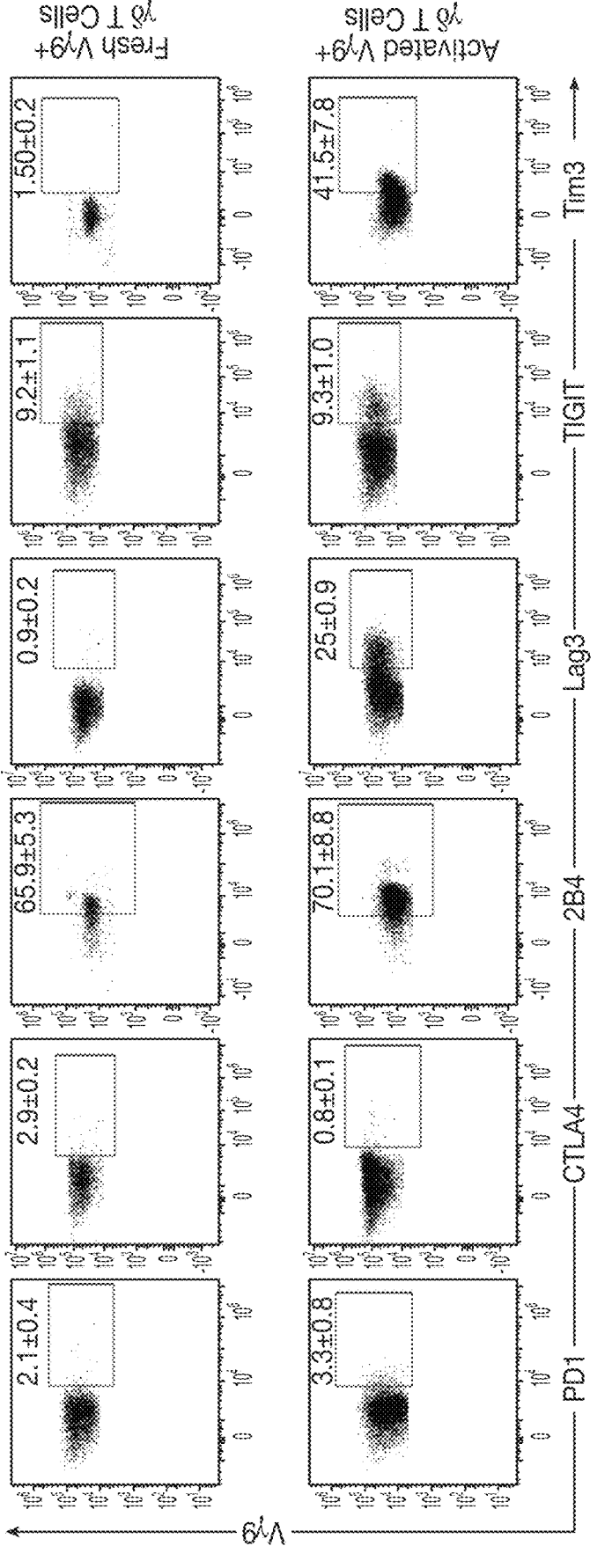
Figure 3D:
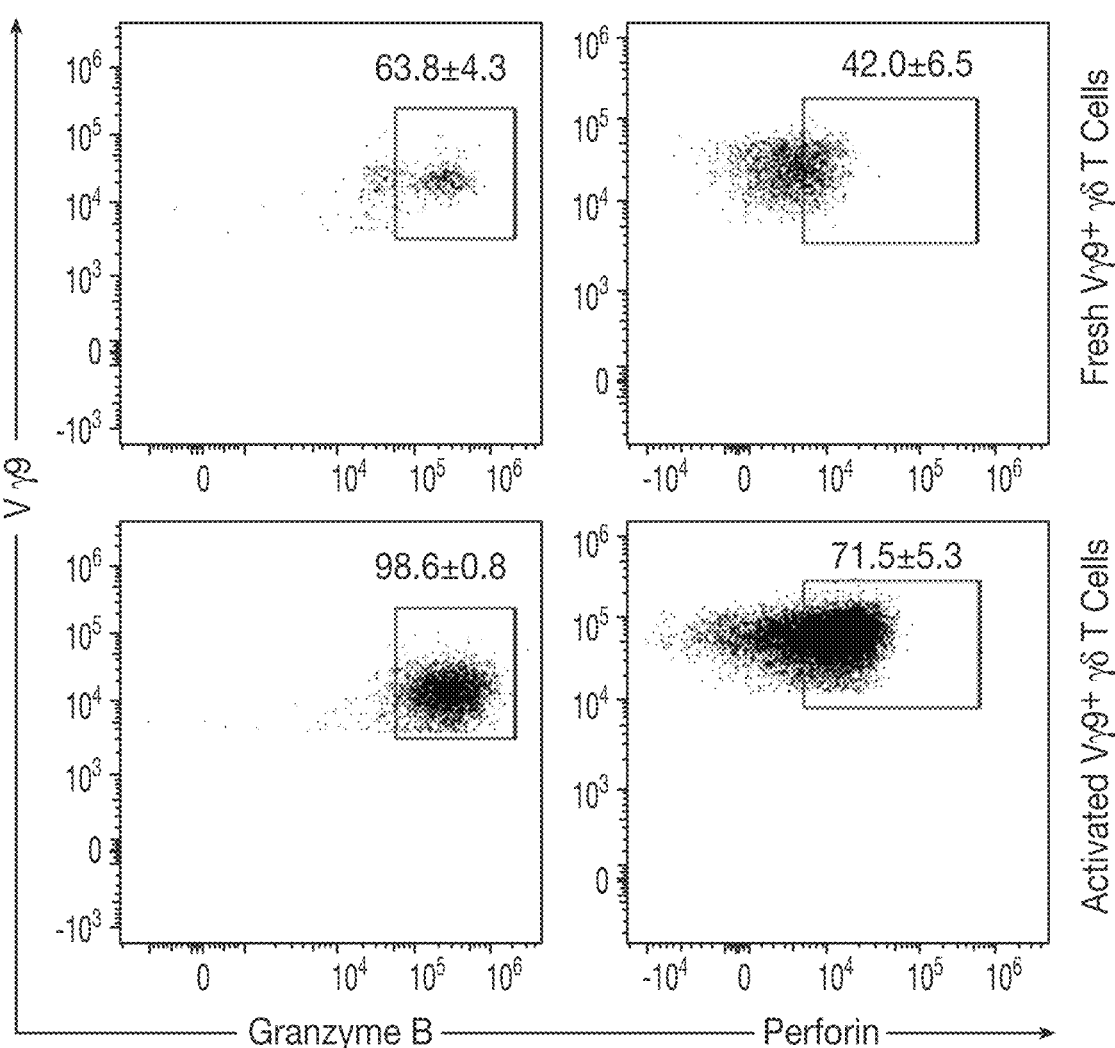
Figure 3E:
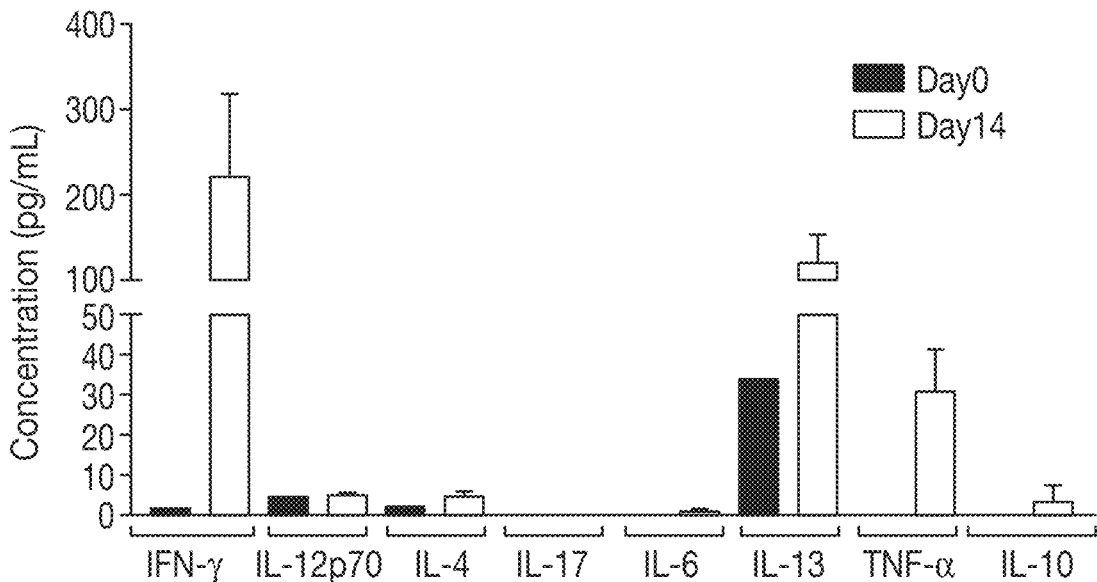

FIGS. 3A to 3E demonstrate the phenotypic characterization of Vγ9+ γδ T cells. FIG. 3A shows a schematic depiction of gates used to describe the differentiation of γδ T cells (left). Representative FACS-dot plots show the differentiation profile of Vγ9+ γδ T cells from fresh PBMCs (left) and PBMCs cultured ex vivo with Zoledronic acid+IL-2+IL-15 for 14 days (right). Numbers in quadrants mirror the frequency (mean±SEM) of the respective population among fresh and activated Vγ9⁺ γδ T cells. Represented data is mean (±SEM) of five donors (n=5) from a single experiment. FIG. 3B shows numbers in representative dot plots mirroring the frequency (mean±SEM) of Vγ9⁺ γδ T cells positive for respective activation marker either from fresh PBMCs (upper row) or PBMCs cultured with Zoledronic acid+IL-2+IL-15 for 14 days (lower row). Represented data is mean (±SEM) of seven donors (n=7) for CD62L, CD69, CD44 expression data from two independent experiments. n=5 donors for NKG2D and 2 donors for CD45RO and CD71 expression data respectively from a single experiment. FIG. 3C shows numbers above gates in dot plots depicting the frequency (mean±SEM) of Vγ9⁺ γδ T cells positive for respective inhibitory receptor surface expression either from fresh PBMCs (upper row) or PBMCs cultured with Zoledronic acid+IL-2+IL-15 for day 14 days (lower row). Data shown here is mean (±SEM) of five donors (n=5) for PD1, CTLA4, TIGIT and LAG3 surface expression and seven donors (n=7) for 2B4 and TIM3 surface expression data from two independent experiments. FIG. 3D shows representative FACS dot plots demonstrating the frequency (mean±SEM) of Vγ9⁺ γδ T cells expressing intracellular Granzyme B (left column) and Perforin (right column) from fresh PBMCs (upper row) and PBMCs cultured ex vivo with Zoledronic acid+IL-2+IL-15 for 14 days (lower row). Depicted data is mean (±SEM) of four (n=4) and seven (n=7) donors for Granzyme B and Perforin data respectively from two independent experiments. FIG. 3E shows bars representing the mean (±SEM) concentration (pg/mL) of cytokine in the cell culture supernatant on day 0 and day 14 of PBMCs culture with Zoledronic acid+IL-2+IL-15. Represented data is mean (±SEM) of four wells (n=4) from a single donor.

Figure 4:
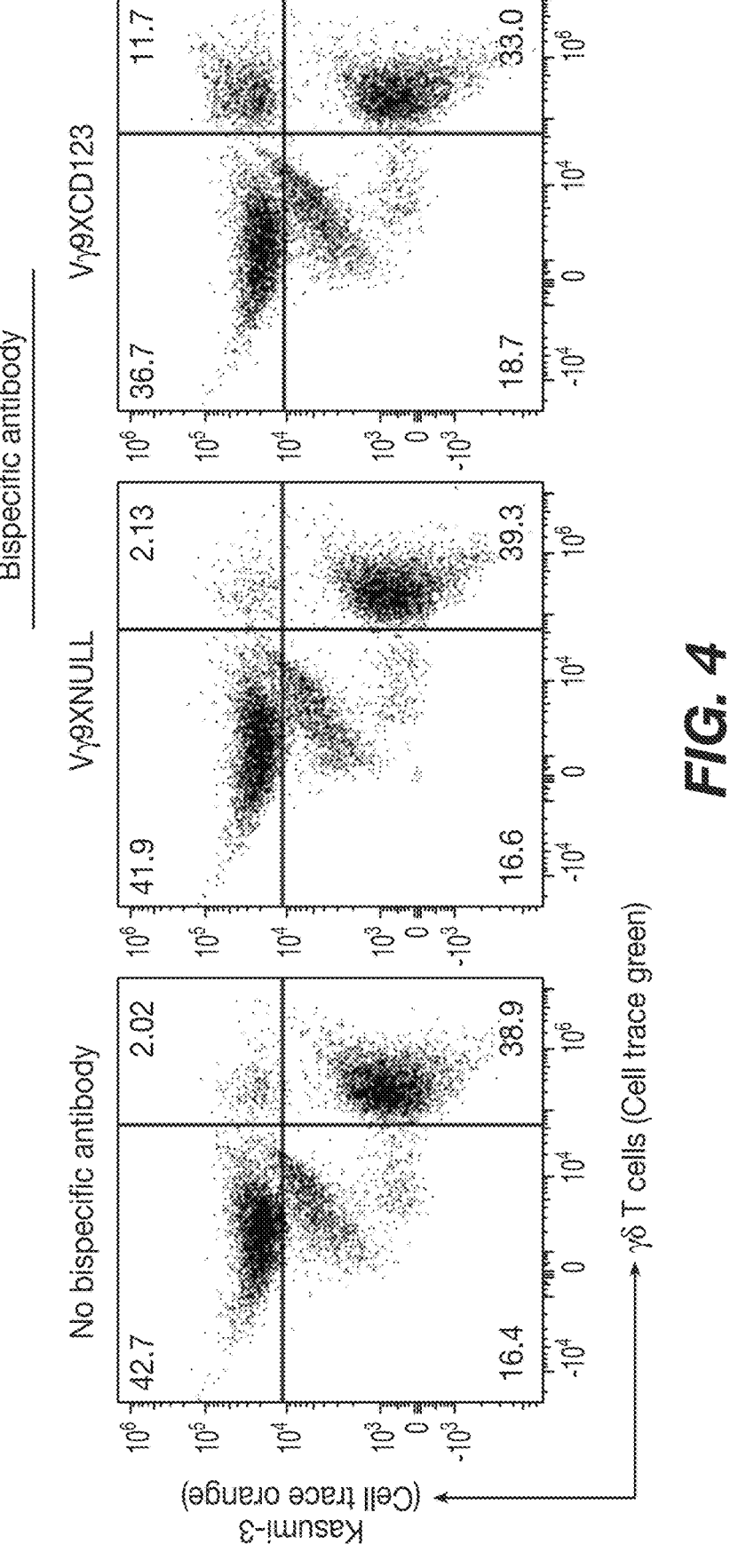
FIG. 4 shows a histogram demonstrating that VG1 (an anti-TRGV9/anti-CD123 bispecific antibody) recruits Vγ9+ T cells as demonstrated by conjugate formation between γδ T cells and Kasumi-3 cells.

FIG. 4 shows that the anti-TRGV9/anti-CD123 bispecific antibody recruits γδ T cells into biphasic cell-cell conjugate. γδ T cells (effector cells) were isolated from whole fresh PBMCs using EASYSEP Human γδ T cell isolation kit (Stem cell Technologies) according to manufacturer instructions. γδ T cells were labelled with 0.25 μM CELL-TRACKER™ Green CMFDA Dye for 30 min. and Kasumi-3 (Targets) cells were labelled with 1 μM CELL-TRACKER™ Orange CMRA Dye in RPMI medium for 30 minutes at 37° C. Both labeled γδ T cells and Kasumi-3 were co-cultured. Labeled Effector (E) and Target (T) cells at an E:T ratio of 1:1 (50,000 cells of each cell type/well) with 1 microgram per ML of bispecific antibody (anti-TRGV9/anti-CD123, anti-TRGV9/anti-NULL) and incubated at 37° C. for 1 hour. At the end of the incubation, cells were spun down at 1200 rpm for 5 minutes and resuspended in FACS buffer. Cells were acquired utilizing the flow cytometer and analysis was performed using FLOWJO analysis software. Numbers in quadrants of representative FACS plots show the frequency of recruited or non-recruited cells to the cell-cell conjugate either in the absence (left dot plot) or presence of anti-TRGV9/anti-NULL (middle dot plot) and anti-TRGV9/anti-CD123 (right dot plot) bispecific antibody. Data shown here is from a single experiment.

Figure 5A:
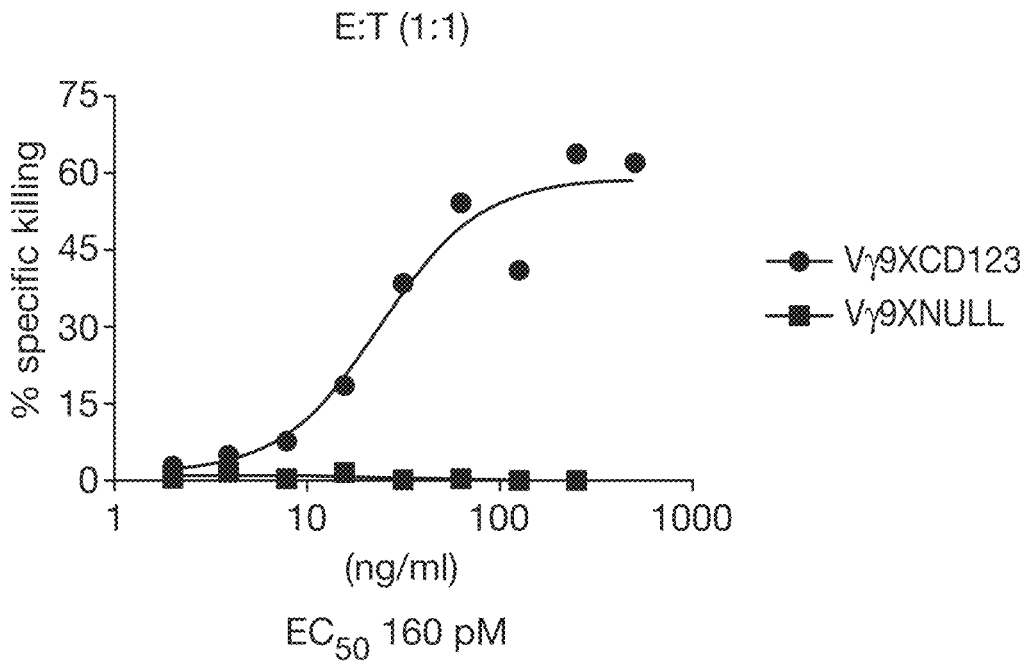
FIGS. 5A-5C show graphs demonstrating VG1 (anti-TRGV9/anti-CD123 bispecific antibody) bispecific mediated γδ T cell cytotoxicity against Kasumi-3 cells at different effector to target cell ratios (1:1 for FIG. 5A; 5:1 for FIG. 5B; and 10:1 for FIG. 5C).
Figure 5B:
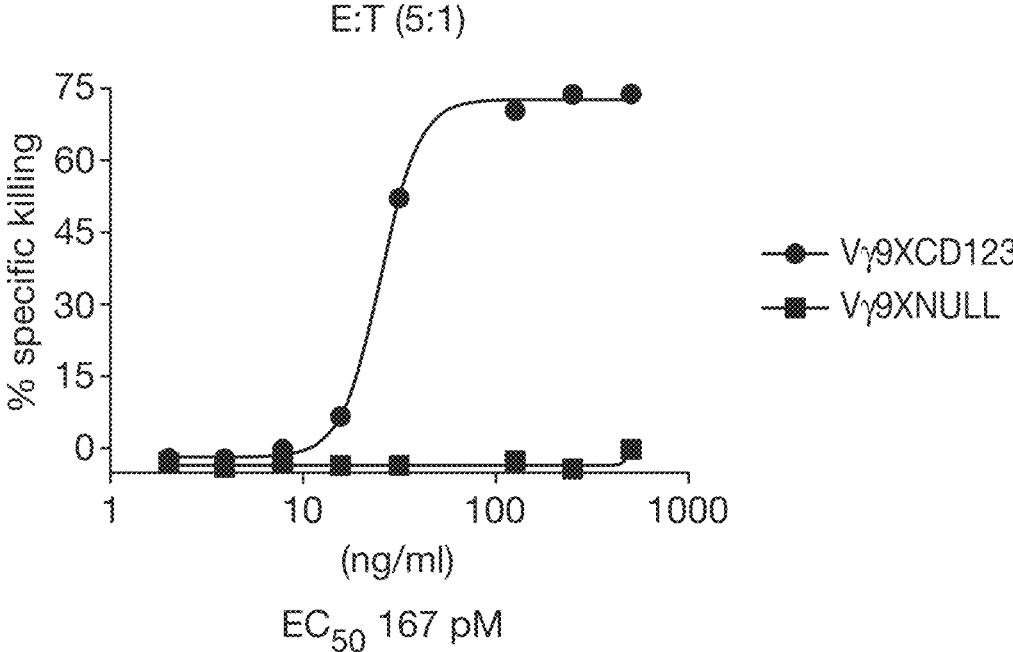
Figure 5C:
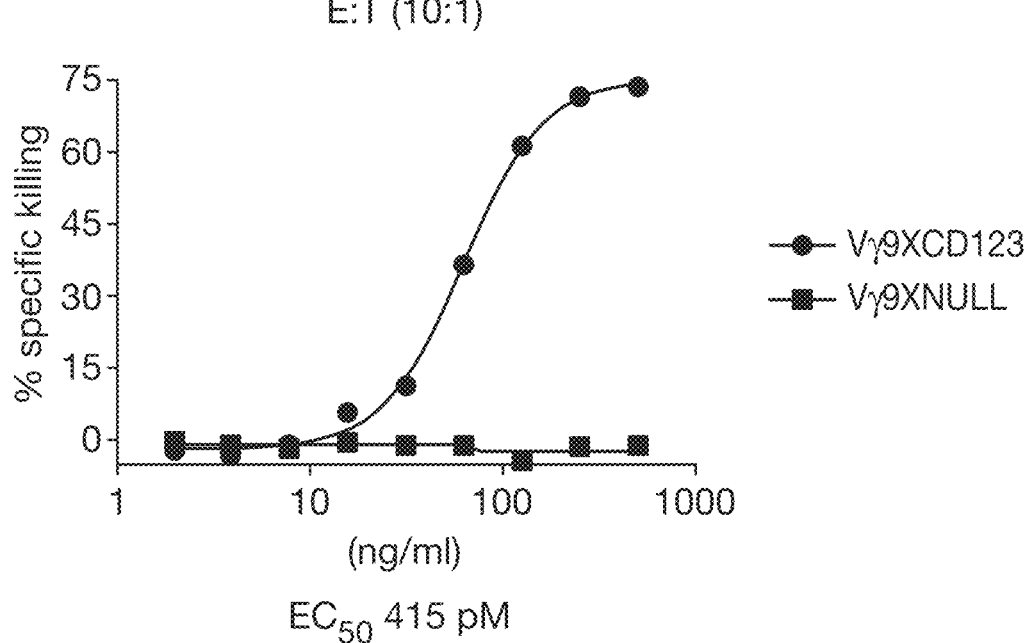

Example 2.4: Evaluation of Binding and Cytotoxic Properties of the Anti-TRGV9/Anti-CD123 Bispecific Antibody Using Kasumi-3 Cells and Human γδ T Cells FIG. 5 shows that the anti-TRGV9/anti-CD123 bispecific antibody mediates γδ T cell cytotoxicity against CD123 expressing Kasumi-3 cells in vitro. Enriched γδ T cells (Effectors), isolated from PBMCs cultured with Zoledronic acid+IL-2+IL-15 for 12 days, were co-cultured with CFSE labelled Kasumi-3 cells (Targets) at 1:1, 5:1 and 10:1 E:T ratios in the presence of various concentrations of the bispecific antibody for 24 hours. Dose response curves show anti-TRGV9/anti-CD123 and anti-TRGV9/anti-NULL bispecific mediated γδ T cell cytotoxicity against CD123 expressing Kasumi-3 cells in a dose dependent manner at 1:1 (FIG. 5A) 5:1 (FIG. 5B) and 10:1 (FIG. 5C) E:T ratios. Cytotoxicity values represented here were subtracted of basal cytotoxicity value observed in the absence of bispecific antibody. EC₅₀ values were calculated as described in methods. Representative data shown here are from a single experiment.

Figure 6A:
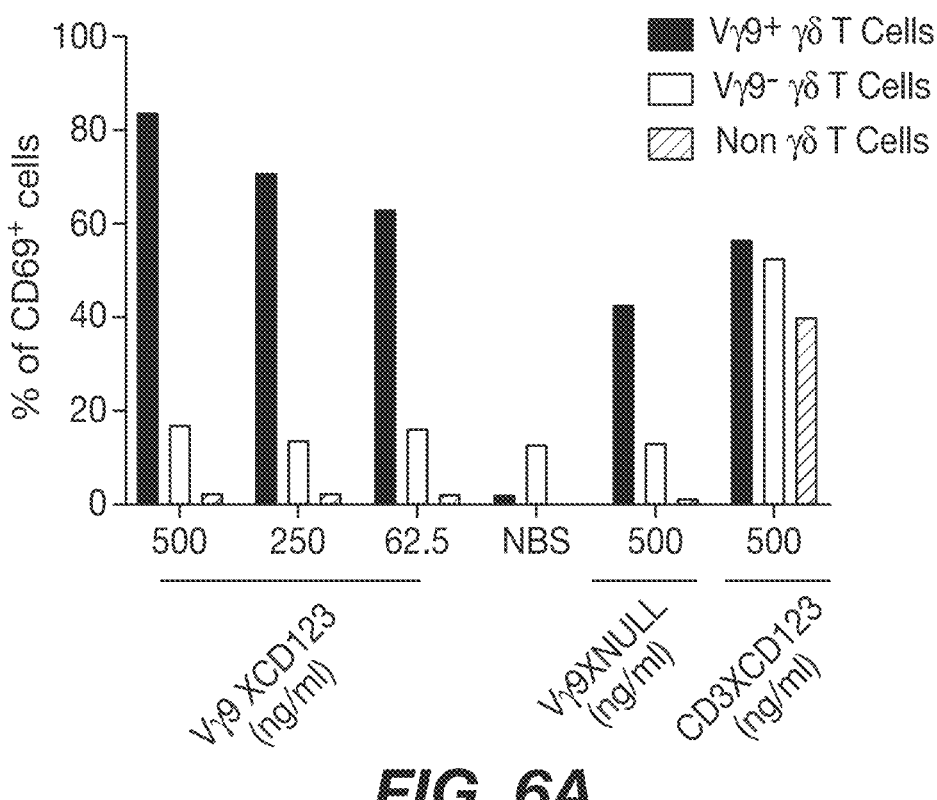
FIGS. 6A-6C show graphs demonstrating CD69 (FIG. 6A), CD25 (FIG. 6B), or Granzyme B (FIG. 6C) expression on Vγ9+ γδ T cells, non-Vγ9+ γδ T cells, and Pan-T cells (non γδ T cells) co-cultured with Kasumi-3 cells and VG1, VG3, or no bispecific antibody.
Figure 6B:
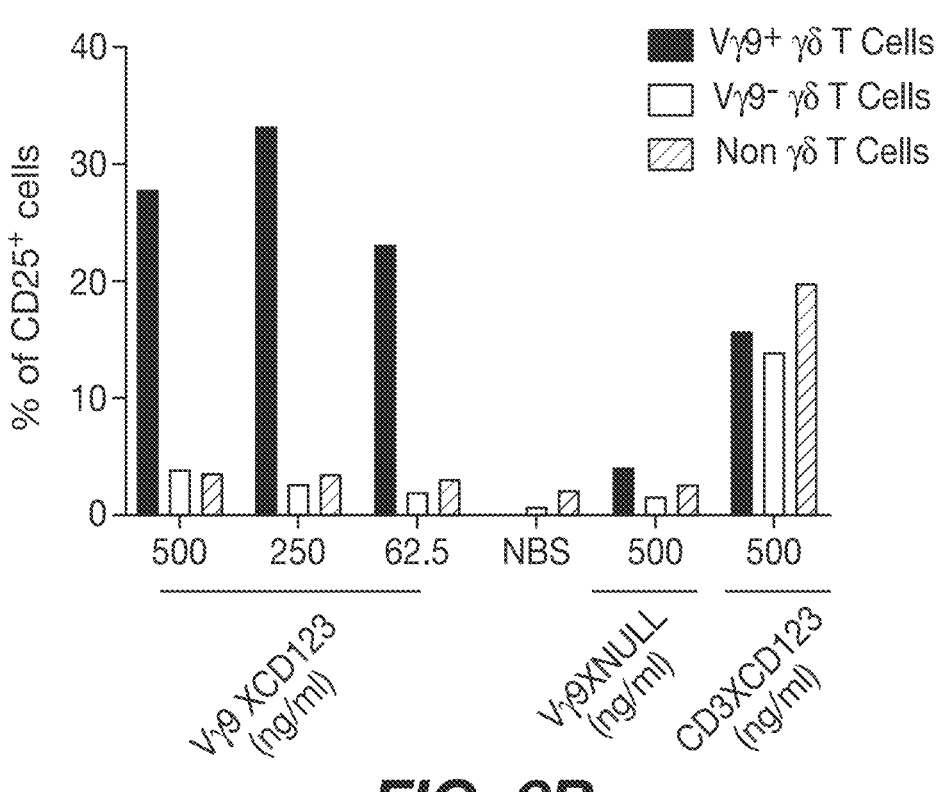
Figure 6C:
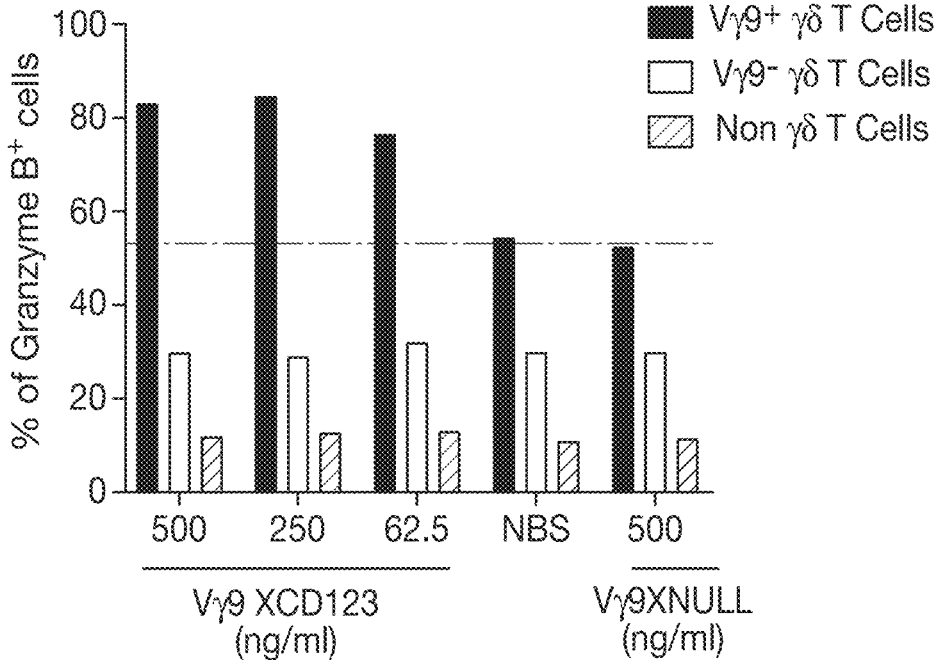

FIG. 6 shows that the anti-TRGV9/anti-CD123 bispecific selectively activates Vγ9⁺ γδ T cells. Whole fresh PBMCs were co-cultured with Kasumi-3 cells in the presence of various concentrations of the anti-TRGV9/anti-CD123 bispecific antibody for 72 hours at 37° C. As a positive and negative control, co-cultured cells were stimulated with anti-CD3/anti-CD123 and anti-TRGV9/anti-NULL bispecifics for 72 hours at 37° C. Bars represent the frequency of Vγ9⁺, Vγ9⁻ γδ T cells and non-γδ T cells positive for CD69 (FIG. 6A, left), CD25 (FIG. 6A, right) surface expression, and intracellular Granzyme B (FIG. 6B) expression. The dotted line in FIG. 6B indicates the basal levels of Granzyme B expression in Vγ9⁺ γδ T cells. NBS denotes no bispecific antibody added to the co-cultured cells. Data shown here are from a single experiment.

Example 3: Humanization of Anti-TRGV9 Clone 7A5

Mouse anti-human Vγ9 clone LP7A5 (7A5) binds to the antigen (Vγ9-Vδ2 fused to human Fc) with a K_D of 1.9 nM. Humanization of murine 7A5 was performed following the approach outlined by Singh et al., mAbs J, 2015. Based on sequence conservation, the heavy chain germline IGHV1-8*01 was chosen for framework adaption. Three somatic hypermutation sites in the heavy chain were chosen for binary library design. A potential Iso-Asp isomerization site (DG motif) in the CDR-H2 was also included in the design to mitigate this potential liability. For light chain frame adaption, IGKV4-1*01 was chosen as the closest homologous human germline. Owing to high sequence homology, only one position (Asn22) was included in the library design. The variants were cloned and expressed in E. coli. The supernatants were screened in single point ELISA and the periplasmic preparation was used for dose response. A mouse/human chimeric 7A5 Fab was used as parental control. Clone 7A5_17 (7A5_var17) maintained the binding activity similar to murine 7A5 and was converted to IgG for additional profiling. The EC₅₀ for primary cell binding for clone 7A5_17 and 7A5 were 200 pM and 159 pM.

The sequences obtained are shown in Tables 12-15. The three VH CDR and three VL CDR sequences of the humanized anti-human TRGV9 clone 7A5_var17 are shown in Table 12 (two versions, depending on CDR type, are provided); and the VH and VL sequences of the humanized anti-human TRGV9 clone 7A5_var17 are shown in Table 14 (SEQ ID NOs:65 and 66, respectively). The three VH CDR and three VL CDR sequences of the humanized anti-human TRGV9 clone 7A5_var29 are shown in Table 13 (two versions, depending on CDR type, are provided); and the VH and VL sequences of the humanized anti-human TRGV9 clone 7A5_var29 are shown in Table 15 (SEQ ID NOs:67 and 68, respectively).

TABLE 12

CDR sequences of humanized anti-human
TRGV9 clone 7A5_var 17.

| mAb ID | HCDR1 | SEQ ID NO: | HCDR2 | SEQ ID NO: | HCDR3 | SEQ ID NO: |
|---|---|---|---|---|---|---|
| 7A5_var17 (CDR v.1) | GFTFTDHY | 60 | IYPGSGNT | 61 | ARNYGD YTIDF | 62 |
| 7A5_var17 (CDR v.2) | DHYIN | 1 | QIYPGSGNT YYNQKFKG | 76 | NYGDYT IDF | 3 |

| mAb ID | LCDR1 | SEQ ID NO: | LCDR2 | SEQ ID NO: | LCDR3 | SEQ ID NO: |
|---|---|---|---|---|---|---|
| 7A5_var17 (CDR v.1) | QSVLYSSN NKNY | 63 | WAS | 64 | QQYYRYHT | 6 |
| 7A5_var17 (CDR v.2) | KSSQSVLYS SNNKNYLA | 77 | WASTRES | 5 | QQYYRYHT | 6 |

TABLE 13

CDR sequences of humanized anti-human
TRGV9 clone 7A5_var 29.

| mAb ID | HCDR1 | SEQ ID NO: | HCDR2 | SEQ ID NO: | HCDR3 | SEQ ID NO: |
|---|---|---|---|---|---|---|
| 7A5_var29 (CDR v.1) | GFTFTDHY | 60 | IYPGSGNT | 61 | ARNYGD YTIDF | 62 |
| 7A5_var29 (CDR v.2) | DHYIN | 1 | QIYPGSGNT YYNQKFKG | 76 | NYGDYT IDF | 3 |

| mAb ID | LCDR1 | SEQ ID NO: | LCDR2 | SEQ ID NO: | LCDR3 | SEQ ID NO: |
|---|---|---|---|---|---|---|
| 7A5_var29 (CDR v.1) | QSVLYSSN NKNY | 63 | WAS | 64 | QQYYRYHT | 6 |
| 7A5_var29 (CDR v.2) | KSSQSVLYS SNNKNYLA | 77 | WASTRES | 5 | QQYYRYHT | 6 |

TABLE 14

Heavy chain and light chain V-region sequences of humanized anti-
human TRGV9 clone 7A5_var17.

| mAb ID | Heavy Chain V-region Amino Acid Sequence | SEQ ID NO: |
|---|---|---|
| 7A5_var17 | QVQLVQSGAE VKKPGASVKV SCKASGFTFT DHYINWVRQA TGQGLEWMGQ IYPGSGNTYY NQKFKGRVTM TRDTSISTAY MELSSLRSED TAVYYCARNY GDYTIDFWGQ GTSVTVSS | 65 |

| mAb ID | Light Chain V-region Amino Acid Sequence | SEQ ID NO: |
|---|---|---|
| 7A5_var17 | DIVMTQSPDS LAVSLGERAT INCKSSQSVL YSSNNKNYLA WYQQKPGQPP KLLIYWASTR ESGVPDRFSG SGSGTDFTLT ISSLQAEDVA VYYCQQYYRY HTFGTGTKLE IK | 66 |

TABLE 15

Heavy chain and light chain V-region sequences of
humanized anti-human TRGV9 clone 7A5_var29.

| mAb ID | Heavy Chain V-region Amino Acid Sequence | SEQ ID NO: |
|---|---|---|
| 7A5_var29 | QVQLVQSGAE VKKPGASVKV SCKASGFTFT DHYINWVRQA TGQGLEWMGQ IYPGSGNTYY NQKFKGRVTM TRNTSISTAY MELSSLRSED TAVYYCARNY GDYTIDFWGQ GTSVTVSS | 67 |

| mAb ID | Light Chain V-region Amino Acid Sequence | SEQ ID NO: |
|---|---|---|
| 7A5_var29 | DIVMTQSPDS LAVSLGERAT ISCKSSQSVL YSSNNKNYLA WYQQKPGQPP KLLIYWASTR ESGVPDRFSG SGSGTDFTLT ISSLQAEDVA VYYCQQYYRY HTFGTGTKLE IK | 68 |

Example 4—Multispecific Antibodies that Bind
TRGV9 and TAA1

T cell acute lymphoblastic leukemia (T-ALL) are aggres-
sive neoplasms characterized by the proliferation and accumulation in blood, bone marrow and lymphoid organs of T
cell precursors abnormally arrested in differentiation. Cur-
rent first-line chemotherapy regimens provide overall sur-
vival rates of approximately 85-90% in children and about
50% in adults (Pui et al. *J. Clin. Oncol. Off J. Am. Soc. Clin.*
*Oncol.* 2015; 33(27):2938-2948; Litzow et al. *Blood.* 2015;
126(7):833-841). T-ALL represent a heterogeneous group of
malignancies classified into different molecular subtypes on
the basis of aberrant expression of specific driver oncogenic
transcription factors and global transcriptomic signatures
(Belver et al. *Nat. Rev. Cancer.* 2016; 16(8):494-507; Nat.
Genet. 2017; 49(8):1211-1218). T-cells are the most abun-
dant (~75% of blood lymphocytes) and potent immune killer
cells. The role of effector T-cells in the anti-cancer immune
response is strongly supported by in vitro studies and the
observation that a high infiltration of CD8$^+$ T cells in several
types of cancers correlates with a favorable clinical prog-
nostic.

V79Vδ2 T lymphocytes, a major γ/δ T cell subset in
humans, recognize phosphoantigens, certain tumor cells,
and cells treated with aminobisphosphonates. This cell
population displays cytolytic activity against various tumor
cells. The γ/δ TCR is a heterodimeric TCR complex com-
posed of covalently bound γ and δ chains involved in antigen
recognition and the non-covalently associated monomorphic
proteins CD3δ, γ, ε, and (chains. The Vγ9 TCR is a variant
of the TCR γ chain expressed on a subset of γ/δ T cells.

Examples 4.1-4.6 are based on the premise that γδ T cells,
which mainly express heterodimers of TRGV9 and Vδ2
chains demonstrate potent anti-tumor functions. These cells
express TCR-TRGV9 and the majority, if not all, of these
cells exhibit efficient cytotoxicity of tumor target cells. This
ability is then harnessed using bispecific antibodies con-
structed such that one arm binds to the TRGV9 structure and
the other arm binds to a T-cell Tumor-Associated Antigen
(TAA1) expressed by the tumor cells (e.g., T cell lympho-
mas). Thus, the bispecific antibody bridges the effector and
target cells together, resulting in tumor cell killing. This
mechanism of action is described in the schematic outlined
in FIG. 1.

The subsequent examples can be divided into the follow-
ing categories: (1) Generation and characterization of bis-
pecific antibodies capable of binding to the TRGV9 arm
expressed on γδ T cells and TAA1 on αβ T cells (Examples
4.1, 4.2, and 4.3); and (2) Evidence for bispecific antibody
binding and bispecific antibody-enabled target cell killing by
γδ T cells expanded in vitro (Example 4.4 and 4.5).

γδ T cell stimulation and expansion was performed.
Expansion of Vγ9-Vδ2 T cells was carried out by treating
PBMCs in complete RPMI media containing rhIL-2 (1000 IU/mL), rhIL-15 (10 ng/mL) and zoledronic acid (5 μM) for
14 days.

Example 4.1: Production and De Novo Sequencing
of Anti-TRGV9 Mab

The mouse IgG1 anti-human T cell receptor anti-TRGV9
clone 7A5 was sourced commercially. Sample preparation
and LC-MS/MS analysis were performed by Lake Pharma
(San Carlos, CA). The sample was reduced and alkylated,
divided into seven aliquots, and proteolytically digested
with Trypsin/LysC, Chymotrypsin, LysC, Pepsin, and AspN,
Elastase, and Proteinase K enzymes. Resulting peptides
were desalted using a ZIPTIP C18 Pipette Tips and separated
on-line using reverse phase chromatography. Mass spec-
trometry was performed on THERMO Q-EXACTIVE spec-
trometer using HCD fragmentation. MS data sets were
analyzed using PEAKS software by matching de novo
sequence tags to an IMGT-based antibody sequences data-
base. Gaps in the sequence were assigned using Contig
sequence assembly of de novo identified peptides. All CDRs
and hyper-mutations were confirmed by inspecting the
MS/MS spectra.

The three VH CDR and three VL CDR sequences of the
mouse anti-human TRGV9 clone 7A5 (LP7A5_1) are pre-
viously shown in Table 3 (SEQ ID NOs:1-6, respectively);
and the VH and VL sequences of the mouse anti-human
TRGV9 clone 7A5 (LP7A5_1) are previously shown in
Table 7 (SEQ ID NOs:7 and 8, respectively).

Example 4.2: Production and De Novo Sequencing
of Anti-TAA1 Mab

The mouse IgG2a monoclonal anti-human TAA1 clone
was commercially sourced. The VH CDR1-3, VL CDR1-3,
VH and VL sequences of this clone (data not shown) were
obtained using a similar procedure as described above for
the anti-TRGV9 clone 7A5.

Example 4.3: Preparation of
Anti-TRGV9/Anti-TAA1 Bispecific Antibodies

The variable region sequence of clone 7A5 (anti-TRGV9
antibody) and the TAA1 clone (anti-TAA1 antibody) were
used to generate a bispecific antibody to be tested for T cell
re-directed killing of acute myeloid leukemia (AML) cells.
The bispecific antibodies VG4 (anti-TRGV9 x TAA1) and
VG3 (anti-TRGV9 x Null) were produced as full-length
antibodies in the knob-into-hole format as human IgG4.
Nucleic acid sequences encoding variable regions were
sub-cloned into a custom mammalian expression vectors
containing constant region of human IgG4 expression cas-
settes using standard PCR restriction enzyme based standard
cloning techniques, and sequenced verified. The bispecific
antibodies were expressed by transient transfection in a
Chinese hamster ovary (CHO) cell line. Sequences of certain
bispecific antibodies expressed in the CHO cells are shown
in Table 16 below. Certain individual heavy and light chain
antibody sequences are shown in Table 17 below

TABLE 16

| | Sequences of antibodies expressed in CHO cells | | |
|---|---|---|---|
| mAb ID | 'Knob' arm and 'hole' arm amino acid sequence | | SEQ ID NO: |
| Anti-TRGV9_7A5_1 (half-mAb) | Heavy Chain A | MAWVWTLLFLMAAAQSIQAEVQLQQSGAELARPGA SVKLSCKASGFTFTDHYINWVKQRTGQGLEWIGQI YPGDGNTYYNQKFKGKATLTADKSSSTAYMQLSSL TSEDSAVYFCAPNYGDYTIDFWGQGTSVTVSSAST | 78 |

TABLE 16-continued

| Sequences of antibodies expressed in CHO cells | | | |
|---|---|---|---|
| mAb ID | 'Knob' arm and 'hole' arm amino acid sequence | | SEQ ID NO: |
| | | KGPSVFPLAPSSKSTSGGTAALGCLVKDYFPEPVT VSWNSGALTSGVHTFPAVLQSSGLYSLSSVVTVPS SSLGTQTYICNVNHKPSNTKVDKKVEPKSCDKTHT CPPCPAPEAAGGPSVFLFPPKPKDTLMISRTPEVT CVVVSVSHEDPEVKFNWYVDGVEVHNAKTKPREEQ YNSTYRVVSVLTVLHQDWLNGKEYKCKVSNKALPA PIEKTISKAKGQPREPQVYVPPSREEMTKNQVSL TCLVKGFYPSDIAVEWESNGQPENNYKTTPPVLDS DGSFALVSKLTVDKSRWQQGNVFSCSVMHEALHNR FTQKSLSLSPGK | |
| | Light Chain | MAWVWTLLFLMAAAQSIQADIVMSQSPSSLAVSVG EKVTMSCKSSQSLLYSSNQKNYLAWYQQKPGQSPK LLIYWASTRESGVPDRFTGSGSGTDFTLTISSVKA EDLAVYYCQQYYRYHTFGTGTKLEIKRTVAAPSVF IFPPSDEQLKSGTASVVCLLNNFYPREAKVQWKVD NALQSGNSQESVTEQDSKDSTYSLSSTLTLSKADY EKHKVYACEVTHQGLSSPVTKSFNRGEC | 79 |
| Anti-TRGV9_7A5_var 17 | Heavy Chain A | MAWVWTLLFLMAAAQSIQAQVQLVQSGAEVKKPGA SVKVSCKASGFTFTDHYINWVRQATGQGLEWMGQI YPGSGNTYYNQKFKGRVTMTRDTSISTAYMELSSL RSEDTAVYYCARNYGDYTIDFWGQGTSVTVSSAST KGPSVFPLAPSSKSTSGGTAALGCLVKDYFPEPVT VSWNSGALTSGVHTFPAVLQSSGLYSLSSVVTVPS SSLGTQTYICNVNHKPSNTKVDKKVEPKSCDKTHT CPPCPAPEAAGGPSVFLFPPKPKDTLMISRTPEVT CVVVSVSHEDPEVKFNWYVDGVEVHNAKTKPREEQ YNSTYRVVSVLTVLHQDWLNGKEYKCKVSNKALPA PIEKTISKAKGQPREPQVYVPPSREEMTKNQVSL TCLVKGFYPSDIAVEWESNGQPENNYKTTPPVLDS DGSFALVSKLTVDKSRWQQGNVFSCSVMHEALHNR FTQKSLSLSPGK | 80 |
| | Light Chain | MAWVWTLLFLMAAAQSIQADIVMTQSPDSLAVSLG ERATINCKSSQSVLYSSNNKNYLAWYQQKPGQPPK LLIYWASTRESGVPDRFSGSGSGTDFTLTISSLQA EDVAVYYCQQYYRYHTFGTGTKLEIKRTVAAPSVF IFPPSDEQLKSGTASVVCLLNNFYPREAKVQWKVD NALQSGNSQESVTEQDSKDSTYSLSSTLTLSKADY EKHKVYACEVTHQGLSSPVTKSFNRGEC | 81 |
| Anti-TRGV9_7A5_var 19 | Heavy Chain A | MAWVWTLLFLMAAAQSIQAQVQLVQSGAEVKKPGA SVKVSCKASGFTFTDHYINWVRQATGQGLEWMGQI YPGSGNTYYNQKFKGRVTMTRNTSISTAYMELSSL RSEDTAVYYCARNYGDYTIDFWGQGTSVTVSSAST KGPSVFPLAPSSKSTSGGTAALGCLVKDYFPEPVT VSWNSGALTSGVHTFPAVLQSSGLYSLSSVVTVPS SSLGTQTYICNVNHKPSNTKVDKKVEPKSCDKTHT CPPCPAPEAAGGPSVFLFPPKPKDTLMISRTPEVT CVVVSVSHEDPEVKFNWYVDGVEVHNAKTKPREEQ YNSTYRVVSVLTVLHQDWLNGKEYKCKVSNKALPA PIEKTISKAKGQPREPQVYVPPSREEMTKNQVSL TCLVKGFYPSDIAVEWESNGQPENNYKTTPPVLDS DGSFALVSKLTVDKSRWQQGNVFSCSVMHEALHNR FTQKSLSLSPGK | 82 |
| | Light Chain | MAWVWTLLFLMAAAQSIQADIVMTQSPDSLAVSLG ERATISCKSSQSVLYSSNNKNYLAWYQQKPGQPPK LLIYWASTRESGVPDRFSGSGSGTDFTLTISSLQA EDVAVYYCQQYYRYHTFGTGTKLEIKRTVAAPSVF IFPPSDEQLKSGTASVVCLLNNFYPREAKVQWKVD NALQSGNSQESVTEQDSKDSTYSLSSTLTLSKADY EKHKVYACEVTHQGLSSPVTKSFNRGEC | 83 |
| Anti-TAA1 (half-mAb) | Heavy Chain B | SEQUENCE NOT SHOWN | — |
| | Light Chain | SEQUENCE NOT SHOWN | — |
| Anti-RSV (half-mAb) | Heavy Chain B | MAWVWTLLFLMAAAQSIQAQITLKESGPTLVKPTQ TLTLTCTFSGESLSTSGMGVSWIRQPPGKALEWLA HIYWDDDKRYNPSLKSRLTITKDTSKNQVVLTMTN MDPVDTATYYCARLYGFTYGFAYWGQGTLVTVSSA STKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPEAAGGPSVFLEPPKPKDTLMISRTPE | 86 |

TABLE 16-continued

| | | Sequences of antibodies expressed in CHO cells | |
| --- | --- | --- | --- |
| mAb ID | | 'Knob' arm and 'hole' arm amino acid sequence | SEQ ID NO: |
| | | VTCVVVSVSHEDPEVKFNWYVDGVEVHNAKTKPRE EQYNSTYRVVSVLTVLHQDWLNGKEYKCKVSNKAL PAPIEKTISKAKGQPREPQVYVLPPSREEMTKNQV SLLCLVKGFYPSDIAVEWESNGQPENNYLTWPPVL DSDGSFFLYSKLTVDKSRWQQGNVFSCSVMHEALH NHYTQKSLSLSPGK | |
| | Light Chain | METHSQVFVYMLLWLSGVEGDIVMTQSPDSLAVSL GERATINCRASQSVDYNGISYMHWYQQKPGQPPKL LIYAASNPESGVPDRFSGSGSGTDFTLTISSLQAE DVAVYYCQQIIEDPWTEGQGTKVEIKRTVAAPSVF IFPPSDEQLKSGTASVVCLLNNFYPREAKVQWKVD NALQSGNSQESVTEQDSKDSTYSLSSTLTLSKADY EKHKVYACEVTHQGLSSPVTKSFNRGEC | 87 | scFv Sequences

| | | | |
| --- | --- | --- | --- |
| Anti- TRGV9_7A5_var 17-scFv | Heavy Chain A | MAWVWTLLFLMAAAQSIQADIVMTQSPDSLAVSLG ERATINCKSSQSVLYSSNNKNYLAWYQQKPGQPPK LLIYWASTRESGVPDRFSGSGSGTDFTLTISSLQA EDVAVYYCQQYYRYHTFGTGTKLEIKGGSEGKSSG SGSESKSTGGSQVQLVQSGAEVKKPGASVKVSCKA SGFTFTDHYINWVRQATGQGLEWMGQIYPGSGNTY YNQKFKGRVTMTRDTSISTAYMELSSLRSEDTAVY YCARNYGDYTIDFWGQGTSVTVSSEPKSSDKTHTC PPCPAPEAAGGPSVFLEPPKPKDTLMISRTPEVTC VVVSVSHEDPEVKFNWYVDGVEVHNAKTKPREEQY NSTYRVVSVLTVLHQDWLNGKEYKCKVSNKALPAP IEKTISKAKGQPREPQVYVYPPSREEMTKNQVSLT CLVKGFYPSDIAVEWESNGQPENNYKTTPPVLDSD GSFALVSKLTVDKSRWQQGNVFSCSVMHEALHNHY TQKSLSLSPGK | 70 |
| Anti- TRGV9_7A5_var 29-scFv | Heavy Chain A | MAWVWTLLFLMAAAQSIQADIVMTQSPDSLAVSLG ERATISCKSSQSVLYSSNNKNYLAWYQQKPGQPPK LLIYWASTRESGVPDRFSGSGSGTDFTLTISSLQA EDVAVYYCQQYYRYHTFGTGTKLEIKGGSEGKSSG SGSESKSTGGSQVQLVQSGAEVKKPGASVKVSCKA SGFTFTDHYINWVRQATGQGLEWMGQIYPGSGNTY YNQKFKGRVTMTRNTSISTAYMELSSLRSEDTAVY YCARNYGDYTIDFWGQGTSVTVSSEPKSSDKTHTC PPCPAPEAAGGPSVFLFPPKPKDTLMISRTPEVTC VVVSVSHEDPEVKFNWYVDGVEVHNAKTKPREEQY NSTYRVVSVLTVLHQDWLNGKEYKCKVSNKALPAP IEKTISKAKGQPREPQVYVYPPSREEMTKNQVSLT CLVKGFYPSDIAVEWESNGQPENNYKTTPPVLDSD GSFALVSKLTVDKSRWQQGNVFSCSVMHEALHNHY TQKSLSLSPGK | 73 |
| Anti-TAA1-scFv | Heavy Chain B | SEQUENCE NOT SHOWN | — |
| Anti-Null-scFv | Heavy Chain B | MAWVWTLLFLMAAAQSIQADIQMTQSPSSLSASVG DRVTITCRASQSISSYLNWYQQKPGCAPKLLIYAA SSLQSGVPSRFSGSGSGTDFTLTISSLQPEDFATY YCQQSYSTPLTFGQGTKVEIKGGGSGGSGGCPPCG GSGGEVQLLESGGGLVQPGGSLRLSCAASGFTFSS YAMSWVRQAPGKGLEWVSAISGSGGSTYYADSVKG RFTISRDNSKNTLYLQMNSLRAEDTAVYYCAKYDG IYGELDFWGCGTLVTVSSEPKSSDKTHTCPPCPAP EAAGGPSVFLFPPKPKDTLMISRTPEVTCVVVSVS HEDPEVKFNWYVDGVEVHNAKTKPREEQYNSTYRV VSVLTVLHQDWLNGKEYKCKVSNKALPAPIEKTIS KAKGQPREPQVYVLPPSREEMTKNQVSLLCLVKGF YPSDIAVEWESNGQPENNYLTWPPVLDSDGSFFLY SKLTVDKSRWQQGNVFSCSVMHEALHNHYTQKSLS LSPGK | 88 |

235

TABLE 17

Anti-TRGV9 Heavy and Light Chain Sequences

| Antibody | Heavy Chaim | Light Chain |
|---|---|---|
| TRGV9_7A5_1 | EVQLQQSGAELARPGASVKLSCKASGF TFTDHYINWVKQRTGQGLEWIGQIYPG DGNTYYNQKFKGKATLTADKSSSTAYM QLSSLTSEDSAVYFCAPNYGDYTIDFW GQGTSVTVSSASTKGPSVFPLAPSSKS TSGGTAALGCLVKDYFPEPVTVSWNSG ALTSGVHTFPAVLQSSGLYSLSSVVTV PSSSLGTQTYICNVNHKPSNTKVDKKV EPKSCDKTHTCPPCPAPEAAGGPSVFL FPPKPKDTLMISRTPEVTCVVVSVSHE NSTYRVVSVLTVLHQDWLNGKEYKCKV SNKALPAPIEKTISKAGQPREPQVYV YPPSREEMTKNQVSLTCLVKGFYPSDI AVEWESNGQPENNYKTTPPVLDSDGSF ALVSKLTVDKSRWQQGNVFSCSVMHEA LHNRFTQKSLSLSPGK (SEQ ID NO: 69) | DIVMSQSPSSLAVSVG EKVTMSCKSSQSLLYS SNQKNYLAWYQQKPGQ SPKLLIYWASTRESGV PDRFTGSGSGTDFTLT ISSVKAEDLAVYYCQQ YYRYHTFGTGTKLEIK RTVAAPSVFIFPPSDE QLKSGTASVVCLLNNF YPREAKDPEVKFNWYV DGVEVHNAKTKPREEQ YVQWKVDNALQSGNSQ ESVTEQDSKDSTYSLS STLTLSKADYEKHKVY ACEVTHQGLSSPVTKS FNRGEC (SEQ ID NO: 24) |
| TRGV9_var17 | QVQLVQSGAEVKKPGASVKVSCKASGF TFTDHYINWVRQATGQGLEWMGQIYPG SGNTYYNQKFKGRVTMTRDTSISTAYM ELSSLRSEDTAVYYCARNYGDYTIDFW GQGTSVTVSSASTKGPSVFPLAPSSKS TSGGTAALGCLVKDYFPEPVTVSWNSG ALTSGVHTFPAVLQSSGLYSLSSVVTV PSSSLGTQTYICNVNHKPSNTKVDKKV EPKSCDKTHTCPPCPAPEAAGGPSVFL FPPKPKDTLMISRTPEVTCVVVSVSHE DPEVKFNWYVDGVEVHNAKTKPREEQY NSTYRVVSVLTVLHQDWLNGKEYKCKV SNKALPAPIEKTISKAGQPREPQVYV YPPSREEMTKNQVSLTCLVKGFYPSDI AVEWESNGQPENNYKTTPPVLDSDGSF ALVSKLTVDKSRWQQGNVFSCSVMHEA LHNRFTQKSLSLSPGK (SEQ ID NO: 71) | DIVMTQSPDSLAVSLG ERATINCKSSQSVLYS SNNKNYLAWYQQKPGQ PPKLLIYWASTRESGV PDRFSGSGSGTDFTLT ISSLQAEDVAVYYCQQ YYRYHTFGTGTKLEIK RTVAAPSVFIFPPSDE QLKSGTASVVCLLNNF YPREAKVQWKVDNALQ SGNSQESVTEQDSKDS TYSLSSTLTLSKADYE KHKVYACEVTHQGLSS PVTKSFNRGEC (SEQ ID NO: 72) |
| TRGV9_var29 | QVQLVQSGAEVKKPGASVKVSCKASGF TFTDHYINWVRQATGQGLEWMGQIYPG SGNTYYNQKFKGRVTMTRNTSISTAYM ELSSLRSEDTAVYYCARNYGDYTIDFW GQGTSVTVSSASTKGPSVFPLAPSSKS TSGGTAALGCLVKDYFPEPVTVSWNSG ALTSGVHTFPAVLQSSGLYSLSSVVTV PSSSLGTQTYICNVNHKPSNTKVDKKV EPKSCDKTHTCPPCPAPEAAGGPSVFL FPPKPKDTLMISRTPEVTCVVVSVSHE DPEVKFNWYVDGVEVHNAKTKPREEQY NSTYRVVSVLTVLHQDWLNGKEYKCKV SNKALPAPIEKTISKAGQPREPQVYV YPPSREEMTKNQVSLTCLVKGFYPSDI AVEWESNGQPENNYKTTPPVLDSDGSF ALVSKLTVDKSRWQQGNVFSCSVMHEA LHNRFTQKSLSLSPGK (SEQ ID NO: 74) | DIVMTQSPDSLAVSLG ERATISCKSSQSVLYS SNNKNYLAWYQQKPGQ PPKLLIYWASTRESGV PDRFSGSGSGTDFTLT ISSLQAEDVAVYYCQQ YYRYHTFGTGTKLEIK RTVAAPSVFIFPPSDE QLKSGTASVVCLLNNF YPREAKVQWKVDNALQ SGNSQESVTEQDSKDS TYSLSSTLTLSKADYE KHKVYACEVTHQGLSS PVTKSFNRGEC (SEQ ID NO: 75) |
| TAA1 | SEQUENCE NOT SHOWN | SEQUENCE NOT SHOWN |

The antibodies were initially purified by MAB SELECT SURE Protein A column (GE Healthcare). The column was equilibrated with PBS pH 7.2 and loaded with fermentation supernatant at a flow rate of 2 mL/min. After loading, the column was washed with 4 column volumes of PBS followed by elution in 30 mM sodium acetate, pH 3.5. Fractions containing protein peaks as monitored by absorbance at 280 nm were pooled and neutralized to pH 5.0 by adding 1% 3 M sodium acetate pH 9.0. The bispecific mAbs were further purified on a preparative SUPERDEX 200 10/300 GL (GE healthcare) size exclusion chromatography (SEC) column equilibrated with PBS buffer. The integrity of the sample was assessed by endotoxin measurement and SDS-PAGE under reducing and non-reducing conditions. The final protein concentrations were 1.0 mg/ml for anti-TRGV9/anti-TAA1 and 1.0 mg/mL for ANTI-TRGV9/Null. The final EU levels of ANTI-TRGV9/anti-TAA1 and ANTI-TRGV9/Null based on these were <3.0 EU/mg.

Example 4.4: Binding Activity of Anti-TAA1 and Anti-TRGV9 Antibodies on Target Cell Lines Binding of antibodies to TAA1 expressing cell line and γδ T cells was carried out by flow cytometry. Briefly, 50,000 target cells or γδ T cells were incubated at 4° C. for 45 minutes with serial dilutions of various antibodies. After washing with wash buffer (PBS+2% FBS), antibody bound to cell surface was detected by incubating the cells with PE labelled mouse anti human IgG1 secondary antibody (Southern Biotech, Birmingham, AL) for 30 minutes at 4° C. Cells were washed with wash buffer (PBS+2% FBS) and the fluorescence of stained cells was measured on Novocyte flow cytometer. Cells were visualized on forward and sideward scatter and doublets were excluded. No secondary antibody control was used to establish background fluorescence and to gate on specific population. Background value was subtracted from main samples to get specific binding value.

Figure 7:
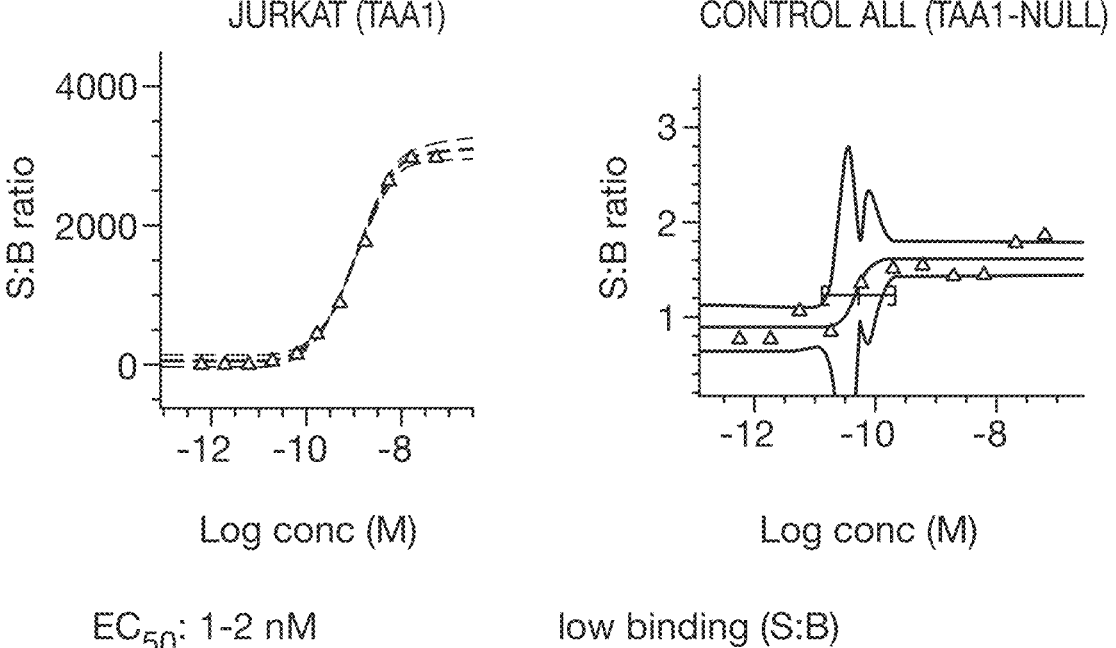
FIG. 7 shows selective cell binding of anti-TAA1 (TAA mIgG2a, TAA1B1) to transfected Jurkat cells. The EC$_{50}$ for binding was ~1 to 2 nM. TAA1B1 did not show any significant binding to a control ALL cell line that endogenously expresses an unrelated protein (TAA1-NULL), but does not express TAA1.

As shown in FIG. 7, the EC50 for binding of anti-TAA1 antibodies (TAA1 mIgG2a, TAA1B1) to TAA1 expressing Jurkat cell lines was ~1 to 2 nM. TAA1B1 did not show any significant binding to a control ALL cell line that endogenously expresses an unrelated protein (TAA1-NULL), but does not express TAA1.

Figure 8:
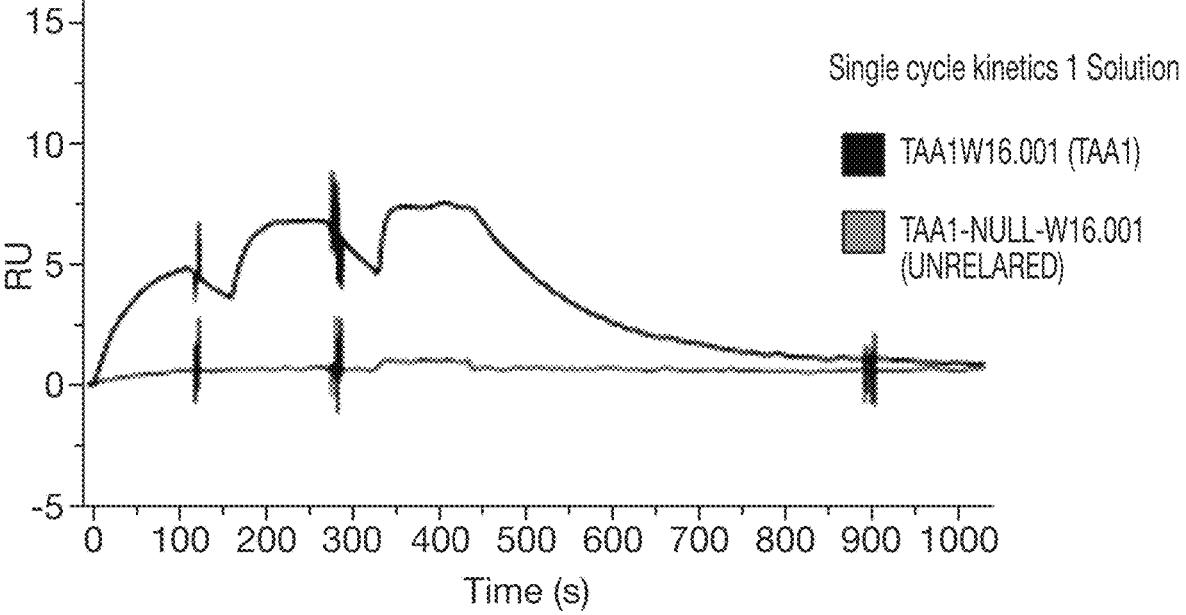
FIG. 8 shows selective protein binding of anti-TAA1 (TAA1 mIgG2a, TAA1B1) to a recombinant TAA1 protein (TAA1W16). TAA1B1 did not show any significant binding to the unrelated protein (TAA1-NULL-W16).

Additional surface plasmon resonance (SPR) experiments were used to determine specific binding of anti-TAA1 mAb to TAA1. Briefly, SPR experiments were carried out in HBSP buffer at 25° C. The experimental set up was following: Goat anti-murine Fc surface was immobilized on a sensor chip, and binding was tested by capturing the mouse anti-human TAA1 clone mAb at different densities. The recombinant TAA1 protein (TAA1W16) and an unrelated protein (TAA1-NULL-W16) were used as analyte to bind in solution in a single cycle kinetics. Raw binding data were processed by double referencing, e.g., interspot on an empty chip surface. As shown in FIG. 8, the anti-TAA1 antibodies (TAA1 mIgG2a, TAA1B1) specifically bound to recombinant TAA1 (TAA1W16). TAA1B1 did not show any significant binding to the unrelated protein (TAA1-NULL-W16).

Figure 9:
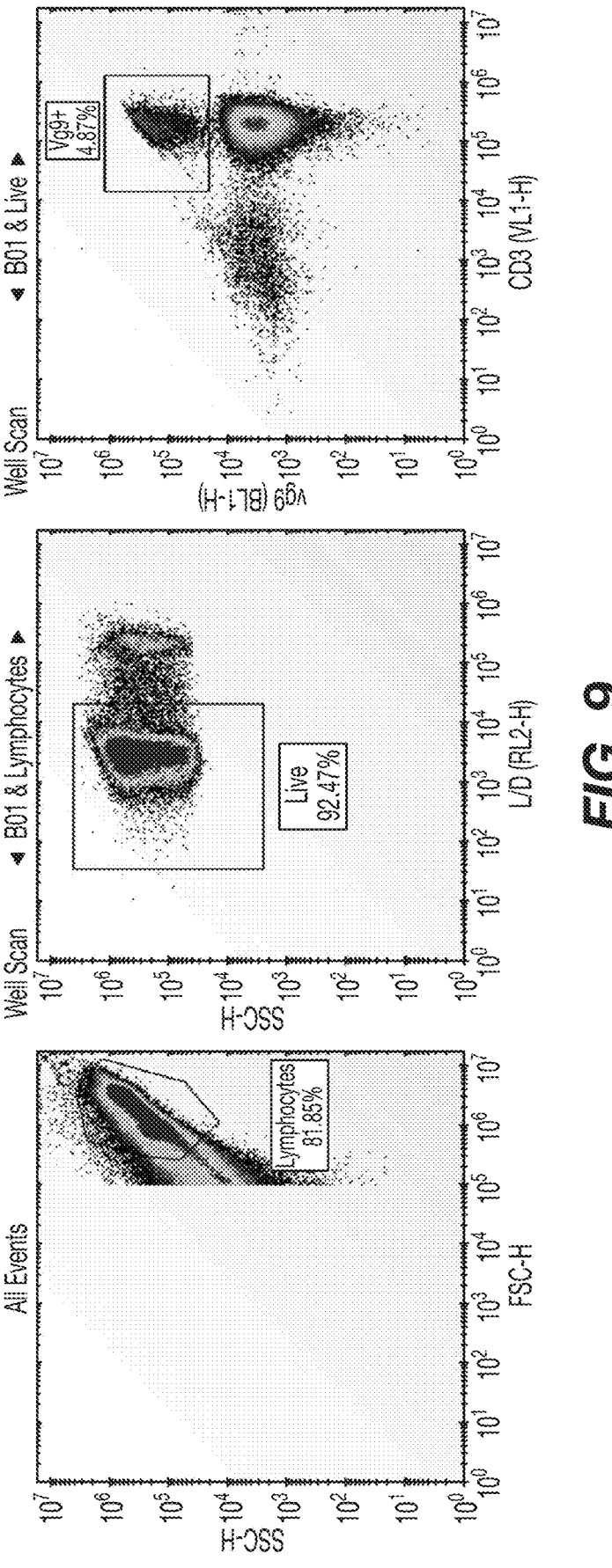
FIG. 9 shows phenotyping of Vg9+ cells used for cytotoxicity studies of a TAA1 x Vγ9 bispecific (TAA1B50) from a healthy donor.
Figure 10:
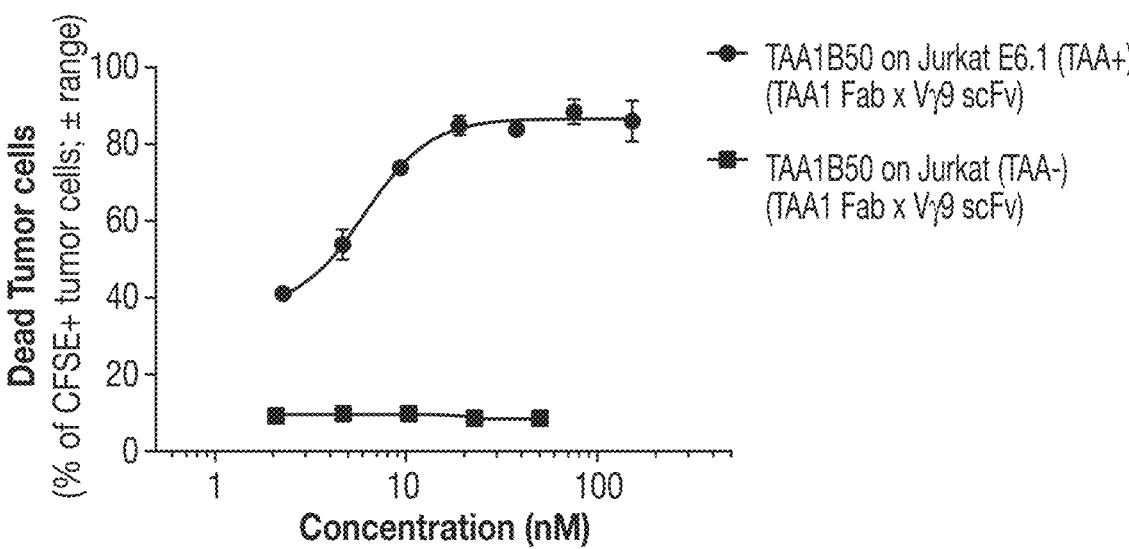
FIG. 10 shows that the anti-TRGV9/anti-TAA1 bispecific antibody mediates γδ T cell cytotoxicity against TAA1 expressing Jurkat cells in vitro. Cytotoxicity values represented here were subtracted of basal cytotoxicity value observed in the absence of bispecific antibody. EC$_{50}$ values were calculated as described in methods. Representative data shown here are from a single experiment.

Example 4.5: Evaluation of Binding and Cytotoxic Properties of the Anti-TRGV9/Anti-TAA1 Bispecific Antibody Using Jurkat Cells and Human γδ T Cells FIG. 9 shows the phenotyping of Vγ9+ cells (TAA1B50) from a healthy donor of used for cytotoxicity studies of an anti-TAA1 x Vγ9 bispecific. FIG. 10 shows that the anti-TRGV9/anti-TAA1 bispecific antibody mediates γδ T cell (TAA1B50) cytotoxicity against TAA1-expressing Jurkat cells in vitro. Enriched γδ T cells (Effectors), isolated from PBMCs cultured with Zoledronic acid+IL-2+IL-15 for 12 days, were co-cultured with CFSE labelled Jurkat cells (Targets) at 0.5:1 to 10:1 E:T ratios in the presence of various concentrations of the bispecific antibody for 24 to 72 hours. Dose response curves show an anti-TRGV9/anti-TAA1 (TAA1 Fab x Vγ9 scFv) bispecific mediated γδ T cell cytotoxicity against TAA1-expressing Jurkat cells in a dose dependent manner, as compared to Jurkat cells that do not endogenously express TAA1. Cytotoxicity values represented here were subtracted of basal cytotoxicity value observed in the absence of bispecific antibody. $EC_{50}$ values were calculated as described above. Representative data shown are from a single experiment.

To additionally study the ability of a Vγ9xTAA1 bispecific to mediate γδ T cell cytotoxicity against Jurkat cells with γδ T cells from different donors, γδ T cells were enriched. In particular, Vγ9Vδ2 T cells from 5 different donors (328337, 328676, 327587, 328630, 326287) were expanded from total PBMC population for 13 days. Briefly, PBMC were cultured in the presence of zoledronic acid (Sigma, SML0223) (350 nM, days 0 to 13), rhIL-2 (Miltenyi, 130-097-748) (1000 U/mL days 0-2, 800 U/mL days 2-5, 100 U/mL days 5-13) and rhIL-15 (Miltenyi, 130-095-765) (10 ng/mL days 0-13) in complete growth media (RPMI, 10% HI FBS, 1% Pen/strep). At day 13 of expansion, cells were harvested and enriched with EASYSEP™ Human Gamma/Delta T Cell Isolation Kit (Stem Cell Technologies, 19255) according to manufacturer's instructions. Following enrichment procedure, cells were seeded at $1\times10^6$/mL in complete growth media with addition of 350 nM zoledronic acid, 100 U/mL IL-2 and 10 ng/mL IL-15 and rested overnight.

Figure 11:
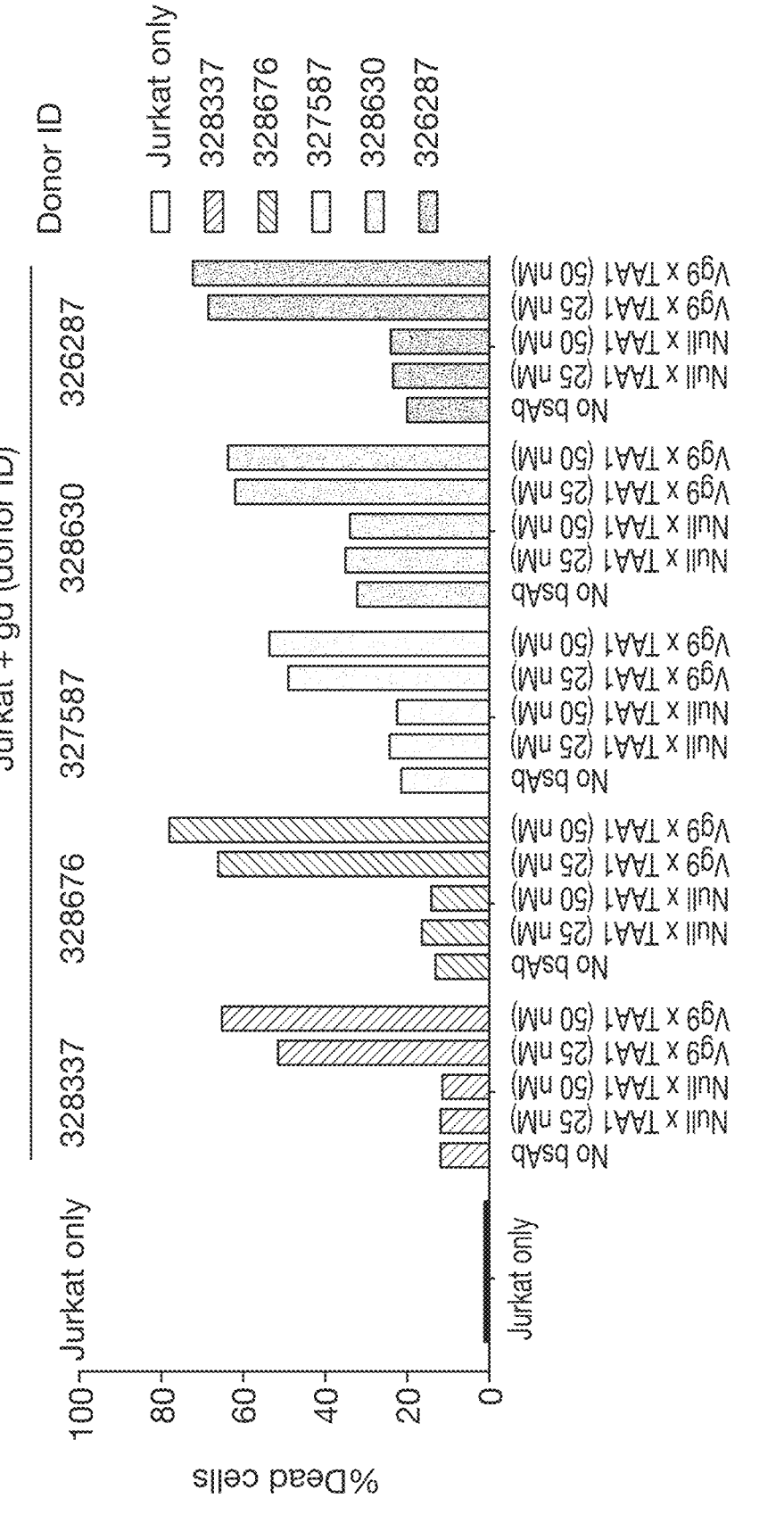
FIG. 11 shows bispecific antibody mediated cytotoxicity. Expanded and enriched Vγ9Vδ2 T cells from various donors were used to induce cytotoxicity to Jurkat cell line (E:T ratio 1:1) in presence of Vγ9xTAA1 at indicated concentrations. Assay was conducted for 16 hrs. Percent dead target cells for various conditions are given in the figure.

For the killing assay, rested γδ T cells were harvested, and cell number and viability were determined. Target cells (Jurkat cells expressing TAA1) were labelled with 0.25 μM CFSE (Thermo, C34554) for 5 min. at room temperature. Cells were washed 3 times and cell number and viability were determined. Killing assay at an E:T ratio of 1:1 ($10^5$ effector cells: $10^5$ target cells) was set up for 16 hours in 96 well plate in complete growth media in the absence on zoledronic acid and cytokines. Vγ9xTAA1 bispecific molecules were adjusted in concentration by limiting dilution to yield final concentration 25 nM and 50 nM in final volume 150 μL/well. After 16 hours, cells were harvested and stained with cocktail containing antibodies against: CD3 (Biolegend, 300424), Vγ9 (Biolegend, 331310), CD25 (Biolegend, 356142), CD69 (Biolegend, 310930), as well as Near-IR (Thermo, L34975) and Fc block (BD, 546219). Cells were washed 3 times, fixed and analysed by flow cytometry. FIG. 11 depicts anti-TRGV9/anti-TAA1 bispecific antibody mediated cytotoxicity. Vγ9xTAA1 bispecific antibodies at both concentrations tested resulted in greater killing in all five of the donor Vγ9Vδ2 T cell populations as compared to the addition of a NULL/TAA1 bispecific or no bispecific antibody. The additional of Vγ9xTAA1 bispecific antibodies also failed to kill Jurkat cells when donor γδ T cells were not present.

Example 5—Multispecific Antibodies that Bind TRGV9 and TAA2

Example 5 is based on the premise that γδ T cells, which mainly express heterodimers of TRGV9 and Vδ2 chains demonstrate potent anti-tumor functions. These cells express TCR-TRGV9 and the majority, if not all, of these cells exhibit efficient cytotoxicity of tumor target cells. This ability is then harnessed using bispecific antibodies constructed such that one arm binds to the TRGV9 structure and the other arm binds to a second T cell Tumor-Associated Antigen (TAA2) expressed by the tumor cells (e.g., certain leukemias and lymphomas). Thus, the bispecific antibody bridges the effector and target cells together, resulting in tumor cell killing. This mechanism of action is described in the schematic outlined in FIG. 1.

The subsequent examples can be divided into the following categories: (1) Generation and characterization of bispecific antibodies capable of binding to the TRGV9 arm expressed on γδ T cells and a certain tumor associated antigen (TAA2) (Examples 5.1, 5.2, 5.3 and 5.4); and (2) Evidence for bispecific antibody-enabled target cell killing by γδ T cells expanded in vitro (Example 5.5).

Example 5.1: Anti-Vg9 Antibody Generation

Immunogen. A recombinant human TCR Vγ9 x Vδ2 fused to a human Fc was used as an immunogen, and the sequence is listed in Table 18.

TABLE 18

| Amino acid sequence of recombinant human TCR Vγ9 x Vδ2 heterodimeric protein fused to human Fc | | |
|---|---|---|
| Name | Protein ID | Sequence |
| Recombinant human [TCR Vg9 x Vd2]-hFc | Vg9 chain | MAWVWTLLFLMAAAQSIQAAGHLEQPQISST KTLSKTARLECVVSGITISATSVYWYRERPG EVIQFLVSISYDGTVRKESGIPSGKFEVDRI PETSTSTLTIHNVEKQDIATYYCALWEAQQE LGKKIKVFGPGTKLIITDKQLDADVSPKPTI FLPSIAETKLQKAGTYLCLLEKFFPDVIKIH WEEKKSNTILGSQEGNTMKTNDTYMKFSWLT VPEKSLDKEHRCIVRHENNKNGVDQEIIFPP IKTDVITMDPKDNEPKSCDKTHTCPPCPAPE LLGGPSVFLFPPKPKDTLMISRIPEVTCVVV DVSHEDPEVKFNWYVDGVEVHNAKTKPREEQ YNSTYRVVSVLTVLHQDWLNGKEYKCKVSNK ALPAPIEKTISKAKGQPREPQVYVYPPSREE MTKNQVSLTCLVKGFYPSDIAVEWESNGQPE NNYKTTPPVLDSDGSFALVSKLTVDKSRWQQ GNVFSCSVMHEALHNHYTQKSLSLSPGK | SEQ ID NO: 156 |
| | Vd2 chain | MAWVWTLLFLMAAAQSIQAAIELVPEHQTVP VSIGVPATLRCSMKGEAIGNYYINWYRKTQG NTMTFIYREKDIYGPGFKDNFQGDIDIAKNL AVLKILAPSERDEGSYYCACDTLGMGGEYTD KLIFGKGTRVIVEPRSQPHTKPSVFVMKNGT NVACLVKEFYPKDIRINLVSSKKITEFDPAI VISPSGKYNAVKLGKYEDSNSVTCSVQHDNK TVHSTDFEVKTDSTDHVKPKETENTKQPSKS EPKSCDKTHTCPPCPAPELLGGPSVFLFPPK PKDTLMISRTPEVTCVVVDVSHEDPEVKFNW YVDGVEVHNAKTKPREEQYNSTYRVVSVLTV LHQDWLNGKEYKCKVSNKALPAPIEKTISKA KGQPREPQVYVLPPSREEMTKNQVSLLCLVK GFYPSDIAVEWESNGQPENNYLTWPPVLDSD GSFFLYSKLTVDKSRWQQGNVFSCSVMHEAL HNHYTQKSLSLSPGK | SEQ ID NO: 157 |

Protein Production of the Immunogen. Expression plasmids encoding the immunogen (see Table 18) were transfected into CHO cell at a DNA ratio of 1:1. Total amount of DNA for a 750 mL expression scale was 750 μg. Final expression volume was 1 L after two feedings and enhancer additions. Using an ÄKTAPRIME plus instrument (GE Healthcare Life Sciences), supernatant (1 L) after 7 days was applied with a flow-rate of 5 mL/min to a MAB SELECT SURE (GE Life Sciences) with a column volume (CV) of 10 mL pre-equilibrated with phosphate buffered saline (PBS), pH 6.8. Non-specific proteins binding to the column material was washed off with PBS supplemented with 500 mM NaCl, pH 6.8 (5 CV). The Fc-containing immunogen was eluted stepwise with 40 mM sodium acetate pH 5.0 (5 CV), pH 4.5 (5 CV), pH 4.0 (10 CV), pH 3.5 (5 CV), and pH 3.0 (5 CV). Fractions were pooled, and applied (5 mL) at a flow-rate of 0.2 mL/min on to a HiLoad 16/600 SUPERDEX (GE Healthcare) column pre-equilibrated with PBS (pH 6.8). Target protein was eluted, pooled, and analyzed by SDS-PAGE, analytic SEC, and intact mass by mass spectrometry. Purity was estimated to >99%.

Antibodies were generated using ALIVAMAB transgenic mice technology (Ablexis). ALIVAMAB mice were immunized with recombinant human Vγ9/Vδ2 TCR protein. Lymphocytes were extracted from secondary lymphoid organs and either fused with FO mouse myeloma cell line for hybridoma generation or subjected to single cell sorting via FACS. Hybridoma supernatants were screened by MSD electrochemiluminescence or by FACS for binding to γδ T cells. Confirmed cell binders were light chain isotyped via ELISA. Single cell sorting supernatants were screened by MSD electrochemiluminescence for binding to recombinant human Vγ9/Vδ2 protein. Several hits with the desired binding profile were selected and sequenced, as provided below.

The CDR sequences of certain VG9 antibodies are provided in Tables 19-22, and the respective VH and VL regions are provided in Tables 23-26, respectively.

TABLE 19

CDR Sequences of anti-TRGV9 antibody (Vγ9 clone).

| Antibody | HCDR1 | SEQ ID NO: | HCDR2 | SEQ ID NO: | HCDR3 | SEQ ID NO: |
|---|---|---|---|---|---|---|
| VG9B420-LH | GFTFSNYD | 98 | ISSSSSYI | 99 | ARDVGVTDYYYYGMDV | 100 |

| Antibody | LCDR1 | SEQ ID NO: | LCDR2 | SEQ ID NO: | LCDR3 | SEQ ID NO: |
|---|---|---|---|---|---|---|
| VG9B420-LH | QSVASSY | 101 | GAS | 102 | QQYGSSPPYT | 103 |

TABLE 20

CDR Sequences of anti-TRGV9 antibody (Vγ9 clone).

| Antibody | HCDR1 | SEQ ID NO: | HCDR2 | SEQ ID NO: | HCDR3 | SEQ ID NO: |
|---|---|---|---|---|---|---|
| VG9SB10SC1087_P18_D08 | GDTFNNYA | 107 | IIPFFGTP | 108 | ARPGSGSPDYYYYDMDV | 109 |

| Antibody | LCDR1 | SEQ ID NO: | LCDR2 | SEQ ID NO: | LCDR3 | SEQ ID NO: |
|---|---|---|---|---|---|---|
| VG9SB10SC1087_P18_D08 | QSLVHSDGNTY | 110 | KIS | 111 | MQATQFPLT | 112 |

TABLE 21

CDR Sequences of anti-TRGV9 antibody (Vγ9 clone).

| Antibody | HCDR1 | SEQ ID NO: | HCDR2 | SEQ ID NO: | HCDR3 | SEQ ID NO: |
|---|---|---|---|---|---|---|
| VG9SB10SC1087_P18_C12 | GGTFSSYA | 117 | NIPIFNTA | 118 | VREGTGYSYGLDY | 119 |

TABLE 21-continued

CDR Sequences of anti-TRGV9 antibody (Vγ9 clone).

| Antibody | LCDR1 | SEQ ID NO: | LCDR2 | SEQ ID NO: | LCDR3 | SEQ ID NO: |
|---|---|---|---|---|---|---|
| VG9SB10SC1087_P18_C12 | QSLIHSDGNTY | 120 | KIS | 121 | MQAKQFPIT | 122 |

TABLE 22

CDR Sequences of anti-TRGV9 antibody (Vγ9 clone).

| Antibody | HCDR1 | SEQ ID NO: | HCDR2 | SEQ ID NO: | HCDR3 | SEQ ID NO: |
|---|---|---|---|---|---|---|
| VG9SB10SC1087_P19_C03 | GGSISSGGSY | 127 | IYNSGST | 128 | ARDSNYEWFFDL | 129 |

| Antibody | LCDR1 | SEQ ID NO: | LCDR2 | SEQ ID NO: | LCDR3 | SEQ ID NO: |
|---|---|---|---|---|---|---|
| VG9SB1-SC1087_P19_C03 | QSVSSY | 130 | DAS | 131 | QQRSNWPLT | 132 |

TABLE 23

Heavy chain and light chain V-region sequences of anti-TRGV9 antibody (Vγ9 clone).

| mAb ID | | SEQ ID NO: |
|---|---|---|
| | Heavy Chain V-region Amino Acid Sequence | |
| VG9B420-LH | EVQLVESGGGLVKPGGSLRLSCSASGFTFSNYDMNW VRQAPGKGLEWVSSISSSSSYIYYADSVKGRFTISR DNAKNSLYLQMNSLRAEDTAVYHCARDVGVTTDYYY YGMDVWGQGTMVTVSS | 104 |
| | Light Chain V-region Amino Acid Sequence | |
| VG9B420-LH | EIVMTQSPGTLSLSPGDRATLSCRASQSVASSYLAW YQQKPGQSPRLLIYGASSRATGIPDRFSGSGSGTDF TLTISRLEPEDFAVYYCQQYGSSPPYTFGQGTRLEI K | 105 |

TABLE 24

Heavy chain and light chain V-region sequences of anti-TRGV9 antibody (Vγ9 clone).

| mAb ID | | SEQ ID NO: |
|---|---|---|
| | Heavy Chain V-region Amino Acid Sequence | |
| VG9SB10SC1087_P18_D08 | EVQLVQSGAEVKKPGSSVKVSCKASGDTFNNYA ISWVRQAPGQGLEWMGGIIPFFGTPDYAQKFQG RVTITADKSTSTAYMELSGLRSEDTAVYYCARP GSGSPDYYYYDMDVWGQGTTVTVSS | 113 |

US 12,673,995 B2

241

TABLE 24-continued

Heavy chain and light chain V-region sequences
of anti-TRGV9 antibody (Vγ9 clone).

| mAb ID | | SEQ ID NO: |
|---|---|---|
| | Light Chain V-region Amino Acid Sequence | |
| VG9SB10SC1 087_P18_D08 | DIVMTQTPLSSPVTLGQPASISCRSSQSLVHSD GNTYLSWLQQRPGQPPRLLIYKISNRFSGVPDR FSGSGAGTDFTLKINRVEAEDVGVYYCMQATQF PLTFGGGTKVEIK | 114 |

TABLE 25

Heavy chain and light chain V-region sequences
of anti-TRGV9 antibody (Vγ9 clone).

| mAb ID | | SEQ ID NO: |
|---|---|---|
| | Heavy Chain V-region Amino Acid Sequence | |
| VG9SB10SC1 087_P18_C12 | EVQLVQSGAEVKKPGSSVKVSCKASGGTFSSYA ISWVRQAPGQGLEWMGGNIPIFNTANYAQKFQD RVTITADKSTSTAYMELSSLRSEDTAVYYCVRE GTGYSYGLDYWGQGTPVTVSS | 123 |
| | Light Chain V-region Amino Acid Sequence | |
| VG9SB10SC1 087_P18_C12 | EIVMTQSPLSSPVTLGQPASISCRSSQSLIHSD GNTYLSWLQQRPGQPPRLLIYKISNRFSGVPDR F4SGSGAGTDFTLKISRVEAEDVGIYYCMQAKQ FPITFGQGTKVDIK | 124 |

TABLE 26

Heavy chain and light chain V-region sequences
of anti-TRGV9 antibody (Vγ9 clone).

| mAb ID | | SEQ ID NO: |
|---|---|---|
| | Heavy Chain V-region Amino Acid Sequence | |
| VG9SB10SC1 087_P19_C03 | QVQLQESGPGLVKPSQTLSLTCTVSGGSISSGG SYWSWIRQHPGKGLEWIGYIYNSGSTYYNPSLK SRVSMSVDTSKNQFSLKLSSVTAADTAVYYCAR DSNYEWFFDLWGPGTLVTVSS | 133 |
| | Light Chain V-region Amino Acid Sequence | |
| VG9SB10SC1 087_P19_C03 | EIVMTQSPATLSLSPGERATLSCRASQSVSSYL AWYQQKPGQAPRLLIYDASNRATGIPARFSGSG SGTDFTLTISSLEPEDFAVYYCQQRSNWPLTFG GGTKVEIK | 134 |

Variable Region Cloning. Both RNA purified by QIA-GEN kit (RNEASY Plus Mini Kit) and B cells lysate were used for cDNA synthesis using the Smarter cDNA synthesis kit (Clontech, Mount View, CA). To facilitate cDNA synthesis, oligodT was used to prime reverse transcription of all messenger RNAs followed by "5' capping" with a SMARTER IIA oligonucleotide. Subsequent amplification of the VH and VL fragments was performed using a two-step PCR amplification using 5' primers targeting the Smarter IIA cap and 3' primers targeting consensus regions in CH1. Briefly, each 50 µl PCR reaction consists of 20 µM of forward and reverse primer mixes, 25 µl of PRIMESTAR MAX DNA polymerase premix (Clontech), 2 µl of unpurified cDNA, and 21 µl of double-distilled H₂ O. The cycling program started at 94° C. for 3 min, followed by 35 cycles (94° C. for 30 Sec, 55° C. for 1 min, 68° C. for 1 min), and ended at 72° C. for 7 min. The second round PCR was performed with VL and VH 2nd round primers containing 15 bp complementary extensions that "overlap" respective regions in their respective Lonza mother vector (VH and VL). Second round PCR was performed with the following program: 94° C. for 3 min; 35 cycles (94° C. for 30 Sec, 55° C. for 1 min, 68° C. for 1 min), and ended at 72° C. for 7 min. IN-FUSION® HD Cloning Kit (Clonetech, U.S.A.) was used for directional cloning of VL gene into Lonza huIgK or Lambda vector and VH gene into Lonza huIgG1 vector. To facilitate IN-FUSION® HD Cloning, PCR products were treated with Cloning Enhancer before IN-FUSION HD Cloning. Cloning and transformation were performed according to manufacturer's protocol (Clonetech, U.S.A.). Mini-prep DNAs were subjected to Sanger sequencing to confirm that complete V-gene fragments were obtained.

Example 5.2: Production and De Novo Sequencing of Anti-TRGV9 Mab

The mouse IgG1 anti-human T cell receptor anti-TRGV9 clone B3 was sourced commercially. Sample preparation and LC-MS/MS analysis were performed by RAPID NOVOR (ON, Canada). Twenty-one in-solution and in-gel digestions were prepared using six different enzymes (Pepsin, Trypsin, Chymotrypsin, Asp N, Lys C, Glu C). The in-solution digestions for the sample was processed with disulfide reduction, alkylation, and then enzyme digestion. Each digestion contains peptides from all immunoglobulin chains. The in-gel digestions were prepared for immunoglobulin chains after gel separation. The sample was processed with disulfide reduction, gel separation, deglycosylation, disulfide reduction a second time, alkylation and then digestion. Digestions were analyzed by LC-MS/MS using THERMO-FISHER Q EXACTIVE™, ORBITRAP FUSION™ mass spectrometers. Peptides were characterized from LC-MS/MS data using de novo peptide sequencing and then assembled into antibody sequences.

The three VH CDR and three VL CDR sequences of anti-human T cell receptor Vγ9 clone B3 are shown in Table 27 (SEQ ID NOs:89-94, respectively); and the VH and VL sequences of the anti-human T cell receptor anti-human T cell receptor Vγ9 clone B3 are shown in Table 28 (SEQ ID NOs:95 and 96, respectively).

TABLE 27

CDR sequences of mouse anti-human TCR Vγ9 clone B3.

| Antibody | HCDR1 | SEQ ID NO: | HCDR2 | SEQ ID NO: | HCDR3 | SEQ ID NO: |
|---|---|---|---|---|---|---|
| Vg9_B3_RN | GFTFSSNY | 89 | IHGGTGGI | 90 | ARRGYGAWFAY | 91 |

| Antibody | LCDR1 | SEQ ID NO: | LCDR2 | SEQ ID NO: | LCDR3 | SEQ ID NO: |
|---|---|---|---|---|---|---|
| Vg9_B3_RN | ENIHNY | 92 | NAK | 93 | QHFWSYPLT | 94 |

TABLE 28

| Heavy chain and light chain sequences of mouse anti-human TCR Vγ9 clone B3. | | |
|---|---|---|
| mAb ID | | SEQ ID NO: |
| | Heavy Chain Amino Acid Sequence (from VG9B2) | |
| Vg9_B3_RN | QGQMQQSGAELVKPGASVKLSCKTSGFTFSSNY ISWLKQKPGQSLEWIAWIHGGTGGIGYNQKFTG KAQLTVDTSSTTAYMQFSSLTTEDSAIYYCARR GYGAWFAYWGQGTLVTVSA | 95 |
| | Light Chain Amino Acid Sequence (from VG9B2) | |
| Vg9_B3_RN | DIQMTQSPASLSASVGETVTITCRASENIHNYL AWYQQKQGKSPQLLVYNAKTLADGVPSRFSGSG SGTQYSLKINSLQPEDFGNYYCQHFWSYPLTFG AGTKLELK | 96 |

Figure 12:
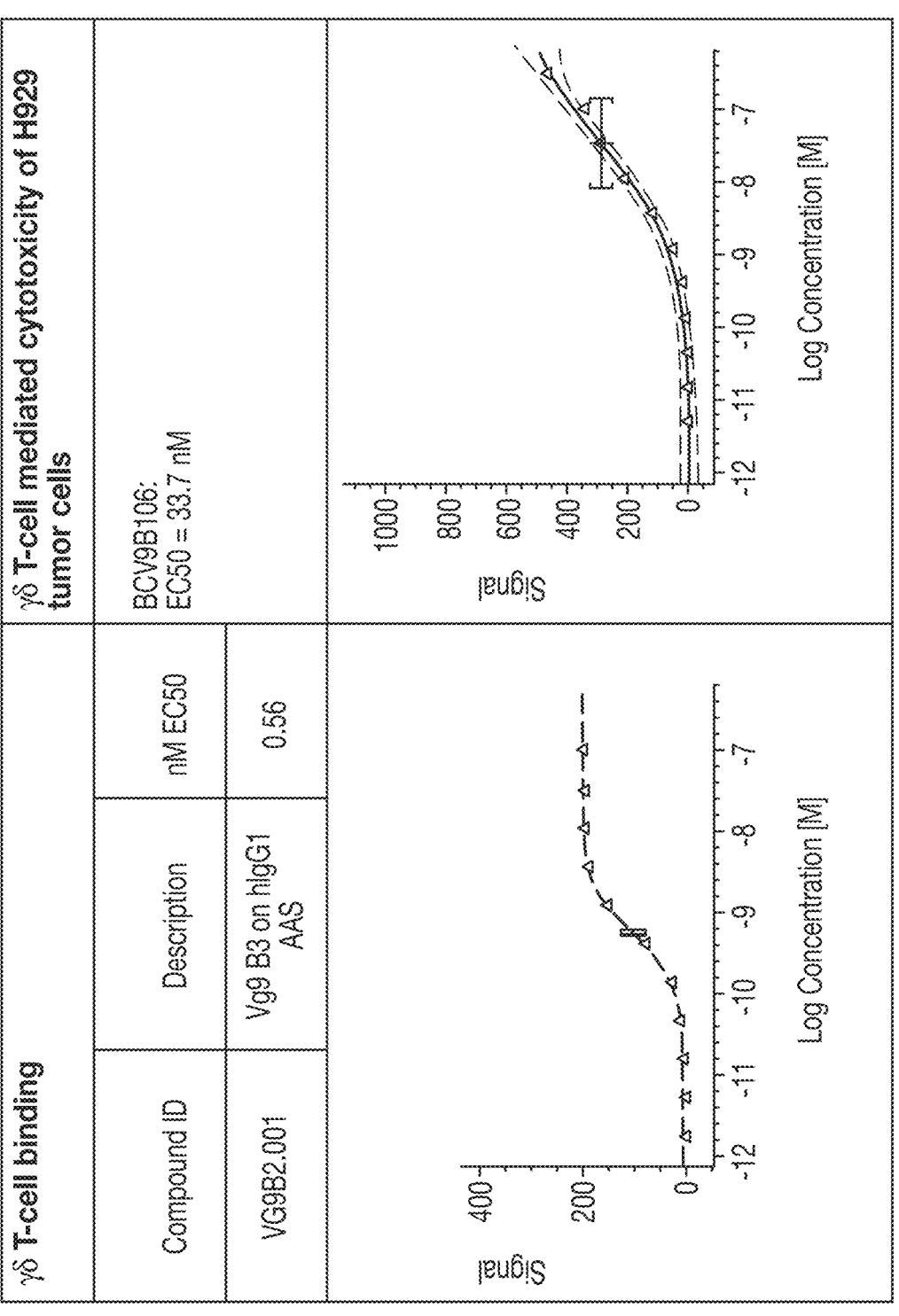
FIG. 12 shows that the anti-TRGV9/anti-TAA2 bispecific antibody (TAA2V9B106 (B3)) binds γδ T cells (left panel) and mediates γδ T cell cytotoxicity against TAA2 expressing H929 cells in vitro (right panel). EC$_{50}$ values were calculated as described in methods. Representative data shown here are from a single experiment.
Figure 13:
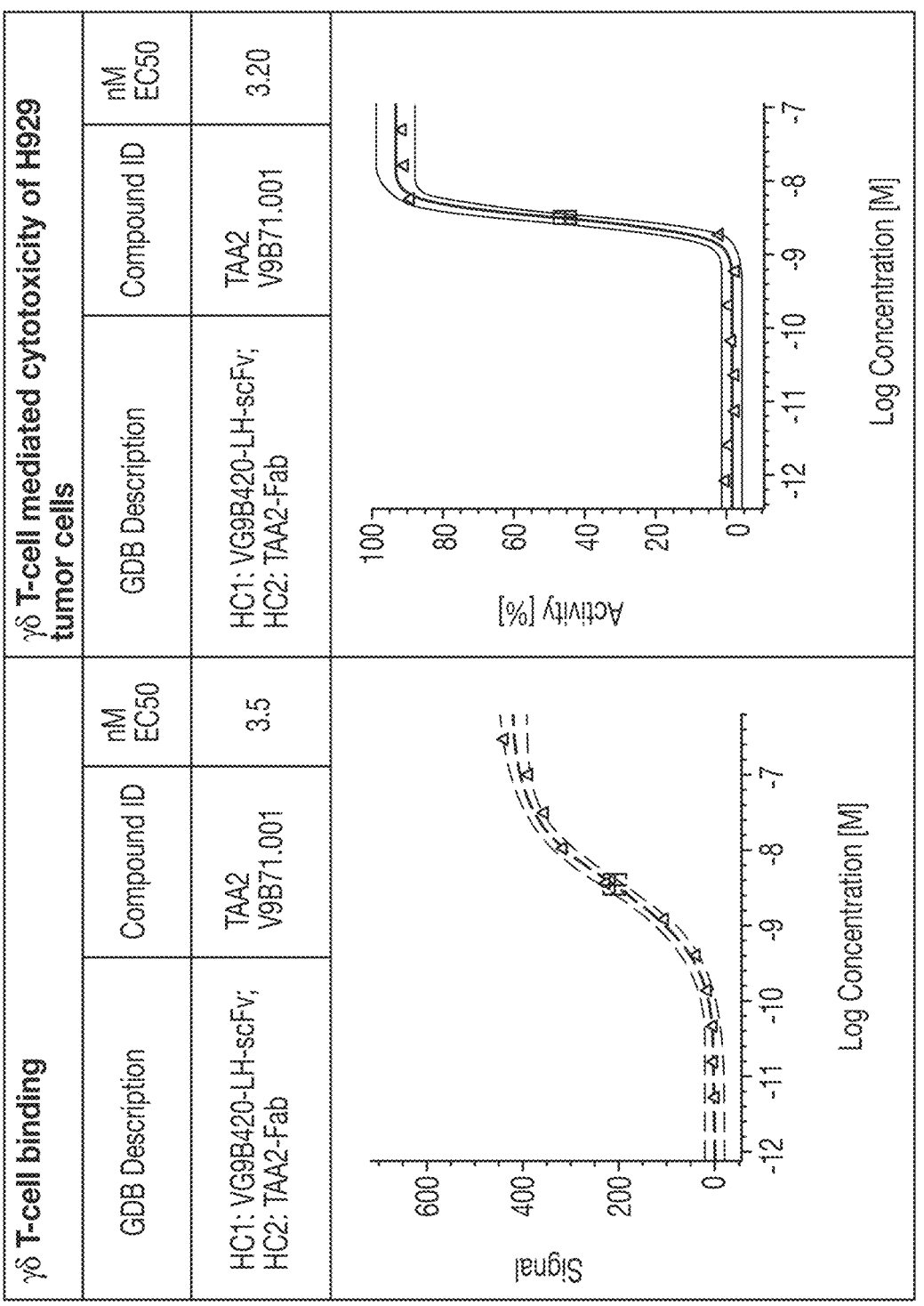
FIG. 13 shows that the anti-TRGV9/anti-TAA2 bispecific antibody (HC1: VG9B420-LH-scFv; HC2: TAA2-Fab (TAA2V9B71.001)) binds γδ T cells (left panel) and mediates γδ T cell cytotoxicity against TAA2 expressing H929 cells in vitro (right panel). EC$_{50}$ values were calculated as described in methods. Representative data shown here are from a single experiment.
Figure 14:
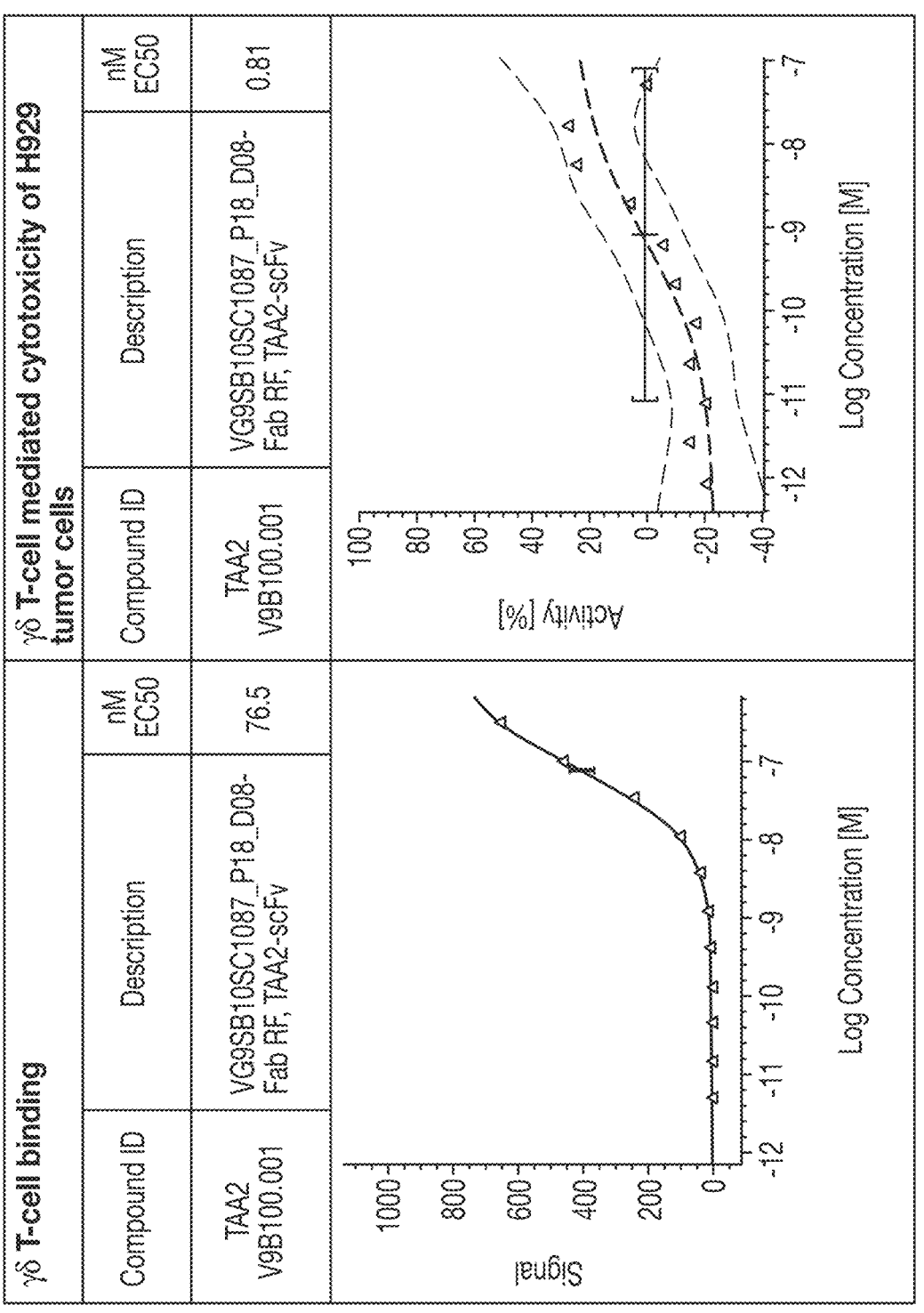
FIG. 14 shows that the anti-TRGV9/anti-TAA2 bispecific antibody (VG9SB10SC1087_P18_D08-Fab RF, TAA2-scFv (TAA2V9B100.001)) binds γδ T cells (left panel) and mediates γδ T cell cytotoxicity against TAA2 expressing H929 cells in vitro (right panel). $EC_{50}$ values were calculated as described in methods. Representative data shown here are from a single experiment.
Figure 16:
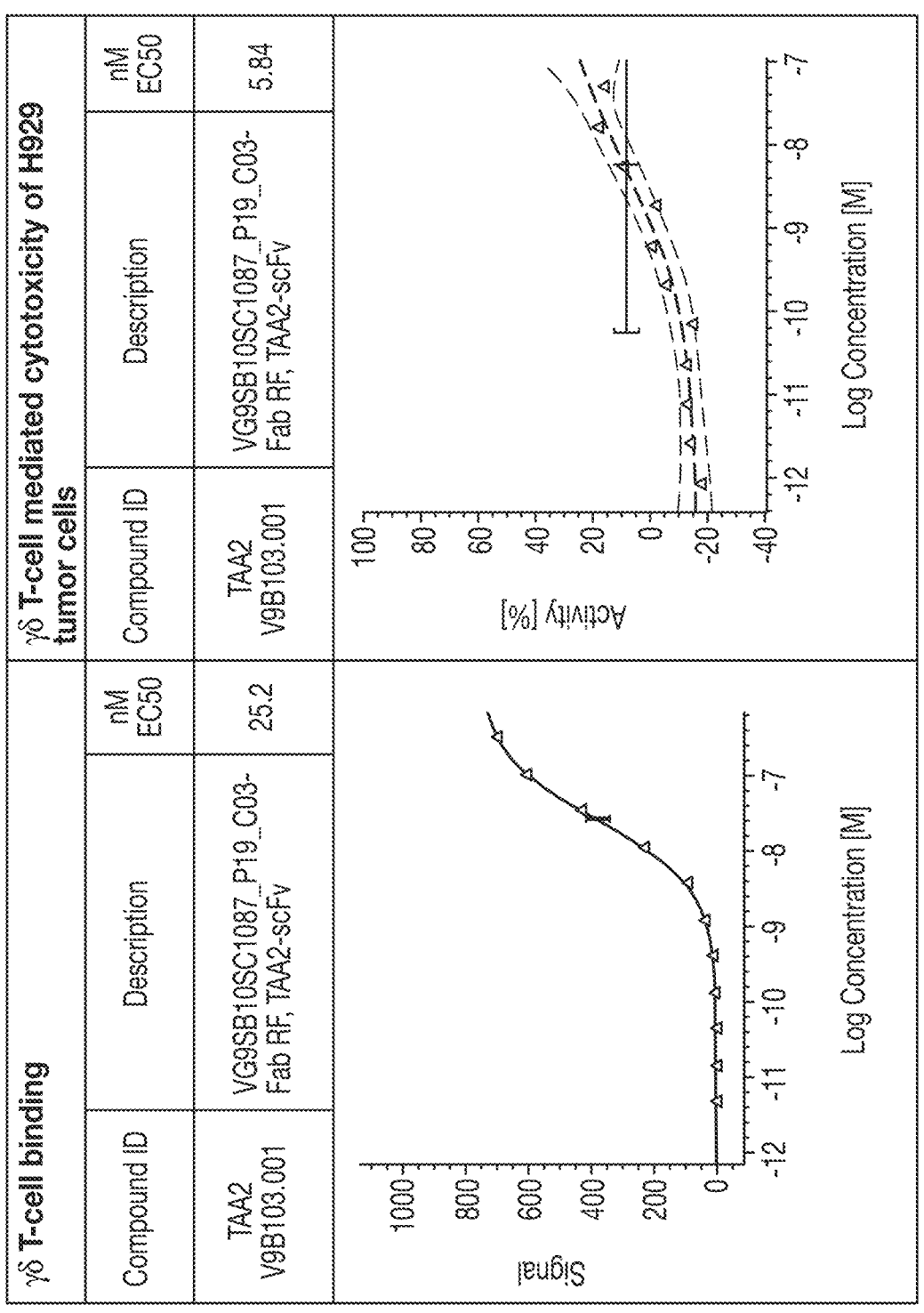
FIG. 16 shows that the anti-TRGV9/anti-TAA2 bispecific antibody (VG9SB10SC1087_P19_C03-Fab RF, TAA2-scFv (TAA2V9B103.001)) binds γδ T cells (left panel) and mediates γδ T cell cytotoxicity against TAA2 expressing H929 cells in vitro (right panel). $EC_{50}$ values were calculated as described in methods. Representative data shown here are from a single experiment.

The two antibodies (VG9B2) were expressed in CHO-Expi cells. The purified chimera human IgG1 mAb (silent Fc) demonstrated binding to human γδ T cells showing specificity toward TCR Vγ9, as shown in FIG. 12 (left panel).

Example 5.3: Production and De Novo Sequencing of Anti-TAA2 Mab

An anti-TAA2 clone was obtained and sequenced (data not shown).

Example 5.4: Preparation of Anti-TRGV9/Anti-TAA2 Bispecific Antibodies

The variable region sequence of anti-TRGV9 and anti-TAA2 antibodies was used to generate a bispecific human IgG1 antibody to be tested for T cell re-directed killing of H929 cells, which express TAA2. A summary of Vγ9 and TAA2 clones is provided in Table 29.

TABLE 29

| Summary of Vγ9 and TAA2 clones | | |
|---|---|---|
| | | B # |
| i. | VG9B420-LH-scFv Half Ab | TAA2V9B101 |
| ii. | VG9SB10SC1087_P18_D08-Fab Half Ab | TAA2V9B100 |
| iii. | VG9SB10SC1087_P18_C12-Fab Half Ab | TAA2V9B101 |
| iv. | TAA2 | Not Shown |
| v. | VG9SB10SC1087_P19_C03-Fab Half Ab | TAA2V9B103 |

The bispecific antibodies were produced as Fab (Vg9) x scFv (TAA2) and scFv (Vg9) x Fab (TAA2) antibodies in the knob-into-hole format as human IgG1 with silent Fc. Nucleic acid sequences encoding variable regions were subcloned into a custom mammalian expression vectors containing constant region of human IgG1 expression cassettes using standard PCR restriction enzyme based standard cloning techniques, and sequenced verified. The bispecific antibodies were expressed by transient transfection in Chinese hamster ovary cell line.

The sequences of the bispecific antibodies expressed in the CHO cells are shown in Table 30 below.

TABLE 30

| Sequences of antibodies expressed in CHO cells | | | |
|---|---|---|---|
| mAb ID | 'Knob' arm and 'hole' arm amino acid sequence | | SEQ ID NO: |
| TAA2-Fab (half-mAb) | Heavy Chain B TAA2V9B71 | SEQUENCE NOT SHOWN | — |
| | Light Chain TAA2V9B71 | SEQUENCE NOT SHOWN | — |
| VG9SB10SC1087_P18_D08-Fab (half-mAb) | Heavy Chain A TAA2V9B100 | MAWVWTLLFLMAAAQSIQAEVQLVQSGAEVKKPGSSVKVSCKASGDTFNNYAISWVRQAPGQGLEWMGGIIPFFGTPDYAQKFQGRVTITADKSTSTAYMELSGLRSEDTAVYYCARPGSGSPDYYYYDMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVSVSHEDPEVKFNWYVDGVEVHNAKTKPREEQYNSTYRVVSVLTVLHQDWLNGKEYKCKVSNKALPAPIEKTISKAKGQPREPQVYVYPPSREEMTKNQVSLTCLVKGFYPSDIAVEWESNGQPENNYKTTPPVLDSDGSFALVSKLTVDKSRWQQGNVFSCSVMHEALHNRFTQKSLSLSPGK | 150 |
| | Light Chain A TAA2V9B100 | MAWVWTLLFLMAAAQSIQADIVMTQTPLSSPVTLGQPASISCRSSQSLVHSDGNTYLSWLQQRPGQPPRLLIYKISNRFSGVPDRFSGSGAGTDFTLKINRVEAEDVGVYYCMQATQFPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 151 |
| VG9SB10SC1087_P18_C12-Fab (half-mAb) | Heavy Chain A TAA2V9B101 | MAWVWTLLFLMAAAQSIQAEVQLVQSGAEVKKPGSSVKVSCKASGGTFSSYAISWVRQAPGQGLEWMGGNIPIFNTANYAQKFQDRVTITADKSTSTAYMELSSLRSEDTAVYYCVREGTGYSYGLDYWGQGTPVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVSVSHEDPEVKFNWYVDGVEVHNAKTKPREEQYNSTYRVVSVLTVLHQDWLNGKEYKCKVSNKALPAPIEKTISKAKGQPREPQVYVYPPSREEMTKNQVSLTCLVKGFYPSDIAVEWESNGQPENNYKTTPPVLDSDGSFALVSKLTVDKSRWQQGNVFSCSVMHEALHNRFTQKSLSLSPGK | 152 |
| | Light Chain A TAA2V9B101 | MAWVWTLLFLMAAAQSIQAEIVMTQSPLSSPVTLGQPASISCRSSQSLIHSDGNTYLSWLQQRPGQPPRLLIYKISNRFSGVPDRFSGSGAGTDFTLKISRVEAEDVGIYYCMQAKQFPITFGGGTKVDIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 153 |

TABLE 30-continued

Sequences of antibodies expressed in CHO cells

| mAb ID | 'Knob' arm and 'hole' arm amino acid sequence | | SEQ ID NO: |
|---|---|---|---|
| VG9SB10 SC1087_ P 19_C03- Fab (half- mAb) | Heavy Chain A TAA2V9B1 03 | MAWVWTLLFLMAAAQSIQAQVQLQ ESGPGLVKPSQTLSLTCTVSGGSI SSSGGGSYWSWIRQHPGKGLEWIGYI YNSGSTYYNPSLKSRVSMSVDTSK NQFSLKLSSVTAADTAVYYCARDS NYEWFFDLWGPGTLVTSSASTKG PSVFPLAPSSKSTSGGTAALGCLV KDYFPEPVTVSWNSGALTSGVHTF PAVLQSSGLYSLSSVVTVPSSSLG TQTYICNVNHKPSNTKVDKKVEPK SCDKTHTCPPCPAPEAAGGPSVFL FPPKPKDTLMISRTPEVTCVVVSV SHEDPEVKFNWYVDGVEVHNAKTK PREEQYNSTYRVVSVLTVLHQDWL NGKEYKCKVSNKALPAPIEKTISK AKGQPREPQVYVYPPSREEMTKNQ VSLTCLVKGFYPSDIAVEWESNGQ PENNYKTTPPVLDSDGSFALVSKL TVDKSRWQQGNVFSCSVMHEALHN RFTQKSLSLSPGK | 154 |
| | Light Chain A TAA2V9B1 03 | MAWVWTLLFLMAAAQSIQAEIVMT QSPATLSLSPGERATLSCRASQSV SSYLAWYQQKPGQAPRLLIYDASN RATGIPARFSGSGSGTDFTLTISS LEPEDFAVYYCQQRSNWPLTFGGG TKVEIKRTVAAPSVFIFPPSDEQL KSGTASVVCLLNNFYPREAKVQWK VDNALQSGNSQESVTEQDSKDSTY SLSSTLTLSKADYEKHKVYACEVT HQGLSSPVTKSFNRGEC | 155 | scFv Sequences

| mAb ID | 'Knob' arm and 'hole' arm amino acid sequence | | SEQ ID NO: |
|---|---|---|---|
| Vg9-B3- LH-scFv (half- mAb) | Heavy Chain A TAA2V9B1 06 | MAWVWTLLFLMAAAQSIQADIQMT QSPASLSASVGETVTITCRASENI HNYLAWYQQKQGKSPQLLVYNAKT LADGVPSRFSGSGSGTQYSLKINS LQPEDFGNYYCQHFWSYPLTFGAG TKLELKGGSEGKSSGSGSESKSTG GSQGQMQQSGAELVKPGASVKLSC KTSGFTFSSNYISWLKQKPGQSLE WIAWIHGGTGGIGYNQKFTGKAQL TVDTSSTTAYMQFSSLTTEDSAIY YCARRGYGAWFAYWGQGTLVTVSA EPKSSDKTHTCPPCPAPEAAGGPS VFLFPPKPKDTLMISRTPEVTCVV VSVSHEDPEVKFNWYVDGVEVHNA KTKPREEQYNSTYRVVSVLTVLHQ DWLNGKEYKCKVSNKALPAPIEKT ISKAKGQPREPQVYVYPPSREEMT KNQVSLTCLVKGFYPSDIAVEWES NGQPENNYKTTPPVLDSDGSFALV SKLTVDKSRWQQGNVFSCSVMHEA LHNHYTQKSLSLSPGK | SEQ ID NO: 97 |
| VG9B420- LH-scFv (half- mAb) | Heavy Chain A TAA2V9B7 1 | MAWVWTLLFLMAAAQSIQAEIVMT QSPGTLSLSPGDRATLSCRASQSV ASSYLAWYQQKPGQSPRLLIYGAS SRATGIPDRFSGSGSGTDFTLTIS RLEPEDFAVYYCQQYGSSPPYTFG QGTRLEIKGGSEGKSSGSGSESKS TGGSEVQLVESGGGLVKPGGSLRL SCSASGFTFSNYDMNWVRQAPGKG LEWVSSISSSSSYIYYADSVKGRF TISRDNAKNSLYLQMNSLRAEDTA VYHCARDVGVTTDYYYGMDVWGQ GTMVTVSSEPKSSDKTHTCPPCPA PEAAGGPSVFLFPPKPKDTLMISR TPEVTCVVVSVSHEDPEVKFNWYV DGVEVHNAKTKPREEQYNSTYRVV SVLTVLHQDWLNGKEYKCKVSNKA LPAPIEKTISKAKGQPREPQVYVY PPSREEMTKNQVSLTCLVKGFYPS | SEQ ID NO: 106 |

TABLE 30-continued

Sequences of antibodies expressed in CHO cells

| mAb ID | 'Knob' arm and 'hole' arm amino acid sequence | | SEQ ID NO: |
|---|---|---|---|
| | | DIAVEWESNGQPENNYKTTPPVLD SDGSFALVSKLTVDKSRWQQGNVF SCSVMHEALHNHYTQKSLSLSPGK | |
| TAA2- scFv (half- mAb) | Heavy Chain B TAA2V9B1 01 | SEQUENCE NOT SHOWN | – |

TABLE 31

Anti-TRGV9 and Anti-TAA2 Heavy and Light
Chain Sequences

| Antibody | Heavy Chain | Light Chain |
|---|---|---|
| VG9SB10 SC1087_ P18_D08 | EVQLVQSGAEVKKPGSSVKVS CKASGDTFNNYAISWVRQAPG QGLEWMGGIIPFFGTPDYAQK FQGRVTITADKSTSTAYMELS GLRSEDTAVYYCARPGSGSPD YYYYDMDVWGQGTTVTVSSAS TKGPSVFPLAPSSKSTSGGTA ALGCLVKDYFPEPVTVSWNSG ALTSGVHTFPAVLQSSGLYSL SSVVTVPSSSLGTQTYICNVN HKPSNTKVDKKVEPKSCDKTH TCPPCPAPEAAGGPSVFLFPP KPKDTLMISRTPEVTCVVVSV SHEDPEVKFNWYVDGVEVHNA KTKPREEQYNSTYRVVSVLTV LHQDWLNGKEYKCKVSNKALP APIEKTISKAKGQPREPQVYV YPPSREEMTKNQVSLTCLVKG FYPSDIAVEWESNGQPENNYK TTPPVLDSDGSFALVSKLTVD KSRWQQGNVFSCSVMHEALHN RFTQKSLSLSPGK (SEQ ID NO: 115) | DIVMTQTPLSSPVT LGQPASISCRSSQS LVHSDGNTYLSWLQ QRPGQPPRLLIYKI SNRFSGVPDRFSGS GAGTDFTLKINRVE AEDVGVYYCMQATQ FPLTFGGGTKVEIK RTVAAPSVFIFPPS DEQLKSGTASVVCL LNNFYPREAKVQWK VDNALQSGNSQESV TEQDSKDSTYSLSS TLTLSKADYEKHKV YACEVTHQGLSSPV TKSFNRGEC (SEQ ID NO: 116) |
| VG9SB1 0SC108 7_P18_ C12 | EVQLVQSGAEVKKPGSSVKVS CKASGGTFSSYAISWVRQAPG QGLEWMGGNIPIFNTANYAQK FQDRVTITADKSTSTAYMELS SLRSEDTAVYYCVREGTGYSY GLDYWGQGTPVTVSSASTKGP SVTSGGTAALGCLVKDYFPEP VTVSWNSGALTSGVHTFPAVL QSSGLYSLSSVVTVPSSSLGT QTYICNVNHKPSNTKVDKKVE PKSCDKTHTCPPCPAPEAAGG PSVFLFPPKPKDTLMISRTPE VTCVVVSVSHEDPEVKFNWYV DGVEVHNAKTKPREEQYNSTY RVVSVLTVLHQDWLNGKEYKC KVSNKALPAPIEKTISKAKGQ PREPQVYVYPPSREEMTKNQV SLTCLVKGFYPSDIAVEWESN GQPENNYKTTPPVLDSDGSFA LVSKLTVDKSRWQQGNVFSCS VMHEALHNRFTQKSLSLSPGK (SEQ ID NO: 125) | EIVMTQSPLSSPVT LGQPASISCRSSQS LIHSDGNTYLSWLQ QRPGQPPRLLIYKI SNRFSGVPDRFSGS GAGTDFTLKISRVE AEDVGIYYCMQAKQ FPITFGQGTKVDIK RTVAAPSVFIFPPS DEQLKSGTASVVCL LNNFYPREAKVQWK VDNALQSGNSQESV TEQDSKDSTYSLSS TLTLSKADYEKHKV YACEVTHQGLSSPV TKSFNRGEC (SEQ ID NO: 126) |
| VG9SB1 0SC108 7_P19_ C03 | QVQLQESGPGLVKPSQTLSLT CTVSGGSISSGGSYWSWIRQH PGKGLEWIGYIYNSGSTYYNP SLKSRVSMSVDTSKNQFSLKL SSVTAADTAVYYCARDSNYEW FFDLWGPGTLVTSSASTKGP SVFPLAPSSKSTSGGTAALGC | EIVMTQSPATLSLS PGERATLSCRASQS VSSYLAWYQQKPGQ APRLLIYDASNRAT GIPARFSGSGSGTD FTLTISSLEPEDFA VYYCQQRSNWPLTE |

US 12,673,995 B2

247

TABLE 31-continued

Anti-TRGV9 and Anti-TAA2 Heavy and Light Chain Sequences

| Antibody | Heavy Chain | Light Chain |
|---|---|---|
| | LVKDYFPEPVTVSWNSGALTS<br>GVHTFPAVLQSSGLYSLSSVV<br>TVPSSSLGTQTYICNVNHKPS<br>NTKVDKKVEPKSCDKTHTCPP<br>CPAPEAAGGPSVFLFPPKPKD<br>TLMISRTPEVTCVVVSVSHED<br>PEVKFNWYVDGVEVHNAKTKP<br>REEQYNSTYRVVSVLTVLHQD<br>WLNGKEYKCKVSNKALPAPIE<br>KTISKAKGQPREPQVYVPPS<br>REEMTKNQVSLTCLVKGFYPS<br>DIAVEWESNGQPENNYKTTPP<br>VLDSDGSFALVSKLTVDKSRW<br>QQGNVFSCSVMHEALHNRFTQ<br>KSLSLSPGK<br>(SEQ ID NO: 135) | GGGTKVEIKRTVAA<br>PSVFIFPPSDEQLK<br>SGTASVVCLLNNFY<br>PREAKVQWKVDNAL<br>QSGNSQESVTEQDS<br>KDSTYSLSSTLTLS<br>KADYEKHKVYACEV<br>THQGLSSPVTKSFN<br>RGEC<br>(SEQ ID<br>NO: 136) |
| TAA2 | SEQUENCE NOT SHOWN | SEQUENCE NOT SHOWN |

The antibodies were initially purified by MABSELECT SURE PROTEIN A column (GE Healthcare). The column was equilibrated with PBS pH 7.2 and loaded with fermentation supernatant at a flow rate of 2 mL/min. After loading, the column was washed with 4 column volumes of PBS followed by elution in 30 mM sodium acetate, pH 3.5. Fractions containing protein peaks as monitored by absorbance at 280 nm were pooled and neutralized to pH 5.0 by adding 1% 3 M sodium acetate pH 9.0. The bispecific mAbs were further purified on a preparative SUPERDEX 200 10/300 GL (GE healthcare) size exclusion chromatography (SEC) column equilibrated with PBS buffer. The integrity of sample was assessed by endotoxin measurement (<3.0 EU/mg), SDS-PAGE under reducing and non-reducing conditions, SEC, and intact mass by MS.

Example 5.5: Evaluation of Binding and Cytotoxic Properties of the Anti-TRGV9/Anti-TAA2 Bispecific Antibody Using H929 Cells and Human γδ T Cells Each of FIGS. 12-16 shows that the anti-TRGV9/anti-TAA2 bispecific antibodies bind γδ T cells (left panels) and mediate γδ T cell cytotoxicity against TAA2 expressing H929 cells in vitro (right panels). For the binding assays, γδ-enriched T cells were used, and samples incubated for 1 hour at 37° C. prior to measurements. For the killing assays, expanded γδ T cells (effectors) were co-cultured with H929 at 5:1 E:T ratios in the presence of various concentrations of the bispecific antibody for 72 hours at 37° C. Bispecific constructs were tested in 11-point titration curve with a 3-fold dilution series starting at 50 nM antibody concentration. Human pan T cells were used as effector cells, as was done previously (see above). H929-WT tumor cell line was used as target cells. Dose response curves show anti-TRGV9/anti-TAA2 bispecific mediated γδ T cell cytotoxicity against TAA2 expressing H929 cells in a dose dependent manner. $EC_{50}$ values were calculated as described in methods. Representative data shown are from a single experiment.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

SEQUENCE LISTING

```
Sequence total quantity: 762
SEQ ID NO: 1          moltype = AA  length = 5
FEATURE               Location/Qualifiers
REGION                1..5
                      note = Description of Artificial Sequence: Synthetic peptide
REGION                1..5
                      note = LP7A5 HCDR1
source                1..5
                      mol_type = protein
                      organism = synthetic construct
SEQUENCE: 1
DHYIN                                                              5

SEQ ID NO: 2          moltype = AA  length = 17
FEATURE               Location/Qualifiers
REGION                1..17
                      note = Description of Artificial Sequence: Synthetic peptide
REGION                1..17
                      note = LP7A5 HCDR2
source                1..17
                      mol_type = protein
                      organism = synthetic construct
SEQUENCE: 2
QIYPGDGNTY YNQKFKG                                                17

SEQ ID NO: 3          moltype = AA  length = 9
FEATURE               Location/Qualifiers
REGION                1..9
                      note = Description of Artificial Sequence: Synthetic peptide
REGION                1..9
                      note = LP7A5_1 HCDR3
source                1..9
                      mol_type = protein
                      organism = synthetic construct
```

-continued

```
SEQUENCE: 3
NYGDYTIDF                                                                    9

SEQ ID NO: 4          moltype = AA  length = 17
FEATURE               Location/Qualifiers
REGION                1..17
                      note = Description of Artificial Sequence: Synthetic peptide
REGION                1..17
                      note = LP7A5 LCDR1
source                1..17
                      mol_type = protein
                      organism = synthetic construct
SEQUENCE: 4
KSSQSLLYSS NQKNYLA                                                            17

SEQ ID NO: 5          moltype = AA  length = 7
FEATURE               Location/Qualifiers
REGION                1..7
                      note = Description of Artificial Sequence: Synthetic peptide
REGION                1..7
                      note = LP7A5 LCDR2
source                1..7
                      mol_type = protein
                      organism = synthetic construct
SEQUENCE: 5
WASTRES                                                                       7

SEQ ID NO: 6          moltype = AA  length = 8
FEATURE               Location/Qualifiers
REGION                1..8
                      note = Description of Artificial Sequence: Synthetic peptide
REGION                1..8
                      note = LP7A5 LCDR3
source                1..8
                      mol_type = protein
                      organism = synthetic construct
SEQUENCE: 6
QQYYRYHT                                                                      8

SEQ ID NO: 7          moltype = AA  length = 118
FEATURE               Location/Qualifiers
REGION                1..118
                      note = Description of Artificial Sequence: Synthetic
                       polypeptide
REGION                1..118
                      note = LP7A5 Heavy Chain Variable Region
source                1..118
                      mol_type = protein
                      organism = synthetic construct
SEQUENCE: 7
EVQLQQSGAE LARPGASVKL SCKASGFTFT DHYINWVKQR TGQGLEWIGQ IYPGDGNTYY  60
NQKFKGKATL TADKSSSTAY MQLSSLTSED SAVYFCAPNY GDYTIDFWGQ GTSVTVSS    118

SEQ ID NO: 8          moltype = AA  length = 112
FEATURE               Location/Qualifiers
REGION                1..112
                      note = Description of Artificial Sequence: Synthetic
                       polypeptide
REGION                1..112
                      note = LP7A5 Light Chain Variable Region
source                1..112
                      mol_type = protein
                      organism = synthetic construct
SEQUENCE: 8
DIVMSQSPSS LAVSVGEKVT MSCKSSQSLL YSSNQKNYLA WYQQKPGQSP KLLIYWASTR  60
ESGVPDRFTG SGSGTDFTLT ISSVKAEDLA VYYCQQYYRY HTFGTGTKLE IK          112

SEQ ID NO: 9          moltype = AA  length = 5
FEATURE               Location/Qualifiers
REGION                1..5
                      note = Description of Artificial Sequence: Synthetic peptide
REGION                1..5
                      note = I3RB217 HCDR1
source                1..5
                      mol_type = protein
                      organism = synthetic construct
SEQUENCE: 9
SYWIS                                                                         5
```

```
SEQ ID NO: 10           moltype = AA  length = 17
FEATURE                 Location/Qualifiers
REGION                  1..17
                        note = Description of Artificial Sequence: Synthetic peptide
REGION                  1..17
                        note = I3RB217 HCDR2
source                  1..17
                        mol_type = protein
                        organism = synthetic construct
SEQUENCE: 10
IIDPSDSDTR YSPSFQG                                                17

SEQ ID NO: 11           moltype = AA  length = 9
FEATURE                 Location/Qualifiers
REGION                  1..9
                        note = Description of Artificial Sequence: Synthetic peptide
REGION                  1..9
                        note = I3RB217 HCDR3
source                  1..9
                        mol_type = protein
                        organism = synthetic construct
SEQUENCE: 11
GDGSTDLDY                                                        9

SEQ ID NO: 12           moltype = AA  length = 11
FEATURE                 Location/Qualifiers
REGION                  1..11
                        note = Description of Artificial Sequence: Synthetic peptide
REGION                  1..11
                        note = I3RB217 LCDR1
source                  1..11
                        mol_type = protein
                        organism = synthetic construct
SEQUENCE: 12
RASQSVSSSY L                                                     11

SEQ ID NO: 13           moltype = AA  length = 7
FEATURE                 Location/Qualifiers
REGION                  1..7
                        note = Description of Artificial Sequence: Synthetic peptide
REGION                  1..7
                        note = I3RB217 LCDR2
source                  1..7
                        mol_type = protein
                        organism = synthetic construct
SEQUENCE: 13
GASSRAT                                                          7

SEQ ID NO: 14           moltype = AA  length = 9
FEATURE                 Location/Qualifiers
REGION                  1..9
                        note = Description of Artificial Sequence: Synthetic peptide
REGION                  1..9
                        note = I3RB217 LCDR3
source                  1..9
                        mol_type = protein
                        organism = synthetic construct
SEQUENCE: 14
QQDYGFPWT                                                        9

SEQ ID NO: 15           moltype = AA  length = 118
FEATURE                 Location/Qualifiers
REGION                  1..118
                        note = Description of Artificial Sequence: Synthetic
                        polypeptide
REGION                  1..118
                        note = I3RB217 Heavy Chain Variable Region
source                  1..118
                        mol_type = protein
                        organism = synthetic construct
SEQUENCE: 15
EVQLVQSGAE VKKPGESLKI SCKGSGYSFT SYWISWVRQM PGKGLEWMGI IDPSDSDTRY  60
SPSFQGQVTI SADKSISTAY LQWSSLKASD TAMYYCARGD GSTDLDYWGQ GTLVTVSS   118

SEQ ID NO: 16           moltype = AA  length = 108
FEATURE                 Location/Qualifiers
REGION                  1..108
                        note = Description of Artificial Sequence: Synthetic
                        polypeptide
```

```
REGION                        1..108
                              note = I3RB217 Light Chain Variable Region
source                        1..108
                              mol_type = protein
                              organism = synthetic construct
SEQUENCE: 16
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QDYGFPWTFG QGTKVEIK               108

SEQ ID NO: 17                 moltype = AA  length = 717
FEATURE                       Location/Qualifiers
REGION                        1..717
                              note = Description of Artificial Sequence: Synthetic
                               polypeptide
REGION                        1..717
                              note = Vgamma9 half antibody
source                        1..717
                              mol_type = protein
                              organism = synthetic construct
SEQUENCE: 17
MAWVWTLLFL MAAAQSIQAD IVMSQSPSSL AVSVGEKVTM SCKSSQSLLY SSNQKNYLAW  60
YQQKPGQSPK LLIYWASTRE SGVPDRFTGS GSGTDFTLTI SSVKAEDLAV YYCQQYYRYH  120
TFGTGTKLEI KRTVAAPSVF IFPPSDEQLK SGTASVVCLL NNFYPREAKV QWKVDNALQS  180
GNSQESVTEQ DSKDSTYSLS STLTLSKADY EKHKVYACEV THQGLSSPVT KSFNRGECGG  240
SEGKSSGSGS ESKSTEGKSS GSGSESKSTG GSEVQLQQSG AELARPGASV KLSCKASGFT  300
FTDHYINWVK QRTGQGLEWI GQIYPGDGNT YYNQKFKGKA TLTADKSSST AYMQLSSLTS  360
EDSAVYFCAP NYGDYTIDFW GQGTSVTVSS ASTKGPSVFP LAPCSRSTSE STAALGCLVK  420
DYFPEPVTVS WNSGALTSGV HTFPAVLQSS GLYSLSSVVT VPSSSLGTKT YTCNVDHKPS  480
NTKVDKRVES KYGPPCPPCP APEAAGGPSV FLFPPKPKDT LMISRTPEVT CVVVDVSQED  540
PEVQFNWYVD GVEVHNAKTK PREEQFNSTY RVVSVLTVLH QDWLNGKEYK CKVSNKGLPS  600
SIEKTISKAK GQPREPQVYT LPPSQEEMTK NQVSLSCAVK GFYPSDIAVE WESNGQPENN  660
YKTTPPVLDS DGSFFLVSRL TVDKSRWQEG NVFSCSVMHE ALHNRFTQKS LSLSLGK     717

SEQ ID NO: 18                 moltype = AA  length = 713
FEATURE                       Location/Qualifiers
REGION                        1..713
                              note = Description of Artificial Sequence: Synthetic
                               polypeptide
REGION                        1..713
                              note = CD123 half antibody
source                        1..713
                              mol_type = protein
                              organism = synthetic construct
SEQUENCE: 18
MAWVWTLLFL MAAAQSIQAE IVLTQSPGTL SLSPGERATL SCRASQSVSS SYLAWYQQKP  60
GQAPRLLIYG ASSRATGIPD RFSGSGSGTD FTLTISRLEP EDFAVYYCQQ DYGFPWTFGQ  120
GTKVEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGECGGSEGK  240
SSGSGSESKS TEGKSSGSGS ESKSTGGSEV QLVQSGAEVK KPGESLKISC KGSGYSFTSY  300
WISWVRQMPG KGLEWMGIID PSDSDTRYSP SFQGQVTISA DKSISTAYLQ WSSLKASDTA  360
MYYCARGDGS TDLDYWGQGT LVTVSSASTK GPSVFPLAPC SRSTSESTAA LGCLVKDYFP  420
EPVTVSWNSG ALTSGVHTFP AVLQSSGLYS LSSVVTVPSS SLGTKTYTCN VDHKPSNTKV  480
DKRVESKYGP PCPPCPAPEA AGGPSVFLFP PKPKDTLMIS RTPEVTCVVV DVSQEDPEVQ  540
FNWYVDGVEV HNAKTKPREE QFNSTYRVVS VLTVLHQDWL NGKEYKCKVS NKGLPSSIEK  600
TISKAKGQPR EPQVYTLPPS QEEMTKNQVS LWCLVKGFYP SDIAVEWESN GQPENNYKTT  660
PPVLDSDGSF FLYSRLTVDK SRWQEGNVFS CSVMHEALHN HYTQKSLSLS LGK         713

SEQ ID NO: 19                 moltype = AA  length = 713
FEATURE                       Location/Qualifiers
REGION                        1..713
                              note = Description of Artificial Sequence: Synthetic
                               polypeptide
REGION                        1..713
                              note = B23B49 half antibody
source                        1..713
                              mol_type = protein
                              organism = synthetic construct
SEQUENCE: 19
MAWVWTLLFL MAAAQSIQAE IVLTQSPGTL SLSPGERATL SCRASQSVSS SYLAWYQQKP  60
GQAPRLLIYG ASSRATGIPD RFSGSGSGTD FTLTISRLEP EDFAVYYCQQ DYGFPWTFGQ  120
GTKVEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGECGGSEGK  240
SSGSGSESKS TEGKSSGSGS ESKSTGGSEV QLVQSGAEVK KPGESLKISC KGSGYSFTSY  300
WISWVRQMPG KGLEWMGIID PSDSDTRYSP SFQGQVTISA DKSISTAYLQ WSSLKASDTA  360
MYYCARGDGS TDLDYWGQGT LVTVSSASTK GPSVFPLAPC SRSTSESTAA LGCLVKDYFP  420
EPVTVSWNSG ALTSGVHTFP AVLQSSGLYS LSSVVTVPSS SLGTKTYTCN VDHKPSNTKV  480
DKRVESKYGP PCPPCPAPEA AGGPSVFLFP PKPKDTLMIS RTPEVTCVVV DVSQEDPEVQ  540
FNWYVDGVEV HNAKTKPREE QFNSTYRVVS VLTVLHQDWL NGKEYKCKVS NKGLPSSIEK  600
TISKAKGQPR EPQVYTLPPS QEEMTKNQVS LWCLVKGFYP SDIAVEWESN GQPENNYKTT  660
```

PPVLDSDGSF FLYSRLTVDK SRWQEGNVFS CSVMHEALHN HYTQKSLSLS LGK          713

```
SEQ ID NO: 20            moltype = DNA   length = 2151
FEATURE                  Location/Qualifiers
misc_feature             1..2151
                         note = Description of Artificial Sequence: Synthetic
                          polynucleotide
misc_feature             1..2151
                         note = Vgamma9 half antibody
source                   1..2151
                         mol_type = other DNA
                         organism = synthetic construct
SEQUENCE: 20
atggcctggg tgtggaccct gctgttcctg atggccgccg cccagagcat ccaggccgac    60
atcgtgatga gccagagccc aagcagcctg gccgtgagcg tgggcgagaa ggtgaccatg   120
agctgcaaga gcagccagag cctgctgtac agcagcaacc agaagaacta cctggcctgg   180
taccagcaga agcaggcca gagcccaaag ctgctgatct actgggccag cacccgcgag    240
agcggcgtgc cagaccgctt caccggcagc ggcagcggca ccgacttcac cctgaccatc   300
agcagcgtga aggccgagga cctgccgtg tactactgcc agcagtacta ccgctaccac    360
accttcggca ccggcaccaa gctggagatc aagcgcaccg tggccgcccc aagcgtgttc   420
atcttcccac caagcgacga gcagctgaag agcggcaccg ccagcgtggt gtgcctgctg   480
aacaacttct acccacgcga ggccaaggtg cagtggaagg tggacaacgc cctgcagagc   540
ggcaacagcc aggagagcgt gaccgagcag gacagcaagg acagcaccta cagcctgagc   600
agcaccctga ccctgagcaa ggccgactac gagaagcaca aggtgtacgc ctgcgaggtg   660
acccaccagg gcctgagcag cccagtgacc aagagcttca accgcggcga gtgcggcggc   720
agcgagggca gagcgaaggc cagcggcagc gagagcaaga gcaccgaggg caagagcgcc   780
ggcagcggca gcgagagcaa gagcaccggc ggcagcgagg tgcagctgca gcagagcggc   840
gccgagctgg cccgcccagg cgccagcgtg aagctgagct gcaaggccag cggcttcacc   900
ttcaccgacc actacatcaa ctgggtgaag cagcgcaccg ccagggcct ggagtggatc    960
ggccagatct acccaggcga cggcaacacc tactacaacc agaagttcaa gggcaaggcc  1020
accctgaccg ccgacaagag cagcagcacc gcctacatgc agctgagcag cctgaccagc  1080
gaggacagcc ccgtgtactt ctgcgcccca aactacggcg actacaccat cgacttctgg  1140
ggccagggca ccagcgtgac cgtgagcagc gccagcacca agggcccaag cgtgttccca  1200
ctggccccat gcagccgcag caccagcgag agcaccgccg ccctgggctg cctggtgaag  1260
gactacttcc cagagccagt gaccgtgagc tggaacagcg gcgccctgac cagcggcgtg  1320
cacaccttcc cagccgtgct gcagagcagc ggcctgtaca gcctgagcag cgtggtgacc  1380
gtgccaagca gcagcctggg caccaagacc tacacctgca acgtggacca caagccaagc  1440
aacaccaagg tggacaagcg cgtggagagc aagtacggcc caccatgccc accatgccca  1500
gccccagagg ccgccggcgg cccaagcgtg ttcctgttcc caccaaagcc aaaggacacc  1560
ctgatgatca gccgcacccc agaggtgacc tgcgtggtgg tggacgtgag ccaggaggac  1620
ccagaggtgc agttcaactg gtacgtggac ggcgtggagg tgcacaacgc caagaccaag  1680
ccacgcgagg agcagttcaa cagcacctac cgcgtggtga gcgtgctgac cgtgctgcac  1740
caggactggc tgaacggcaa ggagtacaag tgcaaggtca gcaacaaggg cctgccaagc  1800
agcatcgaga gaccatcag caaggccaag ggccagccac gcgagccaca ggtgtacacc  1860
ctgccaccaa gccaggagga gatgaccaag aaccaggtga gcctgtggtg cctggtgaag  1920
ggcttctacc caagcgacat cgccgtggag tgggagagca cggccagcc agagaacaac  1980
tacaagacca ccccaccagt gctggacagc gacggcagct tcttcctgta cagccgcctg  2040
accgtggaca gagccgctg gcaggagggc aacgtgttca gctgcagcgt gatgcacgag  2100
gccctgcaca accactacac ccagaagagc ctgagcctga gcctgggcaa g          2151
```

```
SEQ ID NO: 21            moltype = DNA   length = 2139
FEATURE                  Location/Qualifiers
misc_feature             1..2139
                         note = Description of Artificial Sequence: Synthetic
                          polynucleotide
misc_feature             1..2139
                         note = CD123 half antibody
source                   1..2139
                         mol_type = other DNA
                         organism = synthetic construct
SEQUENCE: 21
atggcctggg tgtggaccct gctgttcctg atggccgccg cccagagcat ccaggccgag    60
atcgtgctga cccagagccc aggcaccctg agcctgagcc caggcgagcg cgccaccctg   120
agctgccgcg ccagccagag cgtgagcagc agctacctgg cctggtacca gcagaagcca   180
ggccaggccc cacgcctgct gatctacggc gccagcagc gcgccaccgg catcccagac    240
cgcttcagcg gcagcggcag cggcaccgac ttcaccctga ccatcagccg cctggagcca   300
gaggacttcg ccgtgtacta ctgccagcag gactacggct cccatggac cttcggccag    360
ggcaccaagg tggagatcaa gcgcaccgtg gccgcccca gcgtgttcat cttcccacca    420
agcgacgagc agctgaagag cggcaccgcc agcgtggtgt gcctgctgaa caacttctac    480
ccacgcgagg ccaaggtgca gtggaaggtg gacaacgccc tgcagagcgg caacagccag   540
gagagcgtga ccgagcagga cagcaaggac agcacctaca gcctgagcag caccctgacc   600
ctgagcaagg ccgactacga gaagcacaag gtgtacgcct gcgaggtgac ccaccagggc   660
ctgagcagcc agtgaccaa gagcttcaac cgcggcgagt gcggcggcag cgagggcaag   720
agcggcggca gcgagagcaa gaccgagggg agcggcagcg agagcaagac cgagggcaag   780
gagagcaaga gcaccggcgg cagcgaggtg cagctggtgc agagcggcgc cgaggtgaag   840
aagccaggcg agagcctgaa gatcagctgc aagggcagcg gctacagctt caccagctac   900
tggatcagct gggtgcgcca gatgccaggc aagggcctgg agtggatggg catcatcgac   960
ccaagcgaca gcgacacccg ctacagccca agcttccagg gccaggtgac catcagcgcc  1020
gacaagagca tcagcaccgc ctacctgcag tggagcagcc tgaaggccag cgacaccgcc  1080
```

```
atgtactact gcgcccgcgg cgacggcagc accgacctgg actactgggg ccagggcacc  1140
ctggtgaccg tgagcagcgc cagcaccaag ggcccaagcg tgttcccact ggccccatgc  1200
agccgcagca ccagcgagag caccgccgcc ctgggctgcc tggtgaagga ctacttccca  1260
gagccagtga ccgtgagctg gaacagcggc gccctgacca cgcggcgtgca caccttccca  1320
gccgtgctgc agagcagcgg cctgtacagc ctgagcagcg tggtgaccgt gccaagcagc  1380
agcctgggca ccaagaccta cacctgcaac gtggaccaca agccaagcaa caccaaggtg  1440
gacaagcgcg tggagagcaa gtacggccca ccatgcccac catgcccagc cccagaggcc  1500
gccggcggcc caagcgtgtt cctgttccca ccaaagccaa aggacaccct gatgatcagc  1560
cgcacccag  aggtgacctg cgtggtggtg gacgtgagcc aggaggaccc agaggtgcag  1620
ttcaactggt acgtggacgg cgtggaggtg cacaacgcca agaccaagcc acgcgaggag  1680
cagttcaaca gcacctaccg cgtggtgagc gtgctgaccg tgctgcacca ggactggctg  1740
aacggcaagg agtacaagtg caaggtgagc aacaagggcc tgccaagcag catcgagaag  1800
accatcagca aggccaaggg ccagccacgc gagccacagg tgtacaccct gccaccaagc  1860
caggaggaga tgaccaagaa ccaggtgagc ctgtgtggtg tggtgaagg  cttctaccca  1920
agcgacatcg ccgtggagtg ggagagcaac ggccagccag agaacaacta caagaccacc  1980
ccaccagtgc tggacagcga cggcagcttc ttcctgtaca gccgcctgac cgtggacaag  2040
agccgctggc aggagggcaa cgtgttcagc tgcagcgtga tgcacgaggc cctgcacaac  2100
cactacaccc agaagagcct gagcctgagc ctgggcaag                          2139
```

```
SEQ ID NO: 22          moltype = DNA  length = 2154
FEATURE                Location/Qualifiers
misc_feature           1..2154
                       note = Description of Artificial Sequence: Synthetic
                        polynucleotide
misc_feature           1..2154
                       note = B23B49 half antibody
source                 1..2154
                       mol_type = other DNA
                       organism = synthetic construct
SEQUENCE: 22
atggcctggg tgtggaccct gctgttcctg atggccgccg cccagagcat ccaggccgac  60
atcgtgatga cccagagccc agacagcctg gccgtgagcc tgggcgagcg cgccaccatc  120
aactgccgcg ccagccagag cgtggactac aacggcatca gctacatgca ctggtaccag  180
cagaagccag gccagccacc aaagctgctg atctacgccg ccagcaaccc agagagcggc  240
gtgccagacc gcttcagcgg cagcggcagc ggcaccgact tcaccctgac catcagcagc  300
ctgcaggccg aggacgtggc cgtgtactac tgccagcaga tcatcgagga cccatggacc  360
ttcggccagg gcaccaaggt ggagatcaag cgcaccgtgg ccgccccaag cgtgttcatc  420
ttcccaccaa gcgacgagca gctgaagagc ggcaccgcca gcgtggtgtg cctgctgaac  480
aacttctacc cacgcgaggc caaggtgcag tggaaggtgg acaacgccct gcagagcggc  540
aacagccagg agagcgtgac cgagcaggac agcaaggaca gcacctacag cctgagcagc  600
accctgaccc tgagcaaggc cgactacgag aagcacaagg tgtacgcctg cgaggtgacc  660
caccaggggc tgagcagccc agtgaccaag agcttcaacc gcggcgagtg cggcggcagc  720
gagggcaaga gcagcggcag cggcagcgag agcaagagca ccggcggcgg cagcggcagc  780
agcggcagcg agagcaagag caccggcggc agccagatca ccctgaagga gagcggccca  840
accctggtga gccaacccca gaccctgacc ctgacctgca ccttcagcgg cttcagcctg  900
agcaccagcg gcatgggcgt gagctggatc cgccagccac aggcaaggc  cctggagtgg  960
ctggcccaca tctactggga cgacgacaag cgctacaacc caagcctgaa gagccgcctg  1020
accatcacca aggacaccag caagaaccag gtggtgctga ccatgaccaa catggaccca  1080
gtggacaccg ccacctacta ctgcgcccgc ctgtacggct tcacctacgg cttcgcctac  1140
tggggccagg gcaccctggt gaccgtgagc agcgccagca ccaagggccc aagcgtgttc  1200
ccactgcagcc cagcaccgac gagagcaccg ccgccctggg ctgcctggtg gtgacg   1260
aaggactact tcccagagcc agtgaccgtg agctggaaca gcggcgccct gaccagcggc  1320
gtgcacacct tcccagccgt gctgcagagc agcggcctgt acagcctgag cagcgtggtg  1380
accgtgccaa gcagcagcct gggcaccaag acctacacct gcaacgtgga ccacaagcca  1440
agcaacacca aggtggacaa gcgcgtggag agcaagtacg gcccaccatg cccaccatgc  1500
ccagccccag aggccgccgg cggcccaagc gtgttcctgt tcccaccaaa gccaaaggac  1560
accctgatga tcagccgcac cccagaggtg acctgcgtgg tggtggacgt gagccaggag  1620
gacccagagg tgcagttcaa ctggtacgtg gacggcgtgg aggtgcacaa cgccaagacc  1680
aagccacgcg aggagcagtt caacagcacc taccgcgtgg tgagcgtgct gaccgtgctg  1740
caccaggact ggctgaacgg caaggagtac aagtgcaagg tgagcaacaa gggcctgcca  1800
agcagcatcg agaagaccat cagcaaggcc aagggccagc cacgcgagcc acaggtgtac  1860
accctgccac caagccagga ggagatgacc aagaaccagg tgagcctgtg tgtgcctggtg  1920
aagggcttct acccaagcga catcgccgtg gagtgggaga gcaacggcca gccagagaac  1980
aactacaaga ccaccccacc agtgctggac agcgacggca gcttcttcct gtacagccgc  2040
ctgaccgtgg acaagagccg ctggcaggag ggcaacgtgt tcagctgcag cgtgatgcac  2100
gaggccctgc acaaccacta cacccagaag agcctgagcc tgagcctggg caag        2154
```

```
SEQ ID NO: 23          moltype = AA  length = 445
FEATURE                Location/Qualifiers
REGION                 1..445
                       note = Description of Artificial Sequence: Synthetic
                        polypeptide
REGION                 1..445
                       note = VG1 heavy chain 1
source                 1..445
                       mol_type = protein
                       organism = synthetic construct
SEQUENCE: 23
EVQLQQSGAE LARPGASVKL SCKASGFTFT DHYINWVKQR TGQGLEWIGQ IYPGDGNTYY  60
```

```
NQKFKGKATL TADKSSSTAY MQLSSLTSED SAVYFCAPNY GDYTIDFWGQ GTSVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP EAAGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLSCAVKGF YPSDIAVEWE SNGQPENNYK TTPPVLDSDG SFFLVSRLTV DKSRWQEGNV  420
FSCSVMHEAL HNRFTQKSLS LSLGK                                        445

SEQ ID NO: 24              moltype = AA  length = 219
FEATURE                    Location/Qualifiers
REGION                     1..219
                           note = Description of Artificial Sequence: Synthetic
                            polypeptide
REGION                     1..219
                           note = VG1 light chain 1
source                     1..219
                           mol_type = protein
                           organism = synthetic construct
SEQUENCE: 24
DIVMSQSPSS LAVSVGEKVT MSCKSSQSLL YSSNQKNYLA WYQQKPGQSP KLLIYWASTR   60
ESGVPDRFTG SGSGTDFTLT ISSVKAEDLA VYYCQQYYRY HTFGTGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 25              moltype = AA  length = 445
FEATURE                    Location/Qualifiers
REGION                     1..445
                           note = Description of Artificial Sequence: Synthetic
                            polypeptide
REGION                     1..445
                           note = VG1 heavy chain 2
source                     1..445
                           mol_type = protein
                           organism = synthetic construct
SEQUENCE: 25
EVQLVQSGAE VKKPGESLKI SCKGSGYSFT SYWISWVRQM PGKGLEWMGI IDPSDSDTRY   60
SPSFQGQVTI SADKSISTAY LQWSSLKASD TAMYYCARGD GSTDLDYWGQ GTLVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP EAAGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLWCLVKGF YPSDIAVEWE SNGQPENNYK TTPPVLDSDG SFFLYSRLTV DKSRWQEGNV  420
FSCSVMHEAL HNHYTQKSLS LSLGK                                        445

SEQ ID NO: 26              moltype = AA  length = 215
FEATURE                    Location/Qualifiers
REGION                     1..215
                           note = Description of Artificial Sequence: Synthetic
                            polypeptide
REGION                     1..215
                           note = VG1 light chain 2
source                     1..215
                           mol_type = protein
                           organism = synthetic construct
SEQUENCE: 26
EIVLTQSPGT LSLSPGERAT LSCRASQSVS SSYLAWYQQK PGQAPRLLIY GASSRATGIP   60
DRFSGSGSGT DFTLTISRLE PEDFAVYYCQ QDYGFPWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 27              moltype = AA  length = 447
FEATURE                    Location/Qualifiers
REGION                     1..447
                           note = Description of Artificial Sequence: Synthetic
                            polypeptide
REGION                     1..447
                           note = VG3 heavy chain 1
source                     1..447
                           mol_type = protein
                           organism = synthetic construct
SEQUENCE: 27
QVQLQESGPG LVKPSETLSL TCTVSGYSIT SGYFWNWIRQ PPGKGLEWIG YISYDGSNNY   60
NPSLKSRVTI SRDTSKNQFS LKLSSVTAAD TAVYYCASPS PGTGYAVDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEAAGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLSCAVK GFYPSDIAVE WESNGQPENN YKTTPPVLDS DGSFFLVSRL TVDKSRWQEG  420
NVFSCSVMHE ALHNRFTQKS LSLSLGK                                      447
```

```
SEQ ID NO: 28              moltype = AA  length = 219
FEATURE                    Location/Qualifiers
REGION                     1..219
                           note = Description of Artificial Sequence: Synthetic
                            polypeptide
REGION                     1..219
                           note = VG3 light chain 1
source                     1..219
                           mol_type = protein
                           organism = synthetic construct
SEQUENCE: 28
DIQMTQSPSS LSASVGDRVT ITCRSSQSLV HSNGNTYLHW YQQKPGKAPK FLIYKVSNRF  60
SGVPSRFSGS GSGTDFTLTI SSLQPEDFAT YYCSQSTHVP FTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                          219

SEQ ID NO: 29              moltype = AA  length = 447
FEATURE                    Location/Qualifiers
REGION                     1..447
                           note = Description of Artificial Sequence: Synthetic
                            polypeptide
REGION                     1..447
                           note = VG3 heavy chain 2
source                     1..447
                           mol_type = protein
                           organism = synthetic construct
SEQUENCE: 29
QITLKESGPT LVKPTQTLTL TCTFSGFSLS TSGMGVSWIR QPPGKALEWL AHIYWDDDKR  60
YNPSLKSRLT ITKDTSKNQV VLTMTNMDPV DTATYYCARL YGFTYGFAYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEAAGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLWCLVK GFYPSDIAVE WESNGQPENN YKTTPPVLDS DGSFFLYSRL TVDKSRWQEG  420
NVFSCSVMHE ALHNHYTQKS LSLSLGK                                       447

SEQ ID NO: 30              moltype = AA  length = 218
FEATURE                    Location/Qualifiers
REGION                     1..218
                           note = Description of Artificial Sequence: Synthetic
                            polypeptide
REGION                     1..218
                           note = VG3 light chain 2
source                     1..218
                           mol_type = protein
                           organism = synthetic construct
SEQUENCE: 30
DIVMTQSPDS LAVSLGERAT INCRASQSVD YNGISYMHWY QQKPGQPPKL LIYAASNPES  60
GVPDRFSGSG SGTDFTLTIS SLQAEDVAVY YCQQIIEDPW TFGQGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                           218

SEQ ID NO: 31              moltype = AA  length = 9
FEATURE                    Location/Qualifiers
REGION                     1..9
                           note = Description of Artificial Sequence: Synthetic peptide
REGION                     1..9
                           note = LP7A5_2 HCDR3
source                     1..9
                           mol_type = protein
                           organism = synthetic construct
SEQUENCE: 31
NMGMYTIDF                                                            9

SEQ ID NO: 32              moltype = AA  length = 9
FEATURE                    Location/Qualifiers
REGION                     1..9
                           note = Description of Artificial Sequence: Synthetic peptide
REGION                     1..9
                           note = LP7A5_3 HCDR3
source                     1..9
                           mol_type = protein
                           organism = synthetic construct
SEQUENCE: 32
NMGMYTLDF                                                            9

SEQ ID NO: 33              moltype = AA  length = 9
FEATURE                    Location/Qualifiers
```

```
REGION                    1..9
                          note = Description of Artificial Sequence: Synthetic peptide
REGION                    1..9
                          note = LP7A5_4 HCDR3
source                    1..9
                          mol_type = protein
                          organism = synthetic construct
SEQUENCE: 33
NYGDYTLDF                                                                              9

SEQ ID NO: 34             moltype = AA  length = 118
FEATURE                   Location/Qualifiers
REGION                    1..118
                          note = Description of Artificial Sequence: Synthetic
                           polypeptide
REGION                    1..118
                          note = LP7A5_2 Heavy Chain Variable Region
source                    1..118
                          mol_type = protein
                          organism = synthetic construct
SEQUENCE: 34
EVQLQQSGAE LARPGASVKL SCKASGFTFT DHYINWVKQR TGQGLEWIGQ IYPGDGNTYY  60
NQKFKGKATL TADKSSSTAY MQLSSLTSED SAVYFCAPNM GMYTIDFWGQ GTSVTVSS    118

SEQ ID NO: 35             moltype = AA  length = 118
FEATURE                   Location/Qualifiers
REGION                    1..118
                          note = Description of Artificial Sequence: Synthetic
                           polypeptide
REGION                    1..118
                          note = LP7A5_3 Heavy Chain Variable Region
source                    1..118
                          mol_type = protein
                          organism = synthetic construct
SEQUENCE: 35
EVQLQQSGAE LARPGASVKL SCKASGFTFT DHYINWVKQR TGQGLEWIGQ IYPGDGNTYY  60
NQKFKGKATL TADKSSSTAY MQLSSLTSED SAVYFCAPNM GMYTLDFWGQ GTSVTVSS    118

SEQ ID NO: 36             moltype = AA  length = 118
FEATURE                   Location/Qualifiers
REGION                    1..118
                          note = Description of Artificial Sequence: Synthetic
                           polypeptide
REGION                    1..118
                          note = LP7A5_4 Heavy Chain Variable Region
source                    1..118
                          mol_type = protein
                          organism = synthetic construct
SEQUENCE: 36
EVQLQQSGAE LARPGASVKL SCKASGFTFT DHYINWVKQR TGQGLEWIGQ IYPGDGNTYY  60
NQKFKGKATL TADKSSSTAY MQLSSLTSED SAVYFCAPNY GDYTLDFWGQ GTSVTVSS    118

SEQ ID NO: 37             moltype =   length =
SEQUENCE: 37
000

SEQ ID NO: 38             moltype =   length =
SEQUENCE: 38
000

SEQ ID NO: 39             moltype =   length =
SEQUENCE: 39
000

SEQ ID NO: 40             moltype =   length =
SEQUENCE: 40
000

SEQ ID NO: 41             moltype =   length =
SEQUENCE: 41
000

SEQ ID NO: 42             moltype =   length =
SEQUENCE: 42
000

SEQ ID NO: 43             moltype =   length =
SEQUENCE: 43
000
```

-continued

```
SEQ ID NO: 44          moltype =    length =
SEQUENCE: 44
000

SEQ ID NO: 45          moltype =    length =
SEQUENCE: 45
000

SEQ ID NO: 46          moltype = AA   length = 713
FEATURE                Location/Qualifiers
REGION                 1..713
                       note = Description of Artificial Sequence: Synthetic
                        polypeptide
REGION                 1..713
                       note = Anti-RSV ('knob'-arm) sequence expressed in CHO cells
source                 1..713
                       mol_type = protein
                       organism = synthetic construct
SEQUENCE: 46
MAWVWTLLFL MAAAQSIQAE IVLTQSPGTL SLSPGERATL SCRASQSVSS SYLAWYQQKP    60
GQAPRLLIYG ASSRATGIPD RFSGSGSGTD FTLTISRLEP EDFAVYYCQQ DYGFPWTFGQ   120
GTKVEIKRTV AAPSVFIFPP SDEQLKSGTA SVVCLLNNFY PREAKVQWKV DNALQSGNSQ   180
ESVTEQDSKD STYSLSSTLT LSKADYEKHK VYACEVTHQG LSSPVTKSFN RGECGGSEGK   240
SSGSGSESKS TEGKSSGSGS ESKSTGGSEV QLVQSGAEVK KPGESLKISC KGSGYSFTSY   300
WISWVRQMPG KGLEWMGIID PSDSDTRYSP SFQGQVTISA DKSISTAYLQ WSSLKASDTA   360
MYYCARGDGS TDLDYWGQGT LVTVSSASTK GPSVFPLAPC SRSTSESTAA LGCLVKDYFP   420
EPVTVSWNSG ALTSGVHTFP AVLQSSGLYS LSSVVTVPSS SLGTKTYTCN VDHKPSNTKV   480
DKRVESKYGP PCPPCPAPEA AGGPSVFLFP PKPKDTLMIS RTPEVTCVVV DVSQEDPEVQ   540
FNWYVDGVEV HNAKTKPREE QFNSTYRVVS VLTVLHQDWL NGKEYKCKVS NKGLPSSIEK   600
TISKAKGQPR EPQVYTLPPS QEEMTKNQVS LWCLVKGFYP SDIAVEWESN GQPENNYKTT   660
PPVLDSDGSF FLYSRLTVDK SRWQEGNVFS CSVMHEALHN HYTQKSLSLS LGK          713

SEQ ID NO: 47          moltype = AA   length = 446
FEATURE                Location/Qualifiers
REGION                 1..446
                       note = Description of Artificial Sequence: Synthetic
                        polypeptide
REGION                 1..446
                       note = C33B904 Heavy Chain
source                 1..446
                       mol_type = protein
                       organism = synthetic construct
SEQUENCE: 47
EVQLVESGGG LVQPGRSLRL SCAASGFTFD DYAMHWVRQA PGKGLEWVSG IGWSGGSIVY    60
ADSVKGRFTI SRDNAKNSLY LQMNSLRAED TALYYCAKDS PYGDFFDYWG QGTLVTVSSA   120
STKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEAAGGPSVF   240
LFPPKPKDTL MISRTPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLWCLVKG FYPSDIAVEW ESNGQPENNY KTTPPVLDSD GSFFLYSRLT VDKSRWQEGN   420
VFSCSVMHEA LHNHYTQKSL SLSLGK                                        446

SEQ ID NO: 48          moltype = AA   length = 220
FEATURE                Location/Qualifiers
REGION                 1..220
                       note = Description of Artificial Sequence: Synthetic
                        polypeptide
REGION                 1..220
                       note = C33B904 Light Chain
source                 1..220
                       mol_type = protein
                       organism = synthetic construct
SEQUENCE: 48
DIVMTQSPDS LAVSLGERAT INCKSSQTVF YSSNNKNYLA WYQQKPGQPP KLLISWASTR    60
KSGVPDRFSG SGSGTDFTLT VSSLQAEDVA VYYCQHYYST PYTFGQGTKL EIKRTVAAPS   120
VFIFPPSDEQ LKSGTASVVC LLNNFYPREA KVQWKVDNAL QSGNSQESVT EQDSKDSTYS   180
LSSTLTLSKA DYEKHKVYAC EVTHQGLSSP VTKSFNRGEC                         220

SEQ ID NO: 49          moltype =    length =
SEQUENCE: 49
000

SEQ ID NO: 50          moltype =    length =
SEQUENCE: 50
000

SEQ ID NO: 51          moltype =    length =
SEQUENCE: 51
```

-continued

```
000

SEQ ID NO: 52          moltype =    length =
SEQUENCE: 52
000

SEQ ID NO: 53          moltype =    length =
SEQUENCE: 53
000

SEQ ID NO: 54          moltype =    length =
SEQUENCE: 54
000

SEQ ID NO: 55          moltype =    length =
SEQUENCE: 55
000

SEQ ID NO: 56          moltype =    length =
SEQUENCE: 56
000

SEQ ID NO: 57          moltype =    length =
SEQUENCE: 57
000

SEQ ID NO: 58          moltype = AA   length = 454
FEATURE                Location/Qualifiers
REGION                 1..454
                       note = Description of Artificial Sequence: Synthetic
                        polypeptide
REGION                 1..454
                       note = TRBC1 Heavy Chain
source                 1..454
                       mol_type = protein
                       organism = synthetic construct
SEQUENCE: 58
EVRLQQSGPD LIKPGASVKM SCKASGYTFT GYVMHWVKQR PGQGLEWIGF INPYNDDIQS  60
NERFRGKATL TSDKSSTTAY MELSSLTSED SAVYYCARGA GYNFDGAYRF FDFWGQGTTL  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
AAGGPSVFLF PPKPKDTLMI SRTPEVTCVV VSVSHEDPEV KFNWYVDGVE VHNAKTKPRE  300
EQYNSTYRVV SVLTVLHQDW LNGKEYKCKV SNKALPAPIE KTISKAKGQP REPQVYVLPP  360
SREEMTKNQV SLLCLVKGFY PSDIAVEWES NGQPENNYLT WPPVLDSDGS FFLYSKLTVD  420
KSRWQQGNVF SCSVMHEALH NRFTQKSLSL SPGK                             454

SEQ ID NO: 59          moltype = AA   length = 219
FEATURE                Location/Qualifiers
REGION                 1..219
                       note = Description of Artificial Sequence: Synthetic
                        polypeptide
REGION                 1..219
                       note = TRBC1 Light Chain
source                 1..219
                       mol_type = protein
                       organism = synthetic construct
SEQUENCE: 59
DVVMTQSPLS LPVSLGDQAS ISCRSSQRLV HSNGNTYLHW YLQKPGQSPK LLIYRVSNRF  60
PGVPDRFSGS GSGTDFTLKI SRVEAEDLGI YFCSQSTHVP YTFGGGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 60          moltype = AA   length = 8
FEATURE                Location/Qualifiers
REGION                 1..8
                       note = Description of Artificial Sequence: Synthetic peptide
REGION                 1..8
                       note = TRGV9Ab HCDR1
source                 1..8
                       mol_type = protein
                       organism = synthetic construct
SEQUENCE: 60
GFTFTDHY                                                          8

SEQ ID NO: 61          moltype = AA   length = 8
FEATURE                Location/Qualifiers
REGION                 1..8
                       note = Description of Artificial Sequence: Synthetic peptide
REGION                 1..8
```

```
                            note = TRGV9Ab HCDR2
source                      1..8
                            mol_type = protein
                            organism = synthetic construct
SEQUENCE: 61
IYPGSGNT                                                              8

SEQ ID NO: 62               moltype = AA  length = 11
FEATURE                     Location/Qualifiers
REGION                      1..11
                            note = Description of Artificial Sequence: Synthetic peptide
REGION                      1..11
                            note = TRGV9Ab HCDR3
source                      1..11
                            mol_type = protein
                            organism = synthetic construct
SEQUENCE: 62
ARNYGDYTID F                                                          11

SEQ ID NO: 63               moltype = AA  length = 12
FEATURE                     Location/Qualifiers
REGION                      1..12
                            note = Description of Artificial Sequence: Synthetic peptide
REGION                      1..12
                            note = TRGV9Ab LCDR1
source                      1..12
                            mol_type = protein
                            organism = synthetic construct
SEQUENCE: 63
QSVLYSSNNK NY                                                         12

SEQ ID NO: 64               moltype =    length =
SEQUENCE: 64
000

SEQ ID NO: 65               moltype = AA  length = 118
FEATURE                     Location/Qualifiers
REGION                      1..118
                            note = Description of Artificial Sequence: Synthetic
                             polypeptide
REGION                      1..118
                            note = TRGV9Ab_var17 Heavy Chain Variable Region
source                      1..118
                            mol_type = protein
                            organism = synthetic construct
SEQUENCE: 65
QVQLVQSGAE VKKPGASVKV SCKASGFTFT DHYINWVRQA TGQGLEWMGQ IYPGSGNTYY  60
NQKFKGRVTM TRDTSISTAY MELSSLRSED TAVYYCARNY GDYTIDFWGQ GTSVTVSS     118

SEQ ID NO: 66               moltype = AA  length = 112
FEATURE                     Location/Qualifiers
REGION                      1..112
                            note = Description of Artificial Sequence: Synthetic
                             polypeptide
REGION                      1..112
                            note = TRGV9Ab_var17 Light Chain Variable Region
source                      1..112
                            mol_type = protein
                            organism = synthetic construct
SEQUENCE: 66
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQYYRY HTFGTGTKLE IK          112

SEQ ID NO: 67               moltype = AA  length = 118
FEATURE                     Location/Qualifiers
REGION                      1..118
                            note = Description of Artificial Sequence: Synthetic
                             polypeptide
REGION                      1..118
                            note = TRGV9Ab_var29 Heavy Chain Variable Region
source                      1..118
                            mol_type = protein
                            organism = synthetic construct
SEQUENCE: 67
QVQLVQSGAE VKKPGASVKV SCKASGFTFT DHYINWVRQA TGQGLEWMGQ IYPGSGNTYY  60
NQKFKGRVTM TRNTSISTAY MELSSLRSED TAVYYCARNY GDYTIDFWGQ GTSVTVSS     118

SEQ ID NO: 68               moltype = AA  length = 112
FEATURE                     Location/Qualifiers
```

```
REGION                    1..112
                          note = Description of Artificial Sequence: Synthetic
                           polypeptide
REGION                    1..112
                          note = TRGV9Ab_var29 Light Chain Variable Region
source                    1..112
                          mol_type = protein
                          organism = synthetic construct
SEQUENCE: 68
DIVMTQSPDS LAVSLGERAT ISCKSSQSVL YSSNNKNYLA WYQQKPGQPP KLLIYWASTR  60
ESGVPDRFSG SGSGTDFTLT ISSLQAEDVA VYYCQQYYRY HTFGTGTKLE IK          112

SEQ ID NO: 69             moltype = AA  length = 448
FEATURE                   Location/Qualifiers
REGION                    1..448
                          note = Description of Artificial Sequence: Synthetic
                           polypeptide
REGION                    1..448
                          note = TRGV9_7A5_1 Heavy Chain
source                    1..448
                          mol_type = protein
                          organism = synthetic construct
SEQUENCE: 69
EVQLQQSGAE LARPGASVKL SCKASGFTFT DHYINWVKQR TGQGLEWIGQ IYPGDGNTYY  60
NQKFKGKATL TADKSSSTAY MQLSSLTSED SAVYFCAPNY GDYTIDFWGQ GTSVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVSVSHE DPEVKFNWYV DGVEVHNAKT KPREEQYNST  300
YRVVSVLTVL HQDWLNGKEY KCKVSNKALP APIEKTISKA KGQPREPQVY VYPPSREEMT  360
KNQVSLTCLV KGFYPSDIAV EWESNGQPEN NYKTTPPVLD SDGSFALVSK LTVDKSRWQQ  420
GNVFSCSVMH EALHNRFTQK SLSLSPGK                                     448

SEQ ID NO: 70             moltype = AA  length = 501
FEATURE                   Location/Qualifiers
REGION                    1..501
                          note = Description of Artificial Sequence: Synthetic
                           polypeptide
REGION                    1..501
                          note = TRGV9_var17 scFv
source                    1..501
                          mol_type = protein
                          organism = synthetic construct
SEQUENCE: 70
MAWVWTLLFL MAAAQSIQAD IVMTQSPDSL AVSLGERATI NCKSSQSVLY SSNNKNYLAW  60
YQQKPGQPPK LLIYWASTRE SGVPDRFSGS GSGTDFTLTI SSLQAEDVAV YYCQQYYRYH  120
TFGTGTKLEI KGGSEGKSSG SGSESKSTGG SQVQLVQSGA EVKKPGASVK VSCKASGFTF  180
TDHYINWVRQ ATGQGLEWMG QIYPGSGNTY YNQKFKGRTM MTRDTSISTA YMELSSLRSE  240
DTAVYYCARN YGDYTIDFWG QGTSVTVSSE PKSSDKTHTC PPCPAPEAAG GPSVFLFPPK  300
PKDTLMISRT PEVTCVVVSV SHEDPEVKFN WYVDGVEVHN AKTKPREEQY NSTYRVVSVL  360
TVLHQDWLNG KEYKCKVSNK ALPAPIEKTI SKAKGQPREP QVYVYPPSRE EMTKNQVSLT  420
CLVKGFYPSD IAVEWESNGQ PENNYKTTPP VLDSDGSFAL VSKLTVDKSR WQQGNVFSCS  480
VMHEALHNHY TQKSLSLSPG K                                            501

SEQ ID NO: 71             moltype = AA  length = 448
FEATURE                   Location/Qualifiers
REGION                    1..448
                          note = Description of Artificial Sequence: Synthetic
                           polypeptide
REGION                    1..448
                          note = TRGV9_var17 Heavy Chain
source                    1..448
                          mol_type = protein
                          organism = synthetic construct
SEQUENCE: 71
QVQLVQSGAE VKKPGASVKV SCKASGFTFT DHYINWVRQA TGQGLEWMGQ IYPGSGNTYY  60
NQKFKGRVTM TRDTSISTAY MELSSLRSED TAVYYCARNY GDYTIDFWGQ GTSVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVSVSHE DPEVKFNWYV DGVEVHNAKT KPREEQYNST  300
YRVVSVLTVL HQDWLNGKEY KCKVSNKALP APIEKTISKA KGQPREPQVY VYPPSREEMT  360
KNQVSLTCLV KGFYPSDIAV EWESNGQPEN NYKTTPPVLD SDGSFALVSK LTVDKSRWQQ  420
GNVFSCSVMH EALHNRFTQK SLSLSPGK                                     448

SEQ ID NO: 72             moltype = AA  length = 219
FEATURE                   Location/Qualifiers
REGION                    1..219
                          note = Description of Artificial Sequence: Synthetic
                           polypeptide
REGION                    1..219
```

```
                          note = TRGV9_var17 Light Chain
source                    1..219
                          mol_type = protein
                          organism = synthetic construct
SEQUENCE: 72
DIVMTQSPDS LAVSLGERAT INCKSSQSVL YSSNNKNYLA WYQQKPGQPP KLLIYWASTR   60
ESGVPDRFSG SGSGTDFTLT ISSLQAEDVA VYYCQQYYRY HTFGTGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 73             moltype = AA  length = 501
FEATURE                   Location/Qualifiers
REGION                    1..501
                          note = Description of Artificial Sequence: Synthetic
                           polypeptide
REGION                    1..501
                          note = TRGV9_var29 scFv
source                    1..501
                          mol_type = protein
                          organism = synthetic construct
SEQUENCE: 73
MAWVWTLLFL MAAAQSIQAD IVMTQSPDSL AVSLGERATI SCKSSQSVLY SSNNKNYLAW   60
YQQKPGQPPK LLIYWASTRE SGVPDRFSGS GSGTDFTLTI SSLQAEDVAV YYCQQYYRYH  120
TFGTGTKLEI KGGSEGKSSG SGSESKSTGG SQVQLVQSGA EVKKPGASVK VSCKASGFTF  180
TDHYINWVRQ ATGQGLEWMG QIYPGSGNTY YNQKFKGRVT MTRNTSISTA YMELSSLRSE  240
DTAVYYCARN YGDYTIDFWG QGTSVTVSSE PKSSDKTHTC PPCPAPEAAG GPSVFLFPPK  300
PKDTLMISRT PEVTCVVVSV SHEDPEVKFN WYVDGVEVHN AKTKPREEQY NSTYRVVSVL  360
TVLHQDWLNG KEYKCKVSNK ALPAPIEKTI SKAKGQPREP QVYVYPPSRE EMTKNQVSLT  420
CLVKGFYPSD IAVEWESNGQ PENNYKTTPP VLDSDGSFAL VSKLTVDKSR WQQGNVFSCS  480
VMHEALHNHY TQKSLSLSPG K                                            501

SEQ ID NO: 74             moltype = AA  length = 448
FEATURE                   Location/Qualifiers
REGION                    1..448
                          note = Description of Artificial Sequence: Synthetic
                           polypeptide
REGION                    1..448
                          note = TRGV9_var29 Heavy Chain
source                    1..448
                          mol_type = protein
                          organism = synthetic construct
SEQUENCE: 74
QVQLVQSGAE VKKPGASVKV SCKASGFTFT DHYINWVRQA TGQGLEWMGQ IYPGSGNTYY   60
NQKFKGRVTM TRNTSISTAY MELSSLRSED TAVYYCARNY GDYTIDFWGQ GTSVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVSVSHE DPEVKFNWYV DGVEVHNAKT KPREEQYNST  300
YRVVSVLTVL HQDWLNGKEY KCKVSNKALP APIEKTISKA KGQPREPQVY VYPPSREEMT  360
KNQVSLTCLV KGFYPSDIAV EWESNGQPEN NYKTTPPVLD SDGSFALVSK LTVDKSRWQQ  420
GNVFSCSVMH EALHNRFTQK SLSLSPGK                                     448

SEQ ID NO: 75             moltype = AA  length = 219
FEATURE                   Location/Qualifiers
REGION                    1..219
                          note = Description of Artificial Sequence: Synthetic
                           polypeptide
REGION                    1..219
                          note = TRGV9_var29 Light Chain
source                    1..219
                          mol_type = protein
                          organism = synthetic construct
SEQUENCE: 75
DIVMTQSPDS LAVSLGERAT ISCKSSQSVL YSSNNKNYLA WYQQKPGQPP KLLIYWASTR   60
ESGVPDRFSG SGSGTDFTLT ISSLQAEDVA VYYCQQYYRY HTFGTGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 76             moltype = AA  length = 17
FEATURE                   Location/Qualifiers
REGION                    1..17
                          note = Description of Artificial Sequence: Synthetic peptide
REGION                    1..17
                          note = TRGV9Ab HCDR2
source                    1..17
                          mol_type = protein
                          organism = synthetic construct
SEQUENCE: 76
QIYPGSGNTY YNQKFKG                                                  17
```

```
SEQ ID NO: 77            moltype = AA  length = 17
FEATURE                  Location/Qualifiers
REGION                   1..17
                         note = Description of Artificial Sequence: Synthetic peptide
REGION                   1..17
                         note = TRGV9Ab LCDR1
source                   1..17
                         mol_type = protein
                         organism = synthetic construct
SEQUENCE: 77
KSSQSVLYSS NNKNYLA                                                              17

SEQ ID NO: 78            moltype = AA  length = 467
FEATURE                  Location/Qualifiers
REGION                   1..467
                         note = Description of Artificial Sequence: Synthetic
                         polypeptide
REGION                   1..467
                         note = Anti-TRGV9_7A5_1 (half-mAb) Heavy Chain A
source                   1..467
                         mol_type = protein
                         organism = synthetic construct
SEQUENCE: 78
MAWVVWTLLFL MAAAQSIQAE VQLQQSGAEL ARPGASVKLS CKASGFTFTD HYINWVKQRT  60
GQGLEWIGQI YPGDGNTYYN QKFKGKATLT ADKSSSTAYM QLSSLTSEDS AVYFCAPNYG  120
DYTIDFWGQG TSVTVSSAST KGPSVFPLAP SSKSTSGGTA ALGCLVKDYF PEPVTVSWNS  180
GALTSGVHTF PAVLQSSGLY SLSSVVTVPS SSLGTQTYIC NVNHKPSNTK VDKKVEPKSC  240
DKTHTCPPCP APEAAGGPSV FLFPPKPKDT LMISRTPEVT CVVVSVSHED PEVKFNWYVD  300
GVEVHNAKTK PREEQYNSTY RVVSVLTVLH QDWLNGKEYK CKVSNKALPA PIEKTISKAK  360
GQPREPQVYV YPPSREEMTK NQVSLTCLVK GFYPSDIAVE WESNGQPENN YKTTPPVLDS  420
DGSFALVSKL TVDKSRWQQG NVFSCSVMHE ALHNRFTQKS LSLSPGK             467

SEQ ID NO: 79            moltype = AA  length = 238
FEATURE                  Location/Qualifiers
REGION                   1..238
                         note = Description of Artificial Sequence: Synthetic
                         polypeptide
REGION                   1..238
                         note = Anti-TRGV9_7A5_1 (half-mAb) Light Chain
source                   1..238
                         mol_type = protein
                         organism = synthetic construct
SEQUENCE: 79
MAWVVWTLLFL MAAAQSIQAD IVMSQSPSSL AVSVGEKVTM SCKSSQSLLY SSNQKNYLAW  60
YQQKPGQSPK LLIYWASTRE SGVPDRFTGS GSGTDFTLTI SSVKAEDLAV YYCQQYYRYH  120
TFGTGTKLEI KRTVAAPSVF IFPPSDEQLK SGTASVVCLL NNFYPREAKV QWKVDNALQS  180
GNSQESVTEQ DSKDSTYSLS STLTLSKADY EKHKVYACEV THQGLSSPVT KSFNRGEC   238

SEQ ID NO: 80            moltype = AA  length = 467
FEATURE                  Location/Qualifiers
REGION                   1..467
                         note = Description of Artificial Sequence: Synthetic
                         polypeptide
REGION                   1..467
                         note = Anti- TRGV9_7A5_var17 Heavy Chain A
source                   1..467
                         mol_type = protein
                         organism = synthetic construct
SEQUENCE: 80
MAWVVWTLLFL MAAAQSIQAQ VQLVQSGAEV KKPGASVKVS CKASGFTFTD HYINWVRQAT  60
GQGLEWMGQI YPGSGNTYYN QKFKGRVTMT RDTSISTAYM ELSSLRSEDT AVYYCARNYG  120
DYTIDFWGQG TSVTVSSAST KGPSVFPLAP SSKSTSGGTA ALGCLVKDYF PEPVTVSWNS  180
GALTSGVHTF PAVLQSSGLY SLSSVVTVPS SSLGTQTYIC NVNHKPSNTK VDKKVEPKSC  240
DKTHTCPPCP APEAAGGPSV FLFPPKPKDT LMISRTPEVT CVVVSVSHED PEVKFNWYVD  300
GVEVHNAKTK PREEQYNSTY RVVSVLTVLH QDWLNGKEYK CKVSNKALPA PIEKTISKAK  360
GQPREPQVYV YPPSREEMTK NQVSLTCLVK GFYPSDIAVE WESNGQPENN YKTTPPVLDS  420
DGSFALVSKL TVDKSRWQQG NVFSCSVMHE ALHNRFTQKS LSLSPGK             467

SEQ ID NO: 81            moltype = AA  length = 238
FEATURE                  Location/Qualifiers
REGION                   1..238
                         note = Description of Artificial Sequence: Synthetic
                         polypeptide
REGION                   1..238
                         note = Anti- TRGV9_7A5_var17 Light Chain
source                   1..238
                         mol_type = protein
                         organism = synthetic construct
SEQUENCE: 81
```

```
MAWVWTLLFL MAAAQSIQAD IVMTQSPDSL AVSLGERATI NCKSSQSVLY SSNNKNYLAW  60
YQQKPGQPPK LLIYWASTRE SGVPDRFSGS GSGTDFTLTI SSLQAEDVAV YYCQQYYRYH  120
TFGTGTKLEI KRTVAAPSVF IFPPSDEQLK SGTASVVCLL NNFYPREAKV QWKVDNALQS  180
GNSQESVTEQ DSKDSTYSLS STLTLSKADY EKHKVYACEV THQGLSSPVT KSFNRGEC  238

SEQ ID NO: 82          moltype = AA  length = 467
FEATURE                Location/Qualifiers
REGION                 1..467
                       note = Description of Artificial Sequence: Synthetic
                        polypeptide
REGION                 1..467
                       note = Anti- TRGV9_7A5_var29 Heavy Chain A
source                 1..467
                       mol_type = protein
                       organism = synthetic construct
SEQUENCE: 82
MAWVWTLLFL MAAAQSIQAQ VQLVQSGAEV KKPGASVKVS CKASGFTFTD HYINWVRQAT  60
GQGLEWMGQI YPGSGNTYYN QKFKGRVTMT RNTSISTAYM ELSSLRSEDT AVYYCARNYG  120
DYTIDFWGQG TSVTVSSAST KGPSVFPLAP SSKSTSGGTA ALGCLVKDYF PEPVTVSWNS  180
GALTSGVHTF PAVLQSSGLY SLSSVVTVPS SSLGTQTYIC NVNHKPSNTK VDKKVEPKSC  240
DKTHTCPPCP APEAAGGPSV FLFPPKPKDT LMISRTPEVT CVVVSVSHED PEVKFNWYVD  300
GVEVHNAKTK PREEQYNSTY RVVSVLTVLH QDWLNGKEYK CKVSNKALPA PIEKTISKAK  360
GQPREPQVYV YPPSREEMTK NQVSLTCLVK GFYPSDIAVE WESNGQPENN YKTTPPVLDS  420
DGSFALVSKL TVDKSRWQQG NVFSCSVMHE ALHNRFTQKS LSLSPGK  467

SEQ ID NO: 83          moltype = AA  length = 238
FEATURE                Location/Qualifiers
REGION                 1..238
                       note = Description of Artificial Sequence: Synthetic
                        polypeptide
REGION                 1..238
                       note = Anti- TRGV9_7A5_var29 Light Chain
source                 1..238
                       mol_type = protein
                       organism = synthetic construct
SEQUENCE: 83
MAWVWTLLFL MAAAQSIQAD IVMTQSPDSL AVSLGERATI SCKSSQSVLY SSNNKNYLAW  60
YQQKPGQPPK LLIYWASTRE SGVPDRFSGS GSGTDFTLTI SSLQAEDVAV YYCQQYYRYH  120
TFGTGTKLEI KRTVAAPSVF IFPPSDEQLK SGTASVVCLL NNFYPREAKV QWKVDNALQS  180
GNSQESVTEQ DSKDSTYSLS STLTLSKADY EKHKVYACEV THQGLSSPVT KSFNRGEC  238

SEQ ID NO: 84          moltype = AA  length = 473
FEATURE                Location/Qualifiers
REGION                 1..473
                       note = Description of Artificial Sequence: Synthetic
                        polypeptide
REGION                 1..473
                       note = Anti-TRBC1 (half-mAb) Heavy Chain B
source                 1..473
                       mol_type = protein
                       organism = synthetic construct
SEQUENCE: 84
MAWVWTLLFL MAAAQSIQAE VRLQQSGPDL IKPGASVKMS CKASGYTFTG YVMHWVKQRP  60
GQGLEWIGFI NPYNDDIQSN ERFRGKATLT SDKSSTTAYM ELSSLTSEDS AVYYCARGAG  120
YNFDGAYRFF DFWGQGTTLT VSSASTKGPS VFPLAPSSKS TSGGTAALGC LVKDYFPEPV  180
TVSWNSGALT SGVHTFPAVL QSSGLYSLSS VVTVPSSSLG TQTYICNVNH KPSNTKVDKK  240
VEPKSCDKTH TCPPCPAPEA AGGPSVFLFP PKPKDTLMIS RTPEVTCVVV SVSHEDPEVK  300
FNWYVDGVEV HNAKTKPREE QYNSTYRVVS VLTVLHQDWL NGKEYKCKVS NKALPAPIEK  360
TISKAKGQPR EPQVYVLPPS REEMTKNQVS LLCLVKGFYP SDIAVEWESN GQPENNYLTW  420
PPVLDSDGSF FLYSKLTVDK SRWQQGNVFS CSVMHEALHN RFTQKSLSLS PGK  473

SEQ ID NO: 85          moltype = AA  length = 238
FEATURE                Location/Qualifiers
REGION                 1..238
                       note = Description of Artificial Sequence: Synthetic
                        polypeptide
REGION                 1..238
                       note = Anti-TRBC1 (half-mAb) Light Chain
source                 1..238
                       mol_type = protein
                       organism = synthetic construct
SEQUENCE: 85
MAWVWTLLFL MAAAQSIQAD VVMTQSPLSL PVSLGDQASI SCRSSQRLVH SNGNTYLHWY  60
LQKPGQSPKL LIYRVSNRFP GVPDRFSGSG SGTDFTLKIS RVEAEDLGIY FCSQSTHVPY  120
TFGGGTKLEI KRTVAAPSVF IFPPSDEQLK SGTASVVCLL NNFYPREAKV QWKVDNALQS  180
GNSQESVTEQ DSKDSTYSLS STLTLSKADY EKHKVYACEV THQGLSSPVT KSFNRGEC  238

SEQ ID NO: 86          moltype = AA  length = 469
FEATURE                Location/Qualifiers
```

-continued

```
REGION              1..469
                    note = Description of Artificial Sequence: Synthetic
                     polypeptide
REGION              1..469
                    note = Anti-RSV (half-mAb) Heavy Chain B
source              1..469
                    mol_type = protein
                    organism = synthetic construct
SEQUENCE: 86
MAWVWTLLFL MAAAQSIQAQ ITLKESGPTL VKPTQTLTLT CTFSGFSLST SGMGVSWIRQ   60
PPGKALEWLA HIYWDDDKRY NPSLKSRLTI TKDTSKNQVV LTMTNMDPVD TATYYCARLY   120
GFTYGFAYWG QGTLVTVSSA STKGPSVFPL APSSKSTSGG TAALGCLVKD YFPEPVTVSW   180
NSGALTSGVH TFPAVLQSSG LYSLSSVVTV PSSSLGTQTY ICNVNHKPSN TKVDKKVEPK   240
SCDKTHTCPP CPAPEAAGGP SVFLFPPKPK DTLMISRTPE VTCVVVSVSH EDPEVKFNWY   300
VDGVEVHNAK TKPREEQYNS TYRVVSVLTV LHQDWLNGKE YKCKVSNKAL PAPIEKTISK   360
AKGQPREPQV YVLPPSREEM TKNQVSLLCL VKGFYPSDIA VEWESNGQPE NNYLTWPPVL   420
DSDGSFFLYS KLTVDKSRWQ QGNVFSCSVM HEALHNHYTQ KSLSLSPGK             469

SEQ ID NO: 87       moltype = AA   length = 238
FEATURE             Location/Qualifiers
REGION              1..238
                    note = Description of Artificial Sequence: Synthetic
                     polypeptide
REGION              1..238
                    note = Anti-RSV (half-mAb) Light Chain
source              1..238
                    mol_type = protein
                    organism = synthetic construct
SEQUENCE: 87
METHSQVFVY MLLWLSGVEG DIVMTQSPDS LAVSLGERAT INCRASQSVD YNGISYMHWY   60
QQKPGQPPKL LIYAASNPES GVPDRFSGSG SGTDFTLTIS SLQAEDVAVY YCQQIIEDPW   120
TFGQGTKVEI KRTVAAPSVF IFPPSDEQLK SGTASVVCLL NNFYPREAKV QWKVDNALQS   180
GNSQESVTEQ DSKDSTYSLS STLTLSKADY EKHKVYACEV THQGLSSPVT KSFNRGEC     238

SEQ ID NO: 88       moltype = AA   length = 495
FEATURE             Location/Qualifiers
REGION              1..495
                    note = Description of Artificial Sequence: Synthetic
                     polypeptide
REGION              1..495
                    note = Anti-Null-scFv Heavy Chain B
source              1..495
                    mol_type = protein
                    organism = synthetic construct
SEQUENCE: 88
MAWVWTLLFL MAAAQSIQAD IQMTQSPSSL SASVGDRVTI TCRASQSISS YLNWYQQKPG   60
CAPKLLIYAA SSLQSGVPSR FSGSGSGTDF TLTISSLQPE DFATYYCQQS YSTPLTFGQG   120
TKVEIKGGGS GGSGGCPPCG GSGGGEVQLLE SGGGLVQPGG SLRLSCAASG FTFSSYAMSW   180
VRQAPGKGLE WVSAISGSGG STYYADSVKG RFTISRDNSK NTLYLQMNSL RAEDTAVYYC   240
AKYDGIYGEL DFWGCGTLVT VSSEPKSSDK THTCPPCPAP EAAGGPSVFL FPPKPKDTLM   300
ISRTPEVTCV VVSVSHEDPE VKFNWYVDGV EVHNAKTKPR EEQYNSTYRV VSVLTVLHQD   360
WLNGKEYKCK VSNKALPAPI EKTISKAKGQ PREPQVYVLP PSREEMTKNQ VSLLCLVKGF   420
YPSDIAVEWE SNGQPENNYL TWPPVLDSDG SFFLYSKLTV DKSRWQQGNV FSCSVMHEAL   480
HNHYTQKSLS LSPGK                                                    495

SEQ ID NO: 89       moltype = AA   length = 8
FEATURE             Location/Qualifiers
REGION              1..8
                    note = Description of Artificial Sequence: Synthetic peptide
source              1..8
                    mol_type = protein
                    organism = synthetic construct
SEQUENCE: 89
GFTFSSNY                                                              8

SEQ ID NO: 90       moltype = AA   length = 8
FEATURE             Location/Qualifiers
REGION              1..8
                    note = Description of Artificial Sequence: Synthetic peptide
source              1..8
                    mol_type = protein
                    organism = synthetic construct
SEQUENCE: 90
IHGGTGGI                                                              8

SEQ ID NO: 91       moltype = AA   length = 11
FEATURE             Location/Qualifiers
REGION              1..11
                    note = Description of Artificial Sequence: Synthetic peptide
```

```
source                     1..11
                           mol_type = protein
                           organism = synthetic construct
SEQUENCE: 91
ARRGYGAWFA Y                                                        11

SEQ ID NO: 92              moltype = AA  length = 6
FEATURE                    Location/Qualifiers
REGION                     1..6
                           note = Description of Artificial Sequence: Synthetic peptide
source                     1..6
                           mol_type = protein
                           organism = synthetic construct
SEQUENCE: 92
ENIHNY                                                              6

SEQ ID NO: 93              moltype =    length =
SEQUENCE: 93
000

SEQ ID NO: 94              moltype = AA  length = 9
FEATURE                    Location/Qualifiers
REGION                     1..9
                           note = Description of Artificial Sequence: Synthetic peptide
source                     1..9
                           mol_type = protein
                           organism = synthetic construct
SEQUENCE: 94
QHFWSYPLT                                                           9

SEQ ID NO: 95              moltype = AA  length = 118
FEATURE                    Location/Qualifiers
REGION                     1..118
                           note = Description of Artificial Sequence: Synthetic
                            polypeptide
source                     1..118
                           mol_type = protein
                           organism = synthetic construct
SEQUENCE: 95
QGQMQQSGAE LVKPGASVKL SCKTSGFTFS SNYISWLKQK PGQSLEWIAW IHGGTGGIGY  60
NQKFTGKAQL TVDTSSTTAY MQFSSLTTED SAIYYCARRG YGAWFAYWGQ GTLVTVSA    118

SEQ ID NO: 96              moltype = AA  length = 107
FEATURE                    Location/Qualifiers
REGION                     1..107
                           note = Description of Artificial Sequence: Synthetic
                            polypeptide
source                     1..107
                           mol_type = protein
                           organism = synthetic construct
SEQUENCE: 96
DIQMTQSPAS LSASVGETVT ITCRASENIH NYLAWYQQKQ GKSPQLLVYN AKTLADGVPS  60
RFSGSGSGTQ YSLKINSLQP EDFGNYYCQH FWSYPLTFGA GTKLELK               107

SEQ ID NO: 97              moltype = AA  length = 496
FEATURE                    Location/Qualifiers
REGION                     1..496
                           note = Description of Artificial Sequence: Synthetic
                            polypeptide
source                     1..496
                           mol_type = protein
                           organism = synthetic construct
SEQUENCE: 97
MAWVWTLLFL MAAAQSIQAD IQMTQSPASL SASVGETVTI TCRASENIHN YLAWYQQKQG  60
KSPQLLVYNA KTLADGVPSR FSGSGSGTQY SLKINSLQPE DFGNYYCQHF WSYPLTFGAG  120
TKLELKGGSE GKSSGSGSES KSTGGSQGQM QQSGAELVKP GASVKLSCKT SGFTFSSNYI  180
SWLKQKPGQS LEWIAWIHGG TGGIGYNQKF TGKAQLTVDT SSTTAYMQFS SLTTEDSAIY  240
YCARRGYGAW FAYWGQGTLV TVSAEPKSSD KTHTCPPCPA PEAAGGPSVF LFPPKPKDTL  300
MISRTPEVTC VVVSVSHEDP EVKFNWYVDG VEVHNAKTKP REEQYNSTYR VVSVLTVLHQ  360
DWLNGKEYKC KVSNKALPAP IEKTISKAKG QPREPQVYVY PPSREEMTKN QVSLTCLVKG  420
FYPSDIAVEW ESNGQPENNY KTTPPVLDSD GSFALVSKLT VDKSRWQQGN VFSCSVMHEA  480
LHNHYTQKSL SLSPGK                                                  496

SEQ ID NO: 98              moltype = AA  length = 8
FEATURE                    Location/Qualifiers
REGION                     1..8
                           note = Description of Artificial Sequence: Synthetic peptide
source                     1..8
                           mol_type = protein
```

-continued

```
                    organism = synthetic construct
SEQUENCE: 98
GFTFSNYD                                                              8

SEQ ID NO: 99          moltype = AA   length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 99
ISSSSSYI                                                              8

SEQ ID NO: 100         moltype = AA   length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 100
ARDVGVTDYY YYGMDV                                                     16

SEQ ID NO: 101         moltype = AA   length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 101
QSVASSY                                                               7

SEQ ID NO: 102         moltype =    length =
SEQUENCE: 102
000

SEQ ID NO: 103         moltype = AA   length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 103
QQYGSSPPYT                                                            10

SEQ ID NO: 104         moltype = AA   length = 124
FEATURE                Location/Qualifiers
REGION                 1..124
                       note = Description of Artificial Sequence: Synthetic
                        polypeptide
source                 1..124
                       mol_type = protein
                       organism = synthetic construct
SEQUENCE: 104
EVQLVESGGG LVKPGGSLRL SCSASGFTFS NYDMNWVRQA PGKGLEWVSS ISSSSSYIYY    60
ADSVKGRFTI SRDNAKNSLY LQMNSLRAED TAVYHCARDV GVTTDYYYG MDVWGQGTMV     120
TVSS                                                                  124

SEQ ID NO: 105         moltype = AA   length = 109
FEATURE                Location/Qualifiers
REGION                 1..109
                       note = Description of Artificial Sequence: Synthetic
                        polypeptide
source                 1..109
                       mol_type = protein
                       organism = synthetic construct
SEQUENCE: 105
EIVMTQSPGT LSLSPGDRAT LSCRASQSVA SSYLAWYQQK PGQSPRLLIY GASSRATGIP    60
DRFSGSGSGT DFTLTISRLE PEDFAVYYCQ QYGSSPPYTF GQGTRLEIK               109

SEQ ID NO: 106         moltype = AA   length = 504
FEATURE                Location/Qualifiers
REGION                 1..504
                       note = Description of Artificial Sequence: Synthetic
                        polypeptide
source                 1..504
```

```
                            mol_type = protein
                            organism = synthetic construct
SEQUENCE: 106
MAWVWTLLFL MAAAQSIQAE IVMTQSPGTL SLSPGDRATL SCRASQSVAS SYLAWYQQKP  60
GQSPRLLIYG ASSRATGIPD RFSGSGSGTD FTLTISRLEP EDFAVYYCQQ YGSSPPYTFG  120
QGTRLEIKGG SEGKSSGSGS ESKSTGGSEV QLVESGGGLV KPGGSLRLSC SASGFTFSNY  180
DMNWVRQAPG KGLEWVSSIS SSSSYIYYAD SVKGRFTISR DNAKNSLYLQ MNSLRAEDTA  240
VYHCARDVGV TTDYYYYGMD VWGQGTMVTV SSEPKSSDKT HTCPPCPAPE AAGGPSVFLF  300
PPKPKDTLMI SRTPEVTCVV VSVSHEDPEV KFNWYVDGVE VHNAKTKPRE EQYNSTYRVV  360
SVLTVLHQDW LNGKEYKCKV SNKALPAPIE KTISKAKGQP REPQVYVYPP SREEMTKNQV  420
SLTCLVKGFY PSDIAVEWES NGQPENNYKT TPPVLDSDGS FALVSKLTVD KSRWQQGNVF  480
SCSVMHEALH NHYTQKSLSL SPGK                                          504

SEQ ID NO: 107      moltype = AA  length = 8
FEATURE             Location/Qualifiers
REGION              1..8
                    note = Description of Artificial Sequence: Synthetic peptide
source              1..8
                    mol_type = protein
                    organism = synthetic construct
SEQUENCE: 107
GDTFNNYA                                                             8

SEQ ID NO: 108      moltype = AA  length = 8
FEATURE             Location/Qualifiers
REGION              1..8
                    note = Description of Artificial Sequence: Synthetic peptide
source              1..8
                    mol_type = protein
                    organism = synthetic construct
SEQUENCE: 108
IIPFFGTP                                                             8

SEQ ID NO: 109      moltype = AA  length = 17
FEATURE             Location/Qualifiers
REGION              1..17
                    note = Description of Artificial Sequence: Synthetic peptide
source              1..17
                    mol_type = protein
                    organism = synthetic construct
SEQUENCE: 109
ARPGSGSPDY YYYDMDV                                                   17

SEQ ID NO: 110      moltype = AA  length = 11
FEATURE             Location/Qualifiers
REGION              1..11
                    note = Description of Artificial Sequence: Synthetic peptide
source              1..11
                    mol_type = protein
                    organism = synthetic construct
SEQUENCE: 110
QSLVHSDGNT Y                                                         11

SEQ ID NO: 111      moltype =   length =
SEQUENCE: 111
000

SEQ ID NO: 112      moltype = AA  length = 9
FEATURE             Location/Qualifiers
REGION              1..9
                    note = Description of Artificial Sequence: Synthetic peptide
source              1..9
                    mol_type = protein
                    organism = synthetic construct
SEQUENCE: 112
MQATQFPLT                                                            9

SEQ ID NO: 113      moltype = AA  length = 124
FEATURE             Location/Qualifiers
REGION              1..124
                    note = Description of Artificial Sequence: Synthetic
                     polypeptide
source              1..124
                    mol_type = protein
                    organism = synthetic construct
SEQUENCE: 113
EVQLVQSGAE VKKPGSSVKV SCKASGDTFN NYAISWVRQA PGQGLEWMGG IIPFFGTPDY  60
AQKFQGRVTI TADKSTSTAY MELSGLRSED TAVYYCARPG SGSPDYYYYD MDVWGQGTTV  120
TVSS                                                                124
```

```
SEQ ID NO: 114          moltype = AA   length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 114
DIVMTQTPLS SPVTLGQPAS ISCRSSQSLV HSDGNTYLSW LQQRPGQPPR LLIYKISNRF  60
SGVPDRFSGS GAGTDFTLKI NRVEAEDVGV YYCMQATQFP LTFGGGTKVE IK          112

SEQ ID NO: 115          moltype = AA   length = 454
FEATURE                 Location/Qualifiers
REGION                  1..454
                        note = Description of Artificial Sequence: Synthetic
                         polypeptide
source                  1..454
                        mol_type = protein
                        organism = synthetic construct
SEQUENCE: 115
EVQLVQSGAE VKKPGSSVKV SCKASGDTFN NYAISWVRQA PGQGLEWMGG IIPFFGTPDY  60
AQKFQGRVTI TADKSTSTAY MELSGLRSED TAVYYCARPG SGSPDYYYYD MDVWGQGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
AAGGPSVFLF PPKPKDTLMI SRTPEVTCVV VSVSHEDPEV KFNWYVDGVE VHNAKTKPRE  300
EQYNSTYRVV SVLTVLHQDW LNGKEYKCKV SNKALPAPIE KTISKAKGQP REPQVYVYPP  360
SREEMTKNQV SLTCLVKGFY PSDIAVEWES NGQPENNYKT TPPVLDSDGS FALVSKLTVD  420
KSRWQQGNVF SCSVMHEALH NRFTQKSLSL SPGK                              454

SEQ ID NO: 116          moltype = AA   length = 219
FEATURE                 Location/Qualifiers
REGION                  1..219
                        note = Description of Artificial Sequence: Synthetic
                         polypeptide
source                  1..219
                        mol_type = protein
                        organism = synthetic construct
SEQUENCE: 116
DIVMTQTPLS SPVTLGQPAS ISCRSSQSLV HSDGNTYLSW LQQRPGQPPR LLIYKISNRF  60
SGVPDRFSGS GAGTDFTLKI NRVEAEDVGV YYCMQATQFP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 117          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 117
GGTFSSYA                                                           8

SEQ ID NO: 118          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 118
NIPIFNTA                                                           8

SEQ ID NO: 119          moltype = AA   length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 119
VREGTGYSYG LDY                                                     13

SEQ ID NO: 120          moltype = AA   length = 11
FEATURE                 Location/Qualifiers
REGION                  1..11
                        note = Description of Artificial Sequence: Synthetic peptide
```

```
source                    1..11
                          mol_type = protein
                          organism = synthetic construct
SEQUENCE: 120
QSLIHSDGNT Y                                                                    11

SEQ ID NO: 121            moltype =    length =
SEQUENCE: 121
000

SEQ ID NO: 122            moltype = AA   length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 122
MQAKQFPIT                                                                       9

SEQ ID NO: 123            moltype = AA   length = 120
FEATURE                   Location/Qualifiers
REGION                    1..120
                          note = Description of Artificial Sequence: Synthetic
                           polypeptide
source                    1..120
                          mol_type = protein
                          organism = synthetic construct
SEQUENCE: 123
EVQLVQSGAE VKKPGSSVKV SCKASGGTFS SYAISWVRQA PGQGLEWMGG NIPIFNTANY 60
AQKFQDRVTI TADKSTSTAY MELSSLRSED TAVYYCVREG TGYSYGLDYW GQGTPVTVSS 120

SEQ ID NO: 124            moltype = AA   length = 112
FEATURE                   Location/Qualifiers
REGION                    1..112
                          note = Description of Artificial Sequence: Synthetic
                           polypeptide
source                    1..112
                          mol_type = protein
                          organism = synthetic construct
SEQUENCE: 124
EIVMTQSPLS SPVTLGQPAS ISCRSSQSLI HSDGNTYLSW LQQRPGQPPR LLIYKISNRF 60
SGVPDRFSGS GAGTDFTLKI SRVEAEDVGI YYCMQAKQFP ITFGQGTKVD IK          112

SEQ ID NO: 125            moltype = AA   length = 441
FEATURE                   Location/Qualifiers
REGION                    1..441
                          note = Description of Artificial Sequence: Synthetic
                           polypeptide
source                    1..441
                          mol_type = protein
                          organism = synthetic construct
SEQUENCE: 125
EVQLVQSGAE VKKPGSSVKV SCKASGGTFS SYAISWVRQA PGQGLEWMGG NIPIFNTANY 60
AQKFQDRVTI TADKSTSTAY MELSSLRSED TAVYYCVREG TGYSYGLDYW GQGTPVTVSS 120
ASTKGPSVTS GGTAALGCLV KDYFPEPVTV SWNSGALTSG VHTFPAVLQS SGLYSLSSVV 180
TVPSSSLGTQ TYICNVNHKP SNTKVDKKVE PKSCDKTHTC PPCPAPEAAG GPSVFLFPPK 240
PKDTLMISRT PEVTCVVVSV SHEDPEVKFN WYVDGVEVHN AKTKPREEQY NSTYRVVSVL 300
TVLHQDWLNG KEYKCKVSNK ALPAPIEKTI SKAKGQPREP QVYVPPSRE EMTKNQVSLT 360
CLVKGFYPSD IAVEWESNGQ PENNYKTTPP VLDSDGSFAL VSKLTVDKSR WQQGNVFSCS 420
VMHEALHNRF TQKSLSLSPG K                                            441

SEQ ID NO: 126            moltype = AA   length = 219
FEATURE                   Location/Qualifiers
REGION                    1..219
                          note = Description of Artificial Sequence: Synthetic
                           polypeptide
source                    1..219
                          mol_type = protein
                          organism = synthetic construct
SEQUENCE: 126
EIVMTQSPLS SPVTLGQPAS ISCRSSQSLI HSDGNTYLSW LQQRPGQPPR LLIYKISNRF 60
SGVPDRFSGS GAGTDFTLKI SRVEAEDVGI YYCMQAKQFP ITFGQGTKVD IKRTVAAPSV 120
FIFPPSDEQL KSGTASVVCL LNNFYPREAK VQWKVDNALQ SGNSQESVTE QDSKDSTYSL 180
SSTLTLSKAD YEKHKVYACE VTHQGLSSPV TKSFNRGEC                          219

SEQ ID NO: 127            moltype = AA   length = 10
FEATURE                   Location/Qualifiers
REGION                    1..10
```

```
                          note = Description of Artificial Sequence: Synthetic peptide
source                    1..10
                          mol_type = protein
                          organism = synthetic construct
SEQUENCE: 127
GGSISSGGSY                                                              10

SEQ ID NO: 128            moltype = AA  length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 128
IYNSGST                                                                 7

SEQ ID NO: 129            moltype = AA  length = 12
FEATURE                   Location/Qualifiers
REGION                    1..12
                          note = Description of Artificial Sequence: Synthetic peptide
source                    1..12
                          mol_type = protein
                          organism = synthetic construct
SEQUENCE: 129
ARDSNYEWFF DL                                                           12

SEQ ID NO: 130            moltype = AA  length = 6
FEATURE                   Location/Qualifiers
REGION                    1..6
                          note = Description of Artificial Sequence: Synthetic peptide
source                    1..6
                          mol_type = protein
                          organism = synthetic construct
SEQUENCE: 130
QSVSSY                                                                  6

SEQ ID NO: 131            moltype =    length =
SEQUENCE: 131
000

SEQ ID NO: 132            moltype = AA  length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 132
QQRSNWPLT                                                               9

SEQ ID NO: 133            moltype = AA  length = 120
FEATURE                   Location/Qualifiers
REGION                    1..120
                          note = Description of Artificial Sequence: Synthetic
                           polypeptide
source                    1..120
                          mol_type = protein
                          organism = synthetic construct
SEQUENCE: 133
QVQLQESGPG LVKPSQTLSL TCTVSGGSIS SGGSYWSWIR QHPGKGLEWI GYIYNSGSTY  60
YNPSLKSRVS MSVDTSKNQF SLKLSSVTAA DTAVYYCARD SNYEWFFDLW GPGTLVTVSS  120

SEQ ID NO: 134            moltype = AA  length = 107
FEATURE                   Location/Qualifiers
REGION                    1..107
                          note = Description of Artificial Sequence: Synthetic
                           polypeptide
source                    1..107
                          mol_type = protein
                          organism = synthetic construct
SEQUENCE: 134
EIVMTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPLTFGG GTKVEIK               107

SEQ ID NO: 135            moltype = AA  length = 450
FEATURE                   Location/Qualifiers
REGION                    1..450
                          note = Description of Artificial Sequence: Synthetic
```

-continued

```
                          polypeptide
source                    1..450
                          mol_type = protein
                          organism = synthetic construct
SEQUENCE: 135
QVQLQESGPG LVKPSQTLSL TCTVSGGSIS SGGSYWSWIR QHPGKGLEWI GYIYNSGSTY   60
YNPSLKSRVS MSVDTSKNQF SLKLSSVTAA DTAVYYCARD SNYEWFFDLW GPGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVSVS HEDPEVKFNW YVDGVEVHNA KTKPREEQYN  300
STYRVVSVLT VLHQDWLNGK EYKCKVSNKA LPAPIEKTIS KAKGQPREPQ VYVYPPSREE  360
MTKNQVSLTC LVKGFYPSDI AVEWESNGQP ENNYKTTPPV LDSDGSFALV SKLTVDKSRW  420
QQGNVFSCSV MHEALHNRFT QKSLSLSPGK                                   450

SEQ ID NO: 136           moltype = AA  length = 214
FEATURE                  Location/Qualifiers
REGION                   1..214
                          note = Description of Artificial Sequence: Synthetic
                          polypeptide
source                    1..214
                          mol_type = protein
                          organism = synthetic construct
SEQUENCE: 136
EIVMTQSPAT LSLSPGERAT LSCRASQSVS SYLAWYQQKP GQAPRLLIYD ASNRATGIPA   60
RFSGSGSGTD FTLTISSLEP EDFAVYYCQQ RSNWPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 137           moltype =   length =
SEQUENCE: 137
000

SEQ ID NO: 138           moltype =   length =
SEQUENCE: 138
000

SEQ ID NO: 139           moltype =   length =
SEQUENCE: 139
000

SEQ ID NO: 140           moltype =   length =
SEQUENCE: 140
000

SEQ ID NO: 141           moltype =   length =
SEQUENCE: 141
000

SEQ ID NO: 142           moltype =   length =
SEQUENCE: 142
000

SEQ ID NO: 143           moltype =   length =
SEQUENCE: 143
000

SEQ ID NO: 144           moltype =   length =
SEQUENCE: 144
000

SEQ ID NO: 145           moltype =   length =
SEQUENCE: 145
000

SEQ ID NO: 146           moltype =   length =
SEQUENCE: 146
000

SEQ ID NO: 147           moltype =   length =
SEQUENCE: 147
000

SEQ ID NO: 148           moltype =   length =
SEQUENCE: 148
000

SEQ ID NO: 149           moltype =   length =
SEQUENCE: 149
000
```

-continued

```
SEQ ID NO: 150            moltype = AA  length = 473
FEATURE                   Location/Qualifiers
REGION                    1..473
                          note = Description of Artificial Sequence: Synthetic
                           polypeptide
source                    1..473
                          mol_type = protein
                          organism = synthetic construct
SEQUENCE: 150
MAWVWTLLFL MAAAQSIQAE VQLVQSGAEV KKPGSSVKVS CKASGDTFNN YAISWVRQAP  60
GQGLEWMGGI IPFFGTPDYA QKFQGRVTIT ADKSTSTAYM ELSGLRSEDT AVYYCARPGS  120
GSPDYYYDM DVWGQGTTVT VSSASTKGPS VFPLAPSSKS TSGGTAALGC LVKDYFPEPV  180
TVSWNSGALT SGVHTFPAVL QSSGLYSLSS VVTVPSSSLG TQTYICNVNH KPSNTKVDKK  240
VEPKSCDKTH TCPPCPAPEA AGGPSVFLFP PKPKDTLMIS RTPEVTCVVV SVSHEDPEVK  300
FNWYVDGVEV HNAKTKPREE QYNSTYRVVS VLTVLHQDWL NGKEYKCKVS NKALPAPIEK  360
TISKAKGQPR EPQVYVYPPS REEMTKNQVS LTCLVKGFYP SDIAVEWESN GQPENNYKTT  420
PPVLDSDGSF ALVSKLTVDK SRWQQGNVFS CSVMHEALHN RFTQKSLSLS PGK          473

SEQ ID NO: 151            moltype = AA  length = 238
FEATURE                   Location/Qualifiers
REGION                    1..238
                          note = Description of Artificial Sequence: Synthetic
                           polypeptide
source                    1..238
                          mol_type = protein
                          organism = synthetic construct
SEQUENCE: 151
MAWVWTLLFL MAAAQSIQAD IVMTQTPLSS PVTLGQPASI SCRSSQSLVH SDGNTYLSWL  60
QQRPGQPPRL LIYKISNRFS GVPDRFSGSG AGTDFTLKIN RVEAEDVGVY YCMQATQFPL  120
TFGGGTKVEI KRTVAAPSVF IFPPSDEQLK SGTASVVCLL NNFYPREAKV QWKVDNALQS  180
GNSQESVTEQ DSKDSTYSLS STLTLSKADY EKHKVYACEV THQGLSSPVT KSFNRGEC    238

SEQ ID NO: 152            moltype = AA  length = 469
FEATURE                   Location/Qualifiers
REGION                    1..469
                          note = Description of Artificial Sequence: Synthetic
                           polypeptide
source                    1..469
                          mol_type = protein
                          organism = synthetic construct
SEQUENCE: 152
MAWVWTLLFL MAAAQSIQAE VQLVQSGAEV KKPGSSVKVS CKASGGTFSS YAISWVRQAP  60
GQGLEWMGGN IPIFNTANYA QKFQDRVTIT ADKSTSTAYM ELSSLRSEDT AVYYCVREGT  120
GYSYGLDYWG QGTPVTVSSA STKGPSVFPL APSSKSTSGG TAALGCLVKD YFPEPVTVSW  180
NSGALTSGVH TFPAVLQSSG LYSLSSVVTV PSSSLGTQTY ICNVNHKPSN TKVDKKVEPK  240
SCDKTHTCPP CPAPEAAGGP SVFLFPPKPK DTLMISRTPE VTCVVVSVSH EDPEVKFNWY  300
VDGVEVHNAK TKPREEQYNS TYRVVSLTV LHQDWLNGKE YKCKVSNKAL PAPIEKTISK  360
AKGQPREPQV YVYPPSREEM TKNQVSLTCL VKGFYPSDIA VEWESNGQPE NNYKTTPPVL  420
DSDGSFALVS KLTVDKSRWQ QGNVFSCSVM HEALHNRFTQ KSLSLSPGK             469

SEQ ID NO: 153            moltype = AA  length = 238
FEATURE                   Location/Qualifiers
REGION                    1..238
                          note = Description of Artificial Sequence: Synthetic
                           polypeptide
source                    1..238
                          mol_type = protein
                          organism = synthetic construct
SEQUENCE: 153
MAWVWTLLFL MAAAQSIQAE IVMTQSPLSS PVTLGQPASI SCRSSQSLIH SDGNTYLSWL  60
QQRPGQPPRL LIYKISNRFS GVPDRFSGSG AGTDFTLKIS RVEAEDVGIY YCMQAKQFPI  120
TFGQGTKVDI KRTVAAPSVF IFPPSDEQLK SGTASVVCLL NNFYPREAKV QWKVDNALQS  180
GNSQESVTEQ DSKDSTYSLS STLTLSKADY EKHKVYACEV THQGLSSPVT KSFNRGEC    238

SEQ ID NO: 154            moltype = AA  length = 469
FEATURE                   Location/Qualifiers
REGION                    1..469
                          note = Description of Artificial Sequence: Synthetic
                           polypeptide
source                    1..469
                          mol_type = protein
                          organism = synthetic construct
SEQUENCE: 154
MAWVWTLLFL MAAAQSIQAQ VQLQESGPGL VKPSQTLSLT CTVSGGSISS GGSYWSWIRQ  60
HPGKGLEWIG YIYNSGSTYY NPSLKSRVSM SVDTSKNQFS LKLSSVTAAD TAVYYCARDS  120
NYEWFFDLWG PGTLVTVSSA STKGPSVFPL APSSKSTSGG TAALGCLVKD YFPEPVTVSW  180
NSGALTSGVH TFPAVLQSSG LYSLSSVVTV PSSSLGTQTY ICNVNHKPSN TKVDKKVEPK  240
SCDKTHTCPP CPAPEAAGGP SVFLFPPKPK DTLMISRTPE VTCVVVSVSH EDPEVKFNWY  300
```

-continued

```
VDGVEVHNAK TKPREEQYNS TYRVVSVLTV LHQDWLNGKE YKCKVSNKAL PAPIEKTISK  360
AKGQPREPQV YVYPPSREEM TKNQVSLTCL VKGFYPSDIA VEWESNGQPE NNYKTTPPVL  420
DSDGSFALVS KLTVDKSRWQ QGNVFSCSVM HEALHNRFTQ KSLSLSPGK              469

SEQ ID NO: 155           moltype = AA  length = 233
FEATURE                  Location/Qualifiers
REGION                   1..233
                         note = Description of Artificial Sequence: Synthetic
                          polypeptide
source                   1..233
                         mol_type = protein
                         organism = synthetic construct
SEQUENCE: 155
MAWVWTLLFL MAAAQSIQAE IVMTQSPATL SLSPGERATL SCRASQSVSS YLAWYQQKPG  60
QAPRLLIYDA SNRATGIPAR FSGSGSGTDF TLTISSLEPE DFAVYYCQQR SNWPLTFGGG  120
TKVEIKRTVA APSVFIFPPS DEQLKSGTAS VVCLLNNFYP REAKVQWKVD NALQSGNSQE  180
SVTEQDSKDS TYSLSSTLTL SKADYEKHKV YACEVTHQGL SSPVTKSFNR GEC         233

SEQ ID NO: 156           moltype = AA  length = 493
FEATURE                  Location/Qualifiers
REGION                   1..493
                         note = Description of Artificial Sequence: Synthetic
                          polypeptide
source                   1..493
                         mol_type = protein
                         organism = synthetic construct
SEQUENCE: 156
MAWVWTLLFL MAAAQSIQAA GHLEQPQISS TKTLSKTARL ECVVSGITIS ATSVYWYRER  60
PGEVIQFLVS ISYDGTVRKE SGIPSGKFEV DRIPETSTST LTIHNVEKQD IATYYCALWE  120
AQQELGKKIK VFGPGTKLII TDKQLDADVS PKPTIFLPSI AETKLQKAGT YLCLLEKFFP  180
DVIKIHWEEK KSNTILGSQE GNTMKTNDTY MKFSWLTVPE KSLDKEHRCI VRHENNKNGV  240
DQEIIFPPIK TDVITMDPKD NEPKSCDKTH TCPPCPAPEL LGGPSVFLFP PKPKDTLMIS  300
RTPEVTCVVV DVSHEDPEVK FNWYVDGVEV HNAKTKPREE QYNSTYRVVS VLTVLHQDWL  360
NGKEYKCKVS NKALPAPIEK TISKAKGQPR EPQVYVYPPS REEMTKNQVS LTCLVKGFYP  420
SDIAVEWESN GQPENNYKTT PPVLDSDGSF ALVSKLTVDK SRWQQGNVFS CSVMHEALHN  480
HYTQKSLSLS PGK                                                    493

SEQ ID NO: 157           moltype = AA  length = 480
FEATURE                  Location/Qualifiers
REGION                   1..480
                         note = Description of Artificial Sequence: Synthetic
                          polypeptide
source                   1..480
                         mol_type = protein
                         organism = synthetic construct
SEQUENCE: 157
MAWVWTLLFL MAAAQSIQAA IELVPEHQTV PVSIGVPATL RCSMKGEAIG NYYINWYRKT  60
QGNTMTFIYR EKDIYGPGFK DNFQGDIDIA KNLAVLKILA PSERDEGSYY CACDTLGMGG  120
EYTDKLIFGK GTRVTVEPRS QPHTKPSVFV MKNGTNVACL VKEFYPKDIR INLVSSKKIT  180
EFDPAIVISP SGKYNAVKLG KYEDSNSVTC SVQHDNKTVH STDFEVKTDS TDHVKPKETE  240
NTKQPSKSEP KSCDKTHTCP PCPAPELLGG PSVFLFPPKP KDTLMISRTP EVTCVVVDVS  300
HEDPEVKFNW YVDGVEVHNA KTKPREEQYN STYRVVSVLT VLHQDWLNGK EYKCKVSNKA  360
LPAPIEKTIS KAKGQPREPQ VYVLPPSREE MTKNQVSLLC LVKGFYPSDI AVEWESNGQP  420
ENNYLTWPPV LDSDGSFFLY SKLTVDKSRW QQGNVFSCSV MHEALHNHYT QKSLSLSPGK  480

SEQ ID NO: 158           moltype =   length =
SEQUENCE: 158
000

SEQ ID NO: 159           moltype =   length =
SEQUENCE: 159
000

SEQ ID NO: 160           moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 160
GFTFTDHYIN                                                        10

SEQ ID NO: 161           moltype = AA  length = 17
FEATURE                  Location/Qualifiers
REGION                   1..17
                         note = Description of Artificial Sequence: Synthetic peptide
source                   1..17
                         mol_type = protein
```

```
                        organism = synthetic construct
SEQUENCE: 161
QIYPGDGNTY YNQKFKG                                                    17

SEQ ID NO: 162          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 162
NYGDYTIDF                                                             9

SEQ ID NO: 163          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 163
KSSQSLLYSS NQKNYLA                                                    17

SEQ ID NO: 164          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 164
WASTRES                                                               7

SEQ ID NO: 165          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 165
QQYYRYHT                                                              8

SEQ ID NO: 166          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 166
GFTFTDHY                                                              8

SEQ ID NO: 167          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 167
IYPGDGNT                                                              8

SEQ ID NO: 168          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 168
APNYGDYTID F                                                          11

SEQ ID NO: 169          moltype = AA   length = 12
FEATURE                 Location/Qualifiers
REGION                  1..12
                        note = Description of Artificial Sequence: Synthetic peptide
source                  1..12
```

```
                             mol_type = protein
                             organism = synthetic construct
SEQUENCE: 169
QSLLYSSNQK NY                                                    12

SEQ ID NO: 170          moltype =   length =
SEQUENCE: 170
000

SEQ ID NO: 171          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 171
QQYYRYHT                                                          8

SEQ ID NO: 172          moltype = AA   length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 172
DHYIN                                                             5

SEQ ID NO: 173          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 173
QIYPGDGNTY YNQKFKG                                               17

SEQ ID NO: 174          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 174
NYGDYTIDF                                                         9

SEQ ID NO: 175          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 175
KSSQSLLYSS NQKNYLA                                               17

SEQ ID NO: 176          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 176
WASTRES                                                           7

SEQ ID NO: 177          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 177
QQYYRYHT                                                          8
```

-continued

```
SEQ ID NO: 178          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 178
GFTFTDH                                                              7

SEQ ID NO: 179          moltype = AA   length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 179
PGDG                                                                 4

SEQ ID NO: 180          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 180
YGDYTID                                                              7

SEQ ID NO: 181          moltype = AA   length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 181
SQSLLYSSNQ KNY                                                       13

SEQ ID NO: 182          moltype =    length =
SEQUENCE: 182
000

SEQ ID NO: 183          moltype = AA   length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 183
YYRYH                                                                5

SEQ ID NO: 184          moltype = AA   length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 184
TDHYIN                                                               6

SEQ ID NO: 185          moltype = AA   length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 185
WIGQIYPGDG NTY                                                       13

SEQ ID NO: 186          moltype = AA   length = 10
FEATURE                 Location/Qualifiers
REGION                  1..10
                        note = Description of Artificial Sequence: Synthetic peptide
source                  1..10
```

```
                         mol_type = protein
                         organism = synthetic construct
SEQUENCE: 186
APNYGDYTID                                                        10

SEQ ID NO: 187           moltype = AA   length = 13
FEATURE                  Location/Qualifiers
REGION                   1..13
                         note = Description of Artificial Sequence: Synthetic peptide
source                   1..13
                         mol_type = protein
                         organism = synthetic construct
SEQUENCE: 187
LYSSNQKNYL AWY                                                    13

SEQ ID NO: 188           moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 188
LLIYWASTRE                                                        10

SEQ ID NO: 189           moltype = AA   length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 189
QQYYRYH                                                           7

SEQ ID NO: 190           moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 190
GFTFTDHYIN                                                        10

SEQ ID NO: 191           moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 191
QIYPGDGNTY                                                        10

SEQ ID NO: 192           moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 192
NYGDYTIDF                                                         9

SEQ ID NO: 193           moltype = AA   length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 193
KSSQSLLYSS NQKNYLA                                                17

SEQ ID NO: 194           moltype = AA   length = 7
FEATURE                  Location/Qualifiers
REGION                   1..7
                         note = Description of Artificial Sequence: Synthetic peptide
```

-continued

```
source                    1..7
                          mol_type = protein
                          organism = synthetic construct
SEQUENCE: 194
WASTRES                                                              7

SEQ ID NO: 195            moltype = AA  length = 8
FEATURE                   Location/Qualifiers
REGION                    1..8
                          note = Description of Artificial Sequence: Synthetic peptide
source                    1..8
                          mol_type = protein
                          organism = synthetic construct
SEQUENCE: 195
QQYYRYHT                                                             8

SEQ ID NO: 196            moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 196
GFTFTDHYIN                                                           10

SEQ ID NO: 197            moltype = AA  length = 17
FEATURE                   Location/Qualifiers
REGION                    1..17
                          note = Description of Artificial Sequence: Synthetic peptide
source                    1..17
                          mol_type = protein
                          organism = synthetic construct
SEQUENCE: 197
QIYPGDGNTY YNQKFKG                                                   17

SEQ ID NO: 198            moltype = AA  length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 198
NMGMYTIDF                                                            9

SEQ ID NO: 199            moltype = AA  length = 17
FEATURE                   Location/Qualifiers
REGION                    1..17
                          note = Description of Artificial Sequence: Synthetic peptide
source                    1..17
                          mol_type = protein
                          organism = synthetic construct
SEQUENCE: 199
KSSQSLLYSS NQKNYLA                                                   17

SEQ ID NO: 200            moltype = AA  length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 200
WASTRES                                                              7

SEQ ID NO: 201            moltype = AA  length = 8
FEATURE                   Location/Qualifiers
REGION                    1..8
                          note = Description of Artificial Sequence: Synthetic peptide
source                    1..8
                          mol_type = protein
                          organism = synthetic construct
SEQUENCE: 201
QQYYRYHT                                                             8

SEQ ID NO: 202            moltype = AA  length = 8
FEATURE                   Location/Qualifiers
REGION                    1..8
```

```
                        note = Description of Artificial Sequence: Synthetic peptide
source                  1..8
                        mol_type = protein
                        organism = synthetic construct
SEQUENCE: 202
GFTFTDHY                                                             8

SEQ ID NO: 203          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 203
IYPGDGNT                                                             8

SEQ ID NO: 204          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 204
APNMGMYTID F                                                         11

SEQ ID NO: 205          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 205
QSLLYSSNQK NY                                                        12

SEQ ID NO: 206          moltype =   length =
SEQUENCE: 206
000

SEQ ID NO: 207          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 207
QQYYRYHT                                                             8

SEQ ID NO: 208          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 208
DHYIN                                                                5

SEQ ID NO: 209          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 209
QIYPGDGNTY YNQKFKG                                                   17

SEQ ID NO: 210          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 210
```

```
NMGMYTIDF                                                          9

SEQ ID NO: 211        moltype = AA  length = 17
FEATURE               Location/Qualifiers
REGION                1..17
                      note = Description of Artificial Sequence: Synthetic peptide
source                1..17
                      mol_type = protein
                      organism = synthetic construct
SEQUENCE: 211
KSSQSLLYSS NQKNYLA                                                 17

SEQ ID NO: 212        moltype = AA  length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 212
WASTRES                                                            7

SEQ ID NO: 213        moltype = AA  length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 213
QQYYRYHT                                                           8

SEQ ID NO: 214        moltype = AA  length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 214
GFTFTDH                                                            7

SEQ ID NO: 215        moltype = AA  length = 4
FEATURE               Location/Qualifiers
REGION                1..4
                      note = Description of Artificial Sequence: Synthetic peptide
source                1..4
                      mol_type = protein
                      organism = synthetic construct
SEQUENCE: 215
PGDG                                                               4

SEQ ID NO: 216        moltype = AA  length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 216
MGMYTID                                                            7

SEQ ID NO: 217        moltype = AA  length = 13
FEATURE               Location/Qualifiers
REGION                1..13
                      note = Description of Artificial Sequence: Synthetic peptide
source                1..13
                      mol_type = protein
                      organism = synthetic construct
SEQUENCE: 217
SQSLLYSSNQ KNY                                                     13

SEQ ID NO: 218        moltype =   length =
SEQUENCE: 218
000

SEQ ID NO: 219        moltype = AA  length = 5
FEATURE               Location/Qualifiers
REGION                1..5
```

```
                        note = Description of Artificial Sequence: Synthetic peptide
source                  1..5
                        mol_type = protein
                        organism = synthetic construct
SEQUENCE: 219
YYRYH                                                                          5

SEQ ID NO: 220          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 220
TDHYIN                                                                         6

SEQ ID NO: 221          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 221
WIGQIYPGDG NTY                                                                 13

SEQ ID NO: 222          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 222
APNMGMYTID                                                                     10

SEQ ID NO: 223          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 223
LYSSNQKNYL AWY                                                                 13

SEQ ID NO: 224          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 224
LLIYWASTRE                                                                     10

SEQ ID NO: 225          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 225
QQYYRYH                                                                        7

SEQ ID NO: 226          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 226
GFTFTDHYIN                                                                     10

SEQ ID NO: 227          moltype = AA  length = 10
FEATURE                 Location/Qualifiers
```

-continued

```
REGION                   1..10
                         note = Description of Artificial Sequence: Synthetic peptide
source                   1..10
                         mol_type = protein
                         organism = synthetic construct
SEQUENCE: 227
QIYPGDGNTY                                                                            10

SEQ ID NO: 228           moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 228
NMGMYTIDF                                                                             9

SEQ ID NO: 229           moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 229
KSSQSLLYSS NQKNYLA                                                                    17

SEQ ID NO: 230           moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 230
WASTRES                                                                               7

SEQ ID NO: 231           moltype = AA  length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 231
QQYYRYHT                                                                              8

SEQ ID NO: 232           moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 232
GFTFTDHYIN                                                                            10

SEQ ID NO: 233           moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 233
QIYPGDGNTY YNQKFKG                                                                    17

SEQ ID NO: 234           moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 234
NMGMYTLDF                                                                             9

SEQ ID NO: 235           moltype = AA  length = 17
```

-continued

```
FEATURE           Location/Qualifiers
REGION            1..17
                  note = Description of Artificial Sequence: Synthetic peptide
source            1..17
                  mol_type = protein
                  organism = synthetic construct
SEQUENCE: 235
KSSQSLLYSS NQKNYLA                                              17

SEQ ID NO: 236    moltype = AA  length = 7
FEATURE           Location/Qualifiers
REGION            1..7
                  note = Description of Artificial Sequence: Synthetic peptide
source            1..7
                  mol_type = protein
                  organism = synthetic construct
SEQUENCE: 236
WASTRES                                                          7

SEQ ID NO: 237    moltype = AA  length = 8
FEATURE           Location/Qualifiers
REGION            1..8
                  note = Description of Artificial Sequence: Synthetic peptide
source            1..8
                  mol_type = protein
                  organism = synthetic construct
SEQUENCE: 237
QQYYRYHT                                                         8

SEQ ID NO: 238    moltype = AA  length = 8
FEATURE           Location/Qualifiers
REGION            1..8
                  note = Description of Artificial Sequence: Synthetic peptide
source            1..8
                  mol_type = protein
                  organism = synthetic construct
SEQUENCE: 238
GFTFTDHY                                                         8

SEQ ID NO: 239    moltype = AA  length = 8
FEATURE           Location/Qualifiers
REGION            1..8
                  note = Description of Artificial Sequence: Synthetic peptide
source            1..8
                  mol_type = protein
                  organism = synthetic construct
SEQUENCE: 239
IYPGDGNT                                                         8

SEQ ID NO: 240    moltype = AA  length = 11
FEATURE           Location/Qualifiers
REGION            1..11
                  note = Description of Artificial Sequence: Synthetic peptide
source            1..11
                  mol_type = protein
                  organism = synthetic construct
SEQUENCE: 240
APNMGMYTLD F                                                    11

SEQ ID NO: 241    moltype = AA  length = 12
FEATURE           Location/Qualifiers
REGION            1..12
                  note = Description of Artificial Sequence: Synthetic peptide
source            1..12
                  mol_type = protein
                  organism = synthetic construct
SEQUENCE: 241
QSLLYSSNQK NY                                                   12

SEQ ID NO: 242    moltype =   length =
SEQUENCE: 242
000

SEQ ID NO: 243    moltype = AA  length = 8
FEATURE           Location/Qualifiers
REGION            1..8
                  note = Description of Artificial Sequence: Synthetic peptide
source            1..8
                  mol_type = protein
```

-continued

```
                        organism = synthetic construct
SEQUENCE: 243
QQYYRYHT                                                              8

SEQ ID NO: 244          moltype = AA   length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 244
DHYIN                                                                 5

SEQ ID NO: 245          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 245
QIYPGDGNTY YNQKFKG                                                    17

SEQ ID NO: 246          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 246
NMGMYTLDF                                                             9

SEQ ID NO: 247          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 247
KSSQSLLYSS NQKNYLA                                                    17

SEQ ID NO: 248          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 248
WASTRES                                                               7

SEQ ID NO: 249          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 249
QQYYRYHT                                                              8

SEQ ID NO: 250          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 250
GFTFTDH                                                               7

SEQ ID NO: 251          moltype = AA   length = 4
FEATURE                 Location/Qualifiers
REGION                  1..4
                        note = Description of Artificial Sequence: Synthetic peptide
source                  1..4
```

```
                              mol_type = protein
                              organism = synthetic construct
SEQUENCE: 251
PGDG                                                                    4

SEQ ID NO: 252         moltype = AA   length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 252
MGMYTLD                                                                  7

SEQ ID NO: 253         moltype = AA   length = 13
FEATURE                Location/Qualifiers
REGION                 1..13
                       note = Description of Artificial Sequence: Synthetic peptide
source                 1..13
                       mol_type = protein
                       organism = synthetic construct
SEQUENCE: 253
SQSLLYSSNQ KNY                                                          13

SEQ ID NO: 254         moltype =    length =
SEQUENCE: 254
000

SEQ ID NO: 255         moltype = AA   length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 255
YYRYH                                                                    5

SEQ ID NO: 256         moltype = AA   length = 6
FEATURE                Location/Qualifiers
REGION                 1..6
                       note = Description of Artificial Sequence: Synthetic peptide
source                 1..6
                       mol_type = protein
                       organism = synthetic construct
SEQUENCE: 256
TDHYIN                                                                   6

SEQ ID NO: 257         moltype = AA   length = 13
FEATURE                Location/Qualifiers
REGION                 1..13
                       note = Description of Artificial Sequence: Synthetic peptide
source                 1..13
                       mol_type = protein
                       organism = synthetic construct
SEQUENCE: 257
WIGQIYPGDG NTY                                                          13

SEQ ID NO: 258         moltype = AA   length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 258
APNMGMYTLD                                                              10

SEQ ID NO: 259         moltype = AA   length = 13
FEATURE                Location/Qualifiers
REGION                 1..13
                       note = Description of Artificial Sequence: Synthetic peptide
source                 1..13
                       mol_type = protein
                       organism = synthetic construct
SEQUENCE: 259
LYSSNQKNYL AWY                                                          13
```

```
SEQ ID NO: 260          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 260
LLIYWASTRE                                                       10

SEQ ID NO: 261          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 261
QQYYRYH                                                          7

SEQ ID NO: 262          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 262
GFTFTDHYIN                                                       10

SEQ ID NO: 263          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 263
QIYPGDGNTY                                                       10

SEQ ID NO: 264          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 264
NMGMYTLDF                                                        9

SEQ ID NO: 265          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 265
KSSQSLLYSS NQKNYLA                                               17

SEQ ID NO: 266          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 266
WASTRES                                                          7

SEQ ID NO: 267          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 267
QQYYRYHT                                                         8
```

-continued

```
SEQ ID NO: 268          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 268
GFTFTDHYIN                                                              10

SEQ ID NO: 269          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 269
QIYPGDGNTY YNQKFKG                                                      17

SEQ ID NO: 270          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 270
NYGDYTLDF                                                               9

SEQ ID NO: 271          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 271
KSSQSLLYSS NQKNYLA                                                      17

SEQ ID NO: 272          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 272
WASTRES                                                                 7

SEQ ID NO: 273          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 273
QQYYRYHT                                                                8

SEQ ID NO: 274          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 274
GFTFTDHY                                                                8

SEQ ID NO: 275          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 275
```

```
IYPGDGNT                                                    8

SEQ ID NO: 276      moltype = AA  length = 11
FEATURE             Location/Qualifiers
REGION              1..11
                    note = Description of Artificial Sequence: Synthetic peptide
source              1..11
                    mol_type = protein
                    organism = synthetic construct
SEQUENCE: 276
APNYGDYTLD F                                                11

SEQ ID NO: 277      moltype = AA  length = 12
FEATURE             Location/Qualifiers
REGION              1..12
                    note = Description of Artificial Sequence: Synthetic peptide
source              1..12
                    mol_type = protein
                    organism = synthetic construct
SEQUENCE: 277
QSLLYSSNQK NY                                               12

SEQ ID NO: 278      moltype =   length =
SEQUENCE: 278
000

SEQ ID NO: 279      moltype = AA  length = 8
FEATURE             Location/Qualifiers
REGION              1..8
                    note = Description of Artificial Sequence: Synthetic peptide
source              1..8
                    mol_type = protein
                    organism = synthetic construct
SEQUENCE: 279
QQYYRYHT                                                    8

SEQ ID NO: 280      moltype = AA  length = 5
FEATURE             Location/Qualifiers
REGION              1..5
                    note = Description of Artificial Sequence: Synthetic peptide
source              1..5
                    mol_type = protein
                    organism = synthetic construct
SEQUENCE: 280
DHYIN                                                       5

SEQ ID NO: 281      moltype = AA  length = 17
FEATURE             Location/Qualifiers
REGION              1..17
                    note = Description of Artificial Sequence: Synthetic peptide
source              1..17
                    mol_type = protein
                    organism = synthetic construct
SEQUENCE: 281
QIYPGDGNTY YNQKFKG                                          17

SEQ ID NO: 282      moltype = AA  length = 9
FEATURE             Location/Qualifiers
REGION              1..9
                    note = Description of Artificial Sequence: Synthetic peptide
source              1..9
                    mol_type = protein
                    organism = synthetic construct
SEQUENCE: 282
NYGDYTLDF                                                   9

SEQ ID NO: 283      moltype = AA  length = 17
FEATURE             Location/Qualifiers
REGION              1..17
                    note = Description of Artificial Sequence: Synthetic peptide
source              1..17
                    mol_type = protein
                    organism = synthetic construct
SEQUENCE: 283
KSSQSLLYSS NQKNYLA                                          17

SEQ ID NO: 284      moltype = AA  length = 7
FEATURE             Location/Qualifiers
REGION              1..7
```

```
                              note = Description of Artificial Sequence: Synthetic peptide
source                        1..7
                              mol_type = protein
                              organism = synthetic construct
SEQUENCE: 284
WASTRES                                                                    7

SEQ ID NO: 285                moltype = AA  length = 8
FEATURE                       Location/Qualifiers
REGION                        1..8
                              note = Description of Artificial Sequence: Synthetic peptide
source                        1..8
                              mol_type = protein
                              organism = synthetic construct
SEQUENCE: 285
QQYYRYHT                                                                   8

SEQ ID NO: 286                moltype = AA  length = 7
FEATURE                       Location/Qualifiers
REGION                        1..7
                              note = Description of Artificial Sequence: Synthetic peptide
source                        1..7
                              mol_type = protein
                              organism = synthetic construct
SEQUENCE: 286
GFTFTDH                                                                    7

SEQ ID NO: 287                moltype = AA  length = 4
FEATURE                       Location/Qualifiers
REGION                        1..4
                              note = Description of Artificial Sequence: Synthetic peptide
source                        1..4
                              mol_type = protein
                              organism = synthetic construct
SEQUENCE: 287
PGDG                                                                      4

SEQ ID NO: 288                moltype = AA  length = 7
FEATURE                       Location/Qualifiers
REGION                        1..7
                              note = Description of Artificial Sequence: Synthetic peptide
source                        1..7
                              mol_type = protein
                              organism = synthetic construct
SEQUENCE: 288
YGDYTLD                                                                   7

SEQ ID NO: 289                moltype = AA  length = 13
FEATURE                       Location/Qualifiers
REGION                        1..13
                              note = Description of Artificial Sequence: Synthetic peptide
source                        1..13
                              mol_type = protein
                              organism = synthetic construct
SEQUENCE: 289
SQSLLYSSNQ KNY                                                            13

SEQ ID NO: 290                moltype =   length =
SEQUENCE: 290
000

SEQ ID NO: 291                moltype = AA  length = 5
FEATURE                       Location/Qualifiers
REGION                        1..5
                              note = Description of Artificial Sequence: Synthetic peptide
source                        1..5
                              mol_type = protein
                              organism = synthetic construct
SEQUENCE: 291
YYRYH                                                                     5

SEQ ID NO: 292                moltype = AA  length = 6
FEATURE                       Location/Qualifiers
REGION                        1..6
                              note = Description of Artificial Sequence: Synthetic peptide
source                        1..6
                              mol_type = protein
                              organism = synthetic construct
SEQUENCE: 292
```

```
TDHYIN                                                       6

SEQ ID NO: 293          moltype = AA   length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 293
WIGQIYPGDG NTY                                               13

SEQ ID NO: 294          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 294
APNYGDYTLD                                                   10

SEQ ID NO: 295          moltype = AA   length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 295
LYSSNQKNYL AWY                                               13

SEQ ID NO: 296          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 296
LLIYWASTRE                                                   10

SEQ ID NO: 297          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 297
QQYYRYH                                                      7

SEQ ID NO: 298          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 298
GFTFTDHYIN                                                   10

SEQ ID NO: 299          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 299
QIYPGDGNTY                                                   10

SEQ ID NO: 300          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
```

-continued

```
SEQUENCE: 300
NYGDYTLDF                                                              9

SEQ ID NO: 301          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 301
KSSQSLLYSS NQKNYLA                                                     17

SEQ ID NO: 302          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 302
WASTRES                                                                7

SEQ ID NO: 303          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 303
QQYYRYHT                                                               8

SEQ ID NO: 304          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 304
GFTFTDHYIN                                                             10

SEQ ID NO: 305          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 305
QIYPGSGNTY YNQKFKG                                                     17

SEQ ID NO: 306          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 306
NYGDYTIDF                                                              9

SEQ ID NO: 307          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 307
KSSQSVLYSS NNKNYLA                                                     17

SEQ ID NO: 308          moltype = AA  length = 7
FEATURE                 Location/Qualifiers
REGION                  1..7
                        note = Description of Artificial Sequence: Synthetic peptide
source                  1..7
                        mol_type = protein
```

```
                          organism = synthetic construct
SEQUENCE: 308
WASTRES                                                        7

SEQ ID NO: 309           moltype = AA   length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 309
QQYYRYHT                                                       8

SEQ ID NO: 310           moltype = AA   length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 310
GFTFTDHY                                                       8

SEQ ID NO: 311           moltype = AA   length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 311
IYPGSGNT                                                       8

SEQ ID NO: 312           moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 312
ARNYGDYTID F                                                   11

SEQ ID NO: 313           moltype = AA   length = 12
FEATURE                  Location/Qualifiers
REGION                   1..12
                         note = Description of Artificial Sequence: Synthetic peptide
source                   1..12
                         mol_type = protein
                         organism = synthetic construct
SEQUENCE: 313
QSVLYSSNNK NY                                                  12

SEQ ID NO: 314           moltype =    length =
SEQUENCE: 314
000

SEQ ID NO: 315           moltype = AA   length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 315
QQYYRYHT                                                       8

SEQ ID NO: 316           moltype = AA   length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 316
DHYIN                                                          5

SEQ ID NO: 317           moltype = AA   length = 17
```

-continued

```
FEATURE            Location/Qualifiers
REGION             1..17
                   note = Description of Artificial Sequence: Synthetic peptide
source             1..17
                   mol_type = protein
                   organism = synthetic construct
SEQUENCE: 317
QIYPGSGNTY YNQKFKG                                          17

SEQ ID NO: 318     moltype = AA  length = 9
FEATURE            Location/Qualifiers
REGION             1..9
                   note = Description of Artificial Sequence: Synthetic peptide
source             1..9
                   mol_type = protein
                   organism = synthetic construct
SEQUENCE: 318
NYGDYTIDF                                                   9

SEQ ID NO: 319     moltype = AA  length = 17
FEATURE            Location/Qualifiers
REGION             1..17
                   note = Description of Artificial Sequence: Synthetic peptide
source             1..17
                   mol_type = protein
                   organism = synthetic construct
SEQUENCE: 319
KSSQSVLYSS NNKNYLA                                          17

SEQ ID NO: 320     moltype = AA  length = 7
FEATURE            Location/Qualifiers
REGION             1..7
                   note = Description of Artificial Sequence: Synthetic peptide
source             1..7
                   mol_type = protein
                   organism = synthetic construct
SEQUENCE: 320
WASTRES                                                     7

SEQ ID NO: 321     moltype = AA  length = 8
FEATURE            Location/Qualifiers
REGION             1..8
                   note = Description of Artificial Sequence: Synthetic peptide
source             1..8
                   mol_type = protein
                   organism = synthetic construct
SEQUENCE: 321
QQYYRYHT                                                    8

SEQ ID NO: 322     moltype = AA  length = 7
FEATURE            Location/Qualifiers
REGION             1..7
                   note = Description of Artificial Sequence: Synthetic peptide
source             1..7
                   mol_type = protein
                   organism = synthetic construct
SEQUENCE: 322
GFTFTDH                                                     7

SEQ ID NO: 323     moltype = AA  length = 4
FEATURE            Location/Qualifiers
REGION             1..4
                   note = Description of Artificial Sequence: Synthetic peptide
source             1..4
                   mol_type = protein
                   organism = synthetic construct
SEQUENCE: 323
PGSG                                                        4

SEQ ID NO: 324     moltype = AA  length = 7
FEATURE            Location/Qualifiers
REGION             1..7
                   note = Description of Artificial Sequence: Synthetic peptide
source             1..7
                   mol_type = protein
                   organism = synthetic construct
SEQUENCE: 324
YGDYTID                                                     7
```

```
SEQ ID NO: 325          moltype = AA   length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 325
SQSVLYSSNN KNY                                                    13

SEQ ID NO: 326          moltype =    length =
SEQUENCE: 326
000

SEQ ID NO: 327          moltype = AA   length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 327
YYRYH                                                             5

SEQ ID NO: 328          moltype = AA   length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 328
TDHYIN                                                            6

SEQ ID NO: 329          moltype = AA   length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 329
WMGQIYPGSG NTY                                                    13

SEQ ID NO: 330          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 330
ARNYGDYTID                                                        10

SEQ ID NO: 331          moltype = AA   length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 331
LYSSNNKNYL AWY                                                    13

SEQ ID NO: 332          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 332
LLIYWASTRE                                                        10

SEQ ID NO: 333          moltype = AA   length = 7
FEATURE                 Location/Qualifiers
REGION                  1..7
                        note = Description of Artificial Sequence: Synthetic peptide
source                  1..7
``` mol_type = protein
organism = synthetic construct

SEQUENCE: 333
QQYYRYH                                                                          7

SEQ ID NO: 334        moltype = AA  length = 10
FEATURE               Location/Qualifiers
REGION                1..10
                      note = Description of Artificial Sequence: Synthetic peptide
source                1..10
                      mol_type = protein
                      organism = synthetic construct
SEQUENCE: 334
GFTFTDHYIN                                                                       10

SEQ ID NO: 335        moltype = AA  length = 10
FEATURE               Location/Qualifiers
REGION                1..10
                      note = Description of Artificial Sequence: Synthetic peptide
source                1..10
                      mol_type = protein
                      organism = synthetic construct
SEQUENCE: 335
QIYPGSGNTY                                                                       10

SEQ ID NO: 336        moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 336
NYGDYTIDF                                                                        9

SEQ ID NO: 337        moltype = AA  length = 17
FEATURE               Location/Qualifiers
REGION                1..17
                      note = Description of Artificial Sequence: Synthetic peptide
source                1..17
                      mol_type = protein
                      organism = synthetic construct
SEQUENCE: 337
KSSQSVLYSS NNKNYLA                                                               17

SEQ ID NO: 338        moltype = AA  length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 338
WASTRES                                                                          7

SEQ ID NO: 339        moltype = AA  length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 339
QQYYRYHT                                                                         8

SEQ ID NO: 340        moltype = AA  length = 10
FEATURE               Location/Qualifiers
REGION                1..10
                      note = Description of Artificial Sequence: Synthetic peptide
source                1..10
                      mol_type = protein
                      organism = synthetic construct
SEQUENCE: 340
GFTFTDHYIN                                                                       10

SEQ ID NO: 341        moltype = AA  length = 17
FEATURE               Location/Qualifiers
REGION                1..17
                      note = Description of Artificial Sequence: Synthetic peptide -continued

```
source                    1..17
                          mol_type = protein
                          organism = synthetic construct
SEQUENCE: 341
QIYPGSGNTY YNQKFKG                                              17

SEQ ID NO: 342            moltype = AA   length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 342
NYGDYTIDF                                                       9

SEQ ID NO: 343            moltype = AA   length = 17
FEATURE                   Location/Qualifiers
REGION                    1..17
                          note = Description of Artificial Sequence: Synthetic peptide
source                    1..17
                          mol_type = protein
                          organism = synthetic construct
SEQUENCE: 343
KSSQSVLYSS NNKNYLA                                              17

SEQ ID NO: 344            moltype = AA   length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 344
WASTRES                                                         7

SEQ ID NO: 345            moltype = AA   length = 8
FEATURE                   Location/Qualifiers
REGION                    1..8
                          note = Description of Artificial Sequence: Synthetic peptide
source                    1..8
                          mol_type = protein
                          organism = synthetic construct
SEQUENCE: 345
QQYYRYHT                                                        8

SEQ ID NO: 346            moltype = AA   length = 8
FEATURE                   Location/Qualifiers
REGION                    1..8
                          note = Description of Artificial Sequence: Synthetic peptide
source                    1..8
                          mol_type = protein
                          organism = synthetic construct
SEQUENCE: 346
GFTFTDHY                                                        8

SEQ ID NO: 347            moltype = AA   length = 8
FEATURE                   Location/Qualifiers
REGION                    1..8
                          note = Description of Artificial Sequence: Synthetic peptide
source                    1..8
                          mol_type = protein
                          organism = synthetic construct
SEQUENCE: 347
IYPGSGNT                                                        8

SEQ ID NO: 348            moltype = AA   length = 11
FEATURE                   Location/Qualifiers
REGION                    1..11
                          note = Description of Artificial Sequence: Synthetic peptide
source                    1..11
                          mol_type = protein
                          organism = synthetic construct
SEQUENCE: 348
ARNYGDYTID F                                                    11

SEQ ID NO: 349            moltype = AA   length = 12
FEATURE                   Location/Qualifiers
REGION                    1..12
```

```
                          note = Description of Artificial Sequence: Synthetic peptide
source                    1..12
                          mol_type = protein
                          organism = synthetic construct
SEQUENCE: 349
QSVLYSSNNK NY                                                                12

SEQ ID NO: 350            moltype =    length =
SEQUENCE: 350
000

SEQ ID NO: 351            moltype = AA   length = 8
FEATURE                   Location/Qualifiers
REGION                    1..8
                          note = Description of Artificial Sequence: Synthetic peptide
source                    1..8
                          mol_type = protein
                          organism = synthetic construct
SEQUENCE: 351
QQYYRYHT                                                                     8

SEQ ID NO: 352            moltype = AA   length = 5
FEATURE                   Location/Qualifiers
REGION                    1..5
                          note = Description of Artificial Sequence: Synthetic peptide
source                    1..5
                          mol_type = protein
                          organism = synthetic construct
SEQUENCE: 352
DHYIN                                                                        5

SEQ ID NO: 353            moltype = AA   length = 17
FEATURE                   Location/Qualifiers
REGION                    1..17
                          note = Description of Artificial Sequence: Synthetic peptide
source                    1..17
                          mol_type = protein
                          organism = synthetic construct
SEQUENCE: 353
QIYPGSGNTY YNQKFKG                                                           17

SEQ ID NO: 354            moltype = AA   length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 354
NYGDYTIDF                                                                    9

SEQ ID NO: 355            moltype = AA   length = 17
FEATURE                   Location/Qualifiers
REGION                    1..17
                          note = Description of Artificial Sequence: Synthetic peptide
source                    1..17
                          mol_type = protein
                          organism = synthetic construct
SEQUENCE: 355
KSSQSVLYSS NNKNYLA                                                           17

SEQ ID NO: 356            moltype = AA   length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 356
WASTRES                                                                      7

SEQ ID NO: 357            moltype = AA   length = 8
FEATURE                   Location/Qualifiers
REGION                    1..8
                          note = Description of Artificial Sequence: Synthetic peptide
source                    1..8
                          mol_type = protein
                          organism = synthetic construct
SEQUENCE: 357
```

```
QQYYRYHT                                                              8

SEQ ID NO: 358        moltype = AA   length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 358
GFTFTDH                                                               7

SEQ ID NO: 359        moltype = AA   length = 4
FEATURE               Location/Qualifiers
REGION                1..4
                      note = Description of Artificial Sequence: Synthetic peptide
source                1..4
                      mol_type = protein
                      organism = synthetic construct
SEQUENCE: 359
PGSG                                                                  4

SEQ ID NO: 360        moltype = AA   length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 360
YGDYTID                                                               7

SEQ ID NO: 361        moltype = AA   length = 13
FEATURE               Location/Qualifiers
REGION                1..13
                      note = Description of Artificial Sequence: Synthetic peptide
source                1..13
                      mol_type = protein
                      organism = synthetic construct
SEQUENCE: 361
SQSVLYSSNN KNY                                                        13

SEQ ID NO: 362        moltype =   length =
SEQUENCE: 362
000

SEQ ID NO: 363        moltype = AA   length = 5
FEATURE               Location/Qualifiers
REGION                1..5
                      note = Description of Artificial Sequence: Synthetic peptide
source                1..5
                      mol_type = protein
                      organism = synthetic construct
SEQUENCE: 363
YYRYH                                                                 5

SEQ ID NO: 364        moltype = AA   length = 6
FEATURE               Location/Qualifiers
REGION                1..6
                      note = Description of Artificial Sequence: Synthetic peptide
source                1..6
                      mol_type = protein
                      organism = synthetic construct
SEQUENCE: 364
TDHYIN                                                                6

SEQ ID NO: 365        moltype = AA   length = 13
FEATURE               Location/Qualifiers
REGION                1..13
                      note = Description of Artificial Sequence: Synthetic peptide
source                1..13
                      mol_type = protein
                      organism = synthetic construct
SEQUENCE: 365
WMGQIYPGSG NTY                                                        13

SEQ ID NO: 366        moltype = AA   length = 10
FEATURE               Location/Qualifiers
REGION                1..10
```

-continued

```
                              note = Description of Artificial Sequence: Synthetic peptide
source                        1..10
                              mol_type = protein
                              organism = synthetic construct
SEQUENCE: 366
ARNYGDYTID                                                                     10

SEQ ID NO: 367                moltype = AA   length = 13
FEATURE                       Location/Qualifiers
REGION                        1..13
                              note = Description of Artificial Sequence: Synthetic peptide
source                        1..13
                              mol_type = protein
                              organism = synthetic construct
SEQUENCE: 367
LYSSNNKNYL AWY                                                                 13

SEQ ID NO: 368                moltype = AA   length = 10
FEATURE                       Location/Qualifiers
REGION                        1..10
                              note = Description of Artificial Sequence: Synthetic peptide
source                        1..10
                              mol_type = protein
                              organism = synthetic construct
SEQUENCE: 368
LLIYWASTRE                                                                     10

SEQ ID NO: 369                moltype = AA   length = 7
FEATURE                       Location/Qualifiers
REGION                        1..7
                              note = Description of Artificial Sequence: Synthetic peptide
source                        1..7
                              mol_type = protein
                              organism = synthetic construct
SEQUENCE: 369
QQYYRYH                                                                        7

SEQ ID NO: 370                moltype = AA   length = 10
FEATURE                       Location/Qualifiers
REGION                        1..10
                              note = Description of Artificial Sequence: Synthetic peptide
source                        1..10
                              mol_type = protein
                              organism = synthetic construct
SEQUENCE: 370
GFTFTDHYIN                                                                     10

SEQ ID NO: 371                moltype = AA   length = 10
FEATURE                       Location/Qualifiers
REGION                        1..10
                              note = Description of Artificial Sequence: Synthetic peptide
source                        1..10
                              mol_type = protein
                              organism = synthetic construct
SEQUENCE: 371
QIYPGSGNTY                                                                     10

SEQ ID NO: 372                moltype = AA   length = 9
FEATURE                       Location/Qualifiers
REGION                        1..9
                              note = Description of Artificial Sequence: Synthetic peptide
source                        1..9
                              mol_type = protein
                              organism = synthetic construct
SEQUENCE: 372
NYGDYTIDF                                                                      9

SEQ ID NO: 373                moltype = AA   length = 17
FEATURE                       Location/Qualifiers
REGION                        1..17
                              note = Description of Artificial Sequence: Synthetic peptide
source                        1..17
                              mol_type = protein
                              organism = synthetic construct
SEQUENCE: 373
KSSQSVLYSS NNKNYLA                                                             17

SEQ ID NO: 374                moltype = AA   length = 7
FEATURE                       Location/Qualifiers
```

-continued

```
REGION                  1..7
                        note = Description of Artificial Sequence: Synthetic peptide
source                  1..7
                        mol_type = protein
                        organism = synthetic construct
SEQUENCE: 374
WASTRES                                                                        7

SEQ ID NO: 375          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 375
QQYYRYHT                                                                       8

SEQ ID NO: 376          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 376
GFTFSSNYIS                                                                    10

SEQ ID NO: 377          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 377
WIHGGTGGIG YNQKFTG                                                            17

SEQ ID NO: 378          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 378
RGYGAWFAY                                                                      9

SEQ ID NO: 379          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 379
RASENIHNYL A                                                                  11

SEQ ID NO: 380          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 380
NAKTLAD                                                                        7

SEQ ID NO: 381          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 381
QHFWSYPLT                                                                      9

SEQ ID NO: 382          moltype = AA  length = 8
```

| FEATURE | Location/Qualifiers |
|---|---|
| REGION | 1..8 |
|  | note = Description of Artificial Sequence: Synthetic peptide |
| source | 1..8 |
|  | mol_type = protein |
|  | organism = synthetic construct |

SEQUENCE: 382
GFTFSSNY                                                                                     8

| SEQ ID NO: 383 | moltype = AA  length = 8 |
|---|---|
| FEATURE | Location/Qualifiers |
| REGION | 1..8 |
|  | note = Description of Artificial Sequence: Synthetic peptide |
| source | 1..8 |
|  | mol_type = protein |
|  | organism = synthetic construct |

SEQUENCE: 383
IHGGTGGI                                                                                     8

| SEQ ID NO: 384 | moltype = AA  length = 11 |
|---|---|
| FEATURE | Location/Qualifiers |
| REGION | 1..11 |
|  | note = Description of Artificial Sequence: Synthetic peptide |
| source | 1..11 |
|  | mol_type = protein |
|  | organism = synthetic construct |

SEQUENCE: 384
ARRGYGAWFA Y                                                                                 11

| SEQ ID NO: 385 | moltype = AA  length = 6 |
|---|---|
| FEATURE | Location/Qualifiers |
| REGION | 1..6 |
|  | note = Description of Artificial Sequence: Synthetic peptide |
| source | 1..6 |
|  | mol_type = protein |
|  | organism = synthetic construct |

SEQUENCE: 385
ENIHNY                                                                                       6

| SEQ ID NO: 386 | moltype =   length = |
|---|---|
| SEQUENCE: 386 | |
| 000 | |

| SEQ ID NO: 387 | moltype = AA  length = 9 |
|---|---|
| FEATURE | Location/Qualifiers |
| REGION | 1..9 |
|  | note = Description of Artificial Sequence: Synthetic peptide |
| source | 1..9 |
|  | mol_type = protein |
|  | organism = synthetic construct |

SEQUENCE: 387
QHFWSYPLT                                                                                    9

| SEQ ID NO: 388 | moltype = AA  length = 5 |
|---|---|
| FEATURE | Location/Qualifiers |
| REGION | 1..5 |
|  | note = Description of Artificial Sequence: Synthetic peptide |
| source | 1..5 |
|  | mol_type = protein |
|  | organism = synthetic construct |

SEQUENCE: 388
SNYIS                                                                                        5

| SEQ ID NO: 389 | moltype = AA  length = 17 |
|---|---|
| FEATURE | Location/Qualifiers |
| REGION | 1..17 |
|  | note = Description of Artificial Sequence: Synthetic peptide |
| source | 1..17 |
|  | mol_type = protein |
|  | organism = synthetic construct |

SEQUENCE: 389
WIHGGTGGIG YNQKFTG                                                                           17

| SEQ ID NO: 390 | moltype = AA  length = 9 |
|---|---|
| FEATURE | Location/Qualifiers |
| REGION | 1..9 |
|  | note = Description of Artificial Sequence: Synthetic peptide |
| source | 1..9 |
|  | mol_type = protein |

```
                            organism = synthetic construct
SEQUENCE: 390
RGYGAWFAY                                                       9

SEQ ID NO: 391              moltype = AA  length = 11
FEATURE                    Location/Qualifiers
REGION                     1..11
                           note = Description of Artificial Sequence: Synthetic peptide
source                     1..11
                           mol_type = protein
                           organism = synthetic construct
SEQUENCE: 391
RASENIHNYL A                                                    11

SEQ ID NO: 392              moltype = AA  length = 7
FEATURE                    Location/Qualifiers
REGION                     1..7
                           note = Description of Artificial Sequence: Synthetic peptide
source                     1..7
                           mol_type = protein
                           organism = synthetic construct
SEQUENCE: 392
NAKTLAD                                                         7

SEQ ID NO: 393              moltype = AA  length = 9
FEATURE                    Location/Qualifiers
REGION                     1..9
                           note = Description of Artificial Sequence: Synthetic peptide
source                     1..9
                           mol_type = protein
                           organism = synthetic construct
SEQUENCE: 393
QHFWSYPLT                                                       9

SEQ ID NO: 394              moltype = AA  length = 7
FEATURE                    Location/Qualifiers
REGION                     1..7
                           note = Description of Artificial Sequence: Synthetic peptide
source                     1..7
                           mol_type = protein
                           organism = synthetic construct
SEQUENCE: 394
GFTFSSN                                                         7

SEQ ID NO: 395              moltype = AA  length = 4
FEATURE                    Location/Qualifiers
REGION                     1..4
                           note = Description of Artificial Sequence: Synthetic peptide
source                     1..4
                           mol_type = protein
                           organism = synthetic construct
SEQUENCE: 395
GGTG                                                           4

SEQ ID NO: 396              moltype = AA  length = 7
FEATURE                    Location/Qualifiers
REGION                     1..7
                           note = Description of Artificial Sequence: Synthetic peptide
source                     1..7
                           mol_type = protein
                           organism = synthetic construct
SEQUENCE: 396
GYGAWFA                                                        7

SEQ ID NO: 397              moltype = AA  length = 7
FEATURE                    Location/Qualifiers
REGION                     1..7
                           note = Description of Artificial Sequence: Synthetic peptide
source                     1..7
                           mol_type = protein
                           organism = synthetic construct
SEQUENCE: 397
SENIHNY                                                        7

SEQ ID NO: 398              moltype =   length =
SEQUENCE: 398
000

SEQ ID NO: 399              moltype = AA  length = 6
```

-continued

```
FEATURE               Location/Qualifiers
REGION                1..6
                      note = Description of Artificial Sequence: Synthetic peptide
source                1..6
                      mol_type = protein
                      organism = synthetic construct
SEQUENCE: 399
FWSYPL                                                              6

SEQ ID NO: 400        moltype = AA   length = 6
FEATURE               Location/Qualifiers
REGION                1..6
                      note = Description of Artificial Sequence: Synthetic peptide
source                1..6
                      mol_type = protein
                      organism = synthetic construct
SEQUENCE: 400
SSNYIS                                                              6

SEQ ID NO: 401        moltype = AA   length = 13
FEATURE               Location/Qualifiers
REGION                1..13
                      note = Description of Artificial Sequence: Synthetic peptide
source                1..13
                      mol_type = protein
                      organism = synthetic construct
SEQUENCE: 401
WIAWIHGGTG GIG                                                      13

SEQ ID NO: 402        moltype = AA   length = 10
FEATURE               Location/Qualifiers
REGION                1..10
                      note = Description of Artificial Sequence: Synthetic peptide
source                1..10
                      mol_type = protein
                      organism = synthetic construct
SEQUENCE: 402
ARRGYGAWFA                                                          10

SEQ ID NO: 403        moltype = AA   length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 403
HNYLAWY                                                             7

SEQ ID NO: 404        moltype = AA   length = 10
FEATURE               Location/Qualifiers
REGION                1..10
                      note = Description of Artificial Sequence: Synthetic peptide
source                1..10
                      mol_type = protein
                      organism = synthetic construct
SEQUENCE: 404
LLVYNAKTLA                                                          10

SEQ ID NO: 405        moltype = AA   length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 405
QHFWSYPL                                                            8

SEQ ID NO: 406        moltype = AA   length = 10
FEATURE               Location/Qualifiers
REGION                1..10
                      note = Description of Artificial Sequence: Synthetic peptide
source                1..10
                      mol_type = protein
                      organism = synthetic construct
SEQUENCE: 406
GFTFSSNYIS                                                          10
```

-continued

```
SEQ ID NO: 407         moltype = AA   length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 407
WIHGGTGGIG                                                          10

SEQ ID NO: 408         moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 408
RGYGAWFAY                                                           9

SEQ ID NO: 409         moltype = AA   length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 409
RASENIHNYL A                                                        11

SEQ ID NO: 410         moltype = AA   length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 410
NAKTLAD                                                             7

SEQ ID NO: 411         moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 411
QHFWSYPLT                                                           9

SEQ ID NO: 412         moltype = AA   length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 412
GFTFSNYDMN                                                          10

SEQ ID NO: 413         moltype = AA   length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 413
SISSSSSYIY YADSVKG                                                  17

SEQ ID NO: 414         moltype = AA   length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 414
DVGVTTDYYY YGMDV                                                    15
```

-continued

```
SEQ ID NO: 415          moltype = AA   length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 415
RASQSVASSY LA                                                        12

SEQ ID NO: 416          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 416
GASSRAT                                                              7

SEQ ID NO: 417          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 417
QQYGSSPPYT                                                           10

SEQ ID NO: 418          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 418
GFTFSNYD                                                             8

SEQ ID NO: 419          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 419
ISSSSSYI                                                             8

SEQ ID NO: 420          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 420
ARDVGVTTDY YYYGMDV                                                   17

SEQ ID NO: 421          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 421
QSVASSY                                                              7

SEQ ID NO: 422          moltype =    length =
SEQUENCE: 422
000

SEQ ID NO: 423          moltype = AA   length = 10
FEATURE                 Location/Qualifiers
REGION                  1..10
                        note = Description of Artificial Sequence: Synthetic peptide
```

-continued

```
source                  1..10
                        mol_type = protein
                        organism = synthetic construct
SEQUENCE: 423
QQYGSSPPYT                                                    10

SEQ ID NO: 424          moltype = AA   length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 424
NYDMN                                                         5

SEQ ID NO: 425          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 425
SISSSSSYIY YADSVKG                                            17

SEQ ID NO: 426          moltype = AA   length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 426
DVGVTTDYYY YGMDV                                              15

SEQ ID NO: 427          moltype = AA   length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 427
RASQSVASSY LA                                                 12

SEQ ID NO: 428          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 428
GASSRAT                                                       7

SEQ ID NO: 429          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 429
QQYGSSPPYT                                                    10

SEQ ID NO: 430          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 430
GFTFSNY                                                       7

SEQ ID NO: 431          moltype = AA   length = 4
FEATURE                 Location/Qualifiers
REGION                  1..4
```

-continued

```
                        note = Description of Artificial Sequence: Synthetic peptide
source                  1..4
                        mol_type = protein
                        organism = synthetic construct
SEQUENCE: 431
SSSS                                                                            4

SEQ ID NO: 432          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 432
VGVTTDYYYY GMD                                                                  13

SEQ ID NO: 433          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 433
SQSVASSY                                                                        8

SEQ ID NO: 434          moltype =   length =
SEQUENCE: 434
000

SEQ ID NO: 435          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 435
YGSSPPY                                                                         7

SEQ ID NO: 436          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 436
SNYDMN                                                                          6

SEQ ID NO: 437          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 437
WVSSISSSSS YIY                                                                  13

SEQ ID NO: 438          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 438
ARDVGVTTDY YYYGMD                                                               16

SEQ ID NO: 439          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 439
```

```
ASSYLAWY                                                                       8

SEQ ID NO: 440           moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 440
LLIYGASSRA                                                                     10

SEQ ID NO: 441           moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 441
QQYGSSPPY                                                                      9

SEQ ID NO: 442           moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 442
GFTFSNYDMN                                                                     10

SEQ ID NO: 443           moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 443
SISSSSSYIY                                                                     10

SEQ ID NO: 444           moltype = AA   length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 444
DVGVTTDYYY YGMDV                                                               15

SEQ ID NO: 445           moltype = AA   length = 12
FEATURE                  Location/Qualifiers
REGION                   1..12
                         note = Description of Artificial Sequence: Synthetic peptide
source                   1..12
                         mol_type = protein
                         organism = synthetic construct
SEQUENCE: 445
RASQSVASSY LA                                                                  12

SEQ ID NO: 446           moltype = AA   length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 446
GASSRAT                                                                        7

SEQ ID NO: 447           moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
```

-continued

```
SEQUENCE: 447
QQYGSSPPYT                                                                              10

SEQ ID NO: 448          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 448
GDTFNNYAIS                                                                              10

SEQ ID NO: 449          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 449
GIIPFFGTPD YAQKFQG                                                                      17

SEQ ID NO: 450          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 450
PGSGSPDYYY YDMDV                                                                        15

SEQ ID NO: 451          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 451
RSSQSLVHSD GNTYLS                                                                       16

SEQ ID NO: 452          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 452
KISNRFS                                                                                 7

SEQ ID NO: 453          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 453
MQATQFPLT                                                                               9

SEQ ID NO: 454          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 454
GDTFNNYA                                                                                8

SEQ ID NO: 455          moltype = AA  length = 8
FEATURE                 Location/Qualifiers
REGION                  1..8
                        note = Description of Artificial Sequence: Synthetic peptide
source                  1..8
                        mol_type = protein
```

```
                        organism = synthetic construct
SEQUENCE: 455
IIPFFGTP                                                        8

SEQ ID NO: 456          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 456
ARPGSGSPDY YYYDMDV                                              17

SEQ ID NO: 457          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 457
QSLVHSDGNT Y                                                    11

SEQ ID NO: 458          moltype =   length =
SEQUENCE: 458
000

SEQ ID NO: 459          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 459
MQATQFPLT                                                       9

SEQ ID NO: 460          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 460
NYAIS                                                           5

SEQ ID NO: 461          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 461
GIIPFFGTPD YAQKFQG                                              17

SEQ ID NO: 462          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 462
PGSGSPDYYY YDMDV                                                15

SEQ ID NO: 463          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 463
RSSQSLVHSD GNTYLS                                               16

SEQ ID NO: 464          moltype = AA  length = 7
```

```
FEATURE              Location/Qualifiers
REGION               1..7
                     note = Description of Artificial Sequence: Synthetic peptide
source               1..7
                     mol_type = protein
                     organism = synthetic construct
SEQUENCE: 464
KISNRFS                                                                       7

SEQ ID NO: 465       moltype = AA  length = 9
FEATURE              Location/Qualifiers
REGION               1..9
                     note = Description of Artificial Sequence: Synthetic peptide
source               1..9
                     mol_type = protein
                     organism = synthetic construct
SEQUENCE: 465
MQATQFPLT                                                                     9

SEQ ID NO: 466       moltype = AA  length = 7
FEATURE              Location/Qualifiers
REGION               1..7
                     note = Description of Artificial Sequence: Synthetic peptide
source               1..7
                     mol_type = protein
                     organism = synthetic construct
SEQUENCE: 466
GDTFNNY                                                                       7

SEQ ID NO: 467       moltype = AA  length = 4
FEATURE              Location/Qualifiers
REGION               1..4
                     note = Description of Artificial Sequence: Synthetic peptide
source               1..4
                     mol_type = protein
                     organism = synthetic construct
SEQUENCE: 467
PFFG                                                                          4

SEQ ID NO: 468       moltype = AA  length = 13
FEATURE              Location/Qualifiers
REGION               1..13
                     note = Description of Artificial Sequence: Synthetic peptide
source               1..13
                     mol_type = protein
                     organism = synthetic construct
SEQUENCE: 468
GSGSPDYYYY DMD                                                                13

SEQ ID NO: 469       moltype = AA  length = 12
FEATURE              Location/Qualifiers
REGION               1..12
                     note = Description of Artificial Sequence: Synthetic peptide
source               1..12
                     mol_type = protein
                     organism = synthetic construct
SEQUENCE: 469
SQSLVHSDGN TY                                                                 12

SEQ ID NO: 470       moltype =    length =
SEQUENCE: 470
000

SEQ ID NO: 471       moltype = AA  length = 6
FEATURE              Location/Qualifiers
REGION               1..6
                     note = Description of Artificial Sequence: Synthetic peptide
source               1..6
                     mol_type = protein
                     organism = synthetic construct
SEQUENCE: 471
ATQFPL                                                                        6

SEQ ID NO: 472       moltype = AA  length = 6
FEATURE              Location/Qualifiers
REGION               1..6
                     note = Description of Artificial Sequence: Synthetic peptide
source               1..6
                     mol_type = protein
```

-continued

```
                              organism = synthetic construct
SEQUENCE: 472
NNYAIS                                                          6

SEQ ID NO: 473                moltype = AA  length = 13
FEATURE                       Location/Qualifiers
REGION                        1..13
                              note = Description of Artificial Sequence: Synthetic peptide
source                        1..13
                              mol_type = protein
                              organism = synthetic construct
SEQUENCE: 473
WMGGIIPFFG TPD                                                  13

SEQ ID NO: 474                moltype = AA  length = 16
FEATURE                       Location/Qualifiers
REGION                        1..16
                              note = Description of Artificial Sequence: Synthetic peptide
source                        1..16
                              mol_type = protein
                              organism = synthetic construct
SEQUENCE: 474
ARPGSGSPDY YYYDMD                                               16

SEQ ID NO: 475                moltype = AA  length = 12
FEATURE                       Location/Qualifiers
REGION                        1..12
                              note = Description of Artificial Sequence: Synthetic peptide
source                        1..12
                              mol_type = protein
                              organism = synthetic construct
SEQUENCE: 475
VHSDGNTYLS WL                                                   12

SEQ ID NO: 476                moltype = AA  length = 10
FEATURE                       Location/Qualifiers
REGION                        1..10
                              note = Description of Artificial Sequence: Synthetic peptide
source                        1..10
                              mol_type = protein
                              organism = synthetic construct
SEQUENCE: 476
LLIYKISNRF                                                      10

SEQ ID NO: 477                moltype = AA  length = 8
FEATURE                       Location/Qualifiers
REGION                        1..8
                              note = Description of Artificial Sequence: Synthetic peptide
source                        1..8
                              mol_type = protein
                              organism = synthetic construct
SEQUENCE: 477
MQATQFPL                                                        8

SEQ ID NO: 478                moltype = AA  length = 10
FEATURE                       Location/Qualifiers
REGION                        1..10
                              note = Description of Artificial Sequence: Synthetic peptide
source                        1..10
                              mol_type = protein
                              organism = synthetic construct
SEQUENCE: 478
GDTFNNYAIS                                                      10

SEQ ID NO: 479                moltype = AA  length = 10
FEATURE                       Location/Qualifiers
REGION                        1..10
                              note = Description of Artificial Sequence: Synthetic peptide
source                        1..10
                              mol_type = protein
                              organism = synthetic construct
SEQUENCE: 479
GIIPFFGTPD                                                      10

SEQ ID NO: 480                moltype = AA  length = 15
FEATURE                       Location/Qualifiers
REGION                        1..15
                              note = Description of Artificial Sequence: Synthetic peptide
source                        1..15
```

```
                              mol_type = protein
                              organism = synthetic construct
SEQUENCE: 480
PGSGSPDYYY YDMDV                                                          15

SEQ ID NO: 481          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 481
RSSQSLVHSD GNTYLS                                                         16

SEQ ID NO: 482          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 482
KISNRFS                                                                   7

SEQ ID NO: 483          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 483
MQATQFPLT                                                                 9

SEQ ID NO: 484          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 484
GGTFSSYAIS                                                                10

SEQ ID NO: 485          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 485
GNIPIFNTAN YAQKFQD                                                        17

SEQ ID NO: 486          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 486
EGTGYSYGLD Y                                                              11

SEQ ID NO: 487          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 487
RSSQSLIHSD GNTYLS                                                         16

SEQ ID NO: 488          moltype = AA  length = 7
FEATURE                 Location/Qualifiers
REGION                  1..7
                        note = Description of Artificial Sequence: Synthetic peptide
```

-continued

```
source                    1..7
                          mol_type = protein
                          organism = synthetic construct
SEQUENCE: 488
KISNRFS                                                              7

SEQ ID NO: 489            moltype = AA  length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 489
MQAKQFPIT                                                            9

SEQ ID NO: 490            moltype = AA  length = 8
FEATURE                   Location/Qualifiers
REGION                    1..8
                          note = Description of Artificial Sequence: Synthetic peptide
source                    1..8
                          mol_type = protein
                          organism = synthetic construct
SEQUENCE: 490
GGTFSSYA                                                             8

SEQ ID NO: 491            moltype = AA  length = 8
FEATURE                   Location/Qualifiers
REGION                    1..8
                          note = Description of Artificial Sequence: Synthetic peptide
source                    1..8
                          mol_type = protein
                          organism = synthetic construct
SEQUENCE: 491
NIPIFNTA                                                             8

SEQ ID NO: 492            moltype = AA  length = 13
FEATURE                   Location/Qualifiers
REGION                    1..13
                          note = Description of Artificial Sequence: Synthetic peptide
source                    1..13
                          mol_type = protein
                          organism = synthetic construct
SEQUENCE: 492
VREGTGYSYG LDY                                                       13

SEQ ID NO: 493            moltype = AA  length = 11
FEATURE                   Location/Qualifiers
REGION                    1..11
                          note = Description of Artificial Sequence: Synthetic peptide
source                    1..11
                          mol_type = protein
                          organism = synthetic construct
SEQUENCE: 493
QSLIHSDGNT Y                                                         11

SEQ ID NO: 494            moltype =   length =
SEQUENCE: 494
000

SEQ ID NO: 495            moltype = AA  length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 495
MQAKQFPIT                                                            9

SEQ ID NO: 496            moltype = AA  length = 5
FEATURE                   Location/Qualifiers
REGION                    1..5
                          note = Description of Artificial Sequence: Synthetic peptide
source                    1..5
                          mol_type = protein
                          organism = synthetic construct
SEQUENCE: 496
SYAIS                                                                5
```

```
SEQ ID NO: 497           moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 497
GNIPIFNTAN YAQKFQD                                                       17

SEQ ID NO: 498           moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 498
EGTGYSYGLD Y                                                             11

SEQ ID NO: 499           moltype = AA  length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 499
RSSQSLIHSD GNTYLS                                                        16

SEQ ID NO: 500           moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 500
KISNRFS                                                                  7

SEQ ID NO: 501           moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 501
MQAKQFPIT                                                                9

SEQ ID NO: 502           moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 502
GGTFSSY                                                                  7

SEQ ID NO: 503           moltype = AA  length = 4
FEATURE                  Location/Qualifiers
REGION                   1..4
                         note = Description of Artificial Sequence: Synthetic peptide
source                   1..4
                         mol_type = protein
                         organism = synthetic construct
SEQUENCE: 503
PIFN                                                                     4

SEQ ID NO: 504           moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 504
```

-continued

```
GTGYSYGLD                                                        9

SEQ ID NO: 505         moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 505
SQSLIHSDGN TY                                                    12

SEQ ID NO: 506         moltype =    length =
SEQUENCE: 506
000

SEQ ID NO: 507         moltype = AA  length = 6
FEATURE                Location/Qualifiers
REGION                 1..6
                       note = Description of Artificial Sequence: Synthetic peptide
source                 1..6
                       mol_type = protein
                       organism = synthetic construct
SEQUENCE: 507
AKQFPI                                                           6

SEQ ID NO: 508         moltype = AA  length = 6
FEATURE                Location/Qualifiers
REGION                 1..6
                       note = Description of Artificial Sequence: Synthetic peptide
source                 1..6
                       mol_type = protein
                       organism = synthetic construct
SEQUENCE: 508
SSYAIS                                                           6

SEQ ID NO: 509         moltype = AA  length = 13
FEATURE                Location/Qualifiers
REGION                 1..13
                       note = Description of Artificial Sequence: Synthetic peptide
source                 1..13
                       mol_type = protein
                       organism = synthetic construct
SEQUENCE: 509
WMGGNIPIFN TAN                                                   13

SEQ ID NO: 510         moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 510
VREGTGYSYG LD                                                    12

SEQ ID NO: 511         moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 511
IHSDGNTYLS WL                                                    12

SEQ ID NO: 512         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 512
LLIYKISNRF                                                       10

SEQ ID NO: 513         moltype = AA  length = 8
FEATURE                Location/Qualifiers
REGION                 1..8
```

```
                             note = Description of Artificial Sequence: Synthetic peptide
source                       1..8
                             mol_type = protein
                             organism = synthetic construct
SEQUENCE: 513
MQAKQFPI                                                                          8

SEQ ID NO: 514               moltype = AA  length = 10
FEATURE                      Location/Qualifiers
REGION                       1..10
                             note = Description of Artificial Sequence: Synthetic peptide
source                       1..10
                             mol_type = protein
                             organism = synthetic construct
SEQUENCE: 514
GGTFSSYAIS                                                                        10

SEQ ID NO: 515               moltype = AA  length = 10
FEATURE                      Location/Qualifiers
REGION                       1..10
                             note = Description of Artificial Sequence: Synthetic peptide
source                       1..10
                             mol_type = protein
                             organism = synthetic construct
SEQUENCE: 515
GNIPIFNTAN                                                                        10

SEQ ID NO: 516               moltype = AA  length = 11
FEATURE                      Location/Qualifiers
REGION                       1..11
                             note = Description of Artificial Sequence: Synthetic peptide
source                       1..11
                             mol_type = protein
                             organism = synthetic construct
SEQUENCE: 516
EGTGYSYGLD Y                                                                      11

SEQ ID NO: 517               moltype = AA  length = 16
FEATURE                      Location/Qualifiers
REGION                       1..16
                             note = Description of Artificial Sequence: Synthetic peptide
source                       1..16
                             mol_type = protein
                             organism = synthetic construct
SEQUENCE: 517
RSSQSLIHSD GNTYLS                                                                 16

SEQ ID NO: 518               moltype = AA  length = 7
FEATURE                      Location/Qualifiers
REGION                       1..7
                             note = Description of Artificial Sequence: Synthetic peptide
source                       1..7
                             mol_type = protein
                             organism = synthetic construct
SEQUENCE: 518
KISNRFS                                                                           7

SEQ ID NO: 519               moltype = AA  length = 9
FEATURE                      Location/Qualifiers
REGION                       1..9
                             note = Description of Artificial Sequence: Synthetic peptide
source                       1..9
                             mol_type = protein
                             organism = synthetic construct
SEQUENCE: 519
MQAKQFPIT                                                                         9

SEQ ID NO: 520               moltype = AA  length = 12
FEATURE                      Location/Qualifiers
REGION                       1..12
                             note = Description of Artificial Sequence: Synthetic peptide
source                       1..12
                             mol_type = protein
                             organism = synthetic construct
SEQUENCE: 520
GGSISSGGSY WS                                                                     12

SEQ ID NO: 521               moltype = AA  length = 16
FEATURE                      Location/Qualifiers
```

-continued

```
REGION                    1..16
                          note = Description of Artificial Sequence: Synthetic peptide
source                    1..16
                          mol_type = protein
                          organism = synthetic construct
SEQUENCE: 521
YIYNSGSTYY NPSLKS                                                                16

SEQ ID NO: 522            moltype = AA   length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 522
DSNYEWFFDL                                                                       10

SEQ ID NO: 523            moltype = AA   length = 11
FEATURE                   Location/Qualifiers
REGION                    1..11
                          note = Description of Artificial Sequence: Synthetic peptide
source                    1..11
                          mol_type = protein
                          organism = synthetic construct
SEQUENCE: 523
RASQSVSSYL A                                                                     11

SEQ ID NO: 524            moltype = AA   length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 524
DASNRAT                                                                          7

SEQ ID NO: 525            moltype = AA   length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 525
QQRSNWPLT                                                                        9

SEQ ID NO: 526            moltype = AA   length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 526
GGSISSGGSY                                                                       10

SEQ ID NO: 527            moltype = AA   length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 527
IYNSGST                                                                          7

SEQ ID NO: 528            moltype = AA   length = 12
FEATURE                   Location/Qualifiers
REGION                    1..12
                          note = Description of Artificial Sequence: Synthetic peptide
source                    1..12
                          mol_type = protein
                          organism = synthetic construct
SEQUENCE: 528
ARDSNYEWFF DL                                                                    12

SEQ ID NO: 529            moltype = AA   length = 6
```

-continued

```
FEATURE            Location/Qualifiers
REGION             1..6
                   note = Description of Artificial Sequence: Synthetic peptide
source             1..6
                   mol_type = protein
                   organism = synthetic construct
SEQUENCE: 529
QSVSSY                                                                 6

SEQ ID NO: 530     moltype =    length =
SEQUENCE: 530
000

SEQ ID NO: 531     moltype = AA   length = 9
FEATURE            Location/Qualifiers
REGION             1..9
                   note = Description of Artificial Sequence: Synthetic peptide
source             1..9
                   mol_type = protein
                   organism = synthetic construct
SEQUENCE: 531
QQRSNWPLT                                                              9

SEQ ID NO: 532     moltype = AA   length = 7
FEATURE            Location/Qualifiers
REGION             1..7
                   note = Description of Artificial Sequence: Synthetic peptide
source             1..7
                   mol_type = protein
                   organism = synthetic construct
SEQUENCE: 532
SGGSYWS                                                                7

SEQ ID NO: 533     moltype = AA   length = 16
FEATURE            Location/Qualifiers
REGION             1..16
                   note = Description of Artificial Sequence: Synthetic peptide
source             1..16
                   mol_type = protein
                   organism = synthetic construct
SEQUENCE: 533
YIYNSGSTYY NPSLKS                                                      16

SEQ ID NO: 534     moltype = AA   length = 10
FEATURE            Location/Qualifiers
REGION             1..10
                   note = Description of Artificial Sequence: Synthetic peptide
source             1..10
                   mol_type = protein
                   organism = synthetic construct
SEQUENCE: 534
DSNYEWFFDL                                                             10

SEQ ID NO: 535     moltype = AA   length = 11
FEATURE            Location/Qualifiers
REGION             1..11
                   note = Description of Artificial Sequence: Synthetic peptide
source             1..11
                   mol_type = protein
                   organism = synthetic construct
SEQUENCE: 535
RASQSVSSYL A                                                           11

SEQ ID NO: 536     moltype = AA   length = 7
FEATURE            Location/Qualifiers
REGION             1..7
                   note = Description of Artificial Sequence: Synthetic peptide
source             1..7
                   mol_type = protein
                   organism = synthetic construct
SEQUENCE: 536
DASNRAT                                                                7

SEQ ID NO: 537     moltype = AA   length = 9
FEATURE            Location/Qualifiers
REGION             1..9
                   note = Description of Artificial Sequence: Synthetic peptide
source             1..9
                   mol_type = protein
```

-continued

```
                              organism = synthetic construct
SEQUENCE: 537
QQRSNWPLT                                                              9

SEQ ID NO: 538          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 538
GGSISSGGS                                                              9

SEQ ID NO: 539          moltype =   length =
SEQUENCE: 539
000

SEQ ID NO: 540          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 540
SNYEWFFD                                                               8

SEQ ID NO: 541          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 541
SQSVSSY                                                                7

SEQ ID NO: 542          moltype =   length =
SEQUENCE: 542
000

SEQ ID NO: 543          moltype = AA   length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 543
RSNWPL                                                                 6

SEQ ID NO: 544          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 544
SSGGSYWS                                                               8

SEQ ID NO: 545          moltype = AA   length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 545
WIGYIYNSGS TY                                                          12

SEQ ID NO: 546          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
```

-continued

```
SEQUENCE: 546
ARDSNYEWFF D                                                         11

SEQ ID NO: 547        moltype = AA   length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 547
SSYLAWY                                                              7

SEQ ID NO: 548        moltype = AA   length = 10
FEATURE               Location/Qualifiers
REGION                1..10
                      note = Description of Artificial Sequence: Synthetic peptide
source                1..10
                      mol_type = protein
                      organism = synthetic construct
SEQUENCE: 548
LLIYDASNRA                                                           10

SEQ ID NO: 549        moltype = AA   length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 549
QQRSNWPL                                                             8

SEQ ID NO: 550        moltype = AA   length = 12
FEATURE               Location/Qualifiers
REGION                1..12
                      note = Description of Artificial Sequence: Synthetic peptide
source                1..12
                      mol_type = protein
                      organism = synthetic construct
SEQUENCE: 550
GGSISSGGSY WS                                                        12

SEQ ID NO: 551        moltype = AA   length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 551
YIYNSGSTY                                                            9

SEQ ID NO: 552        moltype = AA   length = 10
FEATURE               Location/Qualifiers
REGION                1..10
                      note = Description of Artificial Sequence: Synthetic peptide
source                1..10
                      mol_type = protein
                      organism = synthetic construct
SEQUENCE: 552
DSNYEWFFDL                                                           10

SEQ ID NO: 553        moltype = AA   length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 553
RASQSVSSYL A                                                         11

SEQ ID NO: 554        moltype = AA   length = 7
FEATURE               Location/Qualifiers
REGION                1..7
                      note = Description of Artificial Sequence: Synthetic peptide
source                1..7
                      mol_type = protein
```

-continued

```
                              organism = synthetic construct
SEQUENCE: 554
DASNRAT                                                                7

SEQ ID NO: 555               moltype = AA   length = 9
FEATURE                      Location/Qualifiers
REGION                       1..9
                             note = Description of Artificial Sequence: Synthetic peptide
source                       1..9
                             mol_type = protein
                             organism = synthetic construct
SEQUENCE: 555
QQRSNWPLT                                                              9

SEQ ID NO: 556               moltype = AA   length = 10
FEATURE                      Location/Qualifiers
REGION                       1..10
                             note = Description of Artificial Sequence: Synthetic peptide
source                       1..10
                             mol_type = protein
                             organism = synthetic construct
SEQUENCE: 556
GYSFTSYWIS                                                             10

SEQ ID NO: 557               moltype = AA   length = 17
FEATURE                      Location/Qualifiers
REGION                       1..17
                             note = Description of Artificial Sequence: Synthetic peptide
source                       1..17
                             mol_type = protein
                             organism = synthetic construct
SEQUENCE: 557
IIDPSDSDTR YSPSFQG                                                     17

SEQ ID NO: 558               moltype = AA   length = 9
FEATURE                      Location/Qualifiers
REGION                       1..9
                             note = Description of Artificial Sequence: Synthetic peptide
source                       1..9
                             mol_type = protein
                             organism = synthetic construct
SEQUENCE: 558
GDGSTDLDY                                                              9

SEQ ID NO: 559               moltype = AA   length = 12
FEATURE                      Location/Qualifiers
REGION                       1..12
                             note = Description of Artificial Sequence: Synthetic peptide
source                       1..12
                             mol_type = protein
                             organism = synthetic construct
SEQUENCE: 559
RASQSVSSSY LA                                                          12

SEQ ID NO: 560               moltype = AA   length = 7
FEATURE                      Location/Qualifiers
REGION                       1..7
                             note = Description of Artificial Sequence: Synthetic peptide
source                       1..7
                             mol_type = protein
                             organism = synthetic construct
SEQUENCE: 560
GASSRAT                                                                7

SEQ ID NO: 561               moltype = AA   length = 9
FEATURE                      Location/Qualifiers
REGION                       1..9
                             note = Description of Artificial Sequence: Synthetic peptide
source                       1..9
                             mol_type = protein
                             organism = synthetic construct
SEQUENCE: 561
QQDYGFPWT                                                              9

SEQ ID NO: 562               moltype = AA   length = 8
FEATURE                      Location/Qualifiers
REGION                       1..8
                             note = Description of Artificial Sequence: Synthetic peptide
source                       1..8
```

-continued

```
                       mol_type = protein
                       organism = synthetic construct
SEQUENCE: 562
GYSFTSYW                                                        8

SEQ ID NO: 563         moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 563
IDPSDSDT                                                        8

SEQ ID NO: 564         moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 564
ARGDGSTDLD Y                                                    11

SEQ ID NO: 565         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 565
QSVSSSY                                                         7

SEQ ID NO: 566         moltype =   length =
SEQUENCE: 566
000

SEQ ID NO: 567         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 567
QQDYGFPWT                                                       9

SEQ ID NO: 568         moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 568
SYWIS                                                           5

SEQ ID NO: 569         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 569
IIDPSDSDTR YSPSFQG                                              17

SEQ ID NO: 570         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 570
GDGSTDLDY                                                       9
```

-continued

```
SEQ ID NO: 571          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 571
RASQSVSSSY LA                                                            12

SEQ ID NO: 572          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 572
GASSRAT                                                                  7

SEQ ID NO: 573          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 573
QQDYGFPWT                                                                9

SEQ ID NO: 574          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 574
GYSFTSY                                                                  7

SEQ ID NO: 575          moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 575
PSDS                                                                     4

SEQ ID NO: 576          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 576
DGSTDLD                                                                  7

SEQ ID NO: 577          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 577
SQSVSSSY                                                                 8

SEQ ID NO: 578          moltype =    length =
SEQUENCE: 578
000

SEQ ID NO: 579          moltype = AA  length = 6
FEATURE                 Location/Qualifiers
REGION                  1..6
                        note = Description of Artificial Sequence: Synthetic peptide
source                  1..6
```

```
                            mol_type = protein
                            organism = synthetic construct
SEQUENCE: 579
DYGFPW                                                                              6

SEQ ID NO: 580              moltype = AA   length = 6
FEATURE                     Location/Qualifiers
REGION                      1..6
                            note = Description of Artificial Sequence: Synthetic peptide
source                      1..6
                            mol_type = protein
                            organism = synthetic construct
SEQUENCE: 580
TSYWIS                                                                              6

SEQ ID NO: 581              moltype = AA   length = 13
FEATURE                     Location/Qualifiers
REGION                      1..13
                            note = Description of Artificial Sequence: Synthetic peptide
source                      1..13
                            mol_type = protein
                            organism = synthetic construct
SEQUENCE: 581
WMGIIDPSDS DTR                                                                      13

SEQ ID NO: 582              moltype = AA   length = 10
FEATURE                     Location/Qualifiers
REGION                      1..10
                            note = Description of Artificial Sequence: Synthetic peptide
source                      1..10
                            mol_type = protein
                            organism = synthetic construct
SEQUENCE: 582
ARGDGSTDLD                                                                          10

SEQ ID NO: 583              moltype = AA   length = 8
FEATURE                     Location/Qualifiers
REGION                      1..8
                            note = Description of Artificial Sequence: Synthetic peptide
source                      1..8
                            mol_type = protein
                            organism = synthetic construct
SEQUENCE: 583
SSSYLAWY                                                                            8

SEQ ID NO: 584              moltype = AA   length = 10
FEATURE                     Location/Qualifiers
REGION                      1..10
                            note = Description of Artificial Sequence: Synthetic peptide
source                      1..10
                            mol_type = protein
                            organism = synthetic construct
SEQUENCE: 584
LLIYGASSRA                                                                          10

SEQ ID NO: 585              moltype = AA   length = 8
FEATURE                     Location/Qualifiers
REGION                      1..8
                            note = Description of Artificial Sequence: Synthetic peptide
source                      1..8
                            mol_type = protein
                            organism = synthetic construct
SEQUENCE: 585
QQDYGFPW                                                                            8

SEQ ID NO: 586              moltype = AA   length = 10
FEATURE                     Location/Qualifiers
REGION                      1..10
                            note = Description of Artificial Sequence: Synthetic peptide
source                      1..10
                            mol_type = protein
                            organism = synthetic construct
SEQUENCE: 586
GYSFTSYWIS                                                                          10

SEQ ID NO: 587              moltype = AA   length = 10
FEATURE                     Location/Qualifiers
REGION                      1..10
                            note = Description of Artificial Sequence: Synthetic peptide
```

-continued

```
source                    1..10
                          mol_type = protein
                          organism = synthetic construct
SEQUENCE: 587
IIDPSDSDTR                                                                    10

SEQ ID NO: 588            moltype = AA  length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 588
GDGSTDLDY                                                                     9

SEQ ID NO: 589            moltype = AA  length = 12
FEATURE                   Location/Qualifiers
REGION                    1..12
                          note = Description of Artificial Sequence: Synthetic peptide
source                    1..12
                          mol_type = protein
                          organism = synthetic construct
SEQUENCE: 589
RASQSVSSSY LA                                                                 12

SEQ ID NO: 590            moltype = AA  length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 590
GASSRAT                                                                       7

SEQ ID NO: 591            moltype = AA  length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 591
QQDYGFPWT                                                                     9

SEQ ID NO: 592            moltype =    length =
SEQUENCE: 592
000

SEQ ID NO: 593            moltype =    length =
SEQUENCE: 593
000

SEQ ID NO: 594            moltype =    length =
SEQUENCE: 594
000

SEQ ID NO: 595            moltype =    length =
SEQUENCE: 595
000

SEQ ID NO: 596            moltype =    length =
SEQUENCE: 596
000

SEQ ID NO: 597            moltype =    length =
SEQUENCE: 597
000

SEQ ID NO: 598            moltype =    length =
SEQUENCE: 598
000

SEQ ID NO: 599            moltype =    length =
SEQUENCE: 599
000

SEQ ID NO: 600            moltype =    length =
```

-continued

```
SEQUENCE: 600
000

SEQ ID NO: 601          moltype =   length =
SEQUENCE: 601
000

SEQ ID NO: 602          moltype =   length =
SEQUENCE: 602
000

SEQ ID NO: 603          moltype =   length =
SEQUENCE: 603
000

SEQ ID NO: 604          moltype =   length =
SEQUENCE: 604
000

SEQ ID NO: 605          moltype =   length =
SEQUENCE: 605
000

SEQ ID NO: 606          moltype =   length =
SEQUENCE: 606
000

SEQ ID NO: 607          moltype =   length =
SEQUENCE: 607
000

SEQ ID NO: 608          moltype =   length =
SEQUENCE: 608
000

SEQ ID NO: 609          moltype =   length =
SEQUENCE: 609
000

SEQ ID NO: 610          moltype =   length =
SEQUENCE: 610
000

SEQ ID NO: 611          moltype =   length =
SEQUENCE: 611
000

SEQ ID NO: 612          moltype =   length =
SEQUENCE: 612
000

SEQ ID NO: 613          moltype =   length =
SEQUENCE: 613
000

SEQ ID NO: 614          moltype =   length =
SEQUENCE: 614
000

SEQ ID NO: 615          moltype =   length =
SEQUENCE: 615
000

SEQ ID NO: 616          moltype =   length =
SEQUENCE: 616
000

SEQ ID NO: 617          moltype =   length =
SEQUENCE: 617
000

SEQ ID NO: 618          moltype =   length =
SEQUENCE: 618
000

SEQ ID NO: 619          moltype =   length =
SEQUENCE: 619
000
```

-continued

```
SEQ ID NO: 620          moltype =   length =
SEQUENCE: 620
000

SEQ ID NO: 621          moltype =   length =
SEQUENCE: 621
000

SEQ ID NO: 622          moltype =   length =
SEQUENCE: 622
000

SEQ ID NO: 623          moltype =   length =
SEQUENCE: 623
000

SEQ ID NO: 624          moltype =   length =
SEQUENCE: 624
000

SEQ ID NO: 625          moltype =   length =
SEQUENCE: 625
000

SEQ ID NO: 626          moltype =   length =
SEQUENCE: 626
000

SEQ ID NO: 627          moltype =   length =
SEQUENCE: 627
000

SEQ ID NO: 628          moltype =   length =
SEQUENCE: 628
000

SEQ ID NO: 629          moltype =   length =
SEQUENCE: 629
000

SEQ ID NO: 630          moltype =   length =
SEQUENCE: 630
000

SEQ ID NO: 631          moltype =   length =
SEQUENCE: 631
000

SEQ ID NO: 632          moltype =   length =
SEQUENCE: 632
000

SEQ ID NO: 633          moltype =   length =
SEQUENCE: 633
000

SEQ ID NO: 634          moltype =   length =
SEQUENCE: 634
000

SEQ ID NO: 635          moltype =   length =
SEQUENCE: 635
000

SEQ ID NO: 636          moltype =   length =
SEQUENCE: 636
000

SEQ ID NO: 637          moltype =   length =
SEQUENCE: 637
000

SEQ ID NO: 638          moltype =   length =
SEQUENCE: 638
000

SEQ ID NO: 639          moltype =   length =
SEQUENCE: 639
000
```

-continued

```
SEQ ID NO: 640              moltype =    length =
SEQUENCE: 640
000

SEQ ID NO: 641              moltype =    length =
SEQUENCE: 641
000

SEQ ID NO: 642              moltype =    length =
SEQUENCE: 642
000

SEQ ID NO: 643              moltype =    length =
SEQUENCE: 643
000

SEQ ID NO: 644              moltype =    length =
SEQUENCE: 644
000

SEQ ID NO: 645              moltype =    length =
SEQUENCE: 645
000

SEQ ID NO: 646              moltype =    length =
SEQUENCE: 646
000

SEQ ID NO: 647              moltype =    length =
SEQUENCE: 647
000

SEQ ID NO: 648              moltype =    length =
SEQUENCE: 648
000

SEQ ID NO: 649              moltype =    length =
SEQUENCE: 649
000

SEQ ID NO: 650              moltype =    length =
SEQUENCE: 650
000

SEQ ID NO: 651              moltype =    length =
SEQUENCE: 651
000

SEQ ID NO: 652              moltype =    length =
SEQUENCE: 652
000

SEQ ID NO: 653              moltype =    length =
SEQUENCE: 653
000

SEQ ID NO: 654              moltype =    length =
SEQUENCE: 654
000

SEQ ID NO: 655              moltype =    length =
SEQUENCE: 655
000

SEQ ID NO: 656              moltype =    length =
SEQUENCE: 656
000

SEQ ID NO: 657              moltype =    length =
SEQUENCE: 657
000

SEQ ID NO: 658              moltype =    length =
SEQUENCE: 658
000

SEQ ID NO: 659              moltype =    length =
SEQUENCE: 659
```

-continued

```
000

SEQ ID NO: 660          moltype =    length =
SEQUENCE: 660
000

SEQ ID NO: 661          moltype =    length =
SEQUENCE: 661
000

SEQ ID NO: 662          moltype =    length =
SEQUENCE: 662
000

SEQ ID NO: 663          moltype =    length =
SEQUENCE: 663
000

SEQ ID NO: 664          moltype =    length =
SEQUENCE: 664
000

SEQ ID NO: 665          moltype =    length =
SEQUENCE: 665
000

SEQ ID NO: 666          moltype =    length =
SEQUENCE: 666
000

SEQ ID NO: 667          moltype =    length =
SEQUENCE: 667
000

SEQ ID NO: 668          moltype =    length =
SEQUENCE: 668
000

SEQ ID NO: 669          moltype =    length =
SEQUENCE: 669
000

SEQ ID NO: 670          moltype =    length =
SEQUENCE: 670
000

SEQ ID NO: 671          moltype =    length =
SEQUENCE: 671
000

SEQ ID NO: 672          moltype =    length =
SEQUENCE: 672
000

SEQ ID NO: 673          moltype =    length =
SEQUENCE: 673
000

SEQ ID NO: 674          moltype =    length =
SEQUENCE: 674
000

SEQ ID NO: 675          moltype =    length =
SEQUENCE: 675
000

SEQ ID NO: 676          moltype =    length =
SEQUENCE: 676
000

SEQ ID NO: 677          moltype =    length =
SEQUENCE: 677
000

SEQ ID NO: 678          moltype =    length =
SEQUENCE: 678
000

SEQ ID NO: 679          moltype =    length =
```

-continued

SEQUENCE: 679
000

SEQ ID NO: 680          moltype =    length =
SEQUENCE: 680
000

SEQ ID NO: 681          moltype =    length =
SEQUENCE: 681
000

SEQ ID NO: 682          moltype =    length =
SEQUENCE: 682
000

SEQ ID NO: 683          moltype =    length =
SEQUENCE: 683
000

SEQ ID NO: 684          moltype =    length =
SEQUENCE: 684
000

SEQ ID NO: 685          moltype =    length =
SEQUENCE: 685
000

SEQ ID NO: 686          moltype =    length =
SEQUENCE: 686
000

SEQ ID NO: 687          moltype =    length =
SEQUENCE: 687
000

SEQ ID NO: 688          moltype =    length =
SEQUENCE: 688
000

SEQ ID NO: 689          moltype =    length =
SEQUENCE: 689
000

SEQ ID NO: 690          moltype =    length =
SEQUENCE: 690
000

SEQ ID NO: 691          moltype =    length =
SEQUENCE: 691
000

SEQ ID NO: 692          moltype =    length =
SEQUENCE: 692
000

SEQ ID NO: 693          moltype =    length =
SEQUENCE: 693
000

SEQ ID NO: 694          moltype =    length =
SEQUENCE: 694
000

SEQ ID NO: 695          moltype =    length =
SEQUENCE: 695
000

SEQ ID NO: 696          moltype =    length =
SEQUENCE: 696
000

SEQ ID NO: 697          moltype =    length =
SEQUENCE: 697
000

SEQ ID NO: 698          moltype =    length =
SEQUENCE: 698
000

-continued

```
SEQ ID NO: 699          moltype =   length =
SEQUENCE: 699
000

SEQ ID NO: 700          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 700
YPGDGN                                                                          6

SEQ ID NO: 701          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 701
NYGDYTID                                                                        8

SEQ ID NO: 702          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 702
YPGDGN                                                                          6

SEQ ID NO: 703          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 703
NMGMYTID                                                                        8

SEQ ID NO: 704          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 704
YPGDGN                                                                          6

SEQ ID NO: 705          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 705
NMGMYTLD                                                                        8

SEQ ID NO: 706          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 706
YPGDGN                                                                          6

SEQ ID NO: 707          moltype = AA  length = 8
FEATURE                 Location/Qualifiers
REGION                  1..8
                        note = Description of Artificial Sequence: Synthetic peptide
source                  1..8
```

```
                            mol_type = protein
                            organism = synthetic construct
SEQUENCE: 707
NYGDYTLD                                                              8

SEQ ID NO: 708             moltype = AA   length = 6
FEATURE                    Location/Qualifiers
REGION                     1..6
                           note = Description of Artificial Sequence: Synthetic peptide
source                     1..6
                           mol_type = protein
                           organism = synthetic construct
SEQUENCE: 708
YPGSGN                                                                6

SEQ ID NO: 709             moltype = AA   length = 8
FEATURE                    Location/Qualifiers
REGION                     1..8
                           note = Description of Artificial Sequence: Synthetic peptide
source                     1..8
                           mol_type = protein
                           organism = synthetic construct
SEQUENCE: 709
NYGDYTID                                                              8

SEQ ID NO: 710             moltype = AA   length = 6
FEATURE                    Location/Qualifiers
REGION                     1..6
                           note = Description of Artificial Sequence: Synthetic peptide
source                     1..6
                           mol_type = protein
                           organism = synthetic construct
SEQUENCE: 710
YPGSGN                                                                6

SEQ ID NO: 711             moltype = AA   length = 8
FEATURE                    Location/Qualifiers
REGION                     1..8
                           note = Description of Artificial Sequence: Synthetic peptide
source                     1..8
                           mol_type = protein
                           organism = synthetic construct
SEQUENCE: 711
NYGDYTID                                                              8

SEQ ID NO: 712             moltype = AA   length = 6
FEATURE                    Location/Qualifiers
REGION                     1..6
                           note = Description of Artificial Sequence: Synthetic peptide
source                     1..6
                           mol_type = protein
                           organism = synthetic construct
SEQUENCE: 712
HGGTGG                                                                6

SEQ ID NO: 713             moltype = AA   length = 8
FEATURE                    Location/Qualifiers
REGION                     1..8
                           note = Description of Artificial Sequence: Synthetic peptide
source                     1..8
                           mol_type = protein
                           organism = synthetic construct
SEQUENCE: 713
RGYGAWFA                                                              8

SEQ ID NO: 714             moltype = AA   length = 6
FEATURE                    Location/Qualifiers
REGION                     1..6
                           note = Description of Artificial Sequence: Synthetic peptide
source                     1..6
                           mol_type = protein
                           organism = synthetic construct
SEQUENCE: 714
SSSSSY                                                                6

SEQ ID NO: 715             moltype = AA   length = 14
FEATURE                    Location/Qualifiers
REGION                     1..14
                           note = Description of Artificial Sequence: Synthetic peptide
```

-continued

```
source                  1..14
                        mol_type = protein
                        organism = synthetic construct
SEQUENCE: 715
DVGVTTDYYY YGMD                                                        14

SEQ ID NO: 716          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 716
IPFFGT                                                                 6

SEQ ID NO: 717          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 717
PGSGSPDYYY YDMD                                                        14

SEQ ID NO: 718          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 718
IPIFNT                                                                 6

SEQ ID NO: 719          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 719
EGTGYSYGLD                                                             10

SEQ ID NO: 720          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 720
YNSGS                                                                  5

SEQ ID NO: 721          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 721
DSNYEWFFD                                                              9

SEQ ID NO: 722          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 722
DPSDSD                                                                 6

SEQ ID NO: 723          moltype = AA  length = 8
FEATURE                 Location/Qualifiers
REGION                  1..8
```

```
                          note = Description of Artificial Sequence: Synthetic peptide
source                    1..8
                          mol_type = protein
                          organism = synthetic construct
SEQUENCE: 723
GDGSTDLD                                                              8

SEQ ID NO: 724            moltype =   length =
SEQUENCE: 724
000

SEQ ID NO: 725            moltype =   length =
SEQUENCE: 725
000

SEQ ID NO: 726            moltype =   length =
SEQUENCE: 726
000

SEQ ID NO: 727            moltype =   length =
SEQUENCE: 727
000

SEQ ID NO: 728            moltype =   length =
SEQUENCE: 728
000

SEQ ID NO: 729            moltype =   length =
SEQUENCE: 729
000

SEQ ID NO: 730            moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 730
GRTFSRYTMG                                                            10

SEQ ID NO: 731            moltype = AA  length = 17
FEATURE                   Location/Qualifiers
REGION                    1..17
                          note = Description of Artificial Sequence: Synthetic peptide
source                    1..17
                          mol_type = protein
                          organism = synthetic construct
SEQUENCE: 731
AISWSGGRTN FAGSVKG                                                    17

SEQ ID NO: 732            moltype = AA  length = 13
FEATURE                   Location/Qualifiers
REGION                    1..13
                          note = Description of Artificial Sequence: Synthetic peptide
source                    1..13
                          mol_type = protein
                          organism = synthetic construct
SEQUENCE: 732
DWLPVPGRES YDY                                                        13

SEQ ID NO: 733            moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 733
GRTFSSYAMG                                                            10

SEQ ID NO: 734            moltype = AA  length = 17
FEATURE                   Location/Qualifiers
REGION                    1..17
                          note = Description of Artificial Sequence: Synthetic peptide
source                    1..17
                          mol_type = protein
                          organism = synthetic construct
SEQUENCE: 734
```

-continued

AISWSGGTTY YADSVKG                                                    17

SEQ ID NO: 735          moltype = AA   length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 735
SLDCSGPGCH TAEYDY                                                     16

SEQ ID NO: 736          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 736
GRTFSEYAMG                                                            10

SEQ ID NO: 737          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 737
AISWTGSKTY YADSVKG                                                    17

SEQ ID NO: 738          moltype = AA   length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 738
SSDCSGPGCH TEEYDY                                                     16

SEQ ID NO: 739          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 739
GRTFSSYAMG                                                            10

SEQ ID NO: 740          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 740
AVSWSGGSTY YADSVKG                                                    17

SEQ ID NO: 741          moltype = AA   length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 741
SQDCSGPGCY TNEYDS                                                     16

SEQ ID NO: 742          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct -continued

```
SEQUENCE: 742
GSIFSNYAMA                                                              10

SEQ ID NO: 743          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 743
AVSWSGGRTY YADSVKG                                                      17

SEQ ID NO: 744          moltype = AA   length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 744
SLSCSGPGCS LEEYDY                                                       16

SEQ ID NO: 745          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 745
GRPFSNYGMG                                                              10

SEQ ID NO: 746          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 746
GITWSGGSTH YADLVKG                                                      17

SEQ ID NO: 747          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 747
VFSGAETAYY PSTEYDY                                                      17

SEQ ID NO: 748          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 748
VRTFSDYRMG                                                              10

SEQ ID NO: 749          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 749
TISWSGGLTY YADSVKG                                                      17

SEQ ID NO: 750          moltype = AA   length = 14
FEATURE                 Location/Qualifiers
REGION                  1..14
                        note = Description of Artificial Sequence: Synthetic peptide
source                  1..14
                        mol_type = protein
```

```
                        organism = synthetic construct
SEQUENCE: 750
GGGYAGGTYY HPEE                                                       14

SEQ ID NO: 751          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 751
EVQLVESGGG LVQAGDSLRL SCAASGRTFS RYTMGWFRQA PGKEREFVAA ISWSGGRTNF   60
AGSVKGRFTI SRDNAKNTVY LQMNSLKPED TAVYYCAADW LPVPGRESYD YWGQGTQVTV   120
SS                                                                   122

SEQ ID NO: 752          moltype = AA  length = 125
FEATURE                 Location/Qualifiers
REGION                  1..125
                        note = Description of Artificial Sequence: Synthetic
                         polypeptide
source                  1..125
                        mol_type = protein
                        organism = synthetic construct
SEQUENCE: 752
EVQLVESGGG LVQAGGSLRL SCTASGRTFS SYAMGWFRQA PGKEREFVAA ISWSGGTTYY   60
ADSVKGRFTI SRDNAKNTVS LQMNSLKPED TAVYFCAASL DCSGPGCHTA EYDYWGQGTQ   120
VTVSS                                                                125

SEQ ID NO: 753          moltype = AA  length = 125
FEATURE                 Location/Qualifiers
REGION                  1..125
                        note = Description of Artificial Sequence: Synthetic
                         polypeptide
source                  1..125
                        mol_type = protein
                        organism = synthetic construct
SEQUENCE: 753
EVQLVESGGG LVQAGGSLRL SCAATGRTFS EYAMGWFRQA PGKEREFAAA ISWIGSKTYY   60
ADSVKGRFTI SRDNAKNTVY LQMNSLKPED TAVYYCAASS DCSGPGCHTE EYDYWGQGTQ   120
VTVSS                                                                125

SEQ ID NO: 754          moltype = AA  length = 125
FEATURE                 Location/Qualifiers
REGION                  1..125
                        note = Description of Artificial Sequence: Synthetic
                         polypeptide
source                  1..125
                        mol_type = protein
                        organism = synthetic construct
SEQUENCE: 754
EVQLVESGGG LVQAGGSLRL SCAASGRTFS SYAMGWFRQA PGKEREFVAA VSWSGGSTYY   60
ADSVKGRFTI SRDNARNTVY LQMNSLNPED TAVYYCAASQ DCSGPGCYTN EYDSWGQGTQ   120
VTVSS                                                                125

SEQ ID NO: 755          moltype = AA  length = 125
FEATURE                 Location/Qualifiers
REGION                  1..125
                        note = Description of Artificial Sequence: Synthetic
                         polypeptide
source                  1..125
                        mol_type = protein
                        organism = synthetic construct
SEQUENCE: 755
EVQLVESGGG LVQPGGSLRL SCAASGSIFS NYAMAWFRQA PEKERDFLAA VSWSGGRTYY   60
ADSVKGRFTI SRDNAKNTVN LQMNSLKPED TAVYYCAASL SCSGPGCSLE EYDYWGQGTQ   120
VTVSS                                                                125

SEQ ID NO: 756          moltype = AA  length = 126
FEATURE                 Location/Qualifiers
REGION                  1..126
                        note = Description of Artificial Sequence: Synthetic
                         polypeptide
source                  1..126
                        mol_type = protein
                        organism = synthetic construct
SEQUENCE: 756
EVQLVESGGG LVQAGGSLRL SCAVSGRPFS NYGMGWFRQA PGKEREFVAG ITWSGGSTHY   60
```

-continued

```
ADLVKGRFTI SRDNAKNTVH LQMNSLKPED TAVYYCAAVF SGAETAYYPS TEYDYWGQGT 120
QVTVSS                                                                126

SEQ ID NO: 757          moltype = AA  length = 123
FEATURE                 Location/Qualifiers
REGION                  1..123
                        note = Description of Artificial Sequence: Synthetic
                         polypeptide
source                  1..123
                        mol_type = protein
                        organism = synthetic construct
SEQUENCE: 757
EVQLVESGGG LVQAGGSLRL SCAVSVRTFS DYRMGWFRQA PGKEREFVST ISWSGGLTYY 60
ADSVKGRFTI SRDNSKNTLY LQMNSLKPED TAVYYCAAGG GYAGGTYYHP EEWGQGTQVT 120
VSS                                                                  123

SEQ ID NO: 758          moltype = AA  length = 11
FEATURE                 Location/Qualifiers
REGION                  1..11
                        note = Description of Artificial Sequence: Synthetic peptide
VARIANT                 4
                        note = MOD_RES - Tyr or Met
VARIANT                 6
                        note = MOD_RES - Met or Asp
VARIANT                 9
                        note = MOD_RES - Ile or Leu
source                  1..11
                        mol_type = protein
                        organism = synthetic construct
SEQUENCE: 758
APNXGXYTXD F                                                          11

SEQ ID NO: 759          moltype =   length =
SEQUENCE: 759
000

SEQ ID NO: 760          moltype =   length =
SEQUENCE: 760
000

SEQ ID NO: 761          moltype =   length =
SEQUENCE: 761
000

SEQ ID NO: 762          moltype = AA  length = 6
FEATURE                 Location/Qualifiers
REGION                  1..6
                        note = Description of Artificial Sequence: Synthetic peptide
VARIANT                 2
                        note = MOD_RES - Ala or Ser
VARIANT                 6
                        note = MOD_RES - Val or Leu
source                  1..6
                        mol_type = protein
                        organism = synthetic construct
SEQUENCE: 762
RXSQSX                                                                6
```

What is claimed is:

1. An antibody that binds to T Cell Receptor Gamma Variable 9 (TRGV9), wherein the antibody comprises a heavy chain variable region (VH) and a light chain variable region (VL), wherein the antibody comprises: (i) a VH comprising a VH CDR1 having the amino acid sequence of SEQ ID NO: 107, a VH CDR2 having the amino acid sequence of SEQ ID NO: 108, and a VH CDR3 having the amino acid sequence of SEQ ID NO: 109; and (ii) a VL comprising a VL CDR1 having the amino acid sequence of SEQ ID NO: 110, a VL CDR2 having the amino acid sequence of SEQ ID NO: 111, and a VL CDR3 having the amino acid sequence of SEQ ID NO:112.

2. The antibody of claim 1, wherein the antibody comprises a VH having the amino acid sequence of SEQ ID NO:113.

3. The antibody of claim 1, wherein the antibody comprises a VL having the amino acid sequence of SEQ ID NO:114.

4. A vector comprising a nucleic acid encoding the antibody of claim 1.

5. A host cell comprising the vector of claim 4.

6. A pharmaceutical composition comprising the antibody of claim 1, and a pharmaceutically acceptable carrier.

* * * * *